(12) United States Patent
Almstead et al.

(10) Patent No.: US 9,611,230 B2
(45) Date of Patent: Apr. 4, 2017

(54) 1,3,4-OXADIAZOLE BENZOIC ACID COMPOUNDS AND THEIR USE FOR NONSENSE SUPPRESSION AND THE TREATMENT OF DISEASE

(75) Inventors: Neil G. Almstead, Princeton, NJ (US); Guangming Chen, Bridgewater, NJ (US); Gary M. Karp, Princeton Junction, NJ (US); Ellen Welch, Califon, NJ (US); Richard Wilde, Somerville, NJ (US); Jeffrey A. Campbell, Bethlehem, PA (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 1513 days.

(21) Appl. No.: 11/577,191

(22) PCT Filed: Oct. 13, 2005

(86) PCT No.: PCT/US2005/036673
§ 371 (c)(1),
(2), (4) Date: Mar. 12, 2009

(87) PCT Pub. No.: WO2006/044456
PCT Pub. Date: Apr. 27, 2006

(65) Prior Publication Data
US 2009/0253699 A1    Oct. 8, 2009

Related U.S. Application Data

(60) Provisional application No. 60/617,653, filed on Oct. 13, 2004, provisional application No. 60/617,670, filed on Oct. 13, 2004, provisional application No. 60/617,633, filed on Oct. 13, 2004, provisional application No. 60/617,634, filed on Oct. 13, 2004, provisional application No. 60/617,655, filed on Oct. 13, 2004, provisional application No. 60/624,170, filed on Nov. 3, 2004.

(51) Int. Cl.

| | | |
|---|---|---|
| C07D 271/10 | (2006.01) |
| C07D 271/107 | (2006.01) |
| C07D 251/24 | (2006.01) |
| C07D 231/12 | (2006.01) |
| C07D 233/64 | (2006.01) |
| C07D 249/08 | (2006.01) |
| C07D 261/08 | (2006.01) |
| C07D 263/32 | (2006.01) |
| C07D 271/06 | (2006.01) |
| C07D 277/30 | (2006.01) |
| C07D 285/12 | (2006.01) |
| C07D 307/68 | (2006.01) |
| C07D 333/24 | (2006.01) |
| C07D 413/12 | (2006.01) |
| C07F 9/653 | (2006.01) |
| C07D 401/04 | (2006.01) |
| C07D 403/04 | (2006.01) |
| C07D 405/04 | (2006.01) |
| C07D 409/04 | (2006.01) |
| C07D 413/04 | (2006.01) |

(52) U.S. Cl.
CPC ......... *C07D 251/24* (2013.01); *C07D 231/12* (2013.01); *C07D 233/64* (2013.01); *C07D 249/08* (2013.01); *C07D 261/08* (2013.01); *C07D 263/32* (2013.01); *C07D 271/06* (2013.01); *C07D 271/10* (2013.01); *C07D 271/107* (2013.01); *C07D 277/30* (2013.01); *C07D 285/12* (2013.01); *C07D 307/68* (2013.01); *C07D 333/24* (2013.01); *C07D 401/04* (2013.01); *C07D 403/04* (2013.01); *C07D 405/04* (2013.01); *C07D 409/04* (2013.01); *C07D 413/04* (2013.01); *C07D 413/12* (2013.01); *C07F 9/65306* (2013.01)

(58) Field of Classification Search
CPC .................... C07D 271/107; C07D 271/10
See application file for complete search history.

(56) References Cited

U.S. PATENT DOCUMENTS

| | | |
|---|---|---|
| 3,679,669 A | 7/1972 | Maeder et al. |
| 3,882,138 A | 5/1975 | Brouwer et al. |
| 3,947,263 A | 3/1976 | Brouwer et al. |
| 3,948,937 A | 4/1976 | Johnson et al. |
| 3,964,896 A | 6/1976 | Brouwer et al. |
| 4,032,644 A | 6/1977 | Nadelson |

(Continued)

FOREIGN PATENT DOCUMENTS

| | | |
|---|---|---|
| AU | 2004229487 B2 | 10/2004 |
| CA | 2 361 816 A1 | 10/2000 |

(Continued)

OTHER PUBLICATIONS

Huisgen et al. Chemishe Berichte, 1960, vol. 93, pp. 2106-2124 (Abstract attached).*

(Continued)

*Primary Examiner* — James D Anderson
(74) *Attorney, Agent, or Firm* — Hoffmann & Baron, LLP

(57) ABSTRACT

The present invention relates to methods, compounds, and compositions for treating or preventing diseases associated with nonsense mutations in an mRNA by administering the compounds or compositions of the present invention. More particularly, the present invention relates to methods, compounds, and compositions for suppressing premature translation termination associated with a nonsense mutation in an mRNA.

3 Claims, 4 Drawing Sheets

(56) References Cited

U.S. PATENT DOCUMENTS

| | | | |
|---|---|---|---|
| 4,035,175 A | 7/1977 | Brouwer et al. | |
| 4,135,910 A | 1/1979 | Howe | |
| 4,140,515 A | 2/1979 | Howe | |
| 4,166,732 A | 9/1979 | Howe | |
| 4,210,762 A | 7/1980 | Howe | |
| 4,229,204 A | 10/1980 | Howe | |
| 4,268,299 A | 5/1981 | Howe | |
| 5,614,520 A | 3/1997 | Kondo et al. | |
| 6,232,290 B1* | 5/2001 | Ohki et al. | 514/3.3 |
| 6,265,536 B1* | 7/2001 | Ohki et al. | 530/317 |
| 6,291,487 B1 | 9/2001 | Chihiro et al. | |
| 7,223,791 B2* | 5/2007 | Maekawa et al. | 514/461 |
| 2003/0187020 A1 | 10/2003 | Astles et al. | |
| 2004/0048863 A1* | 3/2004 | Bunker et al. | 514/242 |
| 2004/0204461 A1 | 10/2004 | Karp et al. | |
| 2005/0272718 A1* | 12/2005 | Ammenn et al. | 514/217.09 |

FOREIGN PATENT DOCUMENTS

| | | |
|---|---|---|
| CN | 1232396 A | 10/1999 |
| DE | 27 22 331 A1 | 11/1977 |
| DE | 38 19 037 A1 | 12/1989 |
| DE | 195 36 811 | 4/1997 |
| DE | 199 04 389 A1 | 8/2000 |
| EP | 0 497 678 A1 | 8/1992 |
| EP | 0497678 A1 * | 8/1992 |
| EP | 0 838 453 A1 | 4/1998 |
| EP | 0 889 032 A1 | 1/1999 |
| EP | 1 405 636 A1 | 4/2004 |
| EP | 0 838 453 B1 | 4/2005 |
| GB | 1 248 070 | 9/1971 |
| GB | 1 494 877 | 12/1977 |
| IE | 920319 | 7/1992 |
| JP | 6-107615 A | 4/1994 |
| JP | 2002-536365 A | 10/2002 |
| JP | 2003-81832 A | 3/2003 |
| JP | 2003-517479 A | 5/2003 |
| JP | 2004-510697 A | 4/2004 |
| JP | 2006-522826 A | 10/2006 |
| WO | WO 97/34869 | 9/1997 |
| WO | 97/44333 A1 | 11/1997 |
| WO | WO 00/08001 | 2/2000 |
| WO | WO 00/46208 | 8/2000 |
| WO | WO 01/44201 A1 | 6/2001 |
| WO | WO 01/64646 A2 | 9/2001 |
| WO | WO 01/90101 * | 11/2001 |
| WO | 02/068417 A2 | 9/2002 |
| WO | WO 02/068417 A2 | 9/2002 |
| WO | 03/027085 A2 | 4/2003 |
| WO | WO 03/027085 A2 | 4/2003 |
| WO | 03/097047 A1 | 11/2003 |
| WO | 2004/009558 A2 | 1/2004 |
| WO | WO 2004/009533 A1 | 1/2004 |
| WO | WO 2004/009558 A2 | 1/2004 |
| WO | 2004/014366 A1 | 2/2004 |
| WO | 2004/072050 A1 | 8/2004 |
| WO | WO 2004/072050 A1 | 8/2004 |
| WO | WO 2004/091502 A2 | 10/2004 |
| WO | 01/90101 A1 | 11/2011 |

OTHER PUBLICATIONS

Pachhamia et al. Journal of the Indian Chemical Society, 1989, vol. 66, No. 4, pp. 250-251 (Abstract Attached).*
Registry No. 384356-23-4 (Entered STN Jan. 19, 2002).*
Registry No. 383894-78-8 (Entered STN Jan. 17, 2002).*
Registry No. 369395-16-4 (Entered STN Nov. 13, 2001).*
Registry No. 352672-90-3 (Entered STN Aug. 27, 2001).*
Registry No. 313483-06-6 (Entered STN Jan. 11, 2001).*
Database Beilstein Beilstein Crossfire Institut Zur Foerderung Der Chemischen Wissenschaften, DE; BRN 244227 1886, XP002398307.
Database Beilstein Beilstein Crossfire Institut Zur Foerderung Der Chemischen Wissenschaften, DE; BRN 246305 1885, XP002398306.
Database Beilstein Beilstein Crossfire Institut Zur Foerderung Der Chemischen Wissenschaften, DE; BRN 305808 1889, XP002398305.
Database Beilstein Beilstein Crossfire Institut Zur Foerderung Der Chemischen Wissenschaften, DE; BRN 538794 1965, XP002398317.
Database Beilstein Beilstein Crossfire Institut Zur Foerderung Der Chemischen Wissenschaften, DE; BRN 547971 1982, XP002398315.
Database Beilstein Beilstein Crossfire Institut Zur Foerderung Der Chemischen Wissenschaften, DE; BRN 555456 1982, XP002398316.
Database Beilstein Beilstein Crossfire Institut Zur Foerderung Der Chemischen Wissenschaften, DE; BRN 617821 1960, XP002398318.
Database Beilstein Beilstein Crossfire Institut Zur Foerderung Der Chemischen Wissenschaften, DE; BRN 935729 1976, XP002398312.
Database Beilstein Beilstein Crossfire Institut Zur Foerderung Der Chemischen Wissenschaften, DE; BRN 998715 1976, XP002398311.
Database Beilstein Beilstein Crossfire Institut Zur Foerderung Der Chemischen Wissenschaften, DE; BRN 999077 1979, XP002398310.
Database Beilstein Beilstein Crossfire Institut Zur Foerderung Der Chemischen Wissenschaften, DE; BRN 1008399 1976, XP002398309.
Database Beilstein Beilstein Crossfire Institut Zur Foederung Der Chemischen Wissenschaften, DE; BRN 1014023 1978, XP002398308.
Database Beilstein Beilstein Crossfire Institut Zur Foerderung Der Chemischen Wissenschaften, DE; BRN 9659924 2003, XP002398313.
Database Beilstein Beilstein Crossfire Institut Zur Foerderung Der Chemischen Wissenschaften, DE; BRN 348134 1914, XP002398314.
Eyrolles L. et al., "Retinobenzoic Acids. 6. Retinoid Antagonists with a Heterocyclic Ring", Journal of Medicinal Chemistry, American Chemical Society, vol. 37, No. 10, pp. 1508-1517, (May 13, 1994), XP002024587 ISSN: 0022-2623.
International Search Report for PCT/US2005/036673, mailed Dec. 29, 2006.
Popova, N. A. et al: "Research in the 2,5-Diaryl-1,3,4-Oxadiazole Series. 1. Electronic Structures and Spectral-Luminescence Properties of Substituted 2,5-Diphenyl-1,3,4-Oxadiazoles", translated from Khimiya Geterotsiklicheskikh Soedinenii, No. 1, pp. 26-32, Jan. 1983.
Kikuchi K. et al., "Syntheses and Evaluation of Quinoline Derivatives as Novel Retinoic Acid Receptor Alpha Antagonists." Bioorganic & Medicinal Chemistry Letters, vol. 11, No. 9, pp. 1215-1218, (2001) XP002398288 ISSN: 0960-894X.
Kitamura S. et al., Orally Active GPIIb/IIIa Antagonists: Synthesis and Biological Activities of Masked Amidines as Prodrugs of 2-[(3S)-4-[(2S)-2-(4-Amidinobenzoylamino)-3-(4-methoxyphenyl)propanoyl]-3-(2-methoxy-2-oxoethyl)-2-oxopiperazinyl]acetic Acid. Chem. Pharm. Bull. 49(3), pp. 268-277 (2001).
Kobayashi Naoki et al., "A Library Construction of 2,5-Disubstituted Pyrrole Compounds by Using Solid/Solution-Phase Syntheses." Bioorganic & Medicinal Chemistry Letters, vol. 12, No. 13, pp. 1747-1750, (2002), XP002398289 ISSN: 0960-894X.
Toja E. et al., "Synthesis and pregnancy terminating activity of 2-aryl pyrazolo [5,1-a] isoindoles and isoquinolines", European Journal of Medicinal Chemistry, Editions Scientifique Elsevier, Paris, FR, vol. 17, No. 3, pp. 223-227, (1982) XP002078326 ISSN: 0223-5234.
Yoshimura Hiroyuki et al., "Discovery of Novel and Potent Retinoic Acid Receptor Alpha Agonists: Syntheses and Evaluation of Benzofuranyl-pyrrole and Benzothiophenyl-pyrrole Derivatives"

(56) References Cited

OTHER PUBLICATIONS

Journal of Medicinal Chemistry, American Chemical Society, vol. 43, pp. 2929-2937, (2000), XP002214937 ISSN: 0022-2623.
Australian Examination Report dated Apr. 29, 2010 for Australian Patent Application No. 2005295778.
Chun-Sing Li et al., "Synthesis of pyran-4-ones from isoxazoles," Tetrahedron Letters 43 (2002) 3565-3568, Published by Elsevier Science Ltd.
MacDonald, G.J. et al., "Design and Synthesis of trans-3-(2-(4-((3-(3-(5-Methyl-1, 2, 4-oxadiazolyl))-phenyl) carboxamido)cyclohexypethyl)-7-methylsulfonyl-2,3,4,5-tetrahydro-1H-3-benzazepine (SB-414796): A Potent and Selective Dopamine D. sub. 3 Receptor Antagonist," Journal of Medicinal Chemistry, American Chemical Society, vol. 46, No. 23, pp. 4952-4964, 2003.
XP-002398313, Beilstein Institute for Organic Chemistry, 2003.
European Search Report for European Application No. 10 18 5126 (date of completion of search: Feb. 2, 2011).
European Search Report for European Application No. 10 18 5128 (date of completion of search: Feb. 8, 2011).
European Search Report for European Application No. 10 18 5130 (date of completion of search: Feb. 8, 2011).
International Preliminary Report on Patentability for International Application No. PCT/US2005/036673 dated Apr. 17, 2007.
Office Action for Chinese Patent Application No. 200580042743.4 dated Mar. 30, 2011.
Communication for European Application No. 05 815 159.8 dated Feb. 17, 2011.
English Translation of Notification of Defects in Patent Application No. 182459 dated Sep. 1, 2010.
Examination Report for New Zealand Patent Application No. 554327 dated May 20, 2009.
Communication for European Application No. 05 815 159.8 dated May 27, 2008.
U.S. Appl. No. 60/461,988 dated Apr. 11, 2003.
Notice of Reasons for Rejection in corresponding Japanese Application No. 2007-536837 with Mailing Date Jan. 31, 2012.
CHEMCATS, Benzoic acid, 4-[5-(4-bromophenyl)-1,3,4-oxadiazol-2-yl]-, Jan. 19, 2002, RN 384357-35-1, XP-002742836.
Dzhaparidze, Z. SH., et al., "Synthesis of new analogs of gramine", XP-002742833, Soobshcheniya Akademii Nauk Gruzinskoi SSR (1988), 130(2), pp. 325-327; 1989:114757 CAPLUS.
Huisgen, R., et al., "Ring opening of azoles. II. The formation of 1,3,4-oxadiazoles in the acylation of 5-substituted tetrazoles", Chemische Berichte (1960), 93, pp. 2106-2124; 1961:13382 CAPLUS, XP-002742835.
Meyer, E., et al., "Synthesis of new 1,2,4- and 1,3,4-oxadiazole derivatives", Synthesis (2003), (6), 899-905; 2003:363333 CAPLUS, XP-002742834.

Pachhamia, V.L. and Parikh, A.R., "Studies on 2,5-disubstituted-1,3,4-oxadiazoles. Part-I. Preparation and antimicrobial activity of 2-aryl-5-(4'-benzenesulfonamidophenyl)/(4'-pyridyl)-1,3,4-oxadiazoles", Journal of the Indian Chemical Society (1989), 66(4), 250-1; 1990:7434 CAPLUS, XP-002742837.
Zambetti, Gerard P. and Levine, Arnold J., "A comparison of the biological activities of wild-type and mutant p53", FASEB J. 7:855-865 1993, XP002141229.
EPO Communication dated Aug. 21, 2015, with accompanying extended European search report including European search report and European search opinion for EP15168072.5, Date of Completion of Search: Jul. 29, 2015.
Chinese Office Action (in Chinese and in English) for Chinese Application No. 200580042743.4 dated 2009.
Notification of Transmittal of the International Search Report and the Written Opinion of the International Searching Authority, or the Declaration with Written Opinion of the International Searching Authority for International Application No. PCT/US2005/036673, Date of mailing: Dec. 29, 2006.
Young, Jonathan R. and DeVita, Robert J., Novel Synthesis of Oxadiazoles via Palladium Catalysis, Tetrahedron Letters 39 (1998) 3931-3934.
Zambetti, Gerard P. and Levine, Arnold J., "A comparison of the biological activities of wild-type and mutant p53", FASEB J. 7:855-865 1993, XP002141229, Feb. 23, 2016.
Meyer, E., et al., "Synthesis of new 1,2,4- and 1,3,4-oxadiazole derivatives", Synthesis (2003), (6), 899-905; 2003:363333 CAPLUS, XP-002742834, Feb. 23, 2016.
Extended European Search Report for European Application No. 15168072.5 which accompanied a Communication dated Aug. 21, 2015.
Yoshimura Hiroyuki et al., "Discovery of Novel and Potent Retinoic Acid Receptor Alpha Agonists: Syntheses and Evaluation of Benzofuranyl-pyrrole and Benzothiophenly-pyrrole Derivatives", Journal of Medicinal Chemistry, American Chemical Society, vol. 43, pp. 2929-2937, (2000), XP002214937 ISSN: 0022-2623.
Eyrolles L. et al., "Retinobenzoic Acids. 6. Retinoid Antagonists with a Heterocyclic Ring", Journal of Medicinal Chemistry, American Chemical Society, vol. 37, No. 10, pp. 1508-1517, (May 13, 1994), XP002024587 ISSN: 0022-2623, Nov. 18, 2009.
Kikuchi K. et al., "Syntheses and Evaluation of Quinoline Derivatives as Novel Retinoic Acid Receptor Alpha Antagonists." Bioorganic & Medicinal Chemistry Letters, vol. 11, No. 9, pp. 1215-1218, (2001) XP002398288 ISSN: 0960-894X, Nov. 18, 2009.
Kobayashi Naoki et al., "A Library Construction of 2,5-Disubstituted Pyrrole Compounds by Using Solid/Solution-Phase Syntheses." Bioorganic & Medicinal Chemistry Letters, vol. 12, No. 13, pp. 1747-1750, (2002), XP002398289 ISSN: 0960-894X, Nov. 18, 2009.

* cited by examiner

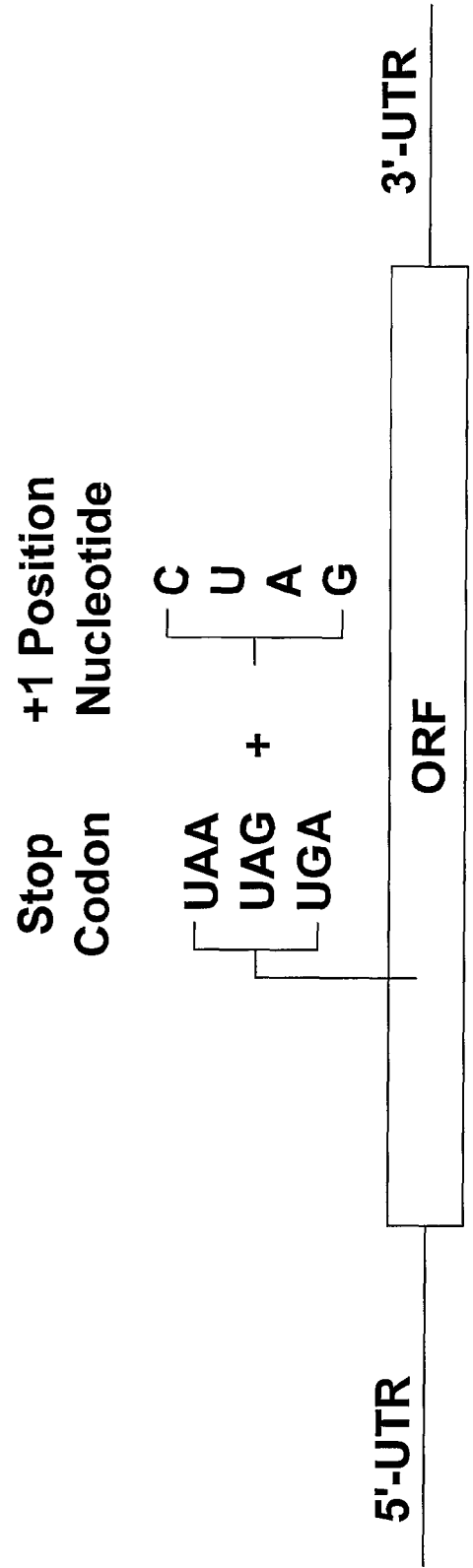
Figure 1: Luminescence Assay

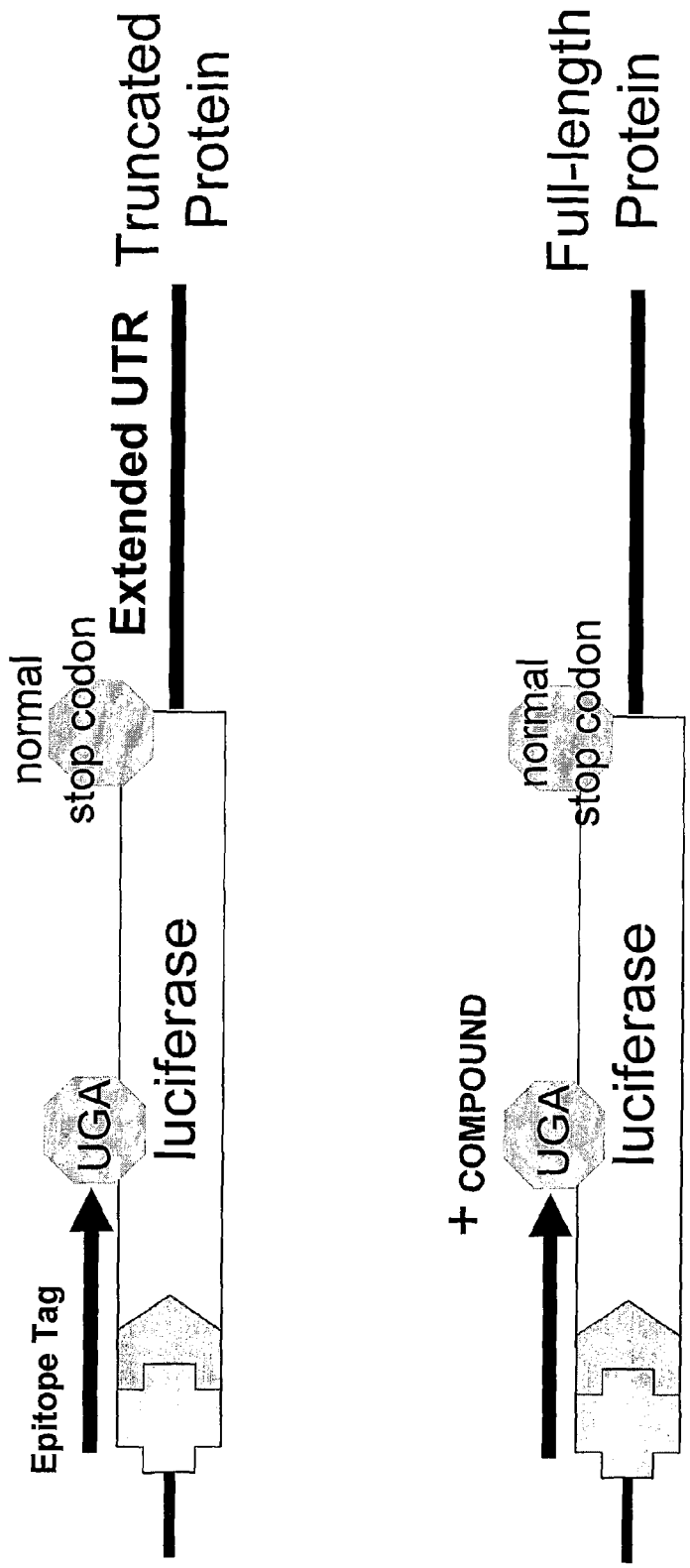

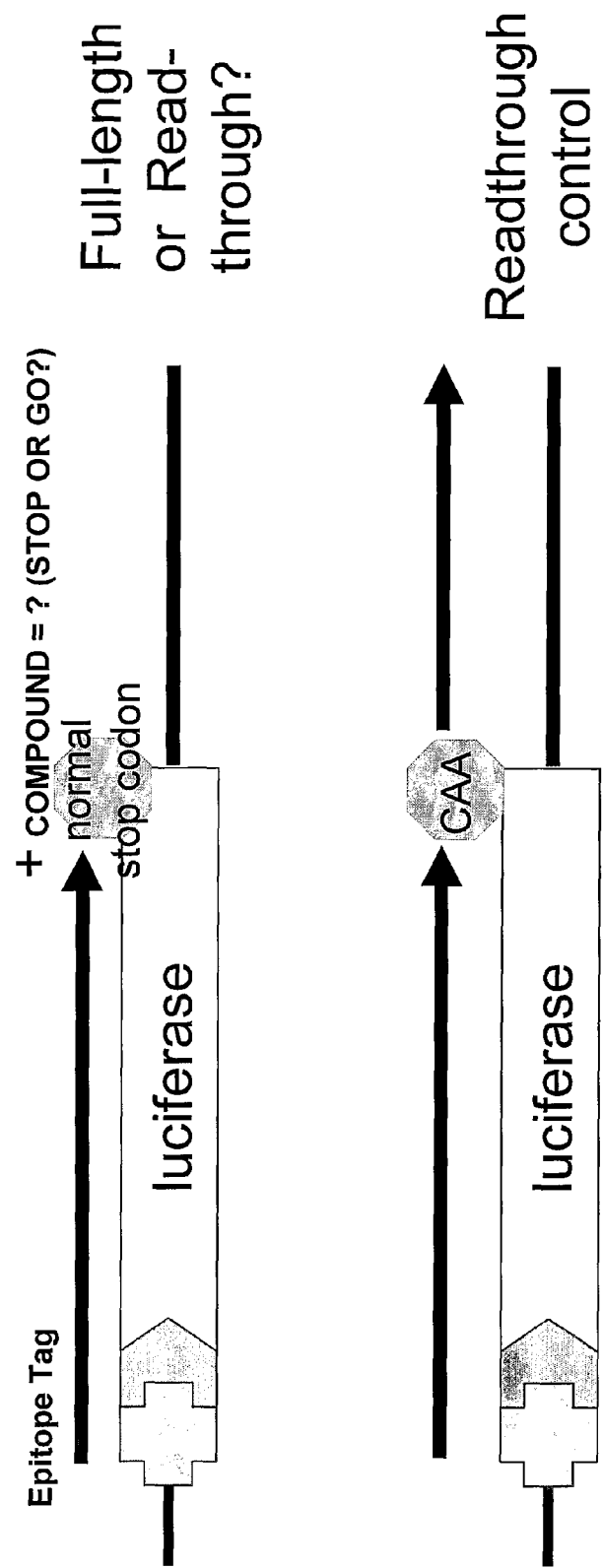
Figure 3: Readthrough Assay

Figure 4: Mice Treated with Compound 6 are Protected from Muscle Injury
A) mdx mice treated with Compound 6 (25 mg/kg) produce full-length dystrophin protein (WT: wild-type)
B) Mice treated with Compound 6 (25 mg/kg) are protected from muscle injury
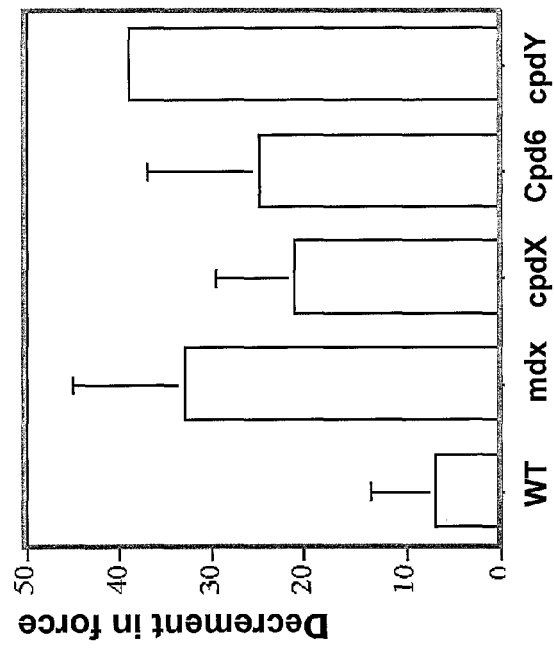

1,3,4-OXADIAZOLE BENZOIC ACID COMPOUNDS AND THEIR USE FOR NONSENSE SUPPRESSION AND THE TREATMENT OF DISEASE

CROSS-REFERENCE TO RELATED APPLICATIONS

The present application is a national phase application under 35 U.S.C. §371 of International Application No. PCT/US2005/036673, filed Oct. 13, 2005, the disclosure of which is hereby incorporated by reference in its entirety, and which claims priority to and the benefit under 35 U.S.C. §119 of U.S. Provisional Application No. 60/617,653, filed Oct. 13, 2004, and U.S. Provisional Application No. 60/624,170, filed Nov. 3, 2004. U.S. Provisional Application No. 60/624,170, filed Nov. 3, 2004, is herein incorporated by reference in its entirety. International Application No. PCT/US2005/036673 also claims priority to and the benefit under 35 U.S.C. §119 of U.S. Provisional Application No. 60/617,655, filed Oct. 13, 2004, U.S. Provisional Application No. 60/617,634, filed Oct. 13, 2004; U.S. Provisional Application No 60/617,633, filed Oct. 13, 2004, and U.S. Provisional Application No. 60/617,670, filed Oct. 13, 2004, all of which are herein incorporated by reference in their entireties. The present application also incorporates by reference herein in their entireties International Application No. PCT/US2005/036761, filed Oct. 13, 2005, International Application No. PCT/US2005/036762 filed Oct. 13, 2005, International Application No. PCT/US2005/036764, filed Oct. 13, 2005, International Application No. PCT/US2005/037052, filed Oct. 13, 2005.

FIELD OF THE INVENTION

The present invention relates to methods and compounds or compositions for treating or preventing diseases associated with nonsense mutations in an mRNA by administering the compounds or compositions of the present invention. More particularly, the present invention relates to methods and compounds or compositions for suppressing premature translation termination associated with a nonsense mutation in an mRNA.

BACKGROUND OF THE INVENTION

Gene expression in cells depends upon the sequential processes of transcription and translation. Together, these processes produce a protein from the nucleotide sequence of its corresponding gene.

Transcription involves the synthesis of mRNA from DNA by RNA polymerase. Transcription begins at a promoter region of the gene and continues until termination is induced, such as by the formation of a stem-loop structure in the nascent RNA or the binding of the rho gene product.

Protein is then produced from mRNA by the process of translation, occurring on the ribosome with the aid of tRNA, tRNA synthetases and various other protein and RNA species. Translation comprises the three phases of initiation, elongation and termination. Translation is initiated by the formation of an initiation complex consisting of protein factors, mRNA, tRNA, cofactors and the ribosomal subunits that recognize signals on the mRNA that direct the translation machinery to begin translation on the mRNA. Once the initiation complex is formed, growth of the polypeptide chain occurs by the repetitive addition of amino acids by the peptidyl transferase activity of the ribosome as well as tRNA and tRNA synthetases. The presence of one of the three termination codons (UAA, UAG, UGA) in the A site of the ribosome signals the polypeptide chain release factors (RFs) to bind and recognize the termination signal. Subsequently, the ester bond between the 3' nucleotide of the tRNA located in the ribosome's P site and the nascent polypeptide chain is hydrolyzed, the completed polypeptide chain is released, and the ribosome subunits are recycled for another round of translation.

Mutations of the DNA sequence in which the number of bases is altered are categorized as insertion or deletion mutations (e.g., frameshift mutations) and can result in major disruptions of the genome. Mutations of the DNA that change one base into another and result in an amino acid substitution are labeled missense mutations. Base substitutions are subdivided into the classes of transitions (one purine to another purine, or one pyrimidine to another pyrimidine) and transversions (a purine to a pyrimidine, or a pyrimidine to a purine).

Transition and transversion mutations can result in a nonsense mutation changing an amino acid codon into one of the three stop codons. These premature stop codons can produce aberrant proteins in cells as a result of premature translation termination. A nonsense mutation in an essential gene can be lethal and can also result in a number of human diseases, such as, cancers, lysosomal storage disorders, the muscular dystrophies, cystic fibrosis and hemophilia, to name a few.

The human p53 gene is the most commonly mutated gene in human cancer (Zambetti, G. P. and Levine, A., *FASEB* 7:855-865 (1993)). Found in both genetic and spontaneous cancers, over 50 different types of human cancers contain p53 mutations and mutations of this gene occur in 50-55% of all human cancers (Hollstein, M., et al., *Nucleic Acids Res.* 22:3551-55 (1994); International Agency for Research on Cancer (IARC) database). Approximately 70% of colorectal cancer, 50% of lung cancer and 40% of breast cancers contain mutant p53 (Koshland, D., *Science* 262: 1953 (1993)). Aberrant forms of p53 are associated with poor prognosis, more aggressive tumors, metastasis, and lower 5 year survival rates (Id.). p53's role in the induction of cell growth arrest and/or apoptosis upon DNA damage is believed to be essential for the destruction of mutated cells that would have otherwise gained a growth advantage. In addition, p53 sensitizes rapidly dividing cells to apoptotic signals. Of greater than 15,000 reported mutations in the p53 gene, approximately 7% are nonsense mutations. Accordingly, there is a need for a safe and effective treatment directed to p53 nonsense mutations.

In bacterial and eukaryotic strains with nonsense mutations, suppression of the nonsense mutation can arise as a result of a mutation in one of the tRNA molecules so that the mutant tRNA can recognize the nonsense codon, as a result of mutations in proteins that are involved in the translation process, as a result of mutations in the ribosome (either the ribosomal RNA or ribosomal proteins), or by the addition of compounds known to alter the translation process (for example, cycloheximide or the aminoglycoside antibiotics). The result is that an amino acid will be incorporated into the polypeptide chain, at the site of the nonsense mutation, and translation will not prematurely terminate at the nonsense codon. The inserted amino acid will not necessarily be identical to the original amino acid of the wild-type protein, however, many amino acid substitutions do not have a gross effect on protein structure or function. Thus, a protein produced by the suppression of a nonsense mutation would be likely to possess activity close to that of the wild-type protein. This scenario provides an opportunity to treat diseases associated with nonsense mutations by avoiding premature termination of translation through suppression of the nonsense mutation.

The ability of aminoglycoside antibiotics to promote read-through of eukaryotic stop codons has attracted interest in these drugs as potential therapeutic agents in human diseases caused by nonsense mutations. One disease for which such a therapeutic strategy may be viable is classical late infantile neuronal ceroid lipofuscinosis (LINCL), a fatal childhood neurodegenerative disease with currently no effective treatment. Premature stop codon mutations in the gene CLN2 encoding the lysosomal tripeptidyl-peptidase 1 (TPP-I) are associated with disease in approximately half of children diagnosed with LINCL. The ability of the aminoglycoside gentamicin to restore TPP-I activity in LINCL cell lines has been examined. In one patient-derived cell line that is compound heterozygous for a commonly seen nonsense mutation (Arg208Stop) and a different rare nonsense mutation, approximately 7% of normal levels of TPP-I were maximally restored with gentamicin treatment. These results suggest that pharmacological suppression of nonsense mutations by aminoglycosides or functionally similar pharmaceuticals may have therapeutic potential in LINCL (Sleat et. al., *Eur. J. Ped. Neurol.* 5:Suppl A 57-62 (2001)).

In cultured cells having premature stop codons in the Cystic Fibrosis Transmembrane Conductance Regulator (CFTR) gene, treatment with aminoglycosides led to the production of full-length CFTR (Bedwell et. al., *Nat. Med.* 3:1280-1284 (1997); Howard et. al. Nat. Med. 2: 467-469 (1996)). In mouse models for Duchenne muscular dystrophy, gentamicin sulfate was observed to suppress translational termination at premature stop codons resulting in full-length dystrophin (Barton-Davis et. al., *J. Clin. Invest.* 104:375-381 (1999)). A small increase in the amount of full-length dystrophin provided protection against contraction-induced damage in the mdx mice. The amino acid inserted at the site of the nonsense codon was not determined in these studies.

Accordingly, small molecule therapeutics or prophylactics that suppress premature translation termination by mediating the misreading of the nonsense codon would be useful for the treatment of a number of diseases. The discovery of small molecule drugs, particularly orally bioavailable drugs, can lead to the introduction of a broad spectrum of selective therapeutics or prophylactics to the public which can be used against disease caused by nonsense mutations is just beginning.

Clitocine (6-Amino-5-nitro-4-(β-D-ribo-furanosylamino) pyrimidine) is a naturally occurring exocyclic amino nucleoside that was first isolated from the mushroom *Clitocybe inversa* (Kubo et al., *Tet. Lett.* 27: 4277 (1986)). The total synthesis of clitocine has also been reported. (Moss et al., *J. Med. Chem.* 31:786-790 (1988) and Kamikawa et al., *J. Chem. Soc. Chem. Commun.* 195 (1988)). Clitocine has been reported to possess insecticidal activity and cytostatic activity against leukemia cell lines (Kubo et al., *Tet. Lett.* 27: 4277 (1986) and Moss et al., *J. Med. Chem.* 31:786-790 (1988)). However, the use of clitocine as a therapeutic for diseases associated with a nonsense mutation has not been disclosed until now. Nor has anyone reported the development of an analogue or derivative of clitocine that has utility as a therapeutic for cancer or a disease associated with a nonsense mutation.

Thus, there remains a need to develop characterize and optimize lead molecules for the development of novel drugs for treating or preventing diseases associated with nonsense mutations of mRNA. Accordingly, it is an object of the present invention to provide such compounds.

All documents referred to herein are incorporated by reference into the present application as though fully set forth herein.

SUMMARY OF THE INVENTION

In accordance with the present invention, compounds that suppress premature translation termination associated with a nonsense mutation in mRNA have been identified, and methods for their use provided.

In one aspect of the invention, compounds of Formula (1) are provided which are useful for suppressing premature translation termination associated with a nonsense mutation in mRNA, and for treating diseases associated with nonsense mutations in mRNA:

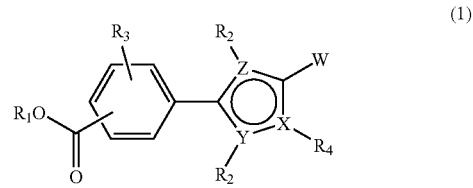

wherein:

X, Y, and Z are independently selected from N, S, O, and C wherein at least one of X, Y or Z is a heteroatom;

$R_1$ is hydrogen, a $C_1$-$C_6$ alkyl, or Na+, or $Mg^{2+}$;

$R_2$ is independently absent; a hydrogen; a —CH=N—OH group; a cyano group; a $C_1$-$C_6$ alkyl which is optionally substituted with a hydroxy group; or a carbonyl group which is optionally substituted with a hydrogen, a hydroxyl, or a $C_1$-$C_4$ alkoxy group;

$R_3$ is independently absent, a halogen, a hydroxy, a $C_1$-$C_6$ alkyl, $C_1$-$C_4$ alkoxy, or a nitro group;

$R_4$ is independently absent, a hydrogen, a $C_1$-$C_6$ alkyl, or when taken together with W, $R_4$ may be a bond, and W and the heterocycle to which $R_4$ and W are attached form an eleven to thirteen membered hetero-tricycle ring structure;

W is selected from:
(a) a $C_2$-$C_6$ alkynyl, optionally substituted with a phenyl;
(b) a $C_1$-$C_8$ straight chain or branched chain alkyl which is optionally substituted with one or more of the following independently selected groups: a $C_1$-$C_6$ alkyl; a halogen; a —C(=O)—NH-phenyl which phenyl is optionally substituted with one or more independently selected halogens or $C_1$-$C_4$ alkyl groups; a five to six-membered heterocycle; a $C_6$-$C_8$ aryl which is optionally substituted with one or more groups independently selected from a hydroxy, a halogen, a $C_1$-$C_4$ alkyl group, a $C_1$-$C_4$ haloalkyl group, a $C_1$-$C_4$ alkoxy group or an amino group which is optionally substituted with one or more $C_1$-$C_4$ alkyl groups; an aryloxy which is optionally substituted with one or more of the following independently selected groups: a hydroxy, a halogen, a $C_1$-$C_4$ alkyl group, a $C_1$-$C_4$ haloalkyl group, a $C_1$-$C_4$ alkoxy group or an amino group which is optionally substituted with one or more $C_1$-$C_4$ alkyl groups;
(c) $C_2$ to $C_8$ alkenyl;
(d) a $C_3$-$C_8$ cycloalkyl optionally substituted with a $C_1$-$C_6$ alkyl;

(e) a $C_6$-$C_8$ aryl which is optionally substituted with one or more of the following independently selected groups: a hydroxy; a halogen; a $C_1$-$C_4$ straight chain or branched chain alkyl which is optionally substituted with one or more independently selected halogen or hydroxy groups; a $C_1$-$C_4$ alkoxy which is optionally substituted with one or more independently selected halogen or phenyl groups; a $C_3$-$C_8$ cycloalkyl which is optionally substituted with one or more independently selected $C_1$-$C_4$ alkyl groups; a $C_6$-$C_8$ aryl which is optionally substituted with one or more independently selected $C_1$-$C_4$ alkyl groups; an aryloxy which is optionally substituted with one or more of the following independently selected groups: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more independently selected $C_1$-$C_4$ alkyl groups; a five to six-membered heterocycle which is optionally substituted with one or more independently selected $C_1$-$C_4$ alkyl, oxo, or $C_6$-$C_8$ aryl which is optionally substituted with one or more of the following independently selected groups: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more independently selected $C_1$-$C_4$ alkyl groups; a naphthyl group which is optionally substituted with an amino or aminoalkyl or alkoxy group; a —C(O)—$NR_xR_y$ group; a —C(O)—$R_x$ group; a isoindole-1,3-dione group; a nitro group; a cyano group; a —$SO_3H$ group; alkylthio group; alkyl sulfonyl group; a —$NR_x$—C(O)—$R_z$ group; a —$NR_xR_y$ group; a —$NR_x$—$SO_2$—$R_z$ group; a —$NR_x$—C(O)—$NR_xR_y$ group; a —$NR_x$—C(O)O—$R_z$ group;

(f) a $C_{10}$-$C_{14}$ aryl group optionally substituted with one or more independently selected halogens, amino groups or aminoalkyl groups, or alkoxy groups;

(g) a —C(O)—$NR_xR_y$ group;

(h) a five or six membered heterocycle which is optionally substituted with one or more independently selected oxo groups; halogens; $C_1$-$C_4$ alkyl groups; $C_1$-$C_4$ alkoxy groups; $C_1$-$C_4$ haloalkyl groups; $C_1$-$C_4$ haloalkoxy groups; aryloxy groups; —$NR_xR_y$ groups; alkylthio groups; —C(O)—$R_x$ groups; or $C_6$ to $C_8$ aryl groups which are optionally substituted with one or more independently selected halogens, $C_1$-$C_4$ alkyl groups, $C_1$-$C_4$ alkoxy groups;

(i) a heterocycle group having two to three ring structures that is optionally substituted with one or more independently selected halogens, oxo groups, $C_1$-$C_4$ alkyl groups, $C_1$-$C_4$ haloalkyl groups, or $C_1$-$C_4$ alkoxy groups;

(j) or W together with $R_4$, including where $R_4$ is a bond, and the heterocycle to which $R_4$ and W are attached form an eleven to thirteen membered hetero-tricycle ring structure;

wherein $R_x$ is hydrogen, a $C_1$-$C_6$ alkyl group, or $R_x$ and $R_y$ together with the atoms to which they are attached form a four to seven membered carbocycle or heterocycle;

$R_y$ is hydrogen, a $C_1$-$C_6$ alkyl group; an aryl group optionally substituted with one or more independently selected $C_1$-$C_4$ alkyl groups, or $R_x$ and $R_y$ together with the atoms to which they are attached form a four to seven membered carbocycle or heterocycle; and $R_z$ is an $C_1$-$C_6$ alkyl optionally substituted with an aryl or a halogen; or aryl optionally substituted with a halogen, a $C_1$-$C_6$ alkyl, or a $C_1$-$C_6$ alkoxy;

or a pharmaceutically acceptable salt, hydrate, solvate, clathrate, racemate, stereoisomer, or polymorph of said compound of Formula 1.

In another aspect of the invention, methods are provided for the suppression of premature translation termination associated with a nonsense mutation, and for the prevention or treatment of diseases associated with nonsense mutations of mRNA. Such diseases include, but are not limited to, genetic diseases caused by premature translation termination associated with a nonsense mutation, such as a CNS disease, an inflammatory disease, a neurodegenerative disease, an autoimmune disease, a cardiovascular disease, or a pulmonary disease; more preferably the disease is cancer (or other proliferative diseases), amyloidosis, Alzheimer's disease, atherosclerosis, giantism, dwarfism, hypothyroidism, hyperthyroidism, cystic fibrosis, aging, obesity, Parkinson's disease, Niemann Pick's disease, familial hypercholesterolemia, retinitis pigmentosa, Marfan syndrome, lysosomal storage disorders, the muscular dystrophies, cystic fibrosis, hemophilia, or classical late infantile neuronal ceroid lipofuscinosis (LINCL).

In one embodiment, the invention is directed to methods for suppressing premature translation termination associated with a nonsense mutation in mRNA comprising administering a nonsense-suppressing amount of at least one compound of the invention to a subject in need thereof.

In yet another embodiment, methods for treating cancer, lysosomal storage disorders, a muscular dystrophy, cystic fibrosis, hemophilia, or classical late infantile neuronal ceroid lipofuscinosis are provided comprising administering a therapeutically effective amount of at least one compound of the invention to a subject in need thereof.

These and other aspects of the invention will be more clearly understood with reference to the following preferred embodiments and detailed description.

Certain Embodiments

1. A method of treating or preventing a disease resulting from a somatic mutation comprising administering to a patient in need thereof an effective amount of a compound of Formula 1, or a pharmaceutically acceptable salt, hydrate, solvate, clathrate, racemate, stereoisomer, or polymorph of said compound of Formula 1.
2. The method of embodiment 1, wherein the compound, or a pharmaceutically acceptable salt, hydrate, solvate, clathrate polymorph, racemate, stereoisomer, or polymorph thereof, is administered as a composition comprising the compound and a pharmaceutically acceptable carrier or diluent.
3. The method of embodiment 1, wherein the administration is intravenous.
4. A method of treating or preventing an autoimmune disease, a blood disease, a collagen disease, diabetes, a neurodegenerative disease, a cardiovascular disease, a pulmonary disease, or an inflammatory disease or central nervous system disease comprising administering to a patient in need thereof an effective amount of a compound of Formula 1, or a pharmaceutically acceptable salt, hydrate, solvate, clathrate, racemate, stereoisomer, or polymorph thereof.
5. The method of embodiment 4, wherein the administration is intravenous.
6. The method of embodiment 4, wherein the autoimmune disease is rheumatoid arthritis or graft versus host disease.
7. The method of embodiment 4, wherein the inflammatory disease is arthritis.
8. The method of embodiment 4, wherein the central nervous system disease is multiple sclerosis, muscular dystrophy, Duchenne muscular dystrophy, Alzheimer's disease, a neurodegenerative disease or Parkinson's disease.

9. The method of embodiment 4, wherein the blood disorder is hemophilia, Von Willebrand disease, ataxia-telangiectasia, β-thalassemia or kidney stones.

10. The method of embodiment 4, wherein the collagen disease is osteogenesis imperfecta or cirrhosis.

11. A method of treating or preventing familial polycythemia, immunodeficiency, kidney disease, cystic fibrosis, familial hypercholesterolemia, retinitis pigmentosa, amyloidosis, hemophilia, Alzheimer's disease, Tay Sachs disease, Niemann Pick disease, Parkinson's disease, atherosclerosis, giantism, dwarfism, hyperthyroidism, aging, obesity, Duchenne muscular dystrophy or Marfan syndrome comprising administering to a patient in need thereof an effective amount of a compound of Formula 1, or a pharmaceutically acceptable salt, hydrate, solvate, clathrate, racemate, stereoisomer, polymorph thereof.

12. The method of embodiment 11, wherein the administration is intravenous.

13. A method of treating or preventing cancer in a human comprising administering to a human in need thereof an effective amount of a compound of Formula 1, or a pharmaceutically acceptable salt, hydrate, solvate, clathrate, racemate, stereoisomer, polymorph thereof.

14. The method of embodiment 13, wherein the administration is intravenous.

15. The method of embodiment 13, wherein the cancer is of the head and neck, eye, skin, mouth, throat, esophagus, chest, bone, blood, lung, colon, sigmoid, rectum, stomach, prostate, breast, ovaries, kidney, liver, pancreas, brain, intestine, heart or adrenals.

16. The method of embodiment 13, wherein the compound, or a pharmaceutically acceptable salt, hydrate, solvate, clathrate, racemate, stereoisomer, or polymorph thereof, comprises a pharmaceutically acceptable carrier or diluent.

17. The method of embodiment 13, wherein the cancer is a solid tumor.

18. The method of embodiment 13, wherein the cancer is sarcoma, carcinoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor or multiple myeloma.

19. The method of embodiment 13, wherein the cancer is acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia, chronic lymphocytic leukemia, hairy cell leukemia, or multiple myeloma.

20. A method of treating or preventing a disease associated with a mutation of the p53 gene comprising administering to a patient in need thereof an effective amount of a compound of Formula 1, or a pharmaceutically acceptable salt, hydrate, solvate, clathrate, racemate, stereoisomer, or polymorph thereof.

21. The method of embodiment 20, wherein the administration is intravenous.

22. The method of embodiment 20, wherein the disease is sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma or retinoblastoma.

23. A method of inhibiting the growth of a cancer cell comprising contacting the cancer cell with an effective amount of a compound of Formula 1, or a pharmaceutically acceptable salt, hydrate, solvate, clathrate, racemate, stereoisomer, or polymorph thereof.

24. A method for selectively producing a protein in a mammal comprising, transcribing a gene containing a nonsense mutation in the mammal; and providing an effective amount of a compound of the present invention to said mammal, wherein said protein is produced by said mammal.

BRIEF DESCRIPTION OF THE DRAWINGS

FIG. 1 provides schematic representations of constructs for luciferase based assays to evaluate the suppression of a nonsense mutation.

FIG. 2 provides schematic representations of the luciferase constructs engineered to harbor one or more epitope tags in the N-terminus of the luciferase protein.

FIG. 3 provides schematic representations of constructs for luciferase based assays to evaluate readthrough efficiency.

FIG. 4 provides results from mdx mouse cells and muscle.

DETAILED DESCRIPTION OF THE INVENTION

Premature translation termination can produce aberrant proteins which can be lethal or can cause a number of diseases, including as non-limiting examples, cancers, lysosomal storage disorders, the muscular dystrophies, cystic fibrosis and hemophilia. In accordance with the present invention, compounds that suppress nonsense mutations have been identified, and methods for their use provided.

A. Compounds of the Invention

In one aspect of the invention, compounds of the invention are provided which are useful in suppression of a nonsense mutation. In certain embodiments, the compounds of the invention specifically suppresses a nonsense mutation, while in other embodiments, the compounds of the invention suppress a nonsense mutation as well as treat a disease, including as non-limiting examples, cancers, lysosomal storage disorders, the muscular dystrophies, cystic fibrosis and hemophilia.

Preferred compounds of the present invention useful in the suppression of a nonsense mutation include those of Formula (1) as shown below.

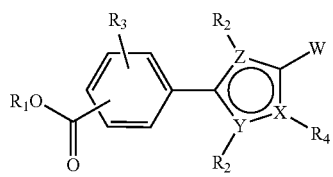

wherein:

X, Y, and Z are independently selected from N, S, O, and C wherein at least one of X, Y or Z is a heteroatom;

$R_1$ is hydrogen, a $C_1$-$C_6$ alkyl, or Na+, or $Mg^{2+}$;

$R_1$ is hydrogen, a $C_1$-$C_6$ alkyl, or Na+, or $Mg^{2+}$;

$R_2$ is independently absent; a hydrogen; a —CH=N—OH group; a cyano group; a $C_1$-$C_6$ alkyl which is optionally substituted with a hydroxy group; or a carbonyl group which is optionally substituted with a hydrogen, a hydroxyl, or a $C_1$-$C_4$ alkoxy group;

$R_3$ is independently absent, a halogen, a hydroxy, a $C_1$-$C_6$ alkyl, $C_1$-$C_4$ alkoxy, or a nitro group;

$R_4$ is independently absent, a hydrogen, a $C_1$-$C_6$ alkyl, or when taken together with W, $R_4$ may be a bond, and W and the heterocycle to which $R_4$ and W are attached form an eleven to thirteen membered hetero-tricycle ring structure;

W is selected from:

(a) a $C_2$-$C_6$ alkynyl, optionally substituted with a phenyl;

(b) a $C_1$-$C_8$ straight chain or branched chain alkyl which is optionally substituted with one or more of the following independently selected groups: a $C_1$-$C_6$ alkyl; a halogen; a —C(=O)—NH-phenyl which phenyl is optionally substituted with one or more independently selected halogens or $C_1$-$C_4$ alkyl groups; a five to six-membered heterocycle; a $C_6$-$C_8$ aryl which is optionally substituted with one or more groups independently selected from a hydroxy, a halogen, a $C_1$-$C_4$ alkyl group, a $C_1$-$C_4$ haloalkyl group, a $C_1$-$C_4$ alkoxy group or an amino group which is optionally substituted with one or more $C_1$-$C_4$ alkyl groups; an aryloxy which is optionally substituted with one or more of the following independently selected groups: a hydroxy, a halogen, a $C_1$-$C_4$ alkyl group, a $C_1$-$C_4$ haloalkyl group, a $C_1$-$C_4$ alkoxy group or an amino group which is optionally substituted with one or more $C_1$-$C_4$ alkyl groups;

(c) $C_2$ to $C_8$ alkenyl;

(d) a $C_3$-$C_8$ cycloalkyl optionally substituted with a $C_1$-$C_6$ alkyl;

(e) a $C_6$-$C_8$ aryl which is optionally substituted with one or more of the following independently selected groups: a hydroxy; a halogen; a $C_1$-$C_4$ straight chain or branched chain alkyl which is optionally substituted with one or more independently selected halogen or hydroxy groups; a $C_1$-$C_4$ alkoxy which is optionally substituted with one or more independently selected halogen or phenyl groups; a $C_3$-$C_8$ cycloalkyl which is optionally substituted with one or more independently selected $C_1$-$C_4$ alkyl groups; a $C_6$-$C_8$ aryl which is optionally substituted with one or more independently selected $C_1$-$C_4$ alkyl groups; an aryloxy which is optionally substituted with one or more of the following independently selected groups: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more independently selected $C_1$-$C_4$ alkyl groups; a five to six-membered heterocycle which is optionally substituted with one or more independently selected $C_1$-$C_4$ alkyl, oxo, or $C_6$-$C_8$ aryl which is optionally substituted with one or more of the following independently selected groups: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more independently selected $C_1$-$C_4$ alkyl groups; a naphthyl group which is optionally substituted with an amino or aminoalkyl or alkoxy group; a —C(O)—$NR_xR_y$ group; a —C(O)—$R_x$ group; a isoindole-1,3-dione group; a nitro group; a cyano group; a —$SO_3H$ group; alkylthio group; alkyl sulfonyl group; a —$NR_x$—C(O)—$R_z$ group; a —$NR_xR_y$ group; a —$NR_x$—$SO_2$—$R_z$ group; a —$NR_x$—C(O)—$NR_xR_y$ group; a —$NR_x$—C(O)O—$R_z$ group;

(f) a $C_{10}$-$C_{14}$ aryl group optionally substituted with one or more independently selected halogens, amino groups or aminoalkyl groups, or alkoxy groups;

(g) a —C(O)—$NR_xR_y$ group;

(h) a five or six membered heterocycle which is optionally substituted with one or more independently selected oxo groups; halogens; $C_1$-$C_4$ alkyl groups; $C_1$-$C_4$ alkoxy groups; $C_1$-$C_4$ haloalkyl groups; $C_1$-$C_4$ haloalkoxy groups; aryloxy groups; —$NR_xR_y$ groups; alkylthio groups; —C(O)—$R_x$ groups; or $C_6$ to $C_8$ aryl groups which are optionally substituted with one or more independently selected halogens, $C_1$-$C_4$ alkyl groups, $C_1$-$C_4$ alkoxy groups;

(i) a heterocycle group having two to three ring structures that is optionally substituted with one or more independently selected halogens, oxo groups, $C_1$-$C_4$ alkyl groups, $C_1$-$C_4$ haloalkyl groups, or $C_1$-$C_4$ alkoxy groups;

(j) or W together with $R_4$, including where $R_4$ is a bond, and the heterocycle to which $R_4$ and W are attached form an eleven to thirteen membered hetero-tricycle ring structure;

wherein $R_x$ is hydrogen, a $C_1$-$C_6$ alkyl group, or $R_x$ and $R_y$ together with the atoms to which they are attached form a four to seven membered carbocycle or heterocycle;

$R_y$ is hydrogen, a $C_1$-$C_6$ alkyl group; an aryl group optionally substituted with one or more independently selected $C_1$-$C_4$ alkyl groups, or $R_x$ and $R_y$ together with the atoms to which they are attached form a four to seven membered carbocycle or heterocycle; and $R_z$ is an $C_1$-$C_6$ alkyl optionally substituted with an aryl or a halogen; or an aryl optionally substituted with a halogen, a $C_1$-$C_6$ alkyl, or a $C_1$-$C_6$ alkoxy;

or a pharmaceutically acceptable salt, hydrate, solvate, clathrate, racemate, stereoisomer, or polymorph of said compound of Formula 1.

In another embodiment, compounds of the present invention useful in the suppression of a nonsense mutation include compounds of Formula (1) wherein:

X, Y, and Z are independently selected from N, S, O, and C wherein at least one of X, Y or Z is a heteroatom;

$R_1$ is hydrogen or a $C_1$-$C_6$ alkyl; or $Na^+$ or $Mg^{2+}$ $R_2$ is independently absent; hydrogen; a $C_1$-$C_6$ alkyl which is optionally substituted with a hydroxy group; a carbonyl group which is optionally substituted with a hydroxyl, a $C_1$-$C_4$ alkoxy group; a —CH=N—OH group; or a cyano group;

$R_3$ is absent, a halogen, a hydroxy, a $C_1$-$C_6$ alkyl, $C_1$-$C_4$ alkoxy, or a nitro group;

$R_4$ is absent; a $C_1$ to $C_6$ alkyl; or together with W and the heterocycle to which $R_4$ and W are attached form an eleven to thirteen membered hetero-tricycle ring structure;

W is selected from:
a $C_1$-$C_8$ straight chain or branched chain alkyl which is optionally substituted with one or more of the following: a $C_1$-$C_6$ alkyl, a halogen, a five to six-membered heterocycle, a $C_6$-$C_8$ aryl which is optionally substituted with one or more of the following: a hydroxy, a halogen, a $C_1$-$C_4$ alkyl group, a $C_1$-$C_4$ haloalkyl group, a $C_1$-$C_4$ alkoxy group or an amino group which is optionally substituted with one or more $C_1$-$C_4$ alkyl groups; an aryloxy which is optionally substituted with one or more of the following: a hydroxy, a halogen, a $C_1$-$C_4$ alkyl group, a $C_1$-$C_4$ haloalkyl group, a $C_1$-$C_4$ alkoxy group or an amino group which is optionally substituted with one or more $C_1$-$C_4$ alkyl groups;

$C_2$ to $C_8$ alkenyl;

a $C_3$-$C_8$ cycloalkyl optionally substituted with a $C_1$ to $C_6$ alkyl;

a $C_6$-$C_8$ aryl which is optionally substituted with one or more of the following: a hydroxy, a halogen; a $C_1$-$C_4$ straight chain or branched chain alkyl which is optionally substituted with one or more independently selected halogen or hydroxy groups; a $C_1$-$C_4$ alkoxy which is optionally substituted with one or more independently selected halogen or phenyl groups; a $C_3$-$C_8$ cycloalkyl which is optionally substituted with one or more independently selected $C_1$-$C_4$ alkyl groups; a $C_6$-$C_8$ aryl which is optionally substituted with one or more independently selected $C_1$-$C_4$ alkyl groups; an aryloxy which is optionally substituted with one or more of the following: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more $C_1$-$C_4$ alkyl groups; a five to six-membered heterocycle which is optionally substituted with one or more independently selected $C_1$-$C_4$ alkyl, oxo, or $C_6$-$C_8$ aryl which is optionally substituted with one or more of the following: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more $C_1$-$C_4$ alkyl groups; a naphthyl group which is optionally substituted with an amino or aminoalkyl group; a —C(O)—$NR_xR_y$ group; a —C(O)—$R_x$ group; a isoindole-1,3-dione group; a nitro group; a cyano group; a —$SO_3H$ group; alkylthio group; alkyl sulfonyl group; a —$NR_x$—C(O)—$R_z$ group; a —$NR_xR_y$ group; a —$NR_x$—$SO_2$—$R_z$ group; a —$NR_x$—C(O)—$NR_xR_y$ group; a —$NR_x$—C(O)O—$R_z$ group;

a —C(O)—$NR_xR_y$ group;

a five or six membered heterocycle which is optionally substituted with one or more oxo groups, halogens, $C_1$ to $C_4$ alkyl groups, $C_1$ to $C_4$ haloalkyl groups, —C(O)—$R_x$ groups, and/or $C_6$ to $C_8$ aryl groups which are optionally substituted with one or more independently selected halogens, $C_1$ to $C_4$ alkyl groups, $C_1$ to $C_4$ alkoxy groups, aryloxy groups, —$NR_xR_y$ groups, and/or alkylthio groups;

a heterocycle group having two to three ring structures that is optionally substituted with one or more halogens, $C_1$ to $C_4$ alkyl groups, $C_1$ to $C_4$ haloalkyl groups, and/or $C_1$ to $C_4$ alkoxy groups;

or W together with $R_4$ and the heterocycle to which $R_4$ and W are attached form an eleven to thirteen membered hetero-tricycle ring structure;

wherein $R_x$ is hydrogen, a $C_1$ to $C_6$ alkyl group, or $R_x$ and $R_y$ together with the atoms to which they are attached form a four to seven membered carbocycle or heterocycle;

$R_y$ is hydrogen, a $C_1$ to $C_6$ alkyl group; an optionally substituted aryl, or $R_x$ and $R_y$ together with the atoms to which they are attached form a four to seven membered carbocycle or heterocycle; and $R_z$ is an $C_1$ to $C_6$ alkyl optionally substituted with an aryl or a halogen; or an aryl optionally substituted with a halogen, a $C_1$ to $C_6$ alkyl, or a $C_1$ to $C_6$ alkoxy;

or a pharmaceutically acceptable salt, hydrate, solvate, clathrate, racemate, stereoisomer, or polymorph of said compound of Formula 1.

In a preferred embodiment of Formula 1, when Y and Z are both N, and X is O, the —C(O)—O—$R_1$ group of the phenyl ring is not in the meta position. In an alternative embodiment, when Y and Z are both N, and X is O, the —C(O)—O—$R_1$ group of the phenyl ring is in the ortho or para position.

In a preferred embodiment of Formula 1, when W is a five or six membered optionally substituted heterocycle, the heterocycle may be selected from the group consisting of: a thienyl group, a furyl group, a pyrazinyl group, a pyrimidinyl group, a pyridazinyl group, a piperidyl group and a pyridyl group; and the heterocycle may be optionally substituted with one or more independently selected oxo groups; halogens; $C_1$ to $C_4$ alkyl groups; $C_1$ to $C_4$ haloalkyl groups; —C(O)—$R_x$ groups; and/or $C_6$ to $C_8$ aryl groups which are optionally substituted with one or more independently selected halogens, $C_1$ to $C_4$ alkyl groups, $C_1$ to $C_4$ alkoxy groups, aryloxy groups, —$NR_xR_y$ groups, and/or alkylthio groups In another preferred embodiment of Formula 1, when W is a five or six membered optionally substituted heterocycle, the optionally substituted heterocycle may be selected from the group consisting of: a thienyl group; a furyl group; a pyrazinyl group which is optionally substituted with a $C_1$-$C_4$ alkyl group; a pyrimidinyl group optionally substituted with one or two oxo groups; a pyridazinyl group which is optionally substituted with one or two oxo groups; a piperidyl group which is optionally substituted with a —C(O)—$R_x$ group; and a pyridyl group which is optionally substituted with one or more of the following: a halogen; a $C_1$-$C_4$ alkyl group; $C_1$-$C_4$ haloalkyl group; a $C_6$-$C_8$ aryl group which is optionally substituted with one more independently selected $C_1$-$C_4$ alkyl groups; a $C_1$-$C_4$ alkoxy group; an aryloxy group; —$NR_xR_y$ group; and an alkylthio group.

In yet another preferred embodiment of Formula 1, when W is an optionally substituted heterocycle having two to three ring structures, the heterocycle may be selected from the group consisting of: a benzodioxolyl group; a benzo[1,3]dioxinyl group which is optionally substituted with one or more independently selected halogens; a benzimidazolyl group which is optionally substituted with one or more independently selected $C_1$-$C_4$ alkyl or $C_1$-$C_4$ haloalkyl groups; a benzothiazolyl group; a benzotriazolyl group which is optionally substituted with one or more independently selected $C_1$-$C_4$ alkyl groups; a benzothienyl group which is optionally substituted with one or more independently selected $C_1$-$C_4$ alkyl groups; a benzo[1,2,5]oxadiazolyl group; a 2,3-dihydrobenzo[1,4]dioxinyl group; a benzofuryl group; a quinoxalinyl group; an indolyl group; a quinolinyl group; and a substituent selected from the group consisting of: (* indicating bond of attachment):

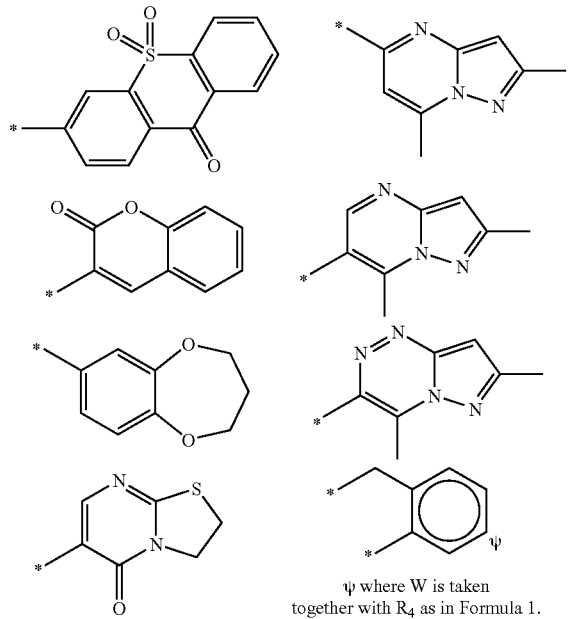

ψ where W is taken together with $R_4$ as in Formula 1.

As recognized by one of skill in the art, certain compounds of the invention may include at least one chiral center, and as such may exist as racemic mixtures or as enantiomerically pure compositions. As used herein, "enantiomerically pure" refers to compositions consisting substantially of a single isomer, preferably consisting of 90%, 92%, 95%, 98%, 99%, or 100% of a single isomer.

As used herein, the term "alkyl" generally refers to saturated hydrocarbyl radicals of straight, branched or cyclic configuration including methyl, ethyl, n-propyl, isopropyl, n-butyl, isobutyl, sec-butyl, tert-butyl, n-pentyl, n-hexyl, cyclohexyl, n-heptyl, octyl, n-octyl, and the like. In some embodiments, alkyl substituents may be $C_1$ to $C_8$, $C_3$ to $C_8$, $C_1$ to $C_6$, or $C_1$ to $C_4$ alkyl groups. In certain embodiments, the alkyl group may be optionally substituted with one or more halogen or alkoxy groups. For instance, the alkyl group may include one or more halogen substituents to form a haloalkyl, including monohaloalkyl, dihaloalkyl, and trihaloalkyl.

As used herein, "alkenyl" generally refers to linear, branched or cyclic alkene radicals having one or more carbon-carbon double bonds, such as $C_2$ to $C_6$ alkylene groups including 3-propenyl.

As used herein, "aryl" refers to a carbocyclic aromatic ring structure. Included in the scope of aryl groups are aromatic rings having from five to twenty carbon atoms. Aryl ring structures include compounds having one or more ring structures, such as mono-, bi-, or tricyclic compounds. Examples of aryl groups that include phenyl, tolyl, anthracenyl, fluorenyl, indenyl, azulenyl, phenanthrenyl (i.e., phenanthrene), and naphthyl (i.e., naphthalene) ring structures. In certain embodiments, the aryl group may be optionally substituted.

As used herein, "heterocycle" refers to cyclic ring structures in which one or more atoms in the ring, the heteroatom(s), is an element other than carbon. Heteroatoms are typically O, S or N atoms. Included within the scope of heterocycle, and independently selectable, are O, N, and S heterocycle ring structures. The heterocyclic ring structure may include compounds having one or more ring structures, such as mono-, bi-, or tricyclic compounds, and may be aromatic, i.e., the ring structure may be a heteroaryl. Heterocycle may include a benzofused heterocyclic ring structure. Non-limiting exemplary heterocyclo groups include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl or tetrahydrothiopyranyl, benzodioxolyl, benzothiazolyl, dihydrobenzodioxine, dihydroisoindolyl, dihydrobenzoimidazolyl and the like. In certain embodiments, the heterocycle may optionally be substituted. As used herein, "heteroaryl" refers to cyclic aromatic ring structures in which one or more atoms in the ring, the heteroatom(s), is an element other than carbon. Heteroatoms are typically O, S or N atoms. Included within the scope of heteroaryl, and independently selectable, are O, N, and S heteroaryl ring structures. The ring structure may include compounds having one or more ring structures, such as mono-, bi-, or tricyclic compounds. In some embodiments, the heteroaryl groups may be selected from heteroaryl groups that contain two or more heteroatoms, three or more heteroatoms, or four or more heteroatoms. Heteroaryl ring structures may be selected from those that contain five or more atoms, six or more atoms, or eight or more atoms. In a preferred embodiment, the heteroaryl including five to ten atoms. Examples of heteroaryl ring structures include: acridine, benzimidazole, benzoxazole, benzodioxole, benzofuran, 1,3-diazine, 1,2-diazine, 1,2-diazole, 1,4-diazanaphthalene, furan, furazan, imidazole, indole, isoxazole, isoquinoline, isothiazole, oxazole, purine, pyridazine, pyrazole, pyridine, pyrazine, pyrimidine, pyrrole, quinoline, quinoxaline, thiazole, thiophene, 1,3,5-triazine, 1,2,4-triazine, 1,2,3-triazine, tetrazole and quinazoline.

As used herein, "alkoxy" generally refers to a group with the structure —O—R. In certain embodiments, R may be an alkyl group, such as a $C_1$ to $C_8$, $C_1$ to $C_6$ alkyl group, or $C_1$ to $C_4$ alkyl group. In certain embodiments, the R group of the alkoxy may optionally be substituted with at least one halogen. For example, the R group of the alkoxy may be a haloalkyl, i.e., haloalkoxy.

Halogen substituents may be independently selected from the halogens such as fluorine, chlorine, bromine, iodine, and astatine.

For the purposes of this invention, where one or more functionalities or substituents are incorporated into a compound of the invention, including preferred embodiments, each functionality or substituent appearing at any location within the disclosed compounds may be independently selected, and as appropriate, independently substituted. Further, where a more generic substituent is set forth for any position in the molecules of the present invention, it is understood that the generic substituent may be replaced with more specific substituents, and the resulting molecules are within the scope of the molecules of the present invention.

With reference is Formula 1, preferred W groups include those shown in the table below (* indicates the bond of attachment).

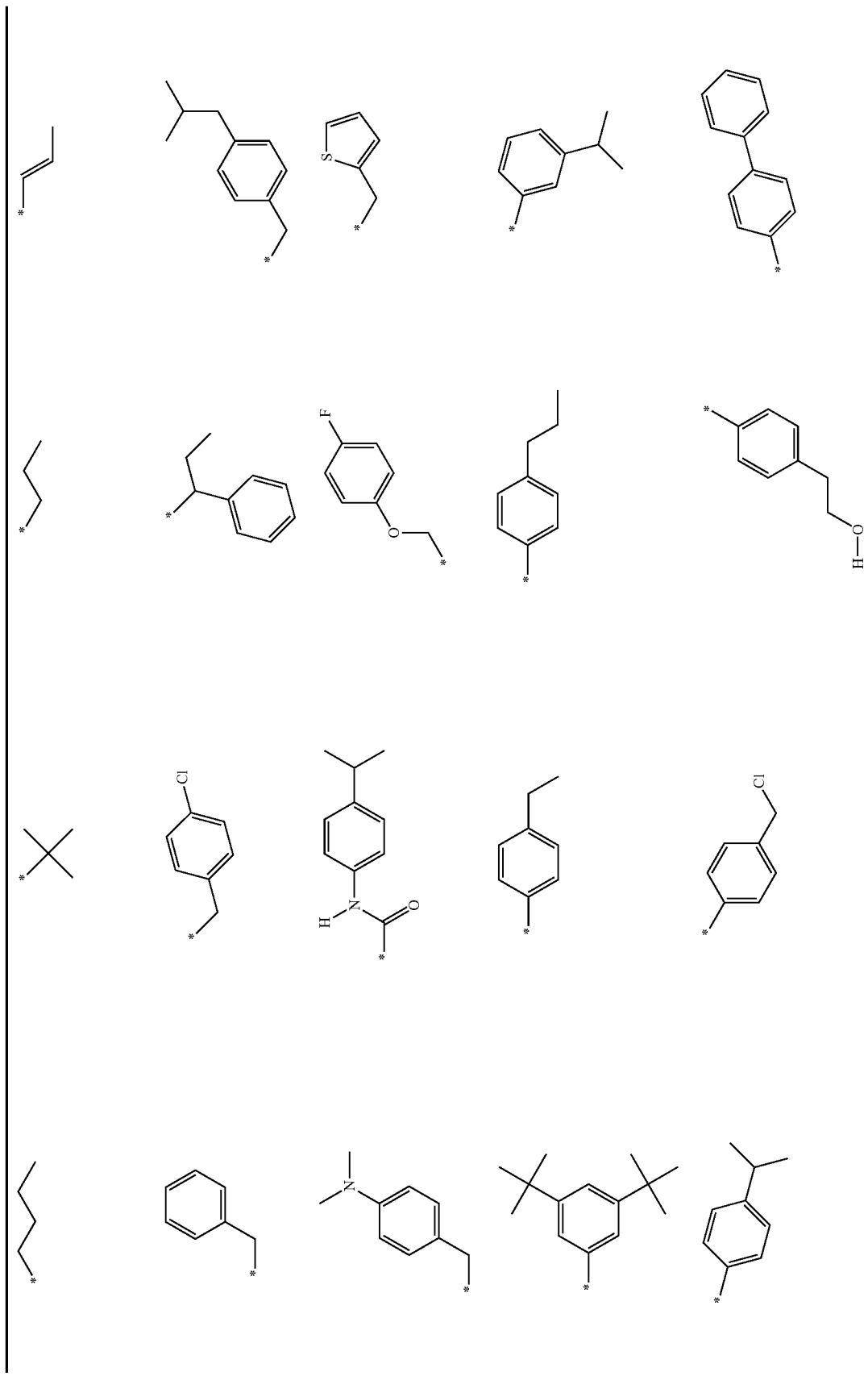

-continued
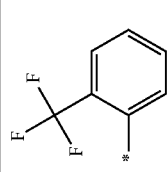 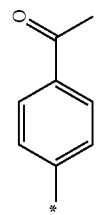 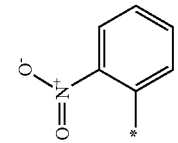
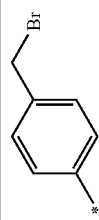 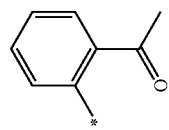 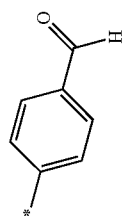 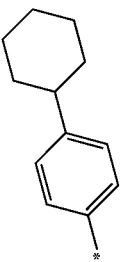
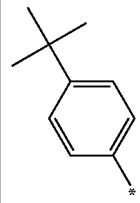 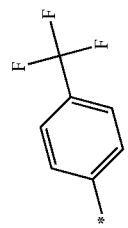 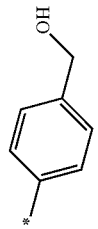 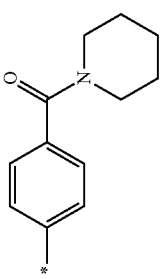 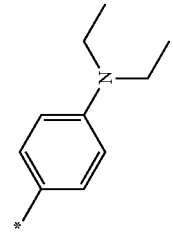
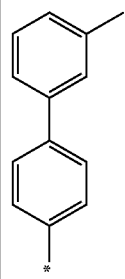 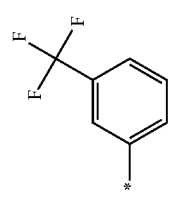 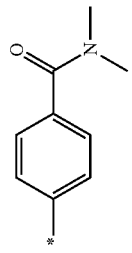 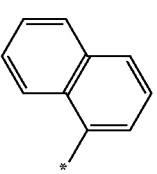 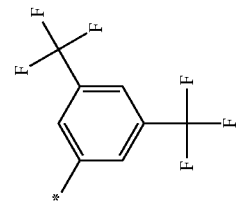

-continued
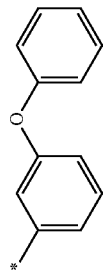 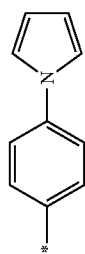 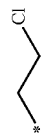 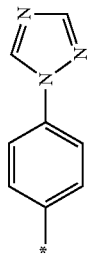
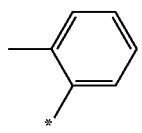 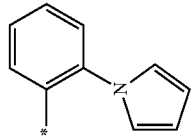 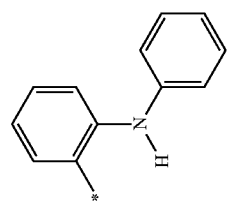 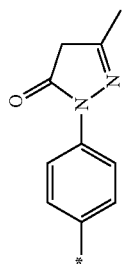
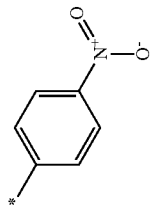 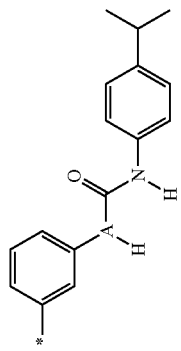 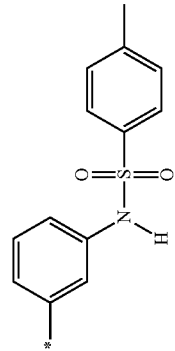 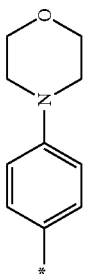
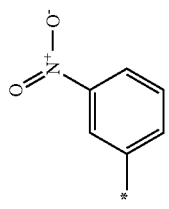 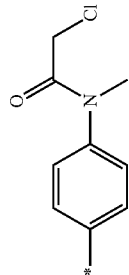 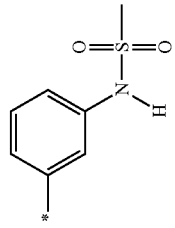 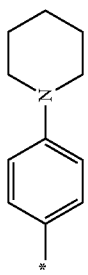

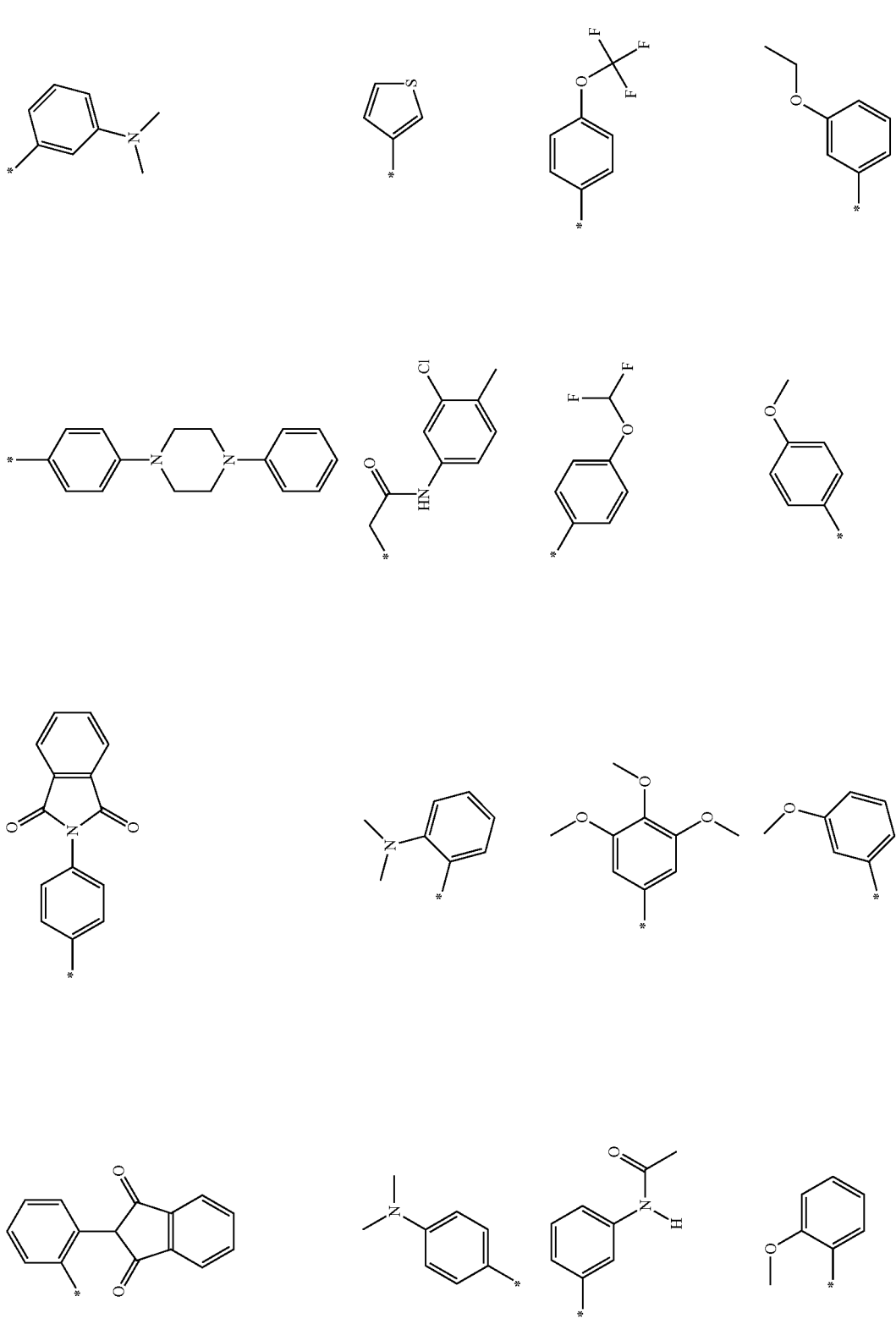

-continued
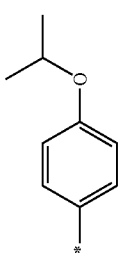 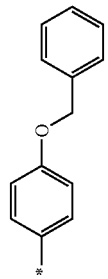 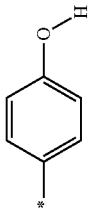 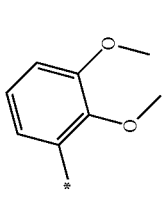 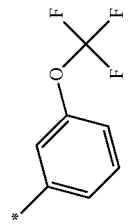
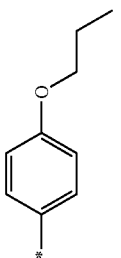 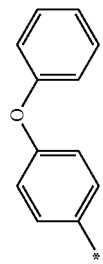 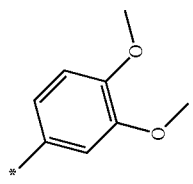 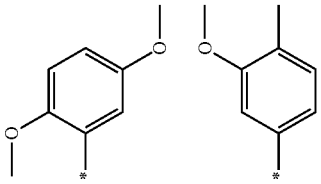
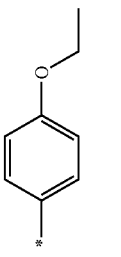 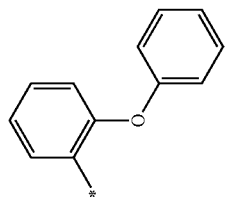 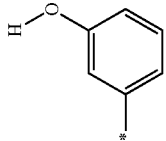 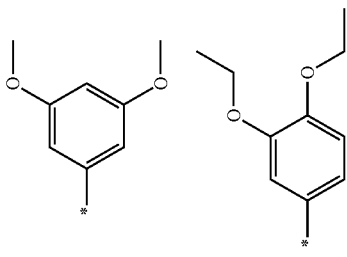
 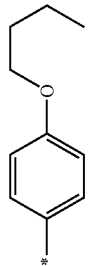 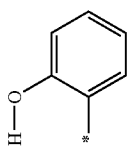 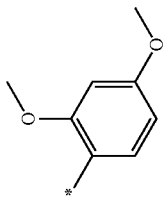

-continued
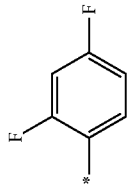 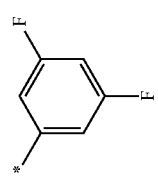 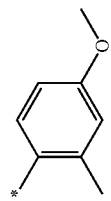 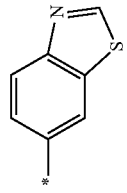
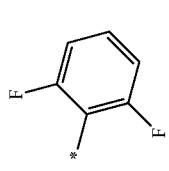 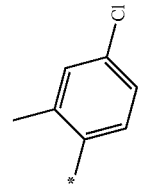 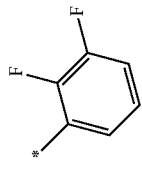 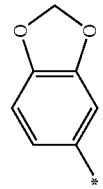 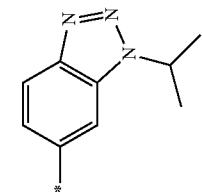
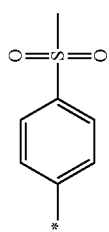 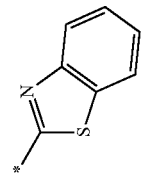 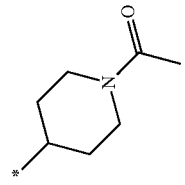 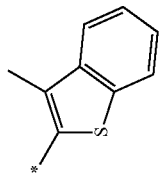 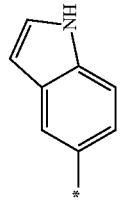
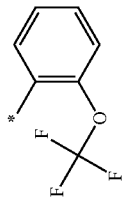 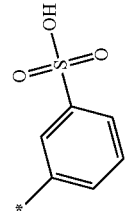  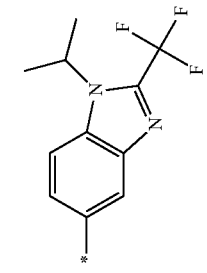

-continued
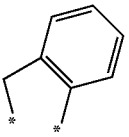 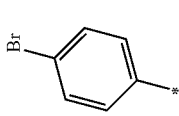 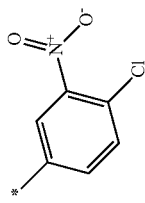 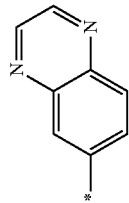 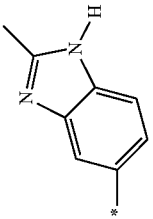
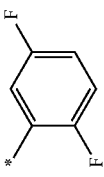 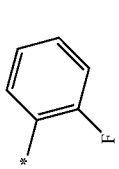 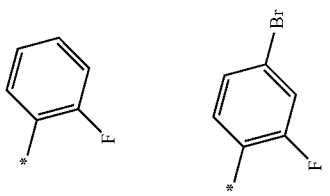 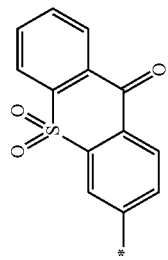
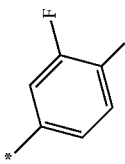 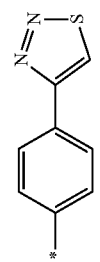 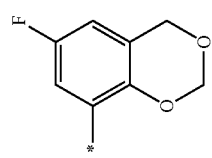
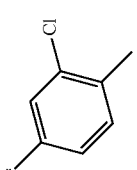 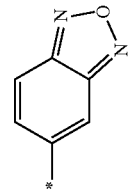 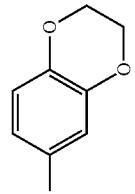

-continued
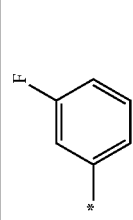 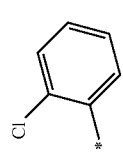 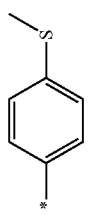 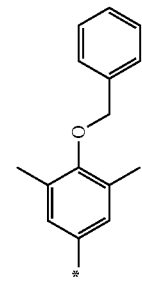 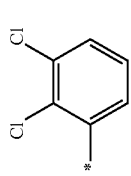 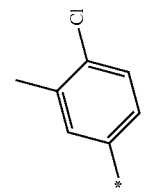
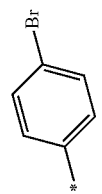 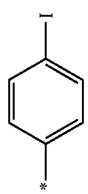 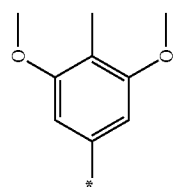 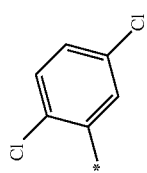 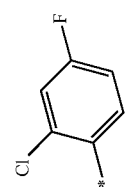
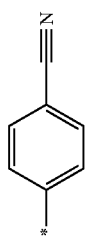 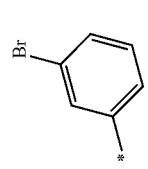 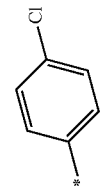 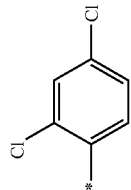 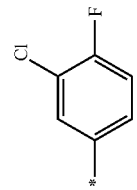
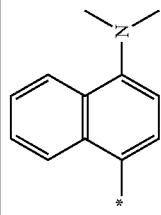 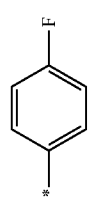 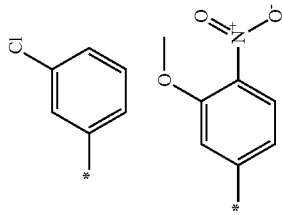 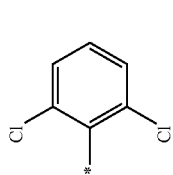 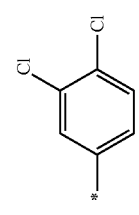

-continued
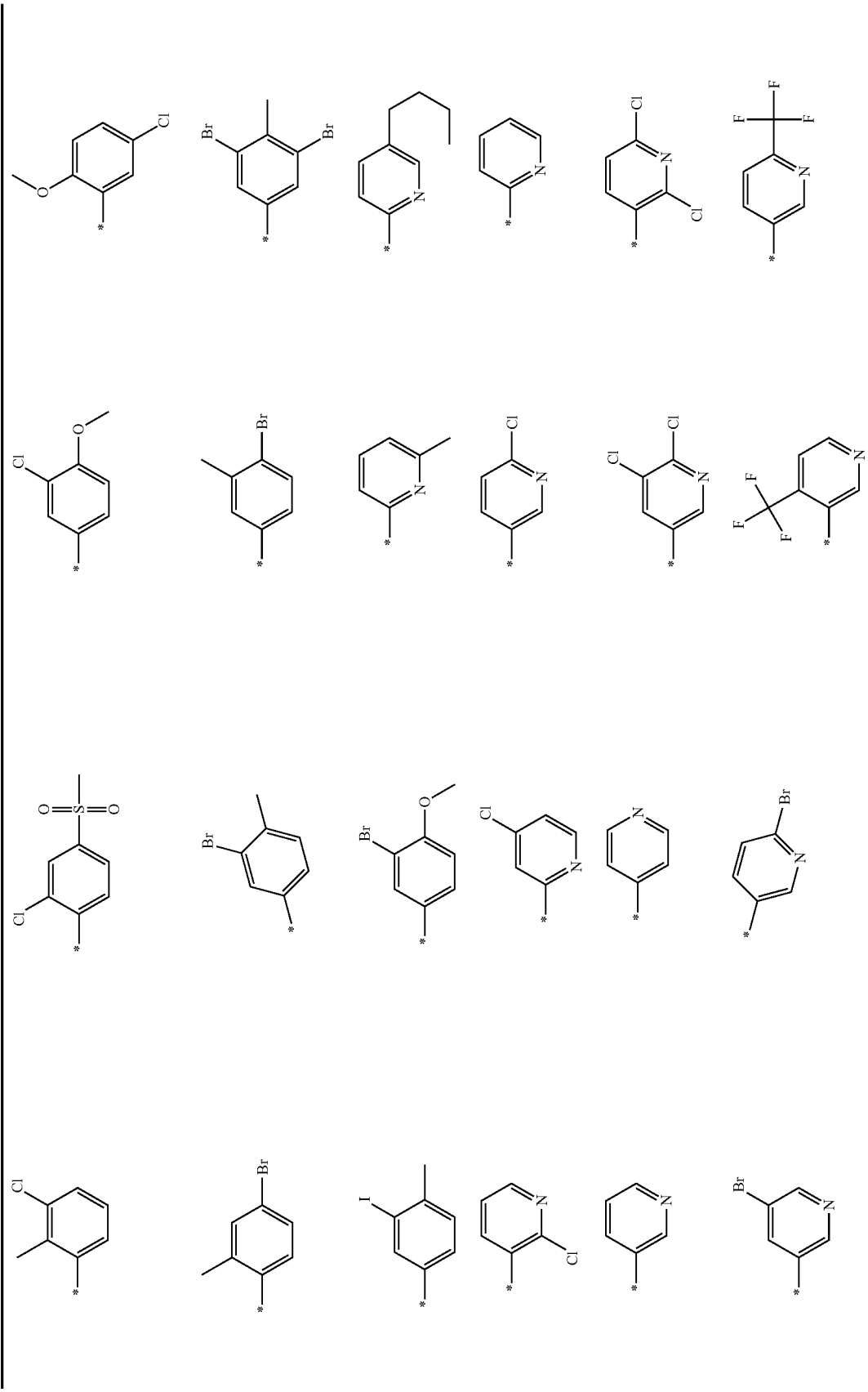

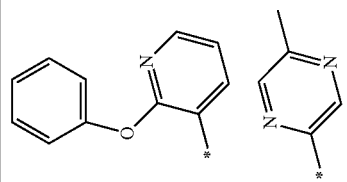 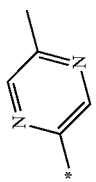 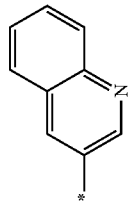 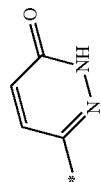 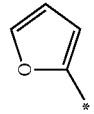
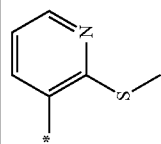 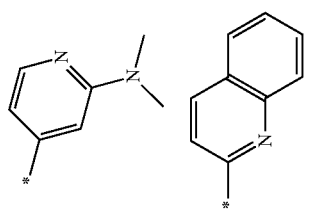 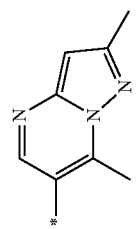 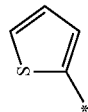 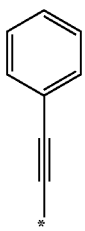
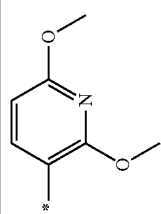 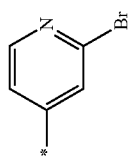 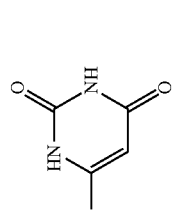 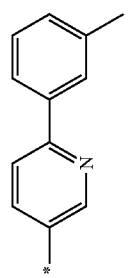 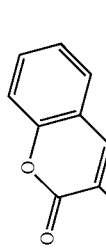 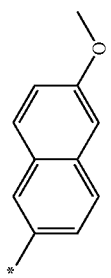
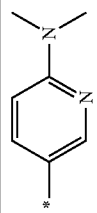 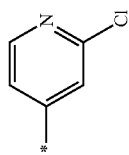 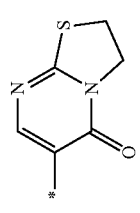 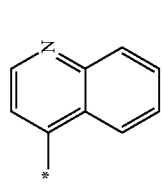 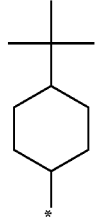 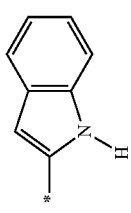

-continued
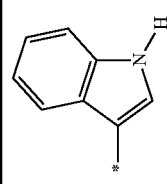 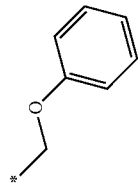 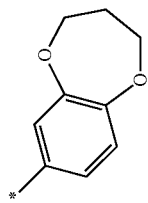 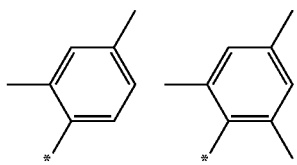
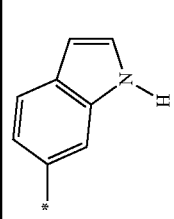 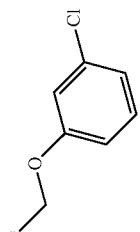 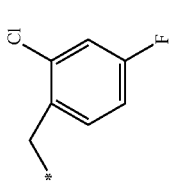 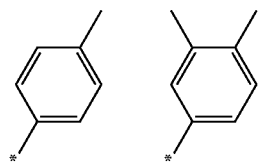
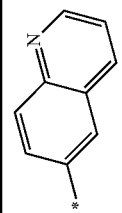 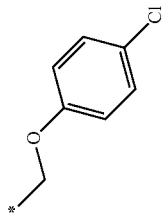 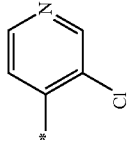 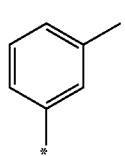 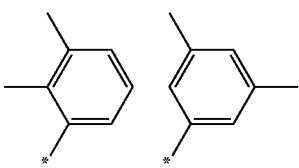
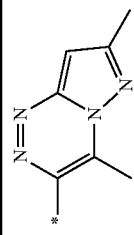 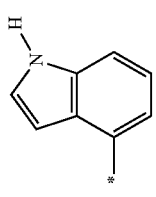  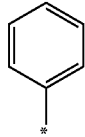 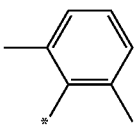

In a preferred embodiment, compounds of Formula 1 include the compounds of Formula 1-A:

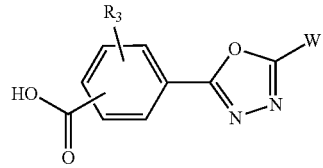

1-A

With reference to Formula 1-A, in a preferred embodiment, the carboxy group is preferably in the meta or para position. In another preferred embodiment, the carboxy group is preferably in the para position. Further, $R_3$ is preferably absent, a halogen, a $C_1$-$C_4$ alkoxy, or a nitro group. In one preferred embodiment of the compounds of Formula 1-A, W is a $C_6$-$C_8$ aryl, optionally substituted as in Formula 1. In another embodiment of Formula 1-A, preferred W groups are shown in the table below.

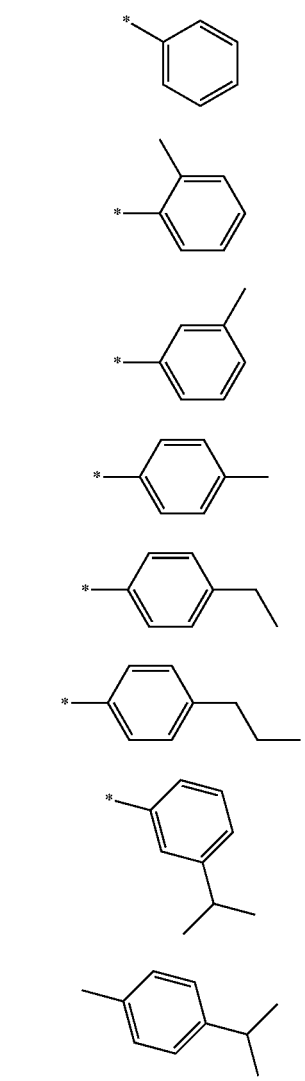

-continued

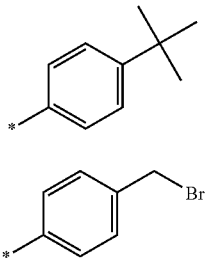

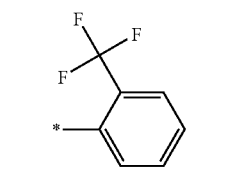 [SMILES: *c1ccccc1C(F)(F)F]

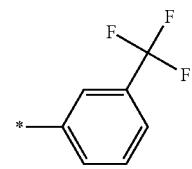 [SMILES: *c1cccc(C(F)(F)F)c1]

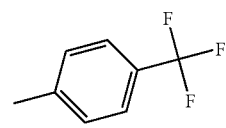

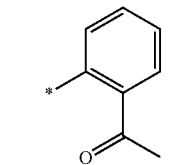 [SMILES: *c1ccccc1C(C)=O]

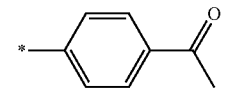

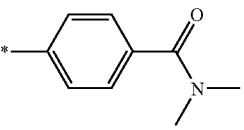

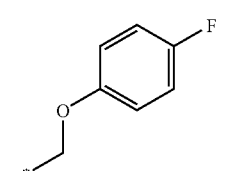

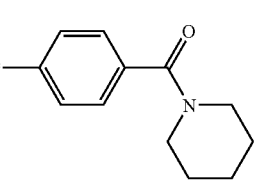

-continued
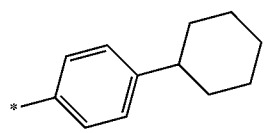 [SMILES: *c1ccc(C2CCCCC2)cc1]
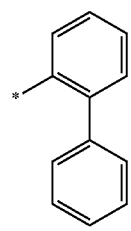 [SMILES: *c1ccccc1-c1ccccc1]
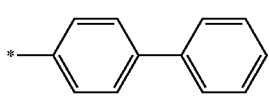 [SMILES: *c1ccc(-c2ccccc2)cc1]
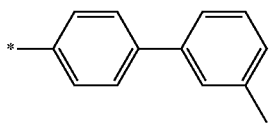
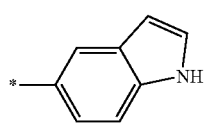
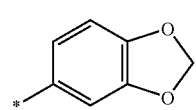
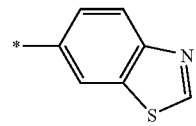 [SMILES: *c1ccc2ncsc2c1]
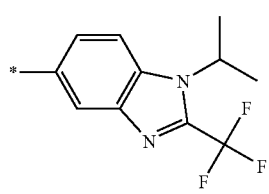 [SMILES: *c1ccc2c(c1)nc(C(F)(F)F)n2C(C)C]
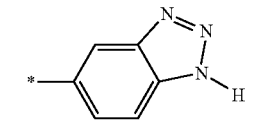
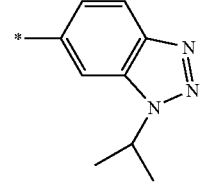 [SMILES: *c1ccc2nnn(C(C)C)c2c1]
-continued
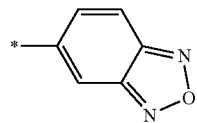
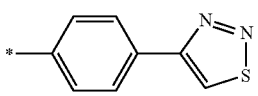
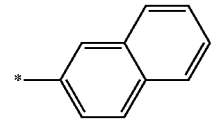
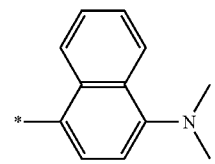
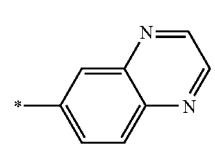 [SMILES: *c1ccc2nccnc2c1]
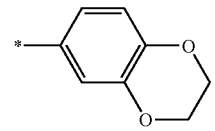
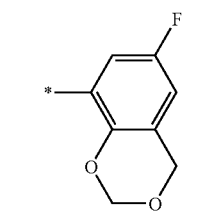 [SMILES: *c1cc(F)cc2c1OCOC2]
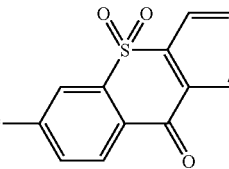
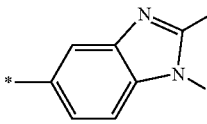
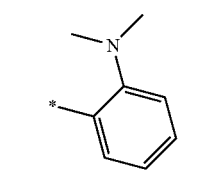 [SMILES: *c1ccccc1N(C)C]

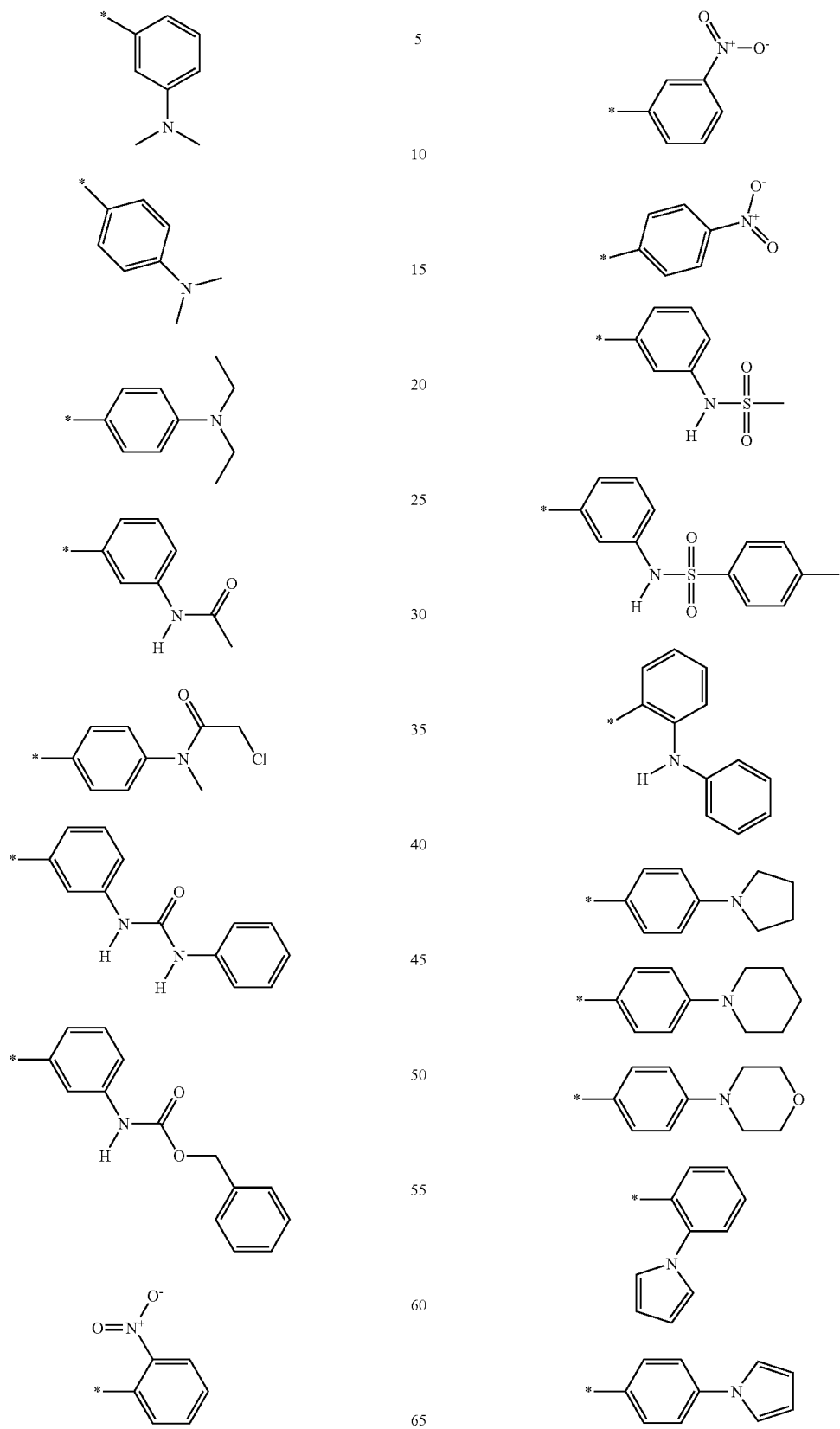

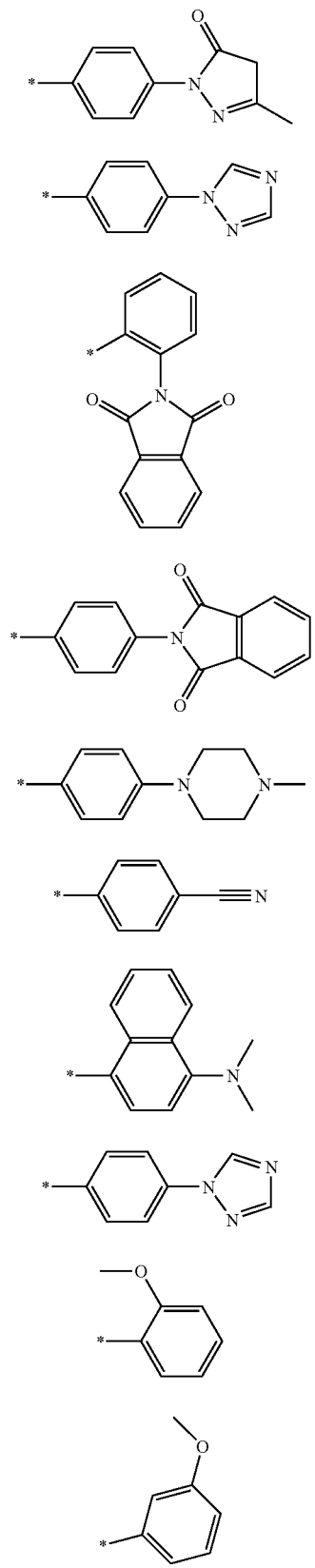
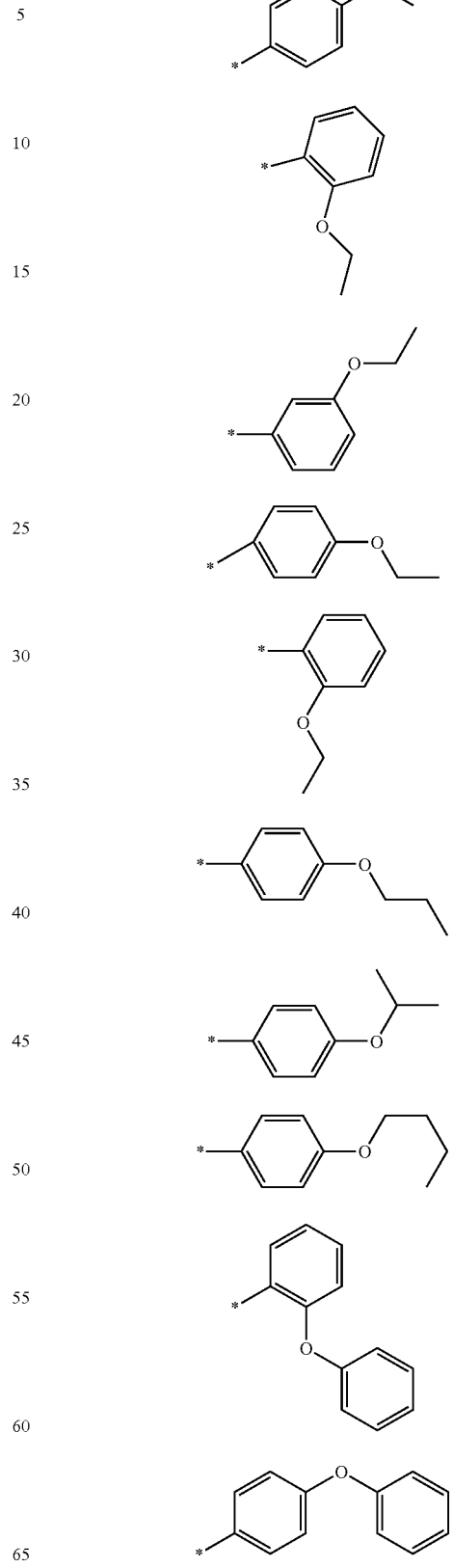

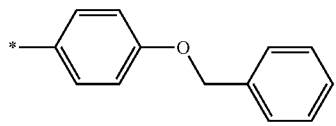 [SMILES: *c1ccc(OCc2ccccc2)cc1]
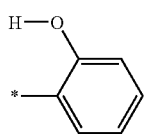
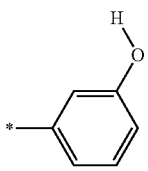
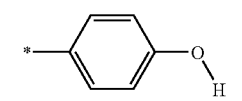 [SMILES: *c1ccc(O)cc1]
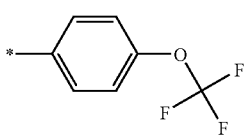 [SMILES: *c1ccc(OC(F)(F)F)cc1]
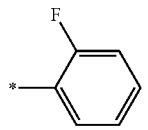 [SMILES: *c1ccccc1F]
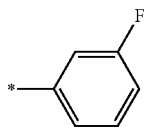 [SMILES: *c1cccc(F)c1]
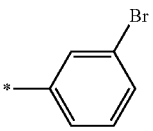
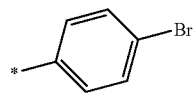
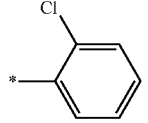 [SMILES: *c1ccccc1Cl]
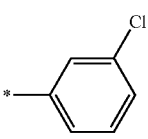 [SMILES: *c1cccc(Cl)c1]
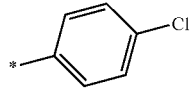 [SMILES: *c1ccc(Cl)cc1]
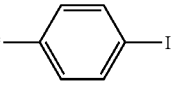
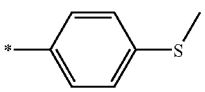
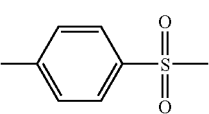
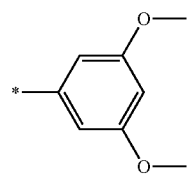
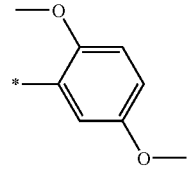 [SMILES: *c1cc(OC)ccc1OC]
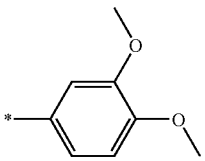
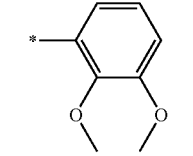 [SMILES: *c1cccc(OC)c1OC]
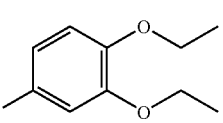
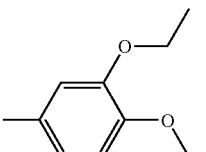
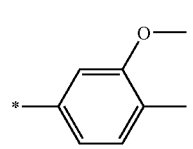

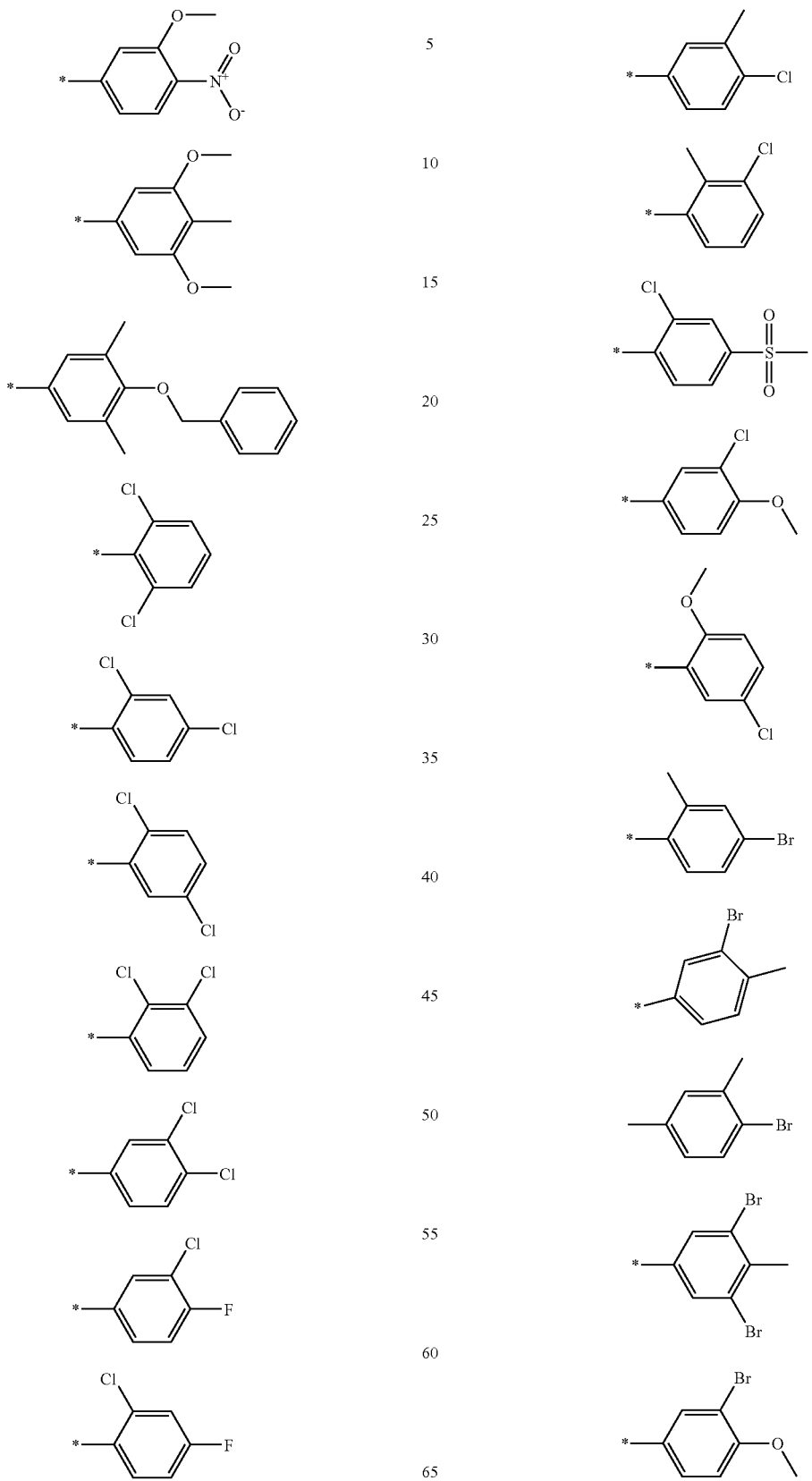

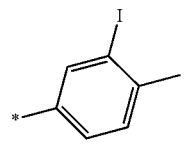
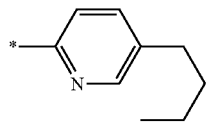
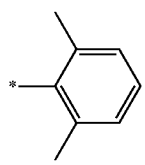 [SMILES: *c1c(C)cccc1C]
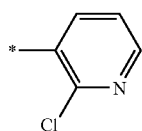
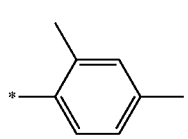 [SMILES: *c1ccc(C)cc1C]
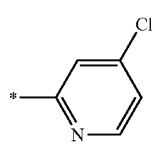
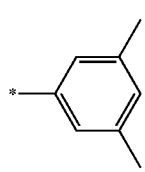 [SMILES: *c1cc(C)cc(C)c1]
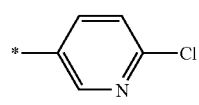
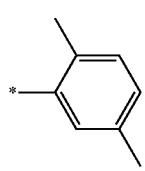 [SMILES: *c1cc(C)ccc1C]
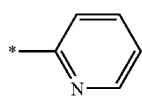
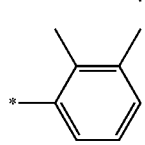
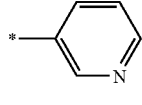
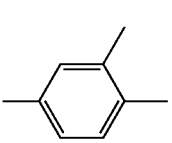
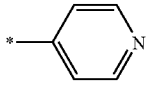
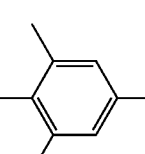
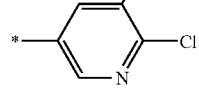
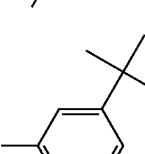
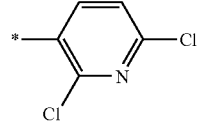
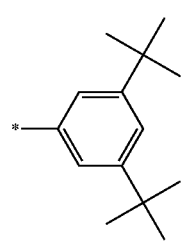 [SMILES: *c1cc(C(C)(C)C)cc(C(C)(C)C)c1]
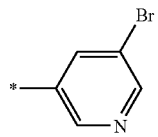
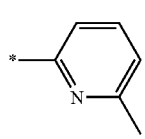 [SMILES: *c1cccc(C)n1]
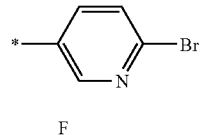
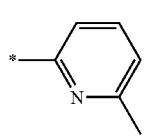

-continued
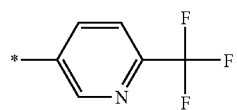
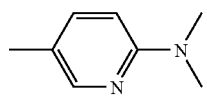
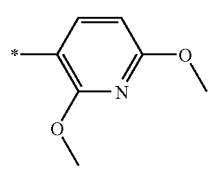 [SMILES: *c1ccc(OC)nc1OC]
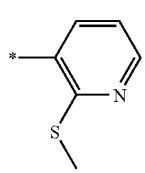 [SMILES: *c1cccnc1SC]
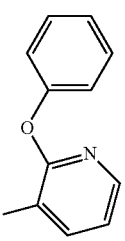
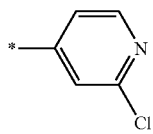
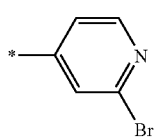
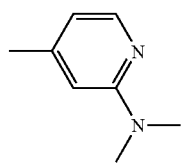
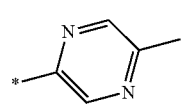
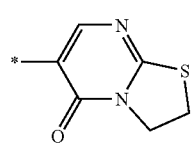 [SMILES: *c1cnc2n(c1=O)CCS2]
-continued
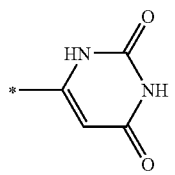
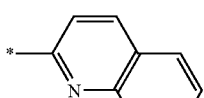
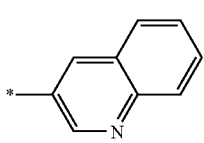
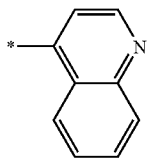 [SMILES: *c1ccnc2ccccc12]
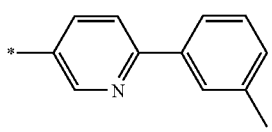
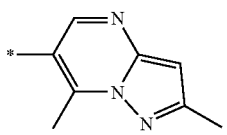 [SMILES: *c1cnc2cc(C)nn2c1C]
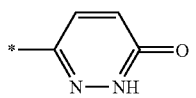
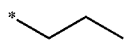
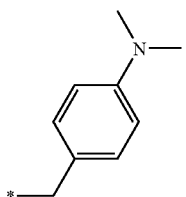
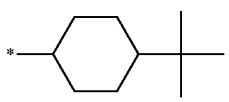 [SMILES: *C1CCC(C(C)(C)C)CC1]
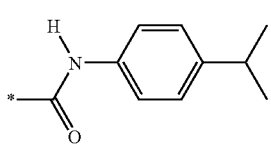 [SMILES: *C(=O)Nc1ccc(C(C)C)cc1]

-continued

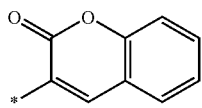
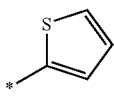
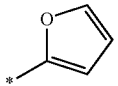
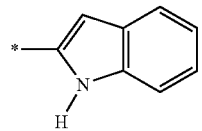 [SMILES: *c1cc2ccccc2[nH]1]
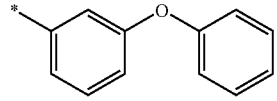 [SMILES: *c1cccc(Oc2ccccc2)c1]

In another preferred embodiment, compounds of Formula 1 include the compounds of Formula 1-B:

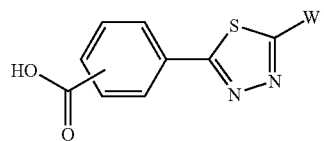
1-B

With reference to Formula 1-B, in an embodiment, the carboxy group is preferably in the para position. In another embodiment, W is preferably a $C_6$-$C_8$ aryl, optionally substituted as in Formula 1; and more preferably a phenyl optionally substituted with a $C_1$-$C_4$ alkyl. A preferred compound of Formula 1-B is shown below.

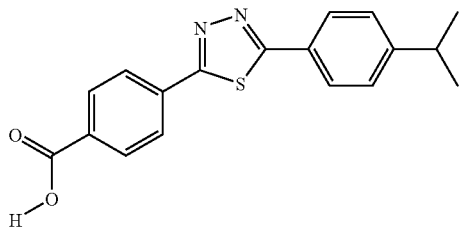 [SMILES: CC(C)c1ccc(-c2nnc(-c3ccc(C(=O)O)cc3)s2)cc1]

In yet another embodiment, preferred compounds of Formula 1 include the compounds of Formula 1-C:

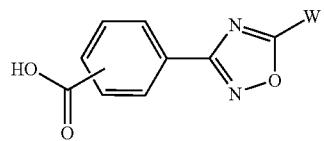
1-C

With reference to Formula 1-C, in an embodiment, the carboxy group is in the para position. In another embodiment, W is preferably a $C_6$-$C_8$ aryl, optionally substituted as in Formula 1.

In another embodiment, preferred W groups include those shown in the table below.

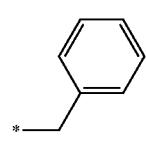

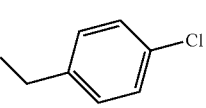

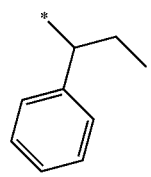 [SMILES: *C(CC)c1ccccc1]

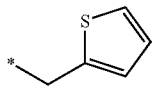

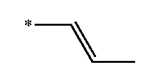 [SMILES: */C=C/C]

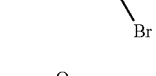

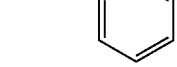

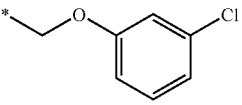 [SMILES: *COc1cccc(Cl)c1]

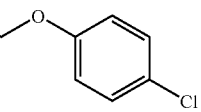

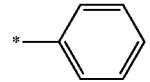

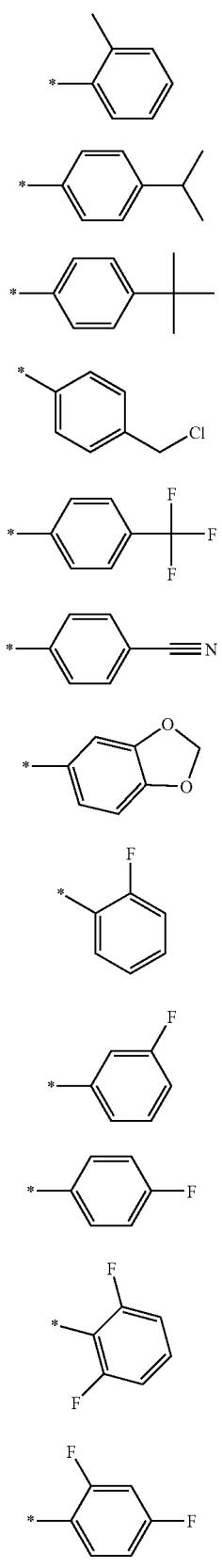
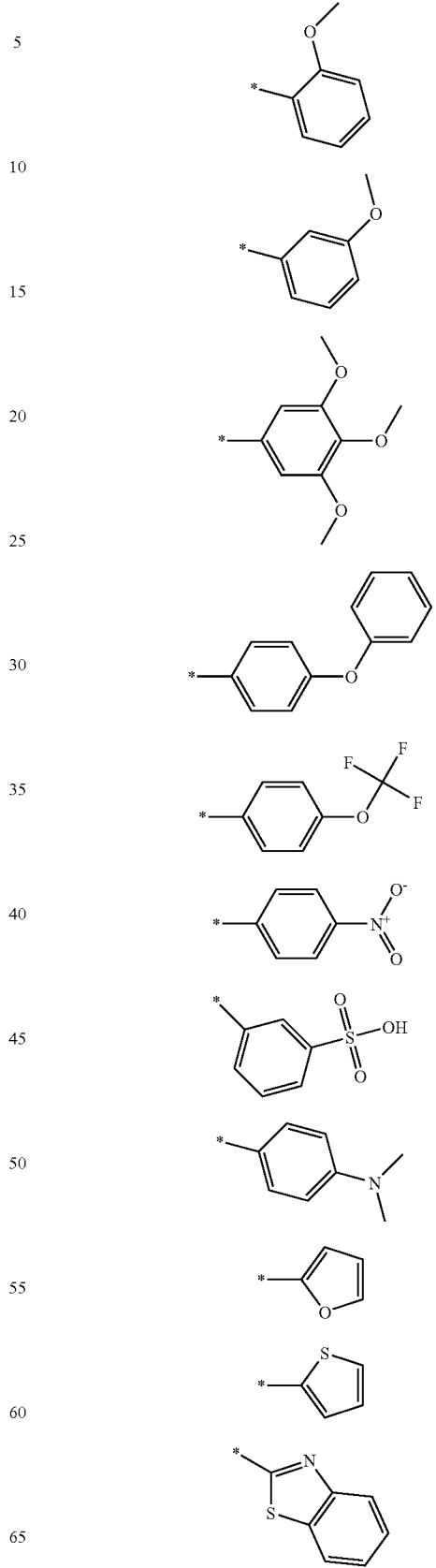

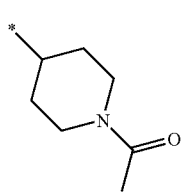
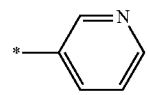
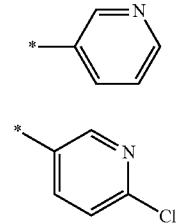
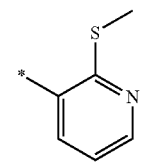 [SMILES: *c1cccnc1SC]
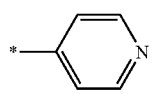
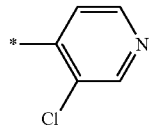 [SMILES: *c1ccncc1Cl]
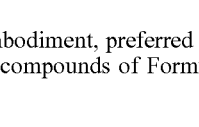
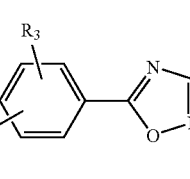

In yet another embodiment, preferred compounds of Formula 1 include the compounds of Formula 1-D:

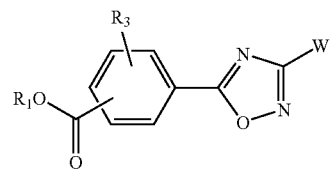

1-D

With reference to Formula 1-D, in an embodiment, the carboxy group is preferably in the meta or para position. Further, $R_1$ is preferably hydrogen or methyl. $R_3$ is preferably in the meta position. In one embodiment, W is preferably a $C_6$-$C_8$ aryl, optionally substituted as in Formula 1. In another embodiment, preferred W groups include those shown in the table below.

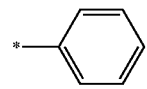 [SMILES: *c1ccccc1]

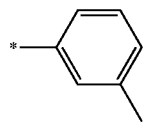
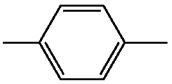
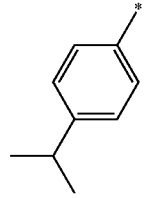 [SMILES: *c1ccc(C(C)C)cc1]
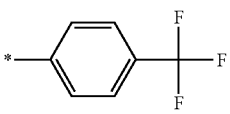
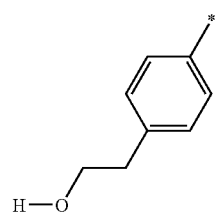 [SMILES: *c1ccc(CCO)cc1]
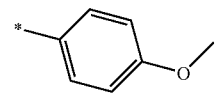
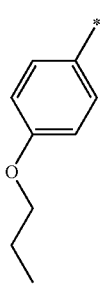
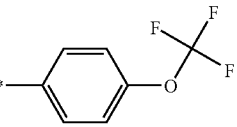
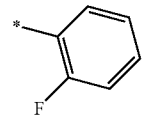
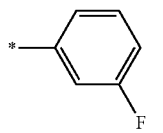 [SMILES: *c1cccc(F)c1]

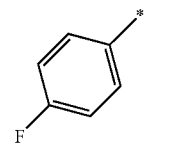
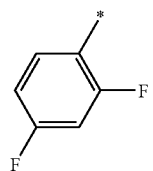
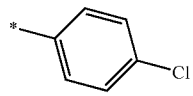 [SMILES: *c1ccc(Cl)cc1]
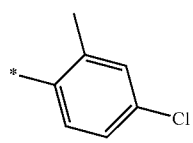 [SMILES: *c1ccc(Cl)cc1C]
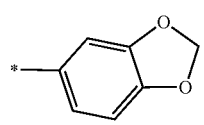
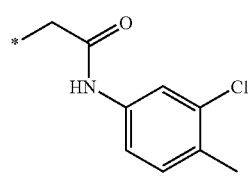 [SMILES: *CC(=O)Nc1ccc(C)c(Cl)c1]

In yet another embodiment, preferred compounds of Formula 1 include the compounds of Formula 1-E:

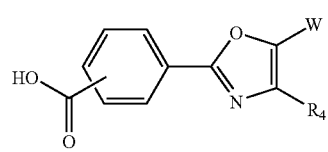

1-E

With reference to Formula 1-E, in an embodiment, the carboxy group is preferably in the meta or para position. Further, in an embodiment, $R_4$ is preferably hydrogen. In one embodiment, W is preferably a $C_6$-$C_8$ aryl, optionally substituted as in Formula 1. In another embodiment, preferred W groups include those shown in the table below.

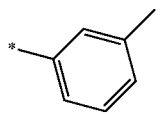 [SMILES: *c1cccc(C)c1]
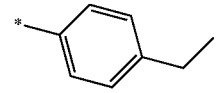
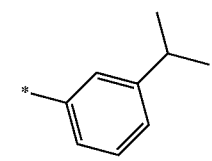
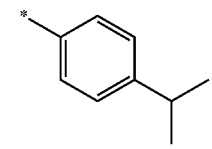 [SMILES: *c1ccc(C(C)C)cc1]
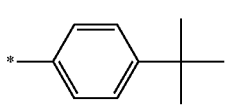
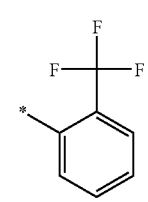 [SMILES: *c1ccccc1C(F)(F)F]
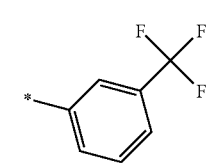 [SMILES: *c1cccc(C(F)(F)F)c1]
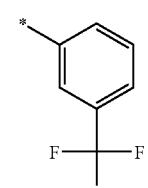
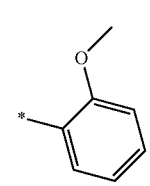 [SMILES: *c1ccccc1OC]
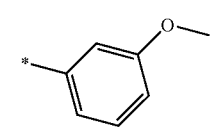

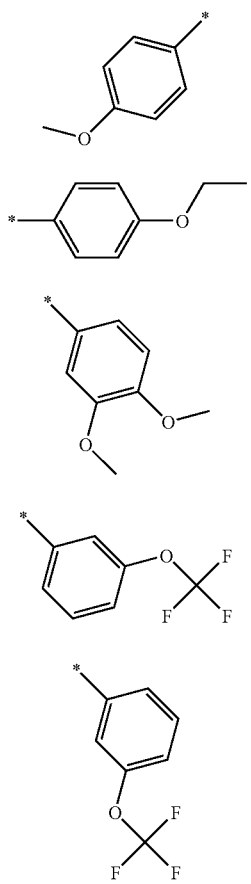

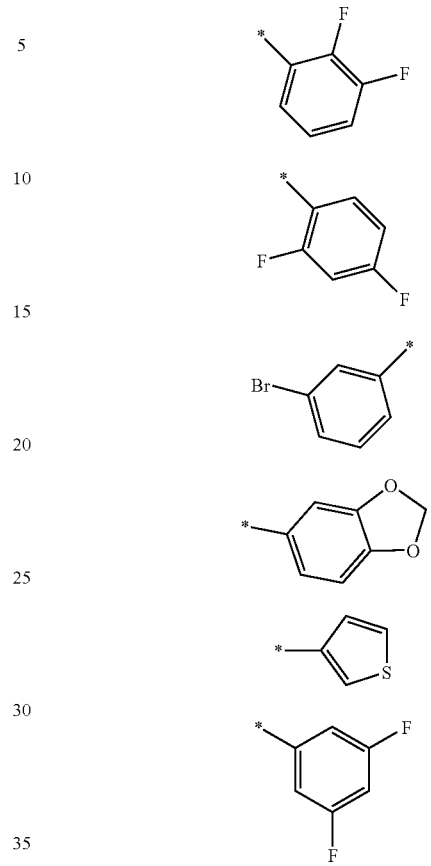

In yet another embodiment, preferred compounds of Formula 1 include the compounds of Formula 1-F:

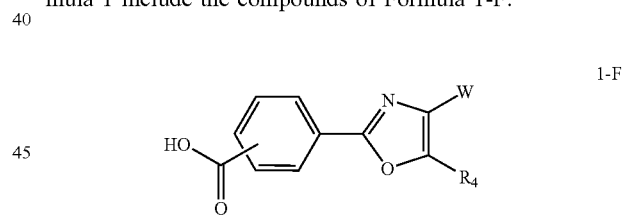

1-F

With reference to Formula 1-F, in an embodiment, the carboxy group is preferably in the meta or para position, more preferably the meta position. In a further embodiment, $R_4$ is preferably hydrogen. In one embodiment, W is preferably a $C_6$-$C_8$ aryl, optionally substituted as in Formula 1. In another embodiment, preferred W groups include those shown in the table below.

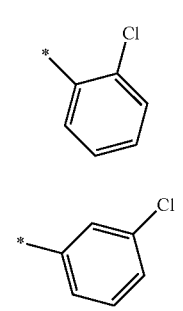

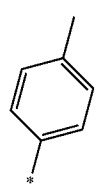

-continued

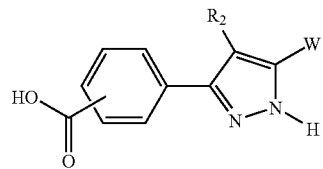

1-G

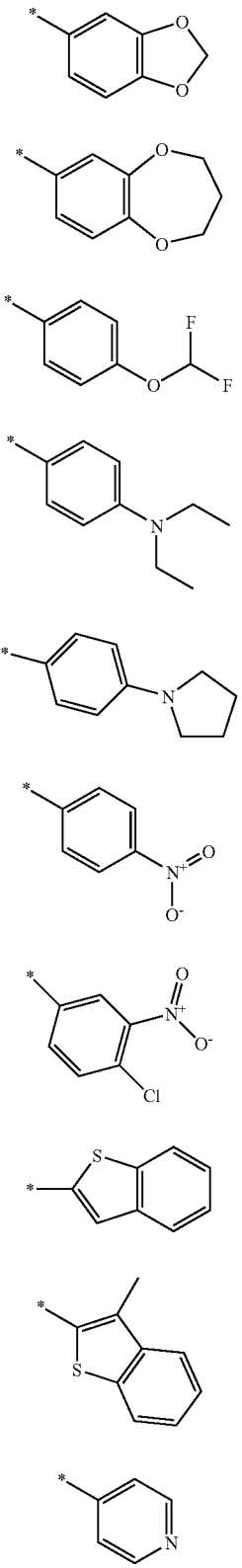

With reference to Formula 1-G, in an embodiment, the carboxy group is preferably in the meta position. In one embodiment, W is preferably a $C_6$-$C_8$ aryl, optionally substituted as in Formula 1. In another embodiment, preferred W groups include those shown in the table below.

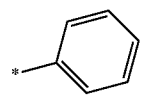

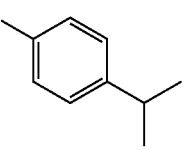

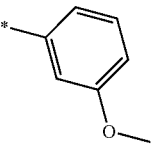 [SMILES: *c1cccc(OC)c1]

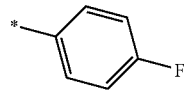

In yet another embodiment, preferred compounds of Formula 1 include the compounds of Formula 1-H:

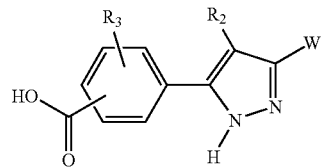

1-H

In yet another embodiment, preferred compounds of Formula 1 include the compounds of Formula 1-G:

With reference to Formula 1-H, in an embodiment, the carboxy group is preferably in the meta position. In a further embodiment, $R_2$ is preferably hydrogen or a $C_1$ to $C_4$ alkyl. $R_3$, if present, is preferably in the ortho position, and is preferably a hydroxy group. In one embodiment, W is preferably a $C_6$-$C_8$ aryl, optionally substituted as in Formula 1, and more preferably a phenyl group. In another embodiment, a preferred compound of Formula 1-His shown below.

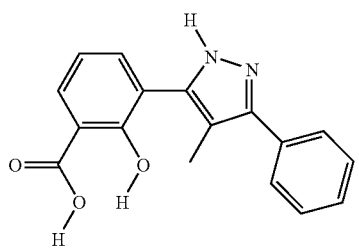 [SMILES: Cc1c(-c2ccccc2)n[nH]c1-c1cccc(C(=O)O)c1O]

In yet another embodiment, preferred compounds of Formula 1 include the compounds of Formula 1-I:

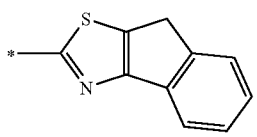

1-I

With reference to Formula 1-I, in an embodiment, the carboxy group is preferably in the meta position. In a further embodiment, $R_4$ is preferably hydrogen. In one embodiment of Formula 1-I, W is preferably a $C_6$-$C_8$ aryl, optionally substituted as in Formula 1. In another embodiment of Formula 1-I, W is preferably a naphthyl group; a pyridyl group; or W together with $R_4$ and the heterocycle to which $R_4$ and W are attached form an eleven to thirteen membered hetero-tricycle ring structure. In a preferred embodiment of Formula 1-I, W together with $R_4$ and the heterocycle to which $R_4$ and W are attached form a hetero-tricycle ring structure as follows, wherein the * indicates the bond of attachment to the phenyl ring of Formula 1-I.

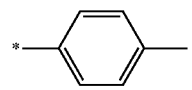

In yet another embodiment, preferred W groups of compounds of Formula 1-I include those shown in the table below.

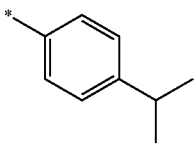 [SMILES: *c1ccc(C(C)C)cc1]

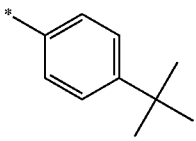 [SMILES: *c1ccc(C(C)(C)C)cc1]

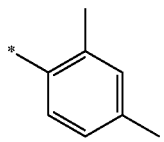

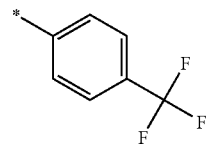 [SMILES: *c1ccc(C(F)(F)F)cc1]

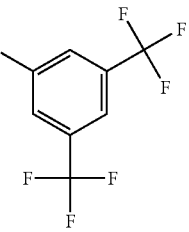

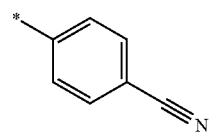 [SMILES: *c1ccc(C#N)cc1]

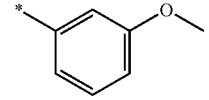 [SMILES: *c1cccc(OC)c1]

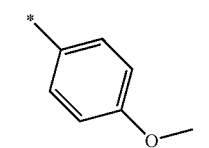 [SMILES: *c1ccc(OC)cc1]

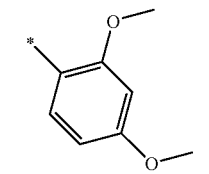 [SMILES: *c1ccc(OC)cc1OC]

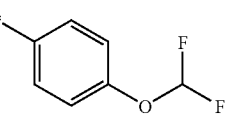

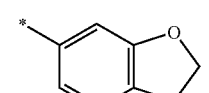

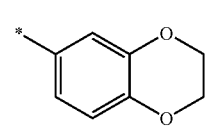

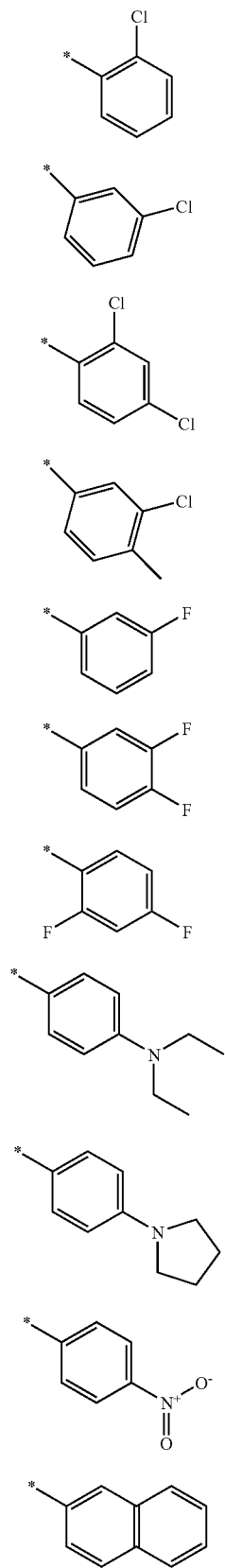

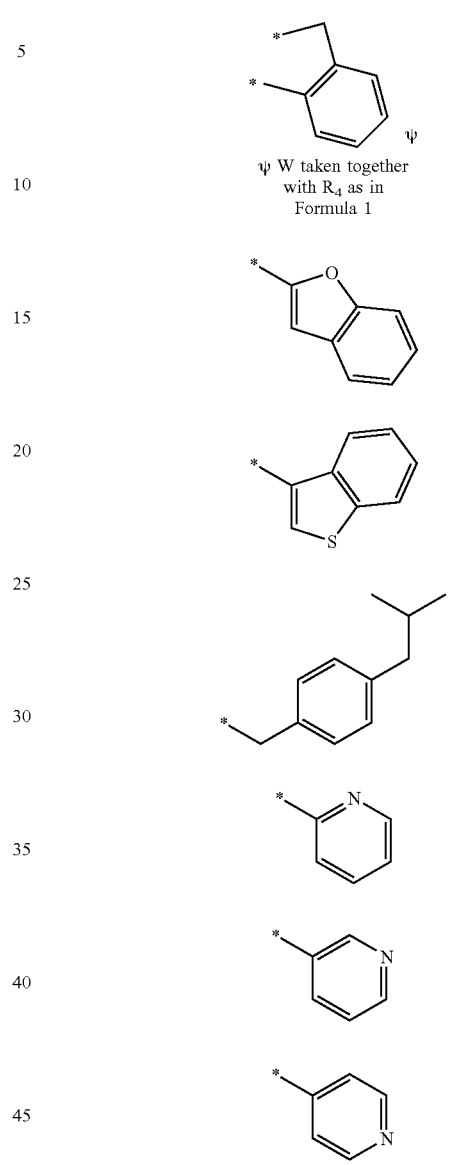

In yet another embodiment, preferred compounds of Formula 1 include the compounds of Formula 1-J:

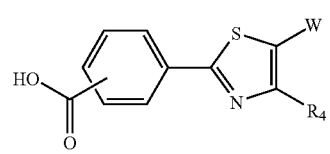

1-J

With reference to Formula 1-J, in an embodiment, the carboxy group is preferably in the meta position. In a further embodiment, $R_4$ is preferably hydrogen. In one embodiment, W is preferably a $C_6$-$C_8$ aryl, optionally substituted as in Formula 1, and more preferably a phenyl optionally substituted with a $C_1$ to $C_4$ alkyl group. In another embodiment, a preferred compound of Formula 1-J is shown below.

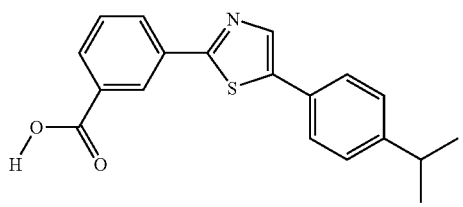 [SMILES: CC(C)c1ccc(-c2cnc(-c3cccc(C(=O)O)c3)s2)cc1]

In yet another embodiment, preferred compounds of Formula 1 include the compounds of Formula 1-K:

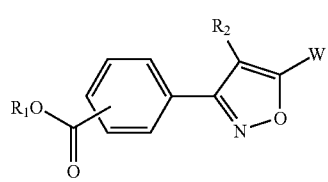

1-K

With reference to Formula 1-K, in an embodiment, the carboxy group is preferably in the meta or para position. In a further embodiment, $R_1$ is preferably hydrogen or a methyl. $R_2$, if present, is preferably hydrogen; a $C_1$-$C_6$ alkyl which is optionally substituted with a hydroxy group; a carbonyl group which is optionally substituted with a hydroxyl or a $C_1$-$C_4$ alkoxy group; a —CH=N—OH group; or a cyano group. In one embodiment, W is preferably a $C_6$-$C_8$ aryl, optionally substituted as in Formula 1, or a naphthyl group optionally substituted as in Formula 1. In another embodiment, preferred W groups include those shown in the table below.

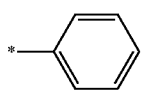

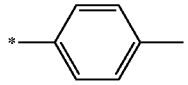

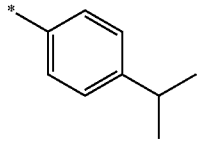

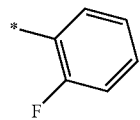

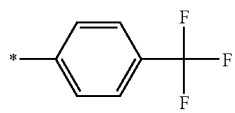

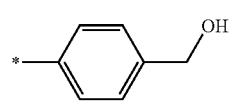

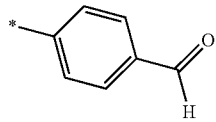

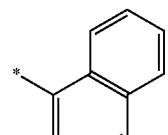

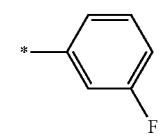 [SMILES: *c1cccc(F)c1]

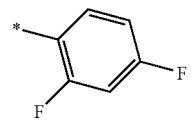

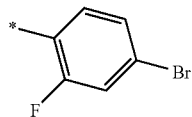 [SMILES: *c1ccc(Br)cc1F]

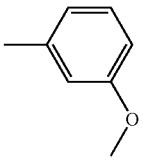

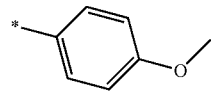 [SMILES: *c1ccc(OC)cc1]

In yet another embodiment, preferred compounds of Formula 1 include the compounds of Formula 1-L:

1-L

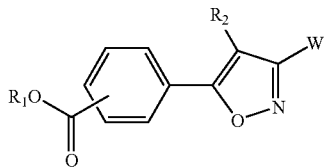

With reference to Formula 1-L, in an embodiment, the carboxy group is preferably in the meta or para position. In a further embodiment, $R_1$ is preferably hydrogen or a $C_1$ to $C_4$ alkyl group. $R_2$ is preferably hydrogen. In one embodiment, W is preferably a $C_6$-$C_8$ aryl, optionally substituted as in Formula 1, and more preferably a phenyl optionally substituted with a $C_1$ to $C_4$ alkyl group. In another embodiment, preferred W groups include those shown in the table below.

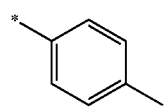

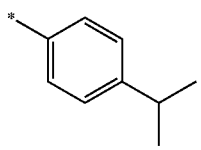 [SMILES: *c1ccc(C(C)C)cc1]

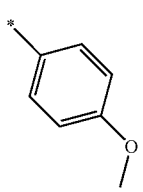

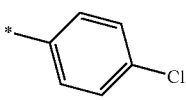 [SMILES: *c1ccc(Cl)cc1]

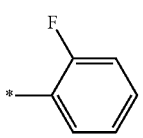

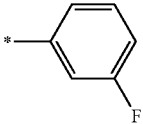

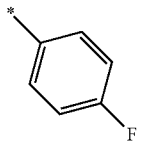

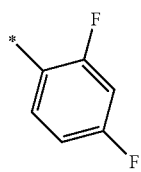 [SMILES: *c1ccc(F)cc1F]

In yet another embodiment, preferred compounds of Formula 1 include the compounds of Formula 1-M:

1-M

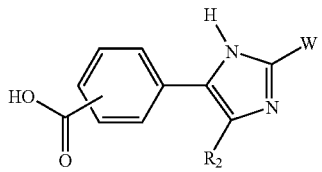

With reference to Formula 1-M, in an embodiment, the carboxy group is preferably in the meta position. In a further embodiment, $R_2$ is preferably hydrogen. In one embodiment, W is preferably a $C_6$-$C_8$ aryl, optionally substituted as in Formula 1, and more preferably a phenyl optionally substituted with a $C_1$ to $C_4$ alkyl group. In another embodiment, a preferred compound of Formula 1-M is shown below.

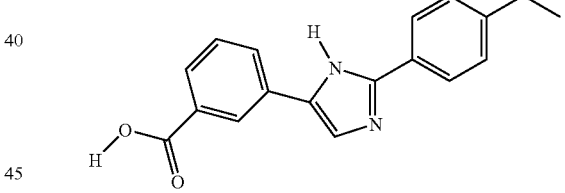

In yet another embodiment, preferred compounds of Formula 1 include the compounds of Formula 1-N:

1-N

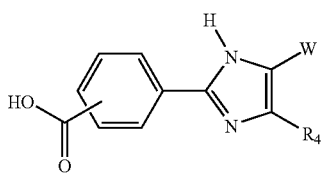

With reference to Formula 1-N, in an embodiment, the carboxy group is preferably in the meta position. In a further embodiment, $R_4$ is preferably hydrogen. In one embodiment, W is preferably a $C_6$-$C_8$ aryl, optionally substituted as in Formula 1, and more preferably a phenyl optionally substituted with a $C_1$ to $C_4$ alkyl group. In another embodiment, a preferred compound of Formula 1-N is shown below.

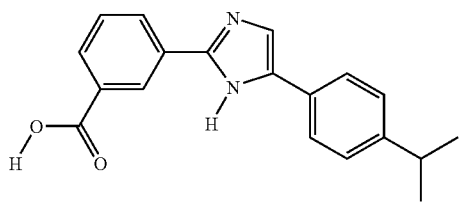 [SMILES: CC(C)c1ccc(-c2cnc(-c3cccc(C(=O)O)c3)[nH]2)cc1]

In yet another embodiment, preferred compounds of Formula 1 include the compounds of Formula 1-O:

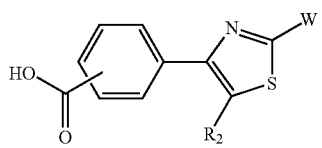

1-O

With reference to Formula 1-O, in an embodiment, the carboxy group is preferably in the meta position. In a further embodiment, $R_2$ is preferably hydrogen. In one embodiment, W is preferably a $C_6$-$C_8$ aryl, optionally substituted as in Formula 1, and more preferably a phenyl optionally substituted with a $C_1$ to $C_4$ alkyl group. In another embodiment, a preferred compound of Formula 1-J is shown below.

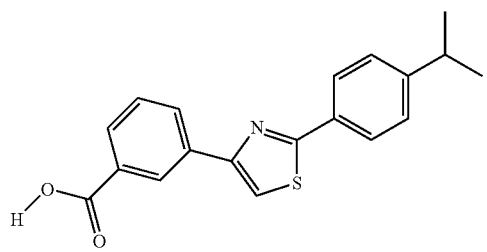 [SMILES: CC(C)c1ccc(-c2nc(-c3cccc(C(=O)O)c3)cs2)cc1]

In yet another embodiment, preferred compounds of Formula 1 include the compounds of Formula 1-P:

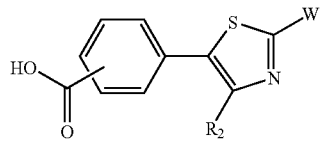

1-P

With reference to Formula 1-P, in an embodiment, the carboxy group is preferably in the meta position. In a further embodiment, $R_2$ is preferably hydrogen. In one embodiment, W is preferably a $C_6$-$C_8$ aryl, optionally substituted as in Formula 1, and more preferably a phenyl optionally substituted with a $C_1$ to $C_4$ alkyl group. In another embodiment, a preferred compound of Formula 1-P is shown below.

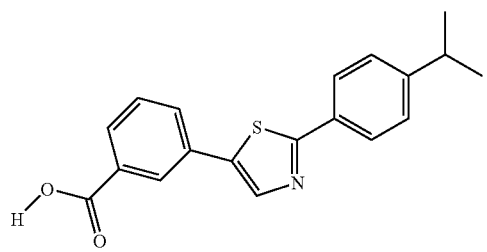 [SMILES: CC(C)c1ccc(-c2ncc(-c3cccc(C(=O)O)c3)s2)cc1]

In yet another embodiment, preferred compounds of Formula 1 include the compounds of Formula 1-Q:

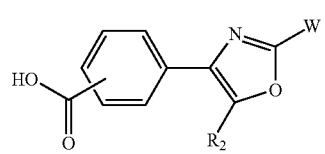

1-Q

With reference to Formula 1-Q, in an embodiment, the carboxy group is preferably in the meta position. In a further embodiment, $R_2$ is preferably hydrogen. In one embodiment, W is preferably a $C_6$-$C_8$ aryl, optionally substituted as in Formula 1, and more preferably a phenyl optionally substituted with a $C_1$ to $C_4$ alkyl group. In another embodiment, a preferred compound of Formula 1-Q is shown below.

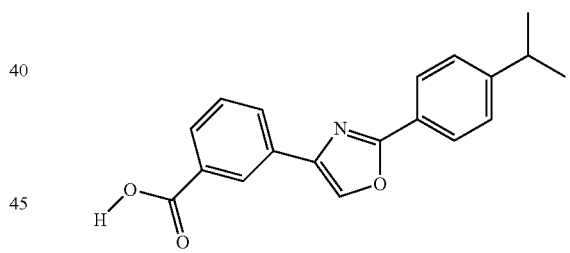

In yet another embodiment, preferred compounds of Formula 1 include the compounds of Formula 1-R:

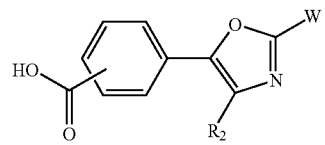

1-R

With reference to Formula 1-R, in an embodiment, the carboxy group is preferably in the meta position. In a further embodiment, $R_2$ is preferably hydrogen. In one embodiment, W is preferably a $C_6$-$C_8$ aryl, optionally substituted as in Formula 1, and more preferably a phenyl optionally substituted with a $C_1$ to $C_4$ alkyl group. In another embodiment, a preferred compound of Formula 1-R is shown below.

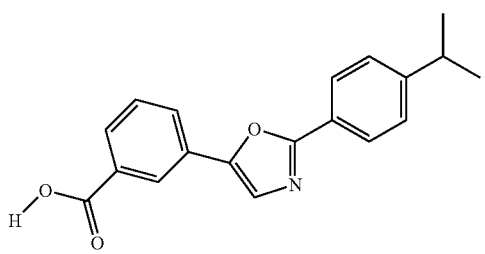 [SMILES: CC(C)c1ccc(-c2ncc(-c3cccc(C(=O)O)c3)o2)cc1]

In yet another embodiment, preferred compounds of Formula 1 include the compounds of Formula 1-S:

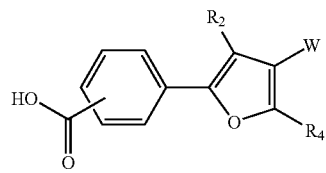

1-S

With reference to Formula 1-S, in an embodiment, the carboxy group is preferably in the meta position. In a further embodiment, $R_2$ is preferably hydrogen or a carbonyl group optionally substituted as in Formula 1. $R_4$ is preferably hydrogen. In one embodiment, W is preferably a $C_6$-$C_8$ aryl, optionally substituted as in Formula 1, and more preferably a phenyl optionally substituted with a $C_1$ to $C_4$ alkyl group. In another embodiment, a preferred compound of Formula 1-S is shown below.

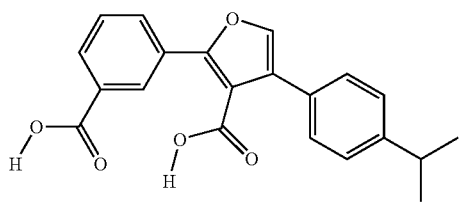 [SMILES: CC(C)c1ccc(-c2coc(-c3cccc(C(=O)O)c3)c2C(=O)O)cc1]

In yet another embodiment, preferred compounds of Formula 1 include the compounds of Formula 1-T:

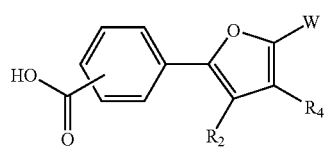

1-T

With reference to Formula 1-T, in an embodiment, the carboxy group is preferably in the meta position. In a further embodiment, $R_2$ is preferably carbonyl optionally substituted as in Formula 1 or hydrogen. $R_4$ is preferably hydrogen. In one embodiment, W is preferably a $C_6$-$C_8$ aryl, optionally substituted as in Formula 1, and more preferably a phenyl optionally substituted with a $C_1$ to $C_4$ alkyl group. In another embodiment, a preferred compound of Formula 1-T is shown below.

In yet another embodiment, preferred compounds of Formula 1 include the compounds of Formula 1-U:

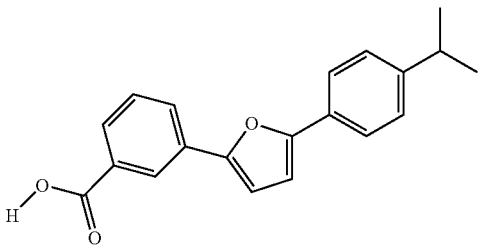 [SMILES: CC(C)c1ccc(-c2ccc(-c3cccc(C(=O)O)c3)o2)cc1]

1-U

With reference to Formula 1-U, in an embodiment, the carboxy group is preferably in the meta position. In one embodiment, W is preferably a $C_6$-$C_8$ aryl, optionally substituted as in Formula 1, and more preferably a phenyl optionally substituted with a $C_1$ to $C_4$ alkyl group. In another embodiment, a preferred compound of Formula 1-U is shown below.

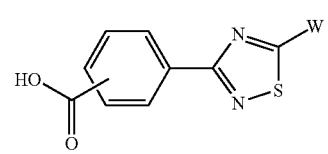

In yet another embodiment, preferred compounds of Formula 1 include the compounds of Formula 1-V:

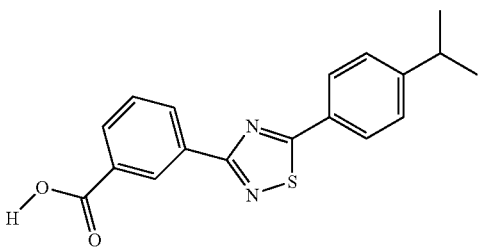 [SMILES: CC(C)c1ccc(-c2nc(-c3cccc(C(=O)O)c3)ns2)cc1]

1-V

With reference to Formula 1-V, in an embodiment, the carboxy group is preferably in the meta position. In one embodiment, W is preferably a $C_6$-$C_8$ aryl, optionally substituted as in Formula 1, and more preferably a phenyl optionally substituted with a $C_1$ to $C_4$ alkyl group. In another embodiment, a preferred compound of Formula 1-V is shown below.

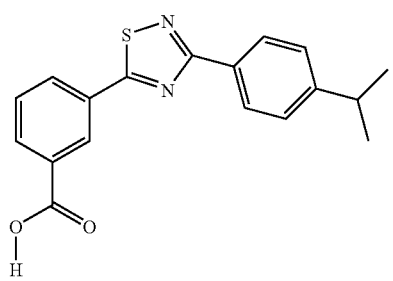 [SMILES: CC(C)c1ccc(-c2nsc(-c3cccc(C(=O)O)c3)n2)cc1]

In yet another embodiment, preferred compounds of Formula 1 include the compounds of Formula 1-W:

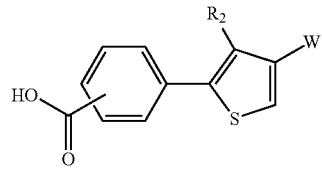

1-W

With reference to Formula 1-W, in an embodiment, the carboxy group is preferably in the meta position. In a further embodiment, $R_2$ is preferably hydrogen. In one embodiment, W is preferably a $C_6$-$C_8$ aryl, optionally substituted as in Formula 1, and more preferably a phenyl optionally substituted with a $C_1$ to $C_4$ alkyl group. In another embodiment, a preferred compound of Formula 1-W is shown below.

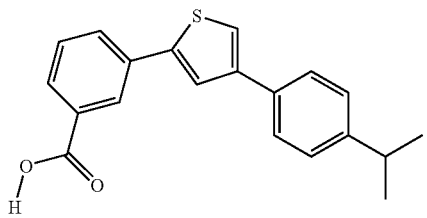 [SMILES: CC(C)c1ccc(-c2csc(-c3cccc(C(=O)O)c3)c2)cc1]

In yet another embodiment, preferred compounds of Formula 1 include the compounds of Formula 1-X:

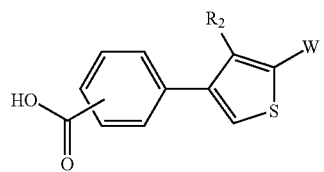

1-X

With reference to Formula 1-X, in an embodiment, the carboxy group is preferably in the meta position. In a further embodiment, $R_2$ is preferably hydrogen. In one embodiment, W is preferably a $C_6$-$C_8$ aryl, optionally substituted as in Formula 1, and more preferably a phenyl optionally substituted with a $C_1$ to $C_4$ alkyl group. In another embodiment, a preferred compound of Formula 1-X is shown below.

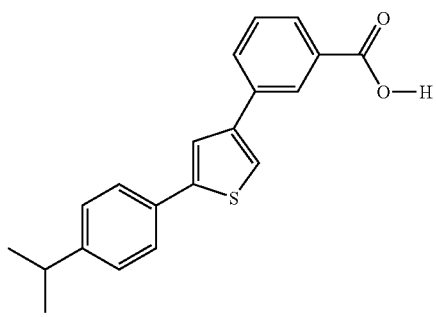 [SMILES: CC(C)c1ccc(-c2cc(-c3cccc(C(=O)O)c3)cs2)cc1]

In yet another embodiment, preferred compounds of Formula 1 include the compounds of Formula 1-Y:

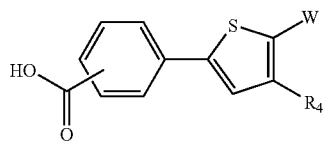

1-Y

With reference to Formula 1-Y, in an embodiment, the carboxy group is preferably in the meta position. In a further embodiment, $R_4$ is preferably hydrogen. In one embodiment, W is preferably a $C_6$-$C_8$ aryl, optionally substituted as in Formula 1, and more preferably a phenyl optionally substituted with a $C_1$ to $C_4$ alkyl group. In another embodiment, a preferred compound of Formula 1-Y is shown below.

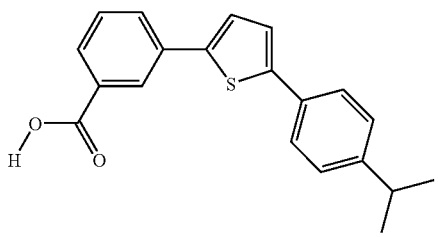 [SMILES: CC(C)c1ccc(-c2ccc(-c3cccc(C(=O)O)c3)s2)cc1]

In yet another embodiment, preferred compounds of Formula 1 include the compounds of Formula 1-Z:

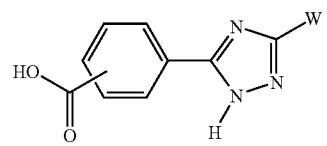

1-Z

With reference to Formula 1-Z, in an embodiment, the carboxy group is preferably in the meta position. In one embodiment, W is preferably a $C_6$-$C_8$ aryl, optionally substituted as in Formula 1; a pyridyl group; or a thienyl group. In another embodiment, preferred W groups include those shown in the table below.

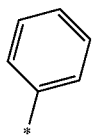

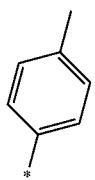

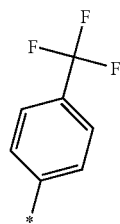 [SMILES: *c1ccc(C(F)(F)F)cc1]

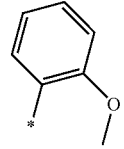

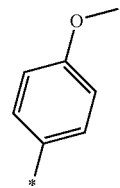 [SMILES: *c1ccc(OC)cc1]

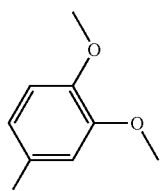

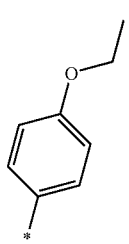 [SMILES: *c1ccc(OCC)cc1]

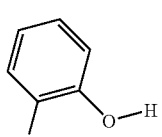

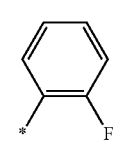

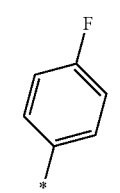

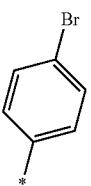 [SMILES: *c1ccc(Br)cc1]

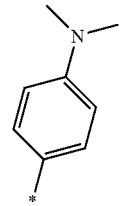 [SMILES: *c1ccc(N(C)C)cc1]

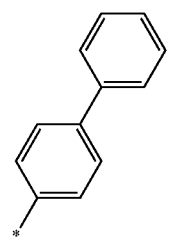 [SMILES: *c1ccc(-c2ccccc2)cc1]

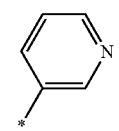

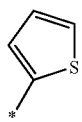

In another aspect of the invention, compounds of Formula (2) are provided which are useful for suppressing premature translation termination associated with a nonsense mutation in mRNA, and for treating diseases associated with nonsense mutations in mRNA:

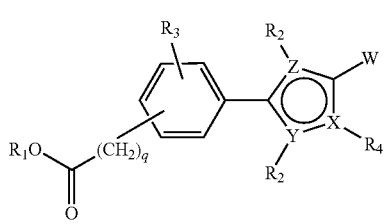

(2)

wherein:

X, Y, and Z are independently selected from N, S, O, and C wherein at least one of X, Y or Z is a heteroatom;

$R_1$ is hydrogen, a $C_1$-$C_6$ alkyl, or Na+, or $Mg^{2+}$;

$R_2$ is independently absent; a hydrogen; a —CH=N—OH group; a cyano group; a $C_1$-$C_6$ alkyl which is optionally substituted with a hydroxy group; or a carbonyl group which is optionally substituted with a hydrogen, a hydroxyl, or a $C_1$-$C_4$ alkoxy group;

$R_3$ is independently absent, a halogen, a hydroxy, a $C_1$-$C_6$ alkyl, $C_1$-$C_4$ alkoxy, or a nitro group;

R4 is independently absent, a hydrogen, a $C_1$-$C_6$ alkyl, or when taken together with W, R4 may be a bond, and W and the heterocycle to which R4 and W are attached form an eleven to thirteen membered hetero-tricycle ring structure;

q is 0, 1, or 2;

W is selected from:
(a) a $C_2$-$C_6$ alkynyl, optionally substituted with a phenyl;
(b) a $C_1$-$C_8$ straight chain or branched chain alkyl which is optionally substituted with one or more of the following independently selected groups: a $C_1$-$C_6$ alkyl; a halogen; a —C(=O)—NH-phenyl which phenyl is optionally substituted with one or more independently selected halogens or $C_1$-$C_4$ alkyl groups; a five to six-membered heterocycle; a $C_6$-$C_8$ aryl which is optionally substituted with one or more groups independently selected from a hydroxy, a halogen, a $C_1$-$C_4$ alkyl group, a $C_1$-$C_4$ haloalkyl group, a $C_1$-$C_4$ alkoxy group or an amino group which is optionally substituted with one or more $C_1$-$C_4$ alkyl groups; an aryloxy which is optionally substituted with one or more of the following independently selected groups: a hydroxy, a halogen, a $C_1$-$C_4$ alkyl group, a $C_1$-$C_4$ haloalkyl group, a $C_1$-$C_4$ alkoxy group or an amino group which is optionally substituted with one or more $C_1$-$C_4$ alkyl groups;
(c) $C_2$ to $C_8$ alkenyl;
(d) a $C_3$-$C_8$ cycloalkyl optionally substituted with a $C_1$-$C_6$ alkyl;
(e) a $C_6$-$C_8$ aryl which is optionally substituted with one or more of the following independently selected groups: a hydroxy; a halogen; a $C_1$-$C_4$ straight chain or branched chain alkyl which is optionally substituted with one or more independently selected halogen or hydroxy groups; a $C_1$-$C_4$ alkoxy which is optionally substituted with one or more independently selected halogen or phenyl groups; a $C_3$-$C_8$ cycloalkyl which is optionally substituted with one or more independently selected $C_1$-$C_4$ alkyl groups; a $C_6$-$C_8$ aryl which is optionally substituted with one or more independently selected $C_1$-$C_4$ alkyl groups; an aryloxy which is optionally substituted with one or more of the following independently selected groups: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more independently selected $C_1$-$C_4$ alkyl groups; a five to six-membered heterocycle which is optionally substituted with one or more independently selected $C_1$-$C_4$ alkyl, oxo, or $C_6$-$C_8$ aryl which is optionally substituted with one or more of the following independently selected groups: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more independently selected $C_1$-$C_4$ alkyl groups; a naphthyl group which is optionally substituted with an amino or aminoalkyl or alkoxy group; a —C(O)—NR$_x$R$_y$ group; a —C(O)—R$_x$ group; a isoindole-1,3-dione group; a nitro group; a cyano group; a —SO$_3$H group; alkylthio group; alkyl sulfonyl group; a —NR$_x$—C(O)—R$_z$ group; a —NR$_x$R$_y$ group; a —NR$_x$—SO$_2$—R$_z$ group; a —NR$_x$—C(O)—NR$_x$R$_y$ group; a —NR$_x$—C(O)O—R$_z$ group;
(f) a $C_{10}$-$C_{14}$ aryl group optionally substituted with one or more independently selected halogens, amino groups or aminoalkyl groups, or alkoxy groups;
(g) a —C(O)—NR$_x$R$_y$ group;
(h) a five or six membered heterocycle which is optionally substituted with one or more independently selected oxo groups; halogens; $C_1$-$C_4$ alkyl groups; $C_1$-$C_4$ alkoxy groups; $C_1$-$C_4$ haloalkyl groups; $C_1$-$C_4$ haloalkoxy groups; aryloxy groups; —NR$_x$R$_y$ groups; alkylthio groups; —C(O)—R$_x$ groups; or $C_6$ to $C_8$ aryl groups which are optionally substituted with one or more independently selected halogens, $C_1$-$C_4$ alkyl groups, $C_1$-$C_4$ alkoxy groups;
(i) a heterocycle group having two to three ring structures that is optionally substituted with one or more independently selected halogens, oxo groups, $C_1$-$C_4$ alkyl groups, $C_1$-$C_4$ haloalkyl groups, or $C_1$-$C_4$ alkoxy groups;
(j) or W together with R4, including where R4 is a bond, and the heterocycle to which R4 and W are attached form an eleven to thirteen membered hetero-tricycle ring structure;

wherein R$_x$ is hydrogen, a $C_1$-$C_6$ alkyl group, or R$_x$ and R$_y$ together with the atoms to which they are attached form a four to seven membered carbocycle or heterocycle;

R$_y$ is hydrogen, a $C_1$-$C_6$ alkyl group; an aryl group optionally substituted with one or more independently selected $C_1$-$C_4$ alkyl groups, or R$_x$ and R$_y$ together with the atoms to which they are attached form a four to seven membered carbocycle or heterocycle; and R$_z$ is an $C_1$-$C_6$ alkyl optionally substituted with an aryl or a halogen; or an aryl optionally substituted with a halogen, a $C_1$-$C_6$ alkyl, or a $C_1$-$C_6$ alkoxy;

or a pharmaceutically acceptable salt, hydrate, solvate, clathrate, racemate, stereoisomer, or polymorph of said compound of Formula 2.

In an embodiment of Formula 2, preferred substituents for Formula 2 may be chosen as for Formula 1. In a preferred embodiment of Formula 2, substituents for Formula 2 may be chosen as described for Formula 1-E.

In a preferred embodiment of Formula 2, q is 0. In another preferred embodiment of Formula 2, q is 1 or 2. In a preferred embodiment of Formula 2, q is 1. In another embodiment of Formula 2, q is 2.

In a preferred embodiment of Formula 2, R$_3$ is hydrogen, q is 1 and the —CH2-COOR1 group is in the para position relative to the 5-membered ring containing the X, Y, and Z substituents.

In other embodiments of compounds of Formula 2, Z is oxygen, Y is nitrogen, and both R$_2$ groups are absent. In a related more preferred embodiment, X is carbon and R4 is hydrogen. In either of the previous two embodiments q is preferably 1.

In even more preferred compounds of Formula 2 embodiments, W is a phenyl ring substituted with one or more independently selected halogens. In another more preferred embodiments, Z is oxygen, Y is nitrogen, both R$_2$ groups are absent, X is carbon, R4 is hydrogen, q is 1, and W is a phenyl ring substituted with two independently selected halogens. In an even more preferred embodiment, the compound of Formula 2 is:

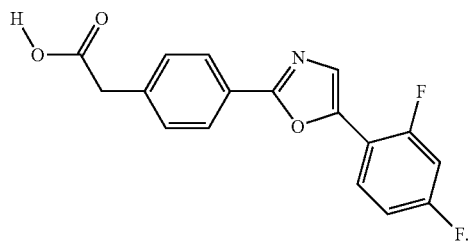 [SMILES: O=C(O)Cc1ccc(-c2ncc(-c3ccc(F)cc3F)o2)cc1]

Compounds of Formula 2 are useful in methods of treatment, and the preparation of pharmaceutical compositions as recited for compounds of Formula 1.

Preferred compounds of the invention include the following compounds in Table X:
TABLE X
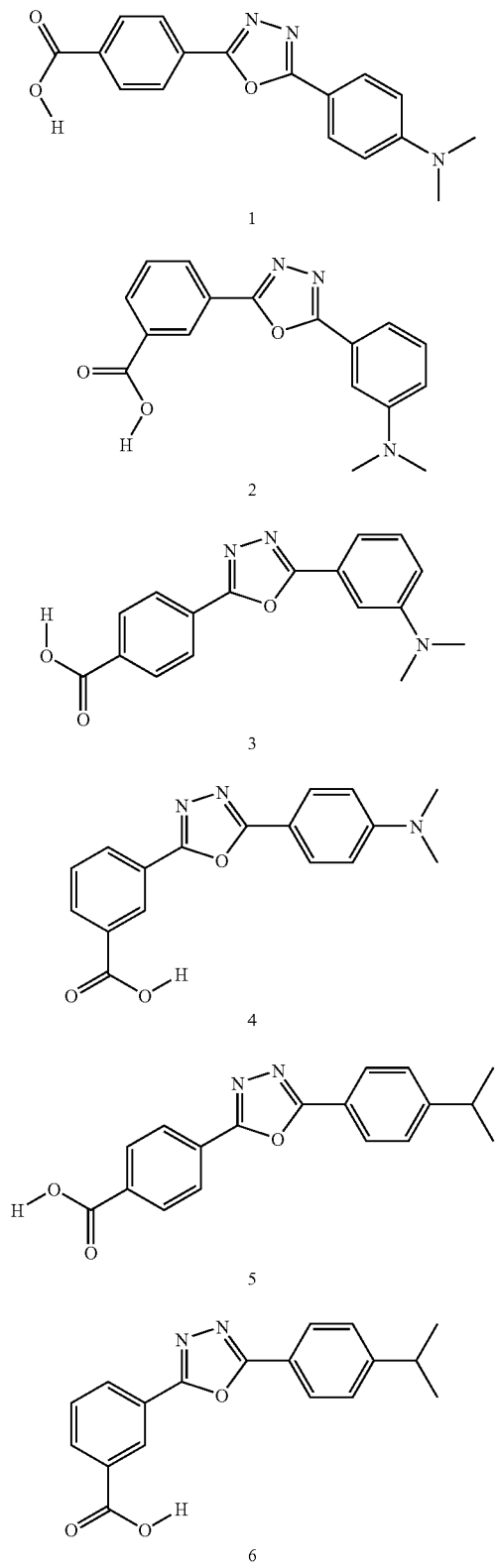
TABLE X-continued
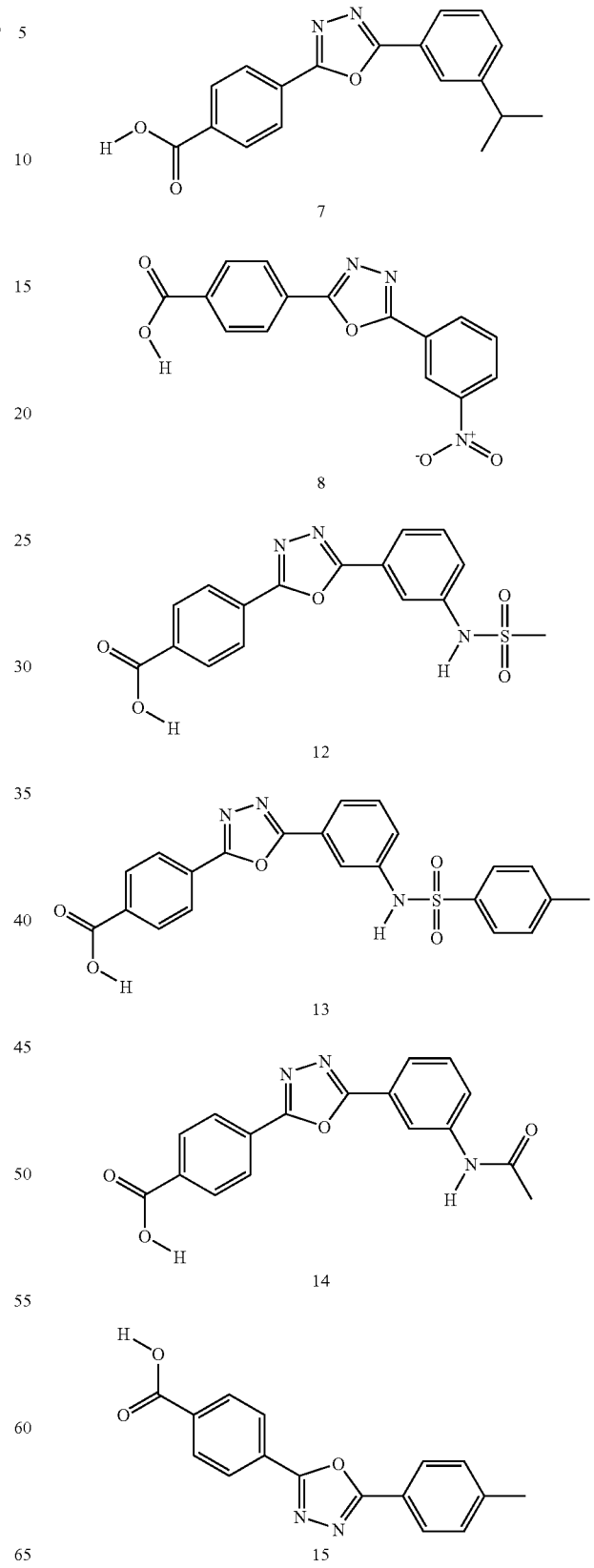

TABLE X-continued
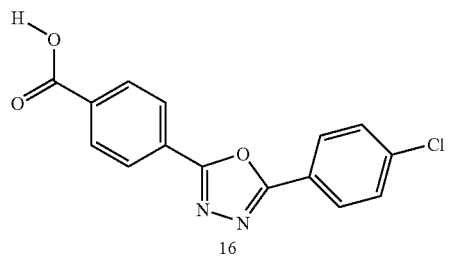
16
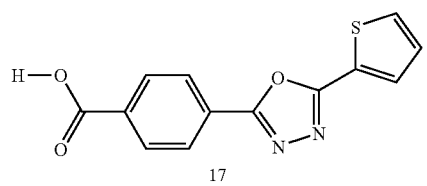
17
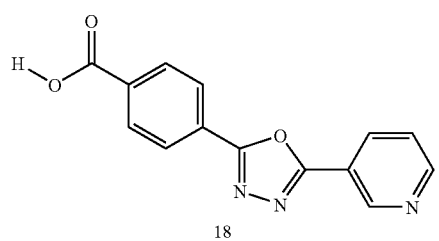
18
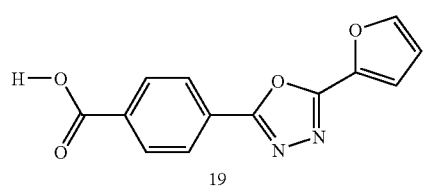
19
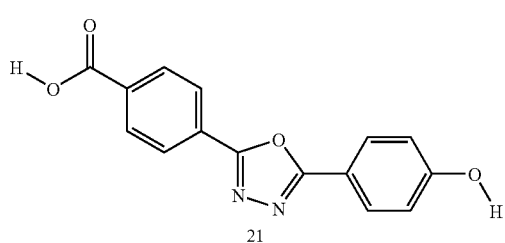
21
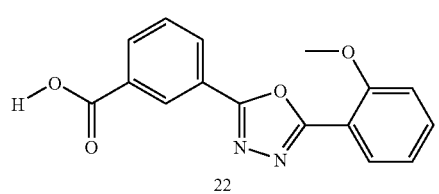
22
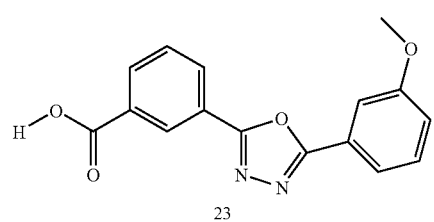
23
TABLE X-continued
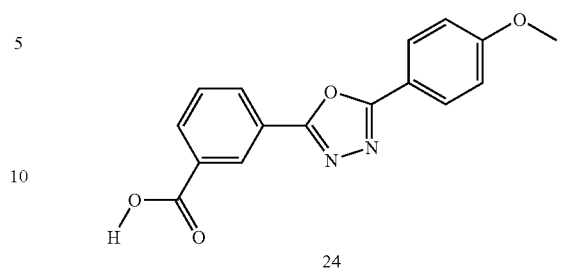
24
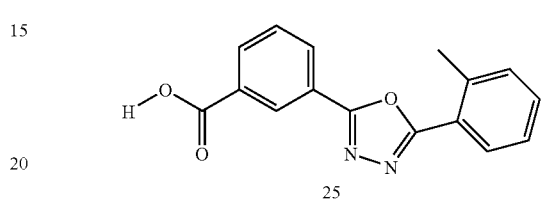
25
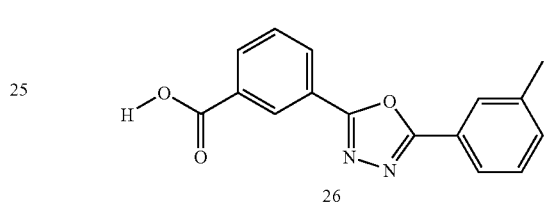
26
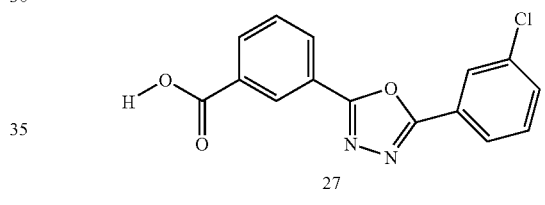
27
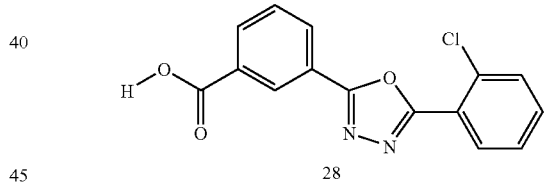
28
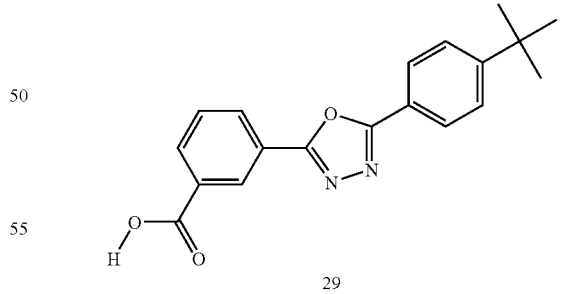
29
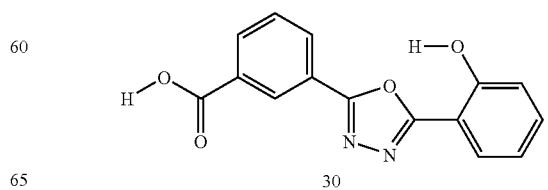
30

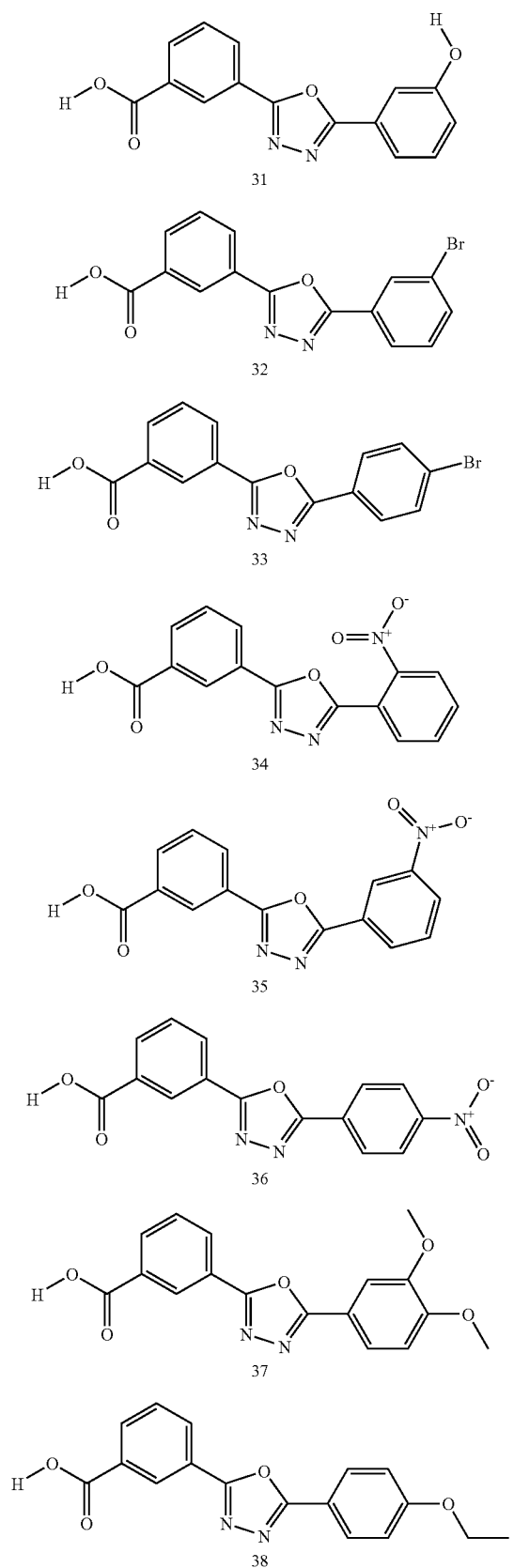

TABLE X-continued
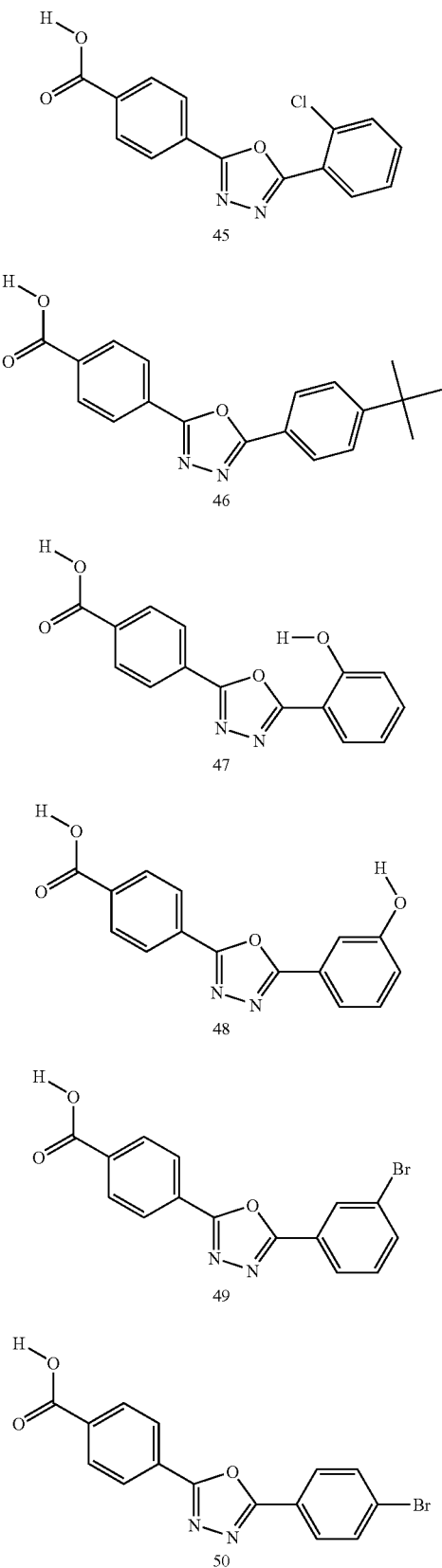
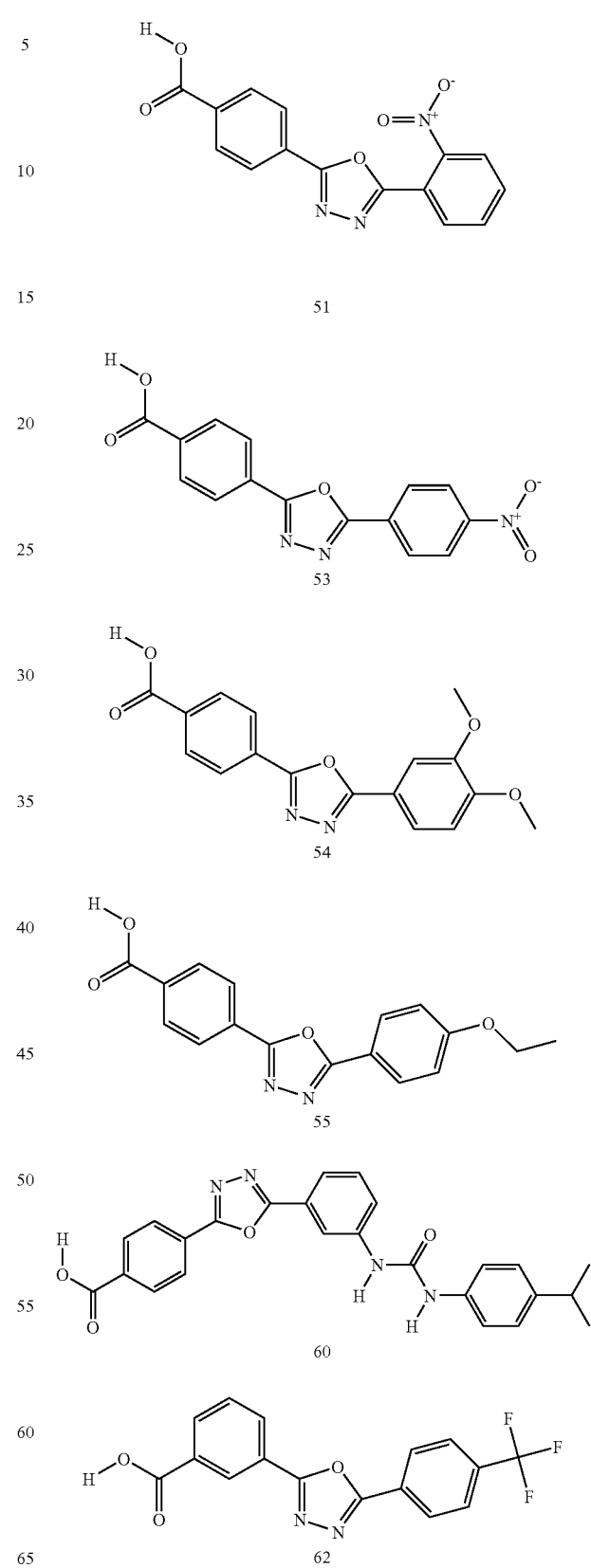

TABLE X-continued
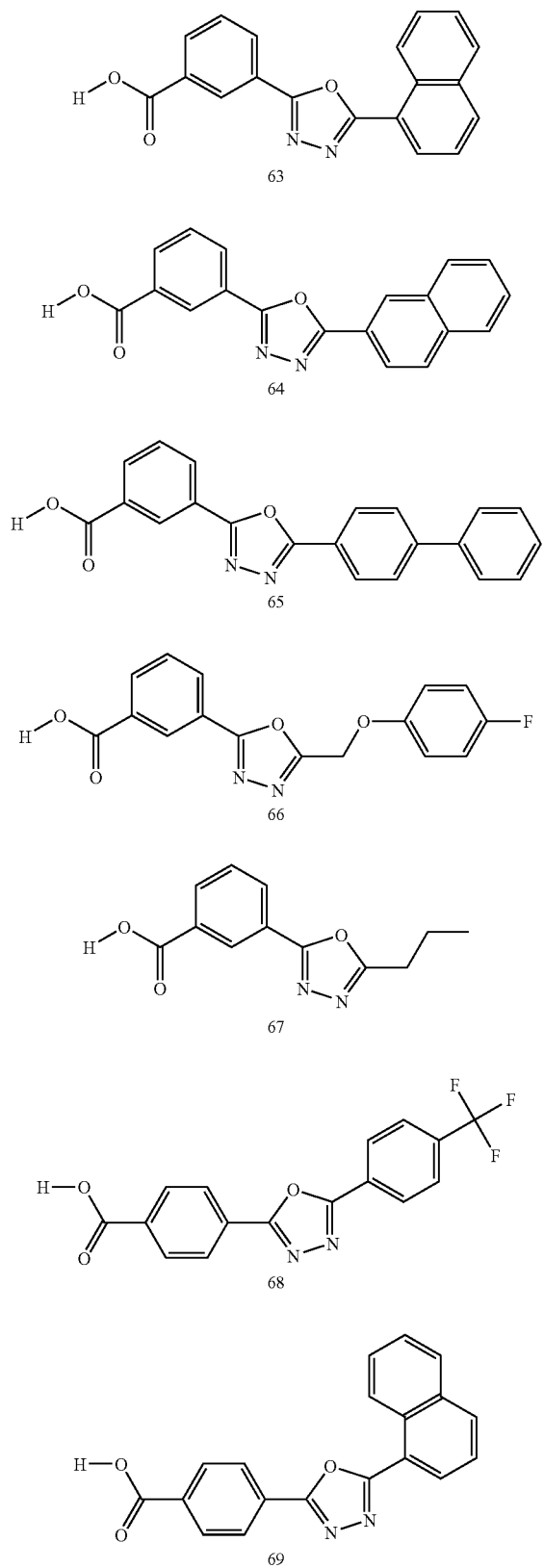
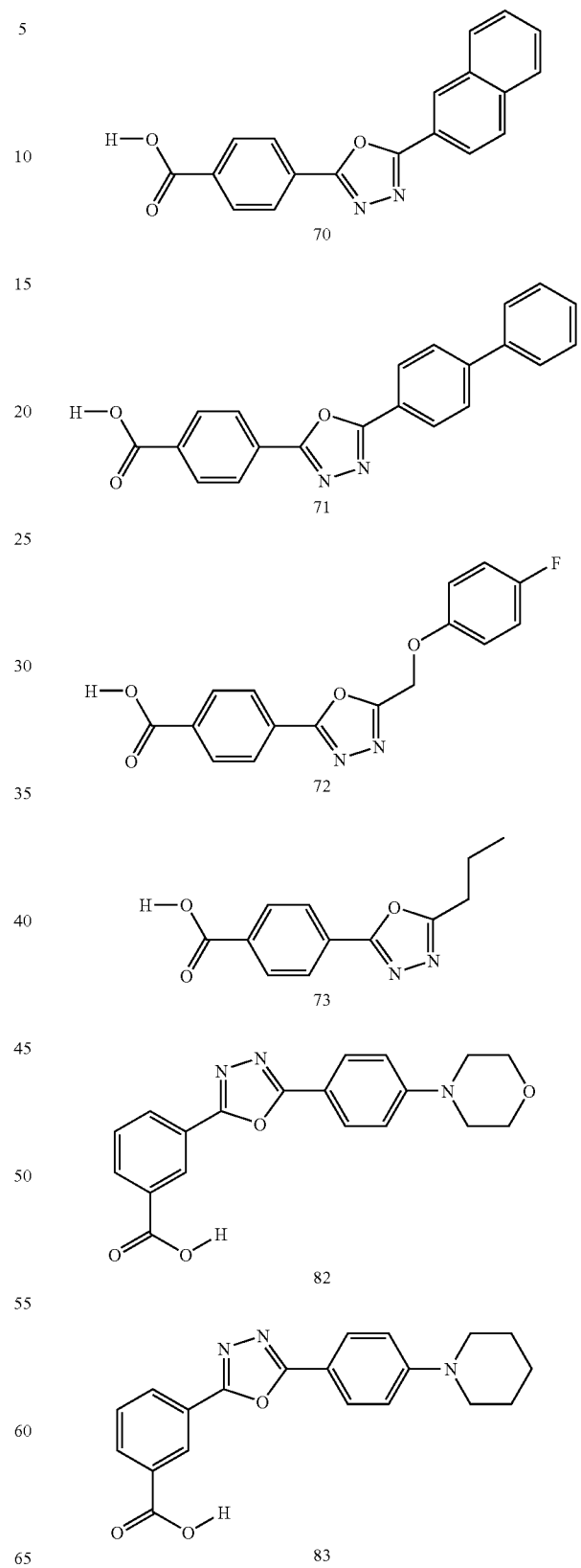

TABLE X-continued
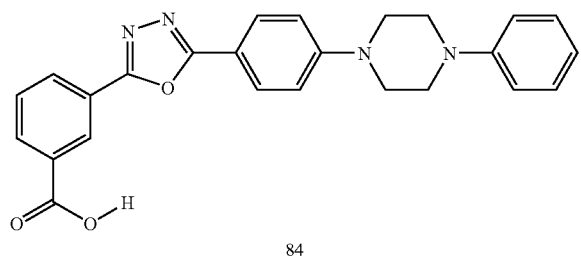
84
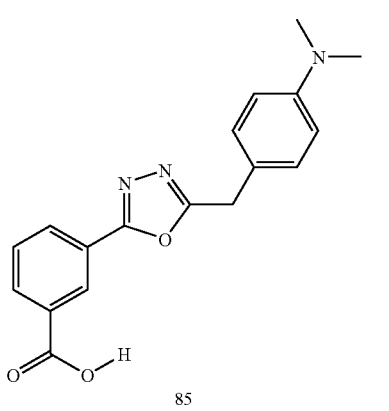
85
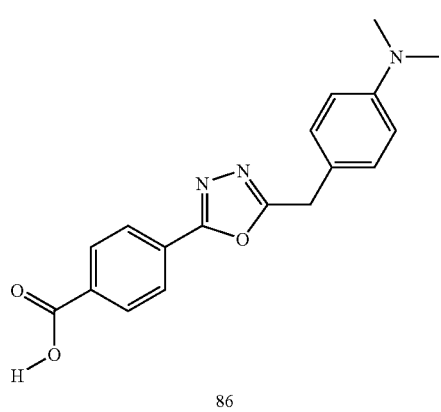
86
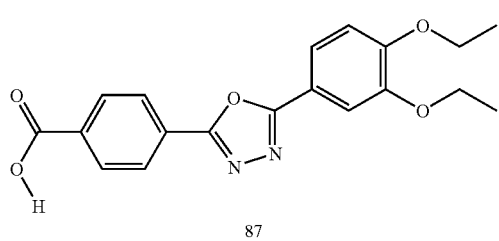
87
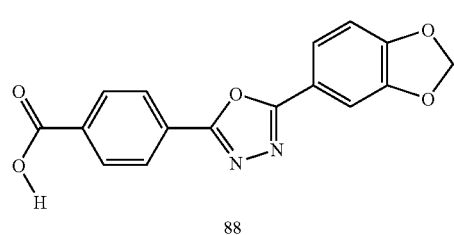
88
TABLE X-continued
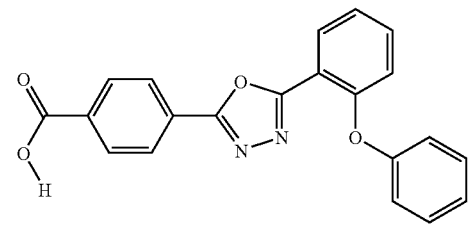 [SMILES: O=C(O)c1ccc(-c2nnc(-c3ccccc3Oc3ccccc3)o2)cc1]
89
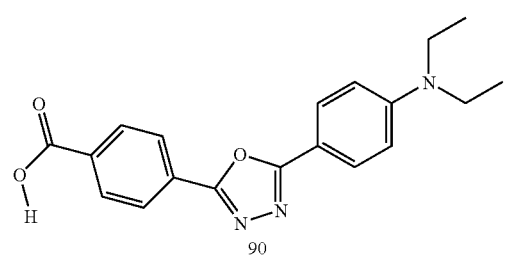
90
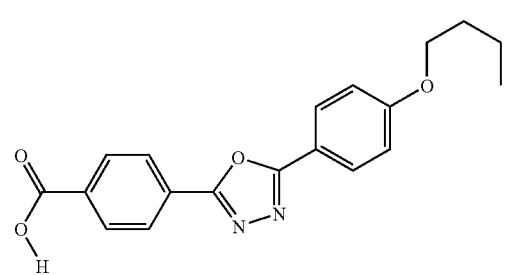 [SMILES: CCCCOc1ccc(-c2nnc(-c3ccc(C(=O)O)cc3)o2)cc1]
91
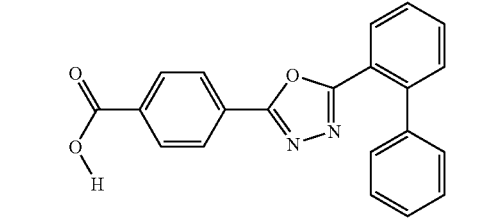 [SMILES: O=C(O)c1ccc(-c2nnc(-c3ccccc3-c3ccccc3)o2)cc1]
92
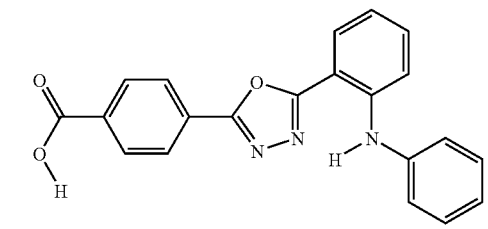 [SMILES: O=C(O)c1ccc(-c2nnc(-c3ccccc3Nc3ccccc3)o2)cc1]
93
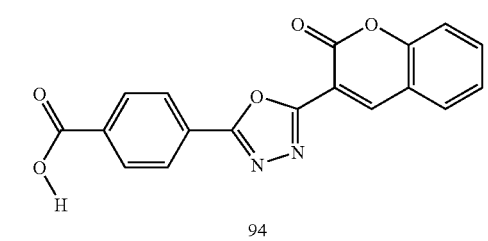
94

TABLE X-continued
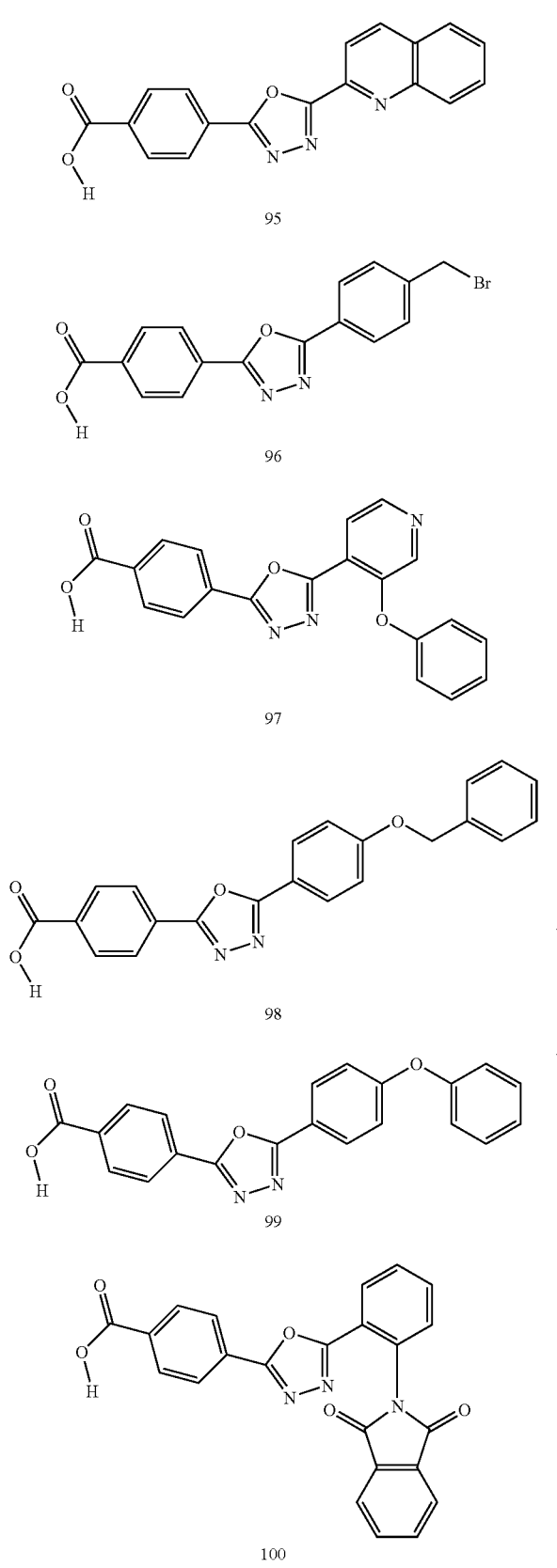
95
96
97
98
99
100
TABLE X-continued
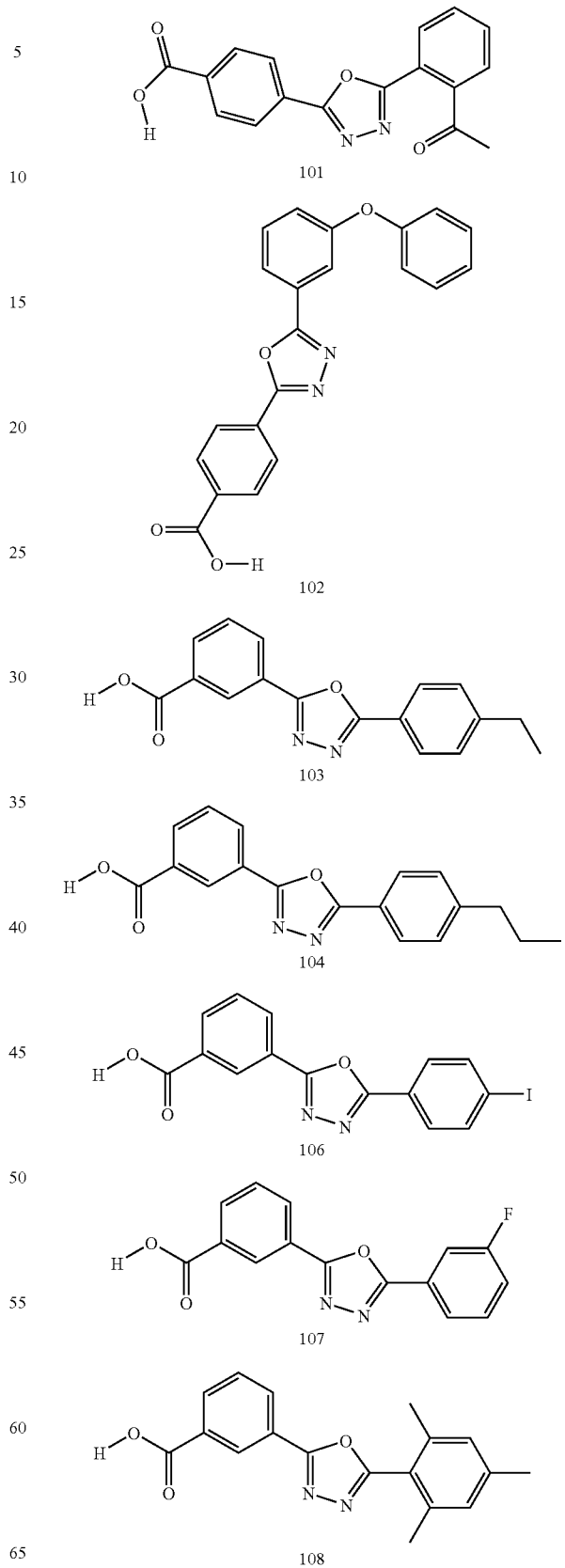
101
102
103
104
106
107
108

TABLE X-continued
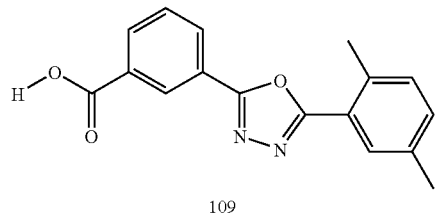
109
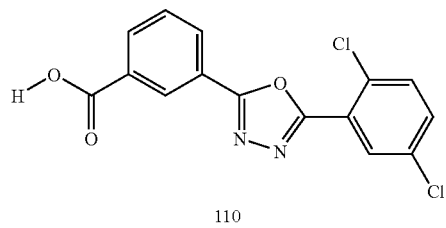
110
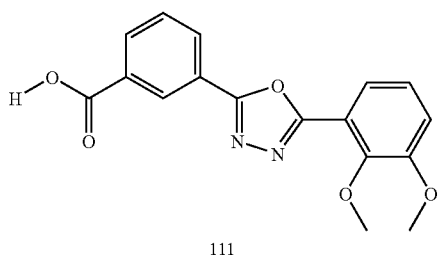
111
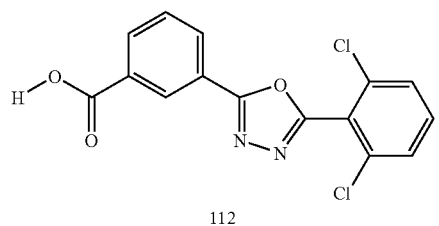
112
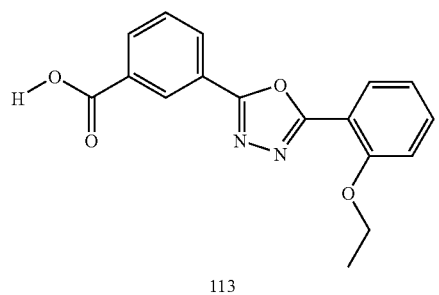
113
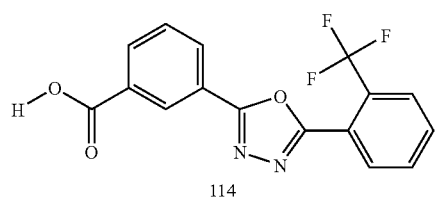
114
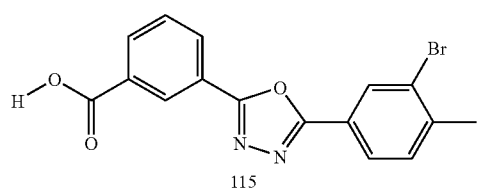
115
TABLE X-continued
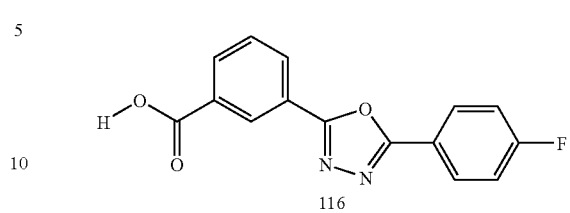
116
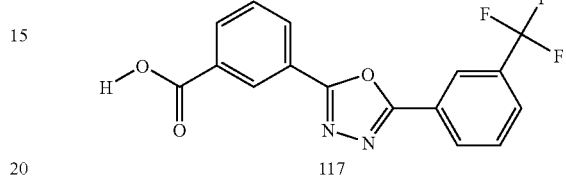
117
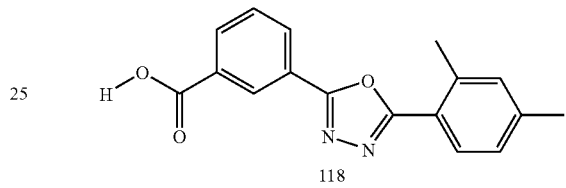
118
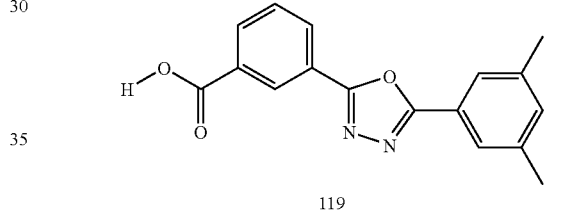
119
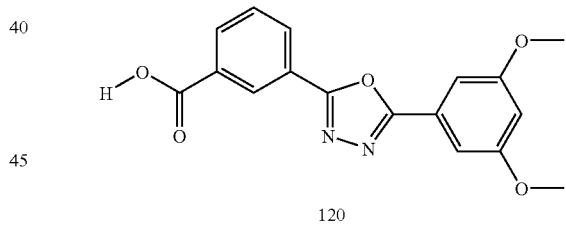
120
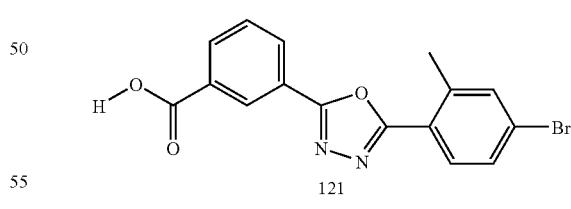
121
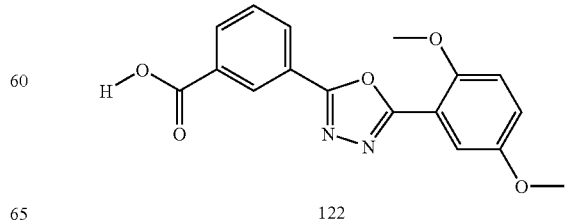
122

TABLE X-continued
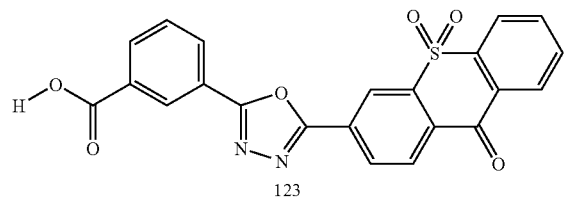
123
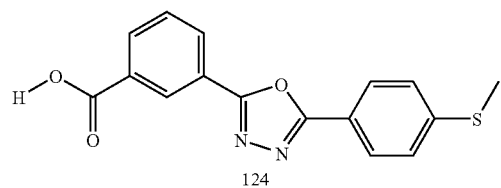
124
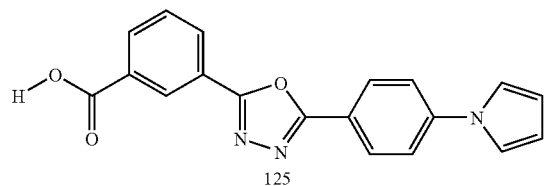
125
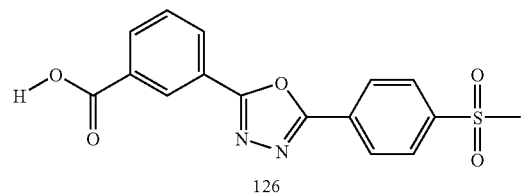
126
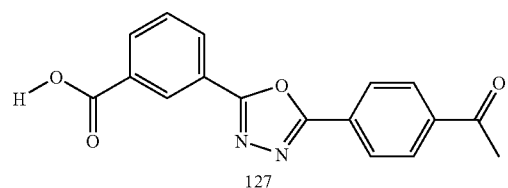
127
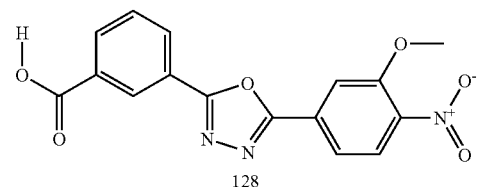
128
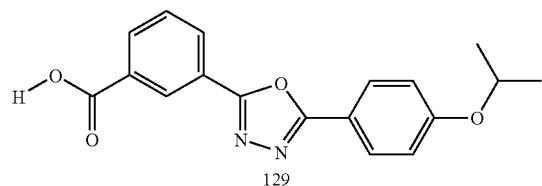
129
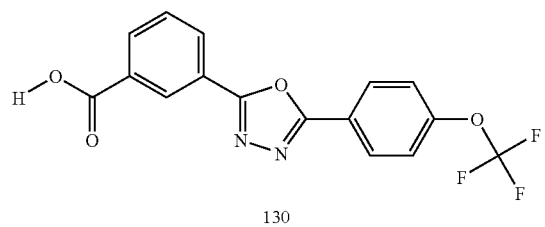
130
TABLE X-continued
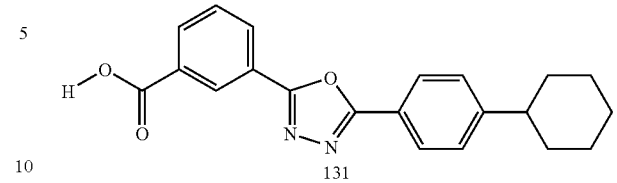
131
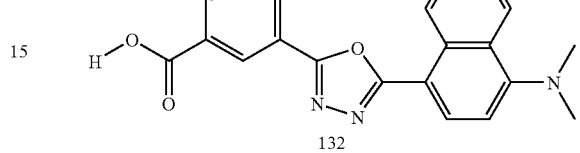
132
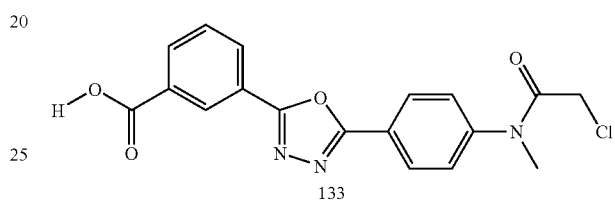
133
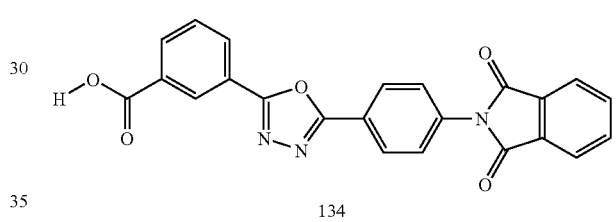
134
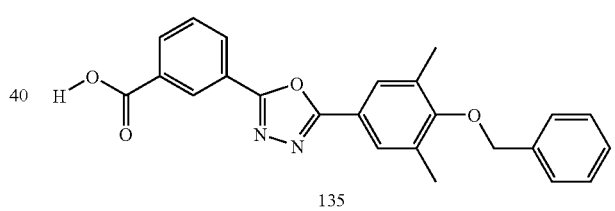
135
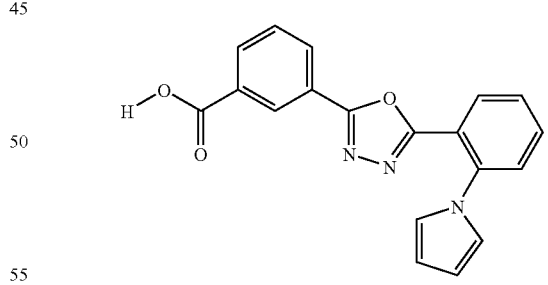
136
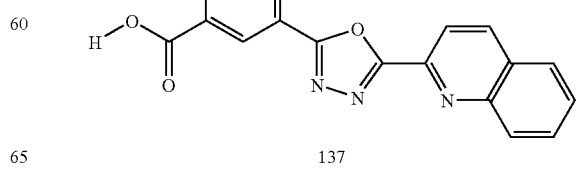
137

TABLE X-continued
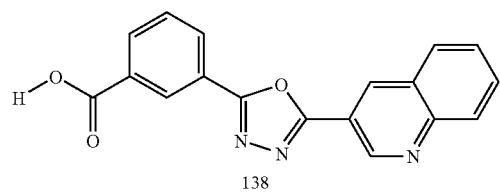
138
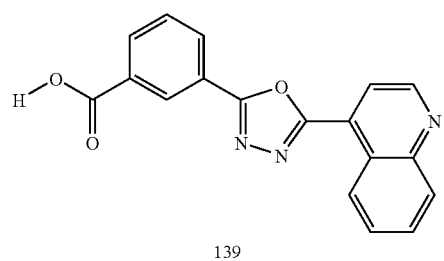
139
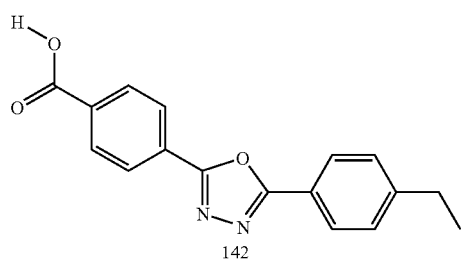
142
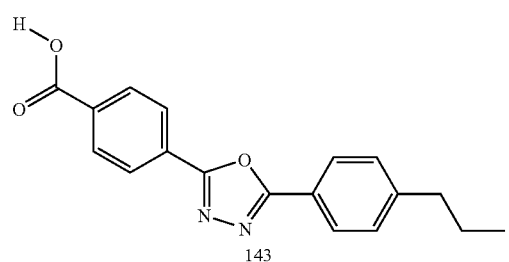
143
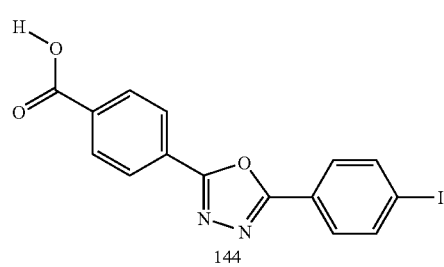
144
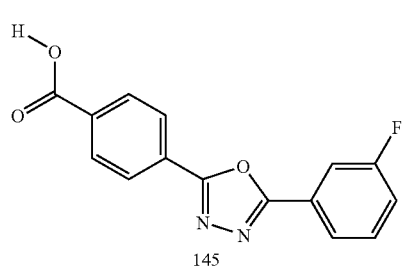
145
TABLE X-continued
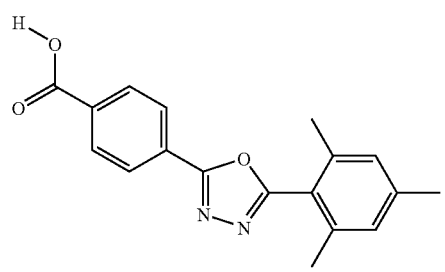 [SMILES: Cc1cc(C)c(-c2nnc(-c3ccc(C(=O)O)cc3)o2)c(C)c1]
146
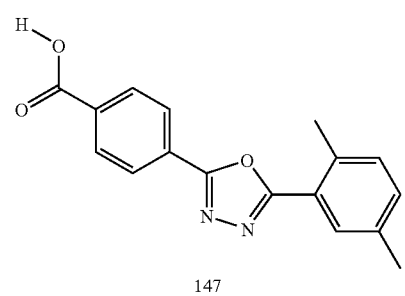
147
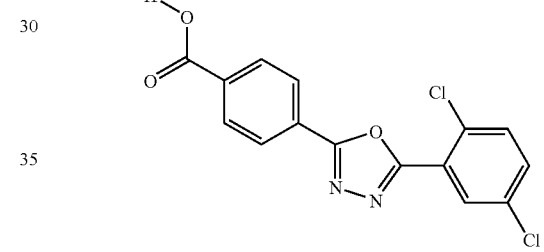
148
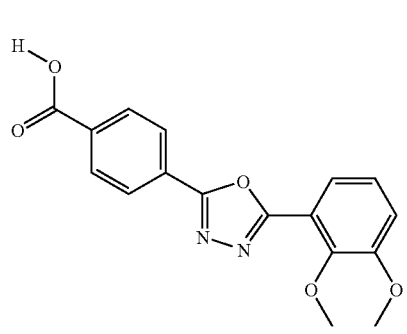 [SMILES: COc1cccc(-c2nnc(-c3ccc(C(=O)O)cc3)o2)c1OC]
149
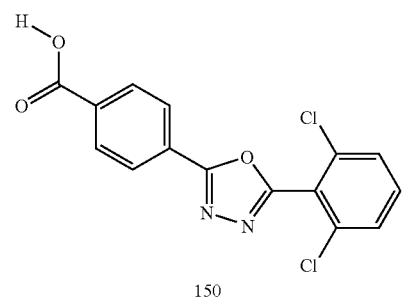
150

TABLE X-continued
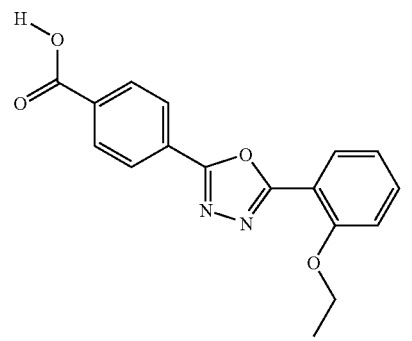 [SMILES: CCOc1ccccc1-c1nnc(-c2ccc(C(=O)O)cc2)o1]
151
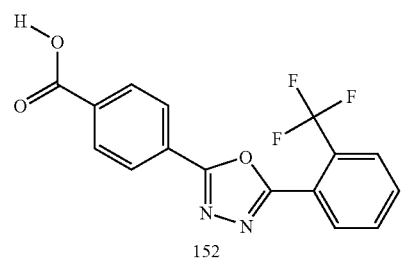
152
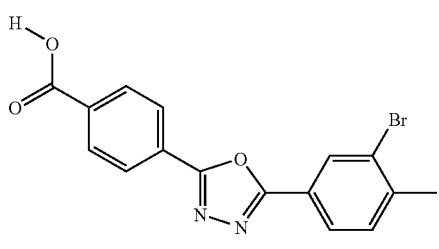 [SMILES: Cc1ccc(-c2nnc(-c3ccc(C(=O)O)cc3)o2)cc1Br]
153
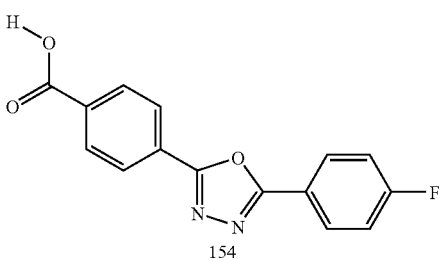
154
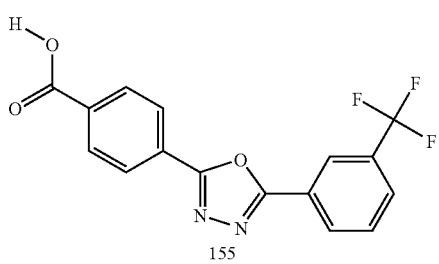
155
TABLE X-continued
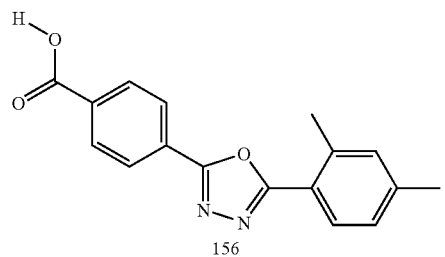
156
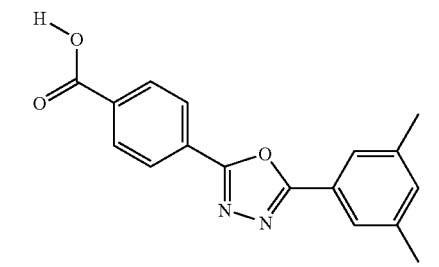 [SMILES: Cc1cc(C)cc(-c2nnc(-c3ccc(C(=O)O)cc3)o2)c1]
157
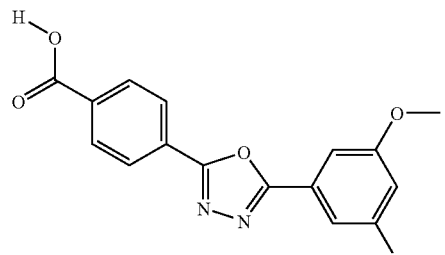
158
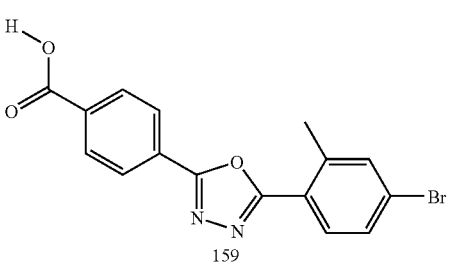
159
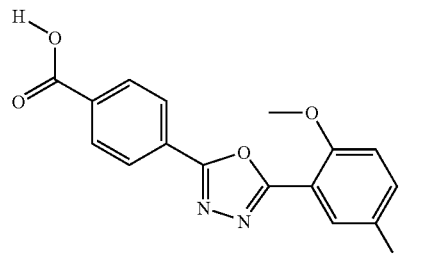
160
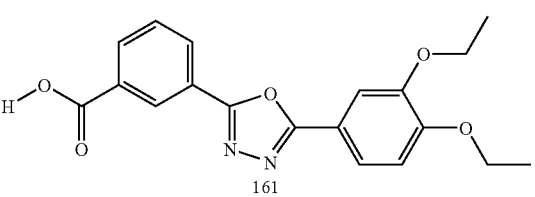
161

TABLE X-continued
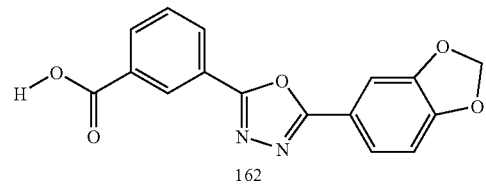
162
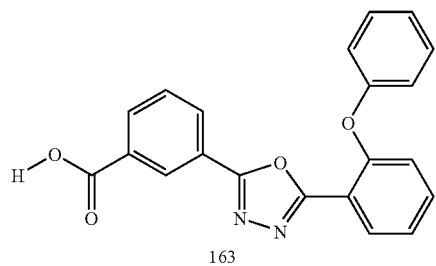
163
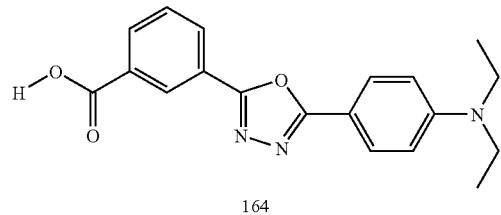
164
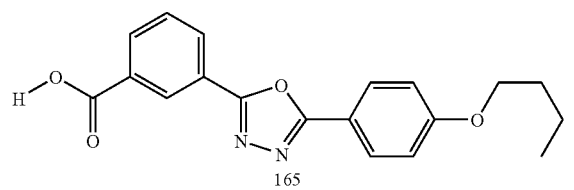
165
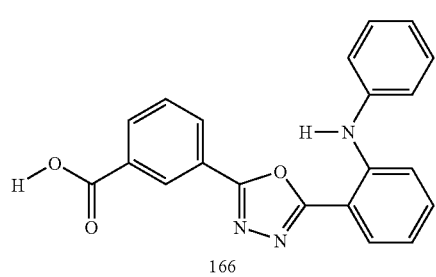
166
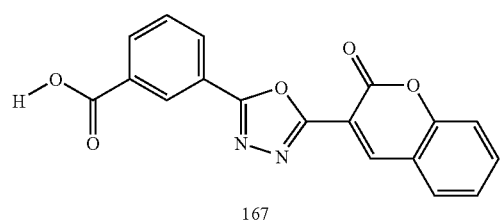
167
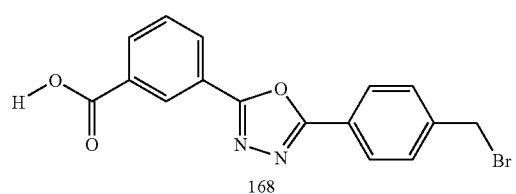
168
TABLE X-continued
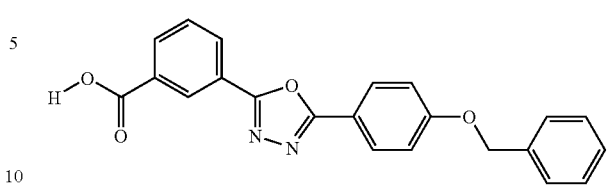
169
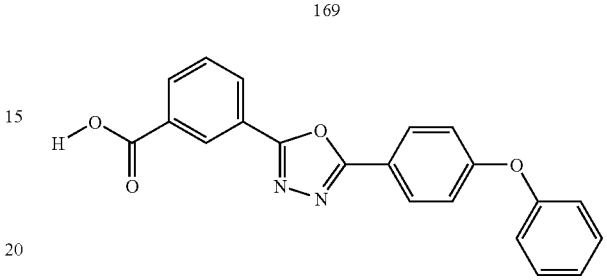
170
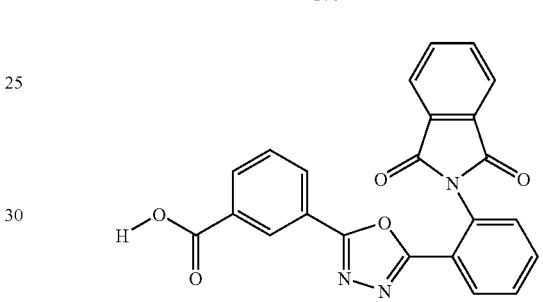
171
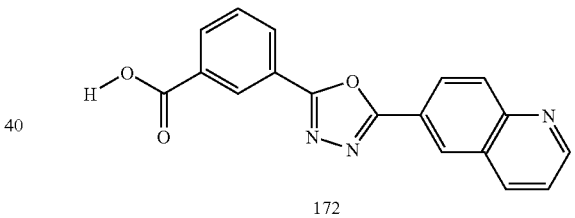
172
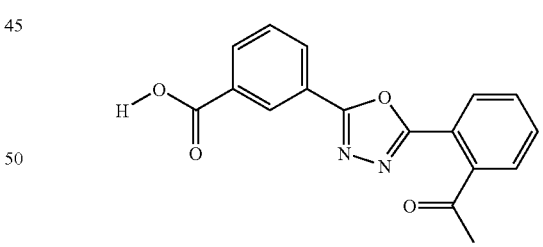
173
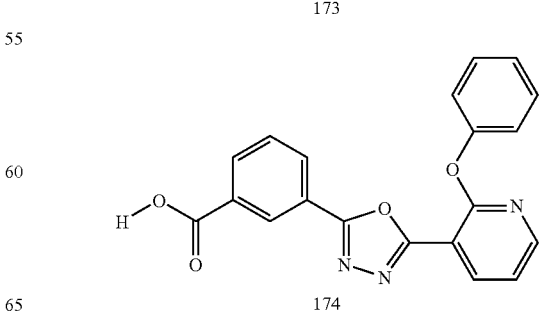
174

TABLE X-continued
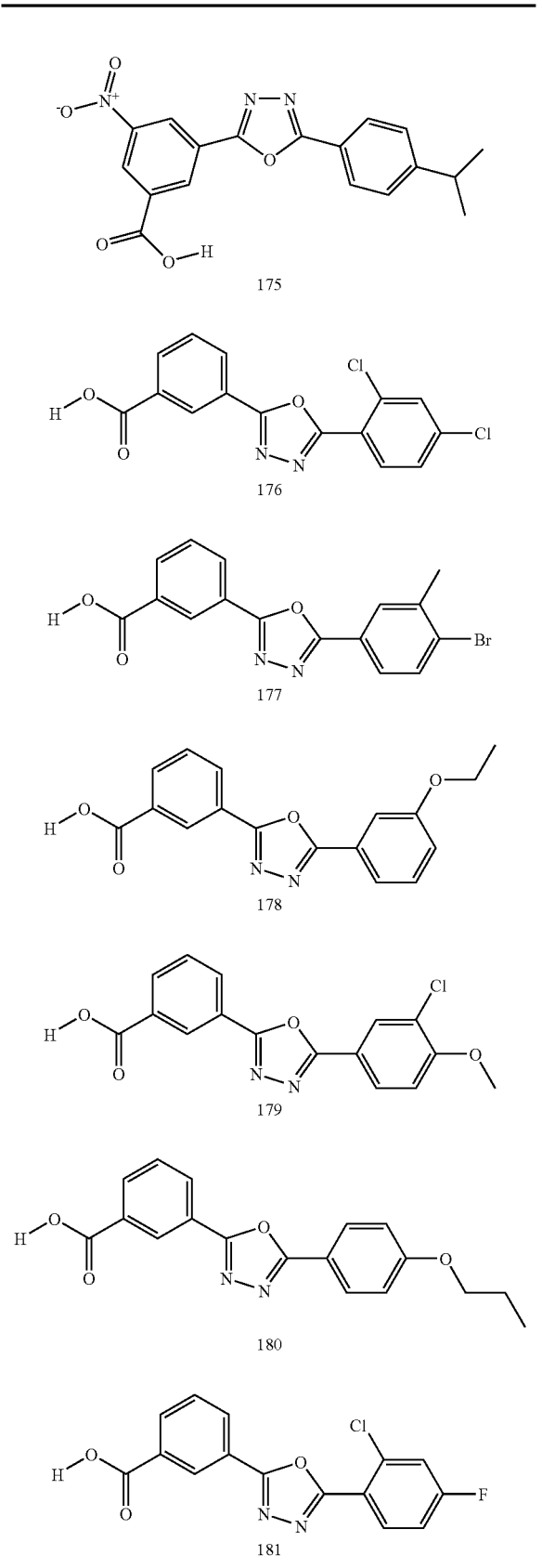
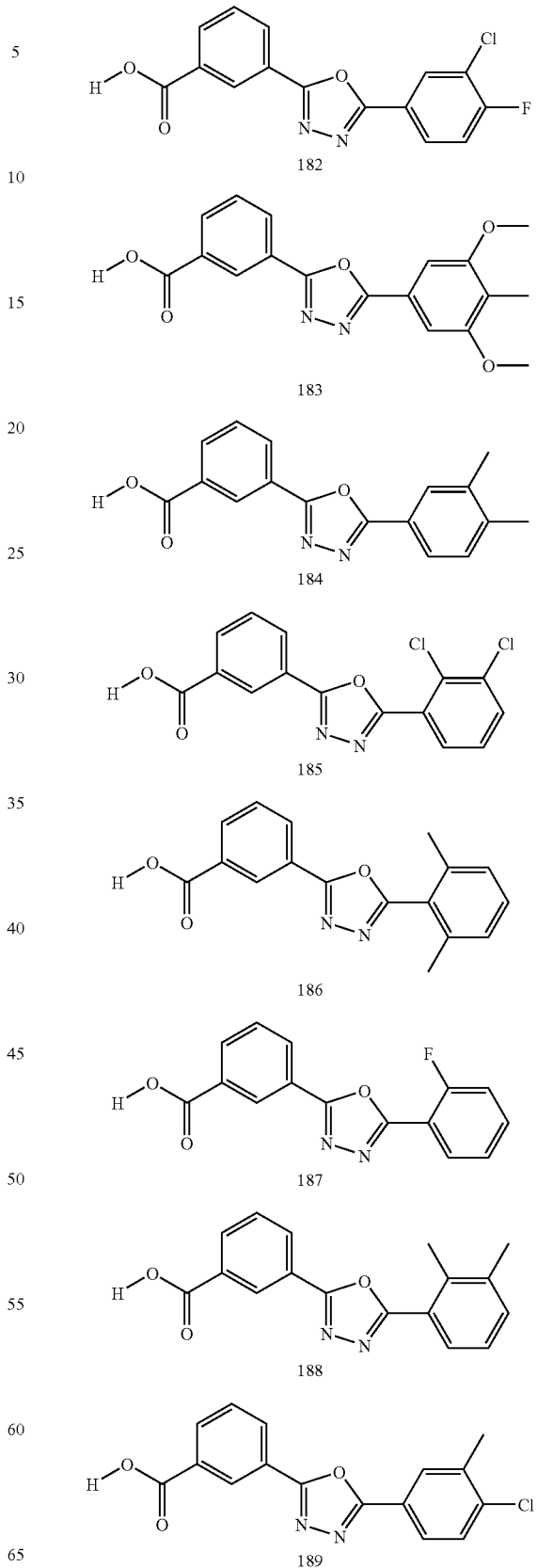

TABLE X-continued
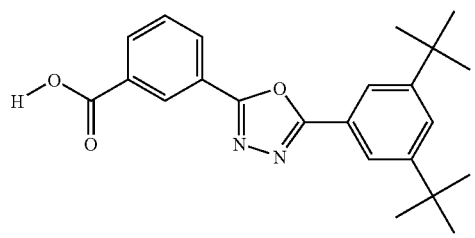 [SMILES: CC(C)(C)c1cc(-c2nnc(-c3cccc(C(=O)O)c3)o2)cc(C(C)(C)C)c1]
190
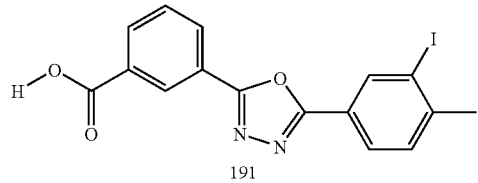
191
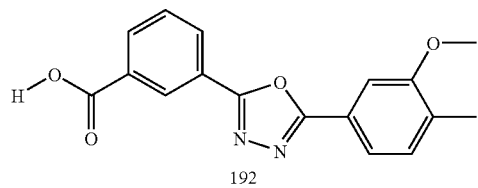
192
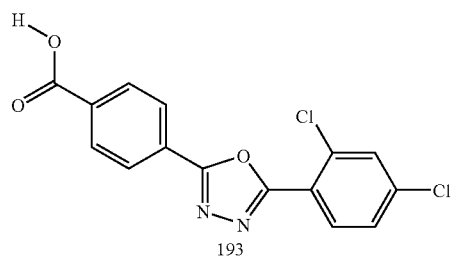
193
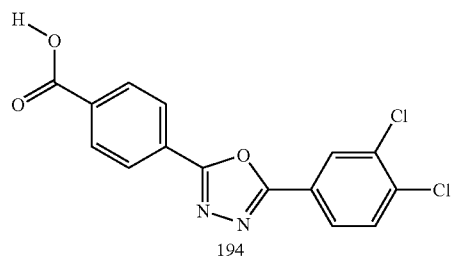
194
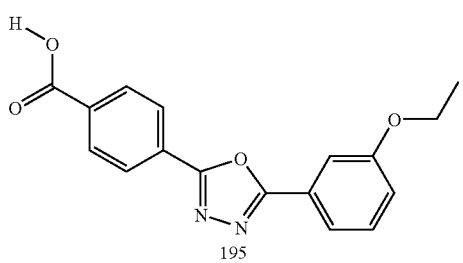
195
TABLE X-continued
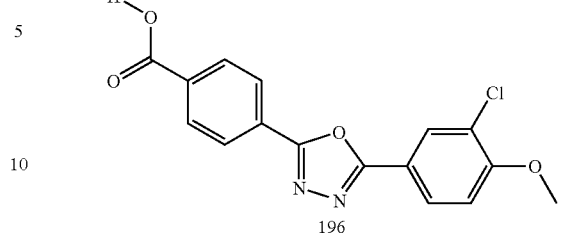
196
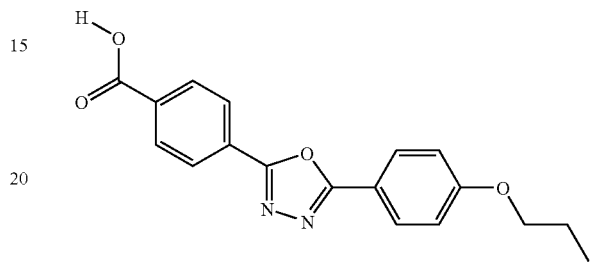
197
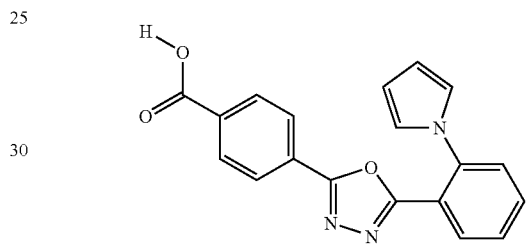
198
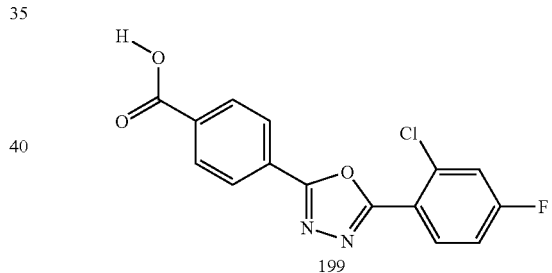
199
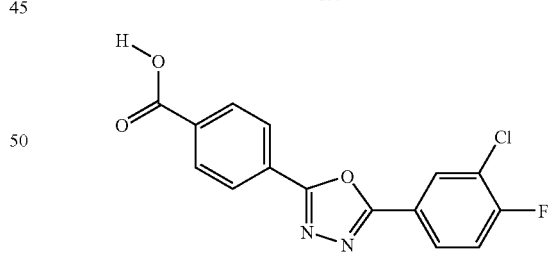
200
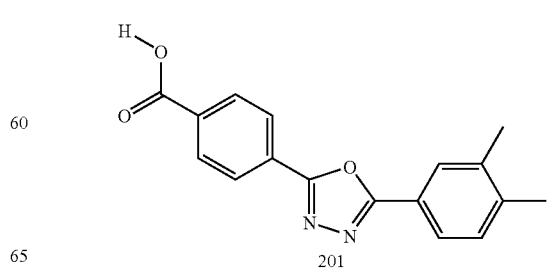
201

TABLE X-continued
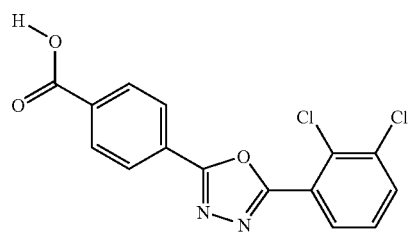 [SMILES: O=C(O)c1ccc(-c2nnc(-c3cccc(Cl)c3Cl)o2)cc1]
202
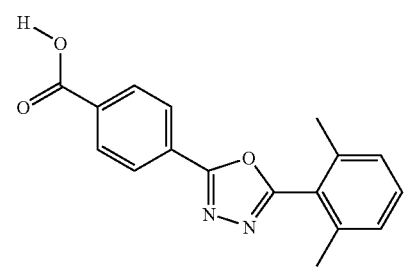 [SMILES: Cc1cccc(C)c1-c1nnc(-c2ccc(C(=O)O)cc2)o1]
203
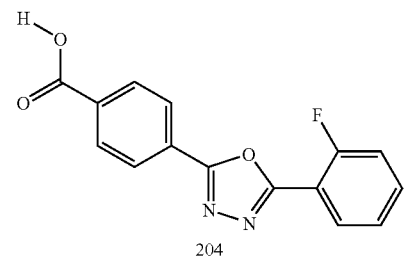
204
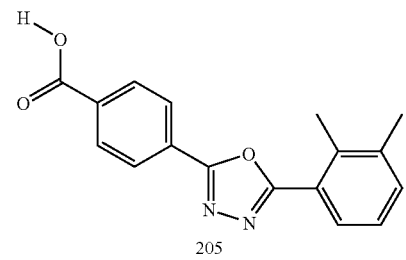
205
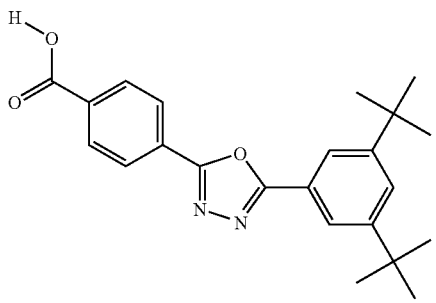 [SMILES: CC(C)(C)c1cc(-c2nnc(-c3ccc(C(=O)O)cc3)o2)cc(C(C)(C)C)c1]
206
TABLE X-continued
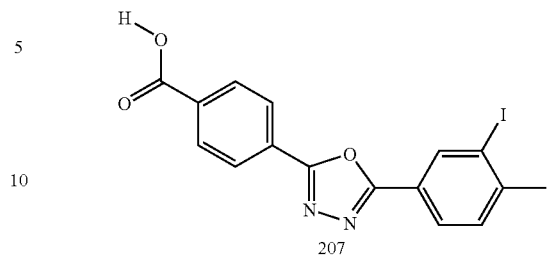
207
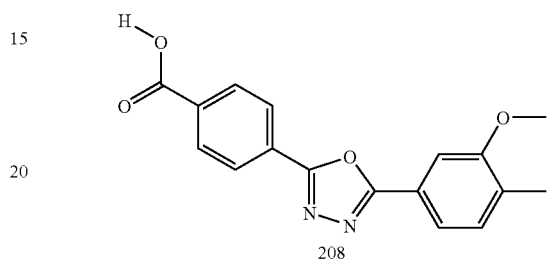
208
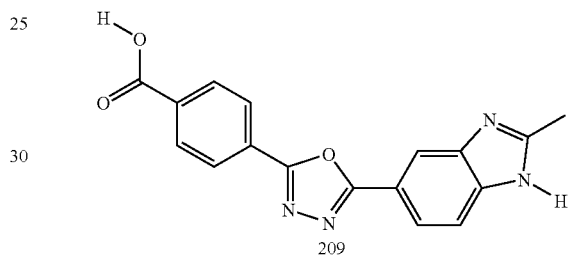
209
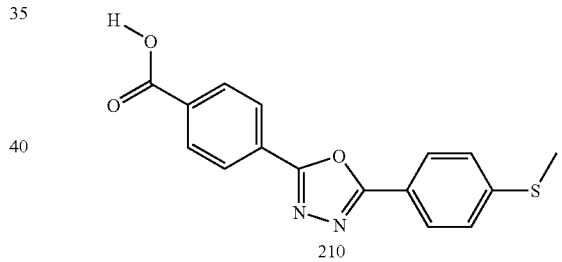
210
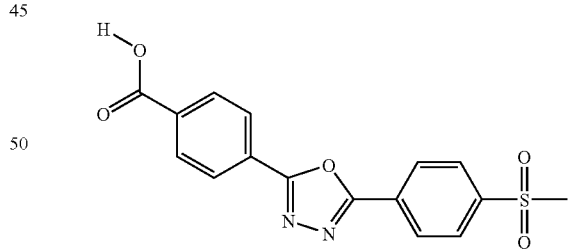
211
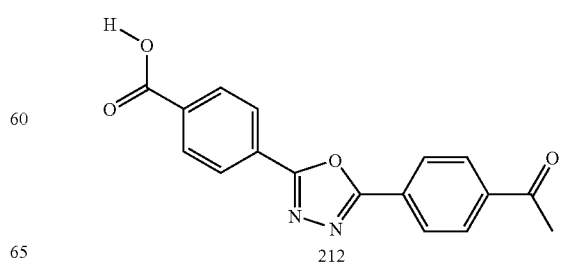
212

TABLE X-continued
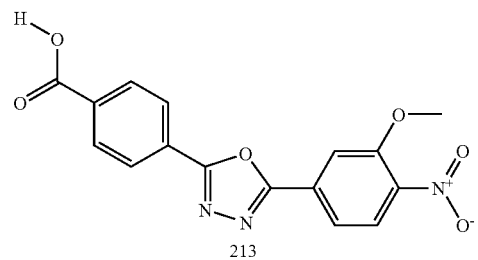
213
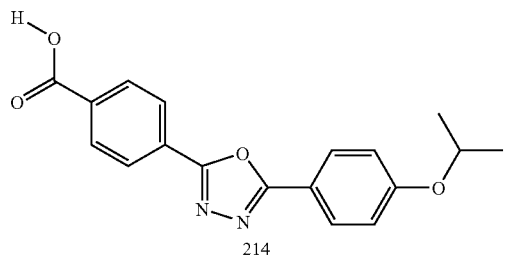
214
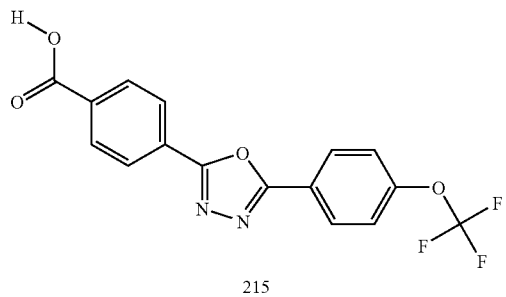
215
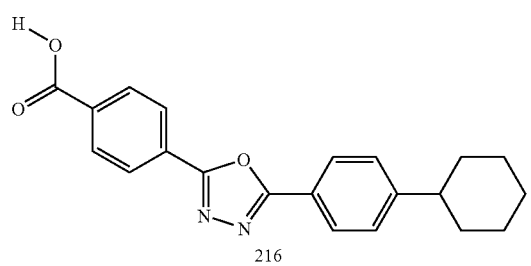
216
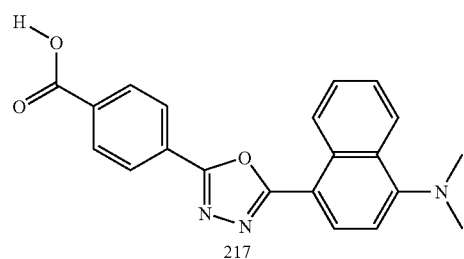
217
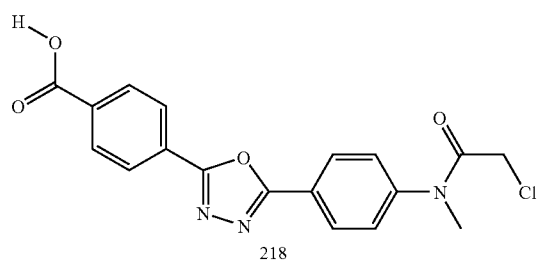
218
TABLE X-continued
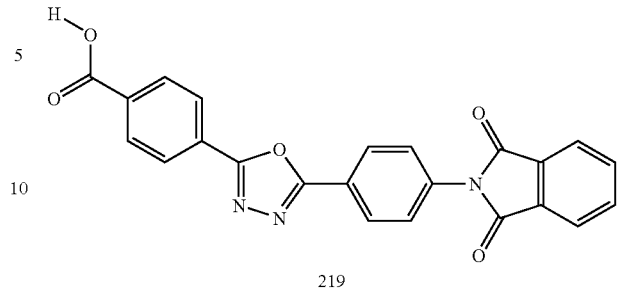
219
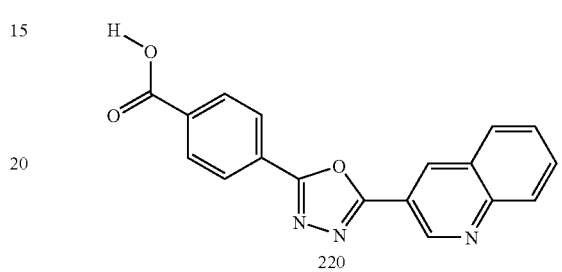
220
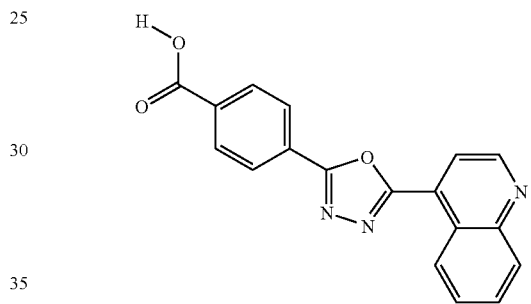
221
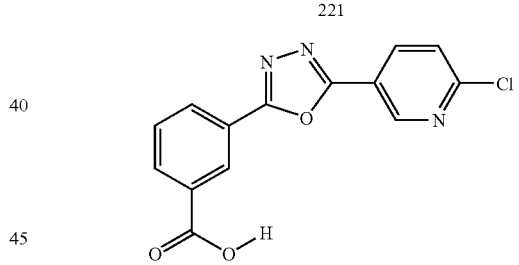
222
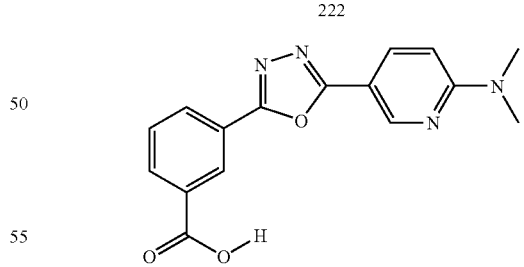
223
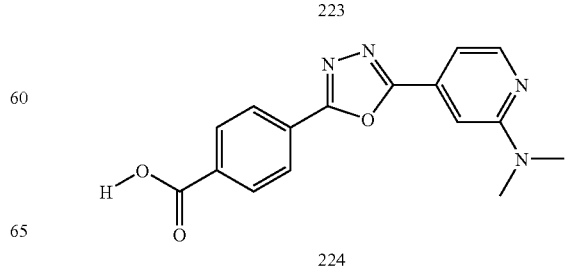
224

TABLE X-continued
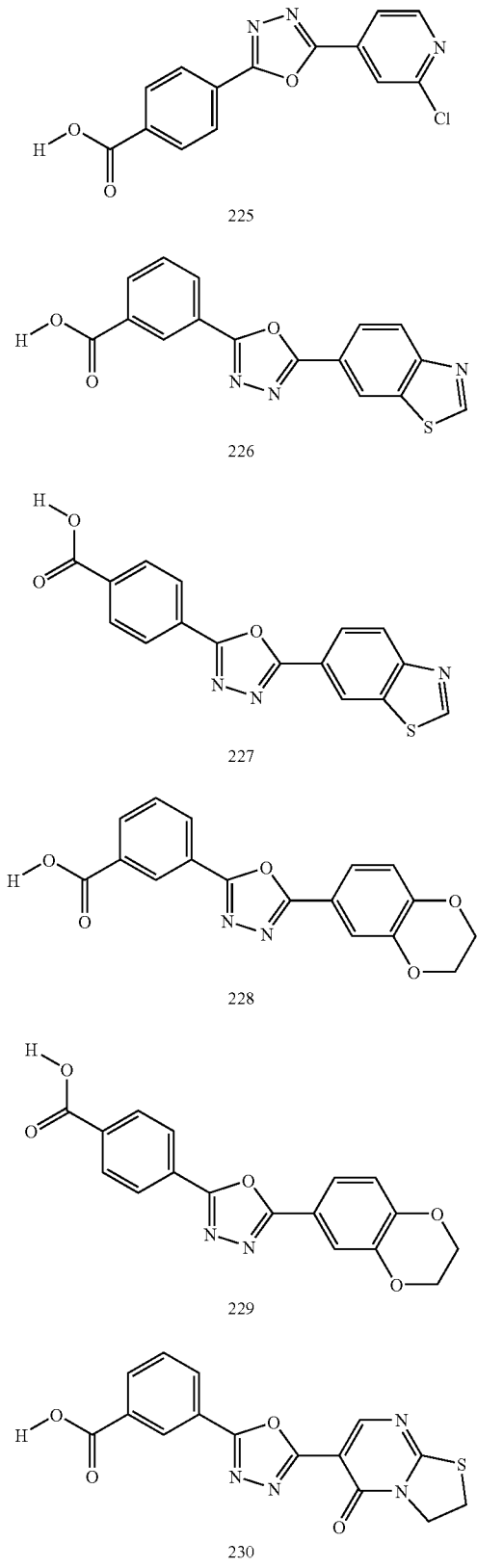
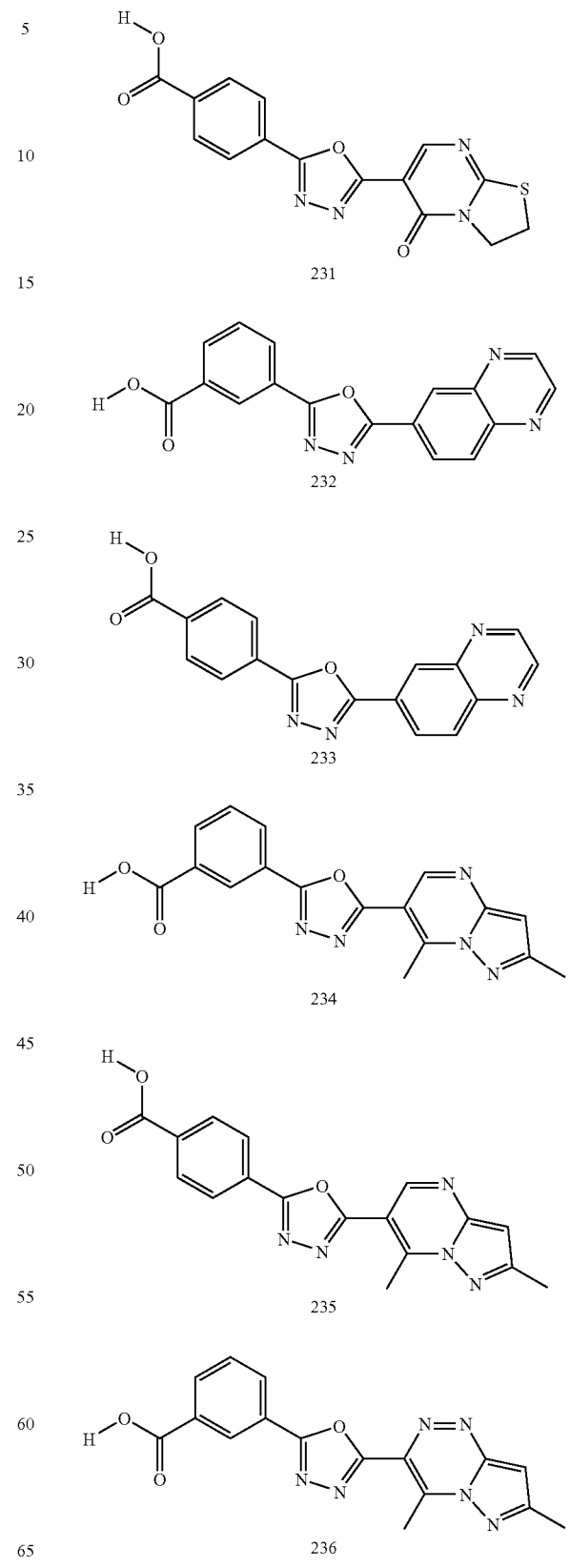

TABLE X-continued
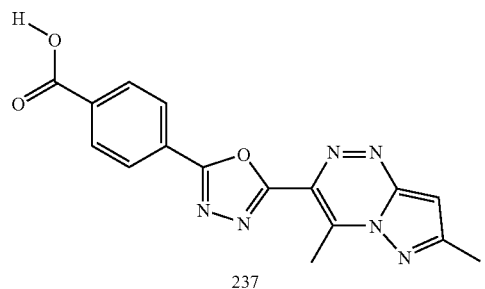
237
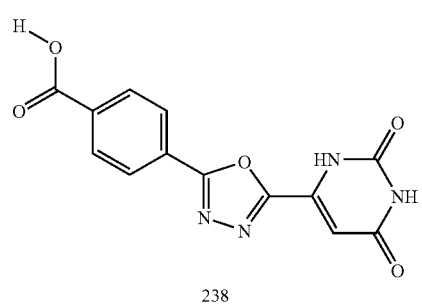
238
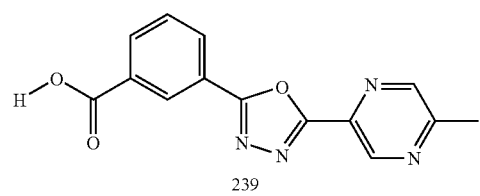
239
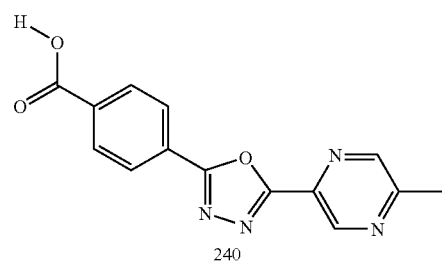
240
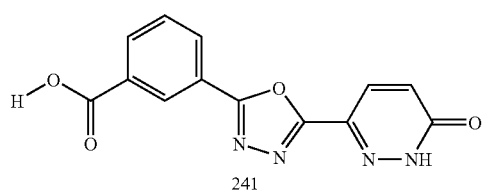
241
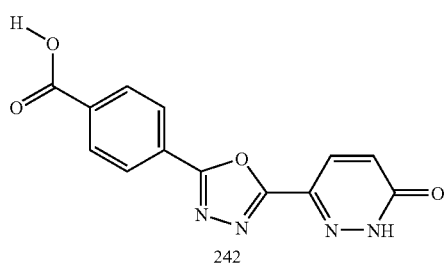
242
TABLE X-continued
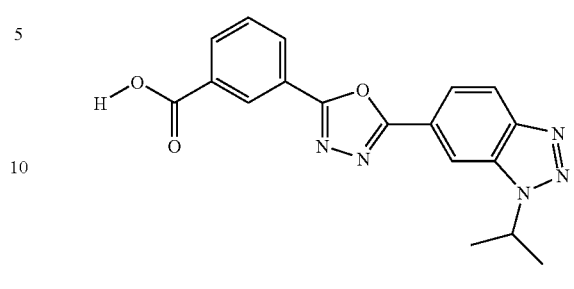
243
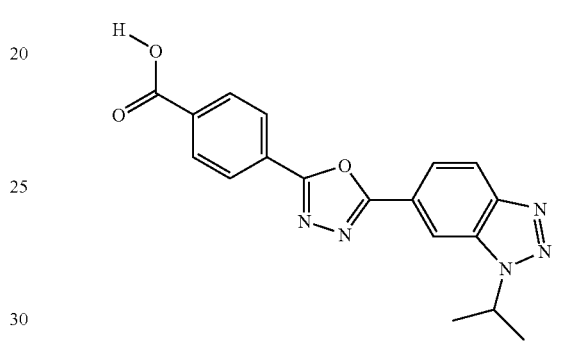
244
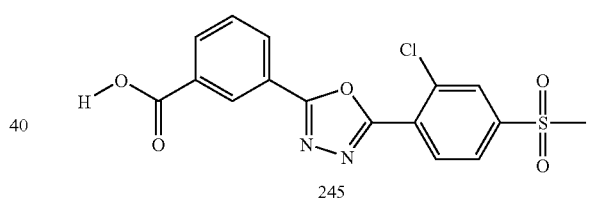
245
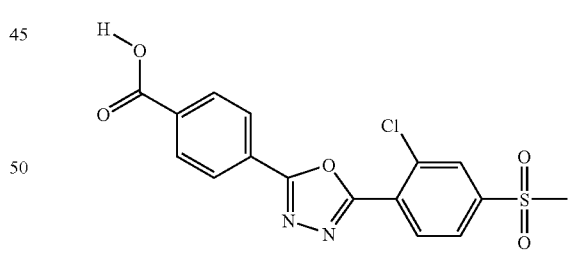
246
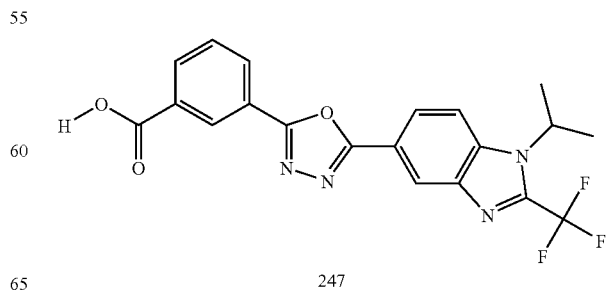
247

TABLE X-continued
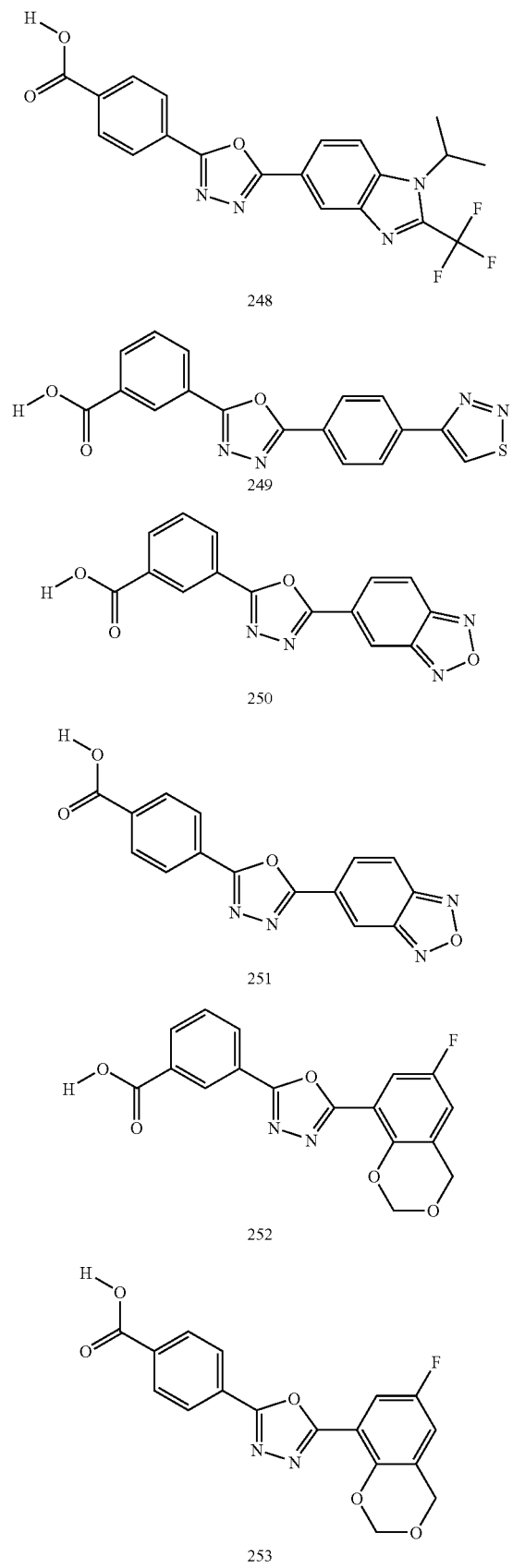
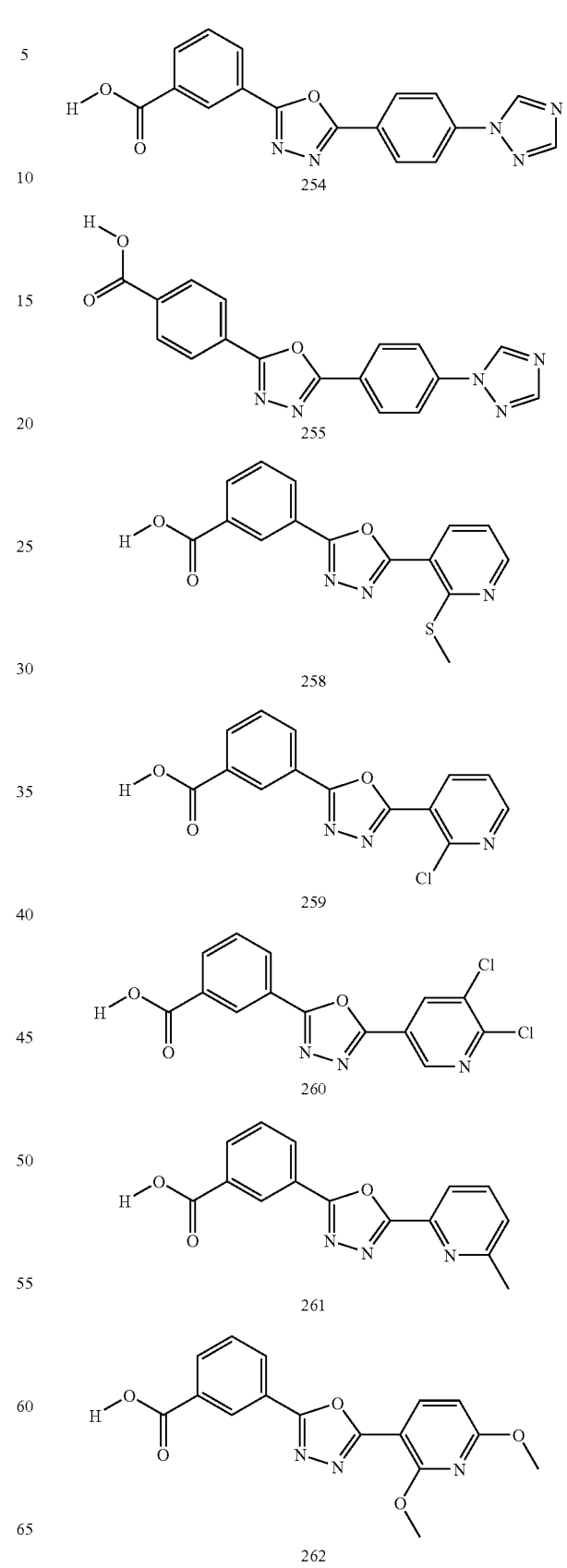

TABLE X-continued
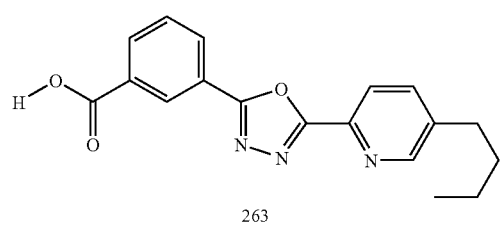
263
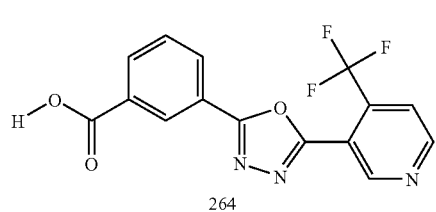
264
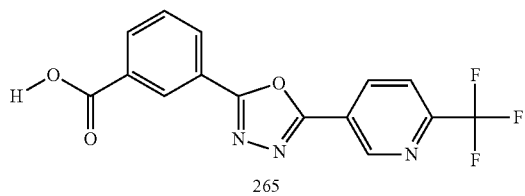
265
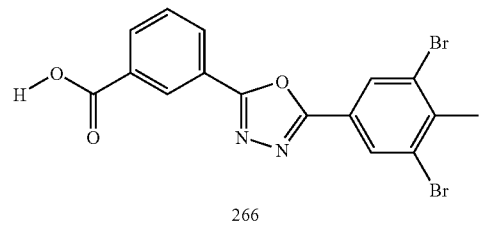
266
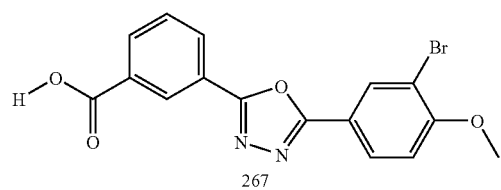
267
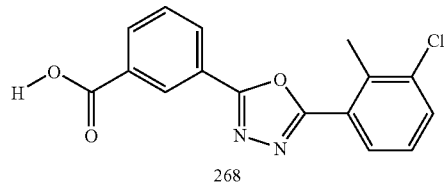
268
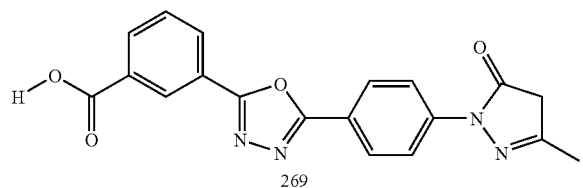
269
TABLE X-continued
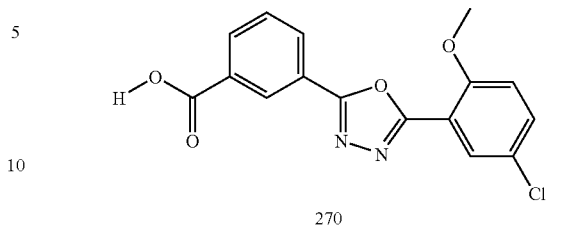
270
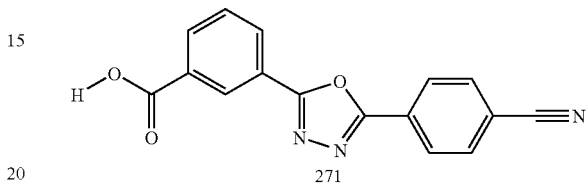
271
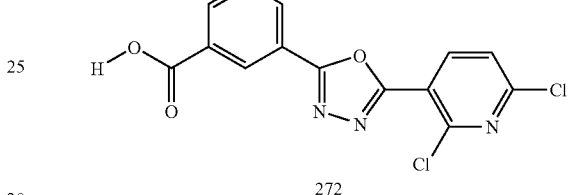
272
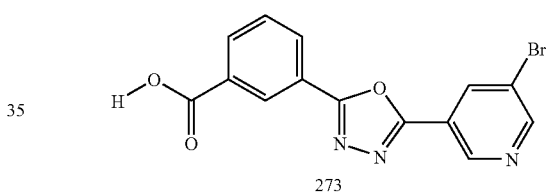
273
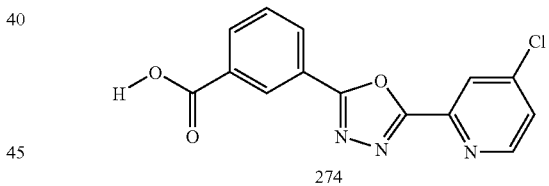
274
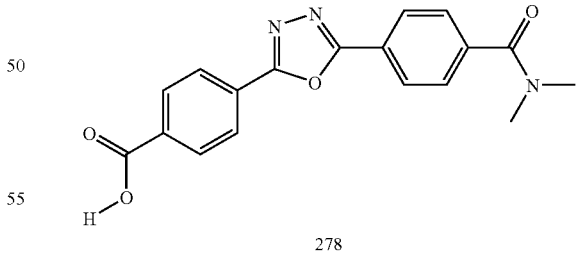
278
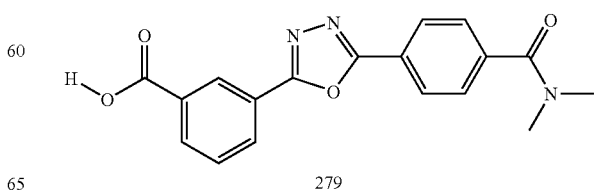
279

TABLE X-continued
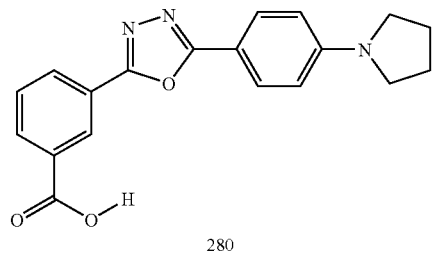
280
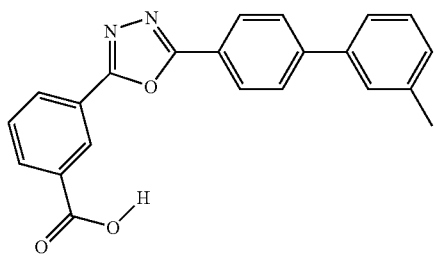
281
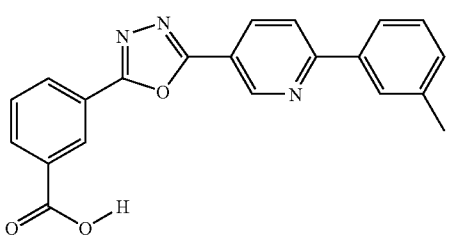 [SMILES: Cc1cccc(-c2ccc(-c3nnc(-c4cccc(C(=O)O)c4)o3)cn2)c1]
282
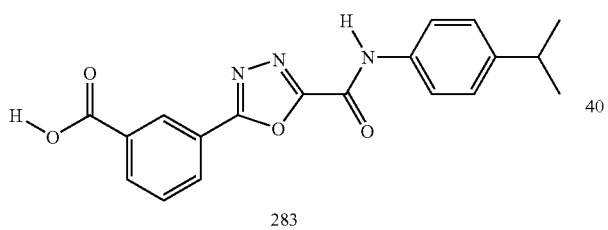
283
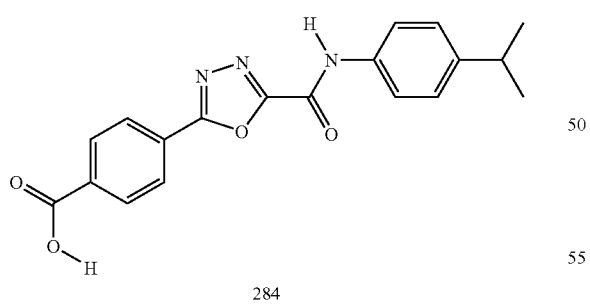
284
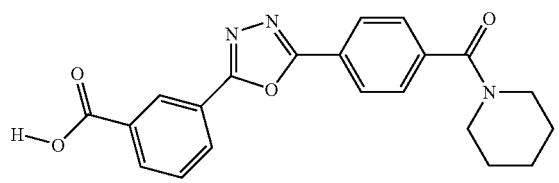 [SMILES: O=C(O)c1cccc(-c2nnc(-c3ccc(C(=O)N4CCCCC4)cc3)o2)c1]
285
TABLE X-continued
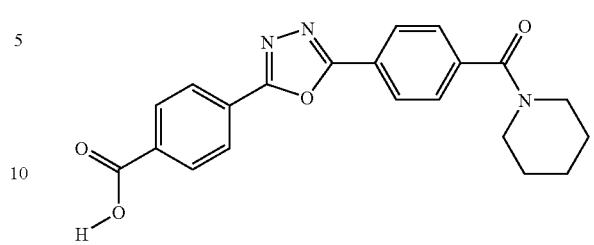
286
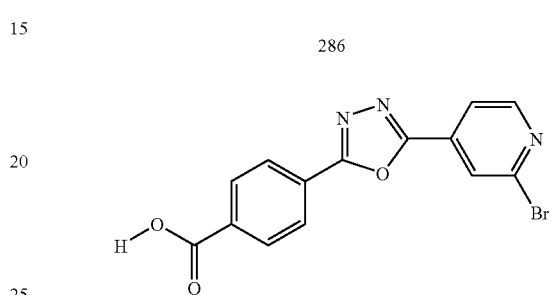
292
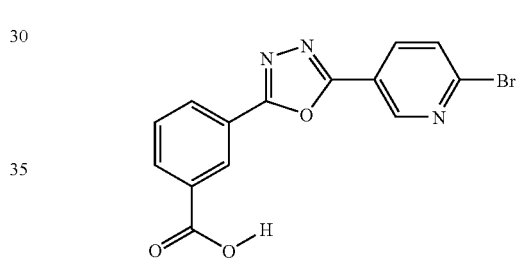
293
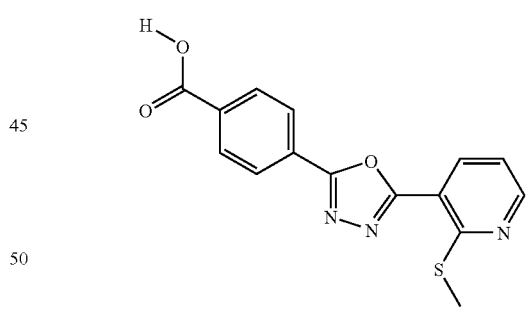
294
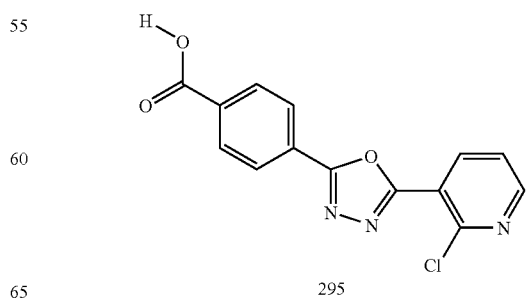
295

TABLE X-continued
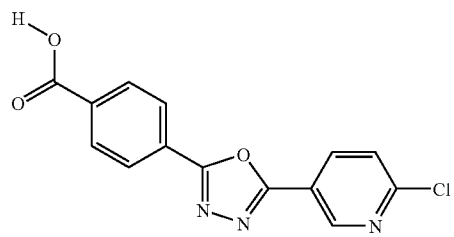 [SMILES: O=C(O)c1ccc(-c2nnc(-c3ccc(Cl)nc3)o2)cc1]
296
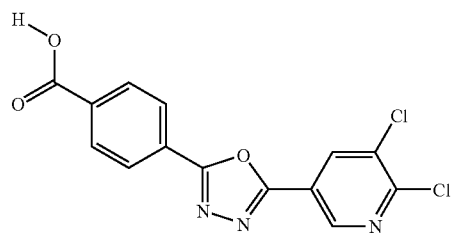 [SMILES: O=C(O)c1ccc(-c2nnc(-c3cnc(Cl)c(Cl)c3)o2)cc1]
297
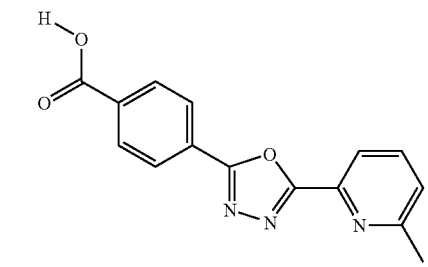 [SMILES: Cc1cccc(-c2nnc(-c3ccc(C(=O)O)cc3)o2)n1]
298
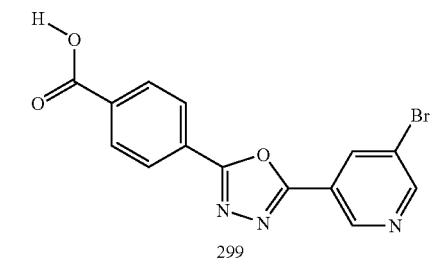
299
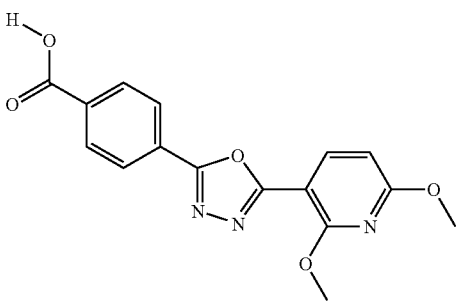 [SMILES: COc1ccc(-c2nnc(-c3ccc(C(=O)O)cc3)o2)c(OC)n1]
300
TABLE X-continued
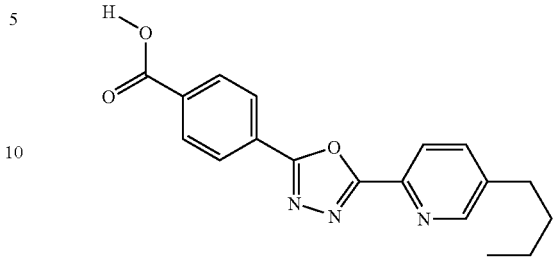
301
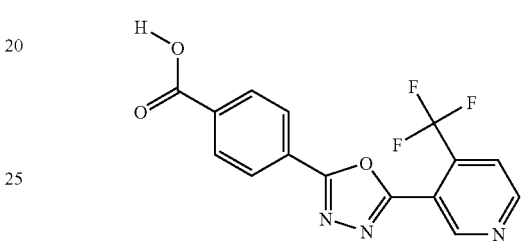
302
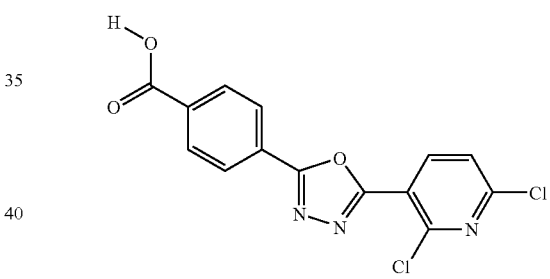
303
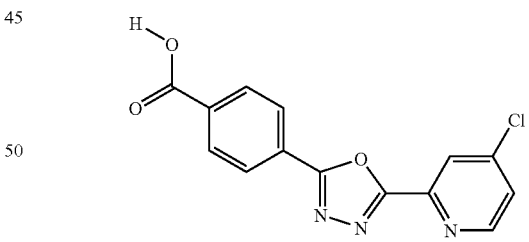
304
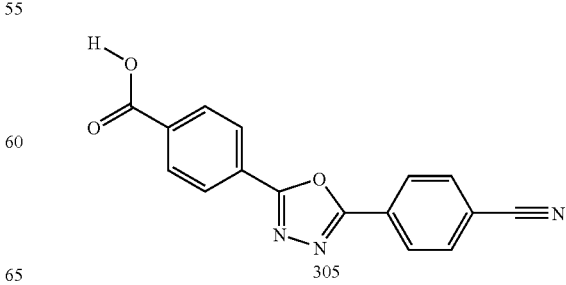
305

TABLE X-continued
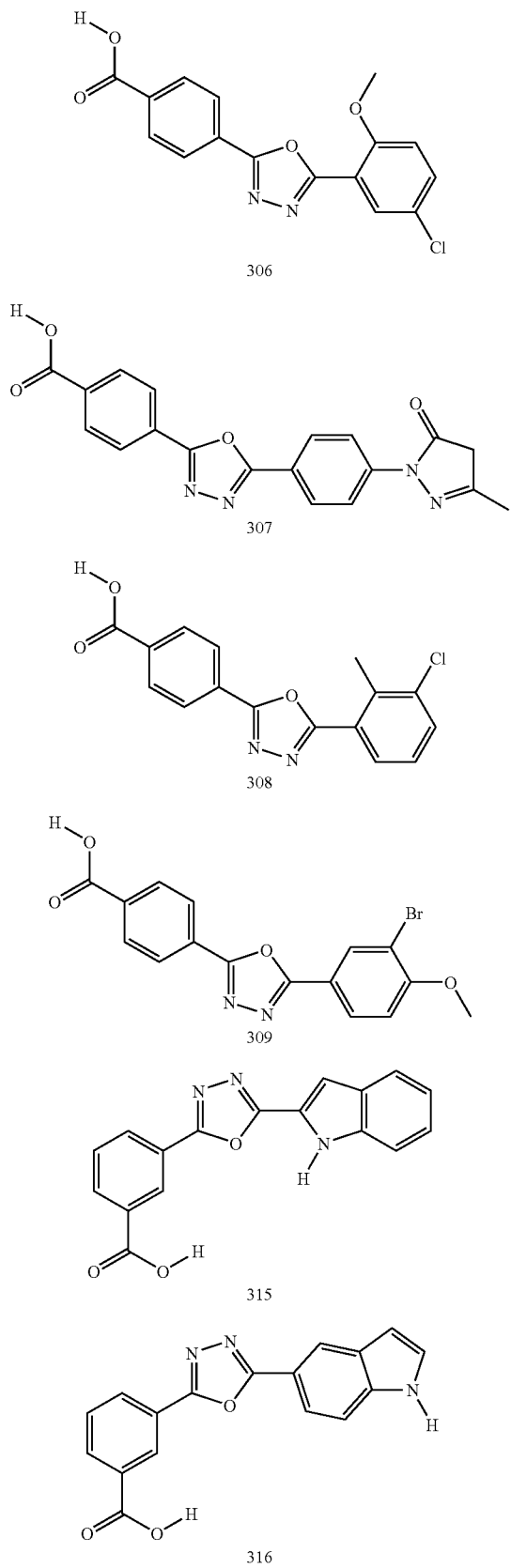
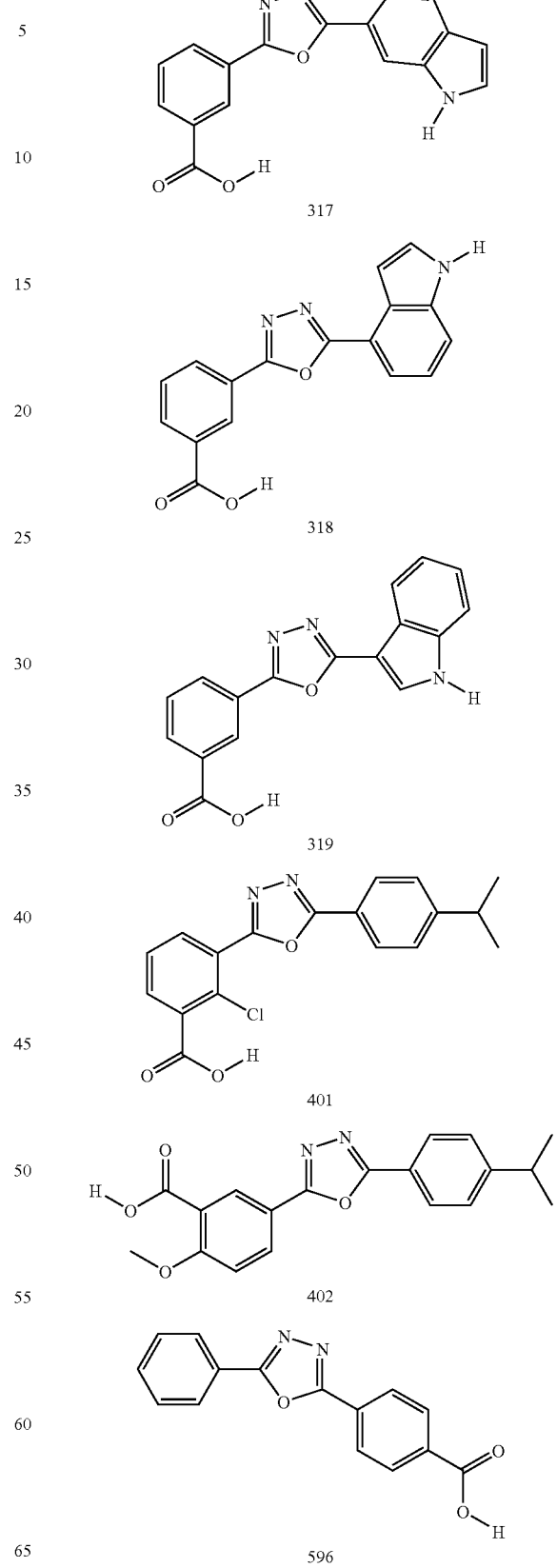

TABLE X-continued
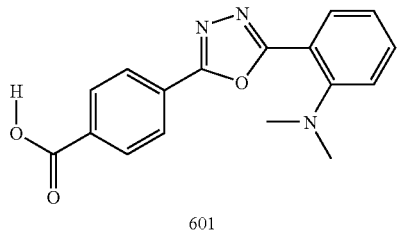
601
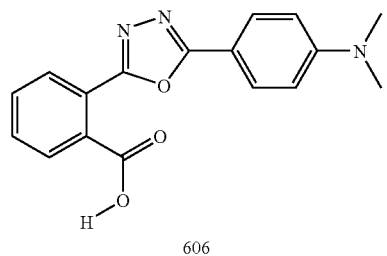
606
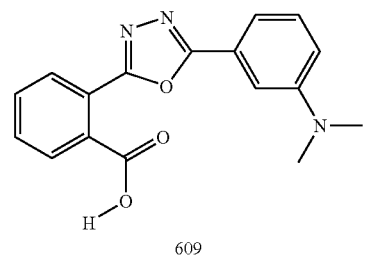
609
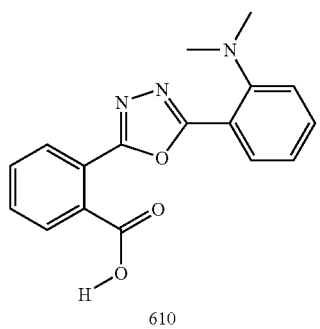
610
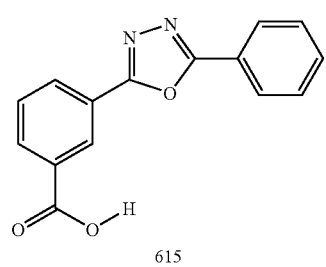
615
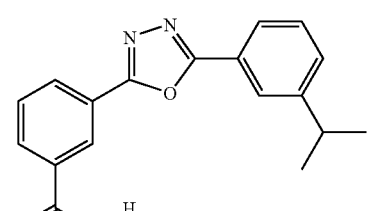
620
TABLE X-continued
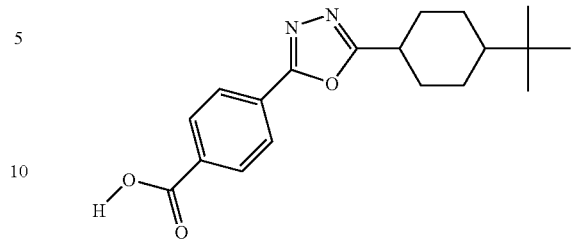
621
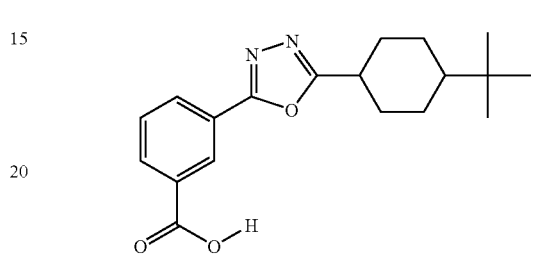
622
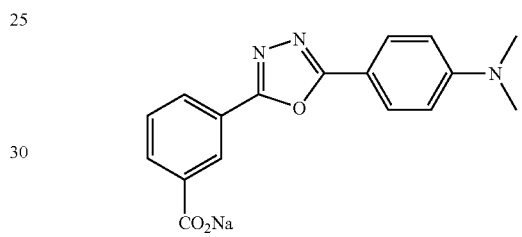
624
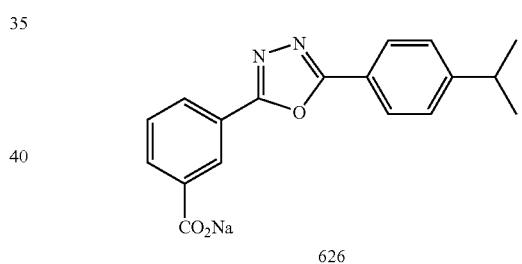
626
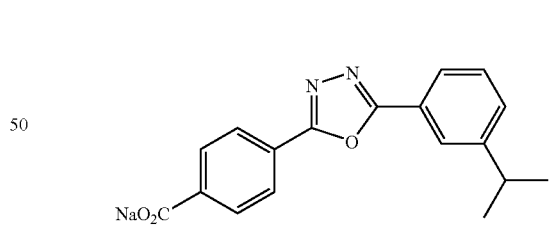
628
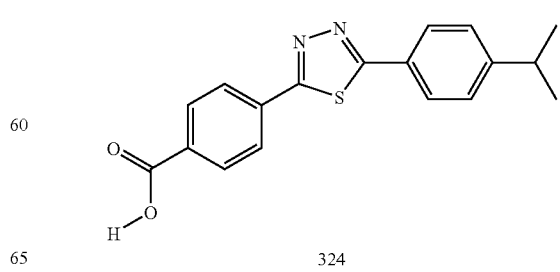
324

TABLE X-continued
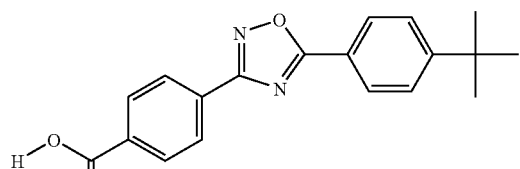
141
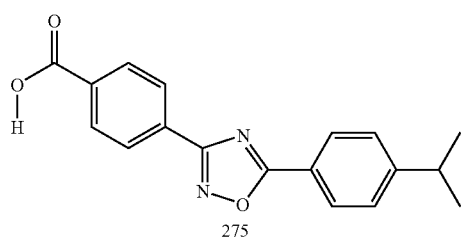
275
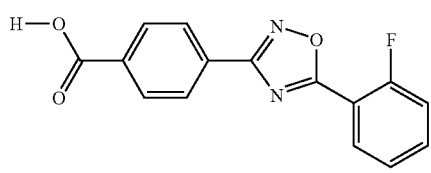
407
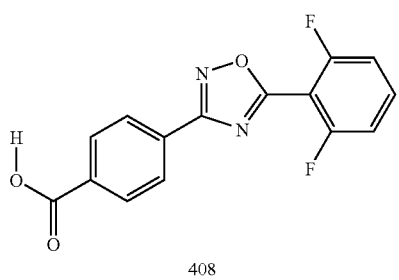
408
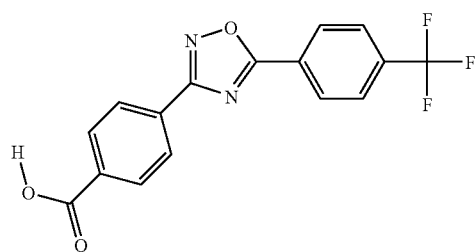 [SMILES: O=C(O)c1ccc(-c2noc(-c3ccc(C(F)(F)F)cc3)n2)cc1]
409
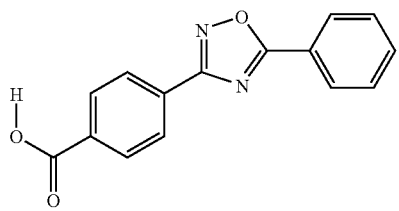 [SMILES: O=C(O)c1ccc(-c2noc(-c3ccccc3)n2)cc1]
410
TABLE X-continued
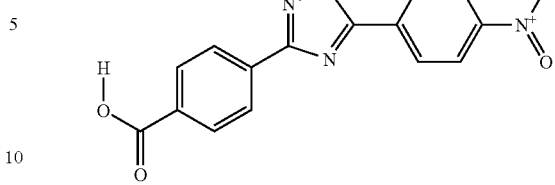
411
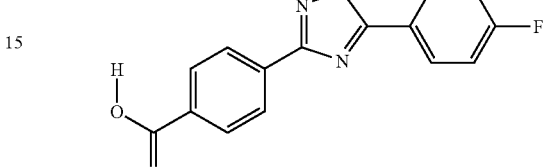
412
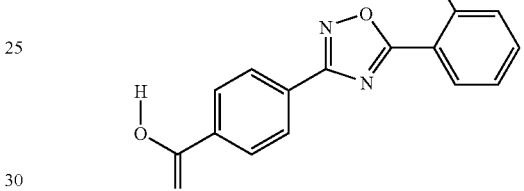
413
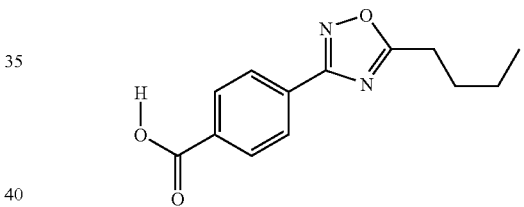
414
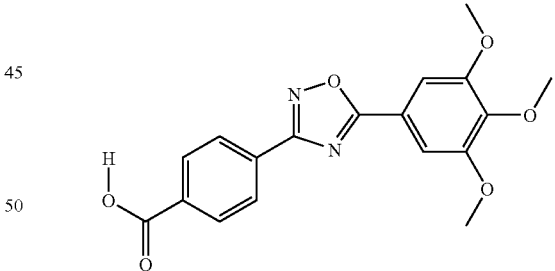
415
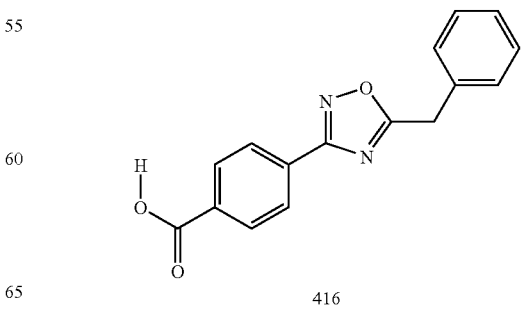
416

TABLE X-continued
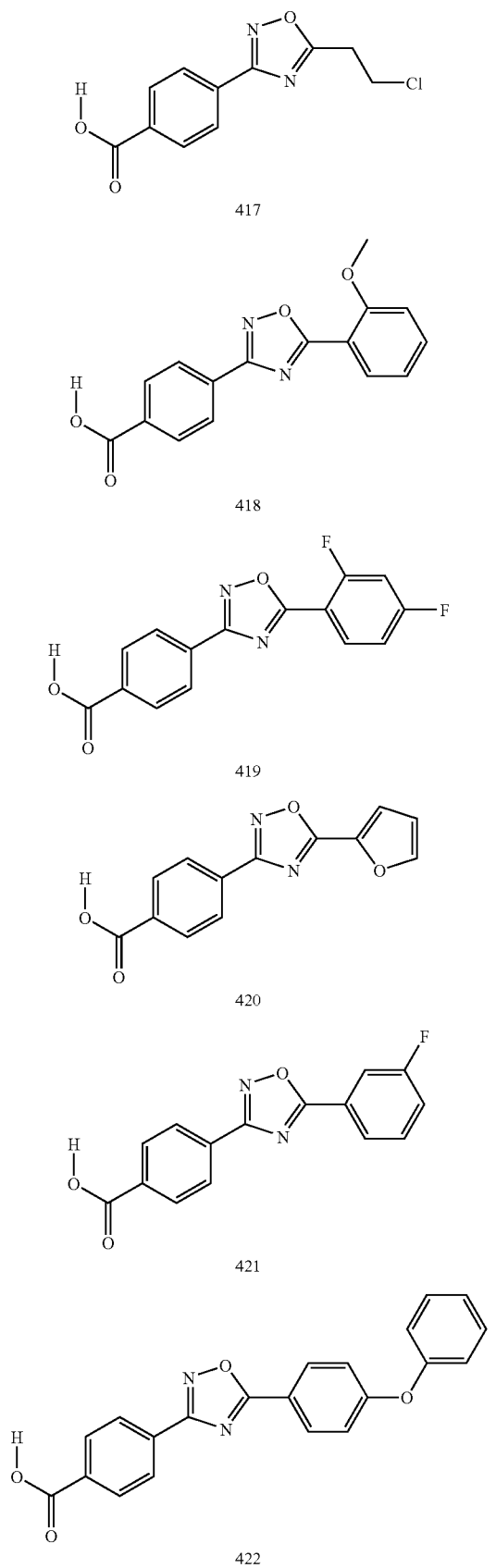
417
418
419
420
421
422
TABLE X-continued
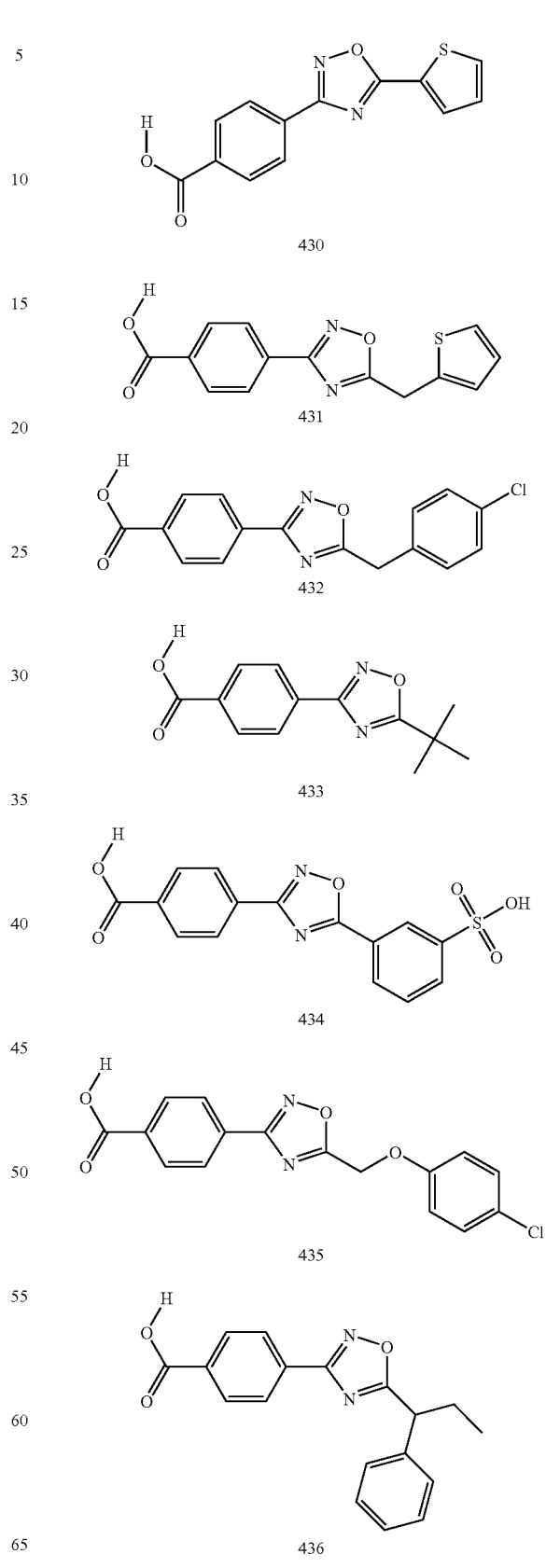
430
431
432
433
434
435
436

TABLE X-continued
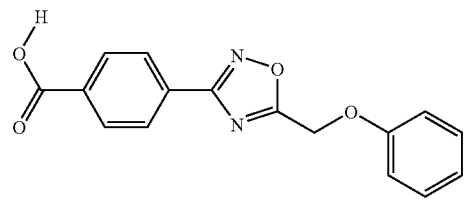 [SMILES: O=C(O)c1ccc(-c2noc(COc3ccccc3)n2)cc1]
437
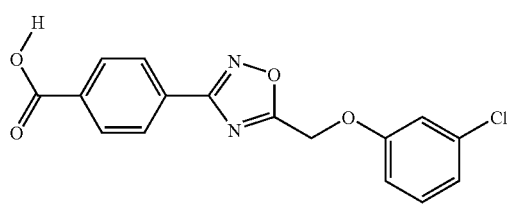 [SMILES: O=C(O)c1ccc(-c2noc(COc3cccc(Cl)c3)n2)cc1]
438
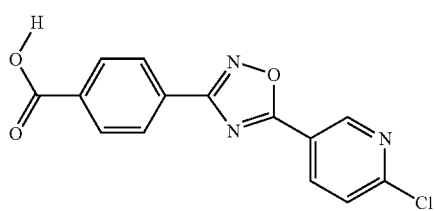 [SMILES: O=C(O)c1ccc(-c2noc(-c3ccc(Cl)nc3)n2)cc1]
439
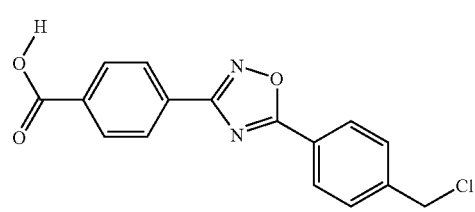 [SMILES: O=C(O)c1ccc(-c2noc(-c3ccc(CCl)cc3)n2)cc1]
440
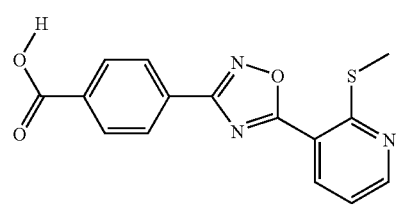 [SMILES: CSc1ncccc1-c1nc(-c2ccc(C(=O)O)cc2)no1]
441
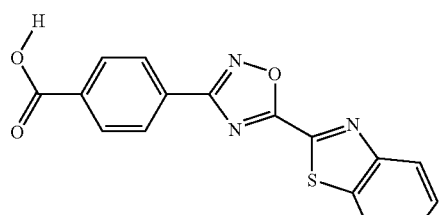
442
TABLE X-continued
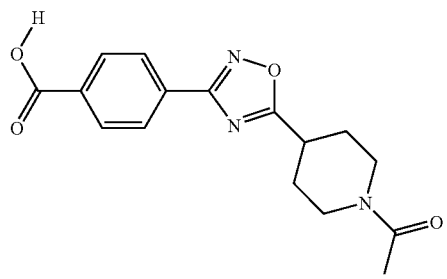 [SMILES: CC(=O)N1CCC(c2nc(-c3ccc(C(=O)O)cc3)no2)CC1]
443
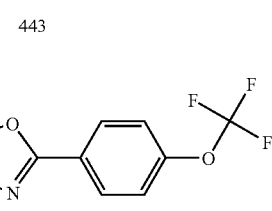
444
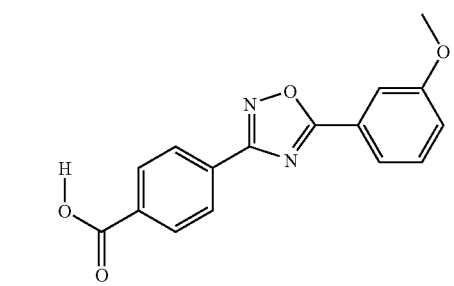 [SMILES: COc1cccc(-c2nc(-c3ccc(C(=O)O)cc3)no2)c1]
445
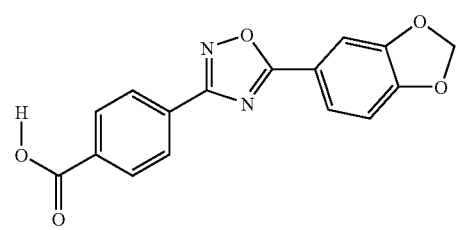 [SMILES: O=C(O)c1ccc(-c2noc(-c3ccc4c(c3)OCO4)n2)cc1]
446
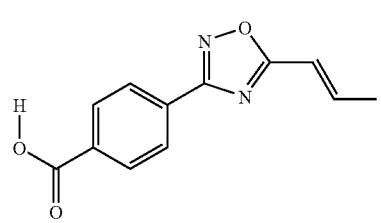 [SMILES: C/C=C/c1nc(-c2ccc(C(=O)O)cc2)no1]
447

TABLE X-continued
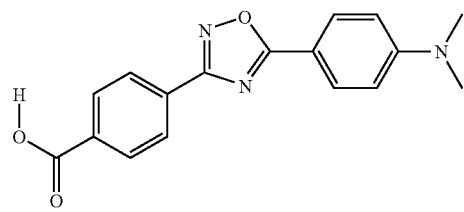 [SMILES: CN(C)c1ccc(-c2nc(-c3ccc(C(=O)O)cc3)no2)cc1]
448
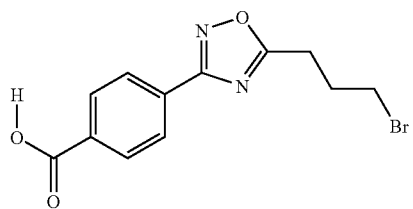 [SMILES: O=C(O)c1ccc(-c2noc(CCCBr)n2)cc1]
449
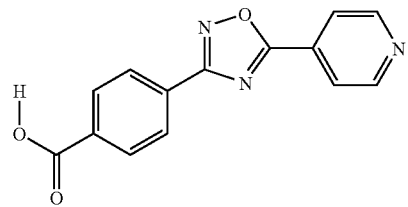 [SMILES: O=C(O)c1ccc(-c2noc(-c3ccncc3)n2)cc1]
450
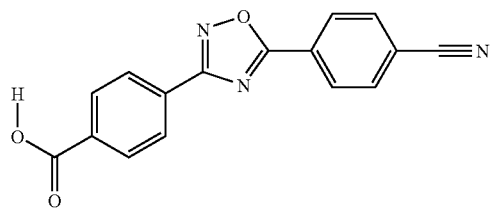 [SMILES: N#Cc1ccc(-c2nc(-c3ccc(C(=O)O)cc3)no2)cc1]
451
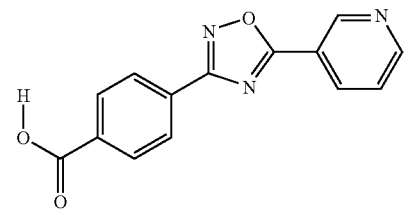 [SMILES: O=C(O)c1ccc(-c2noc(-c3cccnc3)n2)cc1]
452
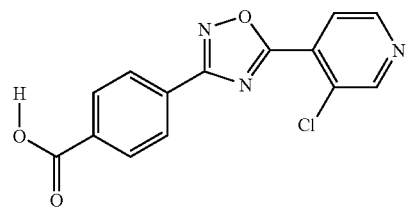 [SMILES: O=C(O)c1ccc(-c2noc(-c3ccncc3Cl)n2)cc1]
453
TABLE X-continued
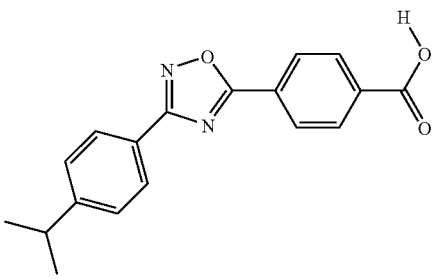 [SMILES: CC(C)c1ccc(-c2noc(-c3ccc(C(=O)O)cc3)n2)cc1]
140
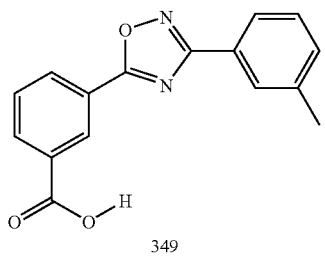
349
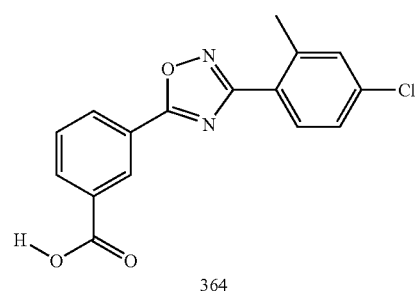
364
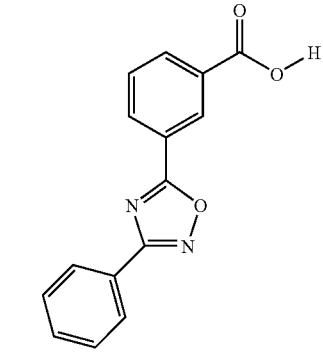 [SMILES: O=C(O)c1cccc(-c2nc(-c3ccccc3)no2)c1]
394
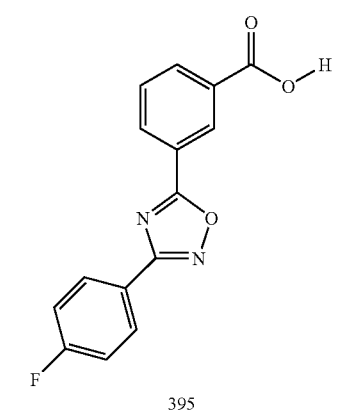
395

TABLE X-continued
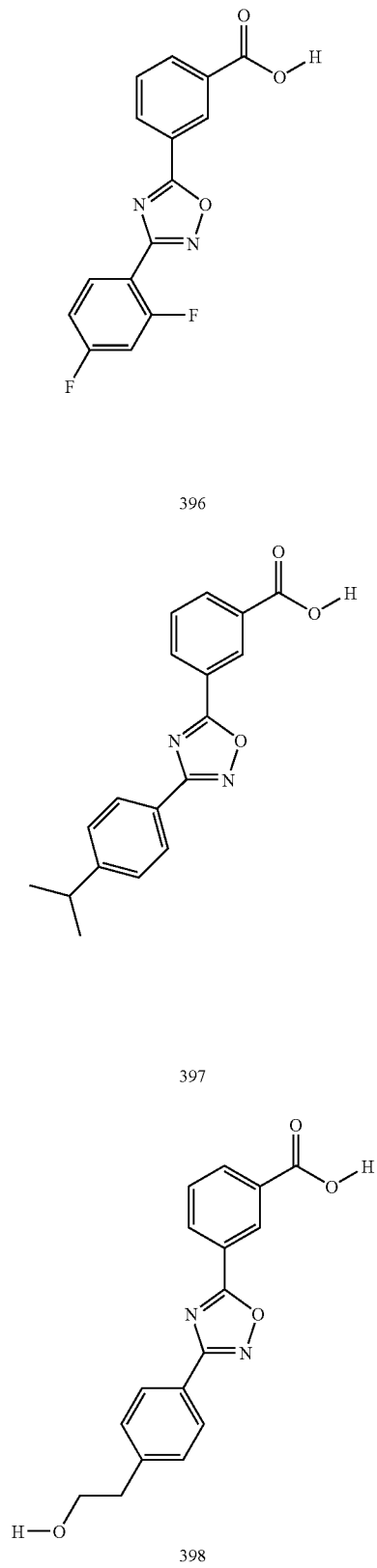
396
397
398
TABLE X-continued
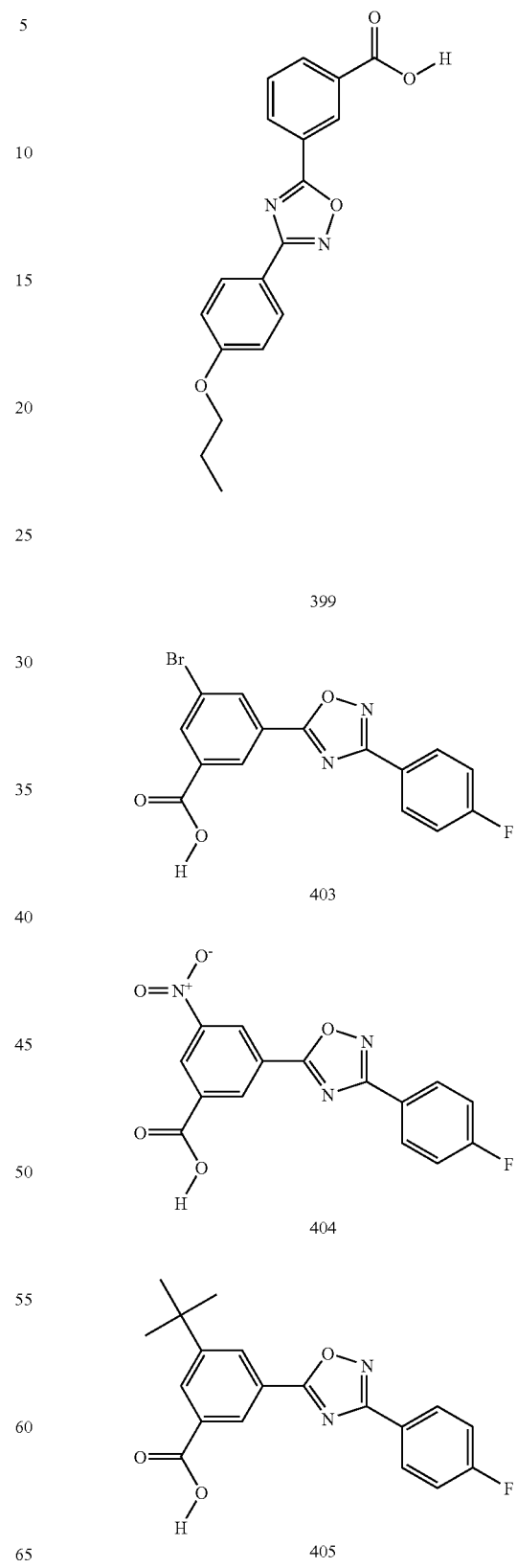
399
403
404
405

TABLE X-continued
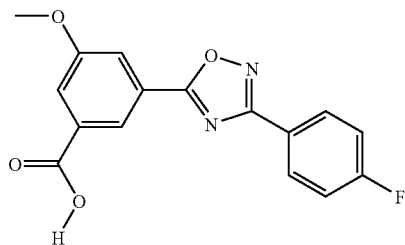 [SMILES: COc1cc(C(=O)O)cc(-c2nc(-c3ccc(F)cc3)no2)c1]
406
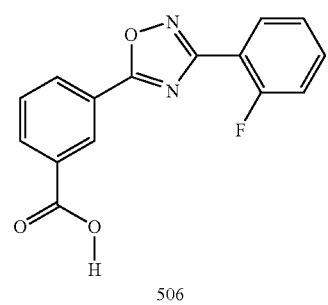
506
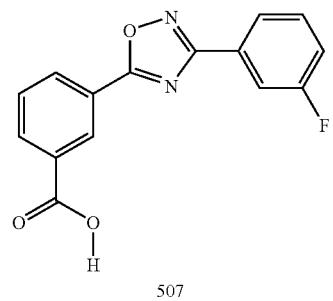
507
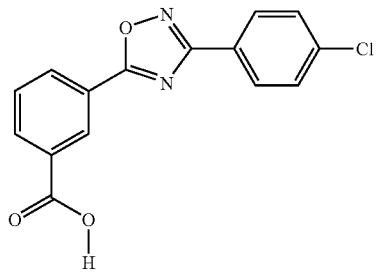 [SMILES: O=C(O)c1cccc(-c2nc(-c3ccc(Cl)cc3)no2)c1]
508
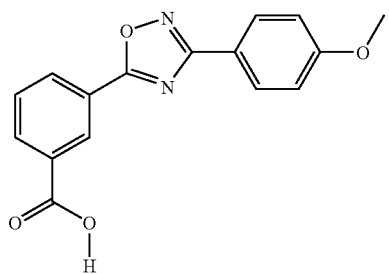 [SMILES: COc1ccc(-c2noc(-c3cccc(C(=O)O)c3)n2)cc1]
509
TABLE X-continued
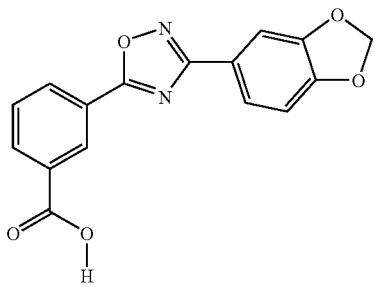 [SMILES: O=C(O)c1cccc(-c2nc(-c3ccc4c(c3)OCO4)no2)c1]
510
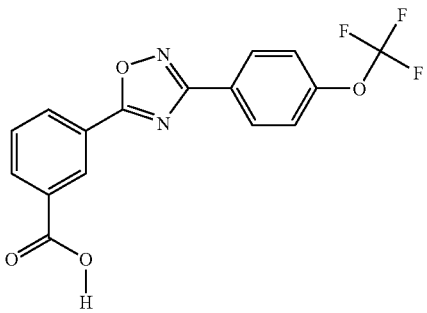 [SMILES: O=C(O)c1cccc(-c2nc(-c3ccc(OC(F)(F)F)cc3)no2)c1]
511
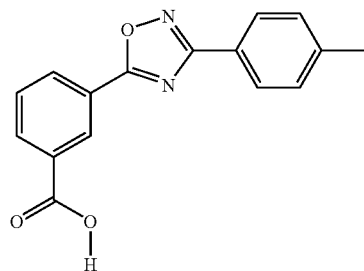 [SMILES: Cc1ccc(-c2noc(-c3cccc(C(=O)O)c3)n2)cc1]
512
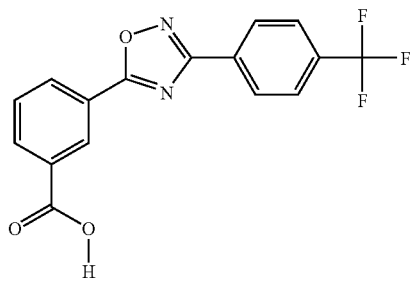 [SMILES: O=C(O)c1cccc(-c2nc(-c3ccc(C(F)(F)F)cc3)no2)c1]
513
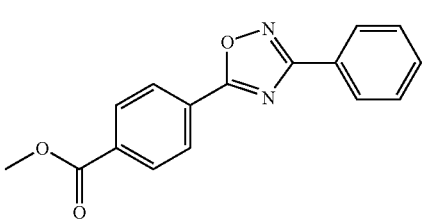 [SMILES: COC(=O)c1ccc(-c2nc(-c3ccccc3)no2)cc1]
559

TABLE X-continued
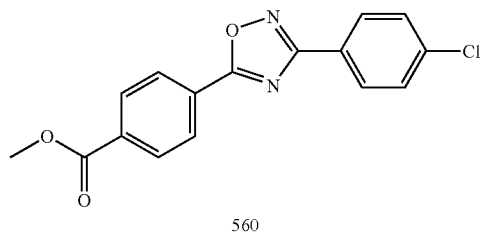
560
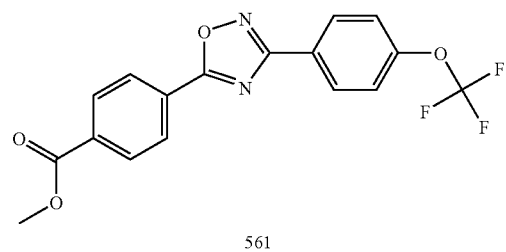
561
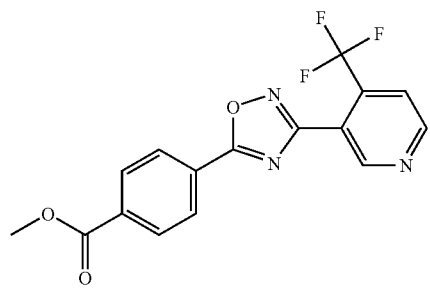 [SMILES: COC(=O)c1ccc(-c2nc(-c3cnccc3C(F)(F)F)no2)cc1]
562
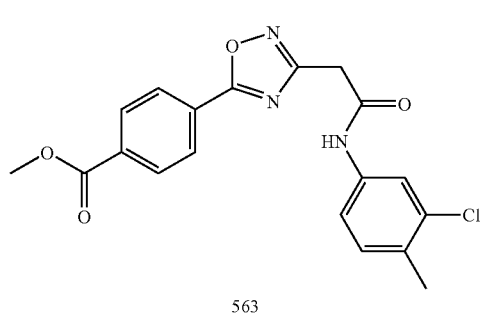
563
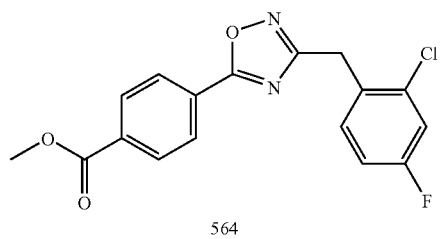
564
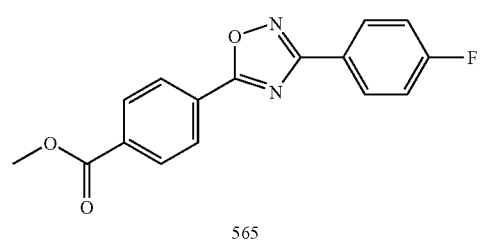
565
TABLE X-continued
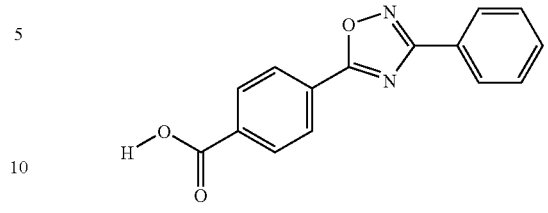
569
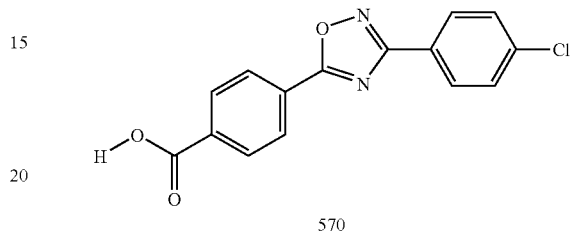
570
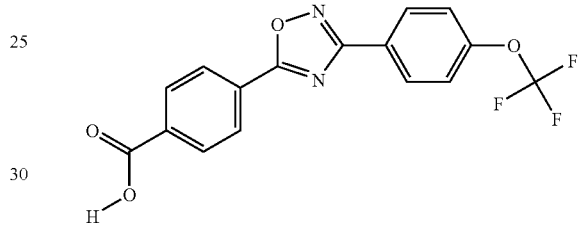
571
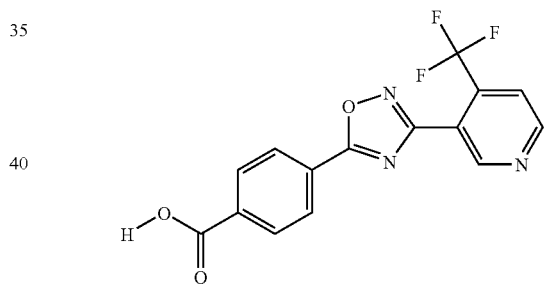
572
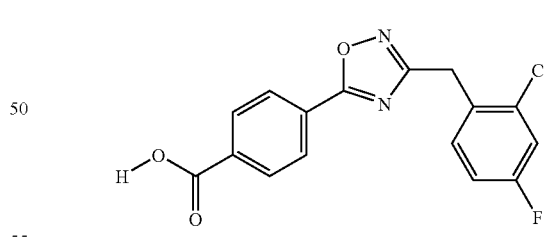
576
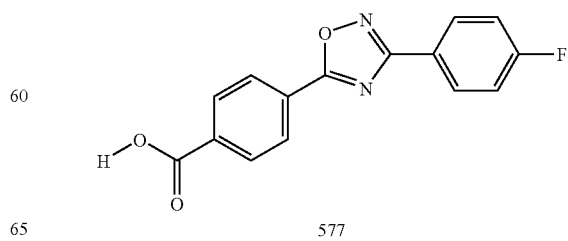
577

TABLE X-continued
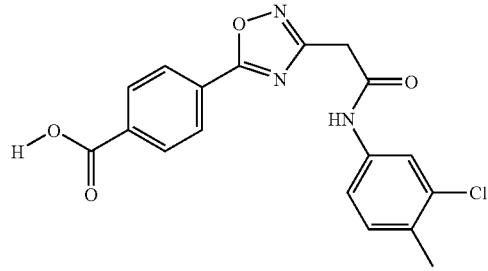 [SMILES: Cc1ccc(NC(=O)Cc2noc(-c3ccc(C(=O)O)cc3)n2)cc1Cl]
578
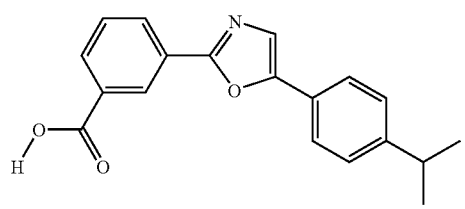
288
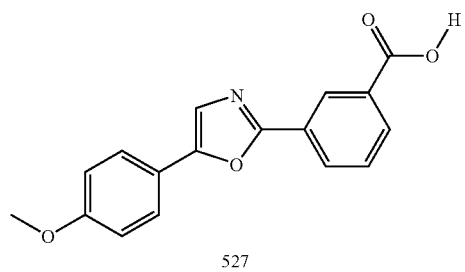
527
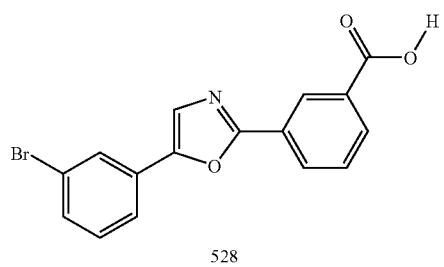
528
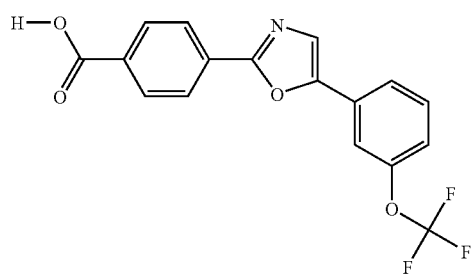
542
TABLE X-continued
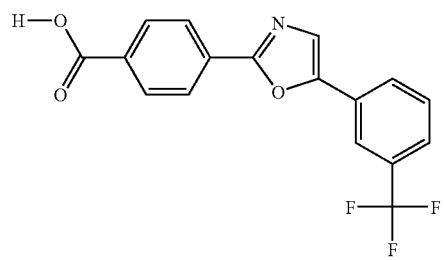 [SMILES: O=C(O)c1ccc(-c2ncc(-c3cccc(C(F)(F)F)c3)o2)cc1]
543
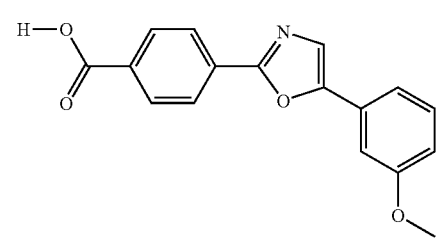 [SMILES: COc1cccc(-c2cnc(-c3ccc(C(=O)O)cc3)o2)c1]
544
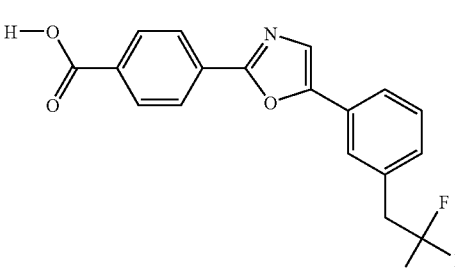
545
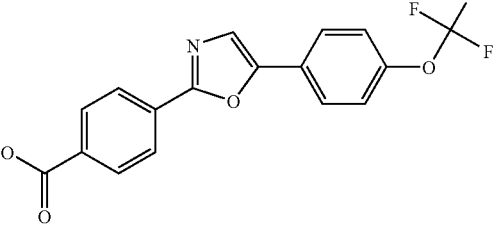
546
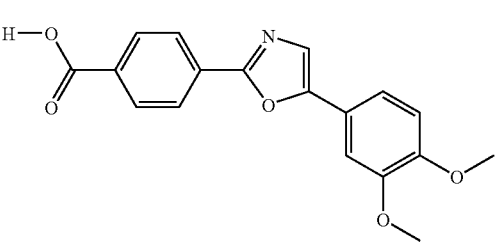 [SMILES: COc1ccc(-c2cnc(-c3ccc(C(=O)O)cc3)o2)cc1OC]
547
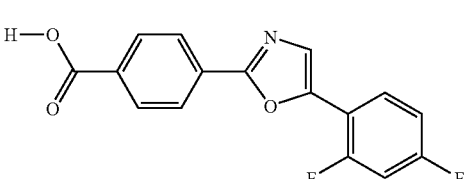
548

TABLE X-continued
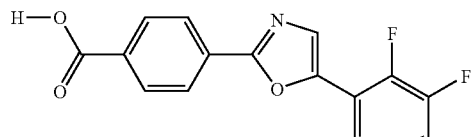
549
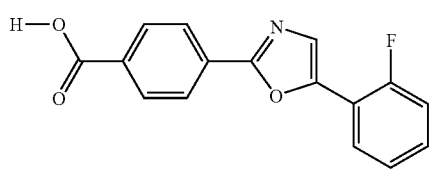 [SMILES: O=C(O)c1ccc(-c2ncc(-c3ccccc3F)o2)cc1]
550
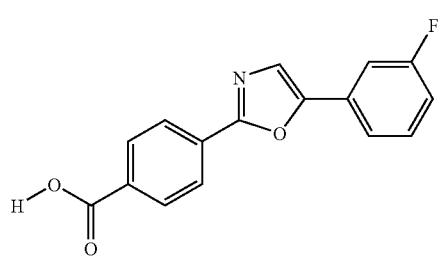 [SMILES: O=C(O)c1ccc(-c2ncc(-c3cccc(F)c3)o2)cc1]
553
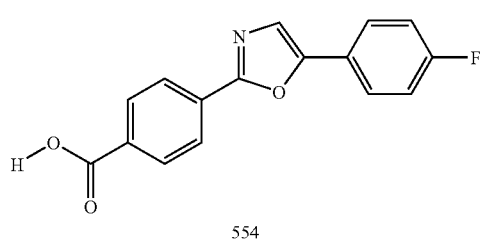
554
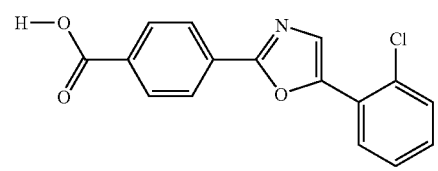
555
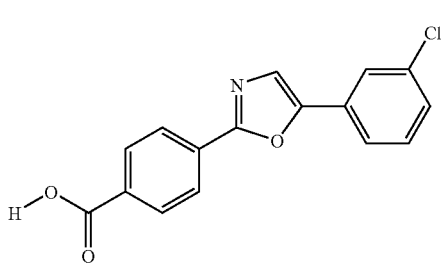 [SMILES: O=C(O)c1ccc(-c2ncc(-c3cccc(Cl)c3)o2)cc1]
556
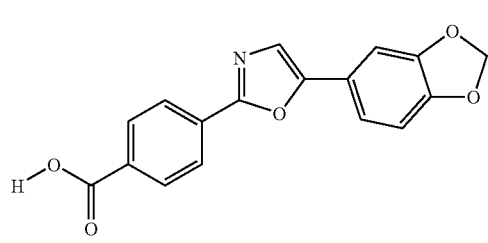 [SMILES: O=C(O)c1ccc(-c2ncc(-c3ccc4c(c3)OCO4)o2)cc1]
557
TABLE X-continued
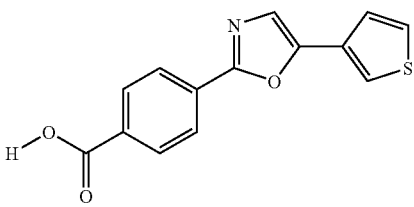 [SMILES: O=C(O)c1ccc(-c2ncc(-c3ccsc3)o2)cc1]
558
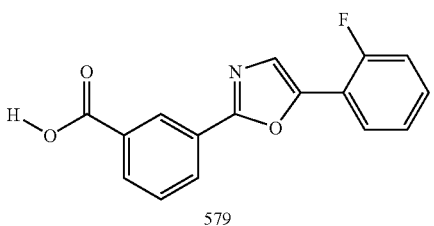
579
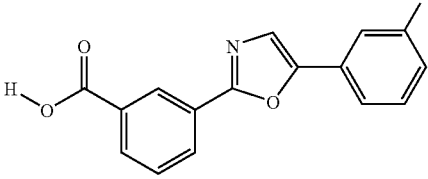
580
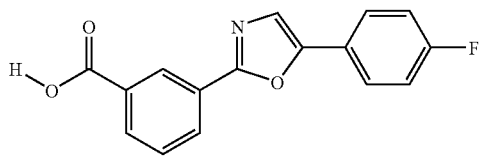 [SMILES: O=C(O)c1cccc(-c2ncc(-c3ccc(F)cc3)o2)c1]
581
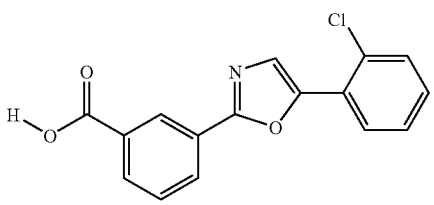 [SMILES: O=C(O)c1cccc(-c2ncc(-c3ccccc3Cl)o2)c1]
582
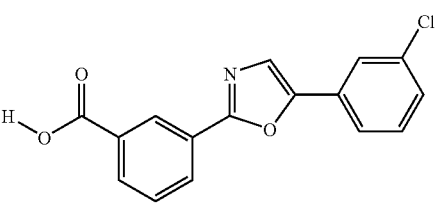 [SMILES: O=C(O)c1cccc(-c2ncc(-c3cccc(Cl)c3)o2)c1]
583
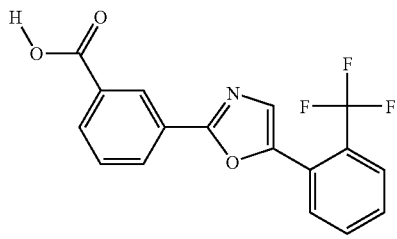 [SMILES: O=C(O)c1cccc(-c2ncc(-c3ccccc3C(F)(F)F)o2)c1]
584

TABLE X-continued
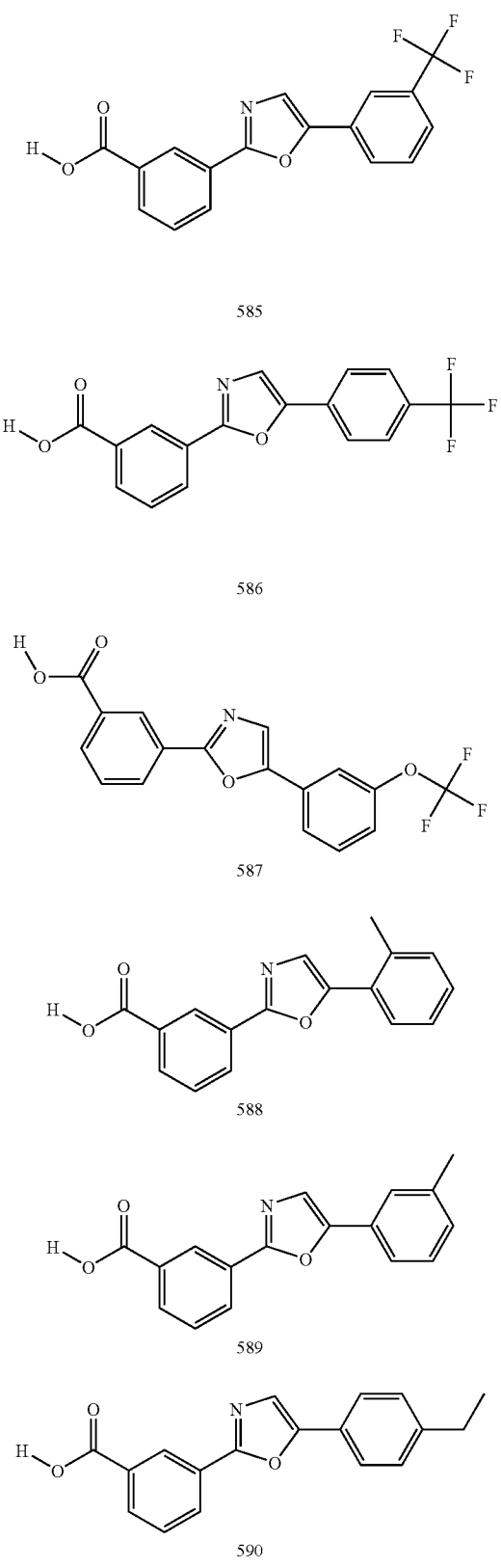
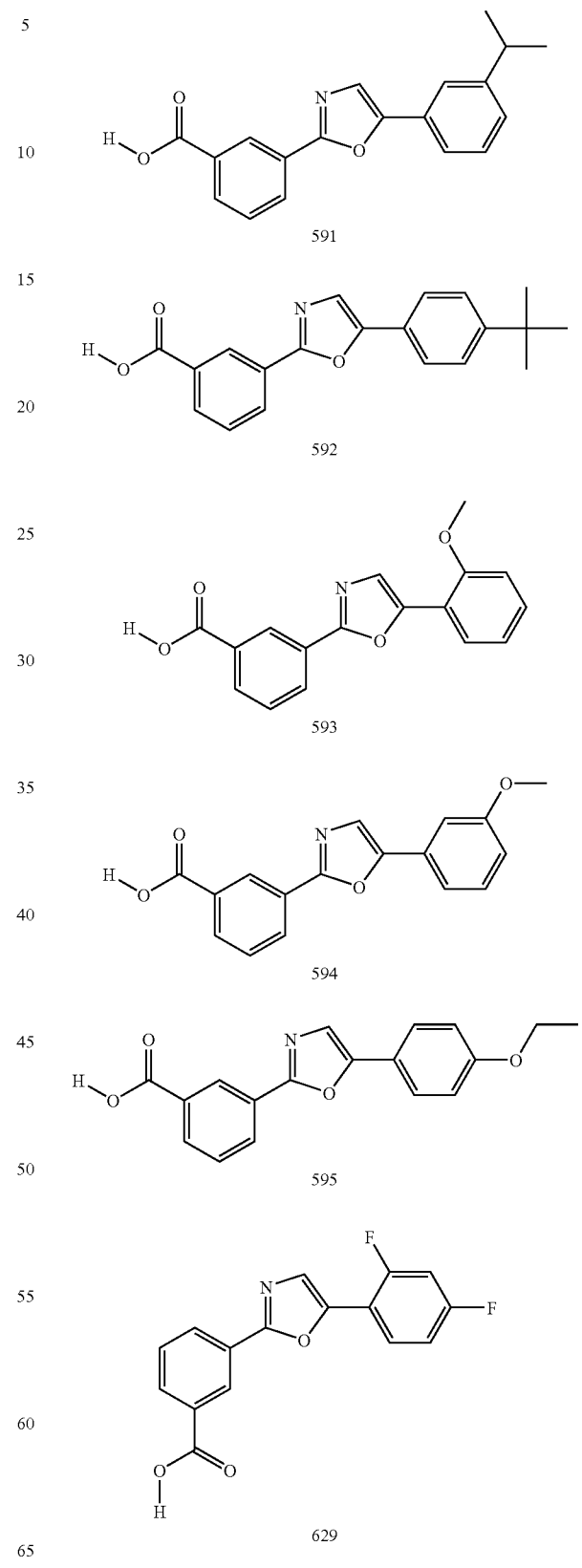

TABLE X-continued
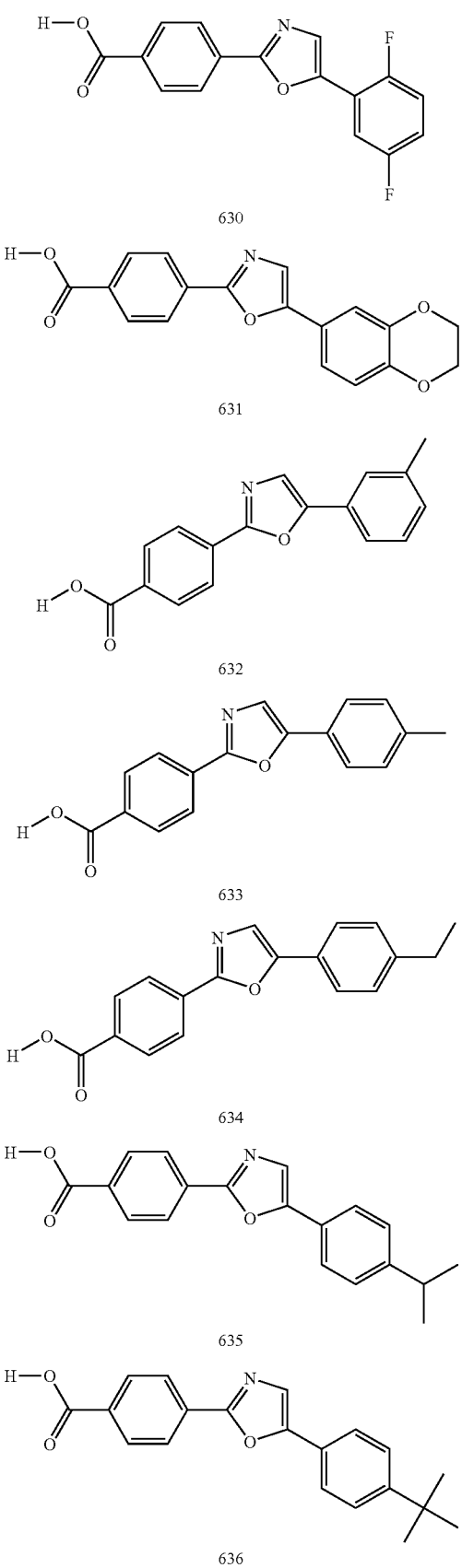
630
631
632
633
634
635
636
TABLE X-continued
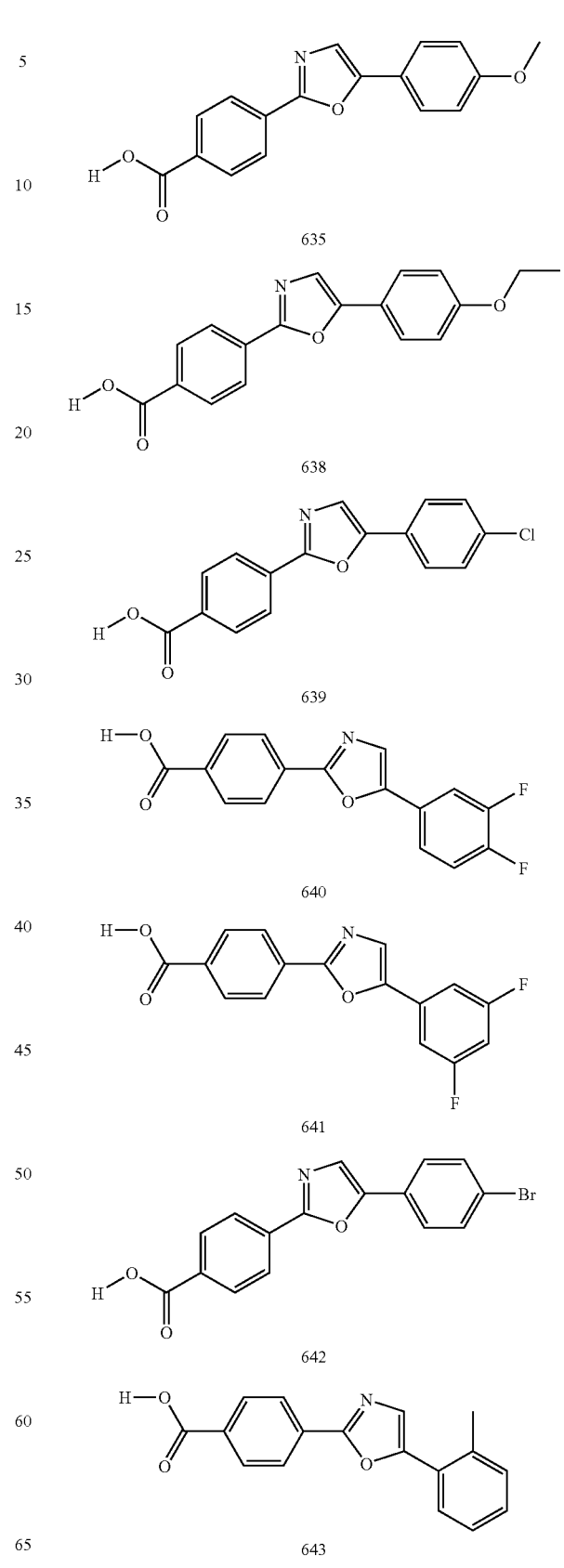
635
638
639
640
641
642
643

TABLE X-continued
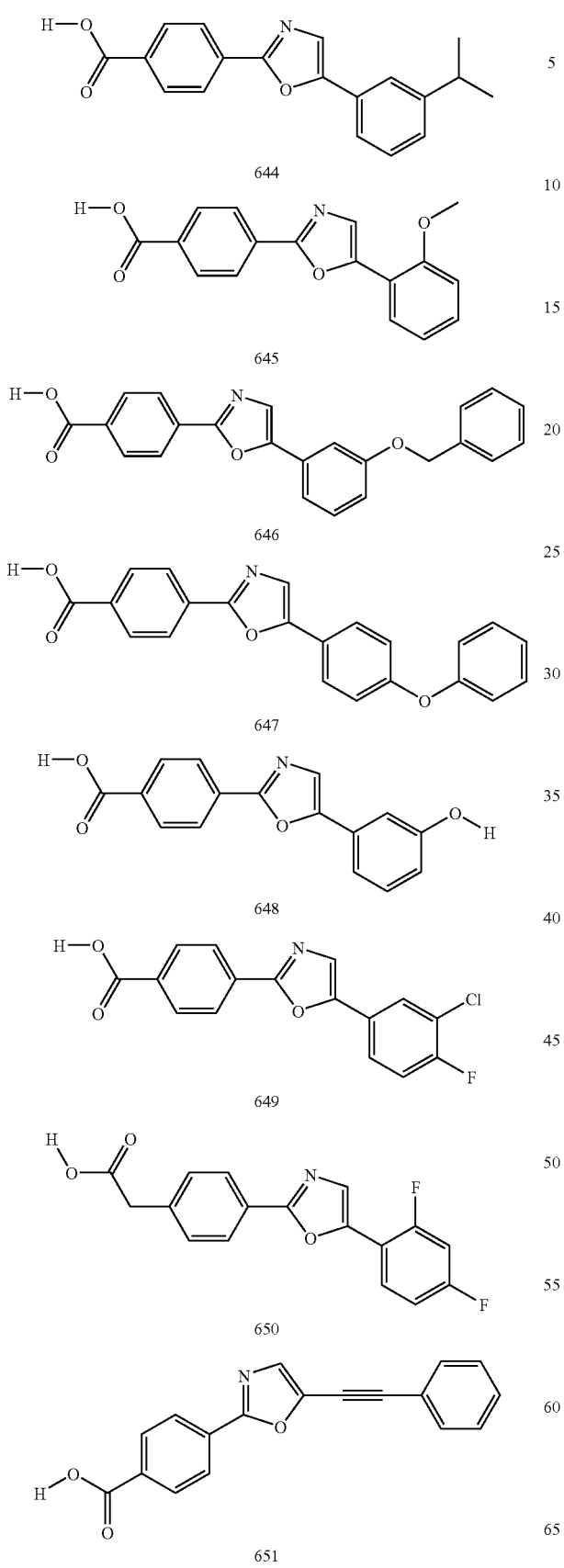
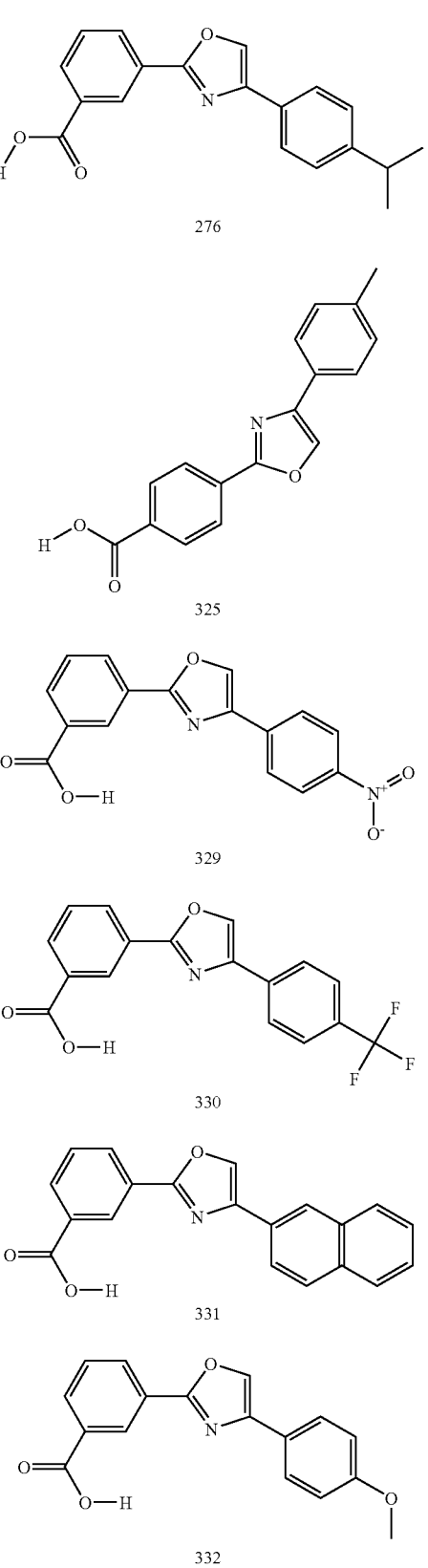

TABLE X-continued
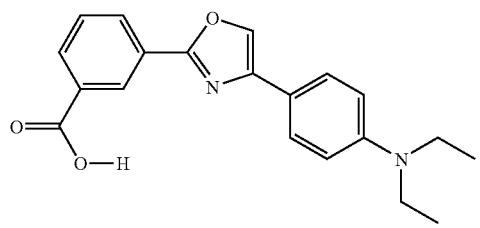 [SMILES: CCN(CC)c1ccc(-c2coc(-c3cccc(C(=O)O)c3)n2)cc1]
333
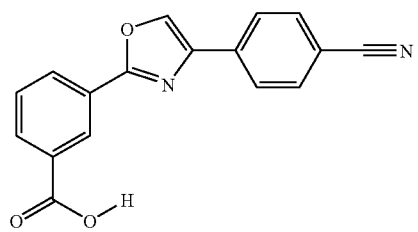 [SMILES: N#Cc1ccc(-c2coc(-c3cccc(C(=O)O)c3)n2)cc1]
334
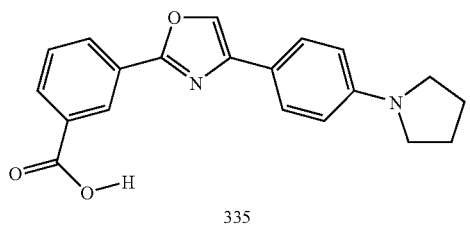
335
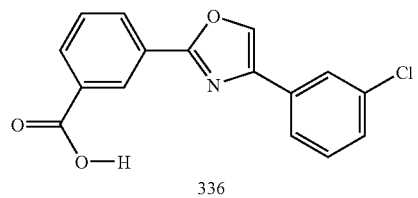
336
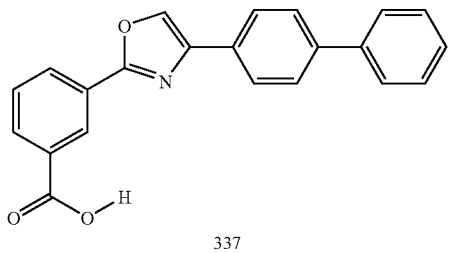
337
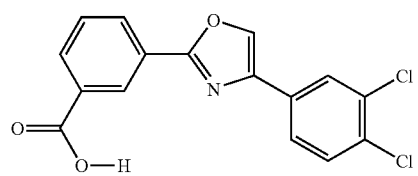
338
TABLE X-continued
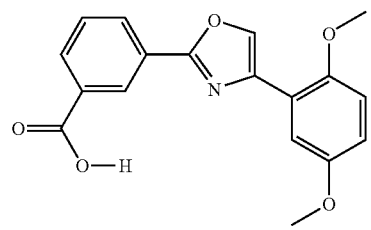 [SMILES: COc1ccc(OC)c(-c2coc(-c3cccc(C(=O)O)c3)n2)c1]
339
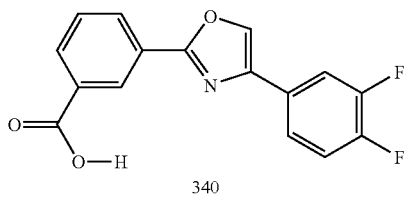
340
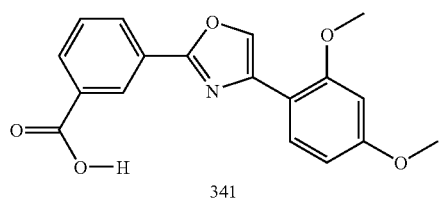
341
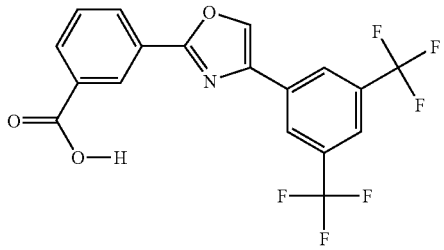 [SMILES: O=C(O)c1cccc(-c2nc(-c3cc(C(F)(F)F)cc(C(F)(F)F)c3)co2)c1]
342
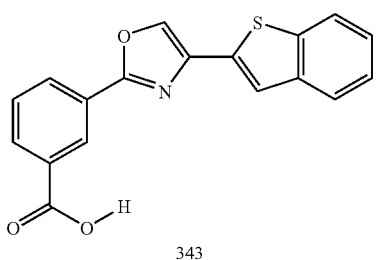
343
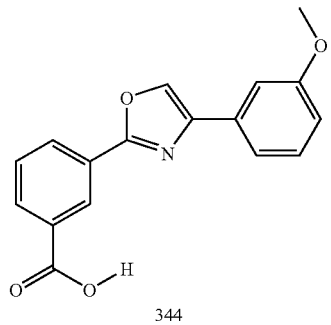
344

TABLE X-continued
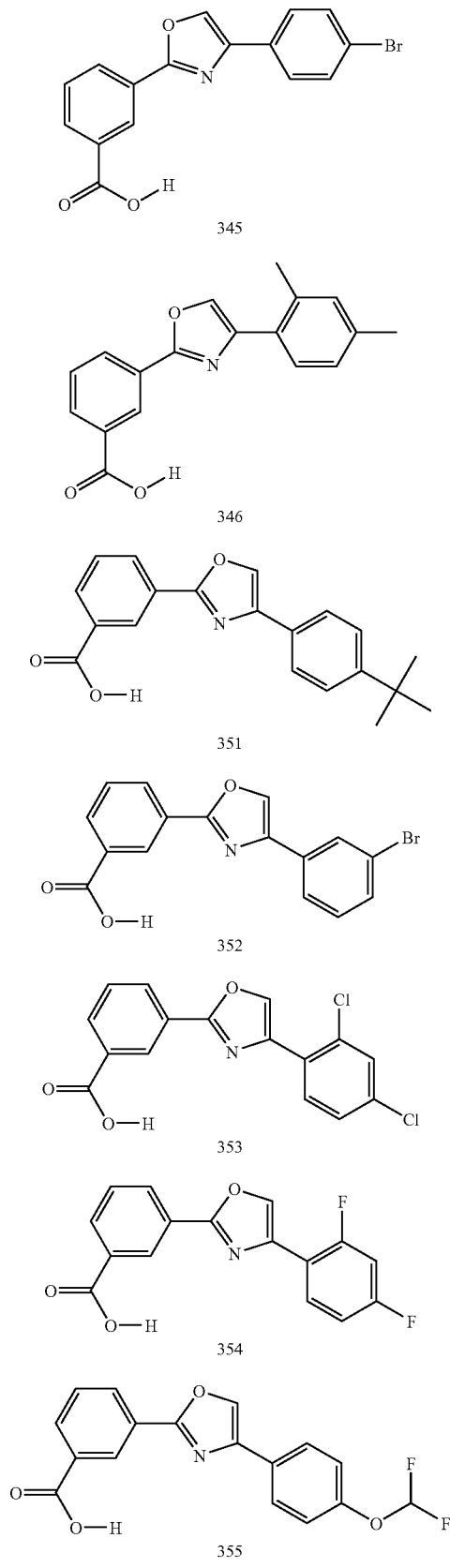
345
346
351
352
353
354
355
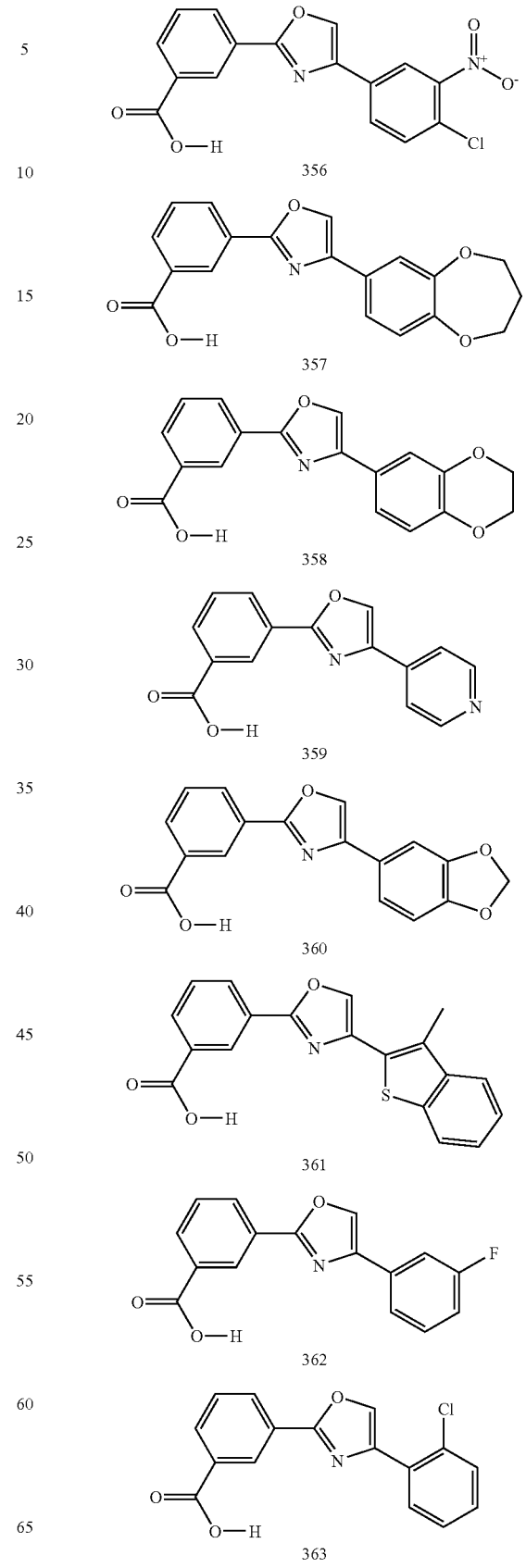
356
357
358
359
360
361
362
363

TABLE X-continued
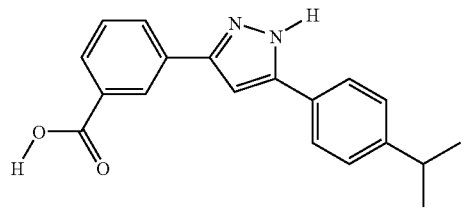 [SMILES: CC(C)c1ccc(-c2cc(-c3cccc(C(=O)O)c3)n[nH]2)cc1]
287
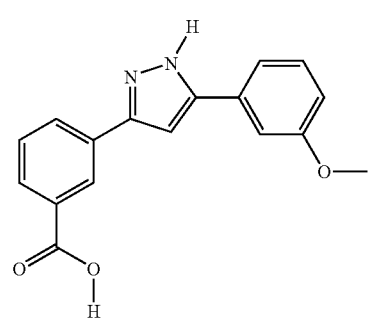 [SMILES: COc1cccc(-c2cc(-c3cccc(C(=O)O)c3)n[nH]2)c1]
551
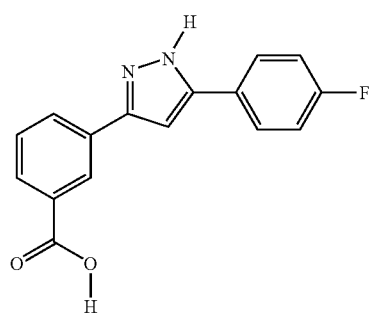 [SMILES: O=C(O)c1cccc(-c2cc(-c3ccc(F)cc3)[nH]n2)c1]
552
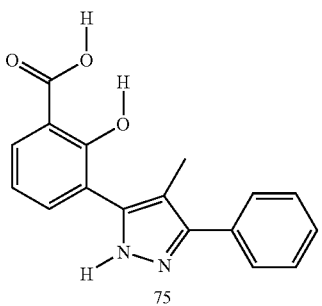
75
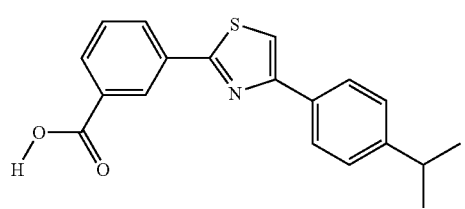 [SMILES: CC(C)c1ccc(-c2csc(-c3cccc(C(=O)O)c3)n2)cc1]
289
TABLE X-continued
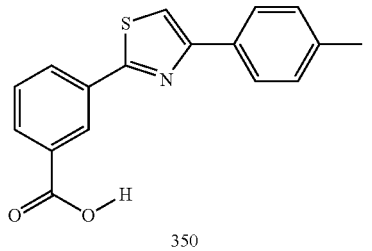
350
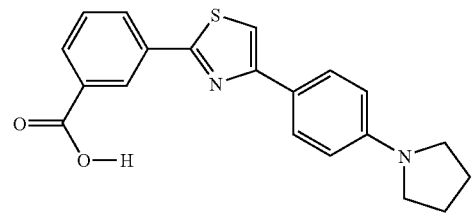 [SMILES: O=C(O)c1cccc(-c2nc(-c3ccc(N4CCCC4)cc3)cs2)c1]
365
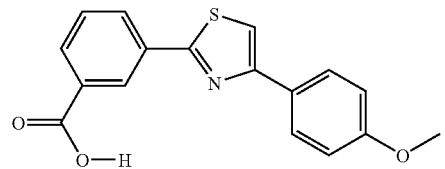 [SMILES: COc1ccc(-c2csc(-c3cccc(C(=O)O)c3)n2)cc1]
366
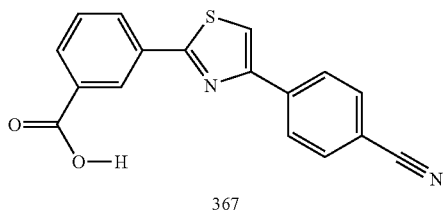
367
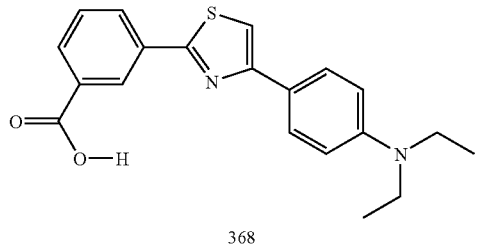
368
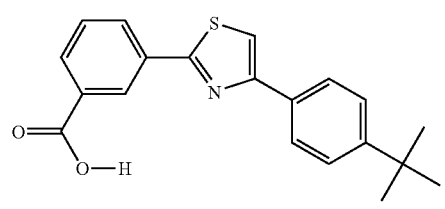 [SMILES: CC(C)(C)c1ccc(-c2csc(-c3cccc(C(=O)O)c3)n2)cc1]
369
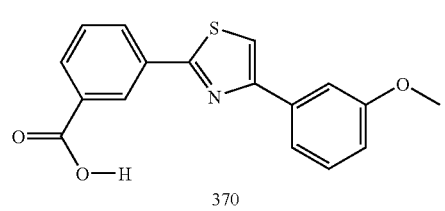
370

TABLE X-continued
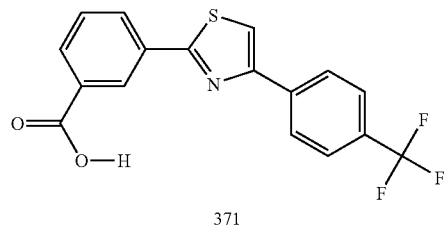
371
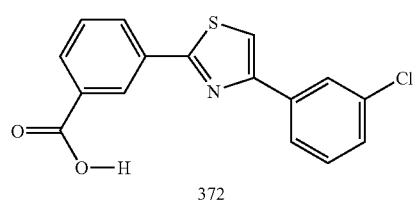
372
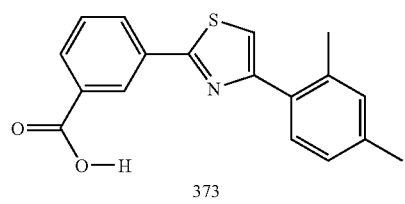
373
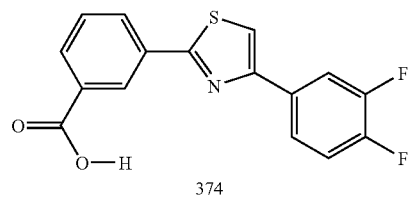
374
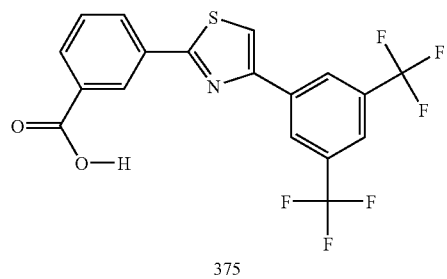
375
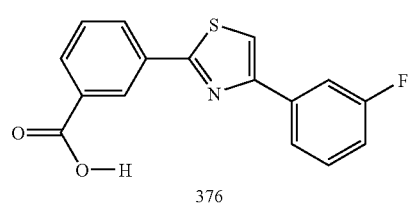
376
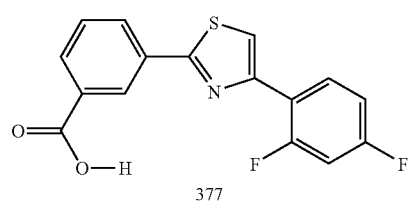
377
TABLE X-continued
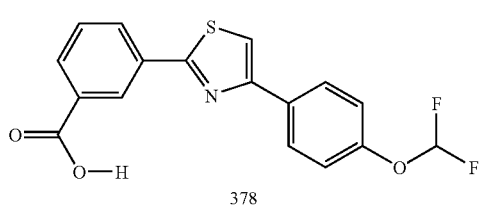
378
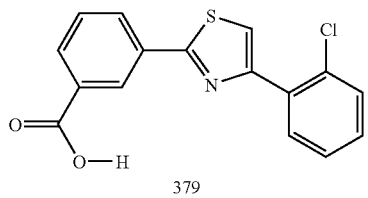
379
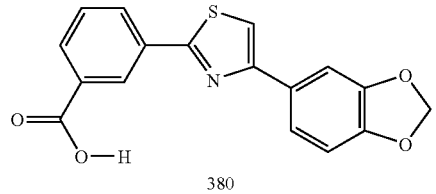
380
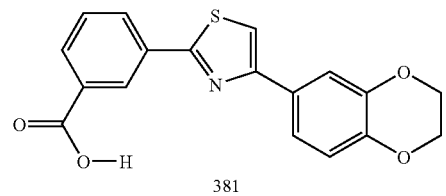
381
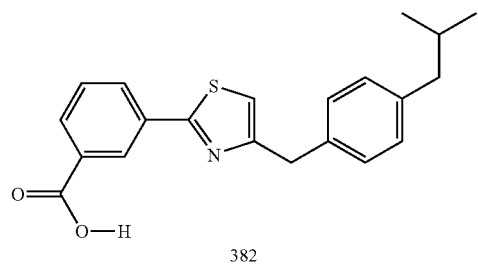
382
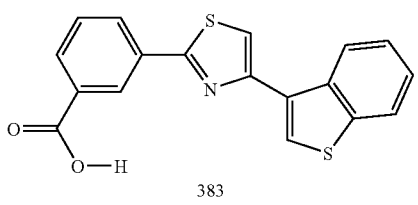
383
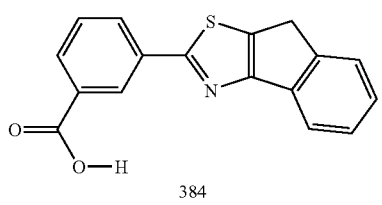
384

TABLE X-continued
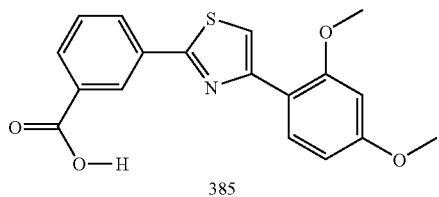
385
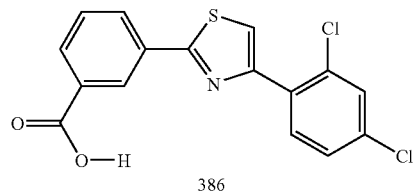
386
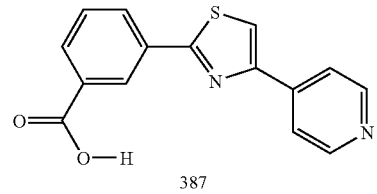
387
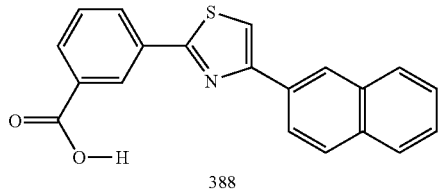
388
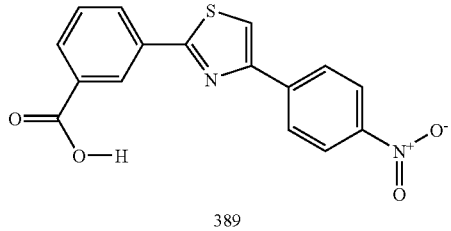
389
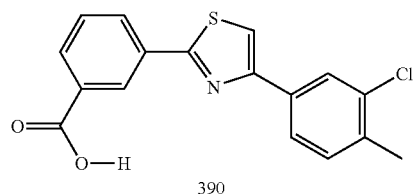
390
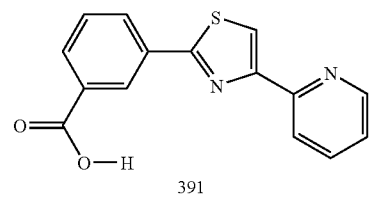
391
TABLE X-continued
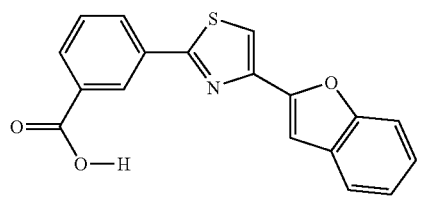 [SMILES: O=C(O)c1cccc(-c2nc(-c3cc4ccccc4o3)cs2)c1]
392
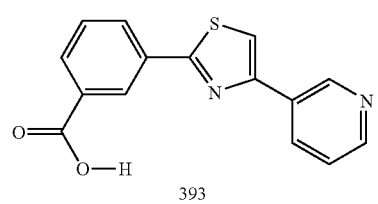
393
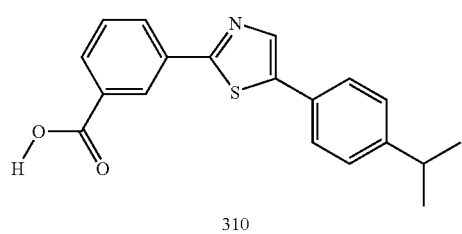
310
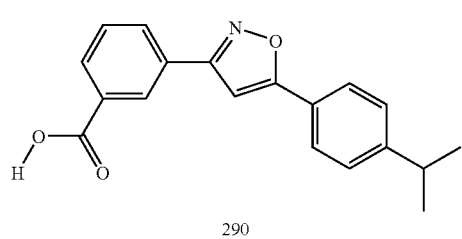
290
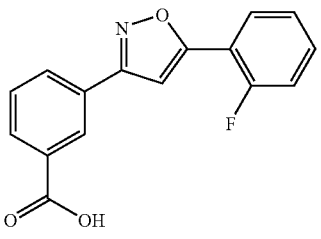 [SMILES: O=C(O)c1cccc(-c2cc(-c3ccccc3F)on2)c1]
463
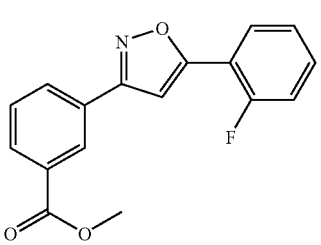 [SMILES: COC(=O)c1cccc(-c2cc(-c3ccccc3F)on2)c1]
464

TABLE X-continued
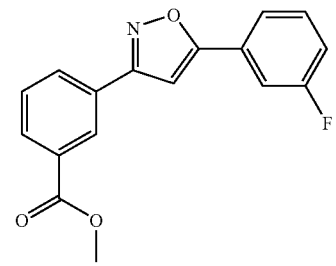
465
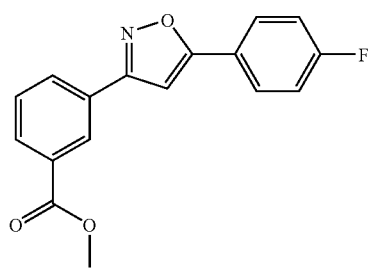 [SMILES: COC(=O)c1cccc(-c2cc(-c3ccc(F)cc3)on2)c1]
466
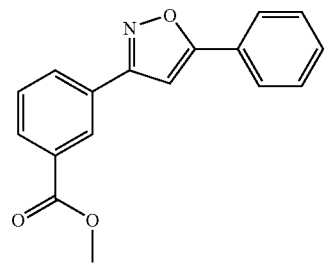 [SMILES: COC(=O)c1cccc(-c2cc(-c3ccccc3)on2)c1]
467
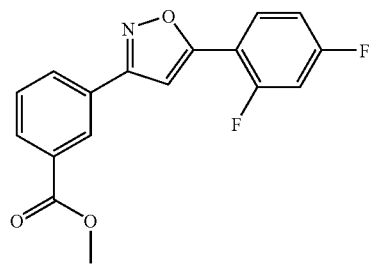 [SMILES: COC(=O)c1cccc(-c2cc(-c3ccc(F)cc3F)on2)c1]
468
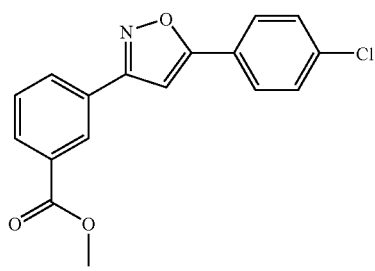 [SMILES: COC(=O)c1cccc(-c2cc(-c3ccc(Cl)cc3)on2)c1]
469
TABLE X-continued
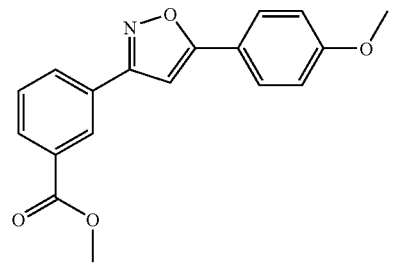 [SMILES: COC(=O)c1cccc(-c2cc(-c3ccc(OC)cc3)on2)c1]
470
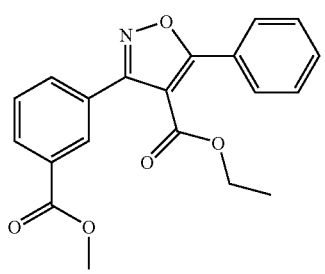 [SMILES: CCOC(=O)c1c(-c2cccc(C(=O)OC)c2)noc1-c1ccccc1]
471
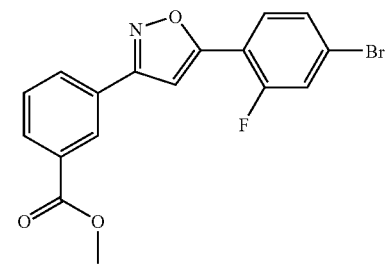 [SMILES: COC(=O)c1cccc(-c2cc(-c3ccc(Br)cc3F)on2)c1]
472
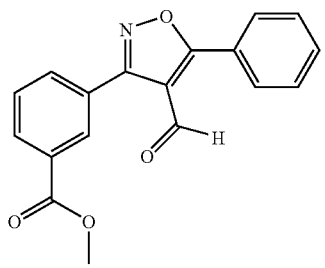 [SMILES: COC(=O)c1cccc(-c2noc(-c3ccccc3)c2C=O)c1]
473
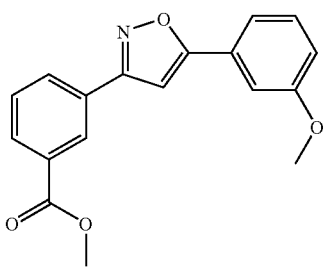 [SMILES: COC(=O)c1cccc(-c2cc(-c3cccc(OC)c3)on2)c1]
474

TABLE X-continued
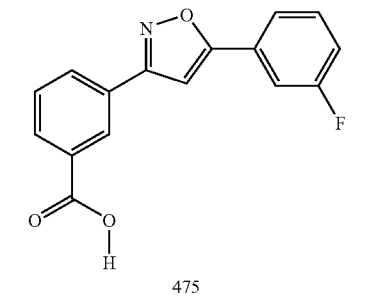
475
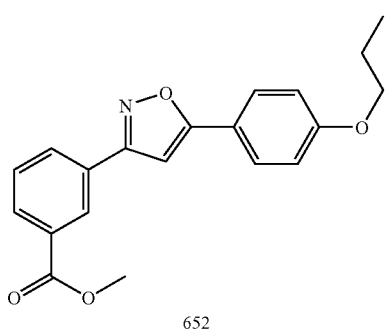
652
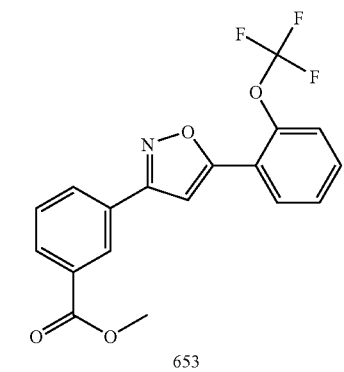
653
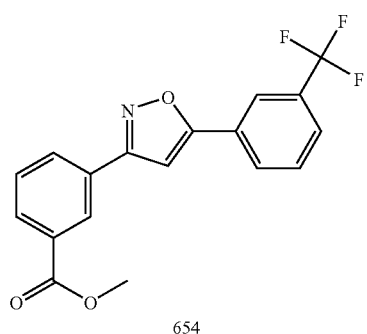
654
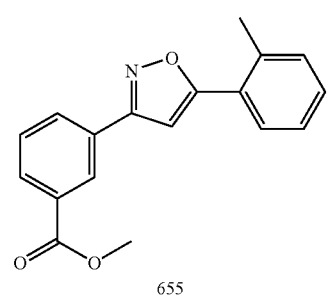
655
TABLE X-continued
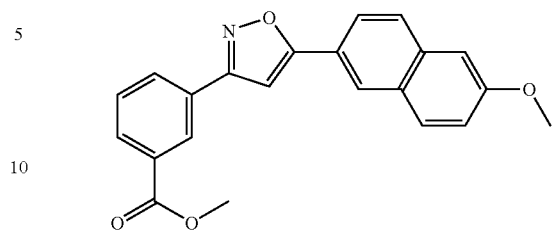
656
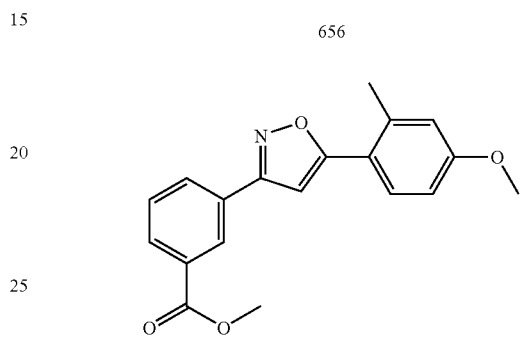
657
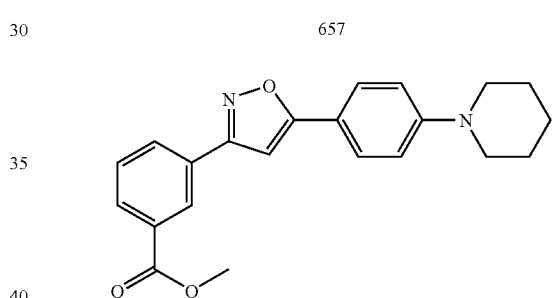
658
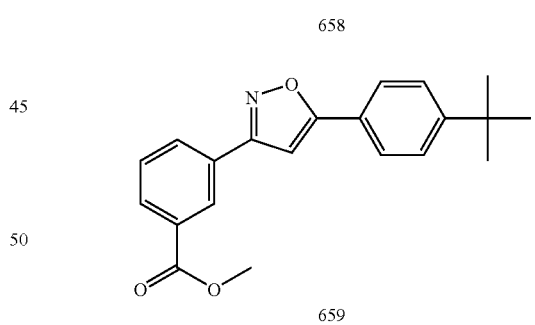
659
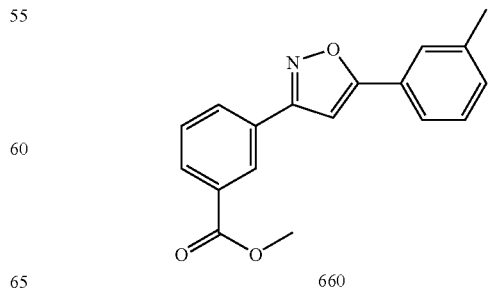
660

TABLE X-continued
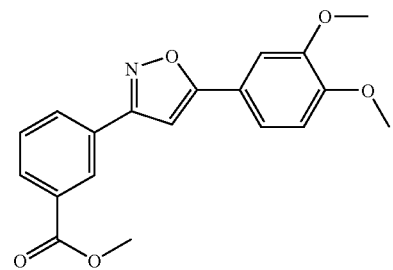 [SMILES: COC(=O)c1cccc(-c2cc(-c3ccc(OC)c(OC)c3)on2)c1]
661
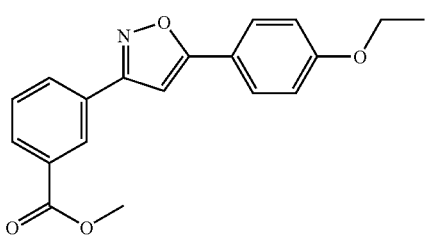 [SMILES: CCOc1ccc(-c2cc(-c3cccc(C(=O)OC)c3)no2)cc1]
662
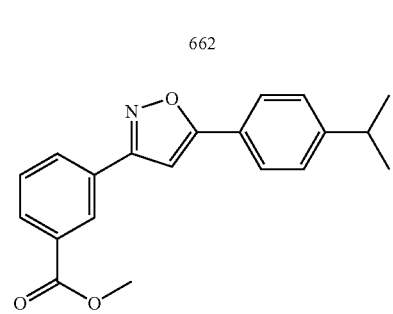
663
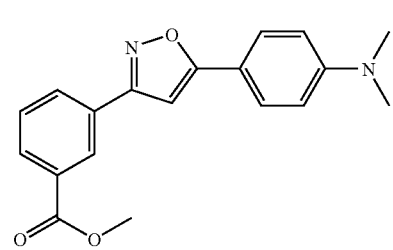 [SMILES: COC(=O)c1cccc(-c2cc(-c3ccc(N(C)C)cc3)on2)c1]
664
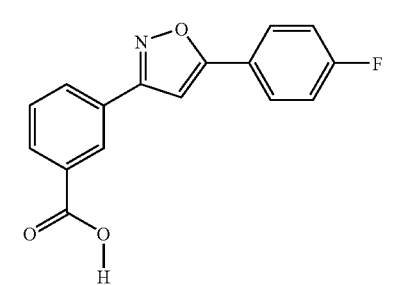 [SMILES: O=C(O)c1cccc(-c2cc(-c3ccc(F)cc3)on2)c1]
476
TABLE X-continued
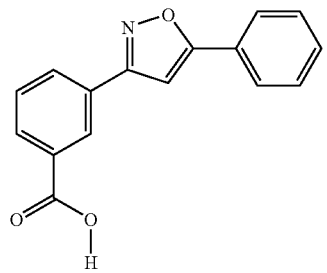 [SMILES: O=C(O)c1cccc(-c2cc(-c3ccccc3)on2)c1]
477
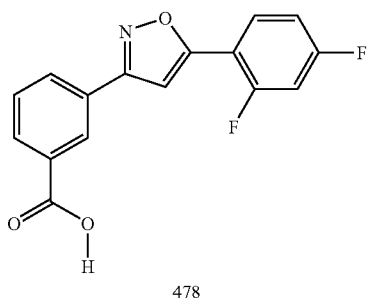
478
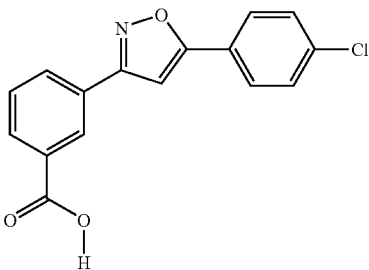 [SMILES: O=C(O)c1cccc(-c2cc(-c3ccc(Cl)cc3)on2)c1]
479
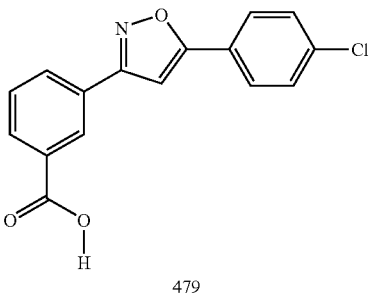
480
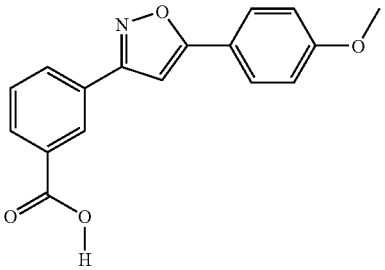 [SMILES: COc1ccc(-c2cc(-c3cccc(C(=O)O)c3)no2)cc1]
481

TABLE X-continued
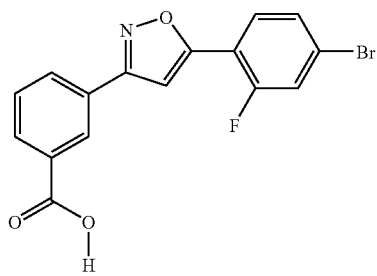 [SMILES: O=C(O)c1cccc(-c2cc(-c3ccc(Br)cc3F)on2)c1]
482
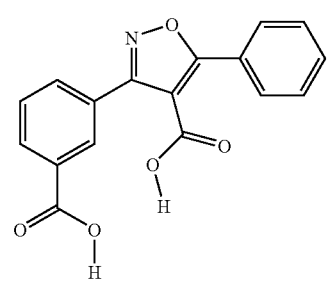 [SMILES: O=C(O)c1cccc(-c2noc(-c3ccccc3)c2C(=O)O)c1]
483
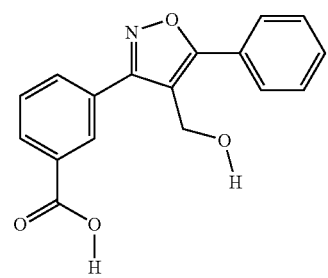 [SMILES: O=C(O)c1cccc(-c2noc(-c3ccccc3)c2CO)c1]
484
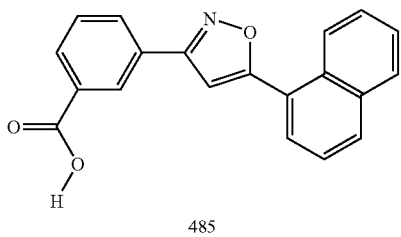
485
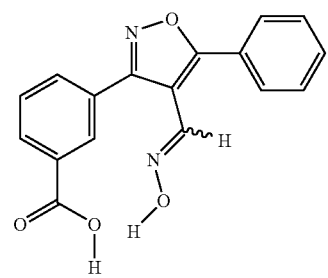 [SMILES: O=C(O)c1cccc(-c2noc(-c3ccccc3)c2C=NO)c1]
486
TABLE X-continued
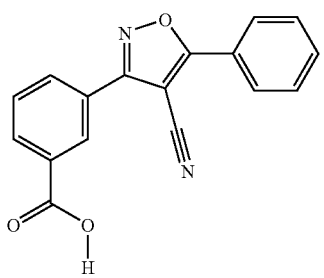 [SMILES: N#Cc1c(-c2cccc(C(=O)O)c2)noc1-c1ccccc1]
487
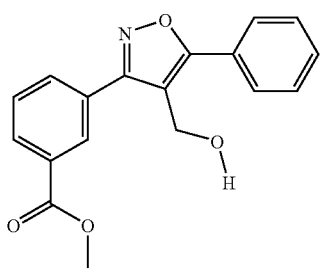 [SMILES: COC(=O)c1cccc(-c2noc(-c3ccccc3)c2CO)c1]
488
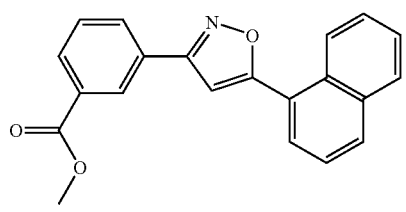 [SMILES: COC(=O)c1cccc(-c2cc(-c3cccc4ccccc34)on2)c1]
489
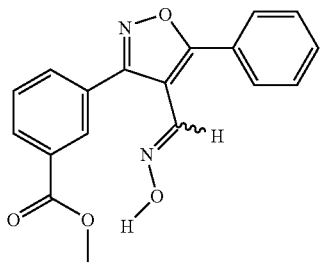 [SMILES: COC(=O)c1cccc(-c2noc(-c3ccccc3)c2C=NO)c1]
490
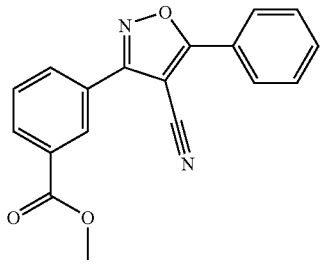 [SMILES: COC(=O)c1cccc(-c2noc(-c3ccccc3)c2C#N)c1]
491

TABLE X-continued
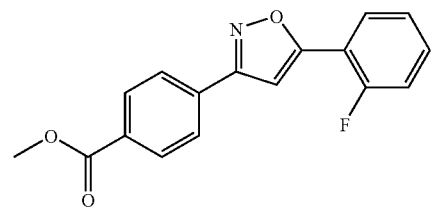 [SMILES: COC(=O)c1ccc(-c2cc(-c3ccccc3F)on2)cc1]
521
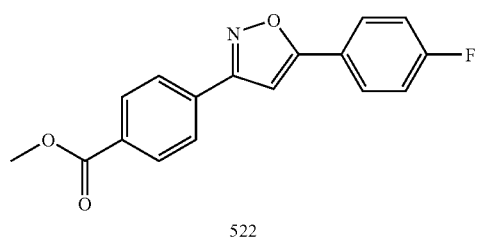
522
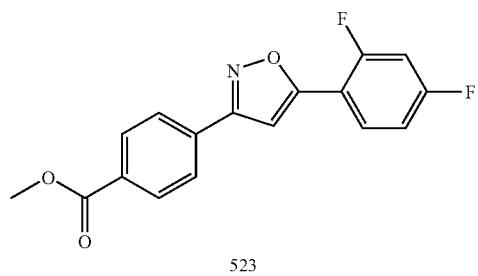
523
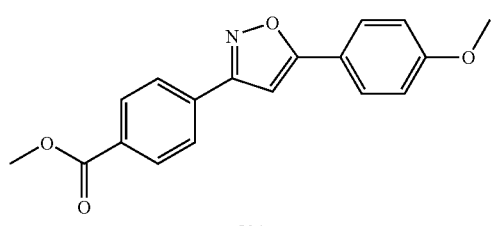
524
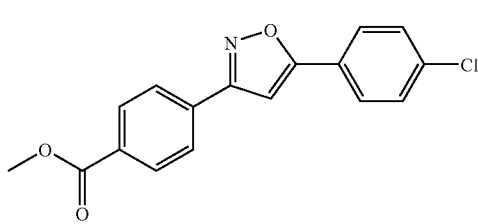 [SMILES: COC(=O)c1ccc(-c2cc(-c3ccc(Cl)cc3)on2)cc1]
525
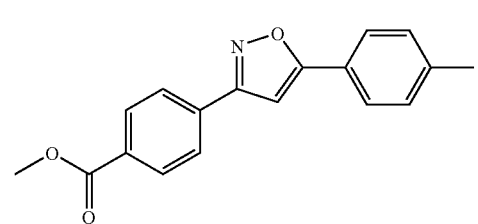
526
TABLE X-continued
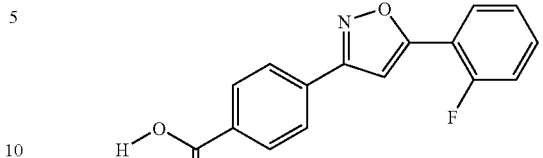
529
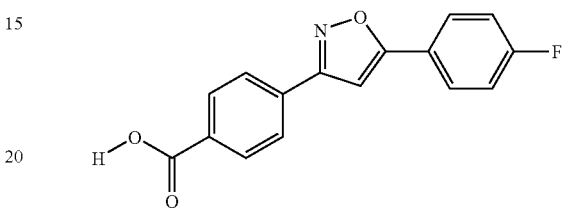
530
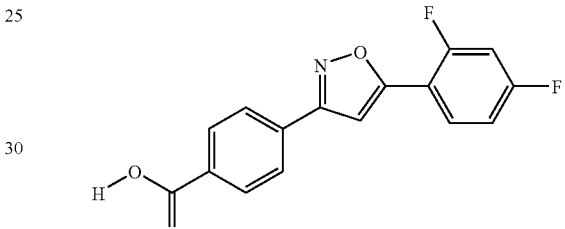
531
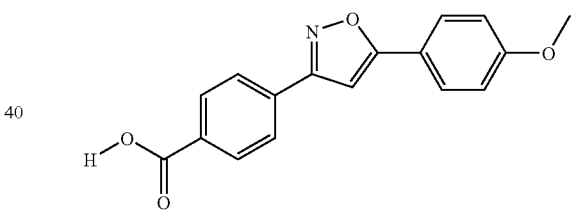
532
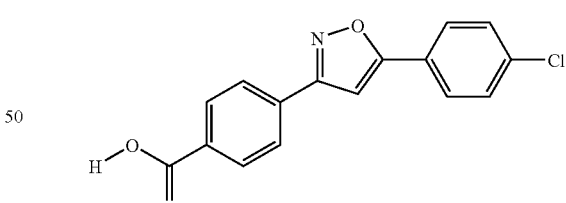
533
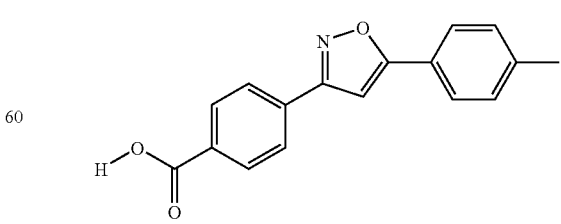
534

TABLE X-continued
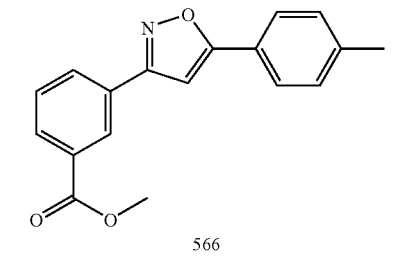
566
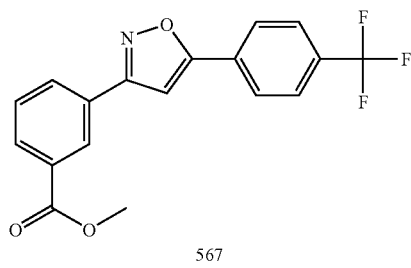
567
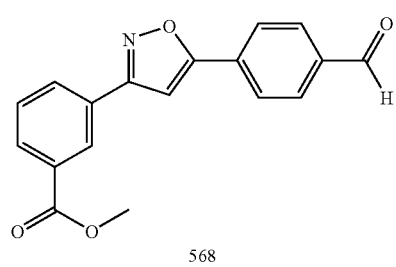
568
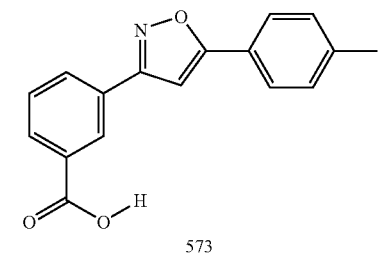
573
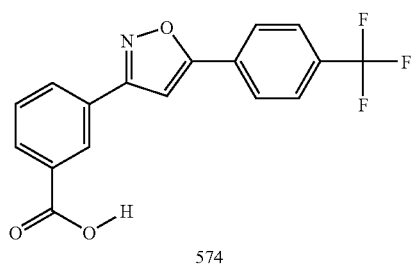
574
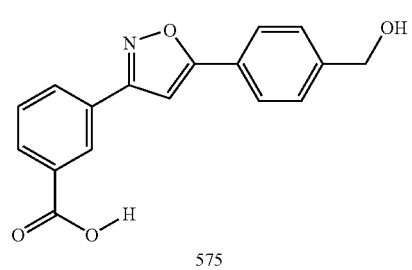
575
TABLE X-continued
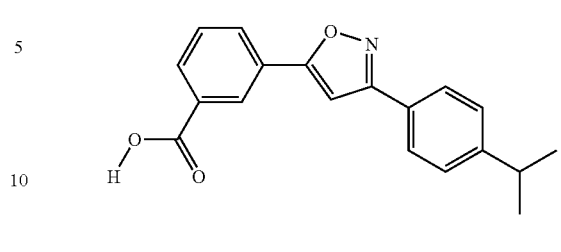
291
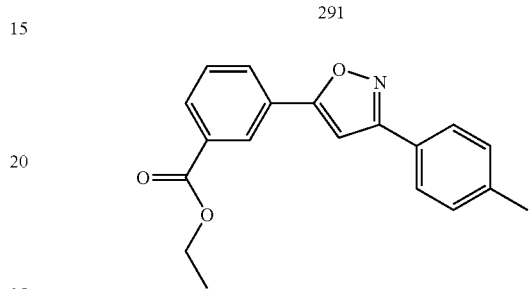
492
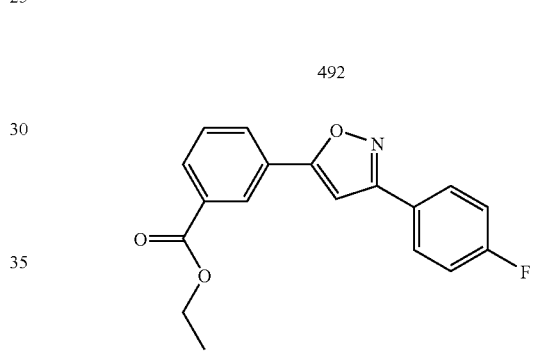
493
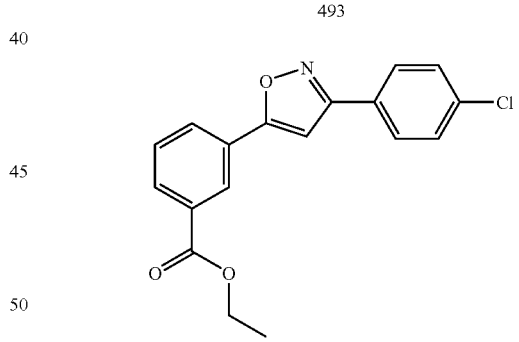
494
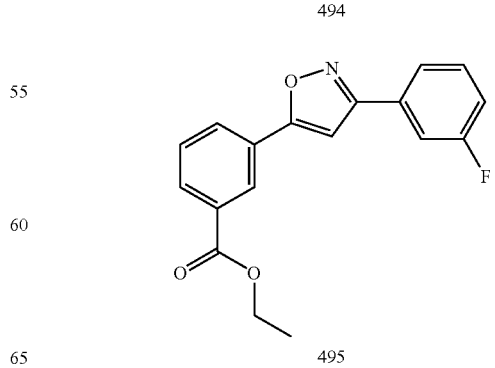
495

TABLE X-continued
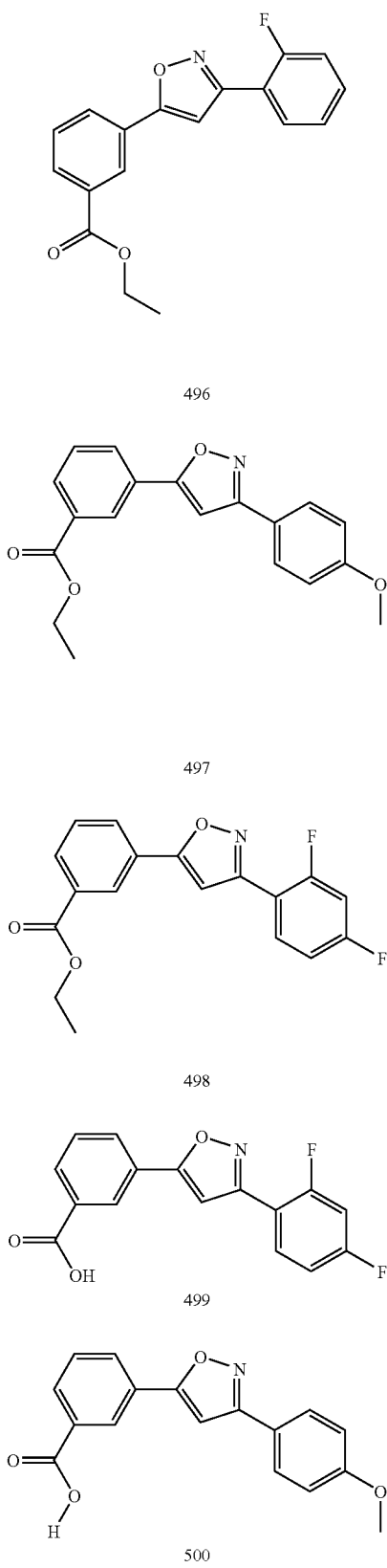
496
497
498
499
500
TABLE X-continued
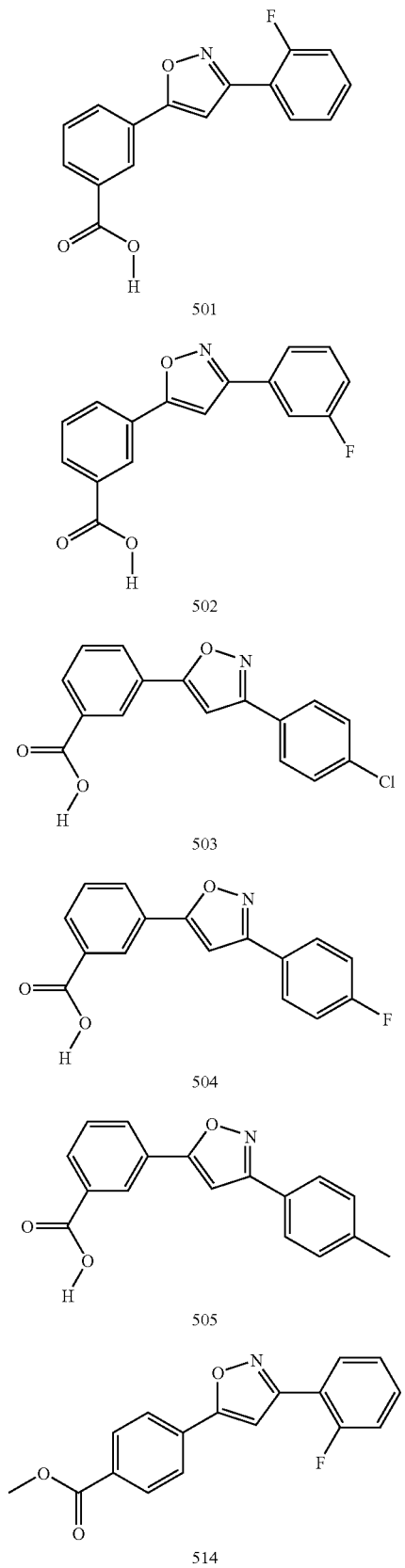
501
502
503
504
505
514

TABLE X-continued
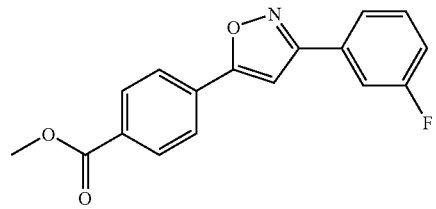 [SMILES: COC(=O)c1ccc(-c2cc(-c3cccc(F)c3)no2)cc1]
515
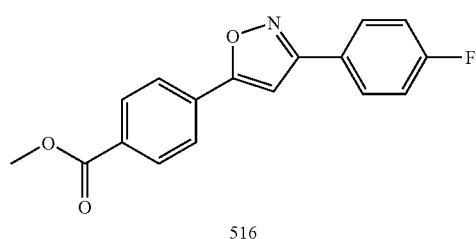
516
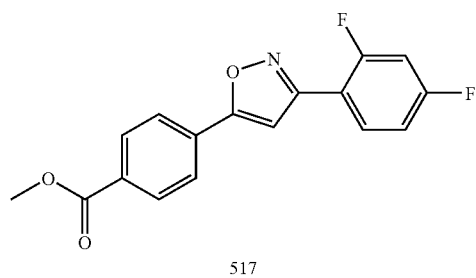
517
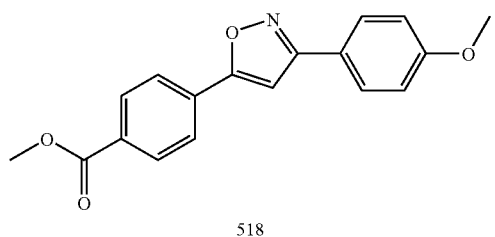
518
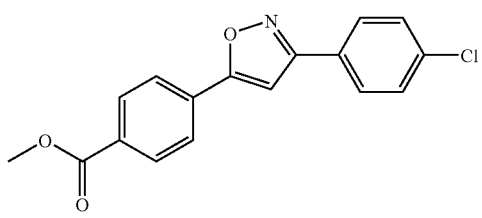 [SMILES: COC(=O)c1ccc(-c2cc(-c3ccc(Cl)cc3)no2)cc1]
519
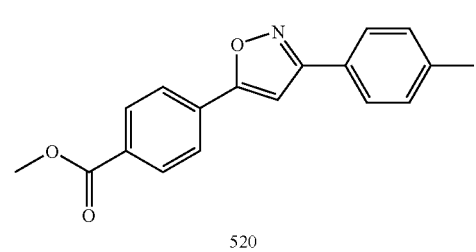
520
TABLE X-continued
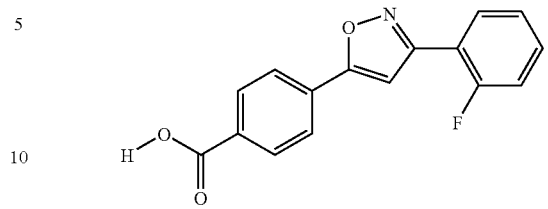
535
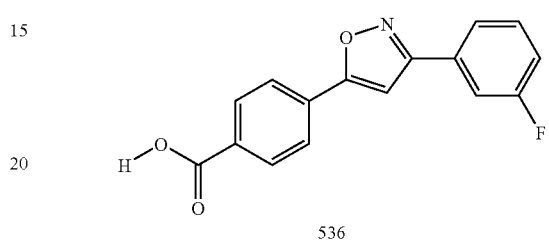
536
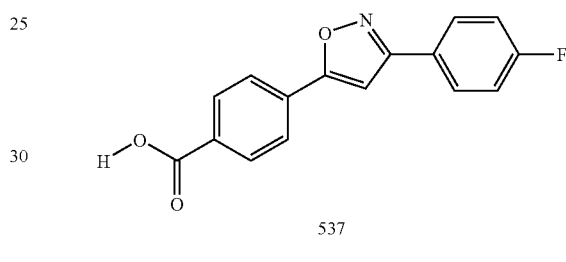
537
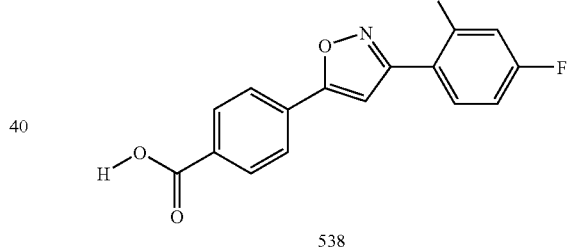
538
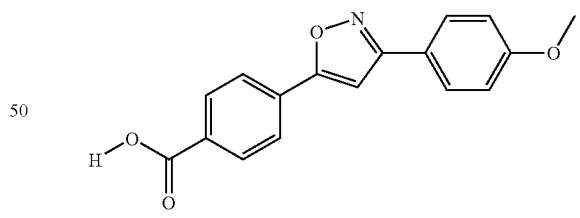
539
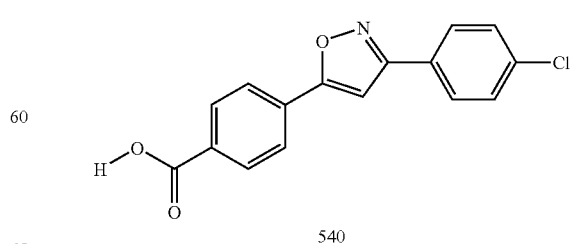
540

TABLE X-continued
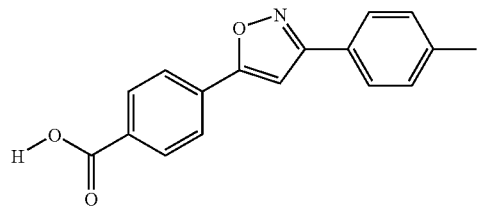 [SMILES: O=C(O)c1ccc(-c2cc(-c3ccc(F)cc3)no2)cc1]
541
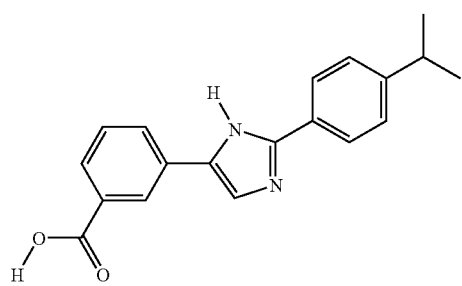 [SMILES: CC(C)c1ccc(-c2ncc(-c3cccc(C(=O)O)c3)[nH]2)cc1]
311
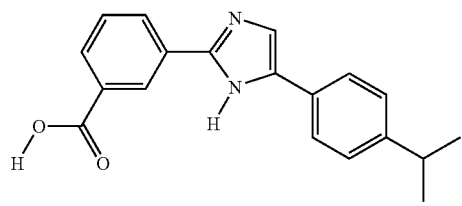 [SMILES: CC(C)c1ccc(-c2cnc(-c3cccc(C(=O)O)c3)[nH]2)cc1]
277
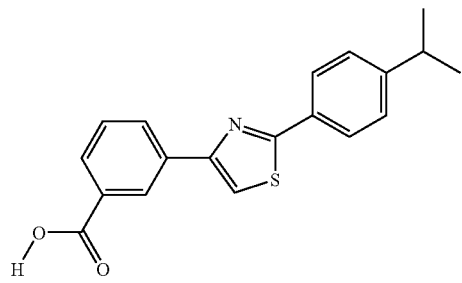 [SMILES: CC(C)c1ccc(-c2nc(-c3cccc(C(=O)O)c3)cs2)cc1]
312
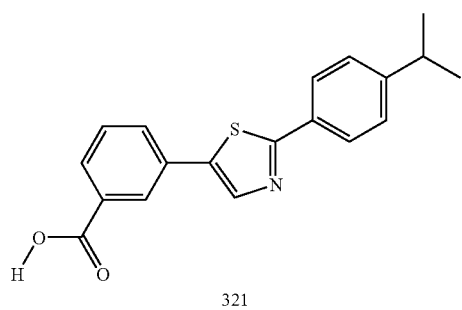
321
TABLE X-continued
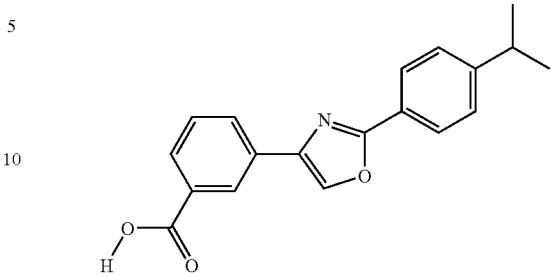
313
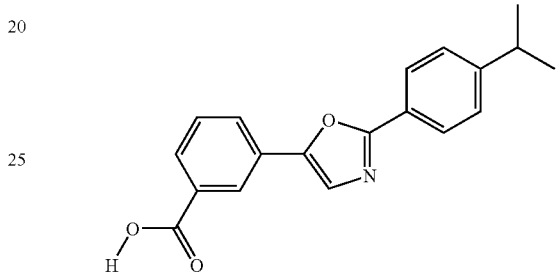
320
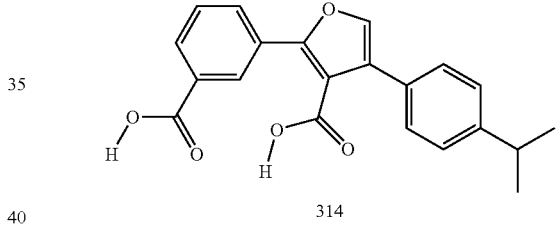
314
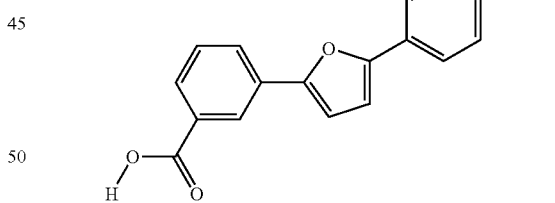
322
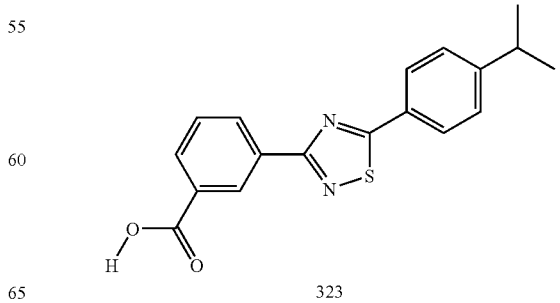
323

TABLE X-continued
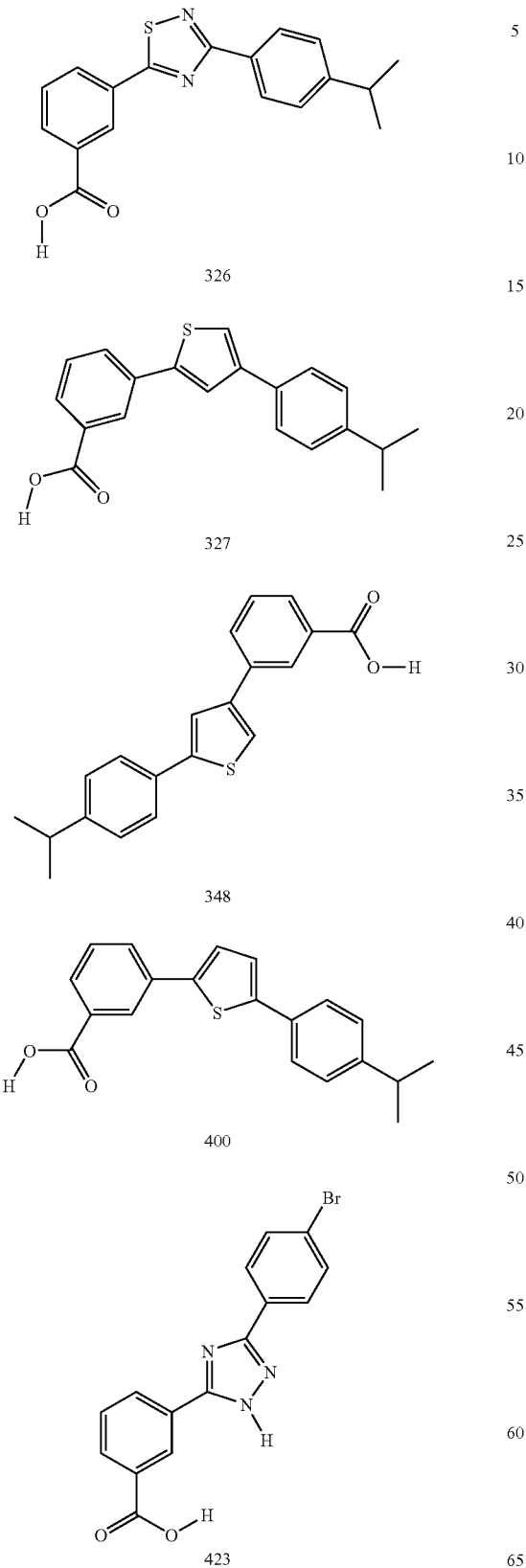
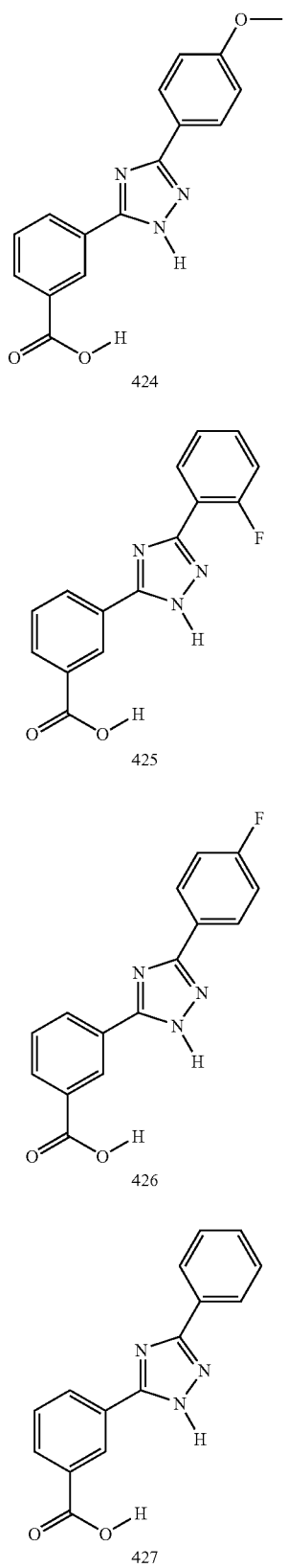

TABLE X-continued
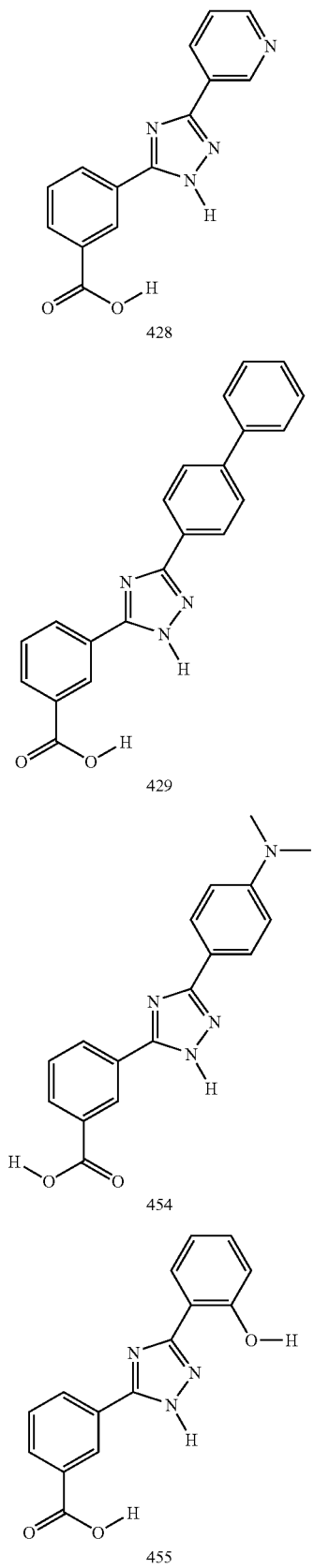
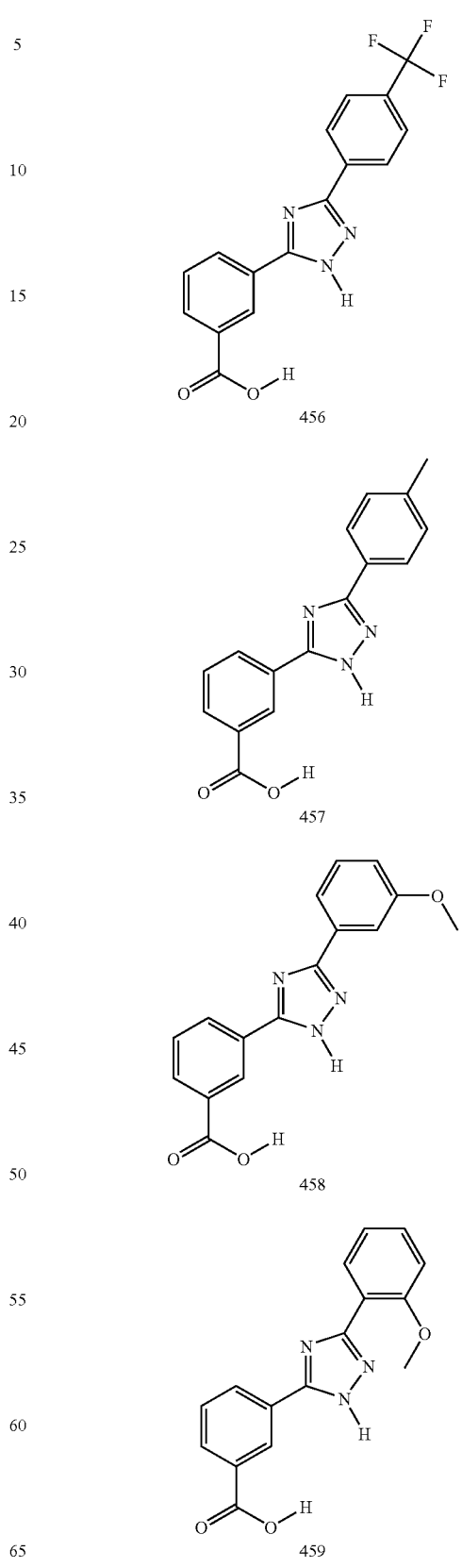

TABLE X-continued

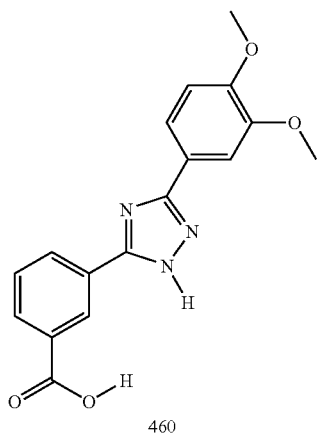

460

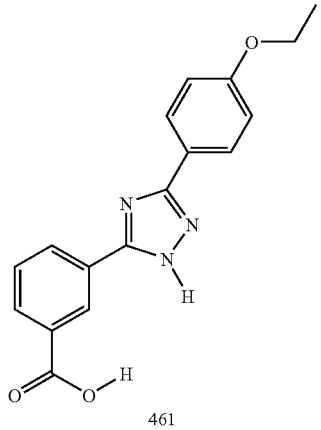

461

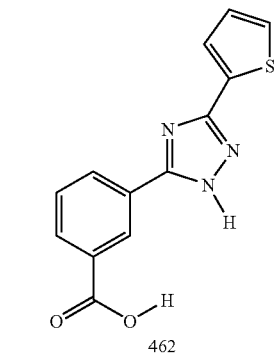

462

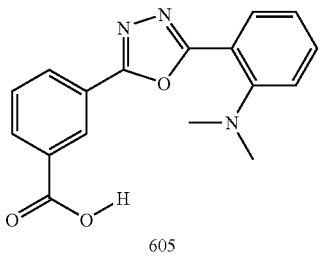

605

The above compounds are listed only to provide examples that may be used in the methods of the invention. Based upon the instant disclosure, the skilled artisan would recognize other compounds intended to be included within the scope of the presently claimed invention that would be useful in the methods recited herein.

B. Preparation of Compounds of the Invention

Compounds of the invention may be produced in any manner known in the art. By way of example, compounds of the invention may be prepared according to the general methodologies described below. For instance, certain 1,3,4-oxadiazoles of Formula 1-A may be prepared by the methodology depicted in Scheme A1 below:

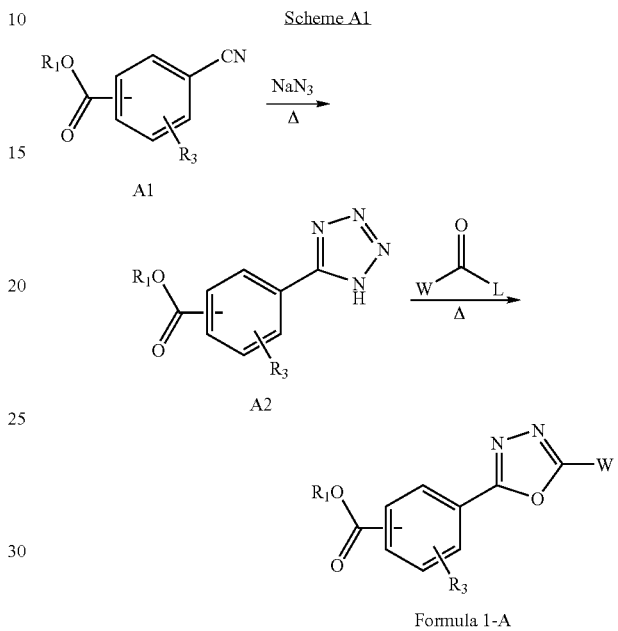

Scheme A1

Formula 1-A

In accordance with Scheme A1, benzonitriles of structure A1 can be converted to tetrazoles of structure A2 by treatment with, e.g., sodium azide. Treatment of the tetrazoles A2 with an activated carboxylic acid, e.g., an acid chloride or an acid activated with a dehydrating agent, e.g., dicyclohexyl carbodiimide in a suitable solvent, affords the 1,3,4-oxadiazole compounds of Formula 1-A. Suitable solvents include, but are not limited to, e.g., toluene or dichloroethane. The reaction can usually carried out within a temperature range of 60-150° C.

In another embodiment, certain 1,3,4-oxadiazoles of Formula 1-A may be prepared by the methodology described in Scheme A2 below.

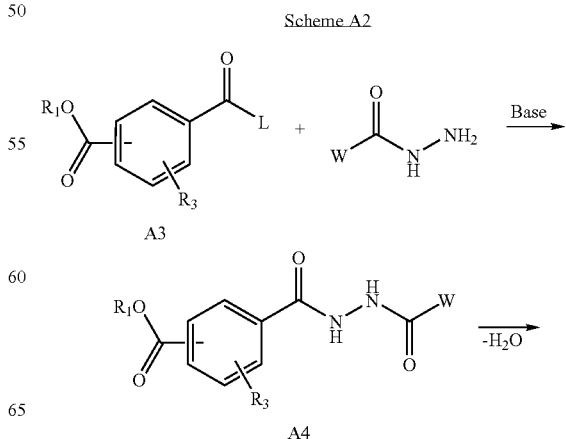

Scheme A2

-continued

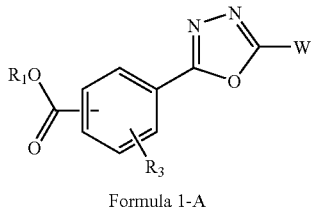

Formula 1-A

In accordance with Scheme A2, activated benzoic acids of structure A3 can be reacted with substituted hydrazides to give substituted benzoyl hydrazides of structure A4. The activating group may be a halide (e.g., an acid chloride or bromide) or derived from treatment of the benzoic acid with a dehydrating agent, e.g., dicyclohexyl carbodiimide). Optionally, a base, e.g., triethylamine, may be employed. Compounds of type A4 can then be dehydrated to form compounds of Formula 1-A. Typical dehydrating agents include, but are not limited to, e.g., dicyclohexyl carbodiimide, or phosphorous oxychloride. The reaction is usually carried out within a range of 20-120° C.

In yet another embodiment, certain 1,3,4-oxadiazoles of Formula 1-A may be prepared by the methodology depicted in Scheme A3 below:

Scheme A3

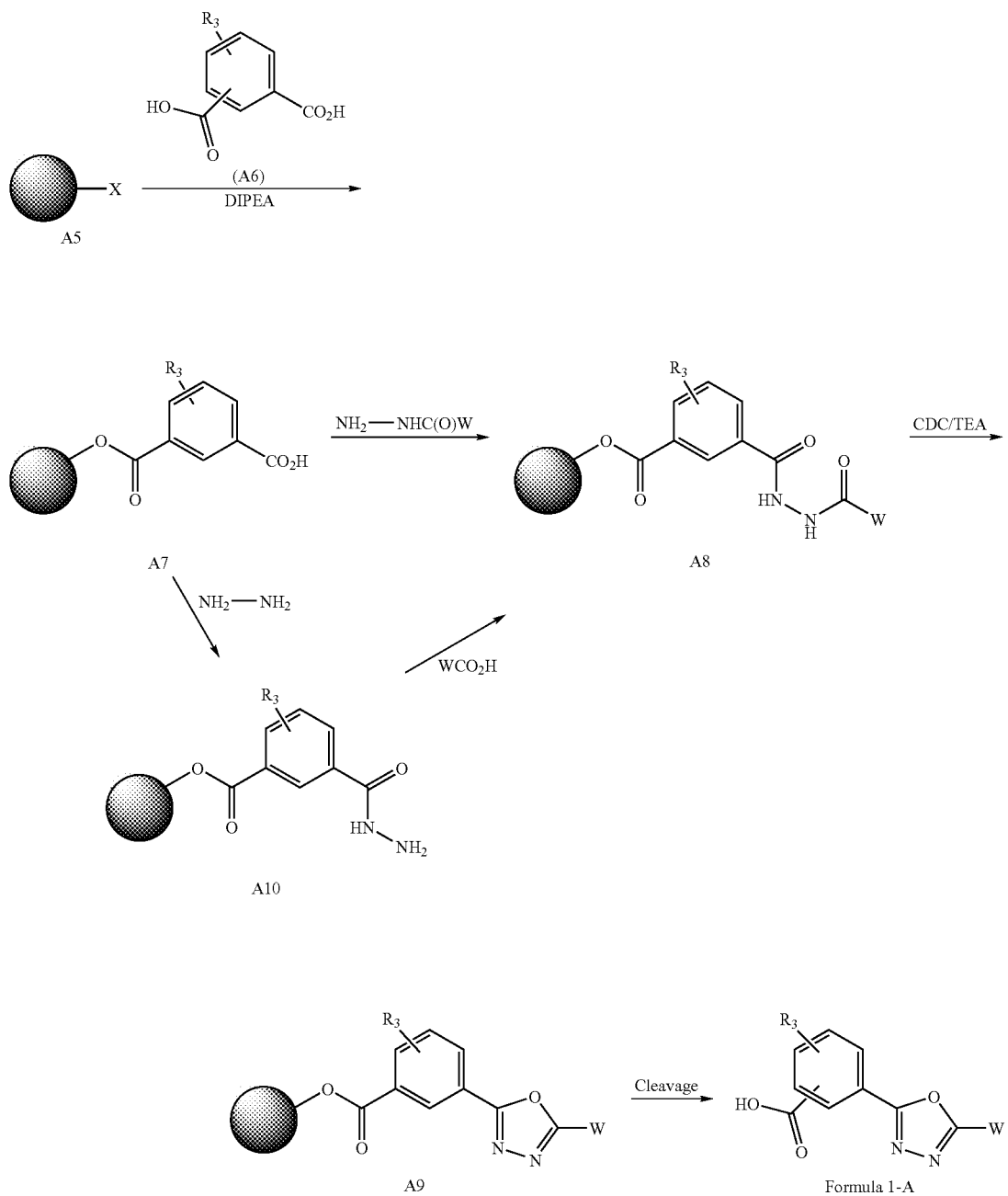

In accordance with Scheme A3, commercially available, acid-labile resin such as trityl resin, 2-chlorotrityl chloride resin, phenylacetamidomethyl (PAM) resin, and p-alkoxybenzyl alcohol resin can be used in this invention. The coupling of carboxylic acid compounds A6 and trityl resin A5 (here X=2-chlorotrityl chloride) can be performed in a suitable solvent such as dichloromethane, dimethylformamide or tetrahydrofuran in the presence of a tertiary amine reagent such as diisopropylethylamine or triethylamine. The resin-bound ester A7 can be treated with hydrazides in the presence of hexafluorophosphate (PYBOP) or equivalents such as diisopropylcarbodiimide, benzotriazole-1-yl-oxytris-pyrrolidino-phosphonium hexafluorophosphate(PyBOP), bromotrispyrrolidinophosphonium hexafluorophosphate (PyBrOP) or 1-ethyl-3-(3-dimethylaminopropyl) carbodiimide hydrochloride (EDC) to give acyl hydrazides A8. Alternatively, the hydrazide resin A10 can be conveniently prepared from A7 under usual amide linkage formation reactions using diisopropyl carbodiimide or equivalents such as benzotriazole-1-yl-oxytrispyrrolidinophosphonium hexafluorophosphate (PyBOP), bromotrispyrrolidinophosphonium hexafluorophosphate (PyBrOP), 1-ethyl-3-(3-dimethylaminopropyl)carbodiimide hydrochloride (EDC) with or without diisopropylethylamine in dimethylformamide. Alternatively, the resin-bound hydrazide resin A10 can be reacted with a carboxylic acid using diisopropylcarbodiimide or equivalents such as benzotriazole-1-yloxytrispyrrolidinophosphonium hexafluorophosphate (PyBOP), bromotrispyrrolidinophosphonium hexafluorophosphate (PyBrOP) or 1-ethyl-3-(3-dimethylaminopropyl)carbodiimide hydrochloride (EDC) to form A8. A ring-closure reaction on resin-bound A8 can be effected by the treatment of 2-chloro-1,3-dimethylimidazolidinium chloride in an inert solvent such as dichloromethane, tetrahydrofuran, dioxane or dimethylformamide with bases such as diisopropylethylamine or triethylamine to afford the 1,3,4-oxdiazole compound A9. The resin-bound oxadiazole compound A9 is cleaved under acidic conditions such as 2N trifluoroacetic acid in dichloromethane, or 3N acetic acid in dichloromethane, to afford the desired compound of Formula 1-A.

Certain 1,3,4-thiadiazoles of Formula 1-B can be prepared by the methodology described in Scheme B below:

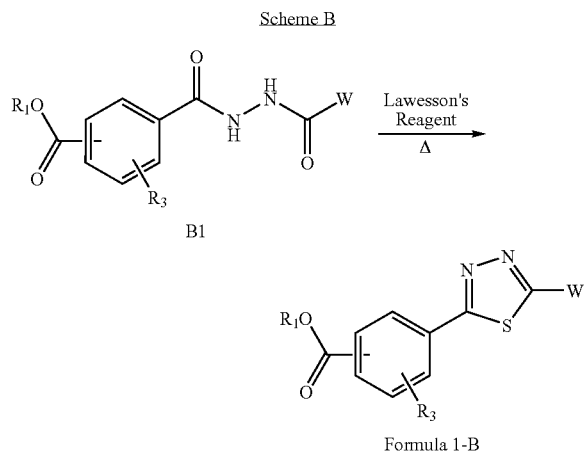

Scheme B

Formula 1-B

In accordance with Scheme B, treatment of benzoyl hydrazides B1 with a thionating reagent, e.g., Lawesson's reagent or phosphorous pentasulfide in a suitably nonreactive organic solvent, e.g., toluene or dioxane, at a temperature range from 50-120° C. can furnish 1,3,4-thiadiazole compounds of Formula 1-B.

Certain 1,2,4-oxadiazoles of Formula 1-C can be prepared by the methodology depicted in Scheme C1 below:

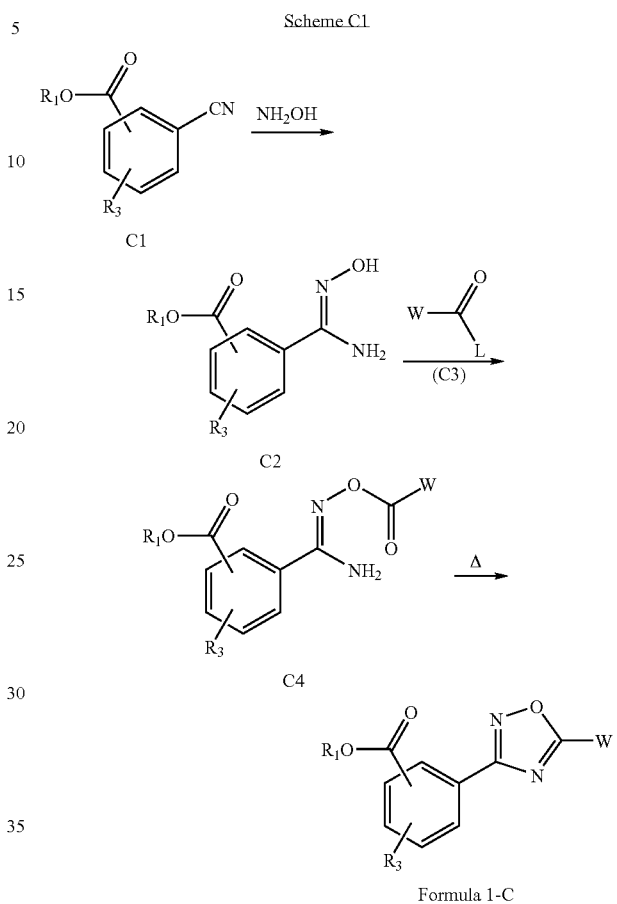

Scheme C1

Formula 1-C

In accordance with Scheme C1, the benzonitrile compound C1 can be converted to the hydroxyamidine C2 by treatment with hydroxylamine or hydroxylamine-HCl. The reaction with hydroxylamine-HCl is usually performed in the presence of a base, such as triethylamine, potassium carbonate or diisopropylethylamine. The reaction can be carried out in a solvent such as methanol, ethanol, tert-butanol, tetrahydrofuran or dimethylformamide, and at temperatures ranging from ambient to the reflux temperature of the chosen solvent. The hydroxyamidine compound C2 is acylated with acyl derivative C3 to give compound C4, wherein the group L represents some leaving group, such as halo, imidazoyl or p-nitrophenol, etc. The reaction is usually carried out with a base, such as triethylamine or diisopropylethylamine, in a solvent such as dichloromethane, tetrahydrofuran or dimethylformamide. In an alternative method, the acylation is conveniently carried out under usual ester linkage formation reactions, wherein the group L represents hydroxy, using diisopropyl carbodiimide or equivalents such as benzotriazole-1-yl-oxytrispyrrolidinophosphonium hexafluorophosphate, bromotrispyrrolidinophosphonium hexafluorophosphate or 1-ethyl-3-(3-dimethylamino-propyl)carbodiimide hydrochloride without or with diisopropylethylamine. The ring-closure of the acylated compound C4 can be accomplished with or without a base such as triethylamine or diisopropylethylamine, in a solvent such as dichloromethane, tetrahydrofuran, toluene or dimethylformamide, and at temperatures ranging from ambient to the reflux temperature of the chosen solvent.

Certain 1,2,4-oxadiazole compounds of Formula 1-C may also be prepared by the method described above using solid phase chemistry as described in Scheme C2, below:

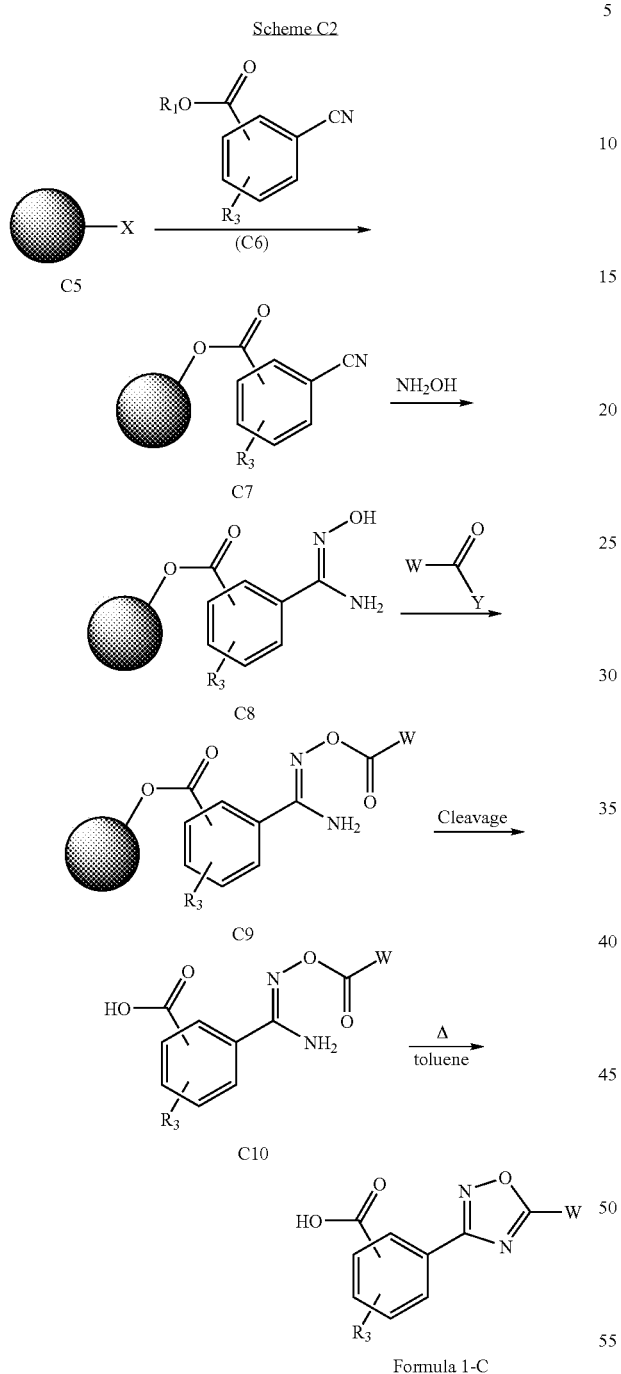

In accordance with Scheme C2, commercially available, acid-labile resin C5 such as trityl resin, 2-chlorotrityl chloride resin, phenylacetamidomethyl (PAM) resin, and p-alkoxybenzyl alcohol resin can be used in this example. The coupling of benzoic acid compounds C6 and trityl resin (here X=2-chlorotrityl chloride) can be performed in a suitable solvent such as dichloromethane, dimethylformamide or toluene in the presence of a tertiary amine reagent such as diisopropylethylamine or triethylamine. The resin-bound cyanobenzoic ester C7 can be treated with hydroxylamine in an inert solvent such as ethanol, tetrahydrofuran, dioxane or dimethylformamide or mixtures with or without diisopropylethylamine to afford the hydroxyamidine compound C8. The resin-bound hydroxyamidine compound C8 can be acylated with a reagent (WCOY), wherein the group Y represents some leaving group, such as halo, imidazoyl, p-nitrophenol, etc. The reaction is typically carried out in the presence of a base, such as diisopropylethylamine or triethylamine, in an inert solvent such as dichloromethane, tetrahydrofuran or dimethylformamide or mixtures. Alternatively, the acylation is conveniently carried out with a reagent (WCOY), wherein the group Y represents hydroxy, using diisopropylcarbodiimide or equivalents such as benzotriazole-1-yloxytrispyrrolidino-phosphonium hexafluorophosphate, bromotrispyrrolidinophosphonium hexafluorophosphate or 1-ethyl-3-(3-dimethylaminopropyl) carbodiimide hydrochloride without or with diisopropylethylamine in dimethylformamide. The resin-bound acylated compound C9 is cleaved under acidic conditions such as 2N trifluoroacetic acid in dichloromethane, or 3N acetic acid in dichloromethane, to afford the desired intermediate compound C10. A ring-closure reaction on free acid compound C10 can be effected by heating in an inert solvent such as toluene, tetrahydrofuran, dioxane or dimethylformamide or mixtures with or without a base reagent such as diisopropylethylamine, triethylamine or tetrabutylammonium fluoride to afford the 1,2,4-oxdiazole compounds of Formula 1-C.

Certain 1,2,4-oxadiazoles of Formula 1-D can be prepared by the methodology depicted in Scheme D1 below:

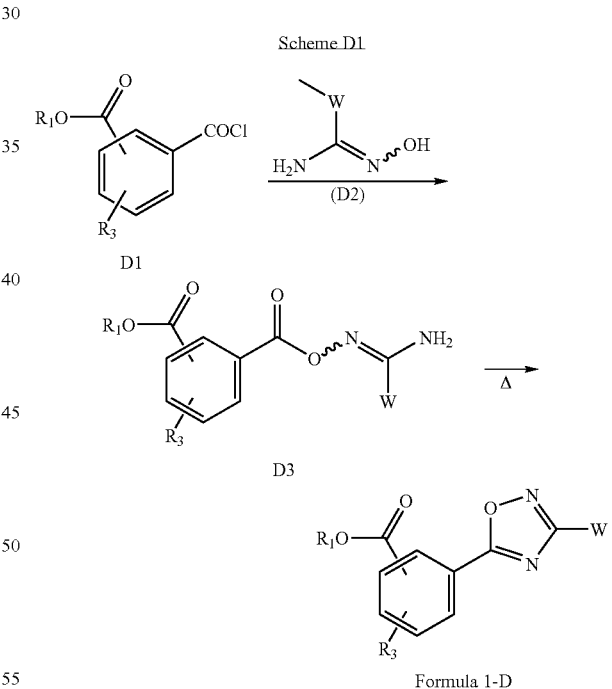

In accordance with Scheme D1, acyl chlorides of structure D1 can be treated with a hydroxyamidine reagent D2 in the presence of a base, such as N-methylmorpholine, N,N-diisopropylethylamine, or triethylamine, in an inert solvent such as dichloromethane, tetrahydrofuran or dimethylformamide or mixtures. Hydroxyamidine compounds D2 can be conveniently prepared from treatment of nitrites with hydroxylamine in an inert solvent such as, e.g., ethanol, dioxane, or tetrahydrofuran. Ring-closure of the compound D3 can be effected by heating in an inert solvent such as toluene, tetrahydrofuran, dioxane or dimethylformamide or mixtures with or without a base reagent such as diisopropylethylamine, triethylamine or tetrabutylammonium fluoride to afford the 1,2,4-oxadiazole compounds of Formula 1-D.

Certain 1,2,4-oxadiazole compounds of Formula 1-D may also be prepared by the method described above using solid phase chemistry as described in Scheme D2, below:

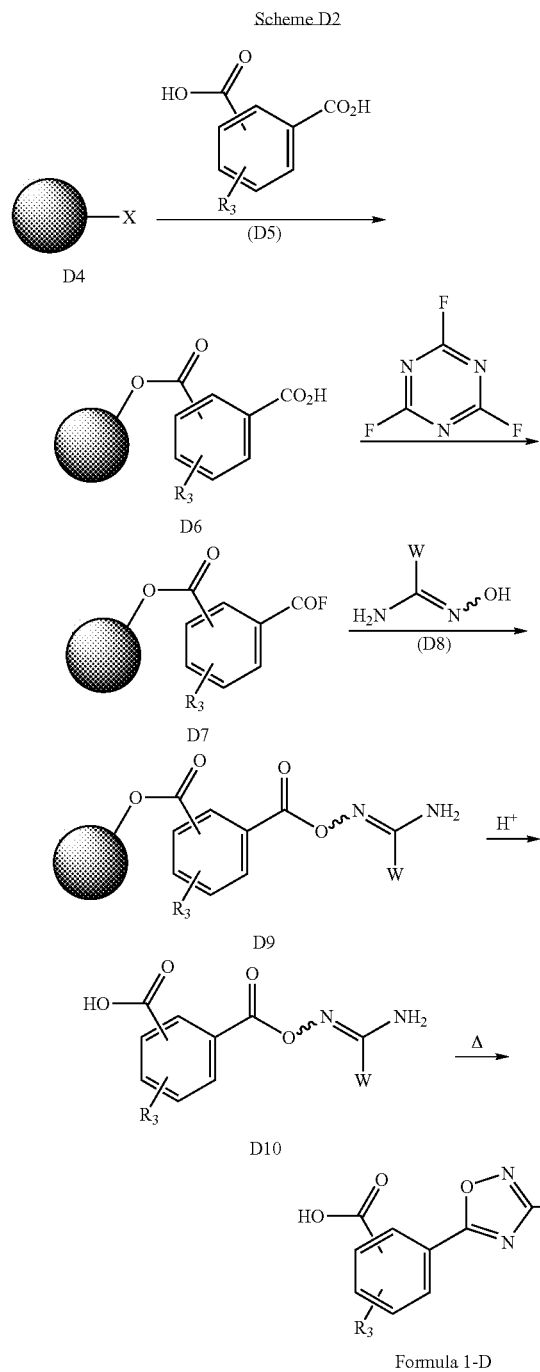

In accordance with Scheme D2, commercially available, acid-labile resin D4, such as trityl resin, 2-chlorotrityl chloride resin, phenylacetamidomethyl (PAM) resin, or p-alkoxybenzyl alcohol resin, is used in this example. The coupling of benzoic acid compound D5 and trityl resin (here X=2-chlorotrityl chloride) can be performed in a suitable solvent such as dichloromethane, dimethylformamide, or toluene in the presence of a tertiary amine reagent such as diisopropylethylamine or triethylamine to give acylated resin D6. In an alternative method, the acylated resin D6 is conveniently prepared by standard ester linkage formation conditions using diisopropylcarbodiimide (for phenylacetamidomethyl resin and p-alkoxybenzyl alcohol resin) or equivalents such as benzotriazole-1-yloxytrispyrrolidinophosphonium hexafluorophosphate (PyBOP), bromotrispyrrolidinophosphonium hexafluorophosphate (PyBrOP) or 1-ethyl-3-(3-dimethylaminopropyl)carbodiimide hydrochloride (EDC) without or with diisopropylethylamine in dimethylformamide. The resin-bound carboxybenzoic ester D6 can be treated with cyanuric fluoride and a tertiary amine base, such as N-methyl morpholine, triethylamine, or N,N-diisopropylethylamine, in an inert solvent such as dichloromethane, dioxane, tetrahydrofuran, or dimethylformamide to afford the acyl fluoride compound D7.

The combinatorial chemistry method may use multi-reaction vessels, where a different combination of reagents used in each vessel to provide library compounds of interest. The resin-bound acyl fluoride compound D7 is treated with a reagents of structure D8 in the presence of a base, such as N-methylmorpholine, N,N-diisopropylethylamine, or triethylamine, in an inert solvent such as dichloromethane, tetrahydrofuran or dimethylformamide or mixtures to give compounds D9. Hydroxyamidines D8 can be conveniently prepared from treatment of nitriles with hydroxylamine in an inert solvent such as ethanol, dioxane, or tetrahydrofuran. The resin-bound acylated compound D9 can be cleaved under acidic conditions such as 2N trifluoroacetic acid in dichloromethane or 3N acetic acid in dichloromethane, to afford the desired compound D10. Ring-closure of free acid compound D10 can be effected by heating in an inert solvent such as toluene, tetrahydrofuran, dioxane or dimethylformamide or mixtures with or without a base reagent such as diisopropylethylamine, triethylamine or tetrabutylammonium fluoride to afford the 1,2,4-oxdiazole compounds of Formula 1-D.

Certain oxazoles of Formula 1-E can be prepared by the methodology described in Scheme E1 below:

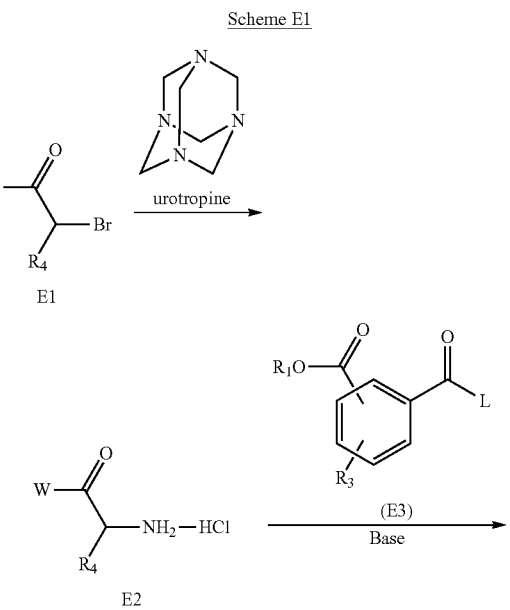

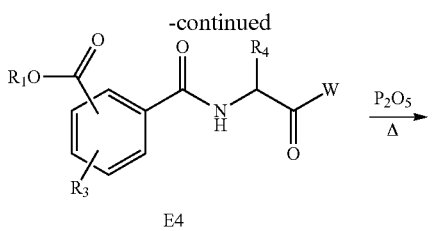

E4

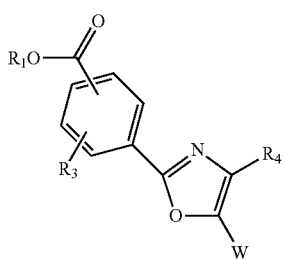

Formula 1-E

In accordance with Scheme E1, α-Bromoketones of structure E1 can be converted to α-aminoketones of structure E2 with such reagents as e.g., urotropine. Reaction of the α-aminoketones E2 with activated acids of type E3 in the presence of base can give compounds of structure E4. The activated acid E3 can be either an acid chloride or an acyl imidazolide. Dehydration of the intermediate E4 with reagents such as phosphorous pentoxide or phosphorous oxychloride within a temperature range from ambient to 120° C. gives the oxazoles of Formula 1-E.

Certain oxazoles of Formula 1-E can also be prepared by the methodology depicted in Scheme E2 below:

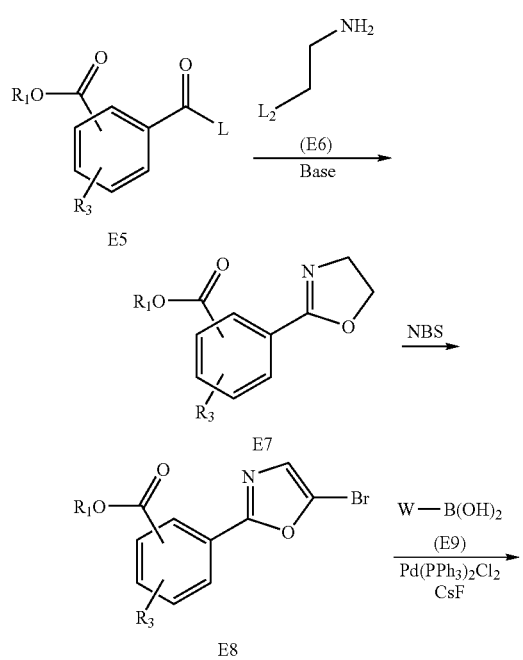

Formula 1-E

In accordance with Scheme E2, carboxylic acids E5 in which one carboxyl group is activated as the acid chloride or similar activating group can react with ethylamines of the type E6 (in which $L_2$ is a leaving group) in the presence of a base, such as triethylamine, to give the dihydrooxazole E7. Reaction of E7 with N-bromosuccinimide in refluxing carbon tetrachloride with a catalytic amount of a radical initiator such as azobisisobutyronitrile gives the bromooxazole E8. The bromooxazole E8 can react with arylboronic acids E9 in the presence of a Pd catalyst such as, but not limited to, tetrakistriphenylphosphine palladium(0) or dichlorobis(triphenylphosphine)palladium(II) and a base such as cesium fluoride or potassium carbonate and a solvent such as toluene, dimethylformamide or dimethoxyethane to give the oxazole compounds Formula 1-E.

Certain oxazoles of Formula 1-F can be prepared by the methodology described in Scheme F below:

Scheme F

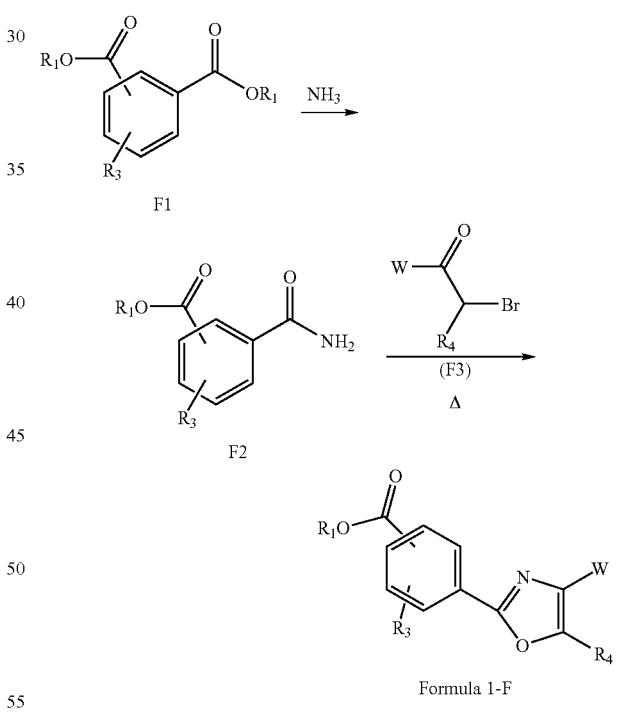

Formula 1-F

In accordance with Scheme F, amide formation of esters of structure F1 and ammonium hydroxide can be performed in a suitable solvent such as water, tetrahydrofuran, dioxane or dimethylformamide or a mixture with heating to give compounds of structure F2. Heating compounds of structure F2 with α-bromoketones in inert solvents such as toluene, tetrahydrofuran, dioxane or dimethylformamide or mixtures, at temperatures of 60-150° C. can afford the desired oxazole compounds of Formula 1-F.

Certain pyrazoles of Formula 1-G can be prepared by the methodology depicted in Scheme G1 shown below or by those skilled in the art.

Scheme G1

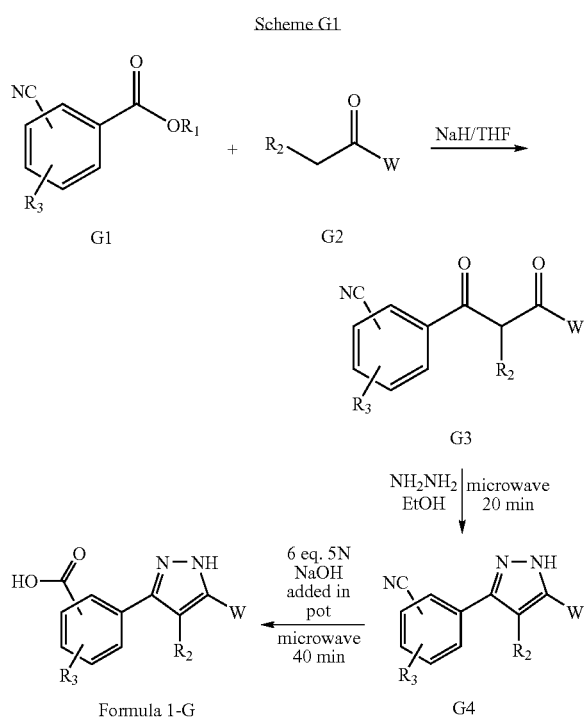

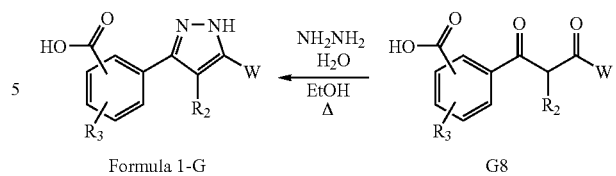

In accordance with Scheme G1, substituted diketones G3 can be prepared by the treatment of substituted acetophenones G2 with sodium hydride in a suitable solvent such as tetrahydrofuran and subsequent reaction with cyanobenzoic esters of type G1. In a 1-pot microwave sequence, the 1,3-diketones of structure G3 can be reacted with 1.1 equivalents of anhydrous hydrazine in a protic solvent such as ethanol at a power of 300 W and a temperature not exceeding 100° C. to afford pyrazole benzonitriles of type G4 which is then subsequently reacted with six equivalents of aqueous 1N sodium hydroxide under identical microwave conditions to afford pyrazole acids of Formula 1-G.

Certain pyrazoles of Formula 1-G can also be prepared by the methodology described in Scheme G2 below:

Scheme G2

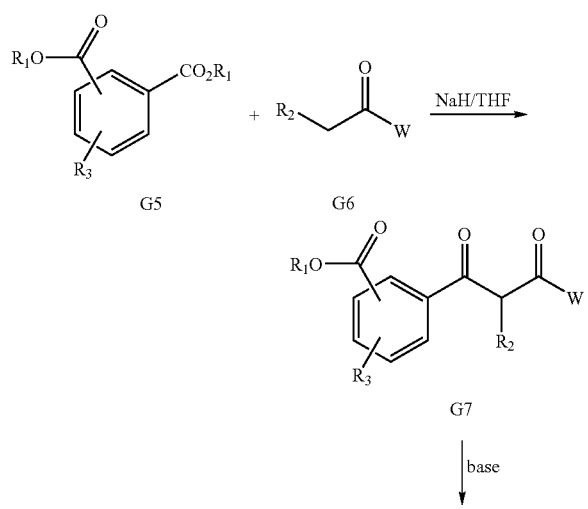

In accordance with Scheme G2, reaction of esters of type G5 with substituted acetophenones of type G6 in the presence of a base, e.g., sodium hydride, in a suitable solvent such as tetrahydrofuran, can give 1,3-diketones of structure G7. Hydrolysis of the ester affords carboxylic acids of structure G8. The acid can then be reacted with hydrazine in a protic solvent such as ethanol at reflux to afford the pyrazoles of Formula 1-G.

Certain thiazoles of Formula 1-I can be prepared by the methodology depicted in Scheme I shown below.

Scheme I

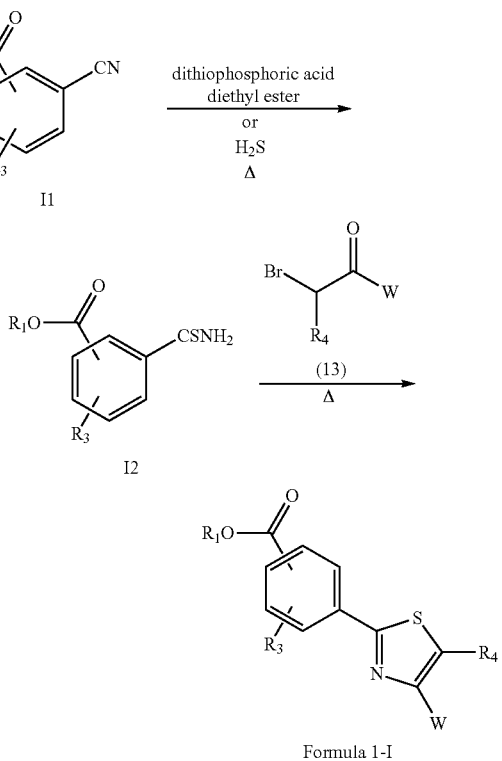

In accordance with Scheme I, benzonitriles of structure I1 can be converted to thioamide compounds of structure I2 by treatment with dithiophosphoric acid diethyl ester in inert solvents such as water, tetrahydrofuran, dioxane or dimethylformamide or mixtures at reflux temperature. Alternatively, hydrogen sulfide gas can be used for the conversion of the nitrile to the thioamide. Reaction of the thioamides I2 with α-bromoketones I3 with heating in inert solvents such as toluene, tetrahydrofuran, dioxane or dimethylformamide or mixtures, afford the desired thiazole compounds of Formula 1-I.

Certain thiazoles of Formula 1-J can be prepared by the methodology depicted in Scheme J below:

Scheme J

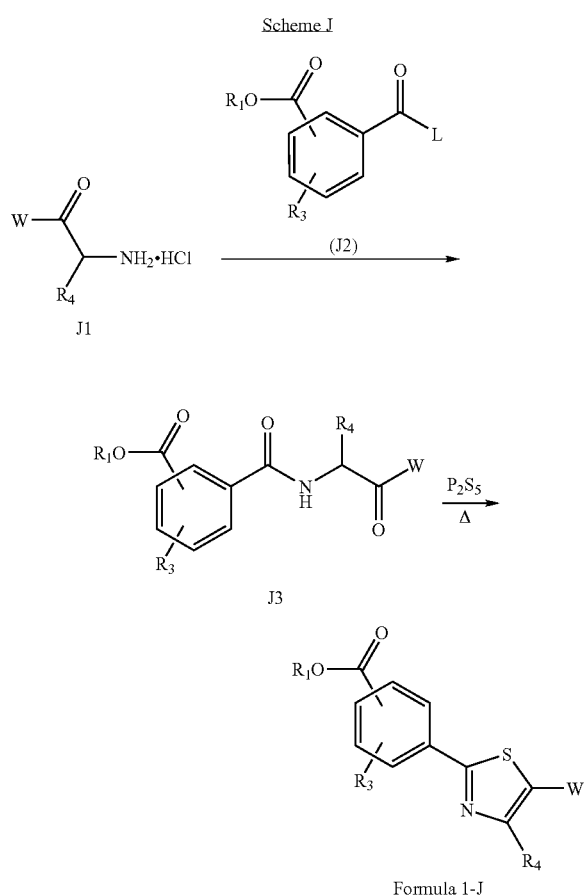

In accordance with Scheme J, α-Aminoketones of structure J1 can be reacted with activated carboxylic acid derivatives of type J2, e.g., acid chlorides or acyl imidazolides, in a suitable non-reactive organic solvent, optionally in the presence of a base, e.g., triethylamine, to give compounds of structure J3. Heating compounds of type J3 with phosphorous pentasulfide in the presence of a solvent, e.g., pyridine, can give the thiazoles of Formula 1-J.

Certain isoxazoles of Formula 1-K can be prepared by the methodology depicted in Scheme K below:

Scheme K

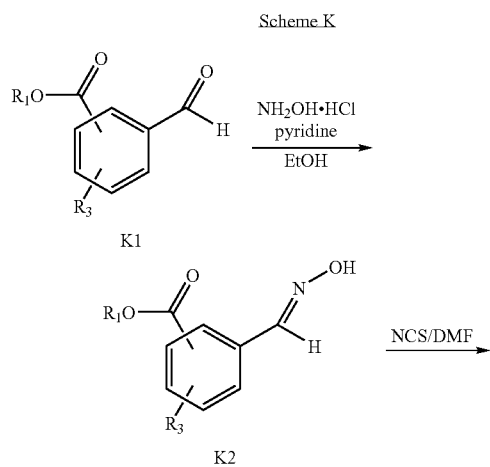

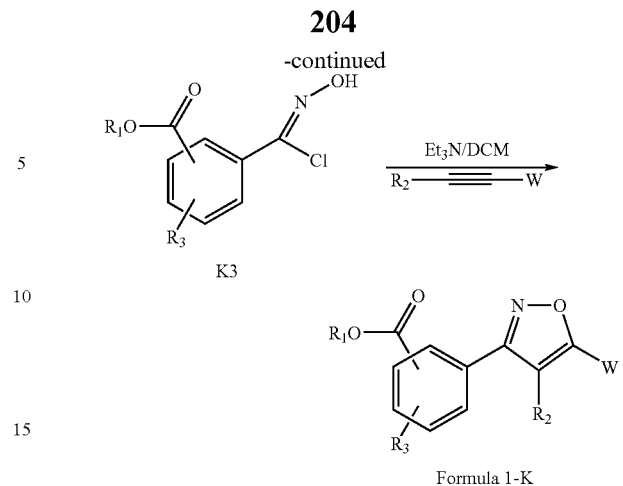

In accordance with Scheme K, oximes of structure K2 can be derived from commercial benzaldehydes of structure K1 using hydroxylamine hydrochloride and a base such as pyridine in a protic solvent, such as ethanol. Reaction of oxime K2 with N-chlorosuccinimide in dimethylformamide in the presence of gaseous hydrochloric acid catalyst can afford α-chlorooximes of structure K3. Treatment of K3 in a suitable organic solvent such as dichloromethane with a base such as triethylamine at 0° C. to room temperature and a substituted acetylene, available commercially or prepared by those skilled in the art, can afford an isoxazole ester of Formula 1-K.

Certain isoxazoles of Formula 1-L can be prepared by the methodology depicted in Scheme L.

Scheme L

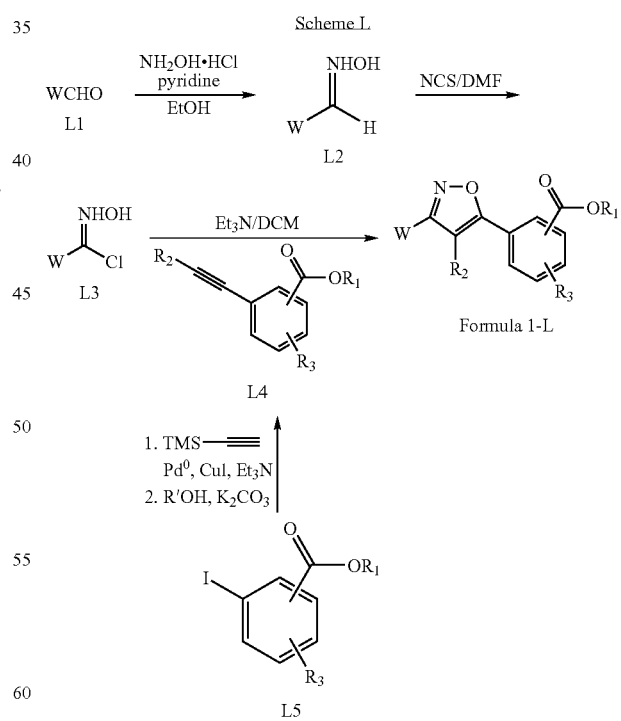

In accordance with Scheme L, oximes of structure L2 can be derived from commercial benzaldehydes of structure L1 using hydroxylamine hydrochloride and a base such as pyridine in a protic solvent, preferably ethanol. Reaction of oxime L2 with N-chlorosuccinimide in dimethylformamide in the presence of gaseous hydrochloric acid catalyst can afford α-chlorooxime of structure L3. Treatment of L3 in a suitable organic solvent such as dichloromethane with a base such as triethylamine at 0° C. or room temperature and a substituted acetylene L4, prepared by those skilled in the art using a two step sequence from the corresponding iodides L5 can afford isoxazoles of Formula 1-L. Alternatively, other halides of formula L5, such as bromides and chlorides in place of the iodide can also be used to effect the two step transformation to acetylene L4 by those skilled in the art.

Certain imidazoles of Formula 1-M can be prepared by the methodology depicted in Scheme M shown below:

Scheme M

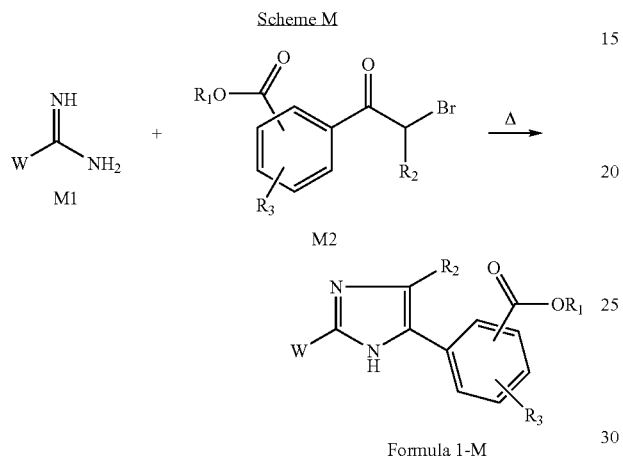

Formula 1-M

In accordance with Scheme M, heating amidines of structure M1 with α-bromoketones of structure M2 in the presence of a non-reactive solvent affords the imidazoles of Formula 1-M. The amidines may be obtained commercially or prepared by methods known by those skilled in the art for example by treatment of the appropriate nitrile precursors with, e.g., sodium amide or sodium hexamethyldisilazide. The reaction between M1 and M2 can be carried out at a temperature range from ambient to 150° C.

Certain imidazoles of Formula 1-N can be prepared by the methodology depicted in Scheme N.

Scheme N

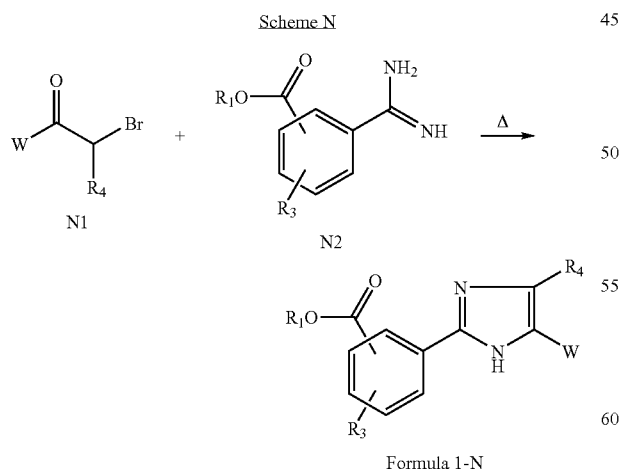

Formula 1-N

In accordance with Scheme N, heating α-bromoketones of structure N1 with amidines of structure N2 in the presence of a non-reactive solvent affords the imidazoles of Formula 1-N. The amidines may be prepared by methods known by those skilled in the art, for example by treatment of the appropriate nitrile precursors with, e.g., lithium or sodium hexamethyldisilazide. The reaction between N1 and N2 can be carried out at a temperature range from ambient to 150° C.

Certain thiazoles of Formula 1-O can be prepared by the methodology depicted in Scheme O shown below:

Scheme O

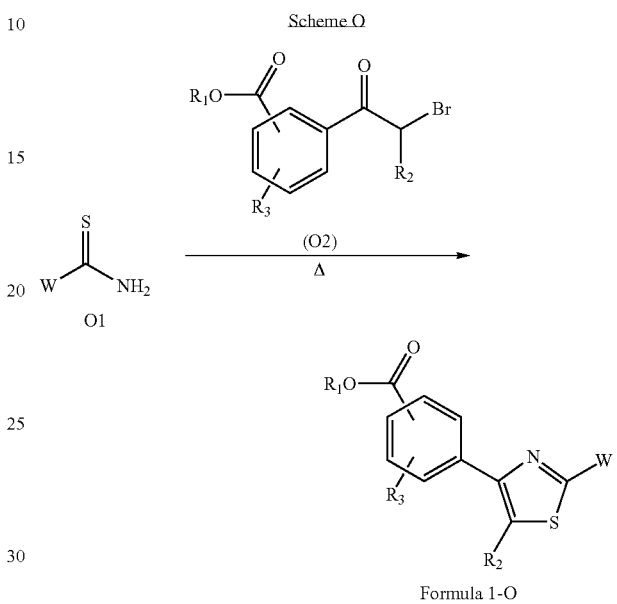

Formula 1-O

In accordance with Scheme O, reaction of the thioamides O1 with α-bromoketones O2 with heating in inert solvents such as toluene, tetrahydrofuran, dioxane or dimethylformamide or mixtures, afford the desired thiazole compounds of Formula 1-O. The thioamides may be purchased commercially, prepared from amides with reagents such as Lawesson's reagent or phosphorous pentasulfide or prepared from nitrites with such reagents as hydrogen sulfide or dithiophosphoric acid diethyl ester.

Certain thiazoles of Formula 1-P can be prepared by the methodology depicted in Scheme P1 shown below:

Scheme P1

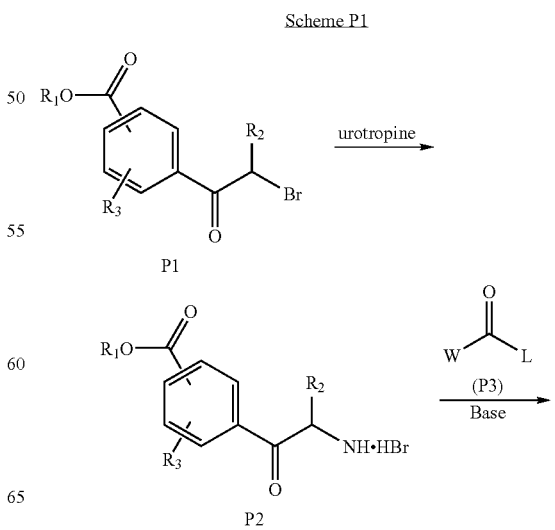

-continued

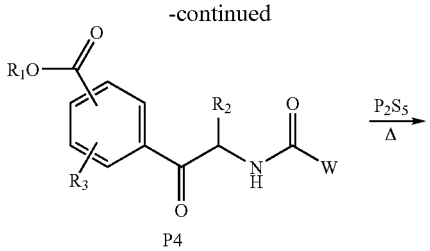

P4

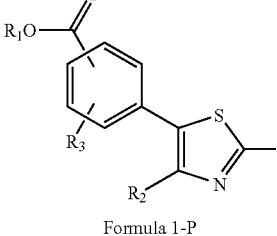

Formula 1-P

In accordance with Scheme P1, α-Bromoketones of structure P1 can be converted to α-aminoketones of structure P2 with, e.g., urotropine. Reaction of the α-aminoketones P2 with carboxylic acid derivatives of type P3 in the presence of base gives compounds of structure P4. Thio-dehydration and concomitant cyclization of the intermediate P4 with reagents such as phosphorous pentasulfide within a temperature range from ambient to 120° C. gives the thiazoles of Formula 1-P.

Certain thiazoles of Formula 1-P can also be prepared by the methodology depicted in Scheme P2 shown below:

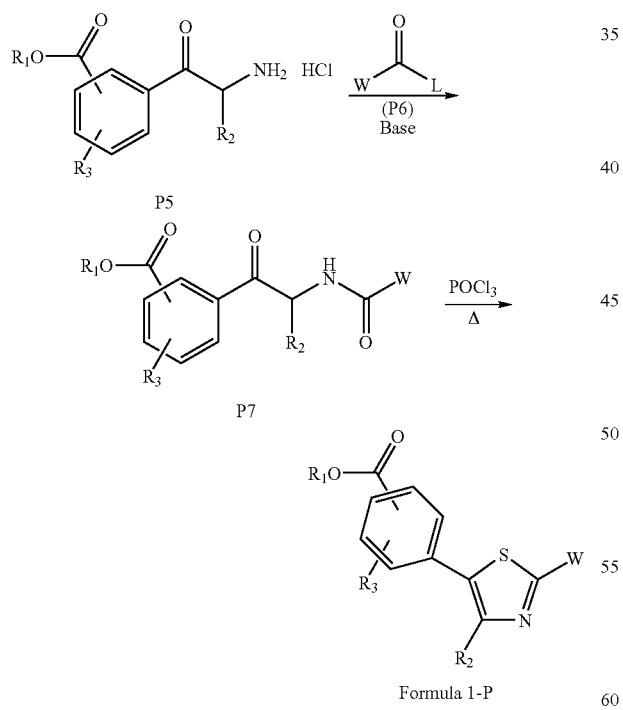

In accordance with Scheme P2, α-Aminoketones P5 (prepared as described in Scheme R) can be reacted with activated carboxylic acid derivatives (P6) e.g., acid chlorides or acyl imidazolides, in a suitable solvent, optionally in the presence of a base, e.g., triethylamine, to give compounds of structure P7. Thiodehydration of P7 with reagents such as phosphorous pentasulfide or Lawesson's reagent within a temperature range from ambient to 120° C. gives thiazole compounds Formula 1-P.

Certain oxazoles of Formula 1-Q can be prepared by the methodology depicted in Scheme Q below:

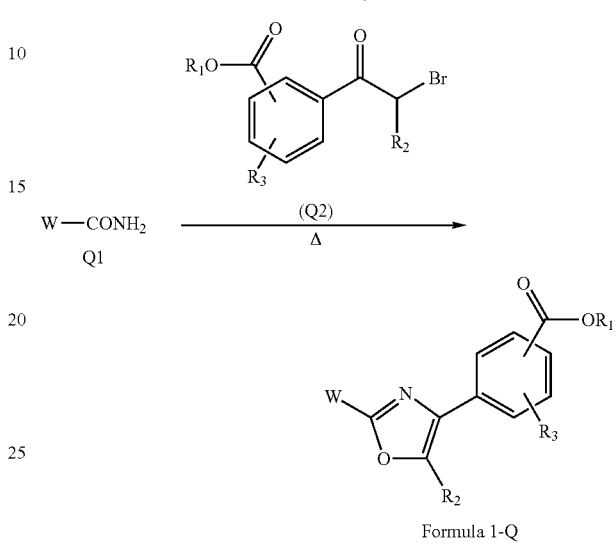

Formula 1-Q

In accordance with Scheme Q, commercially available carboxamides of structure Q1 or carboxamides prepared from commercially available acid chlorides or carboxylic acids can be reacted with α-bromoketones of structure Q2 to give oxazole compounds of Formula 1-Q. The reaction can be carried out in inert solvents such as toluene, tetrahydrofuran, dioxane or dimethylformamide or mixtures, at temperatures of 60-150° C.

Certain oxazoles of the Formula 1-R can be prepared by the methodology described in Scheme R below:

Scheme R

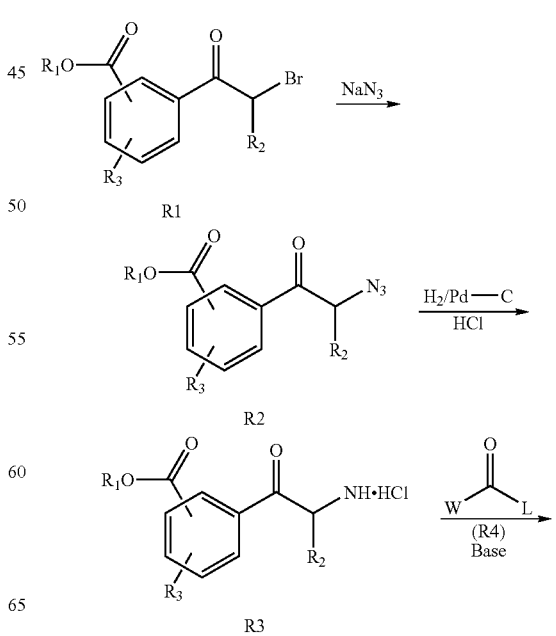

-continued

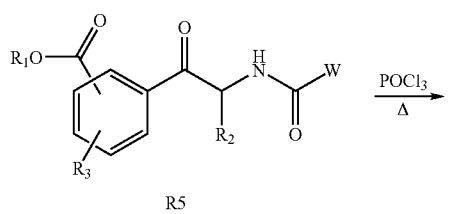

R5

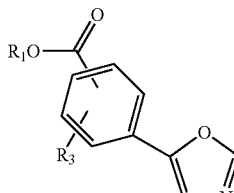

Formula 1-R

In accordance with Scheme R, α-Bromoketones of structure R1 can be converted to α-aminoketones R3 by initial displacement with sodium azide to give the α-azidoketones R2. Conversion to the α-aminoketones R3 can be carried out by reduction of the α-azidoketones via catalytic hydrogenation in the presence of acid, such as hydrochloric acid. The reduction can be carried out from 1-4 atmospheres of pressure in the presence of either protic or non-protic solvents. The active catalyst can be e.g., platinum or palladium metal on charcoal. The α-aminoketones R3 can then be reacted with activated carboxylic acid derivatives (R4) e.g., acid chlorides or acyl imidazolides, in a suitable solvent, optionally in the presence of a base, e.g., triethylamine, to give compounds of structure R5. Dehydration of the intermediate R5 with reagents such as phosphorous pentoxide or phosphorous oxychloride within a temperature range from ambient to 120° C. gives the oxazoles of Formula 1-R.

Certain furans of Formula 1-T can be prepared by the methodology depicted in Scheme T.

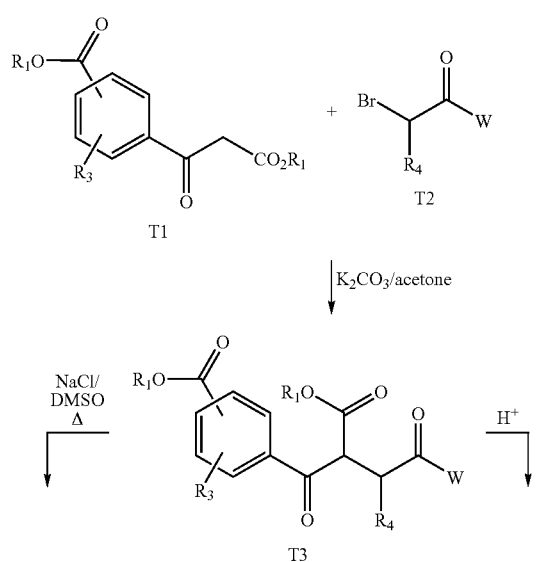

-continued

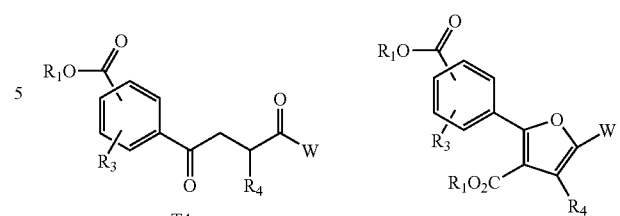

Formula 1-T

Formula 1-T

In accordance with Scheme T, reaction between ketoesters of structure T1 and α-bromoketones of structure T2 afford intermediate compounds of structure T3. Ketoesters T1 can be obtained by a number of methods known by those skilled in the art. Heating intermediate compounds T3 under conditions that facilitate dehydration can give the furan compounds of Formula 1-T, wherein $R_2$ is an ester group. The reaction can be carried out in the presence of an acid, e.g., HCl or p-toluenesulfonic acid, or heated in the presence of a reagent such as phosphorous oxychloride or phosphorous pentoxide to induce dehydration and cyclization.

Decarboxylation of the intermediate T3 gives compounds of type T4. Conditions for the decarboxylation reaction can include heating with a nucleophilic reagent in a nonreactive solvent, e.g., sodium chloride in $H_2O$-DMSO or LiI in pyridine or selective hydrolysis, trifluoroacetic acid if the ester to be decarboxylated is t-butyl or catalytic reduction if the ester to be decarboxylated is a benzyl ester. Heating the resultant intermediate compounds T4 under conditions that facilitate dehydration can give the furan compounds of Formula 1-T. The reaction can be carried out in the presence of an acid, such as HCl or p-toluenesulfonic acid, or heated in the presence of a reagent such as phosphorous oxychloride or phosphorous pentoxide to induce dehydration and cyclization.

Certain 1,2,4-thiadiazoles of Formula 1-U can be prepared by the methodology depicted in Scheme U.

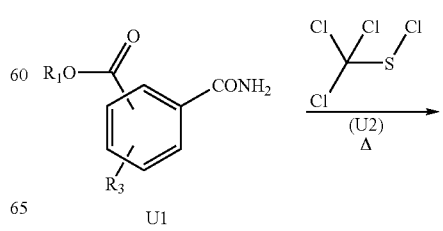

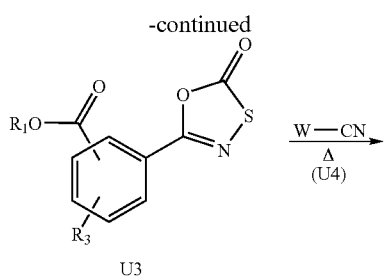

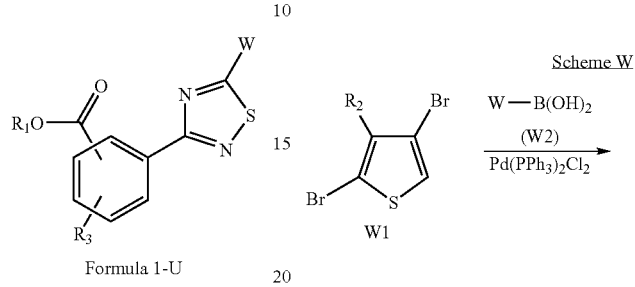

In accordance with Scheme U, heating amide compounds of structure U1 with a thionating agent, e.g., trichloromethyl sulfenyl chloride (U2) can give the oxathiazole intermediate compounds U3. The reaction is typically carried out in a non-reactive solvent, e.g., toluene or xylenes and heated at 80-150° C. Reaction of the oxathiazole compounds thus formed with nitriles of structure U4 at high temperature can give the 1,2,4-thiadiazoles compounds of Formula 1-U.

Certain 1,2,4-thiadiazoles of Formula 1-V can be prepared by the methodology depicted in Scheme V.

trichloromethyl sulfenyl chloride (V2), can give intermediate oxathiazole compounds V3. This reaction is typically carried out in a non-reactive solvent, such as toluene or xylenes, and heated at 80-150° C. Reaction of the oxathiazole compounds thus formed with nitriles of structure V4 at high temperature can give the 1,2,4-thiadiazoles compounds of Formula 1-V.

Certain thiophenes of Formula 1-W can be prepared by the methodology depicted in Scheme W.

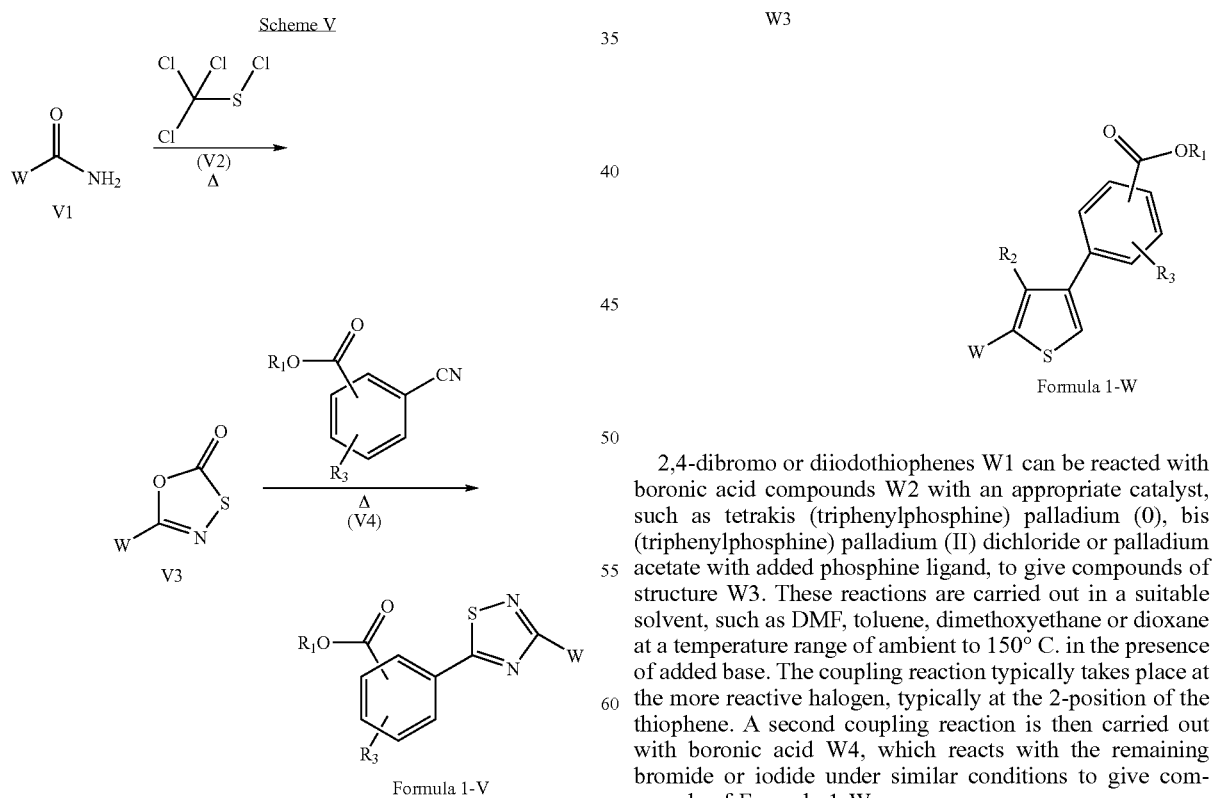

2,4-dibromo or diiodothiophenes W1 can be reacted with boronic acid compounds W2 with an appropriate catalyst, such as tetrakis (triphenylphosphine) palladium (0), bis (triphenylphosphine) palladium (II) dichloride or palladium acetate with added phosphine ligand, to give compounds of structure W3. These reactions are carried out in a suitable solvent, such as DMF, toluene, dimethoxyethane or dioxane at a temperature range of ambient to 150° C. in the presence of added base. The coupling reaction typically takes place at the more reactive halogen, typically at the 2-position of the thiophene. A second coupling reaction is then carried out with boronic acid W4, which reacts with the remaining bromide or iodide under similar conditions to give compounds of Formula 1-W.

Certain thiophenes of Formula 1-X may be prepared by similar methodology as described above. This is depicted in Scheme X.

Scheme X

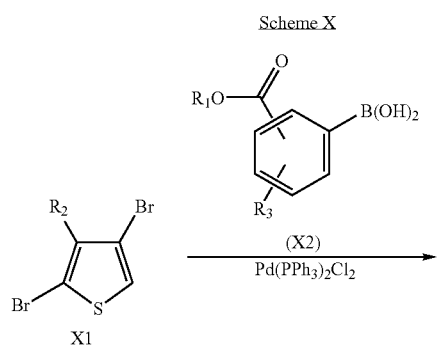

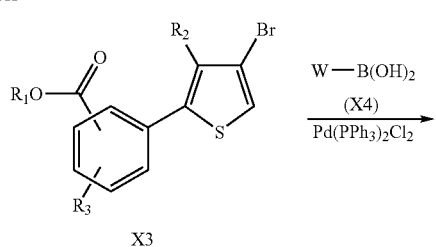

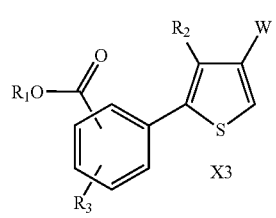

Formula 1-X

In accordance, with Scheme X, 2,4-dibromo or diiodothiophenes X1 can be reacted with boronic acid compounds X2 with an appropriate catalyst, e.g., tetrakis (triphenylphosphine) palladium (0), bis(triphenylphosphine) palladium (II) dichloride or palladium acetate with added phosphine ligand to give compounds of structure X3. The reactions are carried out in a suitable solvent, such as DMF, toluene, dimethoxyethane or dioxane at a temperature range of ambient to 150° C. in the presence of added base. The coupling reaction typically takes place at the more reactive halogen, typically at the 2-position of the thiophene. A second coupling reaction is then carried out with boronic acid X4 which reacts with the remaining bromide or iodide under similar conditions to give compounds of Formula 1-X.

Certain thiophenes of Formula 1-Y can be prepared by the methodology depicted in Scheme Y.

Scheme Y

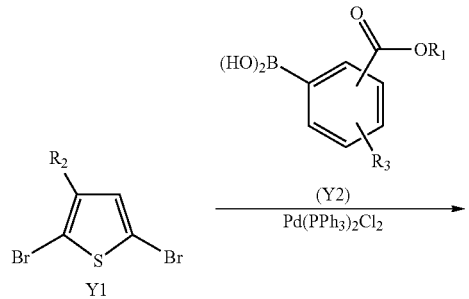

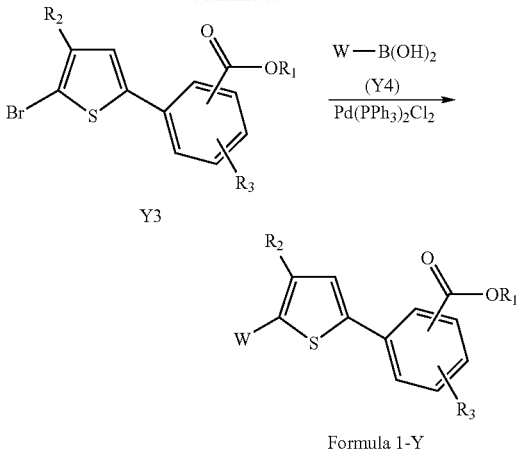

Formula 1-Y

In accordance with Scheme Y, 2,4-dibromo or diiodothiophenes Y1 can be reacted with boronic acid compounds Y2 with an appropriate catalyst, such as tetrakis (triphenylphosphine) palladium (0), bis(triphenylphosphine) palladium (II) dichloride or palladium acetate with added phosphine ligand, to give compounds of structure Y3 as described in the previous examples. A second coupling reaction is then carried out with boronic acid Y4, which reacts with the remaining bromide or iodide under similar conditions to give compounds of Formula 1-Y.

Certain 1,2,4-triazoles of Formula 1-Z can be prepared by the methodology depicted in Scheme Z.

Scheme Z

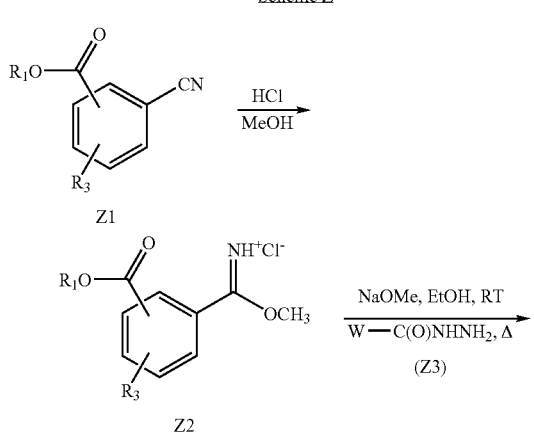

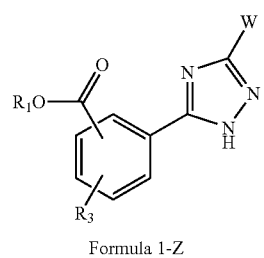

Formula 1-Z

In accordance with Scheme Z, cyanobenzoic acids of structure Z1 can be converted to methoxyimidates Z2 by treatment of Z1 with HCl in methanol in the cold, such as 0° C. Reaction of Z2 with substituted hydrazides (Z3) in the presence of a base and a suitable nonreactive solvent gives an intermediate, which is then heated in the presence of an appropriate solvent (e.g., dioxane) or a mixture of solvents at a temperature range of 60-150° C. to give the desired cyclized compounds of Formula 1-Z.

In certain preferred embodiments, compounds of the invention may be resolved to enantiomerically pure compositions or synthesized as enantiomerically pure compositions using any method known in art. By way of example, compounds of the invention may be resolved by direct crystallization of enantiomer mixtures, by diastereomer salt formation of enantiomers, by the formation and separation of diasteriomers or by enzymatic resolution of a racemic mixture.

These and other reaction methodologies may be useful in preparing the compounds of the invention, as recognized by one of skill in the art. Various modifications to the above schemes and procedures will be apparent to one of skill in the art, and the invention is not limited specifically by the method of preparing the compounds of the invention.

C. Methods of the Invention

In another aspect of the invention, methods are provided for the suppression of premature translation termination, which may be associated with a nonsense mutation, and for the prevention or treatment of diseases. In a preferred embodiment, such diseases are associated with mutations of mRNA, especially nonsense mutations. Exemplary diseases include, but are not limited to, cancer, lysosomal storage disorders, the muscular dystrophies, cystic fibrosis, hemophilia, epidermolysis bullosa and classical late infantile neuronal ceroid lipofuscinosis. In this embodiment, methods for treating cancer, lysosomal storage disorders, a muscular dystrophy, cystic fibrosis, hemophilia, or classical late infantile neuronal ceroid lipofuscinosis are provided comprising administering a therapeutically effective amount of at least one compound of the invention to a subject in need thereof.

In one embodiment, the present invention is directed to methods for increasing the expression of one or more specific, functional proteins. Any compound of the invention can be used to specifically increase expression of functional protein. In another embodiment, a specific increase in expression of functional protein occurs when premature translation termination is suppressed by administering a therapeutically effective amount of at least one compound of the invention to a subject in need thereof. In a preferred embodiment premature translation termination is associated with a nonsense mutation in mRNA. In another embodiment, a specific increase in expression of functional protein occurs when mRNA decay is reduced in a patient. In a preferred embodiment, the abnormality in a patient is caused by mutation-mediated mRNA decay. In a particularly preferred embodiment, mutation-mediated mRNA decay is the result of a nonsense mutation. The methods of the present invention are not limited by any particular theory.

The invention encompasses methods of treating and preventing diseases or disorders ameliorated by the suppression of premature translation termination, nonsense-mediated mRNA decay, or premature translation termination and nonsense-mediated mRNA decay in a patient which comprise administering to a patient in need of such treatment or prevention a therapeutically effective amount of a compound of the invention.

In one embodiment, the present invention encompasses the treatment or prevention of any disease that is associated with a gene exhibiting premature translation termination, nonsense-mediated mRNA decay, or premature translation termination and nonsense-mediated mRNA decay. In one embodiment, the disease is due, in part, to the lack of or reduced expression of the gene resulting from a premature stop codon. Specific examples of genes which may exhibit premature translation termination and/or nonsense-mediated mRNA decay and diseases associated with premature translation termination and/or nonsense-mediated mRNA decay are found in U.S. Provisional Patent Application No. 60/390, 747, titled: Methods For Identifying Small Molecules That Modulate Premature Translation Termination And Nonsense Mediated mRNA Decay, filed Jun. 21, 2002, and International Application PCT/US03/19760, filed Jun. 23, 2003, both of which are incorporated herein by reference in their entirety.

Diseases ameliorated by the suppression of premature translation termination, nonsense-mediated mRNA decay, or premature translation termination and nonsense-mediated mRNA decay include, but are not limited to: genetic diseases, somatic diseases, cancers, autoimmune diseases, blood diseases, collagen diseases, diabetes, neurodegenerative diseases, proliferative diseases, cardiovascular diseases, pulmonary diseases, inflammatory diseases or central nervous system diseases.

In one embodiment, diseases to be treated or prevented by administering to a patient in need thereof an effective amount of a compound of the invention include, but are not limited to, amyloidosis, hemophilia, Alzheimer's disease, Tay Sachs disease, Niemann Pick disease, atherosclerosis, giantism, dwarfism, hypothyroidism, hyperthyroidism, aging, obesity, Parkinson's disease, cystic fibrosis, muscular dystrophy, heart disease, kidney stones, ataxia-telangiectasia, familial hypercholesterolemia, retinitis pigmentosa, Duchenne muscular dystrophy, epidermolysis bullosa and Marfan syndrome. In one embodiment, the diseases are associated with a nonsense mutation.

In one embodiment, the compounds of the invention are useful for treating or preventing an autoimmune disease. In one embodiment, the autoimmune disease is associated with a nonsense mutation. In a preferred embodiment, the autoimmune disease is rheumatoid arthritis or graft versus host disease.

In another embodiment, the compounds of the invention are useful for treating or preventing a blood disease. In one embodiment, the blood disease is associated with a nonsense mutation. In a preferred embodiment, the blood disease is hemophilia, Von Willebrand disease, β-thalassemia In another embodiment, the compounds of the invention are useful for treating or preventing a collagen disease. In one embodiment, the collagen disease is associated with a nonsense mutation. In a preferred embodiment, the collagen disease is osteogenesis imperfecta or cirrhosis.

In another embodiment, the compounds of the invention are useful for treating or preventing diabetes. In one embodiment, the diabetes is associated with a nonsense mutation.

In another embodiment, the compounds of the invention are useful for treating or preventing an inflammatory disease. In one embodiment, the inflammatory disease is associated with a nonsense mutation. In a preferred embodiment, the inflammatory disease is arthritis, rheumatoid arthritis or osteoarthritis.

In another embodiment, the compounds of the invention are useful for treating or preventing a central nervous system disease. In one embodiment, the central nervous system disease is associated with a nonsense mutation. In one embodiment, the central nervous system disease is a neurodegenerative disease. In a preferred embodiment, the central nervous system disease is multiple sclerosis, muscular dystrophy, Duchenne muscular dystrophy, Alzheimer's disease, Tay Sachs disease, Niemann Pick disease, late infantile neuronal ceroid lipofuscinosis (LINCL) or Parkinson's disease.

In another preferred embodiment, the compounds of the invention are useful for treating or preventing cancer, particularly in humans. In a preferred embodiment, the cancer is of the head and neck, eye, skin, mouth, throat, esophagus, chest, bone, blood, lung, colon, sigmoid, rectum, stomach, prostate, breast, ovaries, kidney, liver, pancreas, brain, intestine, heart or adrenals. In one embodiment, the cancer is a solid tumor. In one embodiment, the cancer is associated with a nonsense mutation. In another embodiment, the cancer is associated with a genetic nonsense mutation. In another embodiment, the cancer is associated with a somatic mutation. Without being limited by any theory, the use of the compounds of the invention against cancer may relate to its action against mutations of the p53 gene.

In one embodiment, the cancer is not a blood cancer. In another embodiment, the cancer is not leukemia. In another embodiment, the cancer is not multiple myeloma. In another embodiment, the cancer is not prostate cancer.

In another preferred embodiment, the compounds of the invention are useful for treating or preventing cancer associated with a mutation of tumor suppressor gene. Such genes include, but are not limited to PTEN, BRCA1, BRCA2, Rb, and the p53 gene. In one embodiment, the mutation is a genetic mutation. In another embodiment, the mutation is a somatic mutation. The methods of the invention are particularly useful for treating or preventing a cancer associated with a nonsense mutation in the in a tumor suppressor gene. In a preferred embodiment, the methods of the invention are particularly useful for treating or preventing a cancer associated with a p53 gene due to the role of p53 in apoptosis. Without being limited by theory, it is thought that apoptosis can be induced by contacting a cell with an effective amount of a compound of the invention resulting in suppression of the nonsense mutation, which, in turn, allows the production of full-length p53 to occur. Nonsense mutations have been identified in the p53 gene and have been implicated in cancer. Several nonsense mutations in the p53 gene have been identified (see, e.g., Masuda et al., 2000, Tokai J Exp Clin Med. 25(2):69-77; Oh et al., 2000, Mol Cells 10(3): 275-80; Li et al., 2000, Lab Invest. 80(4):493-9; Yang et al., 1999, Zhonghua Zhong Liu Za Zhi 21(2):114-8; Finkelstein et al., 1998, Mol Diagn. 3(1):37-41; Kajiyama et al., 1998, Dis Esophagus. 11(4):279-83; Kawamura et al., 1999, Leuk Res. 23(2):115-26; Radig et al., 1998, Hum Pathol. 29(11): 1310-6; Schuyer et al., 1998, Int J Cancer 76(3):299-303; Wang-Gohrke et al., 1998, Oncol Rep. 5(1):65-8; Fulop et al., 1998, J Reprod Med. 43(2):119-27; Ninomiya et al., 1997, J Dermatol Sci. 14(3):173-8; Hsieh et al., 1996, Cancer Lett. 100(1-2):107-13; Rall et al., 1996, Pancreas. 12(1):10-7; Fukutomi et al., 1995, Nippon Rinsho. 53(11): 2764-8; Frebourg et al., 1995, Am J Hum Genet. 56(3):608-15; Dove et al., 1995, Cancer Surv. 25:335-55; Adamson et al., 1995, Br J Haematol. 89(1):61-6; Grayson et al., 1994, Am J Pediatr Hematol Oncol. 16(4):341-7; Lepelley et al., 1994, Leukemia. 8(8):1342-9; McIntyre et al., 1994, J Clin Oncol. 12(5):925-30; Horio et al., 1994, Oncogene. 9(4): 1231-5; Nakamura et al., 1992, Jpn J Cancer Res. 83(12): 1293-8; Davidoff et al., 1992, Oncogene. 7(1):127-33; and Ishioka et al., 1991, Biochem Biophys Res Commun. 177 (3):901-6; the disclosures of which are hereby incorporated by reference herein in their entireties). Any disease associated with a p53 gene encoding a premature translation codon including, but not limited to, the nonsense mutations described in the references cited above, can be treated or prevented by compounds of the invention.

In other embodiments, diseases to be treated or prevented by administering to a patient in need thereof an effective amount of a compound of the invention include, but are not limited to, solid tumors such as sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor or multiple myeloma.

In another embodiment, diseases to be treated or prevented by administering to a patient in need thereof an effective amount of a compound of the invention include, but are not limited to, a blood-born tumor such as acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia, chronic lymphocytic leukemia, hairy cell leukemia, or multiple myeloma. See e.g., Harrison's Principles of Internal Medicine, Eugene Braunwald et al., eds., pp. 491-762 (15th ed. 2001).

In yet another embodiment, the invention encompasses the treatment of a human afflicted with a solid tumor or a blood tumor.

In a preferred embodiment, the invention encompasses a method of treating or preventing a disease ameliorated by modulation of premature translation termination, nonsense-mediated mRNA decay, or premature translation termination and nonsense-mediated mRNA decay, or ameliorating one or more symptoms associated therewith comprising contacting a cell with a therapeutically effective amount of a compound of the invention. Cells encompassed by the present methods include animal cells, mammalian cells, bacterial cells, and virally infected cells. In one embodiment, the nonsense mutation is a genetic mutation (i.e., the nonsense codon was present in the progenitor DNA). In another embodiment, the nonsense mutation is a somatic mutation (i.e., the nonsense codon arose spontaneously or from mutagenesis).

In certain embodiments, a compound of the invention is administered to a subject, including but not limited to a plant, reptile, avian, amphibian or preferably a mammal, more preferably a human, as a preventative measure against a disease associated with premature translation termination, nonsense-mediated mRNA decay, or premature translation termination and nonsense-mediated mRNA decay.

In a preferred embodiment, it is first determined that the patient is suffering from a disease associated with premature translation termination and/or nonsense-mediated mRNA decay. In another embodiment, the patient has undergone a screening process to determine the presence of a nonsense mutation comprising the steps of screening a subject, or cells extracted therefrom, by an acceptable nonsense mutation screening assay. In a preferred embodiment, the DNA of the patient can be sequenced or subjected to Southern Blot, polymerase chain reaction (PCR), use of the Short Tandem Repeat (STR), or polymorphic length restriction fragments (RFLP) analysis to determine if a nonsense mutation is present in the DNA of the patient. In one embodiment, it is determined whether the nonsense mutation is a genetic mutation or a somatic mutation by comparison of progenitor DNA. Alternatively, it can be determined if altered levels of the protein with the nonsense mutation are expressed in the patient by western blot or other immunoassays. In another embodiment, the patient is an unborn child who has undergone screening in utero for the presence of a nonsense mutation. Administration of a compound of the invention can occur either before or after birth. In a related embodiment, the therapy is personalized in that the patient is screened for a nonsense mutation screening assay and treated by the administration of one or more compounds of the invention; particularly, the patient may be treated with a compound particularly suited for the mutations in question; e.g., depending upon the disease type, cell type, and the gene in question. Such methods are well known to one of skill in the art.

In another embodiment, the cells (e.g., animal cells, mammalian cells, bacterial cells, plant cells and virally infected cells) are screened for premature translation termination and/or nonsense-mediated mRNA decay with a method such as that described above (i.e., the DNA of the cell can be sequenced or subjected to Southern Blot, polymerase chain reaction (PCR), use of the Short Tandem Repeat (STR), or polymorphic length restriction fragments (RFLP) analysis to determine if a nonsense mutation is present in the DNA of the cell; the RNA of the cell can be subjected to quantitative real time PCR to determine transcript abundance).

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to non-opioid analgesics; non-steroid anti-inflammatory agents; steroids, antiemetics; β-adrenergic blockers; anticonvulsants; antidepressants; $Ca^{2+}$-channel blockers; anticancer agent(s) and antibiotics and mixtures thereof.

In certain embodiments, the compounds of the invention can be administered or formulated in combination with anticancer agents. Suitable anticancer agents include, but are not limited to: alkylating agents; nitrogen mustards; folate antagonists; purine antagonists; pyrimidine antagonists; spindle poisons; topoisomerase inhibitors; apoptosis inducing agents; angiogenesis inhibitors; podophyllotoxins; nitrosoureas; cisplatin; carboplatin; interferon; asparaginase; tamoxifen; leuprolide; flutamide; megestrol; mitomycin; bleomycin; doxorubicin; irinotecan and taxol.

In certain embodiments, the compounds of the invention can be administered or formulated in combination with antibiotics. In certain embodiments, the antibiotic is an aminoglycoside (e.g., tobramycin), a cephalosporin (e.g., cephalexin, cephradine, cefuroxime, cefprozil, cefaclor, cefixime or cefadroxil), a clarithromycin (e.g., clarithromycin), a macrolide (e.g., erythromycin), a penicillin (e.g., penicillin V) or a quinolone (e.g., ofloxacin, ciprofloxacin or norfloxacin). In a preferred embodiment, the antibiotic is active against *Pseudomonas aeruginosa*.

Without intending to be limited by theory, it is believed that the methods of the present invention act through a combination of mechanisms that suppress nonsense mutations. In preferred embodiments, the methods of the invention comprise administering a therapeutically effective amount of at least one compound of the invention, e.g., a compound of Formula 1. Relative activity of the compounds of the invention may be determined by any method known in the art, including the assay described in Example 2 herein.

Compounds of the invention can be characterized with an in vitro luciferase nonsense suppression assay. Luciferase assays are included in the methods of the present invention. Luciferase can be used as a functional reporter gene assay (light is only produced if the protein is functional), and luciferase is extremely sensitive (Light intensity is proportional to luciferase concentration in the nM range). In one embodiment, an assay of the present invention is a cell-based luciferase reporter assay. In a preferred cell-based luciferase reporter assay, a luciferase reporter construct containing a premature termination codon (UGA, UAA, or UAG) is stably transfected in 293 Human Embryonic Kidney cells.

In another assay of the present invention, a preferred assay is a biochemical assay consisting of rabbit reticulocyte lysate and a nonsense-containing luciferase reporter mRNA.

In another assay of the present invention, the assay is a biochemical assay consisting of prepared and optimized cell extract (Lie & Macdonald, 1999, Development 126(22): 4989-4996 and Lie & Macdonald, 2000, Biochem. Biophys. Res. Commun. 270(2):473-481. In the biochemical assay, mRNA containing a premature termination codon (UGA, UAA, or UAG) is used as a reporter in an in vitro translation reaction using rabbit reticulocyte lysate supplemented with tRNA, hemin, creatine kinase, amino acids, KOAc, Mg(OAc)2, and creatine phosphate. Translation of the mRNA is initiated within a virus derived leader sequence, which significantly reduces the cost of the assay because capped RNA is not required. Synthetic mRNA is prepared in vitro using the T7 promoter and the MegaScript in vitro transcription kit (Ambion, Inc.; Austin, Tex.). In assays of the present invention, addition of gentamicin, an aminoglycoside known to allow readthrough of premature termination codons, results in increased luciferase activity and can be used as an internal standard. Assays of the present invention can be used in high-throughput screens. Hundreds of thousands of compounds can be screened in cell-based and biochemical assays of the present invention. In a preferred aspect, a functional cell-based assay similar to the one described.

Compounds of the present invention include compounds capable of increasing specific, functional protein expression from mRNA molecules comprising premature termination codons. In one embodiment, compounds of the present invention can preferentially suppress premature translation termination. For example, a compound of the present invention can be capable of suppressing a nonsense mutation if the mutation results in UAA, but not capable of suppressing a nonsense mutation if the mutation results in UAG. Another non-limiting example can occur when a compound of the present invention can be capable of suppressing a nonsense mutation if the mutation results in UAA and is followed, in-frame by a cytosine at the +1 position, but not capable of suppressing a nonsense mutation if the mutation results in UAA and is followed, in-frame by an adenine at the +1 position.

A stable cell line harboring the UGA nonsense-containing luciferase gene can be treated with a test compound. In this aspect, cells can be grown in standard medium supplemented with 1% penicillin-streptomycin (P/S) and 10% fetal bovine serum (FBS) to 70% confluency and split 1:1 the day before treatment. The next day, cells are trypsinized and 40,000 cells are added to each well of a 96-well tissue culture dish. Serial dilutions of each compound are prepared to generate a six-point dose response curve spanning 2 logs (30 μM to 0.3 μM). The final concentration of the DMSO solvent remains constant at 1% in each well. Cells treated with 1% DMSO serve as the background standard, and cells treated with gentamicin serve as a positive control.

To address the effects of the nonsense-suppressing compounds on mRNAs altered in specific inherited diseases, a bronchial epithelial cell line harboring a nonsense codon at amino acid 1282 (W1282X) can be treated with a compound of the invention and CFTR function is monitored as a cAMP-activated chloride channel using the SPQ assay (Yang et al., *Hum. Mol. Genet.* 2(8):1253-1261 (1993) and Howard et al., *Nat. Med.* 2(4):467-469 (1996)). The increase in SPQ fluorescence in cells treated with a compound of the invention is compared to those treated with cAMP and untreated cells. An increase in SPQ fluorescence in cells is consistent with stimulation of CFTR-mediated halide efflux and an increase in readthrough of the nonsense codon. Full-length CFTR expression from this nonsense-containing allele following treatment with a compound of the invention demonstrates that cystic fibrosis cell lines increase chloride channel activity when treated with a compound of the invention.

D. Metabolites of the Compounds of the Invention

Also falling within the scope of the present invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammalian tissue or a mammal for a period of time sufficient to yield a metabolic product thereof. Such products typically are identified by preparing a radio-labeled (e.g. $C^{14}$ or $H^3$) compound of the invention, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of the invention even if they possess no biological activity of their own.

E. Pharmaceutical Compositions of the Invention

While it is possible for the compounds of the present invention to be administered neat, it may be preferable to formulate the compounds as pharmaceutical compositions. As such, in yet another aspect of the invention, pharmaceutical compositions useful in the methods of the invention are provided. The pharmaceutical compositions of the invention may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In another embodiment, pharmaceutical compositions of the invention may be formulated so that the pH is adjusted to about pH 4 to about pH 7. In alternative embodiments, it may be preferred that the pH is adjusted to a range from about pH 5 to about pH 8.

More particularly, the pharmaceutical compositions of the invention comprise a therapeutically or prophylactically effective amount of at least one compound of the present invention, together with one or more pharmaceutically acceptable excipients. Optionally, the pharmaceutical compositions of the invention may comprise a combination of compounds of the present invention, or may include a second active ingredient useful in the treatment of cancer, diabetic retinopathy, or exudative macular degeneration.

Formulations of the present invention, e.g., for parenteral or oral administration, are most typically solids, liquid solutions, emulsions or suspensions, while inhalable formulations for pulmonary administration are generally liquids or powders, with powder formulations being generally preferred. A preferred pharmaceutical composition of the invention may also be formulated as a lyophilized solid that is reconstituted with a physiologically compatible solvent prior to administration. Alternative pharmaceutical compositions of the invention may be formulated as syrups, creams, ointments, tablets, and the like.

The pharmaceutical compositions of the invention can be administered to the subject via any drug delivery route known in the art. Specific exemplary administration routes include oral, ocular, rectal, buccal, topical, nasal, ophthalmic, subcutaneous, intramuscular, intravenous (bolus and infusion), intracerebral, transdermal, and pulmonary.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by the particular method used to administer the composition. Accordingly, there exists a wide variety of suitable formulations of pharmaceutical compositions of the present invention (see, e.g., Remington's Pharmaceutical Sciences, $18^{th}$ Ed., Mack Publishing Co., 1990).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions of the invention may be formulated as suspensions comprising a compound of the present invention in admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Excipients suitable for use in connection with suspensions include suspending agents, such as sodium carboxymethylcellulose, methylcelluose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

Generally, the compounds of the present invention useful in the methods of the present invention are substantially insoluble in water and are sparingly soluble in most pharmaceutically acceptable protic solvents and in vegetable oils. However, the compounds are generally soluble in medium chain fatty acids (e.g., caprylic and capric acids) or triglycerides and have high solubility in propylene glycol esters of medium chain fatty acids. Also contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In a preferred embodiment, the compounds of the present invention may be formulated for oral administration in a lipid-based formulation suitable for low solubility compounds. Lipid-based formulations can generally enhance the oral bioavailability of such compounds. As such, a preferred pharmaceutical composition of the invention comprises a therapeutically or prophylactically effective amount of a compound of the present invention, together with at least one pharmaceutically acceptable excipient selected from the group consisting of: medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-β-cyclodextrin (HPBC), which may be added to any of the above-described compositions to further improve the aqueous solubility characteristics of the compounds of the present invention. In one embodiment, the composition comprises 0.1% to 20% hydroxypropyl-β-cyclodextrin, more preferably 1% to 15% hydroxypropyl-β-cyclodextrin, and even more preferably from 2.5% to 10% hydroxypropyl-β-cyclodextrin. The amount of solubility enhancer employed will depend on the amount of the compound of the present invention in the composition.

The therapeutically effective amount, as used herein, refers to an amount of a pharmaceutical composition of the invention to treat, ameliorate, or modulate an identified disease or condition, or to exhibit a detectable therapeutic or inhibitory effect. The effect can be detected by, for example, assays of the present invention. The effect can also be the prevention of a disease or condition where the disease or condition is predicted for an individual or a high percentage of a population.

The precise effective amount for a subject will depend upon the subject's body weight, size, and health; the nature and extent of the condition; the therapeutic or combination of therapeutics selected for administration, the protein half-life, the mRNA half-life and the protein localization. Therapeutically effective amounts for a given situation can be determined by routine experimentation that is within the skill and judgment of the clinician.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to the compound(s) of the present invention indicate an initial target plasma concentration ranging from approximately 5 µg/mL to approximately 100 µg/mL, preferably from approximately 10 µg/mL to approximately 50 µg/mL, more preferably from approximately 10 µg/mL to approximately 25 µg/mL. To achieve such plasma concentrations, the compounds of the invention may be administered at doses that vary from 0.1 µg to 100,000 mg, depending upon the route of administration. Guidance as to particular dosages and methods of delivery is provided in the literature and is generally available to practitioners in the art. In general the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children under 40 kg).

The magnitude of a prophylactic or therapeutic dose of a particular active ingredient of the invention in the acute or chronic management of a disease or condition will vary, however, with the nature and severity of the disease or condition, and the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range for the conditions described herein lie within the range of from about 1 mg/kg to about 150 mg/kg per day. In one embodiment, the compound of the invention is given as a single once-a-day dose. In another embodiment, the compound of the invention is given as divided doses throughout a day. More specifically, the daily dose is administered in a single dose or in equally divided doses. Preferably, a daily dose range should be from about 5 mg/kg to about 100 mg/kg per day, more preferably, between about 10 mg/kg and about 90 mg/kg per day, even more preferably 20 mg/kg to 60 mg/kg per day. In managing the patient, the therapy should be initiated at a lower dose, perhaps about 200 mg to about 300 mg, and increased if necessary up to about 600 mg to about 4000 mg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

The phrases "therapeutically effective amount", "prophylactically effective amount" and "therapeutically or prophylactically effective amount," as used herein encompass the above described dosage amounts and dose frequency schedules. Different therapeutically effective amounts may be applicable for different diseases and conditions, as will be readily known by those of ordinary skill in the art. Similarly, amounts sufficient to treat or prevent such diseases, but insufficient to cause, or sufficient to reduce, adverse effects associated with conventional therapies are also encompassed by the above described dosage amounts and dose frequency schedules.

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time, protein of interest half-life, RNA of interest half-life, frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

F. Combination Therapy

It is also possible to combine any compound of the present invention with one or more other active ingredients useful in the treatment of diseases associated with nonsense mutations of mRNA as described herein, including compounds in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the nonsense mutation-suppressing activity of the compounds of the invention.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

G. Gene Therapy

The compounds of the present invention or other nonsense compounds can be utilized in combination with gene therapy. In this embodiment, a gene can be introduced or provided to a mammal, preferably a human that contains a specified nonsense mutation in the desired gene. In a preferred aspect, the desired gene is selected from the group consisting of IGF1, EPO, p53, p19ARF, p21, PTEN, EI 24 and ApoAI. In order to obtain expression of the full-length polypeptide in a patient or mammal, the patient or mammal would be provided with an effective amount of a compound of the present invention or other nonsense compound when such polypeptide is desired.

There are two major approaches to getting nucleic acid that contain a nonsense mutation (optionally contained in a vector) into the patient's cells: in vivo and ex vivo. For in vivo delivery the nucleic acid is injected directly into the patient, usually at the sites where the polypeptide is required, i.e., the site of synthesis of the polypeptide, if known, and the site (e.g. solid tumor) where biological activity of the polypeptide is needed. For ex vivo treatment, the patient's cells are removed, the nucleic acid is introduced into these isolated cells, and the modified cells are administered to the patient either directly or, for example, encapsulated within porous membranes that are implanted into the patient (see e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or transferred in vivo in the cells of the intended host. Techniques suitable for the transfer of nucleic acid into mammalian cells in vitro include the use of liposomes, electroporation, microinjection, transduction, cell fusion, DEAE-dextran, the calcium phosphate precipitation method, etc. Transduction involves the association of a replication-defective, recombinant viral (preferably retroviral) particle with a cellular receptor, followed by introduction of the nucleic acids contained by the particle into the cell. A commonly used vector for ex vivo delivery of the gene is a retrovirus.

The currently preferred in vivo nucleic and transfer techniques include transfection with viral or non-viral vectors (such as adenovirus, lentivirus, Herpes simplex I virus, or adeno-associated virus (AAV)) and lipid-based systems (useful lipids for lipid-mediated transfer of the gene are, for example, DOTMA, DOPE, and DC-Chol; see, e.g., Tonkinson et al, *Cancer Investigation,* 14 (1): 54-65 (1996)). The most preferred vectors for use in gene therapy are viruses, most preferably adenoviruses, AAV, lentiviruses, or retroviruses. A viral vector such as a retroviral vector includes at least one transcriptional promoter/enhancer or locus-defining element(s), or other elements that control gene expression by other means such as alternate splicing, nuclear RNA export, or post-translational modification of messenger. In addition, a viral vector such as a retroviral vector includes a nucleic acid sequence that, when transcribed with a gene encoding a polypeptide, is operably linked to the coding sequence and acts as a translation initiation sequence. Such vector constructs also include a packaging signal, long terminal repeats (LTRs) or portions thereof, and positive and negative strand primer binding sites appropriate to the virus used (if these are not already present in the viral vector). In addition, such vector typically includes a signal sequence for secretion of the polypeptide from a host cell in which it is placed. Preferably the signal sequence for this purpose is a mammalian signal sequence, most preferably the native signal sequence for the polypeptide. Optionally, the vector construct may also include a signal that directs polyadenylation, as well as one or more restriction sites and a translation termination sequences. By way of example, such vectors will typically include a 5' LTR, a tRNA binding site, a packaging signal, a origin of second-strand DNA synthesis, and a 3' LTR or a portion thereof. Other vectors can be used that are non-viral, such as cationic lipids, polylysine, and dendrimers.

In some situations, it is desirable to provide the nucleic acid source with an agent that targets the target cells, such as an antibody specific for a cell-surface membrane protein or the target cell, a ligand for a receptor on the target cell, etc. Where liposomes are employed, proteins that bind to a cell-surface membrane protein associated with endocytosis may be used for targeting and/or to facilitate uptake, e.g., capsid proteins or fragments thereof tropic for a particular cell type, antibodies for proteins that undergo internalization in cycling, and proteins that target intracellular localization and enhance intracellular half-life. The technique of recepto-mediated endocytosis is described, for example, by Wu et al., *J. Biol. Chem.* 262: 4429-4432 (1987); and Wagner et al., *Proc. Natl. Acad. Sci. USA,* 87: 3410-3414 (1990). For a review of the currently known gene marking and gene therapy protocols, see, Anderson et al., *Science* 256: 808-813 (1992). See also WO 93/25673 and the references cited therein.

Suitable gene therapy and methods for making retroviral particles and structural proteins can be found in, e.g. U.S. Pat. Nos. 5,681,746; 6,800,604 and 6,800,731.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

Example 1

Preparation of Compounds of the Invention

Example A

Preparation of 3-[5-(4-isopropylphenyl)-[1,3,4]oxadiazol-2-yl]benzoic acid. (Compound No. 6)

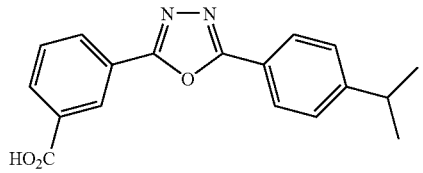 [SMILES: CC(C)c1ccc(-c2nnc(-c3cccc(C(=O)O)c3)o2)cc1]

Step A: A suspension of methyl 3-cyanobenzoate (5.05 g, 31.4 mmol), sodium azide (3.06 g, 47.0 mmol) and triethylamine hydrochloride (6.47 g, 47 mmol) in 60 mL of toluene is heated at reflux for 12 h and then cooled to rt. The heterogeneous mixture is diluted with $H_2O$ and the phases are separated. The organic layer is extracted with saturated $NaHCO_3$, and the aqueous phases are combined and washed with EtOAc. After discarding the organic layer, the combined aqueous phases are acidified with 6N HCl to approximately pH 2 and the resultant thick paste is extracted with EtOAc (2×). The combined organic layers are washed with saturated NaCl and then are dried and are concentrated to give 5.30 g (83%) of methyl 3-(1H-tetrazol-5-yl)benzoate as a white solid: mp 180-181° C.; MS m/z 205.1 [$MH^+$].

Step B: A suspension of methyl 3-(1H-tetrazol-5-yl)benzoate (0.41 g, 2.0 mmol), 4-isopropyl benzoic acid (0.33 g, 2.0 mmol) and dicyclohexyl carbodiimide (0.41 g, 2.0 mmol) in dichloroethane (10 mL) is heated at reflux for 20 h. After cooling to rt, the mixture is filtered and the solids are rinsed with methylene chloride. The filtrate is washed with saturated $NaHCO_3$ and then dried and concentrated to a solid. Flash chromatography over silica gel (EtOAc/$CH_2Cl_2$, 2-5%) gave 0.54 g (84%) of methyl 3-[5-(4-isopropylphenyl)-[1,3,4]oxadiazol-2-yl]benzoate as a tan solid: mp 74-77° C., $^1$H NMR: ($CDCl_3$) δ 8.74 (t, J=1.5, 1H), 8.33 (dt, J=1.5, 7.8, 1H), 8.20 (J=1.5, 7.8, 1H), 8.06 (dt, J=1.5, 8.4, 2H), 7.61 (t, J=7.9, 1H), 7.39 (dd, J=1.8, 8.4, 2H), 3.99 (s, 3H), 3.00 (septet, J=6.9, 1H), 1.31 (d, J=6.9, 6H); MS m/z 323.2 [$MH^+$].

Step C: A solution of methyl 3-[5-(4-isopropylphenyl)-[1,3,4]oxadiazol-2-yl]benzoate (0.48 g, 1.49 mmol) in THF (10 mL) is treated with 1N NaOH (2.25 mL, 2.25 mmol) and is heated at reflux for 5 h. After cooling to rt, and basifying with saturated $NaHCO_3$, the aqueous phase is extracted with EtOAc. The organic layer is then extracted with $NaHCO_3$ (2×). The aqueous phases are combined, acidified to pH 2 and extracted with EtOAc (3×) and then are dried and are concentrated to give a white solid. Recrystallization (EtOAc/hexanes) gives 324 mg (71%) of 3-[5-(4-isopropylphenyl)-[1,3,4]-oxadiazol-2-yl]benzoic acid as white needles: mp 202-204° C., $^1$H NMR: (DMSO-$d_6$) δ 8.54 (br s, 1H), 8.28 (d, J=7.8, 1H), 8.12 (d, J=7.8, 1H), 7.97 (d, J=8.1, 2H), 7.71 (t, J=7.7, 1H), 7.43 (d, J=7.7, 1H), 2.95 (septet, J=6.9, 1H), 1.20 (d, J=6.9, 6H); MS m/z 309.2 [MH⁺], 307.2 [MH⁻].

In similar fashion, utilizing the above steps, the following compounds are prepared from the appropriate cyanobenzoates and carboxylic acid starting materials: Compound Nos: 1, 2, 3, 4, 5, 7, 8, 85, 86, 175, 222, 223, 224, 225, 278, 279, 283, 284, 285, 286, 292, 293, 315, 316, 317, 318, 319, 401, 402, 596, 601, 605, 606, 610, 615, 620, 621, 622, 624, 626, 628.

Example B

Preparation of 3-[5-(4-tertbutylphenyl)-[1,3,4]oxadiazol-2-yl]benzoic acid (Compound No. 29)

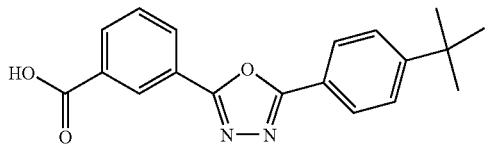 [SMILES: CC(C)(C)c1ccc(-c2nnc(-c3cccc(C(=O)O)c3)o2)cc1]

Step A: 20 g of 2-chlorotrityl chloride resin (Rapp polymere, Germany) is agitated in dry dimethylformamide (100 mL) for 10 min and the solvent is then drained. To the resin is added a solution of isophthalic acid (8.0 g, 48.2 mmol) in 1% disopropylethylamine in dimethylformamide (150 mL) and then is agitated for 4 h at room temperature. The solvents are drained and the resin is washed sequentially with dichloromethane (3×200 mL×1 min), dimethylformamide (3×200 mL×1 min), methanol (3×200 mL×1 min), and dichloromethane (3×200 mL×1 min). The resin is vacuum dried for 4 h at room temperature. The desired product is analyzed by cleavage of a small amount of the reacted resin with triethylsilane/trifluoroacetic acid/dichloromethane.

Step B: To a suspension of isophthalic resin that is prepared in step A above (200 mg, 0.2 mmole) in DMF (3 mL) is added PyBOP (520 mg, 1.0 mmole). After agitation for 5 min at room temperature, 4-t-butylbenzhydrazide (1 mmol) is then added to the reaction mixture. The reaction mixture is agitated overnight at room temperature. The solvents are drained and the resin is washed with dichloromethane (3×20 mL×10 min), DMF (3×20 mL×10 min), MeOH (3×20 mL×10 min), and dichloromethane (3×20 mL×10 min). The resin is vacuum dried for 4 h. The desired product is analyzed by cleavage of a small amount of the reacted resin with triethylsilane/trifluoroacetic acid/dichloromethane.

Step C: To a suspension of hydrazide resin from step B, above (200 mg, 0.1 mmol) in dichloromethane is added 2-chloro-1,3-dimethylimidazolidinium chloride (CDC, 33.6 mg, 0.2 mmol) and triethylamine (56 μL, 0.4 mmole) followed by agitation at room temperature overnight. The solvents are drained and the resin is washed with dichloromethane (3×20 mL×10 min), DMF (3×20 mL×10 min), MeOH (3×20 mL×10 min), and dichloromethane (3×20 mL×10 min). The resin is treated with 20% TFA in dichloromethane (4 mL) for 1 h at room temperature. The resin is removed and the filtrate is concentrated under reduced pressure to afford 3-[5-(4-tert-butylphenyl)-[1,3,4]oxadiazol-2-yl]benzoic acid. The desired product is purified by preparative LC/MS. MS m/z 323.1 [M+H]⁺ (95% purity).

The following compounds are prepared using the procedures described above starting from either isophthalic acid or terephthalic acid in step A and are reacted with the appropriate hydrazine derivatives: Compound Nos: 22, 23, 24, 25, 26, 27, 28, 30, 31, 32, 33, 34, 35, 36, 37, 38, 62, 63, 64, 65, 66, 67, 123, 124, 125, 126, 27, 128, 129, 130, 131, 132, 133, 134, 135, 136, 137, 138, 139, 226, 228, 230, 232, 234, 236, 239, 241, 243, 245, 247, 249, 250, 252, 254, 103, 104, 105, 106, 107, 108, 109, 110, 111, 112, 113, 114, 115, 116, 117, 118, 119, 120, 121, 122, 176, 177, 178, 179, 180, 181, 182, 183, 184, 185, 186, 187, 188, 189, 190, 191, 192, 258, 259, 260, 261, 262, 263, 264, 272, 161, 162, 163, 170, 169, 166, 173, 167, 172, 168, 174, 171, 164, 165, 172, 265, 15, 16, 17, 18, 19, 21, 39, 40, 41, 42, 43, 44, 45, 46, 47, 48, 49, 50, 51, 53, 54, 55, 68, 69, 70, 71, 72, 73, 87, 88, 89, 90, 91, 92, 93, 94, 95, 96, 97 98, 99, 100, 101, 102, 142, 143, 144, 145, 146, 147, 148, 149, 150, 151, 152, 153, 154, 155, 156, 157, 158, 159, 209, 210, 211, 212, 213 214, 215, 216, 217, 218, 219, 220, 221, 193, 194, 195, 196, 197, 198, 199, 200, 201, 202, 203, 204, 205, 206, 207, 208, 294, 295, 296, 297, 298, 299, 300, 301, 302, 303, 304, 227, 229, 231, 233, 235, 237, 238, 240, 242, 244, 246, 248, 251, 253, 255, 266, 267, 268, 269, 270, 271, 273, 274, 305, 306, 307, 308, 309, 160.

Example C

4-{5-[3-(toluene-4-sulfonylamino)phenyl]-[1,3,4]oxadiazol-2-yl}benzoic acid (Compound No. 13)

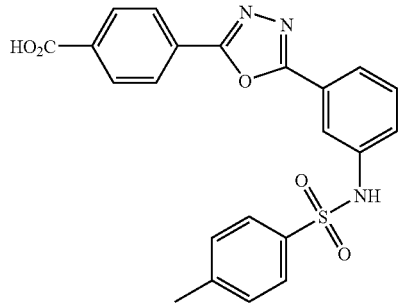 [SMILES: Cc1ccc(S(=O)(=O)Nc2cccc(-c3nnc(-c4ccc(C(=O)O)cc4)o3)c2)cc1]

Step A: A Parr bottle is charged with methyl 4-[5-(3-nitrophenyl)-[1,3,4]oxadiazol-2-yl]benzoate (4.04 g, 12.43 mmol), 0.80 g of 10% Pd—C, THF (200 mL) and EtOAc (50 mL) and the mixture is hydrogenated at 50 psi for 5 h. The reaction mixture is then diluted with saturated NaHCO₃ and EtOAc and then is filtered. The filtrate layers are separated and the aqueous layers are extracted with additional EtOAc. The combined organic phases are washed with H₂O and saturated NaCl and then is dried and concentrated to give 2.34 g (64%) of methyl 4-[5-(3-aminophenyl)-[1,3,4]oxadiazol-2-yl]benzoate a yellow solid: ¹H NMR (DMSO-d₆) δ 8.20-8.14 (m, 4H), 7.31 (t, J=1.4,1H), 7.22 (d, J=3.3, 2H), 6.78 (m, 1H), 5.53 (br s, 2H), 3.88 (s, 3H).

Step B: A suspension of methyl 4-[5-(3-aminophenyl)-[1,3,4]oxadiazol-2-yl]benzoate (0.30 g, 1.02 mmol) pyridine (0.12 mL, 1.53 mmol) and p-toluenesulfonyl chloride (0.23 g, 1.22 mmol) in CH₂Cl₂ (10 mL) is stirred at room temperature overnight. The resultant mixture is diluted with H₂O and CH₂Cl₂ and is filtered to give 0.25 g (55%) of methyl 4-{5-[3-(toluene-4-sulfonylamino)-phenyl]-[1,3,4]oxadiazol-2-yl}benzoate as a white solid: mp 227-228° C.; ¹H NMR (DMSO-d₆) δ 10.67 (s, 1H), 8.20-8.13 (m, 4H), 7.85 (br s, 1H), 7.76-7.69 (m, 3H), 7.46 (dt, J=2.7, 10.2, 1H), 7.36-7.33 (m, 3H), 3.88 (s, 3H), 2.30 (s, 3H); MS m/z 450.0 [MH⁺], 448.0 [MH⁻].

Step C: A suspension of methyl 4-{5-[3-(toluene-4-sulfonylamino)-phenyl]-[1,3,4]oxadiazol-2-yl}benzoate (225 mg, 0.50 mmol) in THF (10 mL) and 1N NaOH (0.55 mL, 0.55 mmol) is heated at reflux overnight. After cooling to room temperature, the reaction mixture is partitioned in EtOAC and saturated NaHCO₃. The phases are separated and the organic layer is extracted with saturated NaHCO₃ (3×). The aqueous phases are combined and acidified to pH 2 with 6N HCl. The resultant heterogeneous mixture is filtered and dried to obtain 129 mg (59%) of 4-{5-[3-(toluene-4-sulfonylamino)-phenyl]-[1,3,4]oxadiazol-2-yl}benzoic acid as a tan powder: mp >275° C.; ¹H NMR: (DMSO-d₆) δ 10.62 (br s, 1H), 8.18-8.11 (m, 4H), 7.84 (t, J=1.8, 1H), 7.76-7.67 (m, 3H), 7.47 (t, J=7.9, 1H), 7.35 (7.32 (m, 3H), 2.30 (s, 3H); MS m/z 436.0 [MH⁺], 434.0 [MH⁻].

Utilizing steps B-C above and substituting other sulfonyl chlorides or acid chlorides the following compounds are prepared: Compound Nos: 12 and 14.

Example D

Preparation of 4-(5-{3-[3-(4-isopropylphenyl)ureido]phenyl}-[1,3,4]oxadiazol-2-yl)benzoic acid (Compound No. 60)

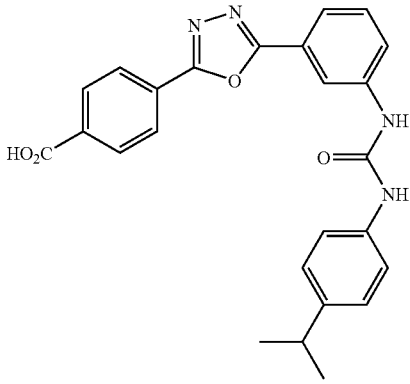 [SMILES: CC(C)c1ccc(NC(=O)Nc2cccc(-c3nnc(-c4ccc(C(=O)O)cc4)o3)c2)cc1]

Step A: A suspension of methyl 4-[5-(3-aminophenyl)-[1,3,4]oxadiazol-2-yl]benzoate from Example C step A (0.30 g, 1.02 mmol) and 4-isopropylphenyl isocyanate (0.20 mL, 1.22 mmol) in dichloroethane (10 mL) is stirred for 3 days at room temperature. The reaction mixture is filtered and the solid is washed with CH₂Cl₂, to afford 0.28 g (60%) of methyl 4-(5-{3-[3-(4-isopropyl-phenyl)-ureido]-phenyl}-[1,3,4]oxadiazol-2-yl)benzoate as a white solid: mp >270° C., ¹H NMR: (DMSO-d₆) ◻ 8.97 (br s, 1H), 8.63 (br s, 1H), 8.33 (t, J=1.8, 1H), 8.22-8.13 (m, 4H), 7.70 (dt, J=1.7, 7.5, 1H), 7.60-7.47 (m, 2H), 7.36 (d, J=8.4, 2H), 7.14 (d, J=8.4, 2H); 2.82 (septet, J=6.8, 1H), 1.18 (d, J=6.8, 6H); MS m/z 457.2 [MH⁺], 455.3 [MH⁻].

Step B: A suspension of methyl 4-(5-{3-[3-(4-isopropylphenyl)ureido]phenyl}-[1,3,4]oxadiazol-2-yl)benzoate (0.23 g, 0.50 mmol) in THF (10 mL) and 1N NaOH (0.56 mL, 0.56 mmol) is heated at reflux for 2.5 h. After cooling to rt, the reaction mixture is diluted with H₂O, acidified to pH 2 with 6N HCl and is extracted with EtOAC (3×) and is dried and concentrated to give 170 mg (77%) of methyl 4-(5-{3-[3-(4-isopropylphenyl)ureido]phenyl}-[1,3,4]oxadiazol-2-yl)benzoate as an off-white solid: mp >270° C., ¹H NMR: ◻ (DMSO-d₆) 8.97 (br s, 1H), 8.63 (br s, 1H), 8.33 (br s, 1H), 8.20-8.10 (m, 4H), 7.70-7.45 (m, 3H), 7.35 (d, J=7.2, 2H), 7.12 (d, J=7.2, 2H), 2.81 (m, 1H), 1.16 (d, J=5.4, 6H); MS m/z 443.2 [MH⁺], 441.2 [MH⁻].

Example E

Preparation of 3-[5-(4-morpholin-4-yl-phenyl)-[1,3,4]oxadiazol-2-yl]benzoic acid (Compound No. 82)

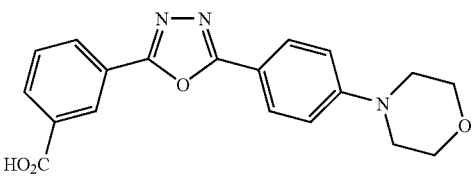 [SMILES: O=C(O)c1cccc(-c2nnc(-c3ccc(N4CCOCC4)cc3)o2)c1]

Step A: A flame-dried tube is charged with Cs₂CO₃ (0.38 g, 1.17 mmol), (tris)-dibenzylidineacetone dipalladium (16 mg, 0.017 mmol), racemic-BINAP (21 mg, 0.033 mmol) and methyl 3-[5-(4-bromophenyl)-[1,3,4]oxadiazol-2-yl]benzoate (preparation by the method of Example A, step B) (0.30 g, 0.83 mmol). After evacuating and flushing with N₂, morpholine (0.09 mL, 1.00 mmol) and toluene (3.6 mL) are added and the reaction is heated at reflux for 24 h and then is cooled to room temperature. The heterogeneous mixture is filtered, washed with EtOAc and is concentrated. The residue is purified by flash chromatography over silica gel (EtOAc/CH₂Cl₂, 5-10%) to afford 0.19 g (63%) of methyl 3-[5-(4-morpholin-4-yl-phenyl)-[1,3,4]oxadiazol-2-yl]-benzoate as a yellow solid: mp 150-151° C., ¹H NMR: (CDCl₃) δ 8.72 (t, J=1.8, 1H), 8.34 (d, J=7.8,1H), 8.19 (d, J=7.8, 1H), 8.03 (d, J=8.7, 2H), 7.61 (t, J=7.8, 1H) 6.99 (d, J=8.7, 2H), 3.99 (s, 3H), 3.89-3.87 (m, 4H), 3.39-3.30 (m,4H).

Step B: A solution of methyl 3-[5-(4-morpholin-4-yl-phenyl)-[1,3,4]oxadiazol-2-yl]benzoate (0.14 g, 0.38 mmol) in THF (10 mL) and 1N NaOH (0.46 mL, 0.46 mmol) is heated at reflux for 15 h. After cooling to room temperature, the reaction mixture is diluted with H₂O and the aqueous phase is extracted with EtOAc. The organic layer is back-extracted with saturated NaHCO₃. The combined aqueous phases are acidified to pH 4.5 with 0.5 N NaH₂PO₄ and extracted with EtOAC (3×) to give, after drying and concentrating, 0.11 g (82%) of 3-[5-(4-morpholin-4-yl-phenyl)-[1,3,4]oxadiazol-2-yl]benzoic acid as a yellow solid: mp 235-237° C.; ¹H NMR: (DMSO-d₆) δ 8.56 (br s,1H), 8.32 (d, J=7.5,1H), 8.13 (d, J=7.5, 1H), 7.95 (d, J=8.4, 2H), 7.73 (t, J=7.8, 1H), 7.11 (d, J=8.4,2H), 3.76-3.72 (m, 4H), 3.32-3.27 (m, 4H); MS m/z 352.3 [MH⁺], 350.3 [MH⁻].

In similar fashion, the following compounds are prepared by reaction of methyl 3-[5-(4-bromophenyl)-[1,3,4]oxadiazol-2-yl]benzoate with the appropriate amines following steps A-B above: Compound Nos: 83, 84, and 280.

Example F

Preparation of 3-[5-(3'-methylbiphenyl-4-yl)-[1,3,4]oxadiazol-2-yl]benzoic acid (Compound No. 281)

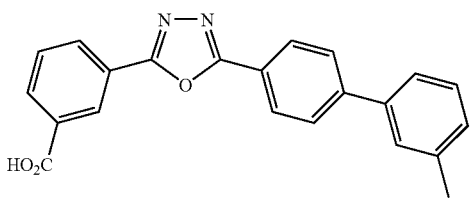 [SMILES: Cc1cccc(-c2ccc(-c3nnc(-c4cccc(C(=O)O)c4)o3)cc2)c1]

Step A: A flame-dried tube is charged with 0.40 g, 1.11 mmol) of methyl 3-[5-(4-bromophenyl)-[1,3,4]oxadiazol-2- yl]benzoate (from Example A, step B) m-tolyl boronic acid (0.21 g, 1.55 mmol), (tris)-dibenzylidineacetone dipalladium (10 mg, 0.011 mmol) and KF (0.19 g, 3.33 mmol). The tube is flushed with $N_2$ followed by the addition of THF (4 mL) and a solution of 0.7 M tri-tert-butyl phosphine in hexane (0.08 mL, 0.027 mmol). The reaction is stirred at room temperature for 15 h and then is heated at reflux for 2 h. After cooling to room temperature, the reaction is filtered, washed with EtOAc, and the filtrate is washed with saturated $NaHCO_3$ and then is dried and is concentrated. Flash chromatography (EtOAc/$CH_2Cl_2$, 0-2%) over silica gel gives 0.18 g (44%) of methyl 3-[5-(3'-methyl-biphenyl-4-yl)-[1,3,4]oxadiazol-2-yl]benzoate as a white solid: mp 147-148° C.; $^1$H NMR: ($CDCl_3$) δ 8.77 (t, J=3.1, 1H), 8.37 (dd, J=1.0,7.5, 1H), 8.24-8.20 (m, 3H), 7.76 (d, J=8.4, 2H), 7.64 (t, J=7.8, 1H), 7.47-7.44 (m, 2H), 3.34 (t, J=7.8, 1H), 7.22 (d, J=7.2, 1H), 4.00 (s, 3H), 2.46 (s, 3H); MS m/z 371.2 [MH$^+$].

Step B: A solution of methyl 3-[5-(3'-methyl-biphenyl-4-yl)-[1,3,4]oxadiazol-2-yl]benzoate (0.15 g, 0.41 mmol) in THF (5 mL) and 1N NaOH (0.51 mL, 0.51 mmol) and $H_2O$ (1 mL) is heated at reflux overnight. After cooling to rt, the reaction mixture is diluted with $H_2O$ and the pH is adjusted to 4.5-5 by addition of $NaH_2PO_4$ and 1N HCl. The mixture is extracted with EtOAc (3×) and then is dried and concentrated to give 3-[5-(3'-methylbiphenyl-4-yl)-[1,3,4]oxadiazol-2-yl]benzoic acid as a white solid: mp 240-242° C.; $^1$H NMR: δ (DMSO-$d_6$) 8.53 (s, 1H), 8.27 (dt, J=1.35, 1H), 8.14-8.08 (m, 3H), 7.80 (d, J=8.1, 2H), 7.70 (t, J=7.8, 1H), 7.49-7.45 (m, 2H), 7.32 (t, J=7.8, 1H), 7.17 (d, J=7.8, 1H), 2.36 (s, 3H); MS m/z 357.2 [MH$^+$], 355.3 [MH$^-$].

The following compound is made by the above procedure by substituting methyl 3-[5-(6-bromopyridin-3-yl)-[1,3,4]oxadiazol-2-yl]benzoate, as prepared as in Example A step B: Compound No. 282.

Example G

Preparation of 4-[5-(4-isopropylphenyl)-[1,3,4]thiadiazol-2-yl]benzoic acid (Compound No. 324)

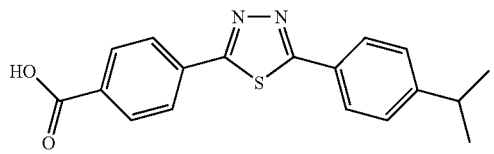 [SMILES: CC(C)c1ccc(-c2nnc(-c3ccc(C(=O)O)cc3)s2)cc1]

Step A: A 0° C. solution of 4-isopropylbenzhydrazide (0.73 g, 4.10 mmol) in THF (20 mL) is treated with $Et_3N$ (0.62 mL) and methyl 4-chlorocarbonylbenzoate (0.90 g, 4.51 mmol). The reaction is then warmed to room temperature and is stirred overnight. The reaction mixture is then washed with $H_2O$ and is extracted with EtOAc (3×). The combined organic phases are washed with $H_2O$ and saturated NaCl and then is dried and concentrated in vacuo to a solid. Purification by flash chromatography over silica gel using EtOAc/$CH_2Cl_2$ (0-15%) as eluent gives 0.86 g (62%) of 4-[N'-(4-isopropylbenzoyl)-hydrazinocarbonyl]benzoic acid as a white solid: mp 235-237° C.; MS m/z 341.2 [MH$^+$], 339.2 [MH$^-$].

Step B: A suspension of 4-[N'-(4-isopropylbenzoyl)-hydrazinocarbonyl]benzoic acid (0.25 g, 0.74 mmol) from step A above and Lawesson's reagent (0.59 g, 1.47 mmol) in $CH_2Cl_2$ (10 mL) is heated at reflux for 18 h and then is cooled to room temperature. The crude reaction mixture is concentrated in vacuo and is purified by flash chromatography (EtOAc/$CH_2Cl_2$, 0-1%) to give 0.22 g (88%) of methyl 4-[5-(4-isopropylphenyl)-[1,3,4]thiadiazol-2-yl]benzoate as a white solid: mp 147-151° C.; $^1$H NMR: (DMSO-$d_6$) δ 8.16-8.09 (m, 4H), 7.93 (d, J=8.1, 2H), 7.45 (d, J=8.1, 2H), 3.89 (s, 3H), 2.98 (septet, J=6.8, 1H), 1.24 (d, J=6.9, 6H); MS m/z 339.2 [MH$^+$].

Step C: A solution of methyl 4-[5-(4-isopropylphenyl)-[1,3,4]thiadiazol-2-yl]-benzoate (96 mg, 0.28 mmol) in THF is treated with 1N NaOH (0.36 mL, 0.36 mmol) and $H_2O$ (0.65 mL) and the biphasic reaction mixture is heated at reflux for 3 h and then is cooled to room temperature. After diluting with additional $H_2O$, sufficient 6N HCl is added until the pH is adjusted to 2, resulting in the formation of a white solid precipitate. The solid is filtered, washed with $H_2O$ and is dried to give 60 mg (65%) of 4-[5-(4-isopropylphenyl)-[1,3,4]thiadiazol-2-yl]-benzoic acid: mp >300° C.; $^1$H NMR: (DMSO-$d_6$) δ 7.99-7.88 (m, 6H), 7.44 (d, J=8.1, 2H), 2.97 (septet, J=6.9, 1H), 1.24 (d, J=6.9, 6H); MS m/z 325.1 [MH$^+$], 323.2 [MH$^-$].

Example H

Preparation of 4-[5-(4-isopropylphenyl)-[1,2,4]oxadiazol-3-yl]benzoic acid (Compound No. 275)

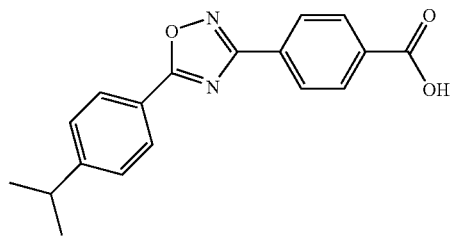 [SMILES: CC(C)c1ccc(-c2nc(-c3ccc(C(=O)O)cc3)no2)cc1]

Step A: To a solution of hydroxylamine, that is prepared from 2.19 g (31.5 mmol) of $NH_2OH.HCl$ and 1.26 g (31.5 mmol) of NaOH, in $H_2O$/EtOH (1/1, 50 mL) is added methyl 4-cyanobenzoate (4.83 g, 30.0 mmol). The reaction mixture is stirred at 90° C. overnight. The solvent is then replaced by EtOH/Hexanes (9/1, 50 mL) and stirred for 0.5 h at room temperature. The solid is removed by filtration and the filtrate is evaporated to dryness to give a white powder, which is further recrystallized from EtOH/Hexane to give white needles (4.53 g, 77.8%): MS m/z 195 [MH$^+$]

Step B: To a 0° C. solution of the above hydroxyamidine (0.39 g, 2.05 mmol), 4-isopropylbenzoic acid (0.34 g, 2.05 mmol) and dichloromethane (10 mL) is added HOBt (0.28 g, 2.05 mmol) followed by DCC (0.42 g, 2.05 mmol). The mixture is stirred at room temperature overnight. The precipitate is removed by filtration and the filtrate is concentrated, followed by chromatography over silica gel to give methyl 4-((Z)-amino{[(4-isopropylbenzoyl)oxy]imino}methyl)benzoate (0.60 g, 77%): MS m/z 341 [MH$^+$].

Step C: The intermediate that is prepared above (0.48 g, 1.4 mmol) is heated in toluene (5.0 mL) at 130° C. overnight, cooled and chromatographed (silica gel, EtOAc/Hexanes, 2/8) to provide methyl 4-[5-(4-isopropylphenyl)-1,2,4-oxadiazol-3-yl]benzoate as a white powder (0.41 g, 91%): MS m/z 323 [MH$^+$].

Step D: The methyl ester prepared as above (0.37 g, 1.15 mmol) is treated with $BBr_3$ (1M in dichloromethane, 2.3 mL, 2.3 mmol) in dichloromethane (10 mL) at room temperature overnight. The volatiles are removed in vacuo and the residue is treated with water and the crude product is recrystallized from chloroform to furnish the desired product, 4-[5-(4-isopropyl-phenyl)-[1,2,4]oxadiazol-3-yl]benzoic acid (0.23 g, 66%): mp 210-213° C.; $^1$H NMR ($CDCl_3$, 300 MHz) δ 1.23 (d, 6H), 2.89-2.99 (m, 1H), 7.33 (d, 2H), 8.03-8.17 (m, 6H); MS m/z 307 [MH$^-$].

The following compounds are prepared essentially following the steps above with substitution of the appropriate carboxylic acid derivative in step B: Compound Nos: 141 and 407.

Example I

Preparation of 4-[5-(4-fluorophenyl)-[1,2,4]oxadiazol-3-yl]benzoic acid (Compound No. 412)

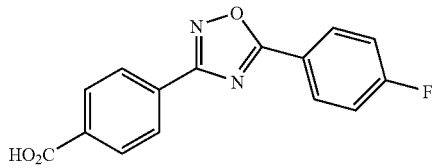 [SMILES: O=C(O)c1ccc(-c2noc(-c3ccc(F)cc3)n2)cc1]

Step A: 40 g of 2-chlorotrityl chloride resin (Rapp polymere, Germany), is agitated in dimethylformamide (200 mL) for 10 min and the solvent is drained. To the resin is added a solution of 4-cyanobenzoic acid (12.71 g, 96.4 mmol) in 300 mL of 1% diisopropylethyl amine/dimethylformamide and is agitated 4 h at room temperature. The solvents are drained and the resin is washed with dichloromethane (3×200 mL×1 min), dimethylformamide (3×200 mL×1 min), methanol (3×200 mL×1 min), and dichloromethane (3×200 mL×1 min). The resin is vacuum dried for 4 h. The desired product is analyzed by cleavage of a small amount of the reacted resin with triethylsilane/trifluoroacetic acid/dichloromethane (10/50/40): MS m/z 148 [MH$^+$] (97% purity).

Step B: The 4-cyanobenzoic resin in ethanol (300 mL) is agitated for 10 min at room temperature, and then the solvent is drained. To a solution of hydroxylamine hydrochloride (35.81 g, 516 mmol) in ethanol (200 mL) is added diisopropylethylamine (89.3 mL, 516 mmol) and the mixture is stirred for 5 min at room temperature. To the resin is added the above reaction mixture and agitated for 24 h at 40° C. The solvents are drained, and the resin is washed with dichloromethane (3×200 mL×10 min), dimethylformamide (3×200 mL×10 min), methanol (3×200 mL×10 min), and dichloromethane (3×200 mL×10 min). The resin is vacuum dried for 4 h. The desired product is analyzed by cleavage of a small amount of the reacted resin with triethylsilane/trifluoroacetic acid/dichloromethane (10/50/40): MS m/z 181 [MH$^+$] (92% purity).

Step C: To a suspension of hydroxyamidine resin (500 mg, 0.4 mmol) in anhydrous dichloromethane (3 mL) is added 4-fluorobenzoyl chloride (95 δL, 0.8 mmol) and diisopropylethylamine (138 δL, 0.8 mmol). The reaction mixture is agitated overnight at room temperature. The solvents are drained, and the resin is washed with dichloromethane (3×10 mL×10 min), dimethylformamide (3×10 mL×10 min), methanol (3×10 mL×10 min), and dichloromethane (3×10 mL×10 min). The resin is vacuum dried for 4 h. The desired product is analyzed by cleavage of a small amount of the reacted resin with triethylsilane/trifluoroacetic acid/dichloromethane (10/50/40): MS m/z 303 [MH$^+$].

Step D: To a suspension of acylated resin in anhydrous dichloromethane (1.5 mL) is added 50% trifluoroacetic acid in dichloromethane (1.5 mL). The reaction mixture is agitated for 2 h at room temperature. The resin is removed and the filtrate is concentrated under reduced pressure. The residue is dissolved in 10% dimethylformide in toluene (4 mL) and then is stirred for 2 h at 130° C. The solvents are removed and the desired product, 4-[5-(4-fluorophenyl)-[1,2,4]oxadiazol-3-yl]benzoic acid, is purified by preparative LC/MS: MS m/z 285 [MH$^+$].

The following compounds are prepared using the procedures described above: Compound Nos: 408, 409, 410, 411, 412, 413, 414, 415, 416, 417, 418, 419, 420, 421, 422, 430, 431, 432, 433, 434, 435, 436, 437, 438, 439, 440, 441, 442, 443, 445, 446, 447, 448, 449, 450, 451, 452, 453, 444.

Example J

Preparation of 4-[3-(4-isopropylphenyl)-1,2,4-oxadiazol-5-yl]benzoic acid (Compound No. 140)

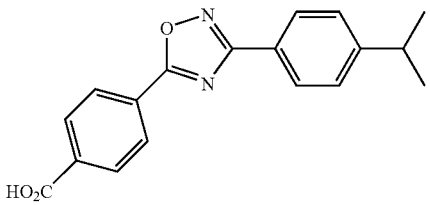 [SMILES: CC(C)c1ccc(-c2noc(-c3ccc(C(=O)O)cc3)n2)cc1]

Step A: To a solution of hydroxylamine, prepared from 3.13 g (45.0 mmol) of NH$_2$OH.HCl and 1.89 g (45 mmol) of NaOH, in H$_2$O/EtOH (1/1, 50 mL) is added 4-isopropylbenzonitrile (4.35 g, 30.0 mmol). The reaction mixture is stirred at 90° C. overnight. The solvent is then replaced by EtOH/Hexanes (9/1, 50 mL) and is stirred for 0.5 h at room temperature. The solid is removed by filtration and the filtrate is evaporated to dryness to give a colorless oil, N'-hydroxy-4-isopropylbenzenecarboximidamide in quantitative yield: MS m/z 195 [MH$^+$].

Step B: To a 0° C. solution of the intermediate prepared above, (0.27 g, 1.50 mmol), triethylamine (0.18 g, 0.25 mL, 1.8 mmol) in dichloromethane (10 mL) is added methyl 4-(chlorocarbonyl)benzoate (0.32 g, 1.58 mmol). The mixture is then stirred at room temperature for 4 h. The mixture is then washed with water and brine, and is dried over anhydrous sodium sulfate and is filtered. The solvent is replaced with toluene and is stirred at 130° C. in a sealed tube overnight. The crude product obtained after the removal of the solvent is chromatographed to provide methyl 4-[3-(4-isopropylphenyl)-1,2,4-oxadiazol-5-yl]benzoate (0.38 g, 79%): MS m/z 323 [MH$^+$].

Step C: The methyl ester prepared above (0.37 g, 1.15 mmol) is treated with BBr$_3$ (1M in dichloromethane, 2.3 mL, 2.3 mmol) in dichloromethane (10 mL) at room temperature overnight. The volatiles are removed in vacuo and the residue is treated with water and the crude product is recrystallized from chloroform to furnish the desired product, 4-[3-(4-isopropylphenyl)-1,2,4-oxadiazol-5-yl]benzoic acid (0.34 g, 97%): mp 253-255° C. $^1$H NMR (CDCl$_3$, 300 MHz) δ 1.25 (d, 6H), 2.90-3.00 (m, 1H), 7.31 (d, 2H), 8.01-8.24 (m, 6H); MS m/z 307 [MH$^-$].

In similar fashion, utilizing the above steps, the following compounds are prepared by substitution of the appropriate benzonitriles in step A above and reaction with methyl 3-(chlorocarbonyl)benzoate starting materials in step B above: Compound Nos: 349, 364, 394, 396, 397, 398, 399, 403, 404, 405, and 406.

Example K

Preparation
3-[3-(2-fluorophenyl)-[1,2,4]oxadiazole-5-yl] benzoic acid (Compound No. 506)

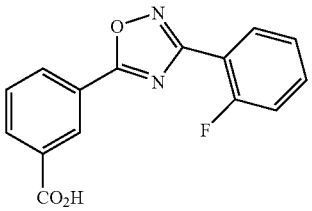 [SMILES: O=C(O)c1cccc(-c2nc(-c3ccccc3F)no2)c1]

Steps A-C (1-pot): To a solution of 2-fluorobenzonitrile (484 mg, 4.00 mmol, Aldrich) in 3 mL of t-BuOH is added 274 μL (4.48 mmol, 1.12 equiv.) of a solution of 50% $NH_2OH/H_2O$. The solution is heated to 73° C. for 20 h, an additional portion of 50% $NH_2OH/H_2O$ is added (100 μL, 1.60 mmol, 0.38 equiv.), and the mixture is heated for 2 days at 73° C. The resulting mixture of crude 2-fluoro-N-hydroxybenzamidine is then cooled to 10° C., diluted with 3 mL of t-BuOH, and treated with $Et_3N$ (836 μL, 6 mmol), followed by 3-chlorocarbonylbenzoic acid methyl ester (1.19 g, 6 mmol) to form the intermediate O-acylated hydroxybenzamidine by slow warming of the mixture to room temperature over a 1-2 h period. This suspension is then heated to 90° C., stirred for 3 days, cooled to room temperature, diluted with 200 mL of 20% $THF/Et_2O$ and filtered. The organic solution is washed with 1N aqueous NaOH (2×50 mL), water (2×50 mL), dried ($MgSO_4$) and concentrated in vacuo to afford 3-[3-(2-fluorophenyl)-[1,2,4]oxadiazol-5-yl]benzoic acid methyl ester which is taken directly into the next reaction without further purification: MS m/z 299.33, calcd for $C_{16}H_{12}FN_3O_3$ ($MH^+$) 299.

Step D: The crude solid from step 3 (>93% pure by LC/MS) is diluted with 40 mL of 50% $THF/H_2O$, is heated to 65° C. for 5 h and cooled to room temperature. The solution is adjusted to pH 4 by the slow addition of 6N aqueous HCl solution and filtered. The resulting solid is washed with 30% $Et_2O$/hexanes and dried overnight at 70° C. (10 torr) to afford 1.07 g (94% over 4-steps) of 3-[3-(2-fluorophenyl)-[1,2,4]oxadiazole-5-yl] benzoic acid as a white fluffy powder: mp 233-234° C.; $^1H$ NMR (300 MHz, DMSO-$d_6$) δ 7.45 (m, 2H), 7.66 (m, 1H), 7.79 (t, J=7.7 Hz, 1H), 8.13 (m, 1H), 8.24 (dt, J=8.0 Hz, 1.4 Hz, 1H), 8.39 (dt, J=8.0, 1.6 Hz, 1H), 8.65 (t, J=1.6 Hz, 1H); MS m/z 285.26, calcd for $C_{15}H_{10}FN_3O_2$ ($MH^+$) 285.

The following compounds are made essentially by the procedures shown above starting from the appropriate substituted nitriles: Compound Nos: 507, 508, 509, 510, 511, 512, 513, 559, 560, 561, 562, 563, 564, 565, 569, 571, 572, 576, 577, 578, and 570.

Example L

Preparation of
3-[5-(4-isopropylphenyl)-oxazol-2-yl]benzoic acid (Compound No. 288)

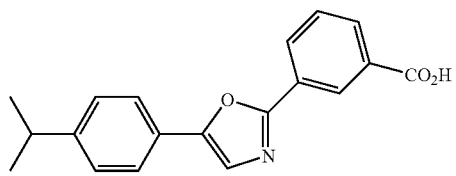 [SMILES: CC(C)c1ccc(-c2cnc(-c3cccc(C(=O)O)c3)o2)cc1]

Step A: To a solution of hexamethylenetetraamine (7.0 g, 50 mmol) in 70 mL of dry toluene is added a solution of 2-bromo-1-(p-isopropylphenyl)ethanone (12 g, 50 mmol) in 40 mL dry toluene at 0° C. The reaction mixture is stirred overnight. The solid formed is removed by filtration, washed with 20 mL of toluene and then the solid (hexamethylenetetraammonium salt) is added to a solution of concentrated hydrochloric acid (8.5 mL) in 80 mL of ethanol. The mixture is stirred for 24 h in the dark at room temperature. The white solid (ammonium chloride) is removed by filtration and the filtrate is evaporated. The residue is recrystallized from ethanol/ether to give 2-amino-1-(p-isopropylphenyl)ethanone hydrochloride (7 g, 33 mmol) as a yellow solid (70%).

Step B: A solution of isophthalic acid mono ethyl ester (5.2 g, 27 mmol) in 20 mL of thionyl chloride is refluxed for 3 h and then is concentrated to remove excess thionyl chloride. The residue is dissolved in dry THF (10 mL) and added dropwise to a solution of 2-amino-1-(p-isopropylphenyl)ethanone hydrochloride (4.7 g, 22 mmol) and pyridine (5 mL, 61 mmol) in dry THF (30 mL) at 0° C. After stirring for 24 h, the solvent is evaporated. The residue is dissolved in 10 mL of water, is extracted with $CH_2Cl_2$, is washed with brine and dried over $Na_2SO_4$. After concentration in vacuo, the residue is purified by column chromatography to give N-[2-(4-isopropylphenyl)-2-oxo-ethyl]-isophthalamic acid ethyl ester as a brown solid (5.5 g, 71%).

Step C: A solution of the above ester (500 mg, 1.42 mmol) in 5 mL of phosphorus oxychloride is refluxed for 2.5 h. After evaporation of the solvent, the residue is dissolved in 20 mL of conc. ammonia solution, is extracted with EtOAC, is washed with brine and dried over $Na_2SO_4$. Concentration of the solvent gives crude ethyl 3-[5-(4-isopropylphenyl)-oxazol-2-yl]benzoate as a brown oil (340 mg, 72%).

Step D: A mixture of ethyl 3-[5-(4-isopropylphenyl)-oxazol-2-yl]benzoate (150 mg, 0.45 mg) and lithium hydroxide (94 mg, 2.24 mmol) in methanol/water (9 mL/3 mL) is stirred for 2 h. After evaporation of the solvent, the residue is dissolved in 10 mL of water, treated with 1 g of citric acid, extracted with EtOAc, washed with brine and dried over $Na_2SO_4$. The solvent is concentrated in vacuo and the product is recrystallized from $CH_2Cl_2$/hexane to give 71 mg (52%) of 3-[5-(4-isopropylphenyl)-oxazol-2-yl]benzoic acid a pale yellow solid: mp 150-153° C.; $^1H$ NMR ($CDCl_3$) δ 8.97 (br s, 1H), 8.33 (d, J=7.6, 1H), 8.21 (d, J=7.6, 1H), 7.68 (d, J=7.6, 2H), 7.62 (t, J=7.8, 1H), 7.50 (br s, 1H), 7.33 (d, J=7.6, 2H), 2.97 (septet, J=6.8, 1H), 1.25 (d, J=6.9, 6H); MS m/z 308.2 [$MH^+$].

Example M

Preparation of
4-[5-(2,4-difluorophenyl)oxazol-2-yl]benzoic acid (Compound No. 548)

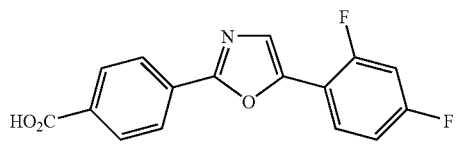 [SMILES: O=C(O)c1ccc(-c2ncc(-c3ccc(F)cc3F)o2)cc1]

Step A: Methyl 4-(4,5-dihydro-oxazol-2-yl)-benzoate: To a solution of methyl 4-chlorocarbonylbenzoate (10.92 g, 54.98 mmol) in toluene (200 mL) at room temperature is added 2-bromoethylamine hydrobromide (10.25 g, 50.0 mmol) with stirring. The reaction mixture is stirred at room temperature as triethylamine (35.0 mL, 251 mmol) is added. The reaction mixture is heated at reflux for 15 h and then cooled to room temperature. Water (200 mL) is added and the mixture is extracted with $CH_2Cl_2$ (4×50 mL). The extract is washed with water (2×50 mL), saturated aqueous NaCl (2×50 mL) and dried over $MgSO_4$, filtered and concentrated on a rotary evaporator to give 6.86 g of methyl 4-(4,5-dihydro-oxazol-2-yl)benzoate as a tan solid in 67% % yield.

Step B: Methyl 4-(5-bromo-oxazol-2-yl)benzoate: Methyl 4-(4,5-dihydrooxazol-2-yl)benzoate (6.86 g, 33.43 mmol) is suspended in $CCl_4$ (335 mL). N-bromosuccinimide (18.45 g, 103.7 mmol) is added followed by addition of azobisisobutyronitrile (50 mg). The reaction mixture is purged with nitrogen (5 vacuum/nitrogen cycles) and is heated to reflux for 17 h. The solid is filtered, washed with $CCl_4$, and discarded. The filtrate is washed with a solution of saturated aqueous $Na_2S_2O_3$ (40 mL), dried over $MgSO_4$, filtered and concentrated on a rotary evaporator to give the crude product. The product is further purified by silica gel chromatography eluting with 1-6% ethyl acetate/hexanes to give 4.42 g (47%) of methyl 4-(5-bromooxazol-2-yl)benzoate as a white solid.

Step C: Methyl 4-[5-(2,4-difluorophenyl)oxazol-2-yl]benzoate: Methyl 4-(5-bromooxazol-2-yl)benzoate (2.23 g, 7.91 mmol) is dissolved in anhydrous dimethoxyethane (26 mL) and stirred at 25° C. 2,4-Difluorophenyl boronic acid (1.39 g, 8.80 mmol), cesium fluoride (2.89 g, 19.0 mmol) and Dichlorobis(triphenylphosphine)palladium(II) (0.281 g, 0.40 mmol) are then added. The reaction mixture is heated to reflux under nitrogen for 16 h. The reaction mixture is cooled to room temperature, the solid is filtered, is washed with dimethoxyethane and is discarded. The filtrate is diluted with water to precipitate the product, which is filtered, washed with water and dried to give the crude product as a tan solid. The product is purified by silica gel chromatography (10-20% ethyl acetate/hexanes) to give 1.16 g (47%) of methyl 4-[5-(2,4-difluorophenyl)oxazol-2-yl]benzoate as a light yellow solid.

Step D: 4-[5-(2,4-Difluoro-phenyl)oxazol-2-yl]benzoic acid: Methyl 4-[5-(2,4-difluorophenyl)-oxazol-2-yl]benzoate is suspended in a mixture of t-butanol (6 mL) and water (2 mL). Sodium hydroxide (0.24 g, 6.0 mmol) is added and the reaction mixture is heated to reflux for 15 h. The reaction mixture is cooled to room temperature and acidified to pH 3 by addition of 10% aqueous hydrochloric acid to precipitate the product. The solid is filtered, washed with water (3×10 mL), and dried to give 1.04 g (94%) of 4-[5-(2,4-difluorophenyl)oxazol-2-yl]benzoic acid as a white solid: mp 301-302° C., $^1H$ NMR (300 MHz, $CDCl_3$): δ 7.30 (1H, dt, J=2.4, 8.1), 7.52 (1H, m), 7.71 (1H, d, J=3.6), 8.03-8.11 (m, 4H), 8.22 (2H, d, J=6.9); MS m/z 302.32 [MH$^+$].

The following compounds are made by the method described above utilizing the appropriate boronic acids: Compounds Nos: 542, 543, 544, 545, 546, 547, 549, 550, 553, 554, 555, 556, 557, 558, 579, 580, 581, 582, 583, 584, 585, 586, 587, 588, 589, 590, 591, 592, 593, 594, 595, 527, 528, 629, 630, 631, 632, 633, 634, 635, 636, 637, 638, 639, 640, 641, 642, 643, 644, 645, 646, 647, 648, 649, 649 and 650.

Example N

Preparation of 3-[4-(4-pyrrolidin-1-yl-phenyl)-oxazol-2-yl]benzoic acid (Compound No. 335)

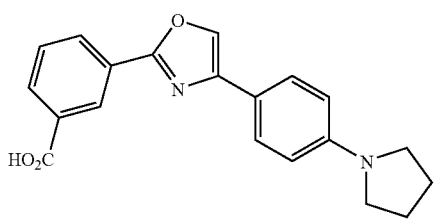 [SMILES: O=C(O)c1cccc(-c2nc(-c3ccc(N4CCCC4)cc3)co2)c1]

Step A: A solution of isophthalic acid methyl ester (20 g) in ammonium hydroxide (100 mL) is stirred for 18 h at 120° C. The solvent is removed under reduced pressure and the desired product is obtained as white solid.

Step B: To a solution of isophthalamic acid above, (160 mg, 0.96 mmol) in DMF (2 mL) is added 2-bromo-1-(4-pyrrolidin-1-yl-phenyl)-ethanone (158 mg, 0.96 mmol) at room temperature. The reaction mixture is stirred for 18 h at 150° C. and then cooled to ambient temperature. The solvent is removed under reduced pressure and the desired product, 3-[4-(4-pyrrolidin-1-yl-phenyl)oxazol-2-yl]benzoic acid, (MH$^+$=355.0) is purified by prep. LC-MS.

The following compounds are prepared using the procedure described above by substitution of the appropriate bromo or chloroketones: Compound Nos: 351, 352, 353, 354, 355, 356, 357, 358, 359, 360, 361, 362, 363, 329, 330, 331, 332, 333, 334, 335, 336, 337, 338, 339, 340, 341, 342, 343, 344, 345, 346, 325, and 276.

Example O

Preparation of 3-[2-(4-isopropylphenyl)-oxazol-4-yl]benzoic acid (Compound No. 313)

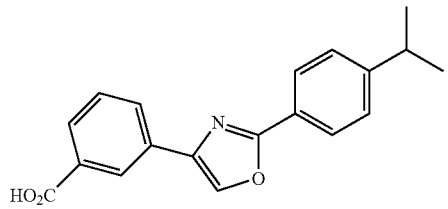 [SMILES: CC(C)c1ccc(-c2nc(-c3cccc(C(=O)O)c3)co2)cc1]

Step A: A solution of 4-isopropylbenzamide (301 mg, 1.85 mmol) and methyl 3-(2-bromoacetyl)benzoate (500 mg, 1.85 mmol) in 5 ml m-xylene is heated at 140-150° C. for 7 h. After cooling, the reaction is poured into water, extracted with EtOAc, dried over $MgSO_4$ and the product is purified by flash chromatography to give 161 mg (27%) of methyl 3-[2-(4-isopropylphenyl)-oxazol-4-yl]-benzoate.

Step B: A solution of methyl 3-[2-(4-isopropylphenyl)oxazol-4-yl]benzoate (100 mg, 0.311 mmol) and LiOH (64 mg, 1.56 mmol) in methanol/$H_2O$ (5 mL/1.7 mL) is stirred at room temperature for 0.5 h. The reaction mixture is then heated to 45° C. and stirred for 3 h. Upon completion of the reaction, the solvent is removed under reduced pressure. The residue is dissolved in 10 mL of water, neutralized, extracted with EtOAc, and then washed with brine, dried over $Na_2SO_4$, and concentrated to afford 90 mg (94%) of 3-[2-(4-isopropylphenyl)oxazol-4-yl]benzoic acid: mp 187-189° C.; $^1H$ NMR ($CDCl_3$) δ 8.53 (br s, 1H), 8.12-8.04 (m, 5H), 7.56 (t, J=7.6, 1H), 7.34 (d, J=7.6, 2H), 2.98 (septet, J=6.8, 1H), 1.30 (d, J=6.8, 6H); MS m/z 308.3 [MH$^+$].

Example P

Preparation of 3-[2-(4-isopropylphenyl)-oxazol-5-yl]-benzoic acid (Compound No. 320)

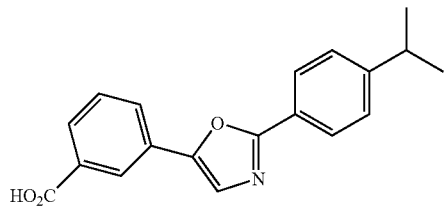 [SMILES: CC(C)c1ccc(-c2ncc(-c3cccc(C(=O)O)c3)o2)cc1]

Step A: A solution of 3-acetylbenzoic acid (0.67 g, 4.1 mmol) and a catalytic amount of TsOH in 50 mL of methanol is refluxed for 20 h. The solvent is removed by evaporation and the residue is dissolved in 50 mL of ether, washed with 20 mL of 5% NaHCO$_3$ and 20 mL of brine, dried (Na$_2$SO$_4$), evaporated to give methyl 3-acetylbenzoate (0.71 g, 97%) as a pale yellow oil.

Step B: A solution of methyl 3-acetylbenzoate (6.6 g, 37 mmol) in a mixture of ethyl ether and 1,4-dioxane (V:V=10:1, total 57.5 mL) is treated dropwise with bromine (1.91 mL, 37 mmol) over 30 min at room temperature. After the addition, the mixture is stirred for an additional 40 min. The mixture is then treated with an aqueous solution of NaHCO$_3$ (4 g, 47 mmol in 40 mL) under ice cooling and extracted with EtOAc (2×100 mL). The organic layer is washed in turn with 50 mL of saturated NaHCO$_3$, 50 mL of water and 50 mL of brine, dried over anhydrous MgSO$_4$, and evaporated. The residue is purified by silica gel column chromatography (petroleum ether-EtOAc, 15:1) to give methyl 3-(bromoacetyl)benzoate (6.5 g, 68%) as a white solid.

Step C: To a solution of methyl 3-(bromoacetyl)benzoate (3.8 g, 14.8 mmol) in 20 mL of DMF is added NaN$_3$ at room temperature and the mixture is stirred for 35 min. The reaction mixture is diluted with 100 mL of ice water and extracted with ether (3×50 mL). The combined organic layer is washed in turn with water (2×40 mL), brine (40 mL) and dried over MgSO$_4$ and concentrated to give methyl 3-(2-azidoacetyl)benzoate (2.1 g, 65%) as a gray solid.

Step D: A mixture of methyl 3-(2-azidoacetyl)benzoate (1.89 g, 8.6 mmol), 0.4 g 10% Pd—C in 40 mL of MeOH and 2.5 mL of conc. HCl is hydrogenated at 1 atm overnight at room temperature. After filtering the catalyst, the filtrate is evaporated and dried to give the amine hydrochloride salt (1.25 g, 63.2%) as a white solid.

Step E: To a solution of the hydrochloride salt of methyl 3-(2-aminoacetyl)benzoate (1.2 g, 5.2 mmol) in 10 mL of dry THF cooled to 0° C. is added 5 mL of absolute pyridine. The mixture is stirred for 30 min and to it is added dropwise a solution of 4-isopropylbenzoyl chloride in THF (10 mmol in 5 mL of solvent) over 15 min. After the addition, the reaction mixture is stirred for 2 h and evaporated. The residue is dissolved in 100 mL of EtOAc and washed with water (3×30 mL), brine (30 mL), and dried over Na$_2$SO$_4$. The residue is purified by silica gel column chromatography (petroleum ether/EtOAc, 3/1) to give methyl 3-[2-(4-isopropylbenzoylamino)acetyl]benzoate (1.2 g, 67.7%) as a pale yellow solid.

Step F: A solution of methyl 3-[2-(4-isopropylbenzoylamino)acetyl]benzoate (0.5 g, 1.5 mmol) in 10 mL of POCl$_3$ is refluxed for 6 hr and cooled to room temperature. The reaction mixture is added to 100 mL of ice water and adjusted to pH 10 with 2N NaOH. Then the mixture is extracted with EtOAc (2×50 mL) and the organic layer is washed with water (2×50 mL), brine (50 mL), dried over Na$_2$SO$_4$ and evaporated. The residue is purified by silica gel column chromatography (petroleum ether/EtOAc, 3/1) to give methyl 3-[2-(4-isopropylphenyl)oxazol-5-yl]benzoate (0.4 g, 84.5%) as a pale yellow solid.

Step G: To a solution of methyl 3-[2-(4-isopropylphenyl)oxazol-5-yl]benzoate (0.4 g, 1.25 mmol) in 5 mL of MeOH is added LiOH (0.1 g) in 10 mL of water and the reaction is heated to reflux for 2 h. The MeOH is removed by evaporation and acidified to pH 3 with 6N HCl and stirred for 15 min. The mixture is filtered and washed with water (3×10 mL), petroleum ether (10 mL) and dried to give 3-[2-(4-isopropylphenyl)oxazol-5-yl]benzoic acid (0.35 g, 91%) as a gray solid: mp 193-195° C.; $^1$H NMR (CDCl$_3$) δ 8.46 (br s, 1H), 8.10-8.05 (m, 3H), 7.95 (d, J=7.6, 2H), 7.58 (t, J=7.6, 1H), 7.56 (s, 1H), 7.37 (d, J=8.4, 2H), 2.99 (septet, J=6.9, 1H), 1.29 (d, J=6.9, 6H); mass spectrum (m/z) 308.2 [MH$^+$].

Example Q

Preparation of 3-[5-(4-fluorophenyl)-1H-pyrazol-3-yl]benzoic acid (Compound No. 552)

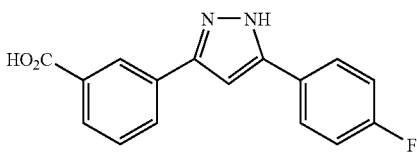 [SMILES: O=C(O)c1cccc(-c2cc(-c3ccc(F)cc3)[nH]n2)c1]

Step A: Preparation of 3-[3-(4-fluorophenyl)-3-oxopropionyl]benzonitrile. To a mixture of methyl 3-cyanobenzoate (1.05 g, 6.52 mmol) and sodium hydride (0.69 g, 60% in hexanes, 17.25 mmol) in THF (15 mL) is added a solution of 4-fluoroacetylphenone (0.86 g, 6.22 mmol) in THF (5 mL). The resulting mixture is heated at reflux under stirring for 1 h until the starting material is consumed as judged by TLC. After cooling to room temperature, the mixture is added to 15 mL of 1N HCl and the solution is extracted with ethyl acetate (2×20 mL). The combined organic layers are washed with saturated NaHCO$_3$, and then brine, dried over MgSO$_4$, and removed under reduced pressure. The residue is further purified by flash column, eluting with hexane and 50% methyl enechloride in hexane in sequence. The solid isolated is suspended in ethyl ether, and filtered to afford 1.28 g (74%) of 3-[3-(4-fluorophenyl)-3-oxopropionyl]benzonitrile as white powder. The obtained compound is >95% pure as determined by $^1$HNMR and LC-MS: $^1$H NMR (300 MHz, CDCl$_3$): δ 8.25 (m, 1H), 8.20 (m, 1H), 8.03 (m, 2H), 7.83 (m, 1H), 7.64 (t, J=7.8, 1H), 7.20 (m, 2H), 6.79 (s, 1H); MS (ES−) 266.25.

Step B: Preparation of 3-[5-(4-fluorophenyl)-1H-pyrazol-3-yl]benzonitrile. To a solution of 3-[3-(4-fluorophenyl)-3-oxo-propionyl]benzonitrile (250 mg, 0.895 mmol) in 3 mL of anhydrous EtOH is added anhydrous hydrazine (30 δL, 0.985 mmol) and the sealed reaction mixture is heated to 100° C. over 21 min in the microwave (Power 300 W, 1 min ramp to 100° C., 20 min hold) to afford a crude solution of 3-[5-(4-fluorophenyl)-1H-pyrazol-3-yl]benzonitrile: MS m/z 264.29, calcd for C$_{16}$H$_{11}$FN$_3$ (MH$^+$) 264.

Step C: Preparation of 3-[5-(4-fluorophenyl)-1H-pyrazol-3-yl]benzoic acid. To the mixture of 3-[5-(4-fluorophenyl)-1H-pyrazol-3-yl]-benzonitrile is added 5N aqueous sodium hydroxide (1 mL, 5 mmol) and the mixture is resealed and is heated to 10° C. over 31 min in the microwave (Power 300 W, 1 min ramp to 100° C., 30 min hold) to afford a crude solution containing 3-[5-(4-fluorophenyl)-1H-pyrazol-3-yl]benzoic acid which is cooled to room temperature. The solution is adjusted to pH 4 by the slow addition of 2N aqueous HCl solution and filtered. The resulting solid is washed with water (2×5 mL), 50% Et$_2$O/hexanes (2×5 mL), and dried (50° C., 1 torr) overnight to afford 211.5 mg (86%-2 steps) of 3-[5-(4-fluorophenyl)-1H-pyrazol-3-yl]benzoic acid as a white powder: mp 270.5-272° C.; $^1$H NMR (300 MHz, DMSO-d$_6$) δ 7.27 (m, 3H), 7.56 (t, J=7.7 Hz, 1H), 7.89 (m, 3H), 8.05 (d, J=7.7 Hz, 1H), 8.39 (m, 1H); MS m/z 283.32, calcd for C$_{16}$H$_{12}$FN$_2$O$_2$ (MH$^+$) 283.

In essentially the same manner the following compound is made: Compound No. 551.

Example R

Preparation of 3-[5-(4-isopropylphenyl)-2H-pyrazol-3-yl]benzoic acid (Compound No. 287)

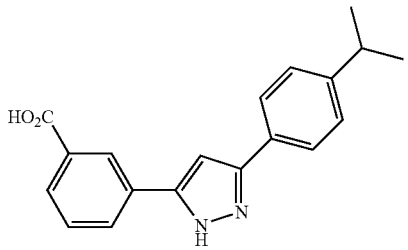 [SMILES: CC(C)c1ccc(-c2cc(-c3cccc(C(=O)O)c3)[nH]n2)cc1]

Step A: To a suspension of sodium hydride (1.56 g, 39 mmol, 60% dispersion in mineral oil) in anhydrous THF (50 mL) is added a 20 mL of a THF solution of 1-(4-isopropylphenyl)ethanone (4.86 g, 30 mmol) and isophthalic acid dimethyl ester (5.83 g, 30 mmol) and stirred for 30 min at room temperature. The mixture is heated at reflux for 5 h, cooled on ice and quenched with the addition of 3.5 mL of concentrated HCl, and then concentrated. The crude methyl 3-[3-(4-isopropylphenyl)-3-oxo-propionyl]-benzoate is dissolved in dichloromethane, purified by flash chromatography using dichloromethane/petroleum ether, 1/1 as eluent to give 6.4 g of intermediate as an oil (66%).

Step B: To 600 mg of methyl 3-[3-(4-isopropylphenyl)-3-oxo-propionyl]benzoate in 25 mL of 4/1 MeOH/H$_2$O is added 518 mg of LiOH.H$_2$O in one portion, and the reaction is heated at reflux for 2 hrs, cooled to room temperature and neutralized with aq. HCl. The precipitate is filtered, washed with water, dried and recrystallized from EtOH to give 350 mg of 3-[3-(4-isopropylphenyl)-3-oxo-propionyl]benzoic acid as a white solid.

Step C: To 310 mg of 3-[3-(4-isopropylphenyl)-3-oxo-propionyl]-benzoic acid in 5 mL of EtOH is added 0.05 mL hydrazine monohydrate. The reaction mixture is refluxed for 24 h, and cooled to room temperature. The precipitate is collected, washed with EtOH, and recrystallized from toluene to give 190 mg of 3-[5-(4-isopropylphenyl)-2H-pyrazol-3-yl]benzoic acid as a white solid: $^1$H NMR (DMSO-d$_6$) δ 8.40 (br s, 1H), 8.04 (d, J=7.2,1H), 7.87 (d, J=7.6, 1H), 7.74 (d, J=7.6, 2H), 7.54 (t, J=7.6, 1H), 7.30 (d, J=7.6, 2H), 7.19 (s, 1H), 2.90 (septet, J=6.8, 1H), 1.21 (d, J=6.8, 6H); MS m/z 308.2 [MH$^+$].

Example S

Preparation of 3-(4-p-tolylthiazol-2-yl)benzoic acid (Compound No. 350)

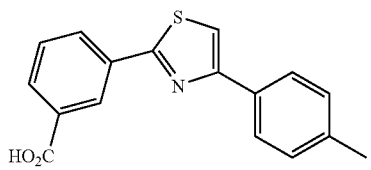 [SMILES: Cc1ccc(-c2csc(-c3cccc(C(=O)O)c3)n2)cc1]

Step A: To a solution of 3-cyanobenzoic acid (1.2 g, 8.2 mmol) in THF (50 mL) is added dithiophosphoric acid diethyl ester and water (5 mL) and the mixture is then stirred for 18 h at 80° C. The solvents are removed under reduced pressure and the desired 3-thiocarbamoyl benzoic acid is obtained as white solid.

Step B: To a solution of the 3-thiocarbamoyl benzoic acid in anhydrous DMF is added 2-bromo-1-p-tolyl-ethanone and the reaction is stirred for 18 h at 150° C. The solvent is removed under a nitrogen stream and the desired product, 3-(4-p-tolylthiazol-2-yl)benzoic acid, is purified by preparative LC-MS.

The following compounds are prepared using the procedures described above: Compound Nos: 365, 366, 367, 368, 369, 370, 371, 372, 373, 374, 375, 376, 377, 378, 379, 380, 381, 382, 383, 384, 385, 386, 387, 388, 389, 390, 391, 392, and 393.

Example T

Preparation of 3-[4-(4-isopropylphenyl)thiazol-2-yl]-benzoic acid (Compound No. 289)

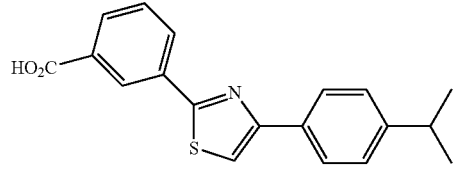 [SMILES: CC(C)c1ccc(-c2csc(-c3cccc(C(=O)O)c3)n2)cc1]

Step A: Ethyl 3-cyanobenzoate (3.36 g, 19.2 mmol) is dissolved in 10 mL of anhydrous DMF and the solution is heated to 70-75° C. H$_2$S is bubbled through the solution and 0.5 mL hexahydropyridine is added. After 2 h, the reaction mixture is poured into 50 mL of water and the precipitate that formed is collected and dried in vacuo to give 3 g of ethyl 3-thiocarbamoylbenzoate.

Step B: A solution of ethyl 3-thiocarbamoylbenzoate (0.5 g, 2.39 mmol) and 2-bromo-1-(4-isopropylphenyl)-ethanone (576 mg, 2.39 mmol) in 2 mL of anhydrous DMF is heated at 60-65° C. for 2 h. After the reaction is complete, the reaction is poured into water, extracted with EtOAc, dried over MgSO$_4$ and purified by flash chromatography affording 0.7 g (84%) of ethyl 3-[4-(4-isopropylphenyl)thiazol-2-yl] benzoate.

Step C: A solution of ethyl 3-[4-(4-isopropylphenyl)thiazol-2-yl]-benzoate (92 mg, 0.26 mmol) and LiOH (55 mg, 1.3 mmol) in methanol/H$_2$O (5 mL/1.7 mL) is stirred at room temperature for 0.5 h. The reaction mixture is then heated to 50° C. and stirred for 3 h. Upon completion, the solvent is removed in vacuo and the residue is dissolved in 10 mL of water, neutralized, extracted with EtOAC, washed with brine and then dried over Na$_2$SO$_4$, and concentrated to afford 82 mg (97.6%) of 3-[4-(4-isopropylphenyl)thiazol-2-yl]benzoic acid: mp 206-208° C.; $^1$H NMR: (CDCl$_3$) δ 8.74 (br s, 1H), 8.33 (d, J=7.6,1H), 8.17 (d, J=7.6, 1H), 7.93 (d, J=8.0, 2H), 7.59 (t, J=7.6, 1H), 7.48 (s, 1H), 7.32 (d, J=8.0, 1H), 2.97 (septet, J=6.9, 1H), 1.30 (d, J=6.8, 6H); MS m/z 324.2 [MH$^+$]. The following compounds are prepared using the procedures described above: Compound Nos: 350, 365, 366, 367, 368, 369, 370, 371, 372, 373, 374, 375, 376, 377, 378, 379, 380, 381, 382, 383, 384, 385, 386, 387, 388, 389, 390, 391, 392, 393.

Example U

Preparation of 3-[5-(4-Isopropyl-phenyl)thiazol-2-yl]benzoic acid (Compound No. 310)

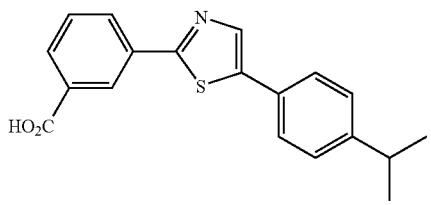 [SMILES: CC(C)c1ccc(-c2cnc(-c3cccc(C(=O)O)c3)s2)cc1]

Step A: A mixture of N-[2-(4-isopropylphenyl)-2-oxo-ethyl]isophthalamic acid ethyl ester (from Example L step B above, 500 mg 1.42 mmol) and phosphorus pentasulphide (1.0 g, 4.5 mmol) in 10 mL of dry pyridine is refluxed for 2 h, and after cooling, the mixture is poured into ice water (20 mL) and saturated ammonia solution (10 mL), The reaction is extracted with EtOAc, washed with brine and dried over $Na_2SO_4$. After concentration, the residue is purified by column chromatography to give ethyl 3-[5-(4-isopropylphenyl)-thiazol-2-yl]-benzoate as a brown oil (150 mg, 30%).

Step B: A mixture of ethyl 3-[5-(4-isopropylphenyl)thiazol-2-yl]benzoate (120 mg, 0.34 mmol) and lithium hydroxide (94 mg 2.24 mmol) in methanol/water (9 mL/3 mL) is stirred for 2 h. After the evaporation of the solvent, the residue is dissolved in 10 mL of water, treated with 1 g of citric acid, and then extracted with EtOAc. The organic phase is washed with brine, dried over $Na_2SO_4$, concentrated and the crude product is recrystallized from $CH_2Cl_2$/hexane to give 3-[5-(4-isopropylphenyl)thiazol-2-yl]benzoic acid as a brown solid (64 mg, 59%): mp 218-220° C.; $^1H$ NMR (DMSO-$d_6$) δ 8.78 (br s, 1H), 8.22-8.16 (m, 2H), 8.07 (s, 1H), 7.61-7.55 (m, 3H), 7.30 (d, J=8.0, 2H), 2.96 (septet, J=6.4, 1H), 1.32 (d, J=6.4, 6H); MS m/z 324.3 [MH$^+$].

Example V

Preparation of 3-[2-(4-isopropylphenyl)thiazol-4-yl]-benzoic acid (Compound No. 312)

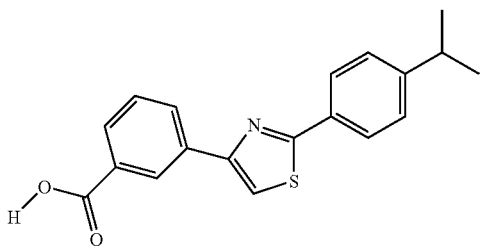 [SMILES: CC(C)c1ccc(-c2nc(-c3cccc(C(=O)O)c3)cs2)cc1]

Step A: 4-isopropylbenzonitrile (2.0 g, 14 mmol) is dissolved in 10 ml of anhydrous DMF and the solution is heated to 70-75° C. $H_2S$ is slowly bubbled through the solution and 0.5 mL of hexahydropyridine is added. After 1.5 h, the reaction mixture is poured into 50 mL of water and the precipitate that formed is collected and dried in vacuo to give 1.5 g of 4-isopropylthiobenzamide.

Step B: A solution of 4-isopropyl-thiobenzamide (331 mg, 1.85 mmol) and ethyl 3-(2-bromoacetyl)benzoate (500 mg, 1.85 mmol) in 5 mL of anhydrous DMF is heated at 60-65° C. for 2 h. The product mixture is poured into water, extracted with EtOAc, dried over $MgSO_4$ and concentrated in vacuo. Purification by flash chromatography gives 468 mg (72%) of methyl 3-[2-(4-isopropylphenyl)thiazol-4-yl]benzoate.

Step C: A solution of methyl 3-[2-(4-isopropylphenyl)thiazol-4-yl]benzoate (92 mg, 0.262 mmol) and LiOH (55 mg, 1.3 mmol) in methanol/$H_2O$ (5 mL/1.7 mL) is stirred at room temperature for 0.5 h. The reaction mixture is then heated to 55° C. and stirred for 3 h. The solvent is then removed under reduced pressure and the residue is dissolved in 10 mL of water, neutralized with acid, extracted with EtOAc, and then is washed with brine, and dried over $Na_2SO_4$, and concentrated to give 92 mg of 3-[2-(4-isopropylphenyl)thiazol-4-yl]benzoic acid: mp 193-195° C.; $^1H$ NMR (CDCl$_3$) δ 8.68 (br s, 1H), 8.29 (d, J=8.0, 2H), 8.08, (d, J=7.6, 1H), 7.98 (d, J=8.0, 2H), 7.59-7.55 (m, 2H), 7.33 (d, J=8.0, 2H), 2.98 (septet, J=6.8, 1H), 1.31 (d, J=6.8, 6H); MS m/z 324.3 [MH$^+$].

Example W

Preparation of 3-[2-(4-isopropylphenyl)thiazol-5-yl]benzoic acid (Compound No. 321)

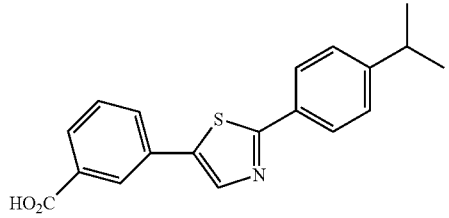 [SMILES: CC(C)c1ccc(-c2ncc(-c3cccc(C(=O)O)c3)s2)cc1]

Step A: A solution of methyl 3-[2-(4-isopropylbenzoylamino)acetyl]benzoate (Example P, Step E) (0.6 g, 1.8 mmol) and 1 g $P_2S_5$ in 5 mL of pyridine is refluxed for 6 h and cooled to room temperature. The reaction mixture is added to 100 mL of ice water and adjusted to pH 10 with 2N NaOH. The mixture is extracted with EtOAc (2×50 mL) and the organic layer is washed with water (2×50 mL), brine (50 mL), dried over $Na_2SO_4$ and evaporated. The residue is purified by silica gel column chromatography (petroleum ether/EtOAc, 3/1) to give methyl 3-[2-(4-isopropylphenyl)thiazol-5-yl]benzoate (0.31 g, 52.0%) as a pale yellow solid.

Step B: To a solution of methyl 3-[2-(4-isopropylphenyl)thiazol-5-yl]benzoate (0.31 g, 0.92 mmol) in 5 mL of MeOH is added LiOH (0.1 g) dissolved in 10 mL of water and the reaction is heated to reflux for 1 h. The MeOH is removed by evaporation and the reaction is acidified to pH 3 with 6N HCl and then stirred for 15 min. The mixture is filtered and washed with water (3×10 mL), petroleum ether (10 mL) and dried to give 3-[2-(4-isopropylphenyl)thiazol-5-yl]benzoic acid (0.28 g, 94%) as a pale yellow solid: mp 237-239° C.; $^1H$ NMR (DMSO-$d_6$) δ 8.37 (s, 1H), 8.17 (br s, 1H), 7.99-7.88 (m, 4H), 7.59 (t, J=7.8, 1H), 7.39 (d, J=8.0, 2H), 2.95 (septet, J=7.2, 1H), 1.22 (d, J=7.2, 6H); MS m/z 322.0 [MH$^+$].

Example X

Preparation of 3-[5-(4-chlorophenyl)isoxazol-3-yl]benzoic acid (Compound No. 479)

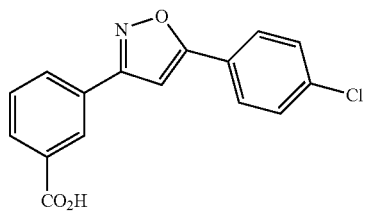 [SMILES: O=C(O)c1cccc(-c2cc(-c3ccc(Cl)cc3)on2)c1]

Step A: Preparation of 3-(hydroxyiminomethyl)benzoic acid methyl ester: To a solution of methyl 3-formylbenzoate (5 g, 30.5 mmol, Acros) in 50 mL of anhydrous EtOH is added hydroxylamine hydrochloride (2.40 g, 33.60 mmol) and pyridine (4.0 mL, 49.5 mmol). The mixture is heated to reflux for 2 h, cooled to room temperature and concentrated in vacuo. The residue is dissolved in 500 mL of $Et_2O$, partitioned with 1N aqueous HCl solution (2×50 mL), water (2×50 mL), dried ($MgSO_4$) and concentrated in vacuo to afford 5.5 g (100%) of methyl 3-(hydroxyiminomethyl)-benzoate as a white powder: mp 107-108° C.; $^1$H NMR (300 MHz, $CDCl_3$) δ 3.94 (s, 3H), 7.46 (t, J=7.5 Hz, 1H), 7.80 (d, J=7.8 Hz, 1H), 8.05 (d, J=7.5 Hz, 1H), 8.20 (m, 2H), 8.41 (s, 1H); MS m/z 178.23 [MH$^+$].

Step B: Preparation of 3-carbomethoxyphenyl hydroximoyl chloride: To a solution of methyl 3-(hydroxyiminomethyl)benzoate (5.5 g, 30.5 mmol) in 7 mL of DMF cooled to 0° C. is added NCS (4.97 g, 36.8 mmol), followed by 1-2 mL of gaseous HCl added by pipette from the headgas of a bottle of concentrated hydrochloric acid. The mixture over 15 min produced a strongly exothermic reaction which is controlled through the use of an ice bath. The mixture is stirred for 90 min, dissolved in 200 mL of 90% $Et_2O$/THF, washed with water (4×50 mL portions), brine (50 mL), and dried ($MgSO_4$). The solution is concentrated in vacuo until about 5 mL of solvent remained, 150 mL of hexane is added to precipitate the product, and the slurry filtered after 1-2 h to afford 4.5 g (61%) of 3-carbomethoxyphenyl hydroximoyl chloride as a white powder. This material is kept in the freezer in a dessicator to maintain stability: MS m/z 214.20 [MH$^+$].

Step C: Preparation of methyl 3-[5-(4-chlorophenyl)isoxazol-3-yl]benzoate: To a solution of 3-carbomethoxyphenyl hydroximoyl chloride (2.0 g, 9.4 mmol) and 1-chloro-4-ethynylbenzene (2.6 g, 19.9 mmol, Aldrich) in 50 mL of $CH_2Cl_2$ cooled to 0° C. is added $Et_3N$ (1.8 mL, 12.9 mmol). The reaction mixture is allowed to warm to room temperature over 1-2 h and is stirred for 24 h. The solution is diluted with 200 mL of $CH_2Cl_2$, washed with 1N aqueous NaOH solution (75 mL), water (75 mL), dried ($MgSO_4$) and concentrated in vacuo until ~15 mL volume remained. The solution is diluted with 8 mL of MeOH, and 110 mL of hexanes is added and the solvent is slowly concentrated at ambient temperature until significant precipitation occurred. The slurry is filtered and the solid product dried (70° C. at 10 torr) to afford 2.25 g (77%) of methyl 3-[5-(4-chlorophenyl)isoxazol-3-yl]benzoate as a white powder. The precipitation procedure is repeated on the concentrated mother liquor to afford an additional 310 mg (11%): $^1$H NMR (300 MHz, Acetone-$d_6$) δ 3.95 (s, 3H), 7.55 (s, 1H), 7.62 (d, J=8.5 Hz, 1.4 Hz, 2H), 7.70 (t, J=7.8 Hz, 2H), 7.98 (d, J=8.4 Hz, 2H), 8.13 (dm, J=7.8 Hz, 1H), 8.20 (dm, J=7.8 Hz, 1H), 8.54 (s, 1H); MS m/z 314.21, calcd for $C_{17}H_{13}ClNO_3$ (MH$^+$) 314.

Step D: Preparation of 3-[5-(4-chlorophenyl)isoxazol-3-yl]benzoic acid: A solution of 2.56 g (8.2 mmol) of methyl 3-[5-(4-chlorophenyl)isoxazol-3-yl]benzoate in 56 mL of 50% THF/$H_2O$ is heated to 65° C. for 3 h and cooled to room temperature. The solution is adjusted to pH 4 by the slow addition of 6N aqueous HCl solution and filtered. The resulting solid is washed with water, 30% $Et_2O$/hexanes and then dried overnight at 70° C. (10 torr) to afford 1.81 g (74%) of 3-[5-(4-chlorophenyl)isoxazol-3-yl]benzoic acid as a white fluffy powder. An additional 376 mg (15%) is obtained from precipitation of the mother liquor: mp 293-295° C.; $^1$H NMR (300 MHz, DMSO-$d_6$) δ 7.65 (m, 3H), 7.80 (s, 1H), 7.94 (d, J=8.8 Hz, 2H), 8.06 (dm, J=8.0 Hz, 1H), 8.14 (dm, J=7.9 Hz, 1H), 8.44 (m, 1H); MS m/z 300.19, calcd for $C_{16}H_{11}ClNO_3$ (MH$^+$) 300.

Utilizing essentially the same procedures described above and substituting other acetylene derivatives in step 4 gave the following compounds: Compound Nos: 463, 464, 465, 466, 467, 468, 469, 470, 471, 472, 473, 474, 475, 476, 477, 478, 480, 481, 482, 483, 484, 485, 486, 487, 488, 489, 490, 491, 521, 522, 523, 524, 525, 526, 529, 530, 531, 532, 533, 534, 566, 567, 568, 573, 574, and 575.

Example Y

Preparation of 3-[3-(4-chlorophenyl)isoxazol-5-yl]benzoic acid (Compound No. 503)

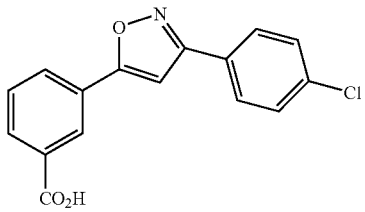 [SMILES: O=C(O)c1cccc(-c2cc(-c3ccc(Cl)cc3)no2)c1]

Step A: Preparation of 4-chlorobenzaldehyde oxime: To a solution of 4-chlorobenzaldehyde (2.83 g, 20.15 mmol, Aldrich) in 17 mL of anhydrous EtOH is added hydroxylamine hydrochloride (1.61 g, 22.5 mmol) and pyridine (2.5 mL, 30.9 mmol). The mixture is heated to reflux for 3 h, cooled to room temperature and concentrated in vacuo. The residue is dissolved in 125 mL of $Et_2O$, partitioned with 1N aqueous HCl solution (2×30 L), water (2×30 mL), dried ($MgSO_4$) and concentrated in vacuo to afford 2.77 g (88.4%) of 4-chlorobenzaldehyde oxime as a white powder: MS m/z 156.00, calcd for $C_7H_7ClNO$ (MH$^+$) 156. For reference regarding preparation, see Luca, L. D.; Giacomelli, G.; Riu, A.; J. Org. Chem. 2001, 66(20), 6823-6825.

Step B: Preparation of 4-chlorophenyl hydroximinoyl chloride: To a solution of 4-chlorobenzaldehyde oxime (1.22 g, 7.9 mmol) in 2 mL of DMF cooled to 0° C. is added NCS (1.20 g, 8.30 mmol), followed 1-2 mL of gaseous HCl added by pipette from the headgas of a bottle of concentrated hydrochloric acid. The mixture over 15 min is produced a strongly exothermic reaction which is controlled through the use of an ice bath. The mixture is stirred 120 min, dissolved in 125 mL of $Et_2O$, washed with water (3×35 mL portions), brine (35 mL), and dried ($MgSO_4$). The solution is concentrated in vacuo to afford 1.46 g (98%) of 4-chlorophenyl hydroximinoyl chloride as a white powder. This material is kept in the freezer in a dessicator to maintain stability: MS m/z 190.02, calcd for $C_7H_6Cl_2NO$ (MH$^+$) 190.

Two Step Preparation of ethyl 3-ethylynylbenzoate from ethyl 3-iodobenzoate: To a solution of ethyl 3-iodobenzoate (25 g, 90.6 mmol) in 43 mL of DMF is added trimethylsilylacetylene (17 mL, 119.5 mmol) and Et$_3$N (25 mL, 181.1 mmol). This mixture is degassed under argon several times, CuI (175 mg, 0.92 mmol) is added, followed by 1.04 g of Pd(PPh$_3$)$_4$ catalyst. The reaction mixture is heated to 50° C. for 24 h, cooled to room temperature and diluted with 400 mL of 50% Et$_2$O/hexanes. This mixture is partitioned with water (4×75 mL portions), dried (MgSO$_4$) and concentrated to afford 23.29 g of a brown oil. This residue is chromatographed over 200 g of SiO$_2$ (eluted with 30% CH$_2$Cl$_2$/hexanes) to afford 22.2 g (99%) of 3-trimethylsilanylethynylbenzoic acid ethyl ester as a pale yellow oil which is taken directly into the next reaction: MS m/z 247.12, calcd for C$_{14}$H$_{19}$SiO$_2$ (MH$^+$) 247.

This material is dissolved in 250 mL of EtOH, 1.25 g (9.0 mmol) of K$_2$CO$_3$ catalyst is added, the mixture stirred at room temperature for 5 h, and concentrated in vacuo. The residue is chromatographed over 200 g of SiO$_2$ (eluted with 40% CH$_2$Cl$_2$/hexanes) to afford 15.7 g (100%) of ethyl 3-ethynylbenzoate (90% pure by LC/MS) as an orange solid. This material is recrystallized from the minimum amount of hexanes to afford 12.2 g (78% overall-two steps) as a pale yellow solid: mp 36-38° C.; $^1$H NMR (300 MHz, CDCl$_3$) δ 1.38 (t, J=7.2 Hz, 3H), 3.12 (s, 1H), 4.36 (q, J=7.2 Hz, 2H), 7.40 (t, J=7.8 Hz, 2H), 7.63 (dt, J=7.8 Hz, 1.5 Hz, 1H), 8.14 (t, J=1.5 Hz, 1H); MS m/z 174.98, calcd for C$_{11}$H$_{11}$O$_2$ (MH$^+$) 175.

Step C: Preparation of ethyl 3-[3-(4-chlorophenyl)isoxazol-5-yl]benzoate: To a solution of 4-chlorophenyl hydroxyiminoyl chloride (0.60 g, 3.15 mmol) and ethyl 3-ethynylbenzoate in 25 mL of CH$_2$Cl$_2$ is added Et$_3$N (0.66 mL, 4.73 mmol) and the mixture is stirred 48 h. The solution is diluted with 60 mL of CH$_2$Cl$_2$, washed with 1N aqueous NaOH solution (30 mL), water (30 mL), dried (MgSO$_4$) and concentrated in vacuo. The solid residue is recrystallized from the minimum amount of Et$_2$O/hexanes to afford 700 mg (68%) of ethyl 3-[3-(4-chlorophenyl)isoxazol-5-yl]benzoate as a white powder: $^1$H NMR (300 MHz, Acetone-d$_6$) δ 1.41 (t, J=7.2 Hz, 3H), 4.41 (q, J=7.2 Hz, 2H), 7.57 (m, 3H), 7.72 (t, J=7.8 Hz, 1H), 7.70 (dt, J=8.4, 1.8 Hz, 2H), 8.15 (tt, J=8.5, 1.8 Hz, 2H), 8.55 (t, J=1.5 Hz, 1H); MS m/z 314.21, calcd for C$_{18}$H$_{15}$ClNO$_3$ (MH$^+$) 328.

Step D: Preparation of 3-[3-(4-chlorophenyl)isoxazol-5-yl]benzoic acid: A solution of 678 mg (2.1 mmol) of ethyl 3-[3-(4-chlorophenyl)isoxazol-5-yl]benzoate in 14 mL of 50% THF/H$_2$O is heated to 60° C. for 5 h and cooled to room temperature. The solution is adjusted to pH 4 by the slow addition of 6N aqueous HCl solution and filtered. The resulting solid is washed with water, hexanes and dried overnight at 70° C. (10 torr) to afford 594 mg (96%) of 3-[3-(4-chlorophenyl)isoxazol-5-yl]benzoic acid as a white fluffy powder: mp 265-266° C.; $^1$H NMR (300 MHz, DMSO-d$_6$) δ 7.61 (dm, J=8.7 Hz, 2H), 7.70 (t, J=7.8 Hz, 1H), 7.82 (s, 1H), 7.95 (dm, J=8.7 Hz, 2H), 8.06 (dm, J=8.0 Hz, 1H), 8.13 (dm, J=8.0 Hz, 1H), 8.41 (m, 1H); MS m/z 300.16, calcd for C$_{16}$H$_{11}$ClNO$_3$ (MH$^+$) 300.

Utilizing essentially the same procedures described above and substituting other benzaldehyde derivatives in Step A gave the following compounds: Compound Nos: 492, 493, 494, 495, 496, 497, 498, 499, 500, 501, 502, 503, 504, 505, 514, 515, 516, 517, 518, 519, 520, 535, 536, 537, 538, 539, 540, and 541.

Example Z

Preparation of 3-[2-(4-isopropylphenyl)-3H-imidazol-4-yl]benzoic acid (Compound No. 311)

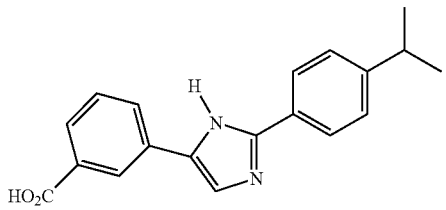 [SMILES: CC(C)c1ccc(-c2ncc(-c3cccc(C(=O)O)c3)[nH]2)cc1]

Step A: 4-Isopropylbenzamidine (356 mg, 2.20 mmol) and 514 mg (2.00 mmol) of methyl 3-(2-bromo-acetyl)-benzoate in 20 mL of CHCl$_3$ is heated at reflux for 8 h, cooled to room temperature and evaporated. The residue is partitioned between aqueous K$_2$CO$_3$ and EtOAc, separated and the organic layer is washed with brine, dried over Na$_2$SO$_4$, filtered and evaporated. The residue is purified by column chromatography to give 210 mg (33%) of methyl 3-[2-(4-isopropylphenyl)-3H-imidazol-4-yl]-benzoate as a yellow solid.

Step B: To a suspension of 190 mg (0.60 mmol) of methyl 3-[2-(4-isopropylphenyl)-3H-imidazol-4-yl]-benzoate in 6 mL of aqueous MeOH (5/1) is added 120 mg LiOH.H$_2$O. The reaction is heated at reflux for 1 h, cooled to room temperature, and neutralized with acetic acid. The precipitate is filtered and washed with water and air-dried. The resulting white solid is recrystallized from acetone to afford 140 mg (76%) of 3-[2-(4-isopropylphenyl)-3H-imidazol-4-yl]-benzoic acid as a white solid: $^1$H NMR (DMSO-d$_6$) δ 8.42 (br s, 1H), 8.06 (d, J=7.6, 1H), 7.91 (d, J=7.6, 2H), 7.83 (br s, 1H), 7.75 (d, J=7.2, 1H), 7.47 (t, J=7.2, 1H), 7.32 (d, J=8.0, 2H), 2.91 (septet, J=6.6, 1H), 1.22 (d, J=6.6, 6H); MS m/z 307.2 [MH$^+$].

Example AA

Preparation of 3-[5-(4-isopropylphenyl)-1H-imidazol-2-yl]benzoic acid (Compound No. 277)

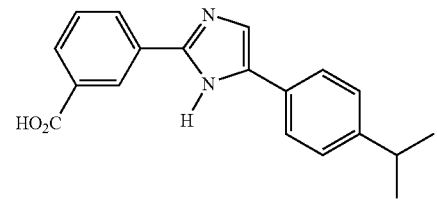 [SMILES: CC(C)c1ccc(-c2cnc(-c3cccc(C(=O)O)c3)[nH]2)cc1]

Step A: To 1.20 g (4.97 mmol) of 2-bromo-1-(4-isopropylphenyl)ethanone in 50 mL of CHCl$_3$ is added 1.05 g (5.47 mmol) of ethyl 3-carbamimidoylbenzoate and the reaction is heated at refluxed for 3 h, then cooled to room temperature, and basified with aqueous K$_2$CO$_3$. The organic layer is separated and dried over K$_2$CO$_3$, filtered and evaporated. The residue is purified by flash column chromatography on silica gel to give 0.85 g of (51%) of methyl 3-[5-(4-isopropylphenyl)-1H-imidazol-2-yl]benzoate as a white solid.

Step B: To a suspension of 480 mg (1.47 mmol) of methyl 3-[5-(4-isopropylphenyl)-1H-imidazol-2-yl]benzoate in 14 mL of aqueous MeOH/H$_2$O (5/1) is added 103 mg LiOH.H₂O, and the reaction is heated at reflux for 1 h, cooled to room temperature, and neutralized with acetic acid. The precipitate is filtered and washed with water and air-dried. The resulting 3-[5-(4-isopropylphenyl)-1H-imidazol-2-yl]benzoic acid is recrystallized from acetone to afford 300 mg (63%) of a white solid: mp 296-298° C.; $^1$H NMR (DMSO-d₆) δ 8.56 (br s, 1H), 8.23 (d, J=8.0, 1H), 7.87 (d, J=8.0, 2H), 7.56 (d, J=8.0, 2H), 7.31 (t, J=8.0, 1H), 7.23 (br s, 1H), 7.10 (d, J=7.6, 2H), 2.93 (septet, J=6.8, 1H), 1.11 (d, J=6.8, 6H).

Example BB

Preparation of 2-(3-carboxyphenyl)-4-(4-isopropylphenyl)furan-3-carboxylic acid (Compound No. 314)

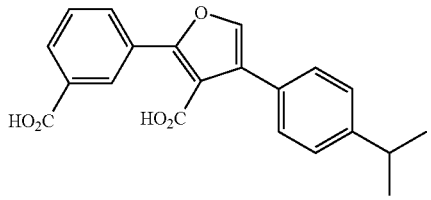 [SMILES: CC(C)c1ccc(-c2coc(-c3cccc(C(=O)O)c3)c2C(=O)O)cc1]

Step A: A mixture of 680 mg (2.90 mmol) of methyl 3-(2-methoxycarbonylacetyl)benzoate, 30 mL of acetone, 4.0 g of K₂CO₃ and 780 mg (3.24 mmol) of 2-bromo-1-(4-isopropylphenyl)-ethanone is heated at reflux for 30 min. The solvent is then removed under reduced pressure, the residue is partitioned between aqueous HCl and EtOAc. The organic layer is washed with brine, dried over Na₂SO₄, filtered and evaporated. The residue is purified by column chromatography to give 660 mg (57%) of methyl 3-[4-(4-isopropylphenyl)-2-methoxycarbonyl-4-oxo-butyryl]benzoate as a yellow oil.

Step B: To 480 mg (1.21 mmol) of methyl 3-[4-(4-isopropylphenyl)-2-methoxycarbonyl-4-oxo-butyryl]-benzoate in 10 mL of MeOH is added 15 mL of 6N HCl and the reaction is heated at reflux for 5 h. The reaction mixture is cooled to room temperature and extracted with EtOAc. The combined organic phases are washed with water, brine, dried over Na₂SO₄, filtered and then evaporated. The residue is purified by chromatography to give 260 mg (57%) of methyl 5-(4-isopropylphenyl)-2-(3-methoxycarbonylphenylfuran-3-carboxylate as a yellow oil.

Step C: To 260 mg (0.69 mmol) of methyl 5-(4-isopropylphenyl)-2-(3-methoxycarbonylphenyl)-furan-3-carboxylate in 12 mL of 5:1 MeOH/H₂O is added 160 mg of LiOH.H₂O and the reaction is heated at reflux for 1 h, cooled to room temperature, and neutralized with acetic acid. The precipitate is collected, washed with water and dried. The crude product is recrystallized from acetone to afford 140 mg (58%) of 2-(3-carboxyphenyl)-5-(4-isopropylphenyl)furan-3-carboxylic acid as a yellow solid: mp 236-239° C.; $^1$H NMR (DMSO-d₆) δ 13.0 (br s, 1H), 8.60 (br s, 1H), 8.28 (d, J=7.6, 1H), 7.98 (d, J=7.6, 1H), 7.74 (d, J=7.6, 2H), 7.74 (t, J=8.0, 1H), 7.33 (d, J=8.0, 2H), 7.25 (s, 1H), 2.91 (septet, J=6.6, 1H), 1.21 (d, J=6.6, 6H); MS m/z 349.0 [MH⁻].

Example CC

Preparation of 3-[5-(4-isopropylphenyl)furan-2-yl]benzoic acid (Compound No. 322)

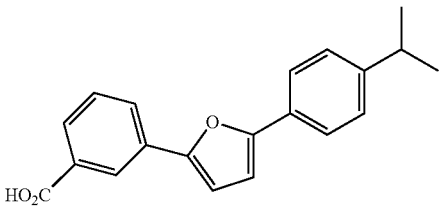

Step A: A suspension of 3-(3-methoxycarbonylphenyl)-3-oxo-propyl acid ethyl ester (1.8 g, 7.2 mmol) and powdered K₂CO₃ (4 g, 29 mmol) and 4-(bromoacetyl) isopropylbenzene (1.8 g, 7.5 mmol) in dry acetone is refluxed for 2 h. The solvent is removed by evaporation and the residue is added into 50 mL of ice water, acidified to pH 4 with 6N HCl and extracted with ethyl acetate (3×30 mL). The organic phase is washed with 30 mL of water and 30 mL of brine, dried over anhydrous Na₂SO₄, evaporated and purified by silica gel column chromatography (petroleum ether/ethyl acetate, 6/1) to give methyl 3-[2-ethoxycarbonyl-4-(4-isopropylphenyl)-4-oxobutyryl]benzoate (1.5 g, 51%) as pale yellow oil.

Step B: A mixture of methyl 3-[2-ethoxycarbonyl-4-(4-isopropylphenyl)-4-oxobutyryl]benzoate (1.5 g, 3.7 mmol), 0.29 g of NaCl and 0.15 mL of water in 20 mL of DMSO is heated to 140-150° C. and stirred for 3.5 hr. The mixture is cooled to room temperature and added into 50 mL of ice-water. Then the mixture is extracted with ether (3×50 mL) and the combined organic layer is washed with water (2×50 mL), brine (50 mL) and then dried over Na₂SO₄ and evaporated. The residue is purified by silica gel column chromatography to obtain methyl 3-[4-(4-isopropylphenyl)-4-oxo-butyryl]benzoate (0.7 g) as a pale yellow solid.

Step C: A solution of methyl 3-[4-(4-isopropylphenyl)-4-oxo-butyryl]benzoate (0.7 g) and a catalytic amount of TsOH in 10 mL of absolute toluene is refluxed overnight. The reaction mixture is diluted with 100 mL of EtOAc and washed with water (2×50 mL), brine (50 mL) and then dried over Na₂SO₄ and evaporated. The residue is purified by silica gel column chromatography to give methyl 3-[5-(4-isopropyl-phenyl)furan-2-yl]benzoate (0.3 g) as yellow oil.

Step D: To a solution of methyl 3-[5-(4-isopropyl-phenyl)furan-2-yl]benzoate (0.3 g) in 5 mL of THF is added LiOH (0.2 g) dissolved in 15 mL water, and the reaction is stirred for 2 h. The reaction mixture is cooled to room temperature and extracted with ether (2×30 mL). The organic layer is washed with water (2×30 mL), brine (30 mL), dried over Na₂SO₄ and evaporated. The residue is purified by preparative HPLC to give 3-[5-(4-isopropylphenyl)furan-2-yl]benzoic acid (7 mg, 0.62%, over 3 steps) as a white solid: mp 172-176° C.; $^1$H NMR (CDCl₃) δ 8.46 (s, 1H), 7.99 (t, J=7.8, 2H), 7.70 (d, J=8, 2H), 7.53 (t, J=7.8, 1H), 7.29, J=8.0, 2H), 6.84 (d, J=3.6, 1H), 6.71 (d, J=3.6, 1H), 2.95 (septet, 6.8, 1H), 1.29 (d, J=6.8, 6H).

Example DD

Preparation of 3-[5-(4-isopropylphenyl)-[1,2,4]thiadiazol-3-yl]-benzoic acid (Compound No. 323)

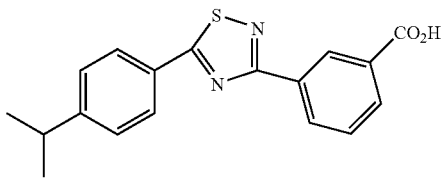 [SMILES: CC(C)c1ccc(-c2nc(-c3cccc(C(=O)O)c3)ns2)cc1]

Step A: A solution of isophthalamic acid methyl ester (1.0 g, 5.6 mmol) and trichloromethyl sulfenyl chloride (1.039 g, 5.6 mmol, 0.6 mL) in 10 mL of anhydrous toluene is heated to reflux overnight under nitrogen. The mixture is cooled to room temperature and water is added to quench the reaction. The residue is partitioned between water and EtOAc and then the organic layer is washed with brine, dried over $Na_2SO_4$, filtered and evaporated. The residue is purified by flash chromatography and 274 mg (21%) of methyl 3-(2-oxo-[1,3,4]oxathiazol-5-yl)benzoate is obtained.

Step B: To 4-isopropylbenzonitrile (795 mg, 5.5 mmol) at 190° C., methyl 3-(2-oxo-[1,3,4]oxathiazol-5-yl)-benzoate (260 mg, 1.1 mmol) is added in three equal portions at 5-minutes interval. The reaction is stirred for another 30 min. The mixture is cooled to room temperature and the residue is partitioned between water and EtOAc. The organic layer is washed with brine, dried over $Na_2SO_4$, filtered and evaporated. The residue is purified by flash chromatography to give 11 mg (3%) of methyl 3-[5-(4-isopropylphenyl)-[1,2,4]thiadiazol-3-yl]benzoate.

Step C: To a solution of 11 mg of the above ester in 4 mL of 3/1 MeOH/$H_2O$ is added 7 mg of LiOH.$H_2O$. The mixture is stirred at 40-50° C. overnight, cooled to room temperature and neutralized with 3N hydrochloric acid. The mixture is extracted with EtOAc, washed with brine and dried over $Na_2SO_4$. Removal of the solvent gave 8 mg (79%) of 3-[5-(4-isopropylphenyl)-[1,2,4]thiadiazol-3-yl]benzoic acid: mp 165-167° C.; $^1H$ NMR (CDCl$_3$) δ 8.75 (br s, 1H), 8.33-8.27 (m, 4H), 7.67 (t, J=7.8, 1H), 7.37 (d, J=7.6, 2H), 3.00 (septet, J=6.8, 1H), 1.31 (d, J=6.8, 6H); MS m/z 325.1 [MH$^+$].

Example EE

Preparation of 3-[3-(4-isopropylphenyl)-[1,2,4]thiadiazol-5-yl]benzoic acid (Compound No. 326)

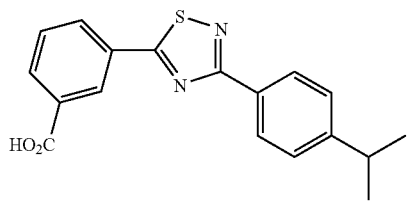 [SMILES: CC(C)c1ccc(-c2nsc(-c3cccc(C(=O)O)c3)n2)cc1]

Step A: A solution of 4-isopropylbenzamide (1.0 g, 6.1 mmol) and trichloromethyl sulfenyl chloride (1.14 g, 6.1 mmol) in 10 mL of anhydrous toluene is heated to reflux overnight. The mixture is cooled to room temperature and water is added to quench the reaction. The residue is partitioned between water and EtOAc and the organic layer is washed with brine, dried over $Na_2SO_4$, filtered and evaporated. The residue is purified by flash chromatography to give 250 mg (18%) of 5-(4-isopropylphenyl)-[1,3,4]oxathiazol-2-one.

Step B: To ethyl 3-cyanobenzoate (2.77 g, 15.8 mmol) at 190° C., 5-(4-isopropylphenyl)-[1,3,4]oxathiazol-2-one (250 mg, 1.1 mmol) is added in three equal portions at 5-minutes interval. The reaction is stirred for another 30 min. The mixture is cooled to room temperature, and the residue is partitioned between water and EtOAc. The organic layer is washed with brine, dried over $Na_2SO_4$, filtered and evaporated. The residue is purified by flash chromatography to give 12 mg (3%) of ethyl 3-[3-(4-isopropylphenyl)-[1,2,4]thiadiazol-5-yl]benzoate.

Step C: To a solution of 12 mg of the above ester in 4 mL of 3/1 MeOH/$H_2O$ is added 7 mg of LiOH.$H_2O$. The mixture is stirred at 40-50° C. overnight, cooled to room temperature and neutralized with 3N hydrochloric acid. The mixture is extracted with EtOAc, washed with brine and dried over $Na_2SO_4$. Removal of the solvent gave 6 mg (54%) of 3-[3-(4-isopropylphenyl)-[1,2,4]thiadiazol-5-yl]benzoic acid: mp 166-168° C.; $^1H$ NMR (CDCl$_3$) δ 8.74 (br s, 1H), 8.33-8.25 (m, 5H), 7.67 (t, J=8.0, 1H), 7.37 (d, J=8.0, 2H), 3.00 (septet, J=6.8, 1H), 1.31 (d, J=6.8, 6H); MS m/z 325.1 [MH$^+$].

Example FF

Preparation of 3-[4-(4-isopropylphenyl)-thiophen-2-yl]-benzoic acid (Compound No. 327)

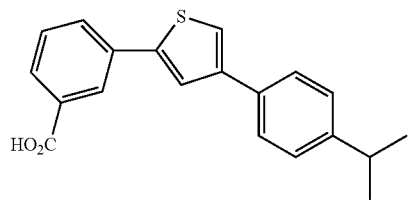 [SMILES: CC(C)c1ccc(-c2csc(-c3cccc(C(=O)O)c3)c2)cc1]

Step A: To a solution of 2,4-dibromothiophene (433 mg, 1.8 mmol) and 3-(ethoxycarbonyl)phenyl boronic acid (347 mg, 1.8 mmol) in ethanol/toluene/water (10 mL/5 mL/3 mL), 568 mg of $Na_2CO_3$ is added. After degasification twice, a catalytic amount of Pd(PPh$_3$)$_4$ is added under a nitrogen atmosphere. The reaction mixture is stirred at 80° C. overnight. The mixture is cooled to room temperature, filtered and evaporated. The residue is partitioned between water and EtOAc. The organic layer is then washed with brine, dried over $Na_2SO_4$, filtered and evaporated. The residue is purified by flash chromatography to give 350 mg (63%) of ethyl 3-(4-bromothiophen-2-yl)-benzoate.

Step B: To a solution of ethyl 3-(4-bromothiophen-2-yl)benzoate (350 mg, 1.1 mmol) and 4-isopropylphenyl boronic acid (187 mg, 1.1 mmol) in ethanol/toluene/water (10 mL/5 mL/3 mL), 358 mg $Na_2CO_3$ is added. After degasification twice, a catalytic amount of Pd(PPh$_3$)$_4$ is added under a nitrogen atmosphere. The reaction mixture is stirred at 80° C. until TLC analysis indicated the reaction is complete. The mixture is cooled to room temperature, filtered and evaporated. The residue is partitioned between water and EtOAc. The organic layer is then washed with brine, dried over $Na_2SO_4$, filtered and evaporated. The residue is purified by flash chromatography to give 150 mg (38%) of ethyl 3-[4-(4-isopropylphenyl)thiophen-2-yl]benzoate.

Step C: To a solution of 50 mg of ethyl 3-[4-(4-isopropylphenyl)thiophen-2-yl]benzoate in 4 mL of 3/1 MeOH/

H₂O is added 30 mg of LiOH.H₂O and the mixture is stirred at 40-50° C. until TLC analysis indicated the reaction is complete. The mixture is cooled to room temperature and neutralized with 3N hydrochloric acid. The mixture is extracted with EtOAc, washed with brine and dried over Na₂SO₄. Removal of the solvent gave 30 mg (65%) of 3-[4-(4-isopropylphenyl)thiophen-2-yl]benzoic acid: mp 220-222° C.; ¹H NMR (CDCl₃) δ 8.35 (br s, 1H), 8.02 (d, J=8.0, 1H), 7.83 (d, J=8.0, 1H), 7.60-7.57 (m, 3H), 7.52 (t, J=8.0, 1H), 7.45 (s, 1H), 7.29 (s, 1H), 2.95 (septet, J=6.8, 1H), 1.28 (d, J=6.8, 6H); MS m/z 323.1 [MH⁺].

Example GG

Preparation of 3-[5-(4-isopropylphenyl)thiophen-3-yl]benzoic acid (Compound No. 348)

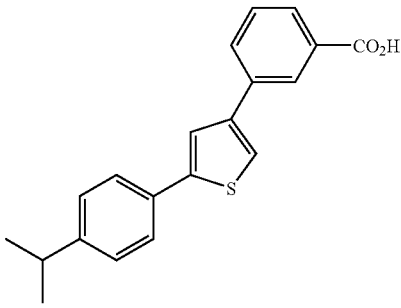 [SMILES: CC(C)c1ccc(-c2cc(-c3cccc(C(=O)O)c3)cs2)cc1]

Step A: To a solution of 2,4-dibromothiophene (500 mg, 2.1 mmol) and 4-isopropylphenyl boronic acid (339 mg, 2.1 mmol) in ethanol/toluene/water (10 mL/5 mL/3 mL), 657 mg Na₂CO₃ is added. After degasification twice, a catalytic amount of Pd(PPh₃)₄ is added under a nitrogen atmosphere. The reaction mixture is stirred at 80° C. overnight. The mixture is cooled to room temperature, filtered and evaporated. The residue is partitioned between water and EtOAc. The organic layer is washed with brine, dried over Na₂SO₄, filtered and evaporated. The residue is purified by flash chromatography to give 207 mg (36%) of 4-bromo-2-(4-isopropylphenyl)thiophene.

Step B: To a solution of 4-bromo-2-(4-isopropylphenyl)thiophene (207 mg, 0.7 mmol) and 3-(ethoxycarbonyl)phenyl boronic acid (143 mg, 0.7 mmol) in ethanol/toluene/water (10 mL/5 mL/3 mL), 234 mg Na₂CO₃ is added. After degasification twice, a catalytic amount of Pd(PPh₃)₄ is added under a nitrogen atmosphere. The reaction mixture is stirred at 80° C. until TLC analysis indicated the reaction is complete. The mixture is cooled to room temperature, filtered and evaporated. The residue is partitioned between water and EtOAc. The organic layer is washed with brine, dried over Na₂SO₄, filtered and evaporated. The residue is purified by flash chromatography to give 180 mg (70%) of ethyl 3-[5-(4-isopropylphenyl)thiophen-3-yl]benzoate.

Step C: To a solution of 100 mg of ethyl 3-[5-(4-isopropylphenyl)thiophen-3-yl]benzoate in 4 mL of 3/1 MeOH/H₂O is added 65 mg LiOH.H₂O. The mixture is stirred at 40-50° C. overnight, cooled to room temperature and neutralized with 3 N hydrochloric acid. The mixture is extracted with EtOAc, washed with brine and dried over Na₂SO₄. After removal of the solvent, 80 mg (87%) of 3-[5-(4-isopropylphenyl)thiophen-3-yl]benzoic acid is obtained: mp 208-209° C.; ¹H NMR (CDCl₃) δ 8.37 (br s, 1H), 8.01 (d, J=7.2, 1H), 7.87 (d, J=7.6, 1H), 7.66 (d, J=1.6, 1H), 7.56 (d, J=8.0, 2H), 7.51 (t, J=8.0, 1H), 7.40 (d, J=1.6, 1H), 7.29 (d, J=8.0, 2H), 2.95 (septet, J=7.2, 1H), 1.28 (d, J=7.2, 6H); MS m/z (m/z) 323.2 [MH⁺].

Example HH

Preparation of 3-[5-(4-isopropylphenyl)thiophen-2-yl]benzoic acid (Compound No. 400)

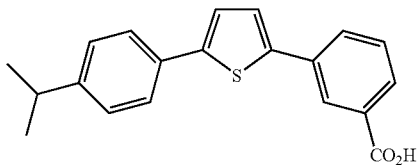 [SMILES: CC(C)c1ccc(-c2ccc(-c3cccc(C(=O)O)c3)s2)cc1]

Step A: To a stirred solution of thiophene (5.94 g, 71 mmol) in an equal volume of toluene at 0° C., bromine (23 g, 142 mmol) in 50 mL of toluene is added as rapidly as possible and stirred for another 0.5 h. Then 5 g sodium hydroxide is added. The mixture is partitioned between water and EtOAc, dried over sodium sulfate and evaporated. The residue, 2,5-dibromothiophene, is purified by distillation.

Step B: To a solution of 2,5-dibromothiophene (1.0 g, 4.0 mmol) and 3-(ethoxycarbonyl)phenyl boronic acid (793 mg, 4.0 mmol) in ethanol/toluene/water (10 mL/5 mL/3 mL), 1.32 g of Na₂CO₃ is added. After degasification twice, a catalytic amount of Pd(PPh₃)₄ is added under a nitrogen atmosphere. The reaction mixture is stirred at 80° C. overnight. The mixture is cooled to room temperature, filtered and evaporated. The residue is partitioned between water and EtOAc. The organic layer is washed with brine, dried over Na₂SO₄, filtered and evaporated. The residue is purified by flash chromatography to give 456 mg (36%) of ethyl 3-(5-bromothiophen-2-yl)-benzoate.

Step C: To a solution of ethyl 3-(5-bromothiophen-2-yl)-benzoate (200 mg, 0.6 mmol) and 4-isopropylphenyl boronic acid (105 mg, 0.6 mmol) in ethanol/toluene/water (10 mL/5 mL/3 mL), 204 mg Na₂CO₃ is added. After degasification twice, a catalytic amount of Pd(PPh₃)₄ is added under a nitrogen atmosphere. The reaction mixture is stirred at 80° C. until TLC analysis indicated the reaction is complete. The mixture is cooled to room temperature, filtered and evaporated. The residue is partitioned between water and EtOAc; the organic layer is washed with brine, dried over Na₂SO₄, filtered and evaporated. The residue is purified by flash chromatography to give 154 mg (69%) of ethyl 3-[5-(4-isopropylphenyl)thiophen-2-yl]benzoate.

Step D: To a solution of 100 mg of ethyl 3-[5-(4-isopropylphenyl)thiophen-2-yl]benzoate in 4 mL of 3/1 MeOH/H₂O is added 46 mg of LiOH.H₂O. The mixture is stirred at 40-50° C. overnight, cooled to room temperature and neutralized with 3N hydrochloric acid. The mixture is extracted with EtOAc, washed with brine and dried over Na₂SO₄. After removal of the solvent, 78 mg (85%) of 3-[5-(4-isopropylphenyl)thiophen-2-yl]benzoic acid is obtained: mp 233-235° C.; ¹H NMR (CDCl₃) δ 8.16 (s, 1H), 7.80 (d, J=7.8, 1H), 7.65 (d, J=8.1, 1H), 7.42 (d, J=8.1, 2H), 7.32 (t, J=7.8, 1H), 7.22 (d, J=3.6, 1H), 7.13 (d, J=3.6, 1H), 7.11 (d, J=8.4, 2H), 2.80 (septet, 6.8, 1H), 1.14 (d, J=6.9, 6H); MS m/z 321.5 [MH⁻].

Example II

Preparation of 3-[5-(4-methoxy-phenyl)-2H-[1,2,4]triazol-3-yl]-benzoic acid (Compound No. 424)

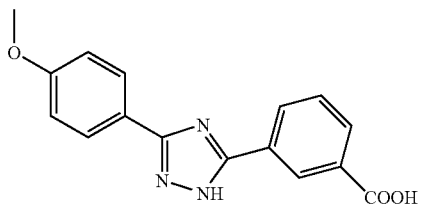 [SMILES: COc1ccc(-c2n[nH]c(-c3cccc(C(=O)O)c3)n2)cc1]

Step A: m-Methoxycarbonyimidoyl benzoic acid methyl ester hydrochloride: To a solution of methyl 3-cyanobenzoate (0.65 g, 4.03 mmol) in methanol (15 mL) is added acetyl chloride (12 mL) dropwise at 0° C. After the addition, the reaction mixture is stirred for 6 h at 0° C. to room temperature. Solvent removal gives a white solid that is purified by washing with diethyl ether and is used immediately in the next step.

Step B: Methyl 3-(5-(4-methoxyphenyl-2H-[1,2,4-]triazol-3-yl)benzoate: A solution of sodium methoxide (0.5 N in methanol) (8.5 mL, 4.25 mmol) in anhydrous ethanol (30 ml) is added to a room temperature solution of m-methoxycarbonyimidoyl benzoic acid methyl ester hydrochloride in ethanol (10 mL). The milky slurry is stirred at room temperature for 30 min and then filtered. The filtrate is condensed to ¼ of the volume, to which is added 4-methoxybenzhydrazide (0.55 g, 3.31 mmol) and dioxane (10 mL). The resulting mixture is heated to reflux for 15 h. Addition of 1N HCl to afford a white solid (0.66 g, 71.0% yield), which is collected by filtration and washed with water, then water/ethanol (1/5). The obtained compound is >90% pure as determined by LC-MS; MS m/z 310 [MH$^+$].

Step C: 3-(5-4-methoxy-phenyl-2H-[1,2,4]triazol-3-yl)benzoic acid: A mixture of methyl 3-[5-(4-methoxyphenyl)-2H-[1,2,4]triazol-3-yl]benzoate (0.32 g, 1.04 mmol) in 1N NaOH (3.0 mL, 3.00 mmol)/THF (1:1) is stirred at reflux for 6 h until complete consumption of the starting material is determined by TLC. The THF is stripped off in vacuo. A white solid is precipitated after addition of 1N HCl. The desired product (0.26 g, 85.2% yield) is collected by filtration and washed with water, then diethyl ether in sequence: mp 287-289° C.; $^1$H NMR (300 MHz, DMSO-d$_6$): δ 13.20 (1H, s), 8.64 (1H, s), 8.27 (1H, dd, J=7.7, 0.8 Hz), 8.01 (3H, m), 7.60 (1H, t, J=1.2 Hz), 7.61 (2H, m), 2.49 (3H, s); MS m/z 296 [MH$^+$].

Melting point and mass spec data for certain preferred compounds of the invention is shown in the table 1 below.

| Compound | Melting Point (° C.) | MS (ES+) |
|---|---|---|
| 1 | >260. | 310.1 |
| 2 | 187-189 | 310.1 |
| 3 | 247-248 | 310.1 |
| 4 | 268-270 | 310.2 |
| 5 | 262-265 | 309.2 |
| 6 | 202-204 | 309.2 |
| 7 | 227-229 | 309.3 |
| 8 | >270 | 312.2 |
| 12 | >270 | 358 |
| 13 | >275 | 436 |
| 14 | >275 | 324.1 |
| 15 | | 281.3 |
| 16 | | 301.1 |
| 17 | | 273.2 |
| 18 | | 268.2 |
| 19 | | 257.2 |
| 21 | | 283.3 |
| 22 | | 297.2 |
| 23 | | 297.2 |
| 24 | | 297.2 |
| 25 | | 281.2 |
| 26 | | 281.2 |
| 27 | | 301.1 |
| 28 | | 301.1 |
| 29 | | 323.3 |
| 30 | | 283.2 |
| 31 | | 283.2 |
| 32 | | 344.1 |
| 33 | | 344.1 |
| 34 | | 312.2 |
| 35 | | 312.2 |
| 36 | | 312.2 |
| 37 | | 327.3 |
| 38 | | 311.3 |
| 39 | | 297.2 |
| 40 | | 297.2 |
| 41 | | 297.2 |
| 42 | | 281.2 |
| 43 | | 281.2 |
| 44 | | 301.1 |
| 45 | | 301.1 |
| 46 | | 323.3 |
| 47 | | 283.2 |
| 48 | | 283.2 |
| 49 | | 344.1 |
| 50 | | 344.1 |
| 51 | | 312.2 |
| 53 | | 312.2 |
| 54 | | 327.3 |
| 55 | | 311.3 |
| 60 | >270 | 443.2 |
| 62 | | 335.2 |
| 63 | | 317.3 |
| 64 | | 317.3 |
| 65 | | 343.3 |
| 66 | | 315.2 |
| 67 | | 232.2 |
| 68 | | 335.2 |
| 69 | | 317.3 |
| 70 | | 317.3 |
| 71 | | 343.3 |
| 72 | | 315.2 |
| 73 | | 233.2 |
| 75 | | |
| 82 | 235-237 | 352.3 |
| 83 | 275-277 | 350.3 |
| 84 | 279-282 | 427.3 |
| 85 | 220-222 | 324.3 |
| 86 | 243-245 | 324.3 |
| 87 | | 355.3 |
| 88 | | 311.2 |
| 89 | | 359.3 |
| 90 | | 338.3 |
| 91 | | 339.3 |
| 92 | | 343.3 |
| 93 | | 358.3 |
| 94 | | 335.3 |
| 95 | | 318.2 |
| 96 | | 359.1 |
| 97 | | 360.3 |
| 98 | | 337.3 |
| 99 | | 359.3 |
| 100 | | 412.3 |
| 101 | | 309.2 |
| 102 | | 359.3 |
| 103 | | 295.2 |
| 104 | | 309.3 |
| 106 | | 393.1 |
| 107 | | 285.2 |
| 108 | | 309.3 |
| 109 | | 295.3 |
| 110 | | 336.1 |

| Compound | Melting Point (° C.) | MS (ES+) |
|---|---|---|
| 111 | | 326.3 |
| 112 | | 336.1 |
| 113 | | 311.3 |
| 114 | | 335.2 |
| 115 | | 360.1 |
| 116 | | 285.2 |
| 117 | | 335.2 |
| 118 | | 295.3 |
| 119 | | 294.3 |
| 120 | | 326.2 |
| 121 | | 359.2 |
| 122 | | 327.3 |
| 123 | | 433.4 |
| 124 | | 313.3 |
| 125 | | 332.3 |
| 126 | | 345.3 |
| 127 | | 309.2 |
| 128 | | 342.2 |
| 129 | | 325.2 |
| 130 | | 351.2 |
| 131 | | 348.3 |
| 132 | | 359.3 |
| 133 | | 371.2 |
| 134 | | 411.3 |
| 135 | | 401.4 |
| 136 | | 331.2 |
| 137 | | 318.2 |
| 138 | | 318.2 |
| 139 | | 318.2 |
| 140 | 253-255 | 307 (ES−) |
| 141 | 237-9 | 323 |
| 142 | | 295.2 |
| 143 | | 309.3 |
| 144 | | 393.1 |
| 145 | | 285.2 |
| 146 | | 309.3 |
| 147 | | 295.3 |
| 148 | | 336.1 |
| 149 | | 327.3 |
| 150 | | 336.1 |
| 151 | | 311.3 |
| 152 | | 335.2 |
| 153 | | 360.1 |
| 154 | | 285.2 |
| 155 | | 335.2 |
| 156 | | 295.3 |
| 157 | | 295.3 |
| 158 | | 327.2 |
| 159 | | 360.2 |
| 160 | | 327.1 |
| 161 | | 355.3 |
| 162 | | 311.2 |
| 163 | | 359.3 |
| 164 | | 338.3 |
| 165 | | 339.3 |
| 166 | | 358.3 |
| 167 | | 335.2 |
| 168 | | 360.1 |
| 169 | | 373.3 |
| 170 | | 359.3 |
| 171 | | 412.3 |
| 172 | | 318.2 |
| 173 | | 309.2 |
| 174 | | 360.3 |
| 175 | 236-238 | 354.1 |
| 176 | | 336.1 |
| 177 | | 360.1 |
| 178 | | 311.3 |
| 179 | | 331.1 |
| 180 | | 325.3 |
| 181 | | 319.4 |
| 182 | | 319.4 |
| 183 | | 341.3 |
| 184 | | 295.3 |
| 185 | | 336.1 |
| 186 | | 295.3 |
| 187 | | 285.2 |
| 188 | | 309.2 |
| 189 | | 336.1 |
| 190 | | 360.1 |
| 191 | | 311.3 |
| 192 | | 331.1 |
| 193 | | 325.3 |
| 194 | | 319.4 |
| 195 | | 319.4 |
| 196 | | 341.3 |
| 197 | | 325.3 |
| 198 | | 332.3 |
| 199 | | 319.4 |
| 200 | | 319.4 |
| 201 | | 295.3 |
| 202 | | 336.1 |
| 203 | | 295.3 |
| 204 | | 285.2 |
| 205 | | 295.3 |
| 206 | | 379.3 |
| 207 | | 407.2 |
| 208 | | 311.2 |
| 209 | | 321.3 |
| 210 | | 313.3 |
| 211 | | 345.3 |
| 212 | | 309.2 |
| 213 | | 342.2 |
| 214 | | 325.3 |
| 215 | | 351.2 |
| 216 | | 349.3 |
| 217 | | 360.3 |
| 218 | | 372.1 |
| 219 | | 412.3 |
| 220 | | 318.2 |
| 221 | | 318.2 |
| 222 | 278-282 | 302.2 |
| 223 | 272-274 | 311.2 |
| 224 | 240-250 | 311.2 |
| 225 | >285 | 302.1 |
| 226 | | 324.2 |
| 227 | | 324.2 |
| 228 | | 325.2 |
| 229 | | 325.2 |
| 230 | | 334.3 |
| 231 | | 334.3 |
| 232 | | 319.2 |
| 233 | | 319.2 |
| 234 | | 336.3 |
| 235 | | 336.3 |
| 236 | | 337.3 |
| 237 | | 337.3 |
| 238 | | 301.2 |
| 239 | | 283.2 |
| 240 | | 283.2 |
| 241 | | 285.2 |
| 242 | | 285.2 |
| 243 | | 350.3 |
| 244 | | 350.3 |
| 245 | | 379.1 |
| 246 | | 379.1 |
| 247 | | 417.3 |
| 248 | | 417.3 |
| 249 | | 351.3 |
| 250 | | 309.2 |
| 251 | | 309.2 |
| 252 | | 343.2 |
| 253 | | 343.2 |
| 254 | | 334.3 |
| 255 | | 334.3 |
| 258 | | 314.3 |
| 259 | | 302.1 |
| 260 | | 337.1 |
| 261 | | 282.2 |
| 262 | | 328.2 |
| 263 | | 324.3 |
| 264 | | 336.2 |
| 265 | | 336.2 |
| 266 | | 439.1 |

| Compound | Melting Point (° C.) | MS (ES+) |
|---|---|---|
| 267 | | 376.2 |
| 268 | | 316.8 |
| 269 | | 363.3 |
| 270 | | 331.7 |
| 271 | | 292.3 |
| 272 | 205-208 | 337.1 |
| 273 | | 347.1 |
| 274 | | 302.7 |
| 275 | 210-213 | 307 (ES−) |
| 276 | 235-237 | 308.4 |
| 277 | 296-298 | 307.4 |
| 278 | >310 | 338.2 |
| 279 | 228-235 | 338.2 |
| 280 | 274-276 | 336.2 |
| 281 | 240-242 | 357.2 |
| 282 | 274-275 | 358.2 |
| 283 | 220-226 | 352.2 |
| 284 | 282-291 | 352.2 |
| 285 | 253-256 | 378.3 |
| 286 | >310 | 378.3 |
| 287 | | 307.2 |
| 288 | 150-153 | 308.2 |
| 289 | 206-208 | 324.2 |
| 290 | 222-225 | 308.2 |
| 291 | 200-212 | |
| 292 | 275-278 | 346.1-348.1 |
| 293 | 274-275 | 346.1-348.1 |
| 294 | | 314.3 |
| 295 | >310 | 306.2 |
| 296 | | 302.7 |
| 297 | | 337.1 |
| 298 | | 282.2 |
| 299 | | 347.1 |
| 300 | | 328.2 |
| 301 | | 324.3 |
| 302 | | 336.2 |
| 303 | | 337.1 |
| 304 | | 302.7 |
| 305 | | 292.2 |
| 306 | | 331.7 |
| 307 | | 363.3 |
| 308 | | 315.7 |
| 309 | | 376.1 |
| 310 | 218-220 | 324.3 |
| 311 | 283-285 | 307.2 |
| 312 | 193-195 | 324.3 |
| 313 | 236-239 | 308.3 |
| 314 | 236-239 | 349.0 (ES−) |
| 315 | >310 | 306.2 |
| 316 | >270 | 306.2 |
| 317 | >290 (decomp) | 306.2 |
| 318 | >310 | 306.2 |
| 319 | 304-320 | 306.1 |
| 320 | 193-195 | 308.2 |
| 321 | 237-239 | 322 |
| 322 | 172-176 | |
| 323 | 165-167 | 325.1 |
| 324 | >300 | 325.1 |
| 325 | | 280.1 |
| 326 | 166-168 | 325.2 |
| 327 | 220-222 | 323.1 |
| 329 | | 311.2 |
| 330 | | 334.2 |
| 331 | | 316.3 |
| 332 | | 296.2 |
| 333 | | 337.3 |
| 334 | | 291.2 |
| 335 | | 335.3 |
| 336 | | 300.1 |
| 337 | | 342.2 |
| 338 | | 335.1 |
| 339 | | 326.3 |
| 340 | | 302.2 |
| 341 | | 326.3 |
| 342 | | 402.2 |
| 343 | | 322.3 |
| 344 | | 296.2 |
| 345 | | 345.1 |
| 346 | | 293.3 |
| 348 | 208-209 | 323.2 |
| 349 | | 281.2 |
| 350 | | 296.1 |
| 351 | | 345.1 |
| 352 | | 322.3 |
| 353 | | 335.1 |
| 354 | | 302.2 |
| 355 | | 332.2 |
| 356 | | 345.1 |
| 357 | | 338.3 |
| 358 | | 324.2 |
| 359 | | 267.2 |
| 360 | | 310.2 |
| 361 | | 336.3 |
| 362 | | 284.2 |
| 363 | | 300.1 |
| 364 | | 315.2 |
| 365 | | 351.4 |
| 366 | | 312.3 |
| 367 | | 307.3 |
| 368 | | 353.4 |
| 369 | | 338.4 |
| 370 | | 312.3 |
| 371 | | 350.3 |
| 372 | | 316.1 |
| 373 | | 310.3 |
| 374 | | 318.3 |
| 375 | | 418.3 |
| 376 | | 300.3 |
| 377 | | 318.3 |
| 378 | | 348.3 |
| 379 | | 316.4 |
| 380 | | 326.3 |
| 381 | | 340.3 |
| 382 | | 352.4 |
| 383 | | 338.4 |
| 384 | | 294.3 |
| 385 | | 342.3 |
| 386 | | 351.2 |
| 387 | | 283.3 |
| 388 | | 332.3 |
| 389 | | 327.3 |
| 390 | | 330.4 |
| 391 | | 383.3 |
| 392 | | 322.3 |
| 394 | | 267.1 |
| 395 | | 285.1 |
| 396 | | 303.1 |
| 397 | | 309.2 |
| 398 | | 311.2 |
| 399 | | 325.2 |
| 400 | 233-235 | 321.5 (ES−) |
| 401 | 152-155 | 343.1 |
| 402 | 174-177 | 338.2 |
| 403 | | 365 |
| 404 | | 330.1 |
| 405 | | 341.2 |
| 406 | | 315.1 |
| 407 | 230-235 | 285.3 |
| 408 | | 303.2 |
| 409 | | 335.2 |
| 410 | | 267.3 |
| 411 | | 312.2 |
| 412 | | 301.3 |
| 413 | | 285.2 |
| 414 | | 247.3 |
| 415 | | 357.3 |
| 416 | | 281.3 |
| 417 | | 253 |
| 418 | | 297.2 |
| 419 | | 303.2 |
| 420 | | 257.2 |
| 421 | | 285.2 |
| 422 | | 359.3 |
| 423 | 309-311 | 346.09 |

-continued

| Compound | Melting Point (° C.) | MS (ES+) |
| --- | --- | --- |
| 424 | 287-289 | 296.18 |
| 425 | >310 | 284.2 |
| 426 | >310 | 284.2 |
| 427 | >300 | 266.38 |
| 428 | >310 | 267.19 |
| 429 | >300 | 342.2 |
| 430 | | 267.3 |
| 431 | | 312.2 |
| 432 | | 301.3 |
| 433 | | 285.2 |
| 434 | | 247.3 |
| 435 | | 357.3 |
| 436 | | 281.3 |
| 437 | | 253 |
| 438 | | 331 |
| 439 | | 302 |
| 440 | | 315 |
| 441 | | 314.1 |
| 442 | | 324 |
| 443 | | 316.1 |
| 444 | | 351.1 |
| 445 | | 297.2 |
| 446 | | 311.2 |
| 447 | | 231.2 |
| 448 | | 310.2 |
| 449 | | 311 |
| 450 | | 268.2 |
| 451 | | 292.2 |
| 452 | | 268.1 |
| 453 | | 302.1 |
| 454 | | 309.19 |
| 455 | >300 | 282.17 |
| 456 | 235-238 | 334.17 |
| 457 | >300 | 280.19 |
| 458 | 247-250 | 296.45 |
| 459 | 287-290 | 296.18 |
| 460 | 275-278 | 326.2 |
| 461 | 295-298 | 310.21 |
| 462 | 282-285 | 272.16 |
| 463 | 221-222 | 284.12 |
| 464 | 112-113.5 | 298.25 |
| 465 | | 298.25 |
| 466 | | 298.25 |
| 467 | | 280.25 |
| 468 | | 316.24 |
| 469 | | 314.21 |
| 470 | | 310.23 |
| 471 | | 352.23 |
| 472 | | 378.10, 380 |
| 473 | | 308.26 |
| 474 | | 310.28 |
| 475 | 242-243 | 284.22 |
| 476 | 266.5-268 | 284.23 |
| 477 | 245-247 | 266.25 |
| 478 | 260-262 | 302.24 |
| 479 | 293-295 | 300.19 |
| 480 | 249.5-251 | 296.22 |
| 481 | 201-203 | 296.22 |
| 482 | 283.5-285 | 364.09, 366 |
| 483 | 255-257 | 310.22 |
| 484 | 215-216 | 296.22 |
| 485 | 224-225 | 296.22 |
| 486 | 198-202 | 309.27 |
| 487 | 249-250 | 291.22 |
| 488 | | 310.27 |
| 489 | | 330.24 |
| 490 | | 323.21 |
| 491 | | 305.23 |
| 492 | | 308.29 |
| 493 | | 312.25 |
| 494 | | 328.22 |
| 495 | | 312.25 |
| 496 | | 312.25 |
| 497 | | 324.29 |
| 498 | | 330.24 |
| 499 | >278.5 | 302.21 |
| 500 | 246-247 | 296.27 |

-continued

| Compound | Melting Point (° C.) | MS (ES+) |
| --- | --- | --- |
| 501 | 231-232 | 284.24 |
| 502 | 264-265 | 284.22 |
| 503 | 265-266 | 300.16 |
| 504 | 273-274.5 | 284.29 |
| 505 | 253-254 | 280.25 |
| 506 | 233-234 | 285.26 |
| 507 | 221.5-223 | 285.23 |
| 508 | 299-300 | 301.15, 299.19 |
| 509 | 281.5-283 | 297.26 |
| 510 | 245-246 | 311.25 |
| 511 | 217-218 | 351.23 |
| 512 | 243-244 | 281.28 |
| 513 | 249.5-251 | 335.27 |
| 514 | | 298.25 |
| 515 | | 298.25 |
| 516 | | 298.25 |
| 517 | | 316.24 |
| 518 | | 310.29 |
| 519 | | 314.17 |
| 520 | | 294.26 |
| 521 | | 298.27 |
| 522 | | 298.27 |
| 523 | | 316.27 |
| 524 | | 310.29 |
| 525 | | 314.27 |
| 526 | | 294.31 |
| 527 | 243-245 | 346.1 |
| 528 | 233-235 | 296.2 |
| 529 | 292.5-293.5 | 284.18 |
| 530 | 318-319 | 284.19 |
| 531 | 317-319 | 302.18 |
| 532 | 298-300 | 296.22 |
| 533 | 273-275 | 300.05 |
| 534 | 297.5-299 | 280.23 |
| 535 | 302-303 | 284.24 |
| 536 | 319-321 | 284.22 |
| 537 | 322-323 | 284.23 |
| 538 | 324-326 | 302.23 |
| 539 | 297.5-299.5 | 296.24 |
| 540 | 320.5-322.5 | 300.19 |
| 541 | 307-308 | 280.25 |
| 542 | 284-285 | 350.2 |
| 543 | 286-287 | 334.24 |
| 544 | 240-242 | 296.22 |
| 545 | 239-240 | 334.24 |
| 546 | 222-224 | 350.2 |
| 547 | 241-243 | 326.25 |
| 548 | 298-299 | 302.19 |
| 549 | 295-296 | 302.22 |
| 550 | 272-273 | 284.18 |
| 551 | 238-239 | 295.34 |
| 552 | 270.5-272 | 283.32 |
| 553 | 264-265 | 284.31 |
| 554 | 245-246 | 284.31 |
| 555 | 276-277 | 300.28 |
| 556 | 272-274 | 300.28 |
| 557 | 269-270 | 310.3 |
| 558 | 246-247 | 272.27 |
| 559 | | 281.22 |
| 560 | | 315.28 |
| 561 | | 365.22 |
| 562 | | 350.29 |
| 563 | | 386.33 |
| 564 | | 347.22 |
| 565 | | 299.4 |
| 566 | | 294.38 |
| 567 | | 348.33 |
| 568 | | 308.3 |
| 569 | 283.5-285 | 281.22 |
| 570 | 292-293 | 315.28 |
| 571 | 282-283 | 365.22 |
| 572 | 298.5-301 | 350.29 |
| 573 | 257-259 | 280.27 |
| 574 | 281-282 | 334.31 |
| 575 | 248-250 | 296.3 |
| 576 | 233-235 | 347.22 |
| 577 | 304-305 | 299.4 |

-continued

| Compound | Melting Point (° C.) | MS (ES+) |
|---|---|---|
| 578 | 234-236 | 386.33 |
| 579 | 228-229 | 284.31 |
| 580 | 223-224.5 | 284.29 |
| 581 | 255-256 | 284.27 |
| 582 | 236-237 | 300.21 |
| 583 | 220-222 | 300.28 |
| 584 | 218-219 | 334.24 |
| 585 | 250-251.5 | 334.33 |
| 586 | 223.5-225 | 334.21 |
| 587 | 210-211 | 350.32 |
| 588 | 207-208 | 280.32 |
| 589 | 194-195 | 280.3 |
| 590 | 174-175 | 294.32 |
| 591 | 213-215 | 308.33 |
| 592 | 224-225 | 322.34 |
| 593 | 244-246 | 296.29 |
| 594 | 207-208 | 296.29 |
| 595 | 223-224 | 310.29 |
| 596 | >275 | 267.1 |
| 601 | 177-178 | 310.1 |
| 605 | 170-172 | 310.2 |
| 606 | 197-200 | 310.2 |
| 609 | 71-78 | 310.2 |
| 610 | 180-183 | 310.2 |
| 615 | 190-192 | 267.2 |
| 620 | 190-192 | 309.3 |
| 621 | 258-261 | 329.4 |
| 622 | 245-247 | 329.4 |
| 624 | 227-235 (decomp) | |
| 626 | 200-205 (decomp) | |
| 628 | >300 | |
| 629 | | 302.35 |
| 630 | 301-302 | 302.32 |
| 631 | 308-309 | 324.35 |
| 632 | 248-249 | 280.36 |
| 633 | 256-257 | 280.36 |
| 634 | 233-234 | 294.37 |
| 635 | 233-234 | 308.37 |
| 636 | 258-259 | 322.44 |
| 637 | 249-251 | 296.34 |
| 638 | 245-246 | 310.36 |
| 639 | 260-263 | 300.26 |
| 640 | 291-292 | 302.25 |
| 641 | 273-274 | 302.25 |
| 642 | 259-261 | 344.20 |
| 643 | 284-286 | 280.24 |
| 644 | 236-237 | 308.30 |
| 645 | 305-306 | 296.27 |
| 646 | 210-211 | 373.27 |
| 647 | 220-222 | 358.27 |
| 648 | 291-292 | 282.20 |
| 649 | 295-297 | 318.18 |
| 650 | 191-193 | 316.26 |
| 651 | 251-253 | 290.29 |
| 652 | | 338.27 |
| 653 | | 364.35 |
| 654 | | 348.2 |
| 655 | | 394.32 |
| 656 | | 360.31 |
| 657 | | 324.27 |
| 658 | | 363.33 |
| 659 | | 336.4 |
| 660 | | 294.32 |
| 661 | | 340.23 |
| 662 | | 324.26 |
| 663 | | 322.38 |
| 664 | | 323.32 |

Example 2

Nonsense Suppression Activity

A functional, cell-based translation assay based on luciferase-mediated chemoluminescence (International Application PCT/US2003/023185, filed on Jul. 23, 2003, hereby incorporated by reference in its entirety) permits quantitative assessment of the level of nonsense suppression. Human embryonic kidney cells (293 cells) are grown in medium containing fetal bovine serum (FBS). These cells can be stably transfected with the luciferase gene containing a premature termination codon at amino acid position 190. In place of the threonine codon (ACA) normally present in the luciferase gene at this site, each of the 3 possible nonsense codons (TAA, TAG, or TGA) and each of the 4 possible nucleotides (adenine, thymine, cytosine, or guanine) at the contextually important downstream +1 position following the nonsense codon are introduced by site-directed mutagenesis. As such, amino acid 190 in the luciferase gene containing a premature termination codon is either TAA, TAG, or TGA. For each stop codon, the nucleotide following amino acid 190 of luciferase gene containing a premature termination codon can be replaced with an adenine, thymine, cytosine, or guanine (A, T, C, G) such that these mutations do not change the reading frame of the luciferase gene. Schematics of these constructs are depicted in FIG. 1.

The nonsense suppression activity from a cell-based luciferase reporter assay of the present invention as described above shown in the table below (Table 2). Human Embryonic Kidney 293 cells are stably transfected with a luciferase reporter construct comprising a UGA nonsense mutation at position 190, which is followed, in-frame by an adenine nucleotide.

Activity measurements in Table 2 are determined in a cell-based luciferase reporter assay of the present invention construct containing a UGA premature termination codon. Gentamicin, an aminoglycoside antibiotic known to allow readthrough of premature termination codons, is used as an internal standard. Activity measurements are based on the qualitative ratio between the minimum concentration of compound required to produce a given protein in a cell versus the amount of protein produced by the cell at that concentration. Compounds which are found to have either or both very high potency and very high efficacy of protein synthesis are classified as "***". Compounds which are found to have intermediate potency and/or efficacy of protein synthesis are classified as ""; "*"; or "**". Similarly, compounds which are found to have lower potency and/or efficacy of protein synthesis are classified as "*".

Activity of the certain preferred compounds of the invention is shown in the table below:

| Compound No. | Activity |
|---|---|
| 1 | **** |
| 2 | *** |
| 3 | *** |
| 4 | **** |
| 5 | ** |
| 6 | **** |
| 7 | *** |
| 8 | * |
| 12 | * |
| 13 | * |
| 14 | * |
| 15 | ** |
| 16 | ** |
| 17 | ** |
| 18 | * |
| 19 | ** |
| 21 | * |
| 22 | * |
| 23 | ** |
| 24 | ** |
| 25 | ** |
| 26 | * |
| 27 | * |
| 28 | ** |

| Compound No. | Activity |
|---|---|
| 29 | ** |
| 30 | ** |
| 31 | * |
| 32 | * |
| 33 | ** |
| 34 | * |
| 35 | * |
| 36 | * |
| 37 | * |
| 38 | * |
| 39 | * |
| 40 | * |
| 41 | ** |
| 42 | ** |
| 43 | ** |
| 44 | ** |
| 45 | ** |
| 46 | ** |
| 47 | * |
| 48 | * |
| 49 | * |
| 50 | *** |
| 51 | * |
| 53 | * |
| 54 | * |
| 55 | ** |
| 60 | * |
| 62 | * |
| 63 | * |
| 64 | * |
| 65 | ** |
| 66 | * |
| 67 | * |
| 68 | ** |
| 69 | * |
| 70 | ** |
| 71 | * |
| 72 | * |
| 73 | * |
| 75 | * |
| 82 | * |
| 83 | ** |
| 84 | ** |
| 85 | * |
| 86 | * |
| 87 | * |
| 88 | **** |
| 89 | * |
| 90 | ** |
| 91 | * |
| 92 | * |
| 93 | * |
| 94 | * |
| 95 | * |
| 96 | * |
| 97 | * |
| 98 | * |
| 99 | *** |
| 100 | * |
| 101 | * |
| 102 | *** |
| 103 | **** |
| 104 | *** |
| 106 | **** |
| 107 | ** |
| 108 | * |
| 109 | *** |
| 110 | **** |
| 111 | * |
| 112 | * |
| 113 | * |
| 114 | ** |
| 115 | *** |
| 116 | ** |
| 117 | *** |
| 118 | **** |
| 119 | *** |
| 120 | * |
| 121 | **** |
| 122 | * |
| 123 | * |
| 124 | ** |
| 125 | ** |
| 126 | * |
| 127 | ** |
| 128 | * |
| 129 | *** |
| 130 | *** |
| 131 | ** |
| 132 | * |
| 133 | * |
| 134 | ** |
| 135 | * |
| 136 | *** |
| 137 | * |
| 138 | ** |
| 139 | ** |
| 140 | ** |
| 141 | *** |
| 142 | *** |
| 143 | *** |
| 144 | * |
| 145 | * |
| 146 | * |
| 147 | * |
| 148 | * |
| 149 | ** |
| 150 | * |
| 151 | * |
| 152 | * |
| 153 | * |
| 154 | ** |
| 155 | * |
| 156 | *** |
| 157 | * |
| 158 | * |
| 159 | ** |
| 160 | * |
| 161 | * |
| 162 | ** |
| 163 | * |
| 164 | * |
| 165 | * |
| 166 | * |
| 167 | * |
| 168 | ** |
| 169 | * |
| 170 | ** |
| 171 | * |
| 172 | ** |
| 173 | * |
| 174 | * |
| 175 | * |
| 176 | **** |
| 177 | * |
| 178 | * |
| 179 | * |
| 180 | ** |
| 181 | *** |
| 182 | * |
| 183 | * |
| 184 | ** |
| 185 | ** |
| 186 | * |
| 187 | ** |
| 188 | ** |
| 189 | *** |
| 190 | * |
| 191 | * |
| 192 | * |
| 193 | * |
| 194 | ** |
| 195 | ** |
| 196 | *** |

-continued

| Compound No. | Activity |
|---|---|
| 197 | * |
| 198 | ** |
| 199 | *** |
| 200 | * |
| 201 | **** |
| 202 | *** |
| 203 | * |
| 204 | ** |
| 205 | *** |
| 206 | ** |
| 207 | ** |
| 208 | ** |
| 209 | * |
| 210 | *** |
| 211 | ** |
| 212 | * |
| 213 | * |
| 214 | ** |
| 215 | ** |
| 216 | * |
| 217 | * |
| 218 | ** |
| 219 | ** |
| 220 | ** |
| 221 | *** |
| 222 | * |
| 223 | *** |
| 224 | * |
| 225 | * |
| 226 | * |
| 227 | * |
| 228 | *** |
| 229 | *** |
| 230 | * |
| 231 | * |
| 232 | * |
| 233 | * |
| 234 | * |
| 235 | * |
| 236 | * |
| 237 | * |
| 238 | * |
| 239 | * |
| 240 | * |
| 241 | * |
| 242 | * |
| 243 | ** |
| 244 | * |
| 245 | *** |
| 246 | * |
| 247 | ** |
| 248 | * |
| 249 | * |
| 250 | * |
| 251 | ** |
| 252 | * |
| 253 | * |
| 254 | ** |
| 255 | * |
| 258 | * |
| 259 | * |
| 260 | ** |
| 261 | * |
| 262 | ** |
| 263 | * |
| 264 | * |
| 265 | * |
| 266 | * |
| 267 | * |
| 268 | ** |
| 269 | * |
| 270 | * |
| 271 | * |
| 272 | *** |
| 273 | ** |
| 274 | ** |
| 275 | *** |

-continued

| Compound No. | Activity |
|---|---|
| 276 | *** |
| 277 | ** |
| 278 | ** |
| 279 | ** |
| 280 | **** |
| 281 | ** |
| 282 | ** |
| 283 | ** |
| 284 | ** |
| 285 | * |
| 286 | ** |
| 287 | **** |
| 288 | **** |
| 289 | *** |
| 290 | **** |
| 291 | **** |
| 292 | ** |
| 293 | * |
| 294 | * |
| 295 | * |
| 296 | * |
| 297 | ** |
| 298 | * |
| 299 | ** |
| 300 | * |
| 301 | * |
| 302 | * |
| 303 | ** |
| 304 | * |
| 305 | * |
| 306 | * |
| 307 | * |
| 308 | ** |
| 309 | ** |
| 310 | *** |
| 311 | *** |
| 312 | *** |
| 313 | *** |
| 314 | * |
| 315 | ** |
| 316 | * |
| 317 | * |
| 318 | *** |
| 319 | * |
| 320 | *** |
| 321 | **** |
| 322 | *** |
| 323 | *** |
| 324 | * |
| 325 | *** |
| 326 | *** |
| 327 | **** |
| 329 | **** |
| 330 | ** |
| 331 | **** |
| 332 | ** |
| 333 | *** |
| 334 | *** |
| 335 | *** |
| 336 | **** |
| 337 | ** |
| 338 | *** |
| 339 | *** |
| 340 | *** |
| 341 | *** |
| 342 | *** |
| 343 | ** |
| 344 | *** |
| 345 | *** |
| 346 | *** |
| 348 | **** |
| 349 | **** |
| 350 | **** |
| 351 | *** |
| 352 | *** |
| 353 | *** |
| 354 | ** |

| Compound No. | Activity |
|---|---|
| 355 | *** |
| 356 | **** |
| 357 | *** |
| 358 | *** |
| 359 | *** |
| 360 | **** |
| 361 | ** |
| 362 | *** |
| 363 | *** |
| 364 | ** |
| 365 | *** |
| 366 | *** |
| 367 | *** |
| 368 | *** |
| 369 | *** |
| 370 | *** |
| 371 | *** |
| 372 | ** |
| 373 | *** |
| 374 | *** |
| 375 | *** |
| 376 | *** |
| 377 | *** |
| 378 | ** |
| 379 | *** |
| 380 | *** |
| 381 | *** |
| 382 | *** |
| 383 | ** |
| 384 | ** |
| 385 | *** |
| 386 | *** |
| 387 | ** |
| 388 | *** |
| 389 | *** |
| 390 | ** |
| 391 | * |
| 392 | ** |
| 393 | * |
| 394 | *** |
| 395 | *** |
| 396 | * |
| 397 | *** |
| 398 | *** |
| 399 | **** |
| 400 | **** |
| 401 | * |
| 402 | ** |
| 403 | * |
| 404 | ** |
| 405 | * |
| 406 | ** |
| 407 | **** |
| 408 | ** |
| 409 | **** |
| 410 | **** |
| 411 | ** |
| 412 | **** |
| 413 | *** |
| 414 | *** |
| 415 | *** |
| 416 | * |
| 417 | * |
| 418 | * |
| 419 | **** |
| 420 | * |
| 421 | ** |
| 422 | * |
| 423 | **** |
| 424 | * |
| 425 | ** |
| 426 | * |
| 427 | * |
| 428 | * |
| 429 | *** |
| 430 | ** |
| 431 | ** |
| 432 | * |
| 433 | ** |
| 434 | * |
| 435 | * |
| 436 | * |
| 437 | * |
| 438 | * |
| 439 | * |
| 440 | *** |
| 441 | * |
| 442 | *** |
| 443 | * |
| 444 | *** |
| 445 | **** |
| 446 | **** |
| 447 | * |
| 448 | *** |
| 449 | * |
| 450 | * |
| 451 | * |
| 452 | * |
| 453 | * |
| 454 | *** |
| 455 | ** |
| 456 | *** |
| 457 | **** |
| 458 | * |
| 459 | ** |
| 460 | ** |
| 461 | * |
| 462 | * |
| 463 | **** |
| 464 | ** |
| 465 | *** |
| 466 | *** |
| 467 | *** |
| 468 | **** |
| 469 | *** |
| 470 | *** |
| 471 | *** |
| 472 | *** |
| 473 | *** |
| 474 | *** |
| 475 | **** |
| 476 | **** |
| 477 | **** |
| 478 | **** |
| 479 | **** |
| 480 | **** |
| 481 | **** |
| 482 | **** |
| 483 | * |
| 484 | ** |
| 485 | * |
| 486 | ** |
| 487 | ** |
| 488 | ** |
| 489 | *** |
| 490 | ** |
| 491 | ***** |
| 492 | ** |
| 493 | *** |
| 494 | *** |
| 495 | **** |
| 496 | **** |
| 497 | ** |
| 498 | ** |
| 499 | ***** |
| 500 | ***** |
| 501 | ***** |
| 502 | **** |
| 503 | **** |
| 504 | **** |
| 505 | ***** |
| 506 | **** |
| 507 | **** |
| 508 | **** |

-continued

| Compound No. | Activity |
| --- | --- |
| 509 | ***** |
| 510 | **** |
| 511 | **** |
| 512 | ***** |
| 513 | ***** |
| 514 | ** |
| 515 | ** |
| 516 | ** |
| 517 | * |
| 518 | ** |
| 519 | ** |
| 520 | *** |
| 521 | *** |
| 522 | **** |
| 523 | *** |
| 524 | *** |
| 525 | **** |
| 526 | *** |
| 527 | **** |
| 528 | *** |
| 529 | *** |
| 530 | ***** |
| 531 | ***** |
| 532 | ***** |
| 533 | *** |
| 534 | *** |
| 535 | *** |
| 536 | ** |
| 537 | ** |
| 538 | *** |
| 539 | **** |
| 540 | **** |
| 541 | **** |
| 542 | *** |
| 543 | *** |
| 544 | ***** |
| 545 | **** |
| 546 | **** |
| 547 | **** |
| 548 | **** |
| 549 | **** |
| 550 | ***** |
| 551 | *** |
| 552 | *** |
| 553 | *** |
| 554 | **** |
| 555 | **** |
| 556 | *** |
| 557 | ***** |
| 558 | **** |
| 559 | ** |
| 560 | ** |
| 561 | * |
| 562 | ** |
| 563 | * |
| 564 | * |
| 565 | ** |
| 566 | ** |
| 567 | ** |
| 568 | ** |
| 569 | ** |
| 570 | ** |
| 571 | *** |
| 572 | * |
| 573 | **** |
| 574 | **** |
| 575 | *** |
| 576 | ** |
| 577 | *** |
| 578 | * |
| 579 | *** |
| 580 | *** |
| 581 | *** |
| 582 | *** |
| 583 | *** |
| 584 | *** |
| 585 | *** |
| 586 | *** |
| 587 | *** |
| 588 | *** |
| 589 | **** |
| 590 | **** |
| 591 | *** |
| 592 | **** |
| 593 | *** |
| 594 | *** |
| 595 | **** |
| 596 | * |
| 601 | * |
| 605 | * |
| 606 | ** |
| 609 | * |
| 610 | * |
| 615 | * |
| 620 | * |
| 621 | *** |
| 622 | * |
| 624 | ***** |
| 626 | **** |
| 628 | *** |
| 629 | *** |
| 630 | *** |
| 631 | ***** |
| 632 | ***** |
| 633 | ***** |
| 634 | ***** |
| 635 | ***** |
| 636 | ***** |
| 637 | ***** |
| 638 | ***** |
| 639 | **** |
| 640 | **** |
| 641 | ** |
| 642 | **** |
| 643 | *** |
| 644 | **** |
| 645 | *** |
| 646 | *** |
| 647 | **** |
| 648 | **** |
| 649 | * |
| 650 | **** |
| 651 | **** |
| 652 | ** |
| 653 | ** |
| 654 | ** |
| 655 | **** |
| 656 | * |
| 657 | ** |
| 658 | ** |
| 659 | ** |
| 660 | ** |
| 661 | ** |
| 662 | ** |
| 663 | ** |
| 664 | ** |

The nonsense suppression activity in an assay as described above is shown in the Table 3 below, for a construct with a UAG nonsense mutation at position 190, followed by an adenine nucleotide in-frame, (UAGA); and a construct with a UAA nonsense mutation at position 190, followed by an adenine nucleotide in-frame, (UAAA). "POS WB" indicates that a positive signal is produced on a western blot when the compound of the invention is used in an assay of the present invention. "ND" indicates that the result is not determined.

| Compound No. | UAG | UAA |
|---|---|---|
| 4 | ** | ** |
|  | (FA) | (FA) |
|  | ** | ** |
|  | (Na) | (Na) |
| 5 | ** |  |
| 6 | *** | *** |
|  | (FA) | (FA) |
|  | ** | ** |
|  | (Na) | (Na) |
| 7 | *** | *** |
|  | (FA) | (FA) |
|  | **** | *** |
|  | (Na) | (Na) |
| 499 | *** |  |
| 500 | ** |  |
| 501 | * |  |
| 502 | * |  |
| 503 | * |  |
| 504 | * |  |
| 505 | *** |  |
| 506 | ** | *** |
| 507 | * | * |
| 508 | ** | * |
| 509 | **** | *** |
| 510 | *** | ** |
| 511 | *** | ** |
| 512 | **** | *** |
| 513 | *** | ** |

| Compound No. | UAGA | UAAA |
|---|---|---|
| 527 | **** | * |
| 528 | *** | ** |
| 548 |  | POSWB |
| 554 | * | * |
| 557 | * | * |
| 590 | ** | ** |
| 592 | *** | *** |
| 595 | ** | ** |
|  |  | POSWB |
| 478 | *** | ** |
| 479 | *** | ** |
|  |  | POSWB |
| 480 | ***** | *** |
| 481 | *** | *** |
| 482 | *** | *** |
| 525 | *** | * |
| 573 | ** | * |
| 574 | ** | * |

Example 3

Readthrough Assay

A functional, cell-based translation assay based on luciferase-mediated chemoluminescence (International Application PCT/US2003/023185, filed on Jul. 23, 2003 and incorporated by reference in its entirety) permits assessment of translation-readthough of the normal stop codon in a mRNA. Human embryonic kidney cells (293 cells) are grown in medium containing fetal bovine serum (FBS). These cells are stably transfected with the luciferase gene containing a premature termination codon at amino acid position 190. In place of the threonine codon (ACA) normally present in the luciferase gene at this site, each of the 3 possible nonsense codons (TAA, TAG, or TGA) and each of the 4 possible nucleotides (adenine, thymine, cytosine, or guanine) at the contextually important downstream +1 position following the nonsense codon are introduced by site-directed mutagenesis. As such, amino acid 190 in the luciferase gene containing a premature termination codon is either TAA, TAG, or TGA. For each stop codon, the nucleotide following amino acid 190 of luciferase gene containing a premature termination codon are replaced with an adenine, thymine, cytosine, or guanine (A, T, C, G) such that these mutation do not change the reading frame of the luciferase gene. Schematics of these constructs are depicted above in FIG. 1.

Another assay of the present invention can evaluate compounds that promote nonsense mutation suppression. The luciferase constructs described above in FIG. 1 are engineered to harbor two epitope tags in the N-terminus of the luciferase protein. Based on luciferase protein production, these constructs qualitatively assess the level of translation-readthrough. The presence of the full-length luciferase protein produced by suppression of the premature termination codon is measured by immunoprecipitation of the suppressed luciferase protein (using an antibody against a His tag) followed by western blotting using an antibody against the second epitope (the Xpress™ epitope; Invitrogen®; Carlsbad, Calif.). These constructs are depicted in FIG. 2.

Cells that harbor the constructs of FIG. 2 show increased full-length protein production when treated with a compound of the present invention. After treatment for 20 hours, cells containing the constructs of FIG. 2 are collected and an antibody recognizing the His epitope is used to immunoprecipitate the luciferase protein. Following immunoprecipitation, western blotting is performed using the antibody to the Xpress™ epitope (Invitrogen®; Carlsbad, Calif.) to detect the truncated luciferase (produced when no nonsense suppression occurs) and to detect the full-length protein (produced by suppression of the nonsense codon). Treatment of cells with a test compound produces full-length protein and not a readthrough protein (See e.g. FIG. 3). The readthrough protein is produced if suppression of the normal termination codon occurs. Compounds of the present invention suppress the premature, i.e. nonsense mutation, but not the normal termination codon in the luciferase mRNA.

Compounds of the present invention selectively act on premature termination codons but not normal termination codons in mammals.

Rats and dogs are administered high doses of compound (up to 1800 mg/kg) by gavage (oral) once daily for 14 days. After the treatment, tissues are collected, lysates are prepared, and Western blot analysis is performed. Selection of the proteins for evaluation of normal termination codon readthrough is based primarily on the corresponding mRNA having a second stop codon in the 3'-UTR that is in-frame with the normal termination codon. Between these 2 stop codons, each selected protein has an intervening sequence of nucleotides that codes for an extension of the protein in the event of ribosomal readthrough of the first termination codon. If the compound has the capacity to induce nonspecific, ribosomal readthrough, an elongated protein is differentiated from the wild-type protein using Western blot. Tissues are collected from rats and are analyzed for suppression of the normal termination codon (UAA) in the vimentin mRNA. No evidence of suppression is apparent. Tissues are collected from dogs treated with compounds of the present invention. There is no evidence of suppression of the normal termination codon of beta actin, which harbors a UAG stop codon.

In healthy human volunteers, a single dose of a compound of the present invention (200 mg/kg) is administered orally. Blood samples are collected, plasma is prepared, and a Western blot is conducted using plasma samples from female and male subjects. C-reactive protein (CRP), which harbors a UGA termination codon, is used to determine if treatment of subjects with compounds of the present invention result in suppression of the normal termination codon in the CRP mRNA. A luciferase assay in combination with a premature termination assay demonstrates selective suppression of premature termination codons but not normal termination codons.

Example 4

Animal Models

Animal model systems can also be used to demonstrate the safety and efficacy of a compound of the present invention. The compounds of the present invention can be tested for biological activity using animal models for a disease, condition, or syndrome of interest. These include animals engineered to contain the target RNA element coupled to a functional readout system, such as a transgenic mouse.

Cystic Fibrosis

Examples of animal models for cystic fibrosis include, but are not limited to, cftr(−/−) mice (see, e.g., Freedman et al., 2001, *Gastroenterology* 121(4):950-7), cftr(tm1HGU/tm1HGU) mice (see, e.g., Bernhard et al., 2001, *Exp Lung Res* 27(4):349-66), CFTR-deficient mice with defective cAMP-mediated Cl(−) conductance (see, e.g., Stotland et al., 2000, *Pediatr Pulmonol* 30(5):413-24), and C57BL/6-Cftr (m1UNC)/Cftr(m1UNC) knockout mice (see, e.g., Stotland et al., 2000, *Pediatr Pulmonol* 30(5):413-24).

Muscular Dystrophy

Examples of animal models for muscular dystrophy include, but are not limited to, mouse, hamster, cat, dog, and *C. elegans*. Examples of mouse models for muscular dystrophy include, but are not limited to, the dy−/− mouse (see, e.g., Connolly et al., 2002, *J Neuroimmunol* 127(1-2):80-7), a muscular dystrophy with myositis (mdm) mouse mutation (see, e.g., Garvey et al., 2002, *Genomics* 79(2):146-9), the mdx mouse (see, e.g., Nakamura et al., 2001, *Neuromuscul Disord* 11(3):251-9), the utrophin-dystrophin knockout (dko) mouse (see, e.g., Nakamura et al., 2001, *Neuromuscul Disord* 11(3):251-9), the dy/dy mouse (see, e.g., Dubowitz et al., 2000, *Neuromuscul Disord* 10(4-5):292-8), the mdx (Cv3) mouse model (see, e.g., Pillers et al., 1999, *Laryngoscope* 109(8):1310-2), and the myotonic ADR-MDX mutant mice (see, e.g., Kramer et al., 1998, *Neuromuscul Disord* 8(8):542-50). Examples of hamster models for muscular dystrophy include, but are not limited to, sarcoglycan-deficient hamsters (see, e.g., Nakamura et al., 2001, *Am J Physiol Cell Physiol* 281(2):C690-9) and the BIO 14.6 dystrophic hamster (see, e.g., Schlenker & Burbach, 1991, *J Appl Physiol* 71(5):1655-62). An example of a feline model for muscular dystrophy includes, but is not limited to, the hypertrophic feline muscular dystrophy model (see, e.g., Gaschen & Burgunder, 2001, *Acta Neuropathol* (Berl) 101(6):591-600). Canine models for muscular dystrophy include, but are not limited to, golden retriever muscular dystrophy (see, e.g., Fletcher et al., 2001, *Neuromuscul Disord* 11(3):239-43) and canine X-linked muscular dystrophy (see, e.g., Valentine et al., 1992, Am J Med Genet. 42(3):352-6). Examples of *C. elegans* models for muscular dystrophy are described in Chamberlain & Benian, 2000, *Curr Biol* 10(21):R795-7 and Culette & Sattelle, 2000, *Hum Mol Genet* 9(6):869-77.

Familial Hypercholesterolemia

Examples of animal models for familial hypercholesterolemia include, but are not limited to, mice lacking functional LDL receptor genes (see, e.g., Aji et al., 1997, *Circulation* 95(2):430-7), Yoshida rats (see, e.g., Fantappie et al., 1992, *Life Sci* 50(24):1913-24), the JCR:LA-cp rat (see, e.g., Richardson et al., 1998, *Atherosclerosis* 138(1):135-46), swine (see, e.g., Hasler-Rapacz et al., 1998, *Am J Med Genet* 76(5):379-86), and the Watanabe heritable hyperlipidaemic rabbit (see, e.g., Tsutsumi et al., 2000, *Arzneimittelforschung* 50(2):118-21; Harsch et al., 1998, *Br J Pharmacol* 124(2):227-82; and Tanaka et al., 1995, *Atherosclerosis* 114(1):73-82).

Human Cancer

An example of an animal model for human cancer, in general includes, but is not limited to, spontaneously occurring tumors of companion animals (see, e.g., Vail & MacEwen, 2000, *Cancer Invest* 18(8):781-92). Examples of animal models for lung cancer include, but are not limited to, lung cancer animal models described by Zhang & Roth (1994, *In Vivo* 8(5):755-69) and a transgenic mouse model with disrupted p53 function (see, e.g., Morris et al., 1998, *J La State Med Soc* 150(4):179-85). An example of an animal model for breast cancer includes, but is not limited to, a transgenic mouse that overexpresses cyclin D1 (see, e.g., Hosokawa et al., 2001, *Transgenic Res* 10(5):471-8). An example of an animal model for colon cancer includes, but is not limited to, a TCRbeta and p53 double knockout mouse (see, e.g., Kado et al., 2001, *Cancer Res* 61(6):2395-8). Examples of animal models for pancreatic cancer include, but are not limited to, a metastatic model of Panc02 murine pancreatic adenocarcinoma (see, e.g., Wang et al., 2001, *Int J Pancreatol* 29(1):37-46) and nu-nu mice generated in subcutaneous pancreatic tumours (see, e.g., Ghaneh et al., 2001, *Gene Ther* 8(3):199-208). Examples of animal models for non-Hodgkin's lymphoma include, but are not limited to, a severe combined immunodeficiency ("SCID") mouse (see, e.g., Bryant et al., 2000, *Lab Invest* 80(4):553-73) and an IgHmu-HOX11 transgenic mouse (see, e.g., Hough et al., 1998, *Proc Natl Acad Sci USA* 95(23):13853-8). An example of an animal model for esophageal cancer includes, but is not limited to, a mouse transgenic for the human papillomavirus type 16 E7 oncogene (see, e.g., Herber et al., 1996, *J Virol* 70(3):1873-81). Examples of animal models for colorectal carcinomas include, but are not limited to, Apc mouse models (see, e.g., Fodde & Smits, 2001, *Trends Mol Med* 7(8):369-73 and Kuraguchi et al., 2000, *Oncogene* 19(50):5755-63). An example of an animal model for neurofibromatosis includes, but is not limited to, mutant NF1 mice (see, e.g., Cichowski et al., 1996, *Semin Cancer Biol* 7(5):291-8). Examples of animal models for retinoblastoma include, but are not limited to, transgenic mice that expression the simian virus 40 T antigen in the retina (see, e.g., Howes et al., 1994, *Invest Opthalmol V is Sci* 35(2):342-51 and Windle et al, 1990, Nature 343(6259):665-9) and inbred rats (see, e.g., Nishida et al., 1981, *Curr Eye Res* 1(1):53-5 and Kobayashi et al., 1982, *Acta Neuropathol* (Berl) 57(2-3):203-8). Examples of animal models for Wilm's tumor include, but are not limited to, a WT1 knockout mice (see, e.g., Scharnhorst et al., 1997, *Cell Growth Differ* 8(2):133-43), a rat subline with a high incidence of neuphroblastoma (see, e.g., Mesfin & Breech, 1996, *Lab Anim Sci* 46(3):321-6), and a Wistar/Furth rat with Wilms' tumor (see, e.g., Murphy et al., 1987, *Anticancer Res* 7(4B):717-9).

Retinitis Pigmentosa

Examples of animal models for retinitis pigmentosa include, but are not limited to, the Royal College of Surgeons ("RCS") rat (see, e.g., Vollrath et al., 2001, *Proc Natl Acad Sci USA* 98(22); 12584-9 and Hanitzsch et al., 1998, *Acta Anat* (Basel) 162(2-3):119-26), a rhodopsin knockout mouse (see, e.g., Jaissle et al., 2001, *Invest Opthalmol Vis Sci* 42(2):506-13), and Wag/Rij rats (see, e.g., Lai et al., 1980, *Am J Pathol* 98(1):281-4).

Cirrhosis

Examples of animal models for cirrhosis include, but are not limited to, $CCl_4$-exposed rats (see, e.g., Kloehn et al., 2001, *Horm Metab Res* 33(7):394-401) and rodent models instigated by bacterial cell components or colitis (see, e.g., Vierling, 2001, *Best Pract Res Clin Gastroenterol* 15(4): 591-610).

Hemophilia

Examples of animal models for hemophilia include, but are not limited to, rodent models for hemophilia A (see, e.g., Reipert et al., 2000, *Thromb Haemost* 84(5):826-32; Jarvis et al., 1996, *Thromb Haemost* 75(2):318-25; and Bi et al., 1995, *Nat Genet* 10(1):119-21), canine models for hemophilia A (see, e.g., Gallo-Penn et al., 1999, *Hum Gene Ther* 10(11):1791-802 and Connelly et al, 1998, *Blood* 91(9); 3273-81), murine models for hemophilia B (see, e.g., Snyder et al., 1999, *Nat Med* 5(1):64-70; Wang et al., 1997, *Proc Natl Acad Sci USA* 94(21):11563-6; and Fang et al., 1996, *Gene Ther* 3(3):217-22), canine models for hemophilia B (see, e.g., Mount et al., 2002, *Blood* 99(8):2670-6; Snyder et al., 1999, *Nat Med* 5(1):64-70; Fang et al., 1996, *Gene Ther* 3(3):217-22); and Kay et al., 1994, *Proc Natl Acad Sci USA* 91(6):2353-7), and a rhesus macaque model for hemophilia B (see, e.g., Lozier et al., 1999, *Blood* 93(6):1875-81).

Von Willebrand Disease

Examples of animal models for von Willebrand disease include, but are not limited to, an inbred mouse strain RIIIS/J (see, e.g., Nichols et al., 1994, 83(11):3225-31 and Sweeney et al., 1990, 76(11):2258-65), rats injected with botrocetin (see, e.g., Sanders et al., 1988, *Lab Invest* 59(4): 443-52), and porcine models for von Willebrand disease (see, e.g., Nichols et al., 1995, *Proc Natl Acad Sci USA* 92(7):2455-9; Johnson & Bowie, 1992, *J Lab Clin Med* 120(4):553-8); and Brinkhous et al., 1991, *Mayo Clin Proc* 66(7):733-42).

β-Thalassemia

Examples of animal models for β-thalassemia include, but are not limited to, murine models with mutations in globin genes (see, e.g., Lewis et al., 1998, *Blood* 91(6):2152-6; Raja et al., 1994, *Br J Haematol* 86(1):156-62; Popp et al., 1985, 445:432-44; and Skow et al., 1983, *Cell* 34(3):1043-52).

Kidney Stones

Examples of animal models for kidney stones include, but are not limited to, genetic hypercalciuric rats (see, e.g., Bushinsky et al., 1999, *Kidney Int* 55(1):234-43 and Bushinsky et al., 1995, *Kidney Int* 48(6):1705-13), chemically treated rats (see, e.g., Grases et al., 1998, *Scand J Urol Nephrol* 32(4):261-5; Burgess et al., 1995, *Urol Res* 23(4): 239-42; Kumar et al., 1991, *J Urol* 146(5):1384-9; Okada et al., 1985, *Hinyokika Kiyo* 31(4):565-77; and Bluestone et al., 1975, *Lab Invest* 33(3):273-9), hyperoxaluric rats (see, e.g., Jones et al., 1991, *J Urol* 145(4):868-74), pigs with unilateral retrograde flexible nephroscopy (see, e.g., Seifmah et al., 2001, 57(4):832-6), and rabbits with an obstructed upper urinary tract (see, e.g., Itatani et al., 1979, *Invest Urol* 17(3):234-40).

Ataxia-Telangiectasia

Examples of animal models for ataxia-telangiectasia include, but are not limited to, murine models of ataxia-telangiectasia (see, e.g., Barlow et al., 1999, *Proc Natl Acad Sci USA* 96(17):9915-9 and Inoue et al., 1986, *Cancer Res* 46(8):3979-82).

Lysosomal Storage Diseases

Examples of animal models for lysosomal storage diseases include, but are not limited to, mouse models for mucopolysaccharidosis type VII (see, e.g., Brooks et al., 2002, *Proc Natl Acad Sci USA*. 99(9):6216-21; Monroy et al., 2002, *Bone* 30(2):352-9; Vogler et al., 2001, *Pediatr Dev Pathol*. 4(5):421-33; Vogler et al., 2001, *Pediatr Res*. 49(3): 342-8; and Wolfe et al., 2000, *Mol Ther.* 2(6):552-6), a mouse model for metachromatic leukodystrophy (see, e.g., Matzner et al., 2002, *Gene Ther.* 9(1):53-63), a mouse model of Sandhoff disease (see, e.g., Sango et al., 2002, *Neuropathol Appl Neurobiol*. 28(1):23-34), mouse models for mucopolysaccharidosis type III A (see, e.g., Bhattacharyya et al., 2001, *Glycobiology* 11(1):99-10 and Bhaumik et al., 1999, *Glycobiology* 9(12):1389-96.), arylsulfatase A (ASA)-deficient mice (see, e.g., D'Hooge et al., 1999, *Brain Res*. 847(2):352-6 and D'Hooge et al, 1999, *Neurosci Lett*. 273 (2):93-6); mice with an aspartylglucosaminuria mutation (see, e.g., Jalanko et al., 1998, *Hum Mol Genet*. 7(2):265-72); feline models of mucopolysaccharidosis type VI (see, e.g., Crawley et al., 1998, *J Clin Invest*. 101(1):109-19 and Norrdin et al., 1995, *Bone* 17(5):485-9); a feline model of Niemann-Pick disease type C (see, e.g., March et al., 1997, *Acta Neuropathol (Berl)*. 94(2):164-72); acid sphingomyelinase-deficient mice (see, e.g., Otterbach & Stoffel, 1995, *Cell* 81(7):1053-6), and bovine mannosidosis (see, e.g., Jolly et al., 1975, *Birth Defects Orig Arctic Ser.* 11(6):273-8).

Tuberous Sclerosis

Examples of animal models for tuberous sclerosis ("TSC") include, but are not limited to, a mouse model of TSC1 (see, e.g., Kwiatkowski et al., 2002, *Hum Mol Genet*. 11(5):525-34), a Tsc1 (TSC1 homologue) knockout mouse (see, e.g., Kobayashi et al., 2001, *Proc Natl Acad Sci USA*. 2001 Jul. 17; 98(15):8762-7), a TSC2 gene mutant (Eker) rat model (see, e.g., Hino 2000, *Nippon Rinsho* 58(6):1255-61; Mizuguchi et al., 2000, *J Neuropathol Exp Neurol*. 59(3): 188-9; and Hino et al., 1999, *Prog Exp Tumor Res*. 35:95-108); and Tsc2(+/−) mice (see, e.g., Onda et al., 1999, *J Clin Invest*. 104(6):687-95).

Example 5

Mdx Mouse, an Animal Model Study

The mutation in the mdx mouse that causes premature translation termination of the 427 kDa dystrophin polypeptide has been shown to be a C to T transition at position 3185 in exon 23 (Sicinski et al., *Science* 244(4912):1578-1580 (1989)). Mouse primary skeletal muscle cultures derived from 1-day old mdx mice are prepared as described previously (Barton-Davis et al., *J. Clin. Invest.* 104(4):375-381 (1999)). Cells are cultured for 10 days in the presence of a compound of the invention. Culture medium is replaced every four days and the presence of dystrophin in myoblast cultures is detected by immunostaining as described previously (Barton-Davis et al., *J. Clin. Invest.* 104(4):375-381 (1999)). A primary monoclonal antibody to the C-terminus of the dystrophin protein is used undiluted and rhodamine conjugated anti-mouse IgG is used as the secondary antibody. The antibody detects the full-length protein produced by suppression of the nonsense codon. Staining is viewed using a Leica DMR microscope, digital camera, and associated imaging software.

As previously described (Barton-Davis et al., *J. Clin. Invest.* 104(4):375-381 (1999), compound is delivered by Alzet osmotic pumps implanted under the skin of anesthetized mice. Two doses of a compound of the invention are administered. Gentamicin serves as a positive control and pumps filled with solvent only serve as the negative control. Pumps are loaded with appropriate compound such that the calculated doses to which tissue is exposed are 10 mM and 20 mM. The gentamicin concentration is calculated to achieve tissue exposure of approximately 200 mM. In the initial experiment, mice are treated for 14 days, after which animals are anesthetized with ketamine and exsanguinated. The tibialis anterior (TA) muscle of the experimental animals is then excised, frozen, and used for immunofluorescence analysis of dystrophin incorporation into striated muscle. The presence of dystrophin in TA muscles is detected by immunostaining, as described previously (Barton-Davis et al., J. Clin. Invest. 104(4):375-381 (1999).

Western Blot Analysis

Quadricep muscles from an mdx mouse treated with a compound of the present invention for 4 weeks are analyzed by western blot using a commercially available antibody to dystrophin. Protein extracted from the quadriceps of a wild-type mouse serve as a positive control. Production of full-length dystrophin is observed in the treated animal. The amount of full-length dystrophin produced, as a result of nonsense suppression, but not limited by this theory, is approximately 10% of wild-type levels of expression.

Immunofluorescence

Male mdx mice (age 9-11 weeks) are treated with different compounds of the present invention (n=2 at least for each compound). These compounds are injected SQ once per day for two weeks at 25 mg/kg. After 2 weeks of treatment, mice are sacrificed for the removal of muscles to determine dystrophin readthrough efficiency.

Immunofluorescence (IF) is performed on 10 µm cryosections using a dystrophin antibody. The antibody recognizes an epitope C-terminal to the premature stop mutation found in mdx mice. Image analysis is performed in an identical manner in all sections. Images from treated and untreated mice are analyzed and a signal greater than the signal on the untreated control is deemed positive and indicates that suppression of the premature termination codon in the dystrophin mRNA occurred.

Muscle Mechanics

Isolated whole muscle mechanics is performed on EDL muscles from animals. Optimum muscle length (Lo) is defined as the length that produced maximum twitch tension. Maximum tetanic force at Lo is measured using a 120 Hz, 500 msec pulse at supramaximal voltage. Protection against mechanical injury, induced by a series of 5 eccentric tetanic contractions, is monitored. These measurements are performed using a 700 msec stimulation period during which the muscle is held in an isometric contraction for the first 500 msec followed by a stretch of 8 or 10% Lo at a rate of 0.5 Lo/sec. Protection against mechanical injury is evaluated at 80 Hz stimulation frequency. Damage is determined as the loss in force between the first and last eccentric contraction. As shown in FIG. 4, treatment with compounds of the present invention result in protection from damage induced by eccentric contractions of the EDL muscle compared to the untreated control.

Example 6

Suppression of a Nonsense Mutation in the p53 Gene

For an animal model system, CAOV-3 cells (1×10$^7$) are injected into the flanks of nude/nude mice. After 12 days, mice are randomized (10 mice per group) and treated subcutaneously (5 days per week) with 3 mg/kg of a compound of the present invention or intraperitonealy (1 day per week) with 30 mg/kg of a compound of the present invention. Tumor volumes are measured weekly. Suppression of nonsense mutations in the p53 gene by a compound of the present invention can inhibit cancer growth in vivo.

Example 7

Access to Specific Nucleotides of the 28S rRNA can be Modified by Compounds of the Present Invention Previous studies have demonstrated that gentamicin and other members of the aminoglycoside family that decrease the fidelity of translation bind to the A site of the 16S rRNA. By chemical footprinting, UV cross-linking and NMR, gentamicin has been shown to bind at the A site (comprised of nucleotides 1400-1410 and 1490-1500, E. coli numbering) of the rRNA at nucleotides 1406, 1407, 1494, and 1496 (Moazed & Noller, Nature 327(6121):389-394 (1978); Woodcock et al., EMBO J. 10(10):3099-3103 (1991); and Schroeder et al., EMBO J. 19:1-9 (2000).

Ribosomes prepared from HeLa cells are incubated with the small molecules (at a concentration of 100 mM), followed by treatment with chemical modifying agents (dimethyl sulfate [DMS] and kethoxal [KE]). Following chemical modification, rRNA is phenol-chloroform extracted, ethanol precipitated, analyzed in primer extension reactions using end-labeled oligonucleotides hybridizing to different regions of the three rRNAs and resolved on 6% polyacrylamide gels. Probes for primer extension cover the entire 18S (7 oligonucleotide primers), 28S (24 oligonucleotide primers), and 5S (one primer) rRNAs. Controls in these experiments include DMSO (a control for changes in rRNA accessibility induced by DMSO), paromomycin (a marker for 18S rRNA binding), and anisomycin (a marker for 28S rRNA binding).

All publications and patent applications cited herein are incorporated by reference to the same extent as if each individual publication or patent application is specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the claims of the invention.

What is claimed:

1. A compound of Formula 1-A:

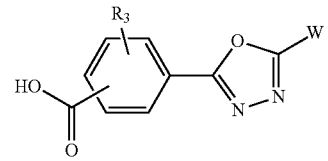

1-A wherein:
R$_3$ is absent;
W is selected from the group consisting of:

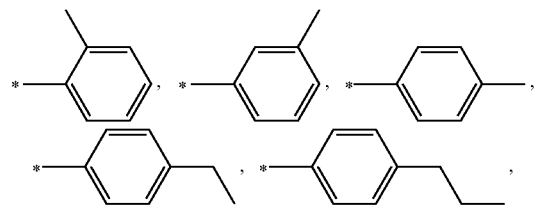

283
-continued
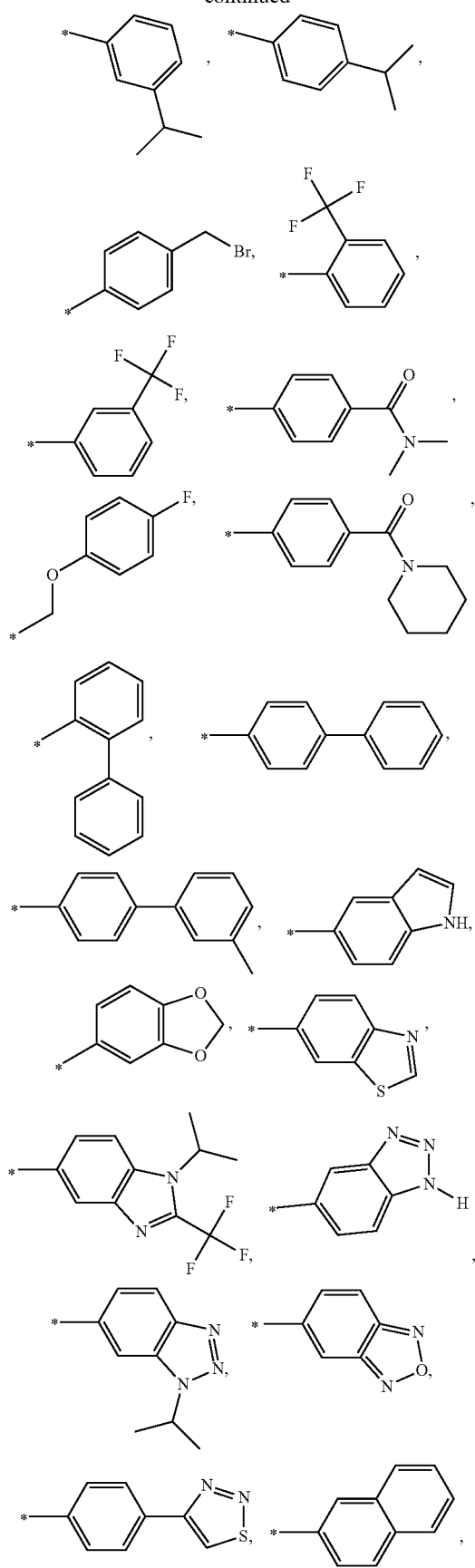
284
-continued
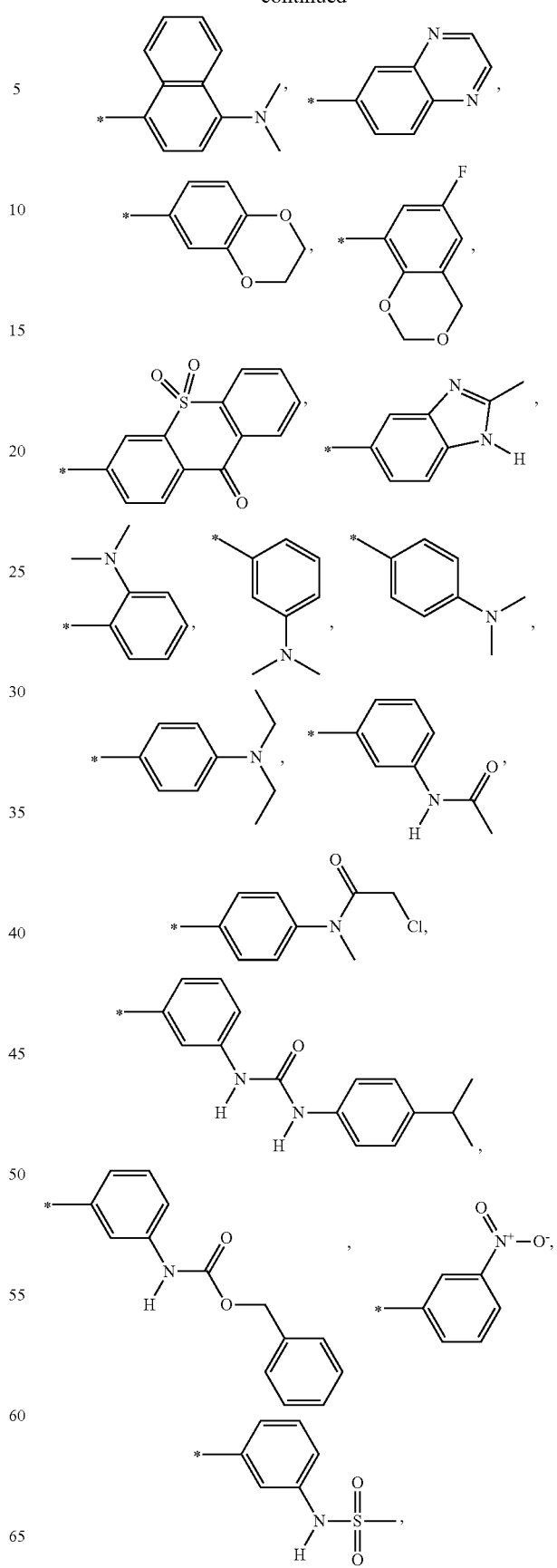

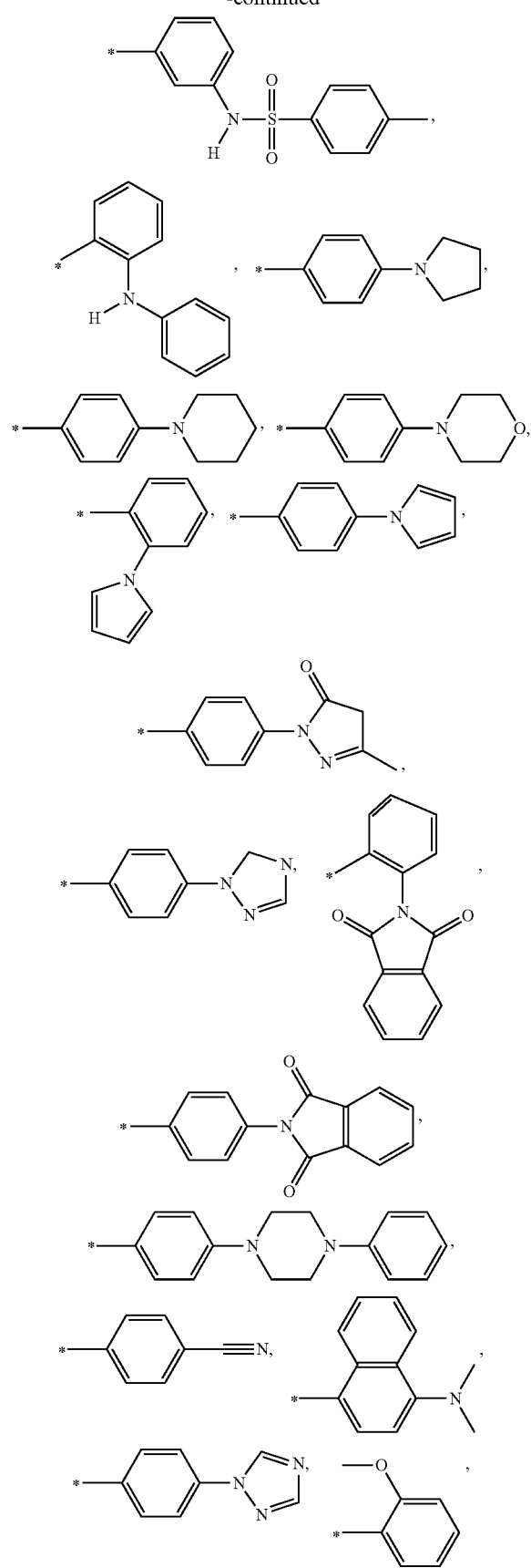
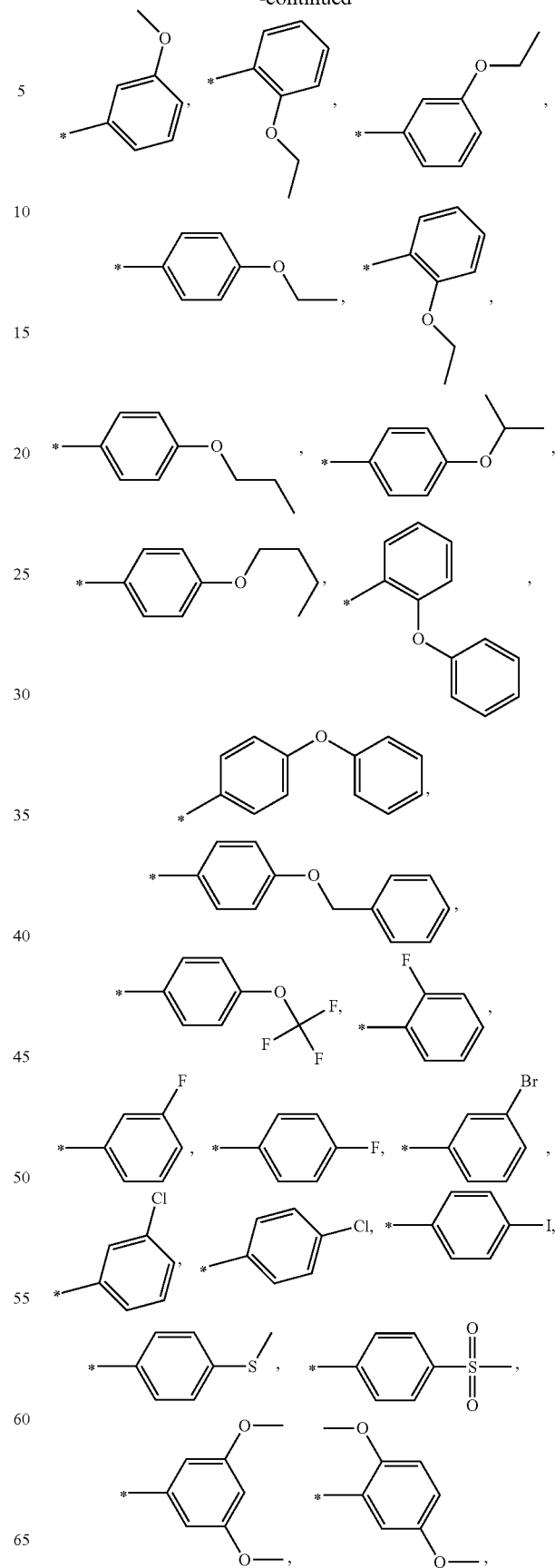

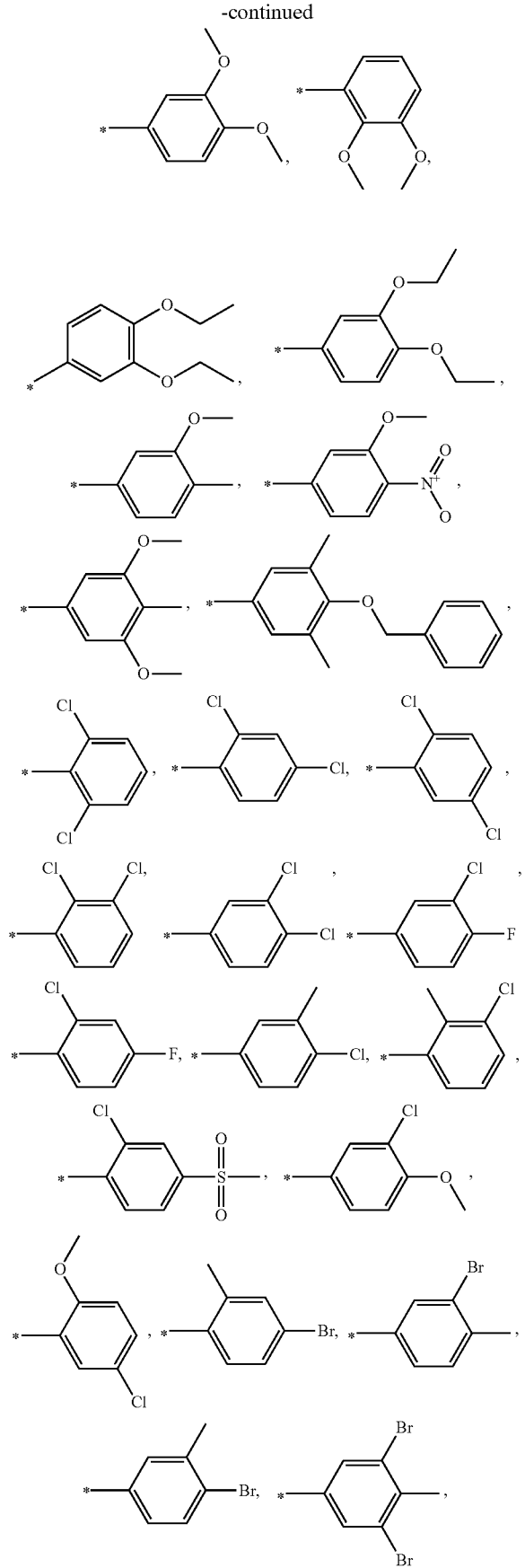
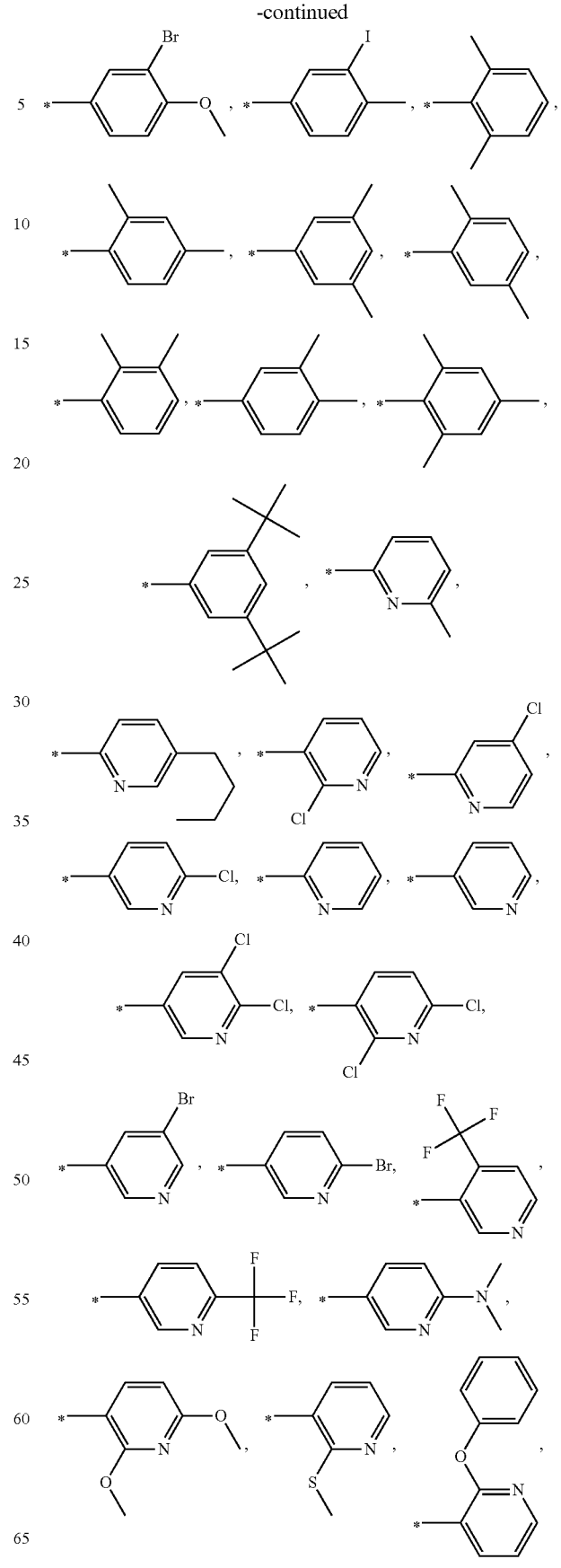

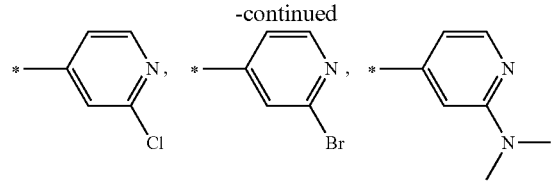
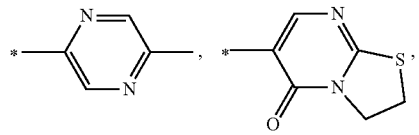
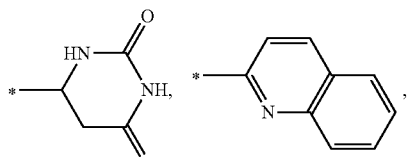
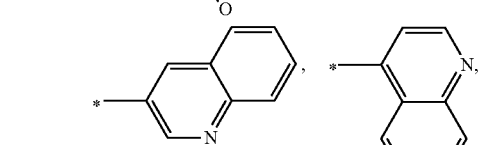
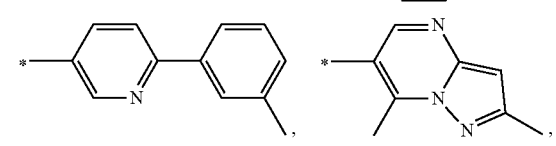
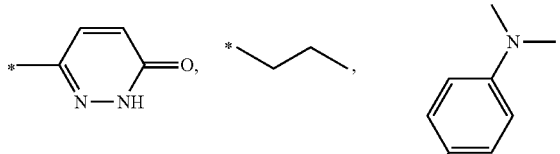
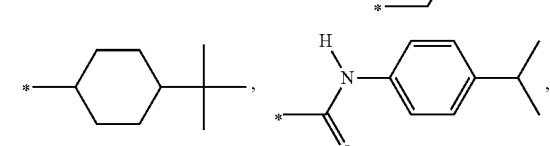
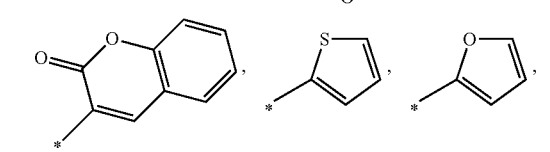
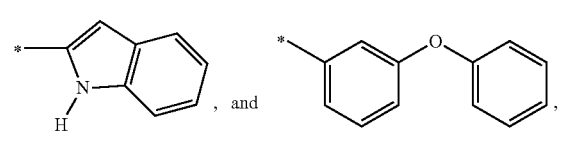
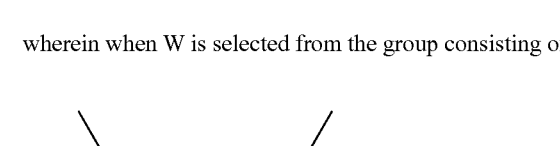, and
wherein when W is selected from the group consisting of:
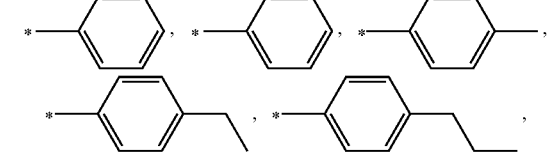
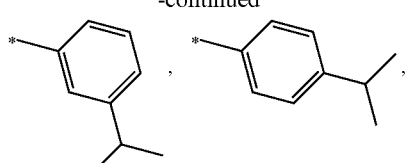
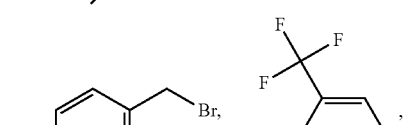
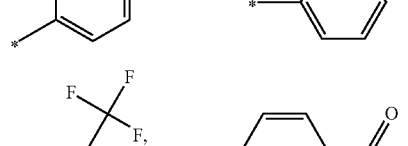
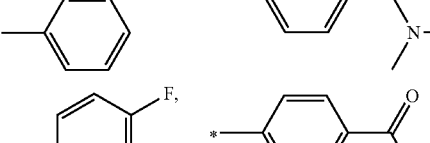
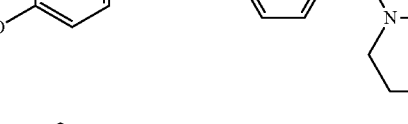
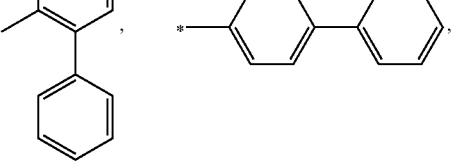
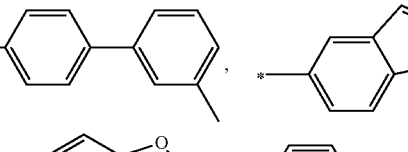
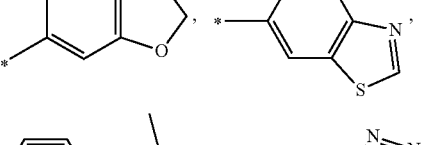
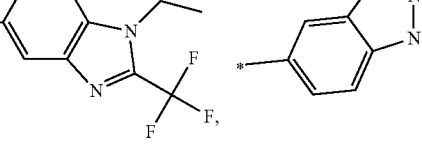
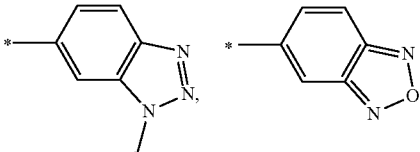
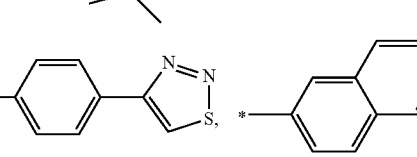

291
-continued
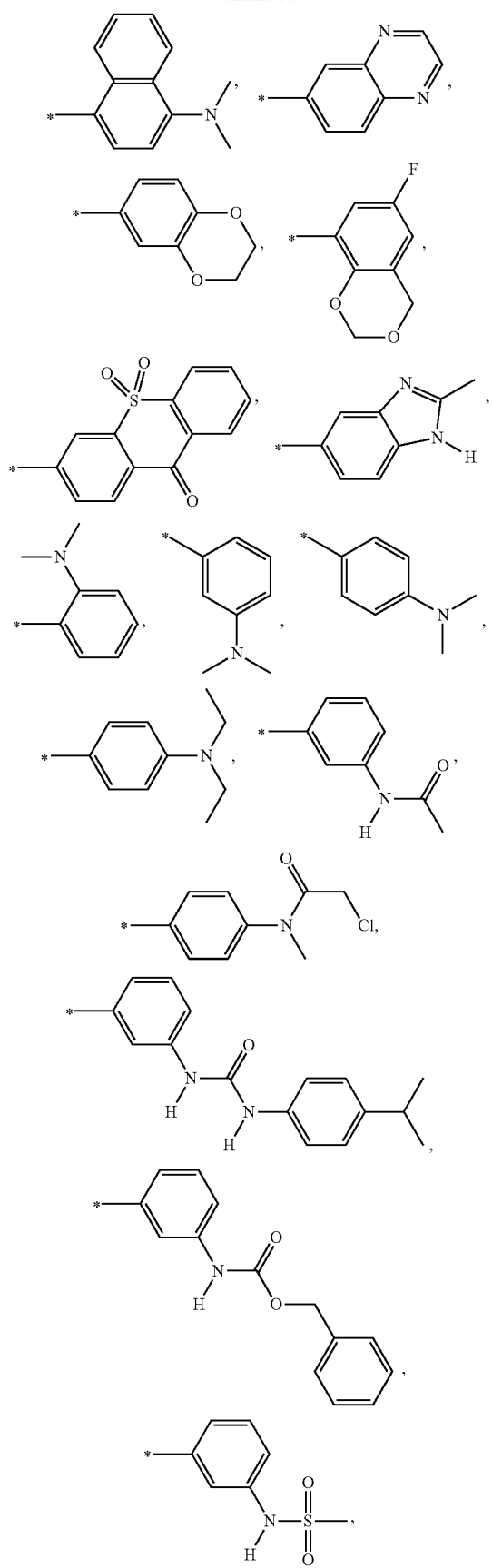
292
-continued
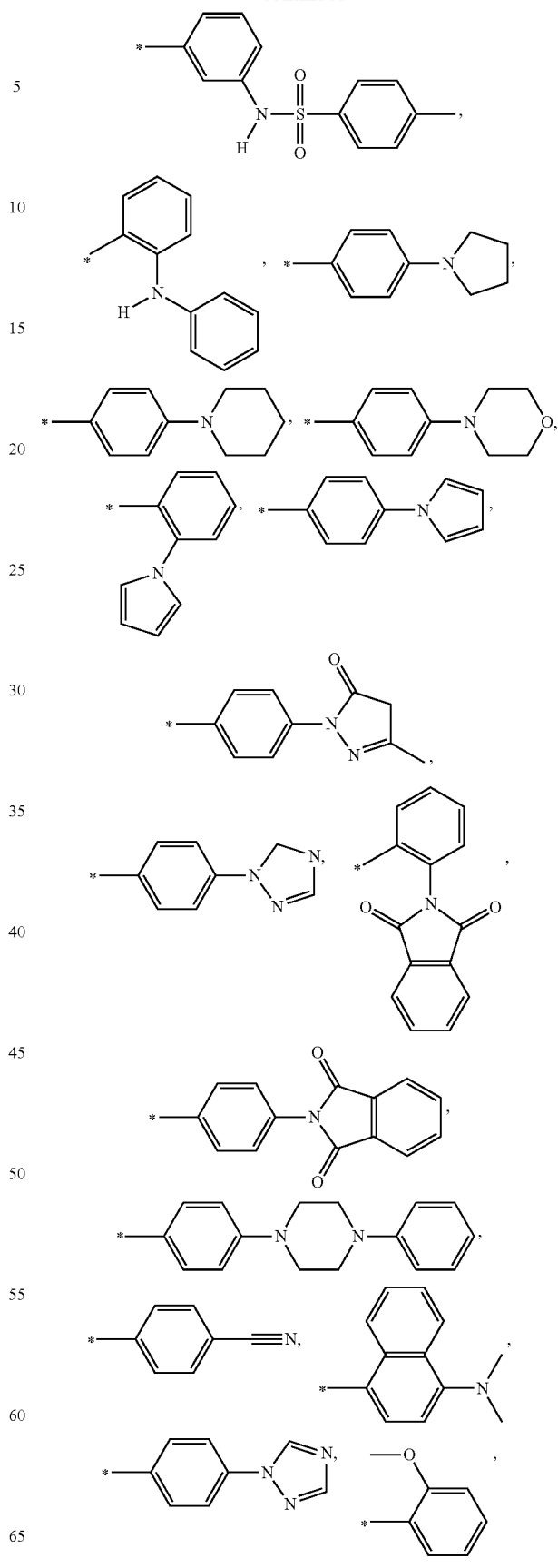

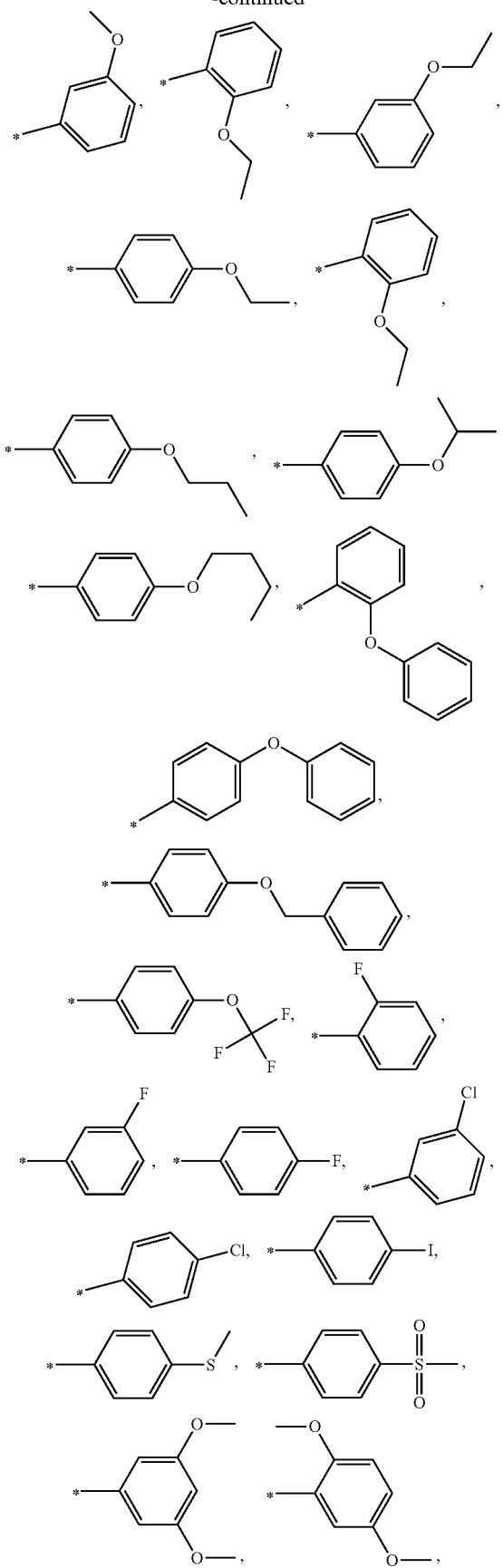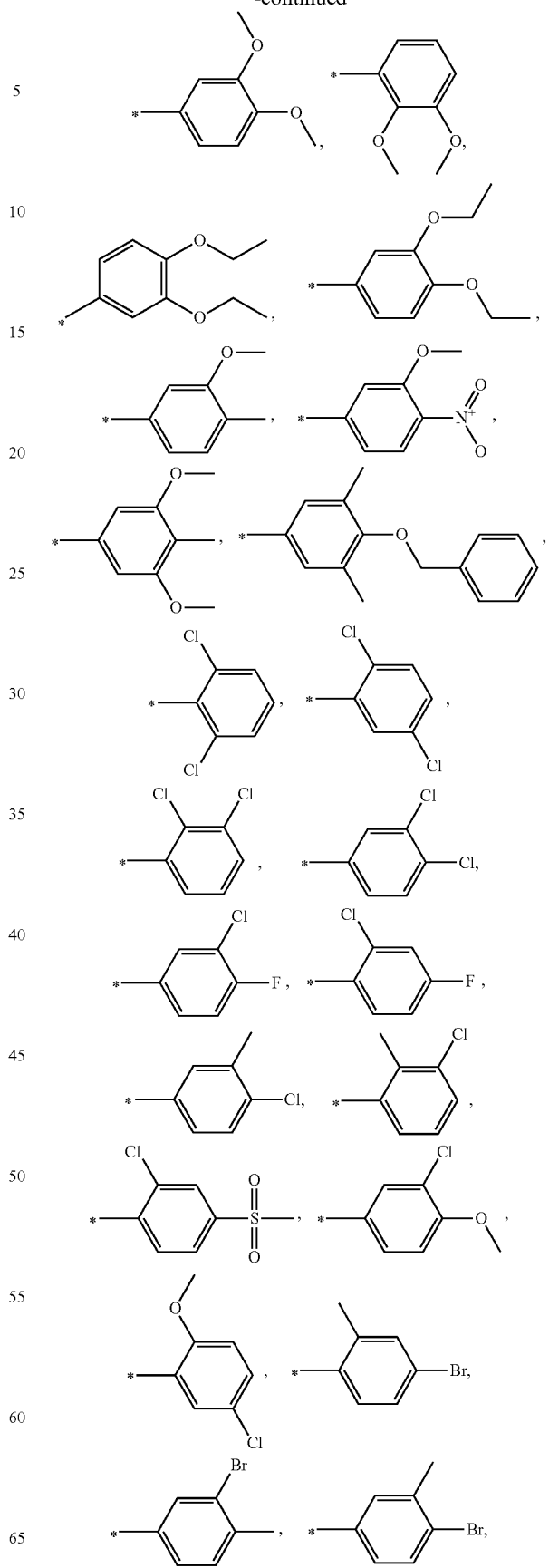

-continued then

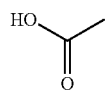

shown in Formula 1-A is in the meta or para position; and
wherein when W is selected from the group consisting of

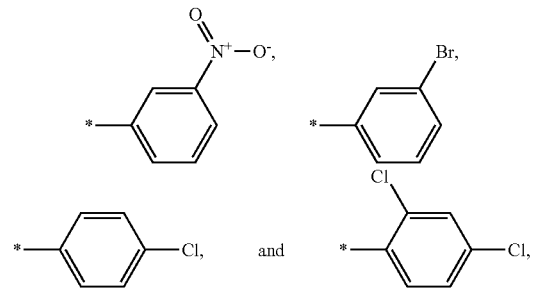

then

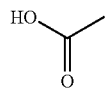

shown in Formula 1-A is in the meta position;
and a pharmaceutically acceptable salt of said compound of Formula 1-A, wherein * indicates the only bond of attachment for W, and wherein said bond of attachment is a direct bond of attachment.

2. A compound selected from the group consisting of:

1
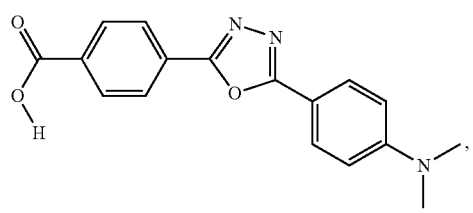

2
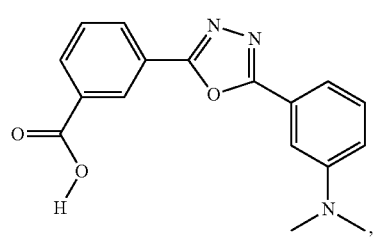

3
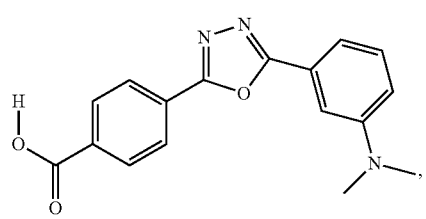

-continued

4
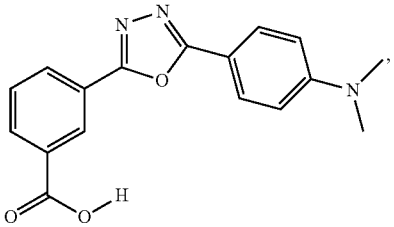

5
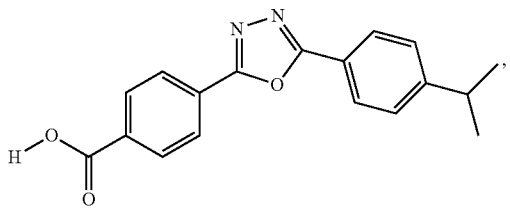

6
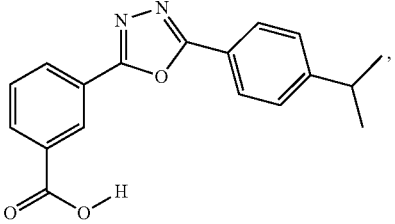

7
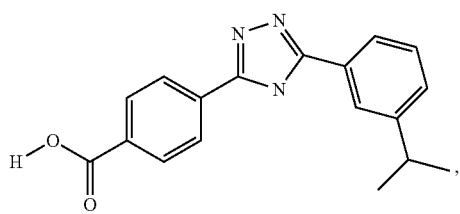

12
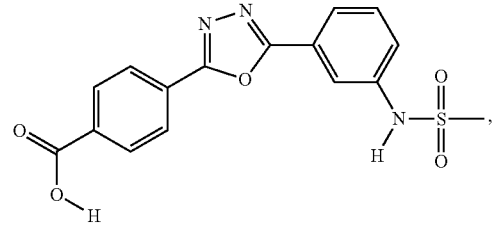

13
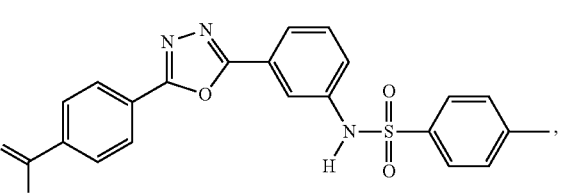

14
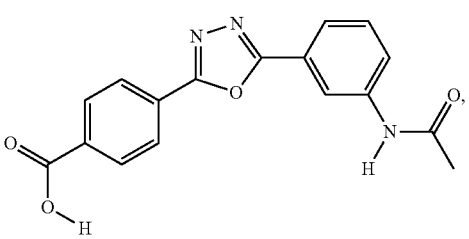

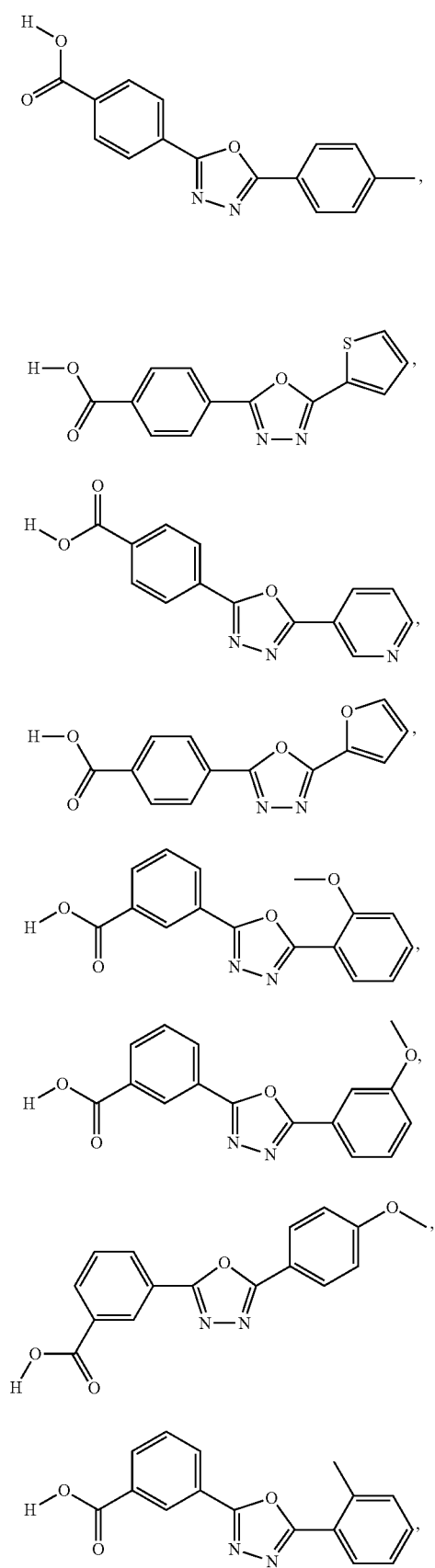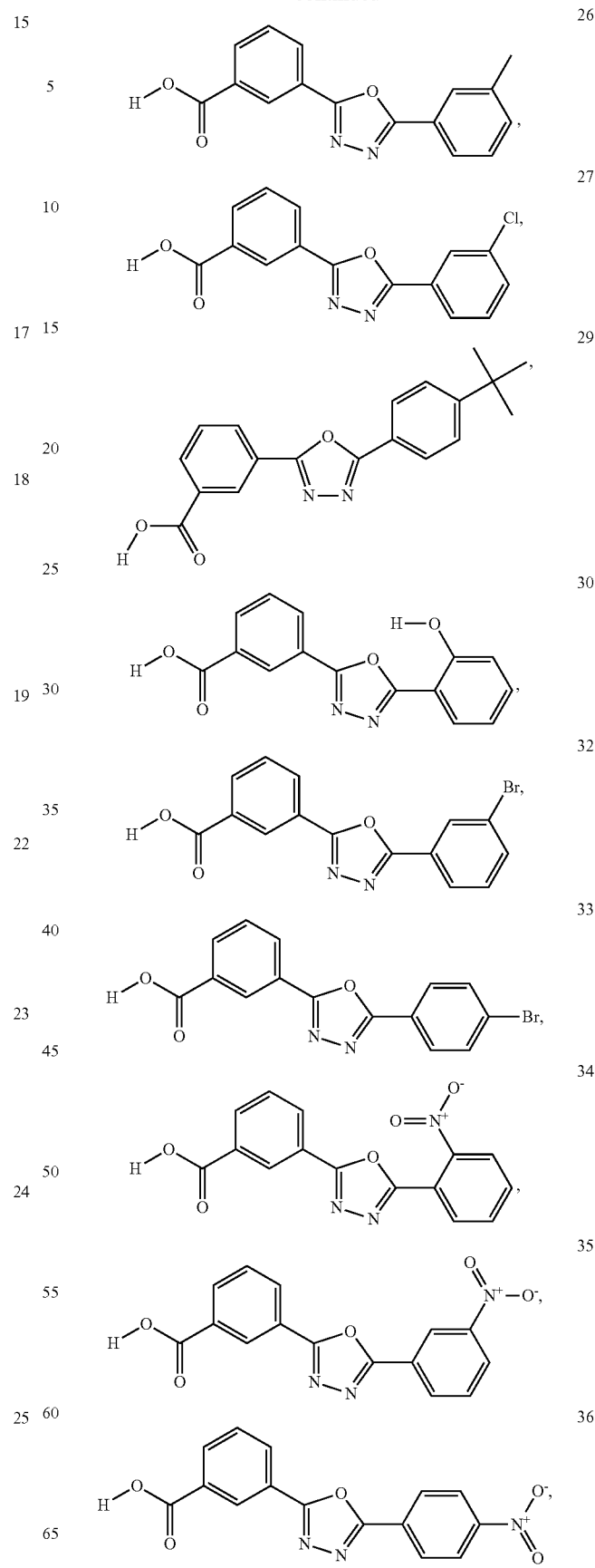

301
-continued
37
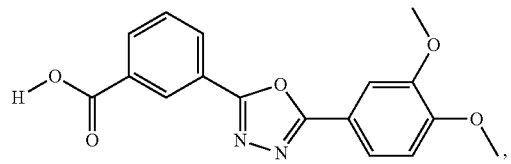
38
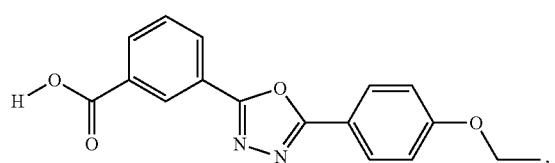
39
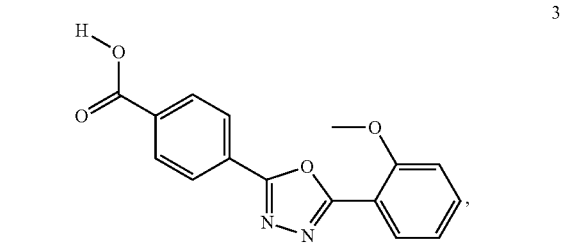
40
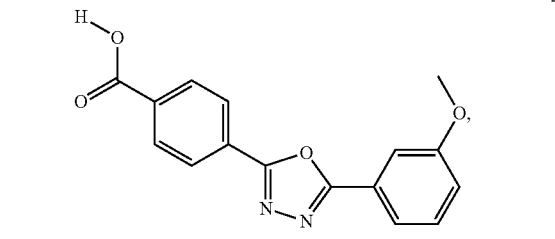
42
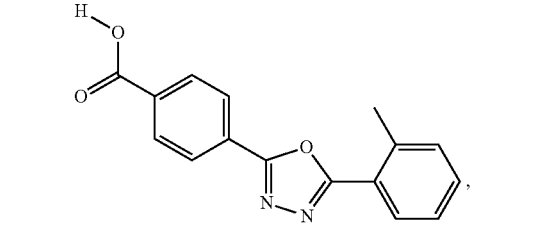
43
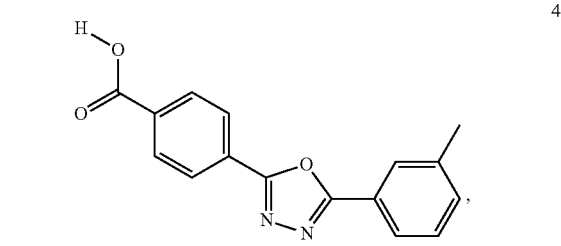
44
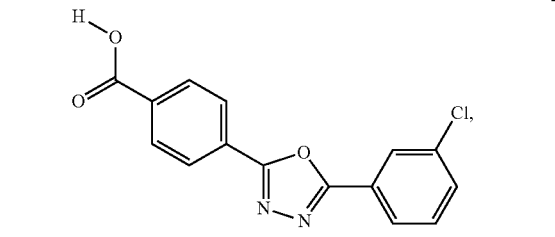
302
-continued
47
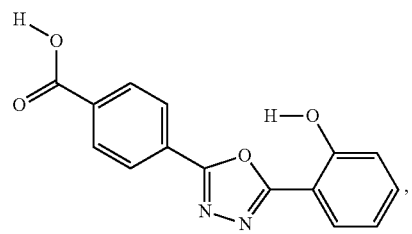
54
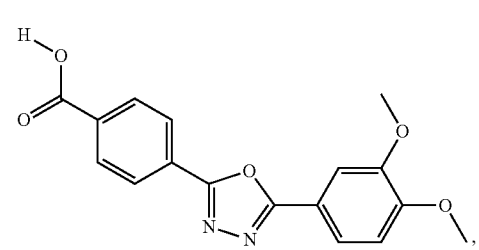
55
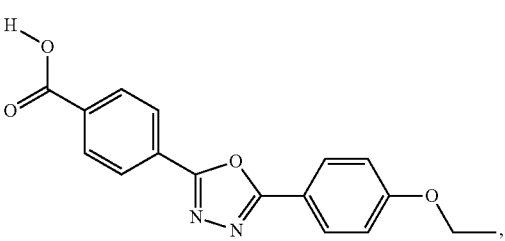
60
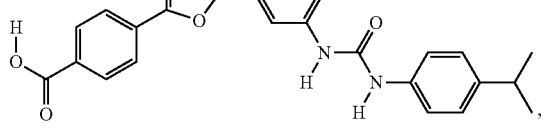
62
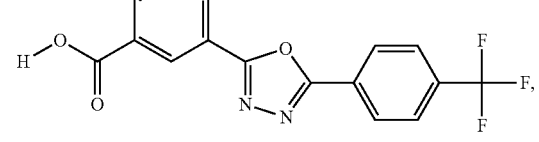
63
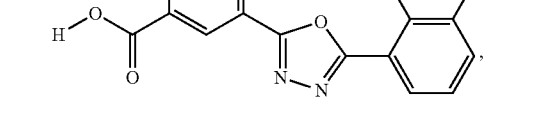
64
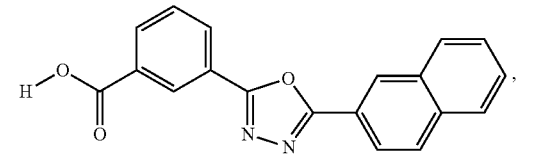

65
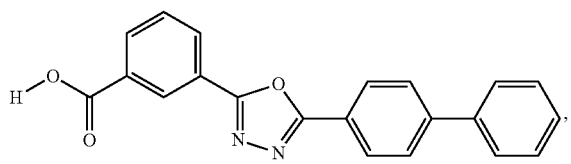
66
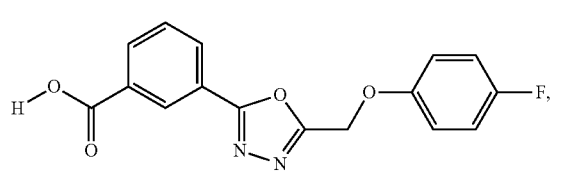
67
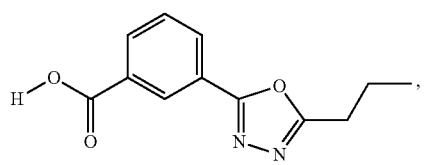
69
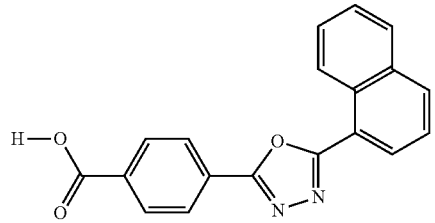
70
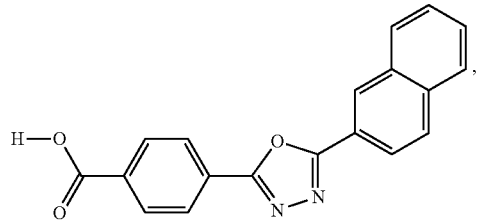
71
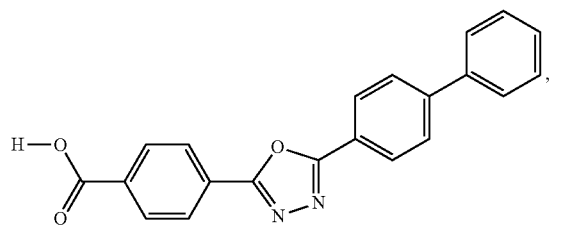
72
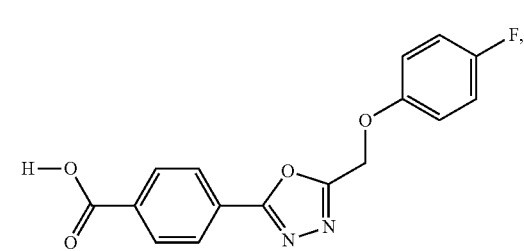
73
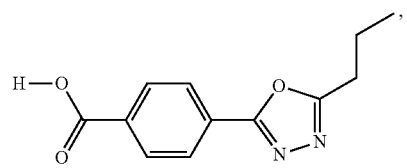
82
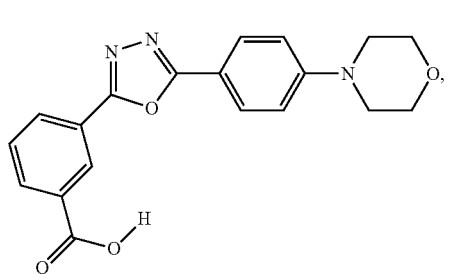
83
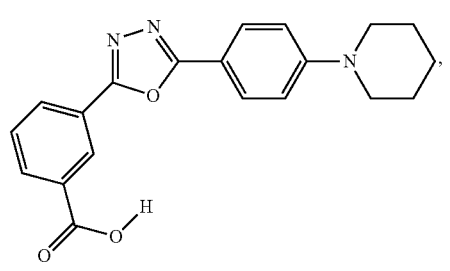
84
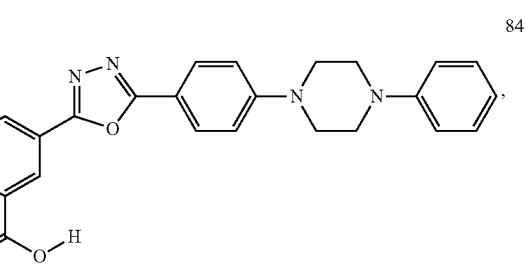
85
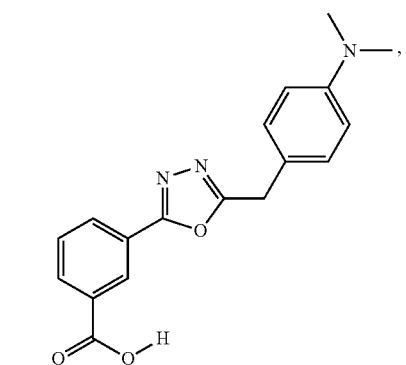

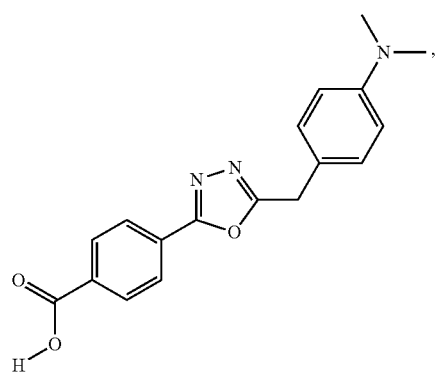
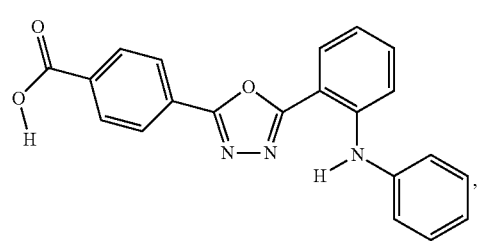
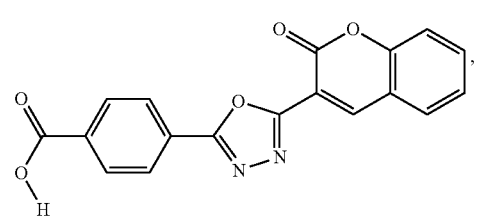
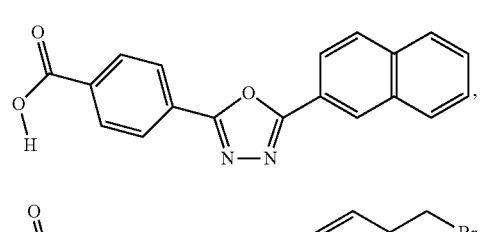
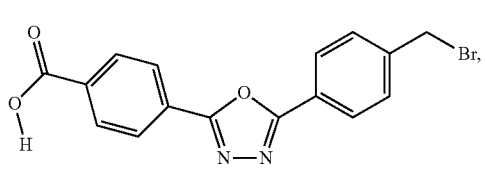
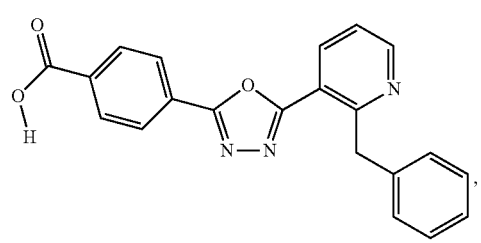
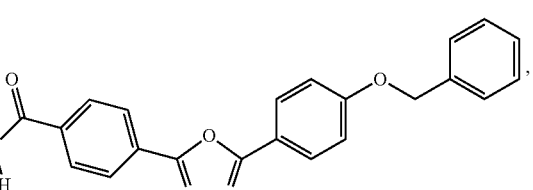
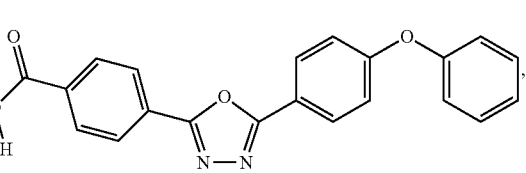

307
-continued
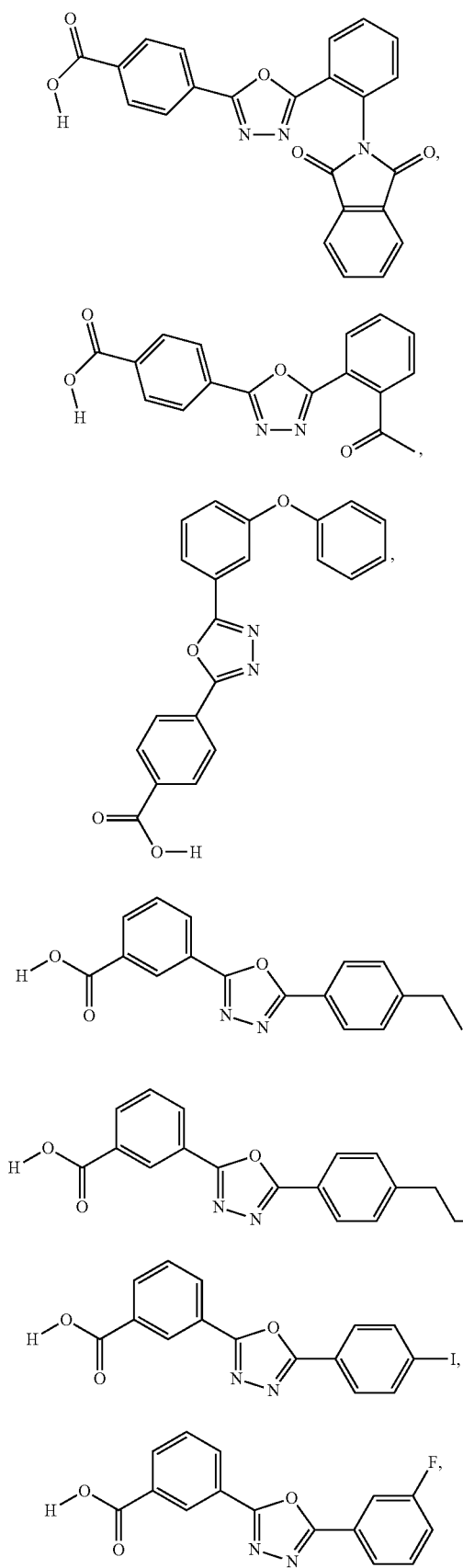
308
-continued
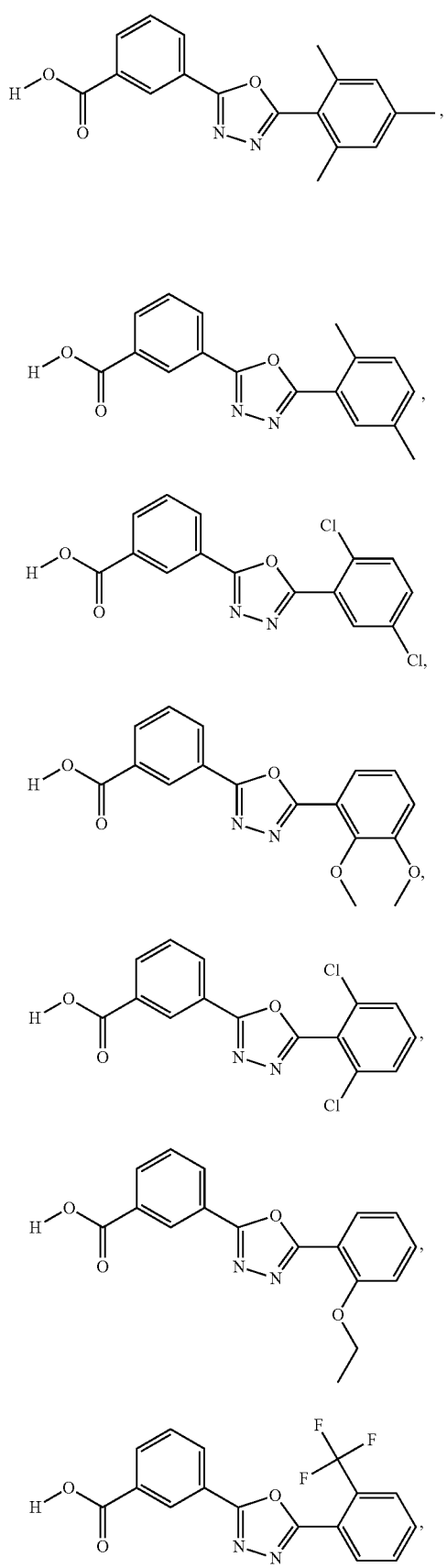

115
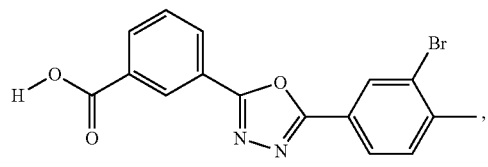
116
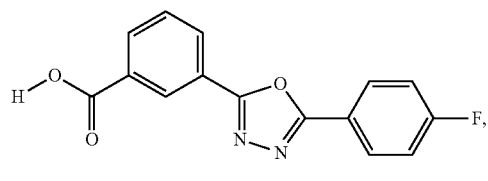
117
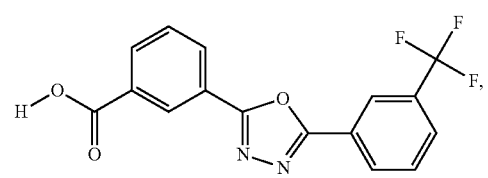
118
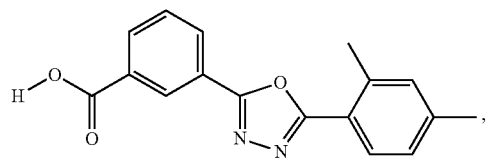
119
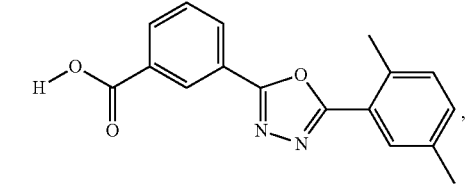
120
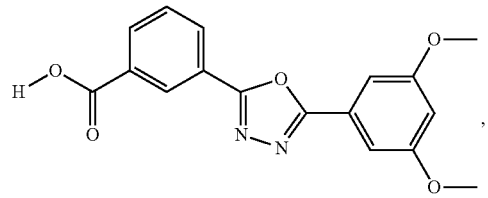
121
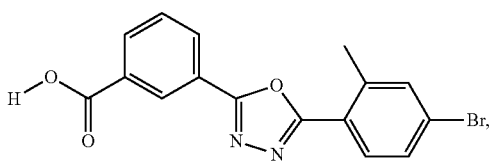
122
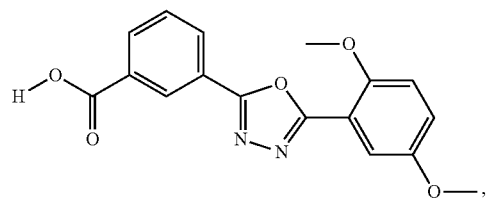
123
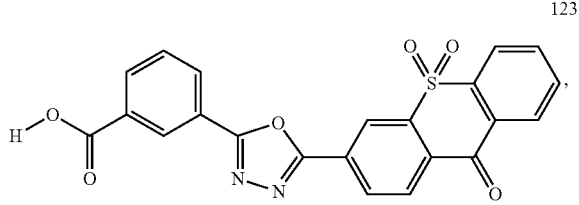
124
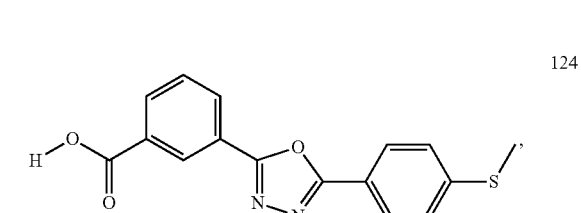
125
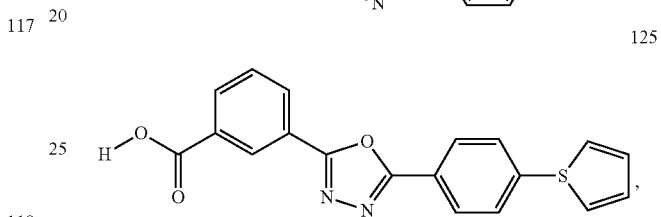
126
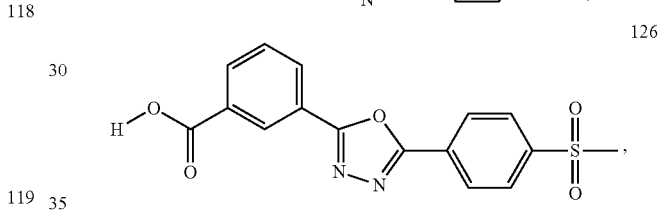
127
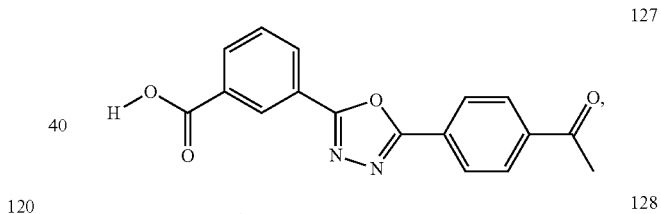
128
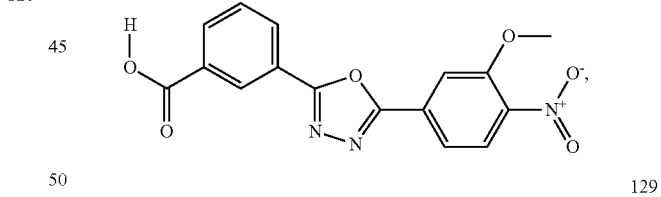
129
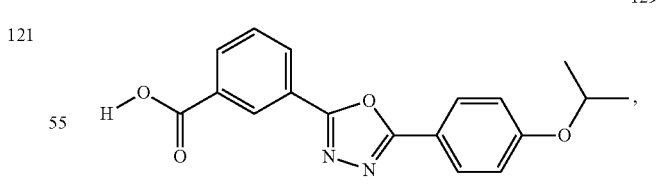
130
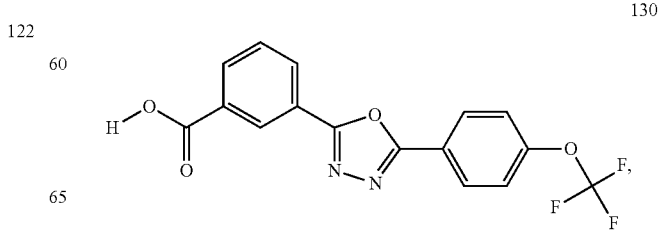

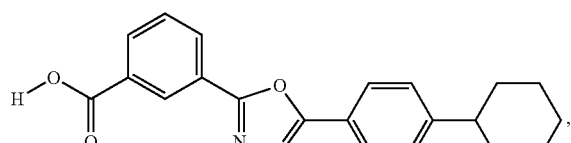 131,
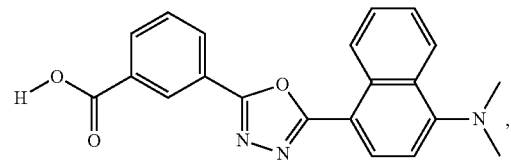 132,
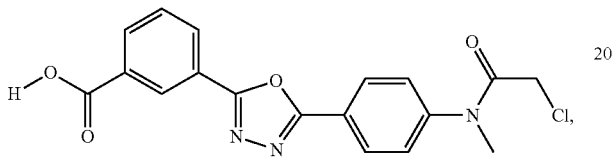 133,
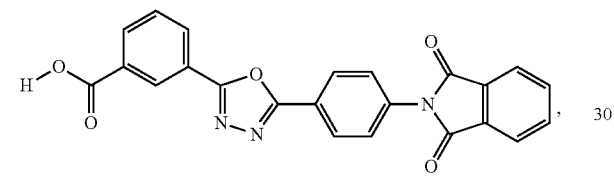 134,
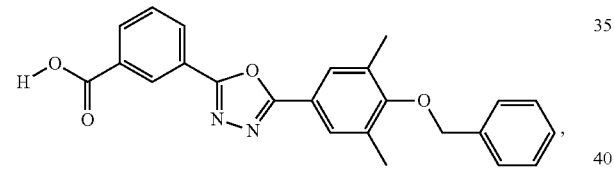 135,
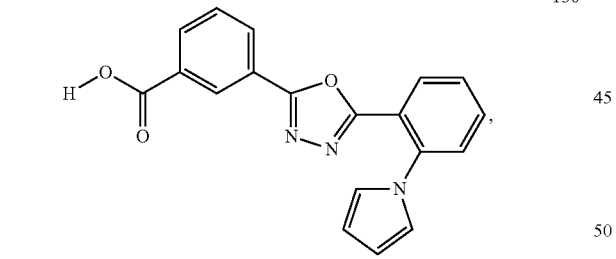 136,
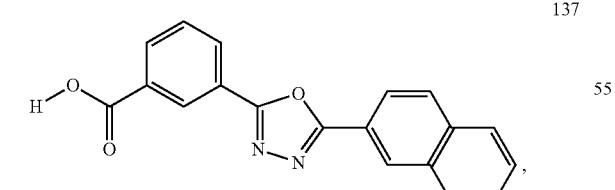 137,
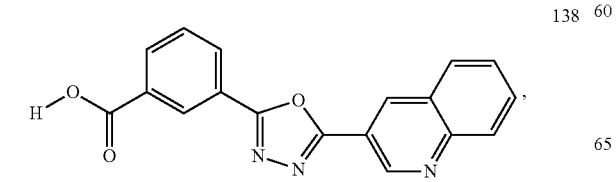 138,
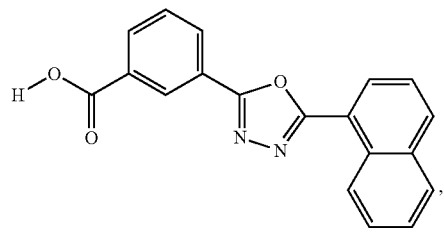 139,
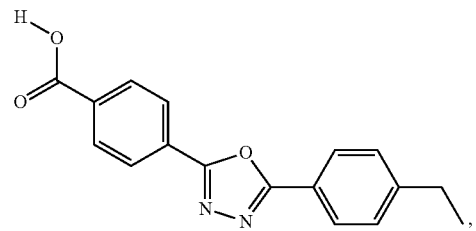 142,
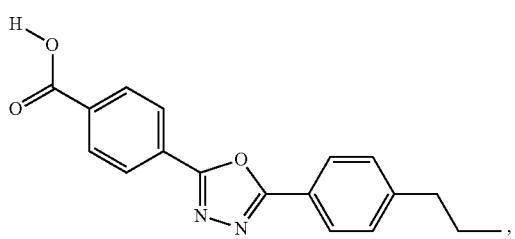 143,
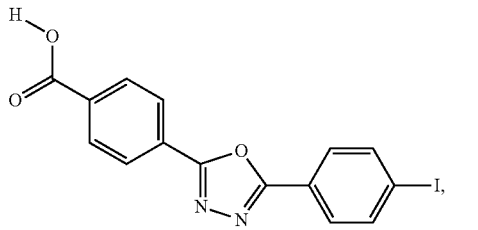 144,
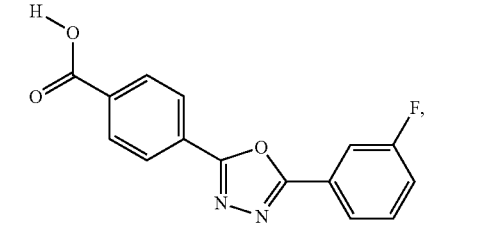 145,
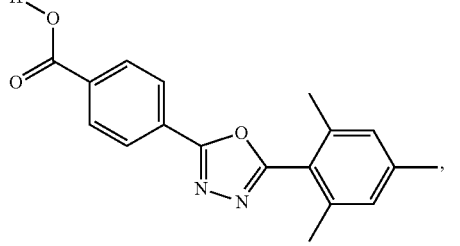 146, 313
-continued
147
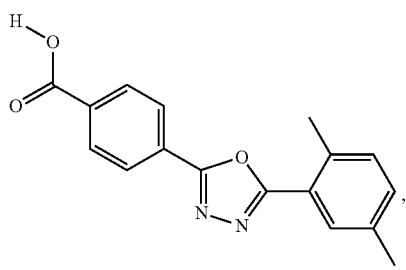
148
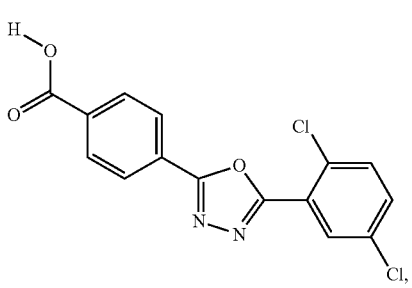
149
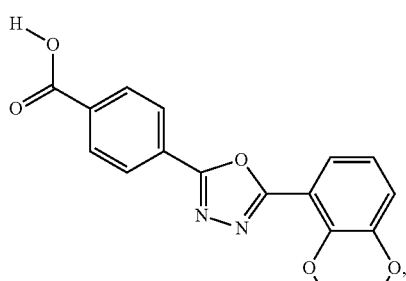
150
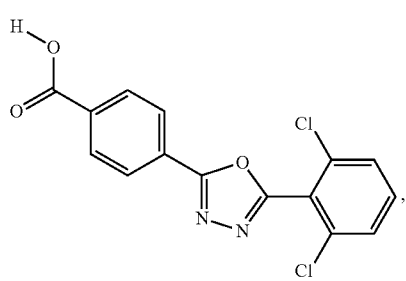
151
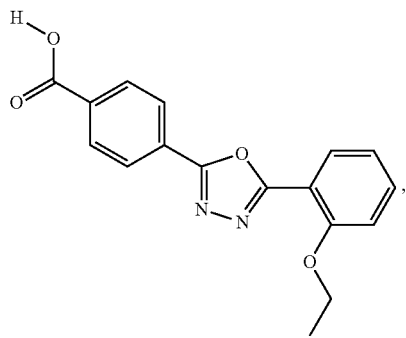
314
-continued
152
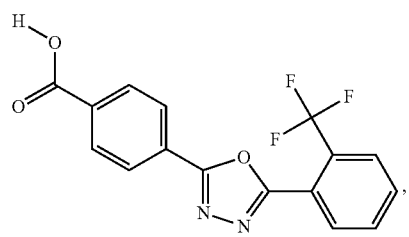
153
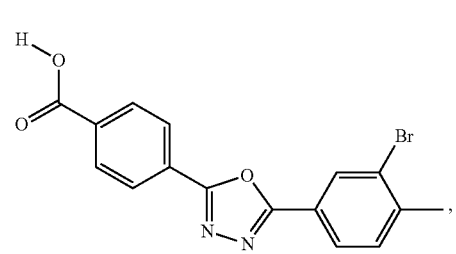
154
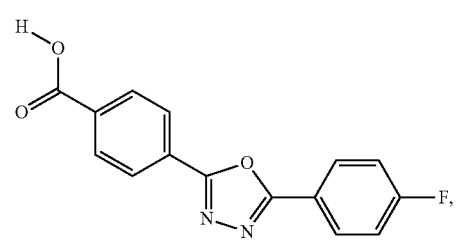
155
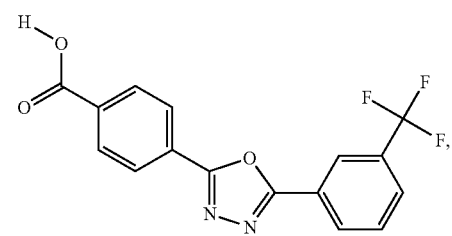
156
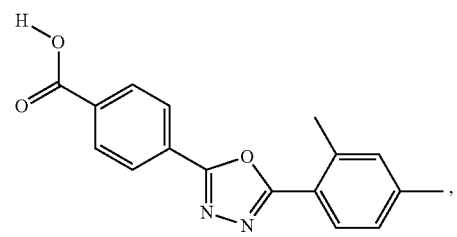
157
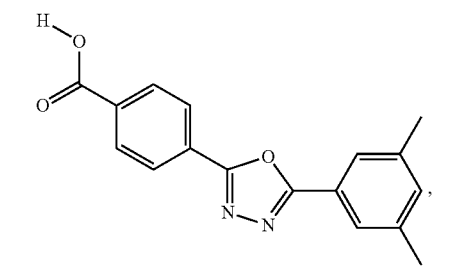

158 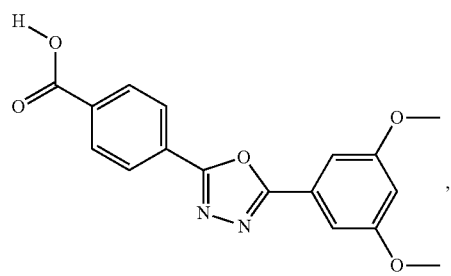
159 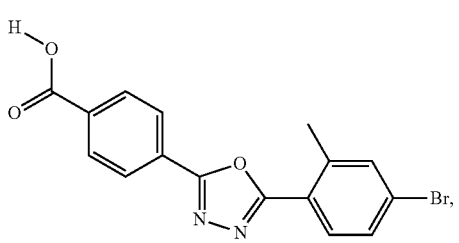
160 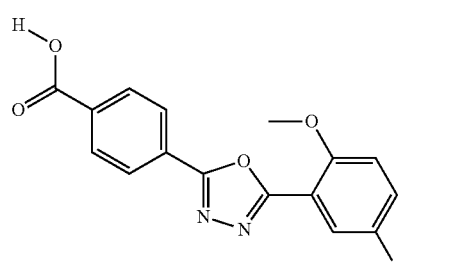
161 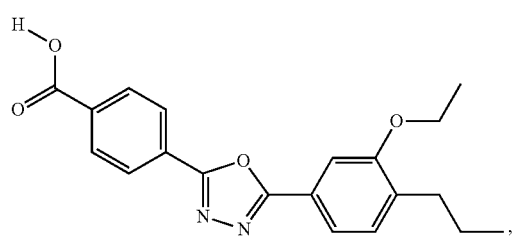
162 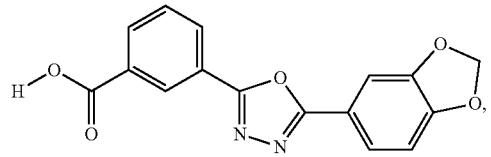
163 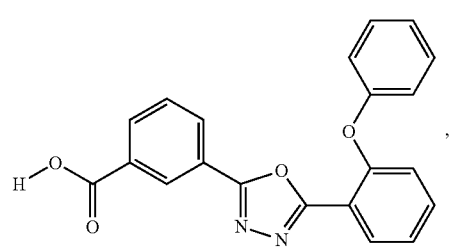
164 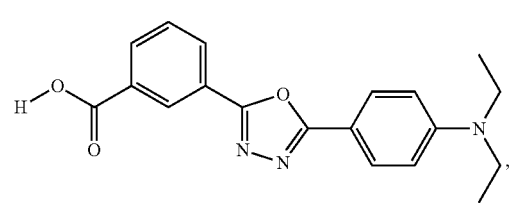
165 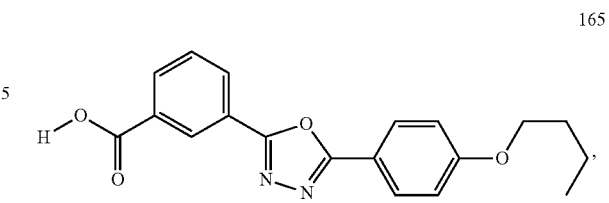
166 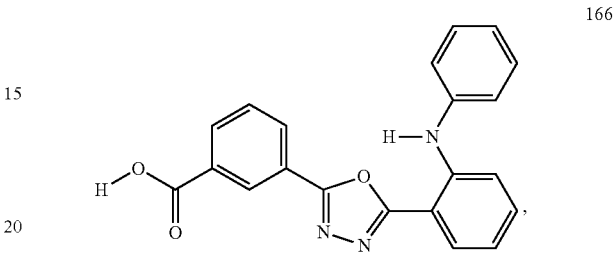
167 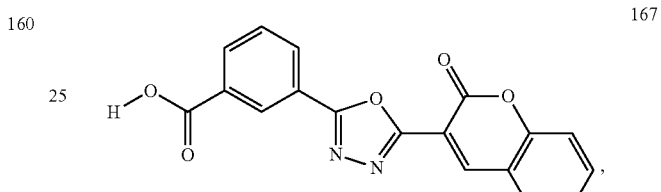
168 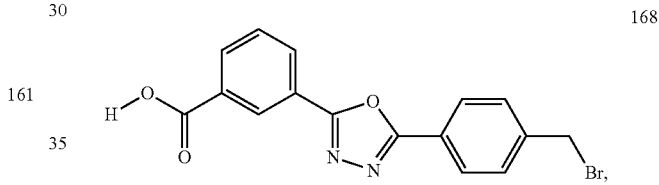
169 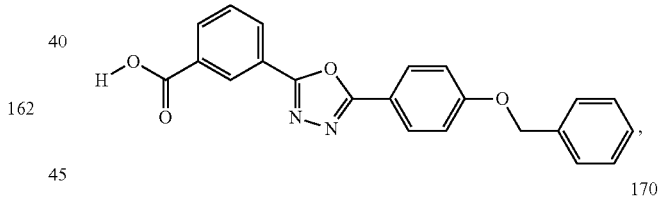
170 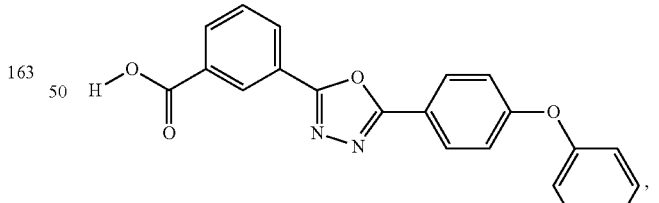
171 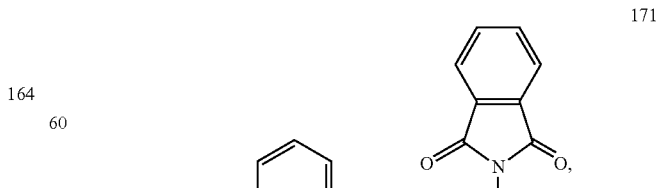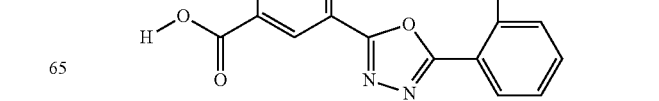

-continued
172
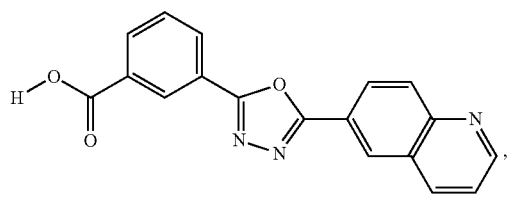
173
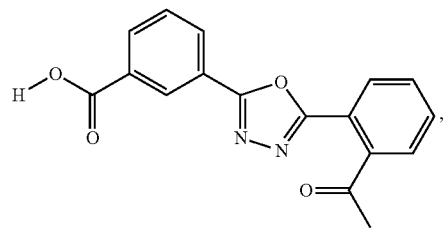
174
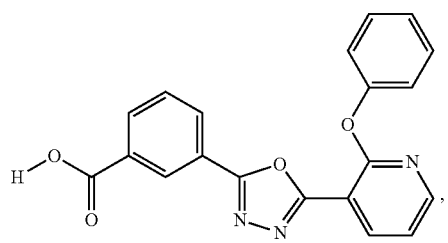
175
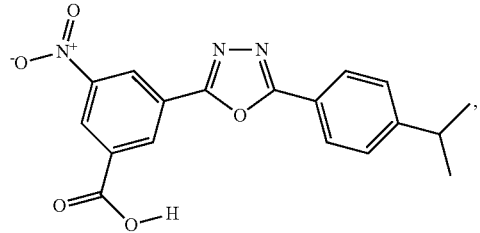
176
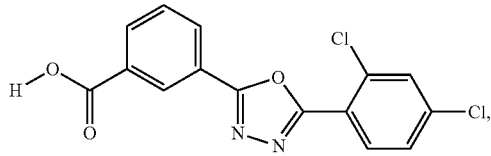
177
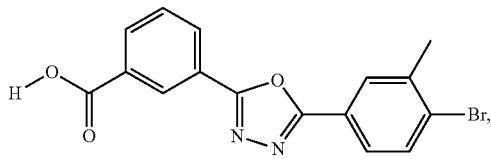
178
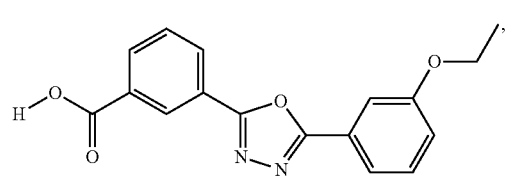
179
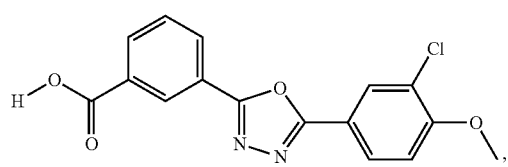
-continued
180
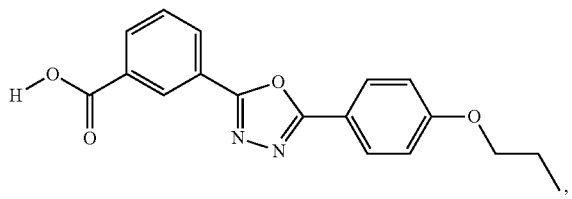
181
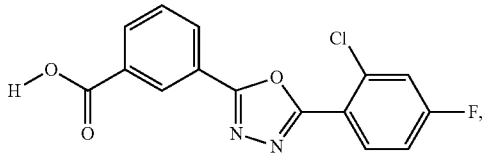
182
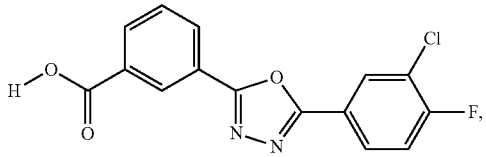
183
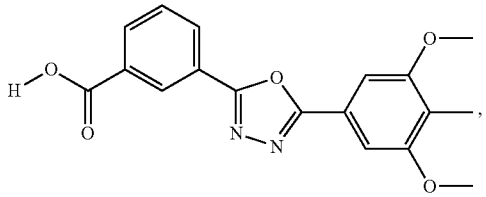
184
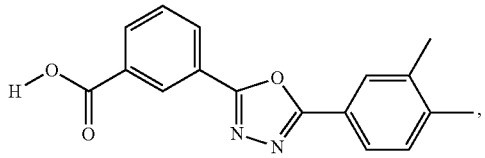
185
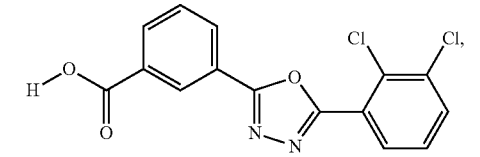
186
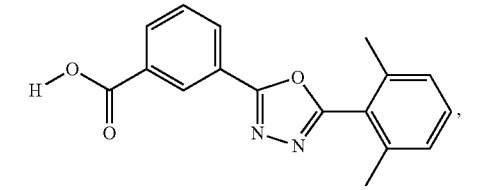
187
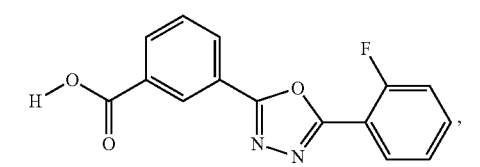

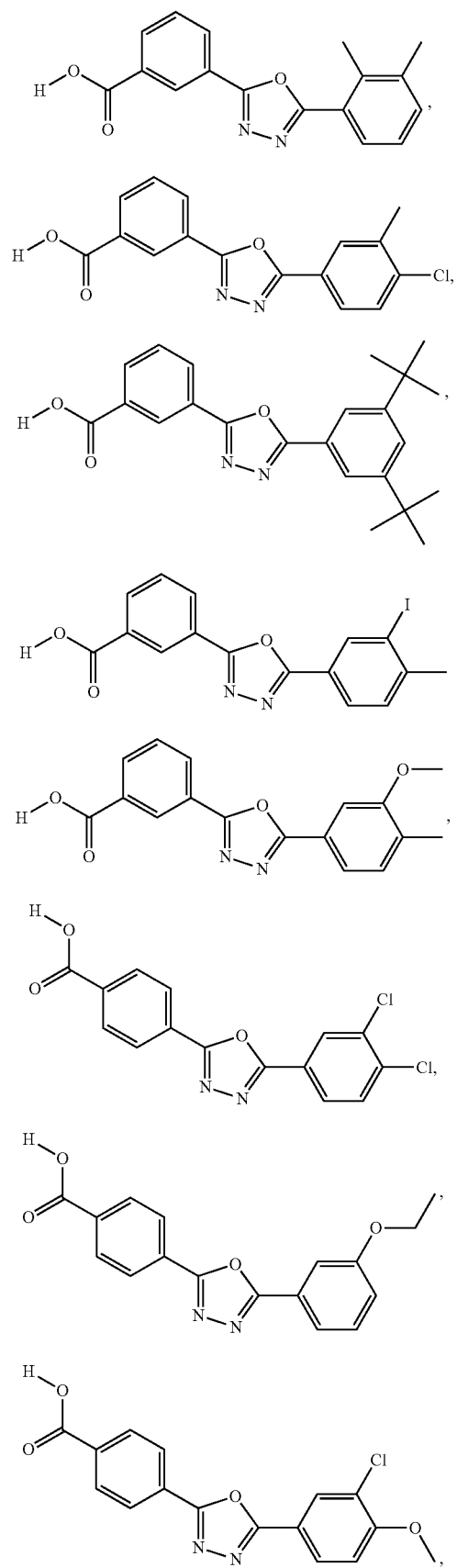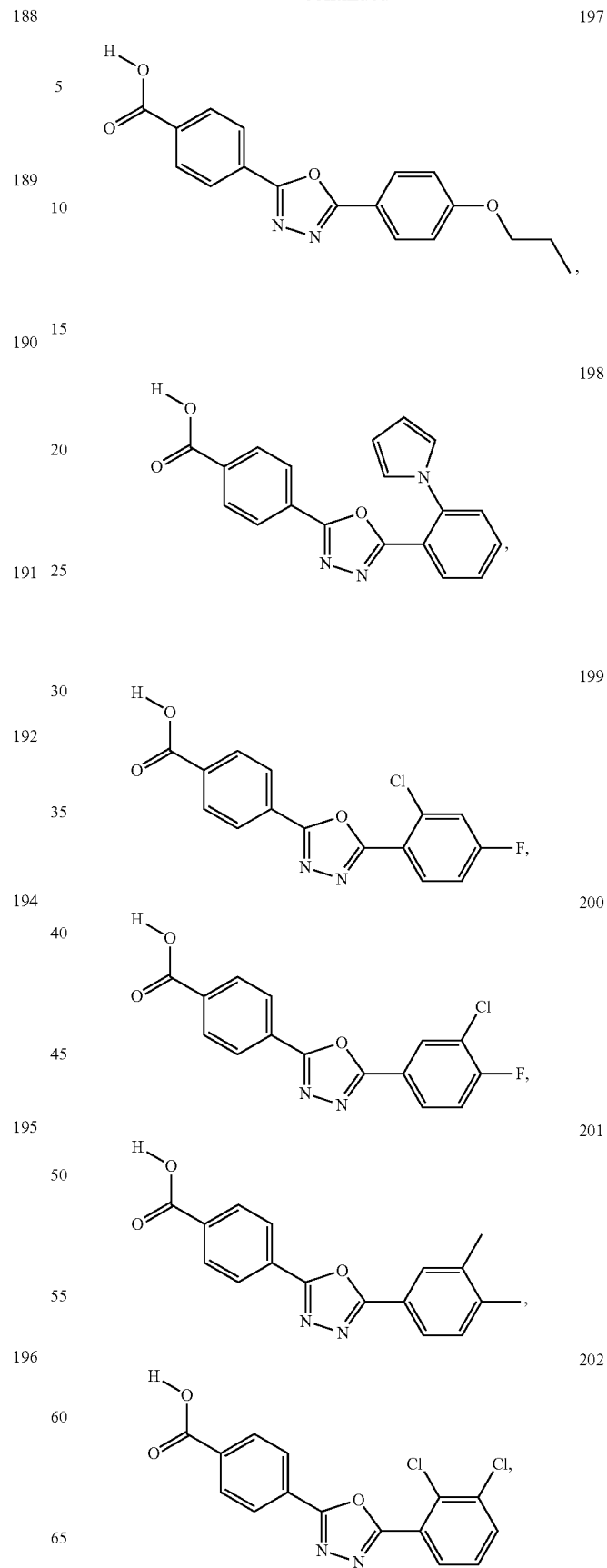

203 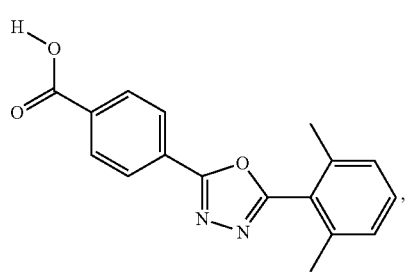
204 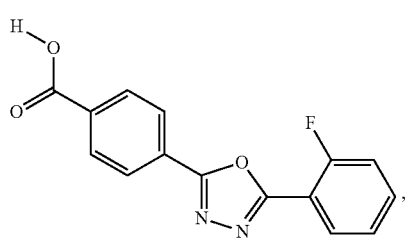
205 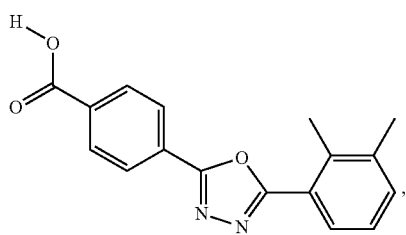
206 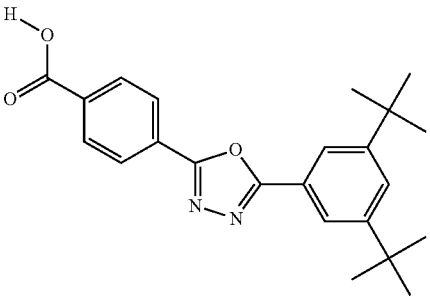
207 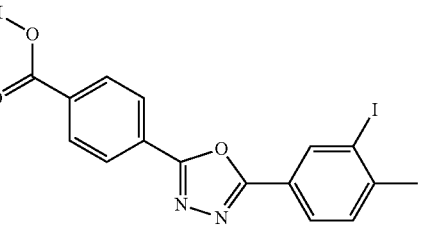
208 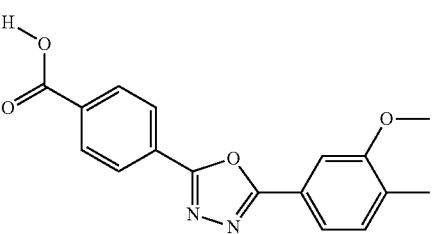
209 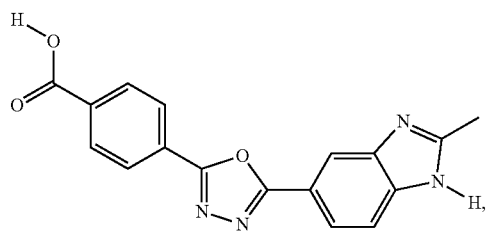
210 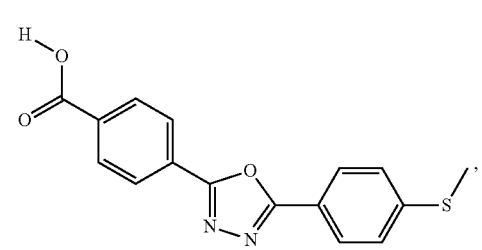
211 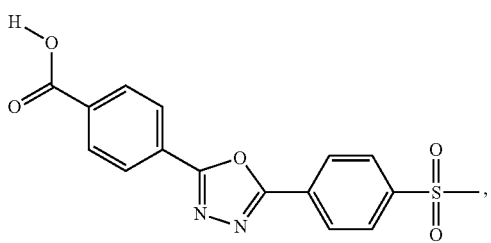
212 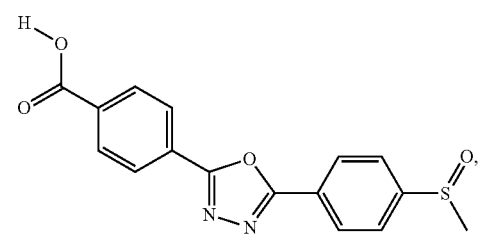
213 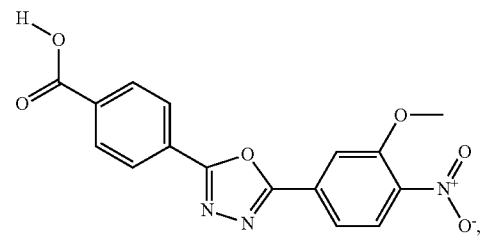
214 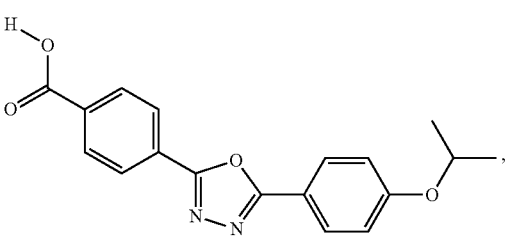

215 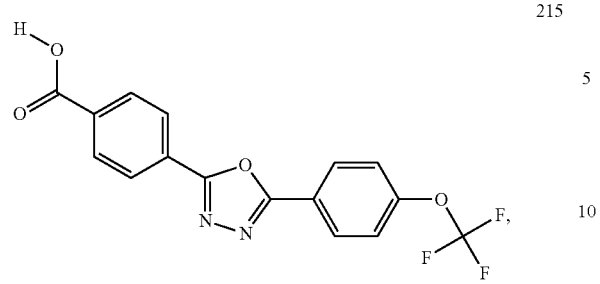
217 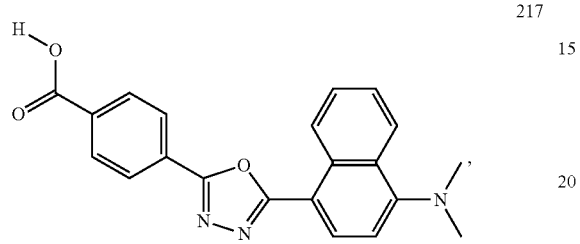
218 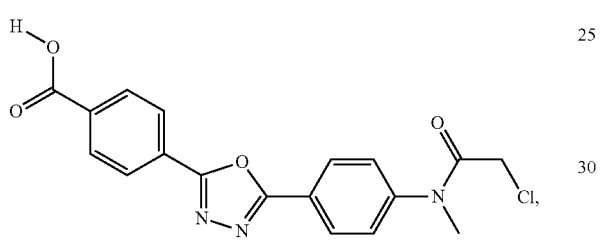
219 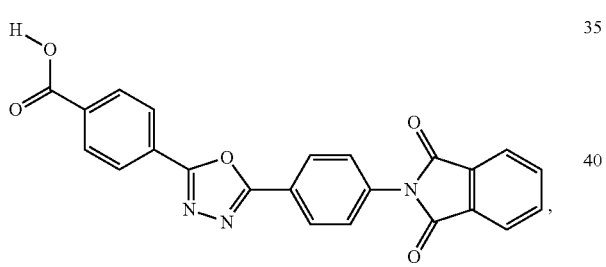
220 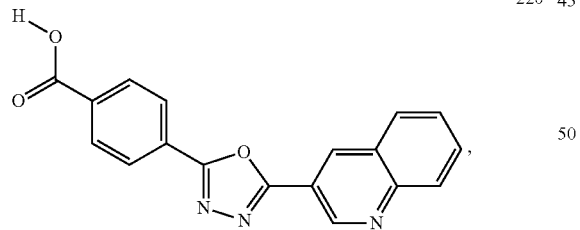
221 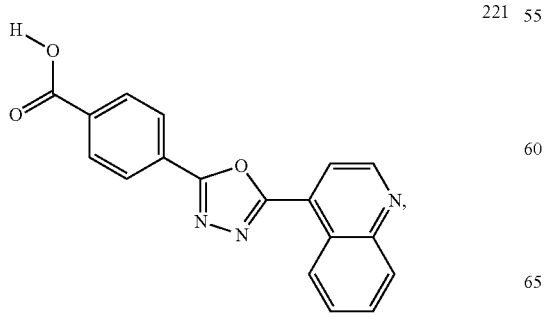
222 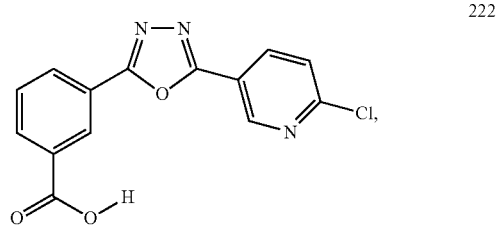
223 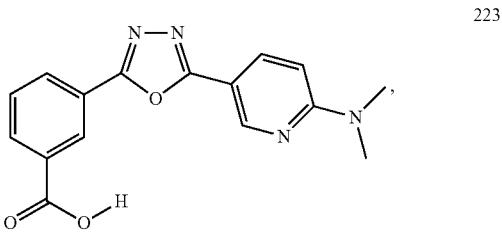
224 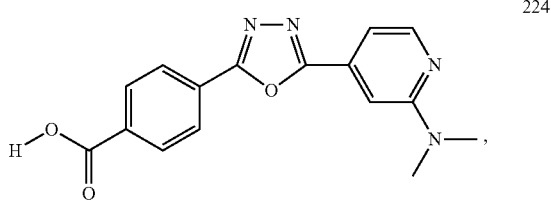
225 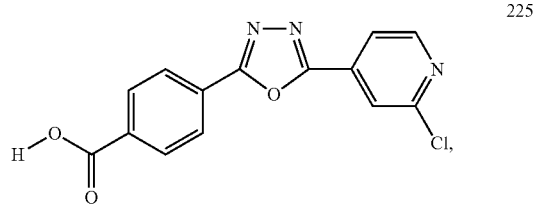
226 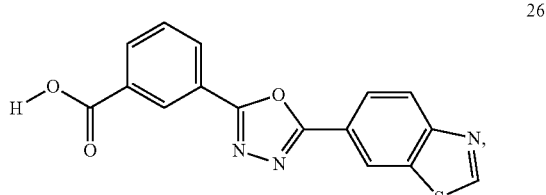
227 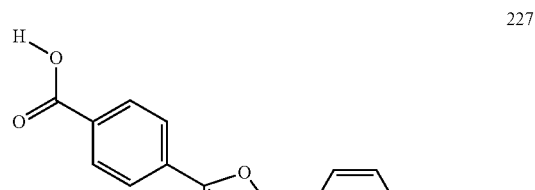
228 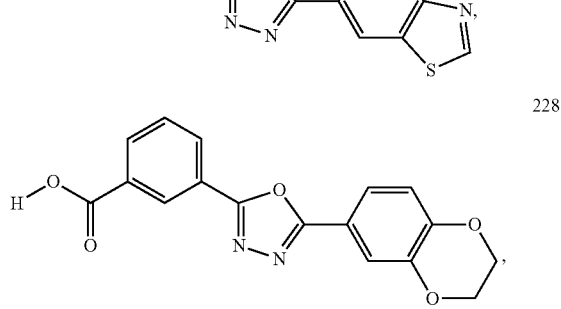

229
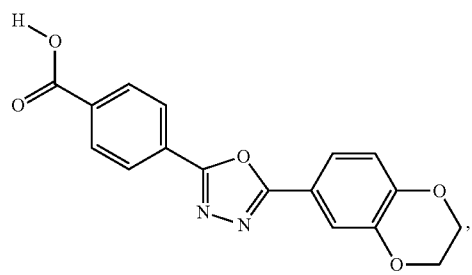
230
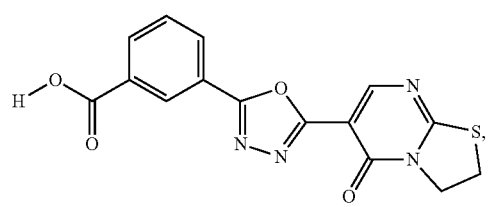
231
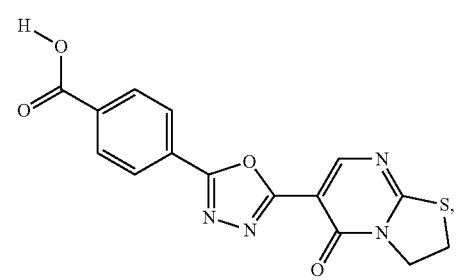
232
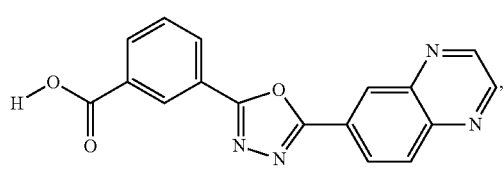
233
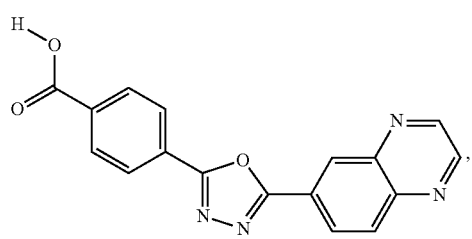
234
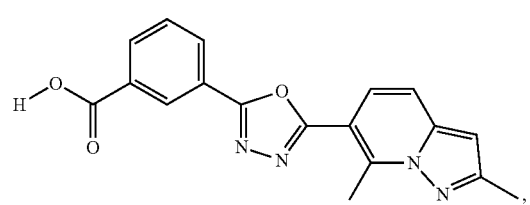
235
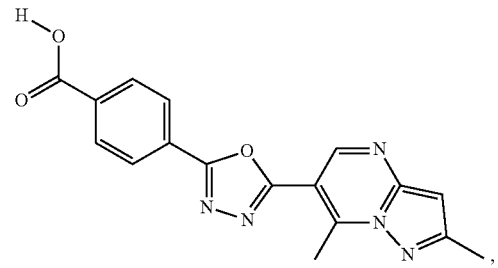
236
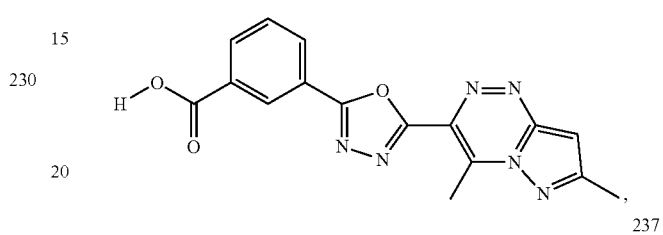
237
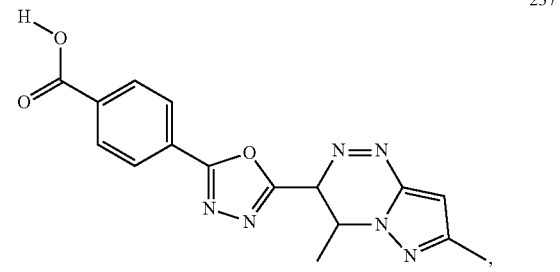
238
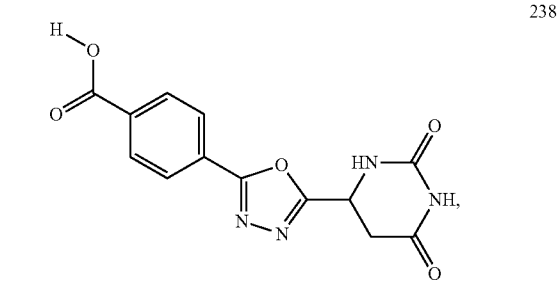
239
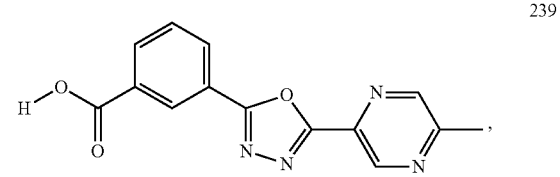
240
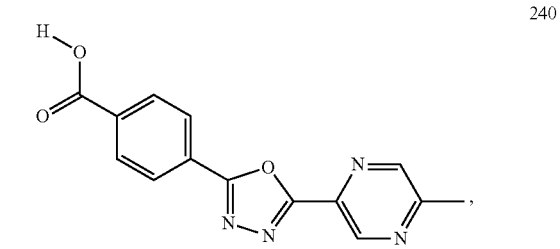
241
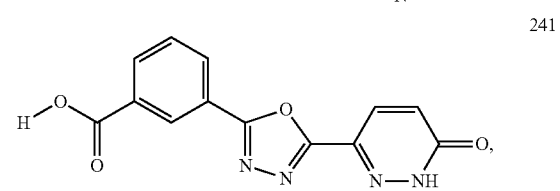

242
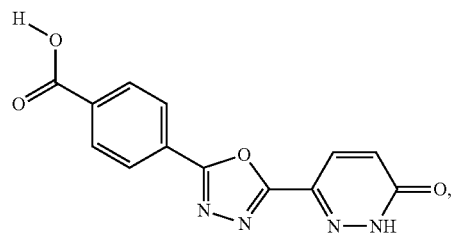
243
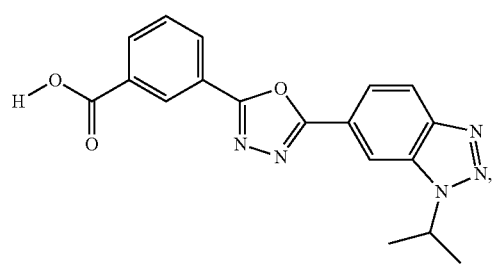
244
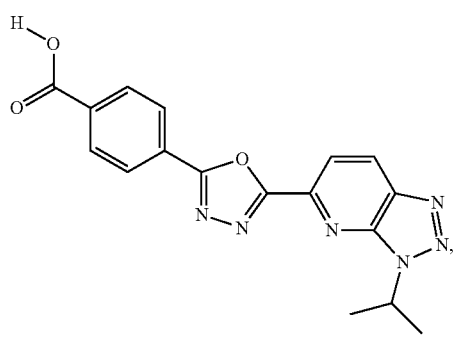
245
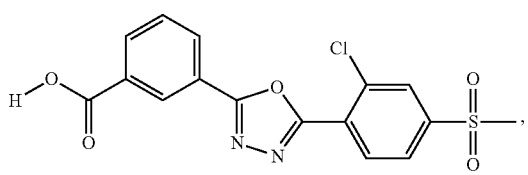
246
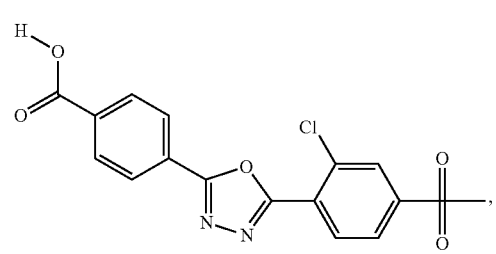
247
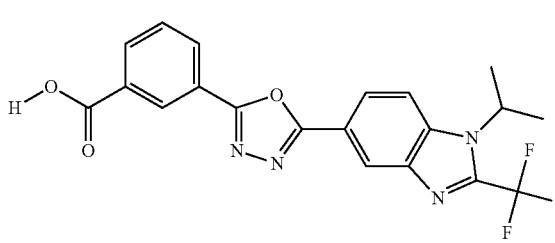
248
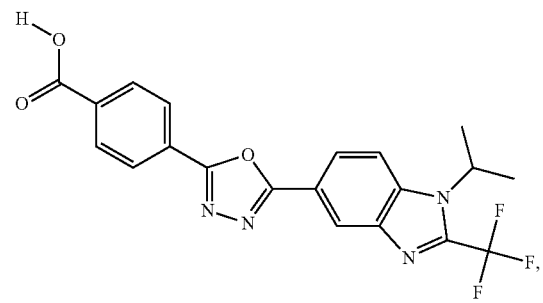
249
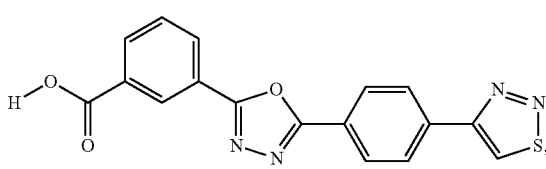
250
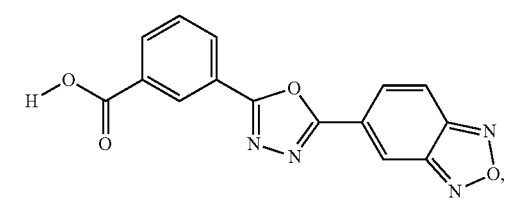
251
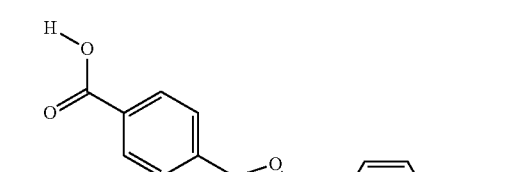
252
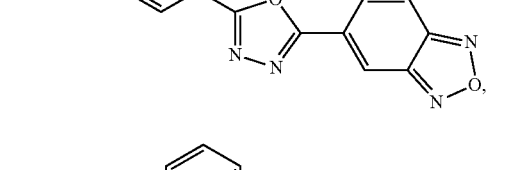
253
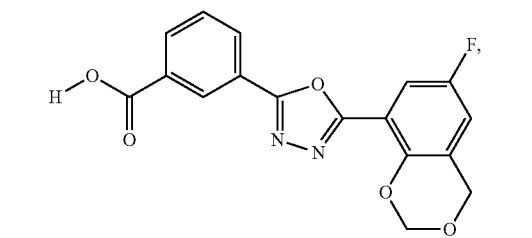

254
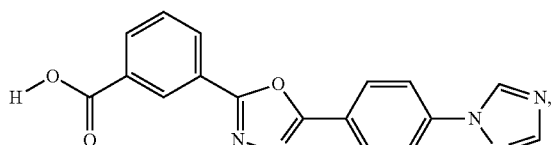
255
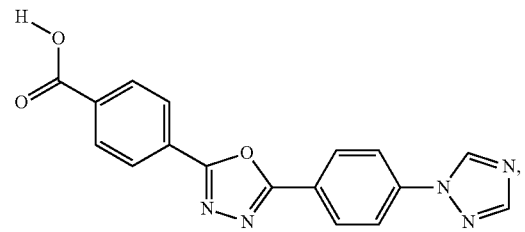
258
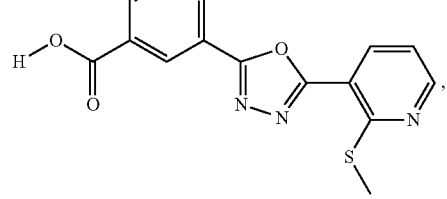
259
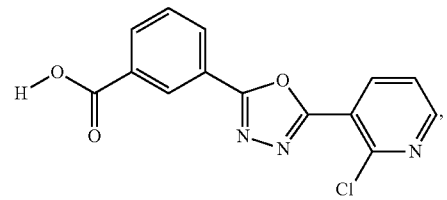
260
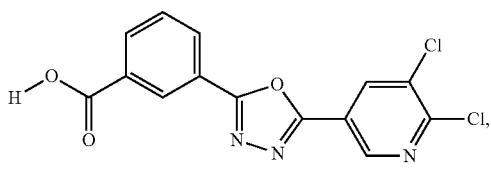
261
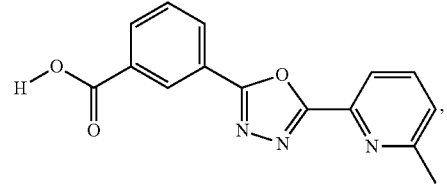
262
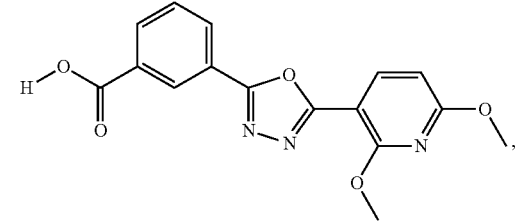
263
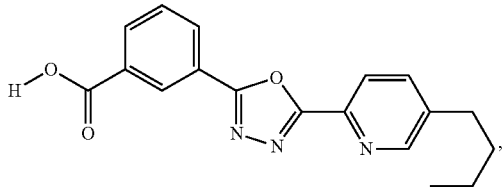
264
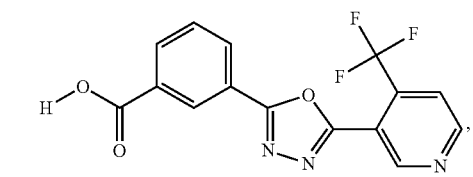
265
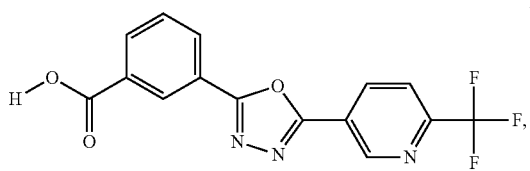
266
267
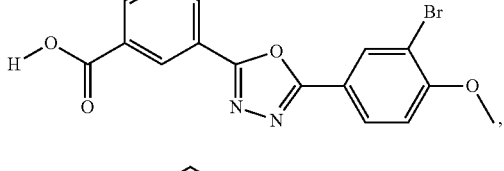
268
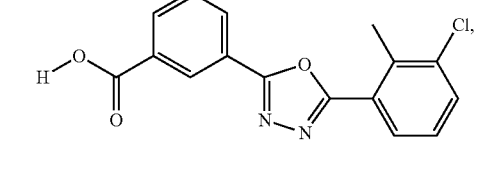
269
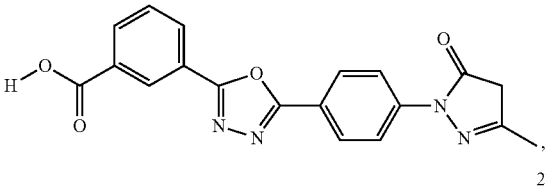
270
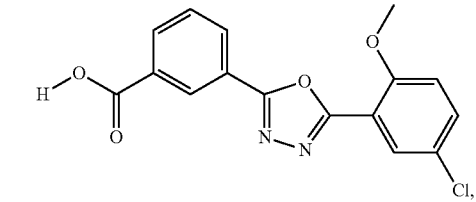

-continued

333
-continued
292 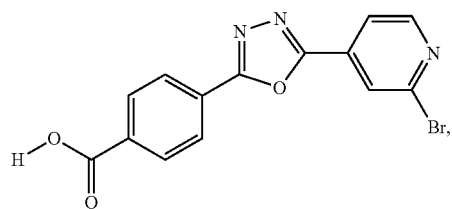
293 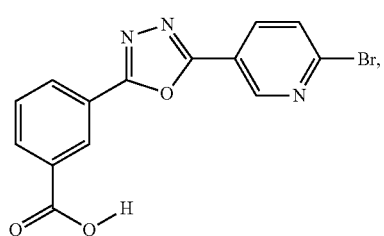
294 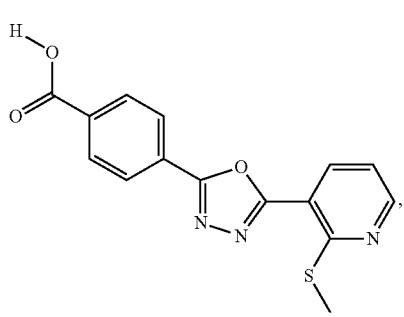
295 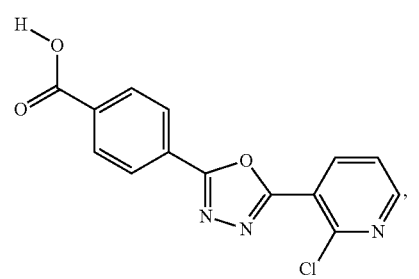
296 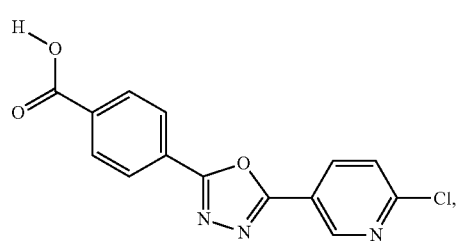
297 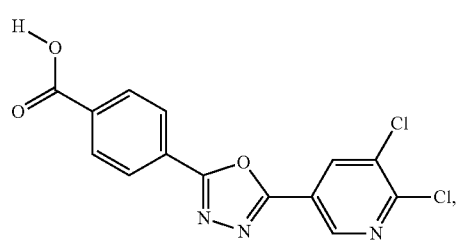
334
-continued
298 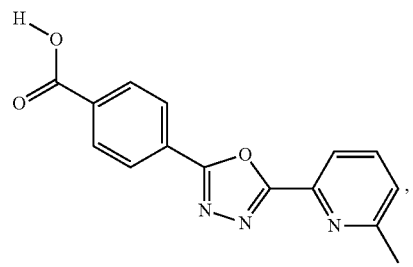
299 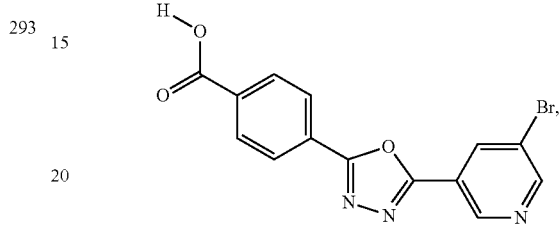
300 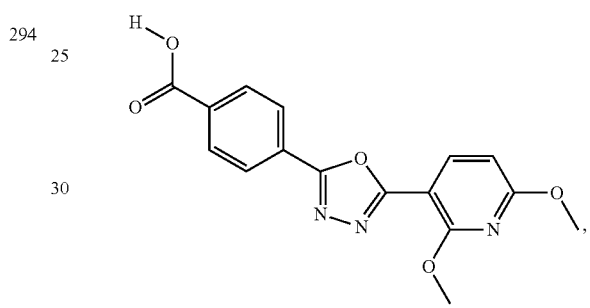
301 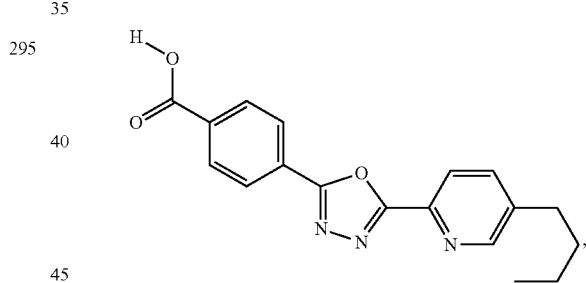
302 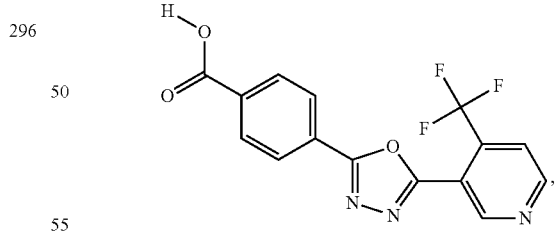
303 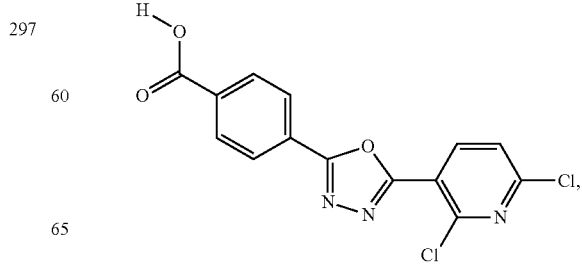

304
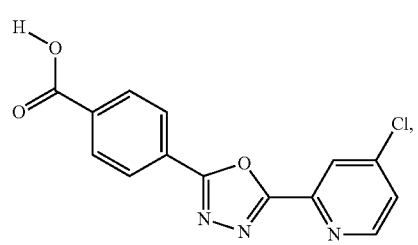
305
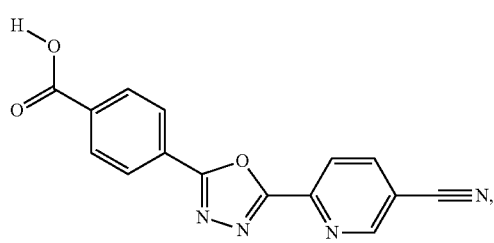
306
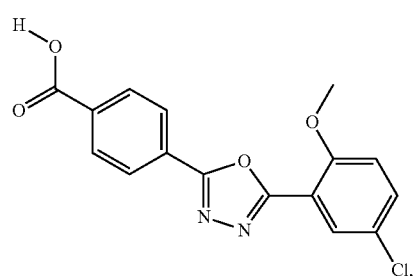
307
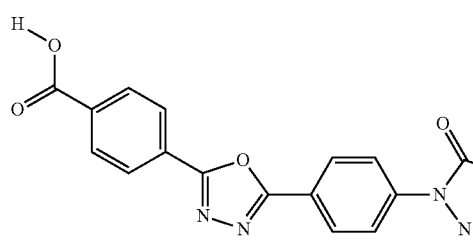
308
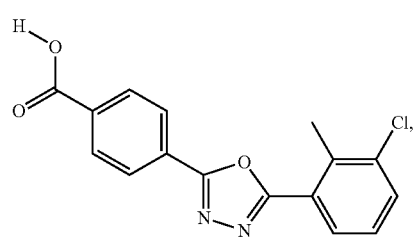
309
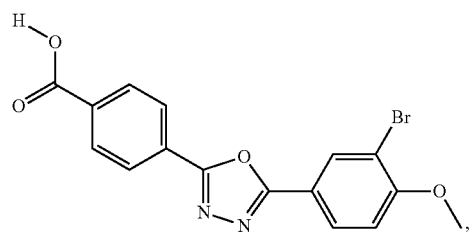
315
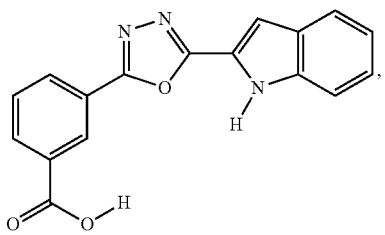
316
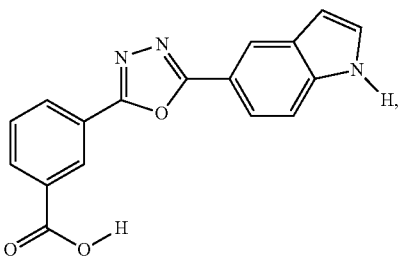
317
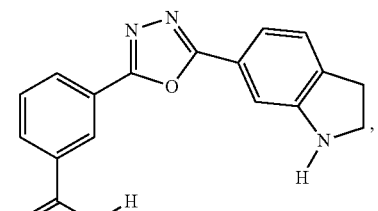
318
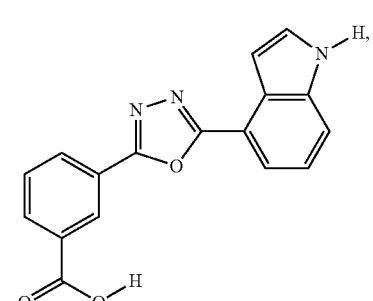
319
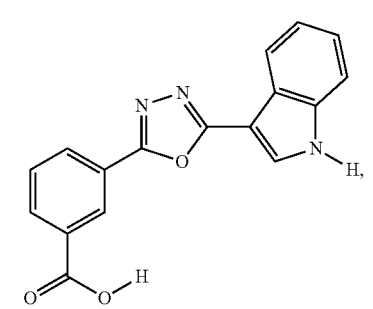
401
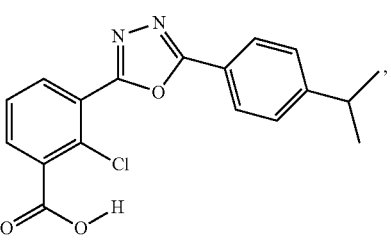

402
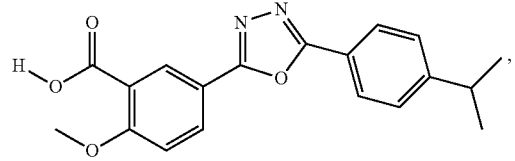
601
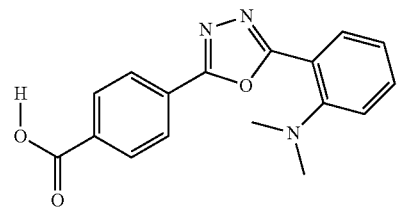
605
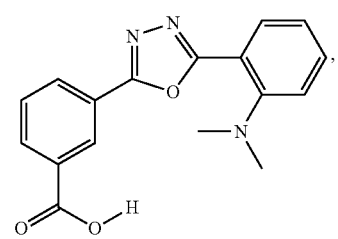
606
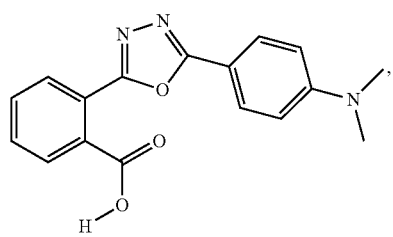
609
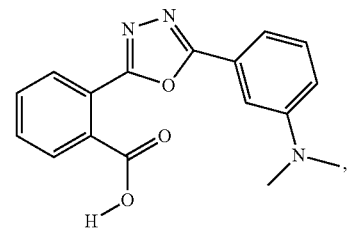
610
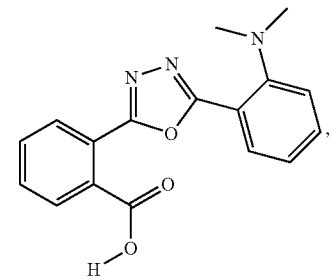
615
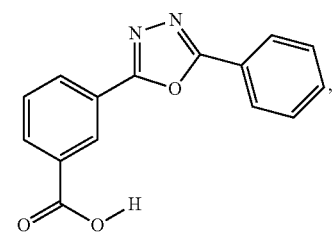
620
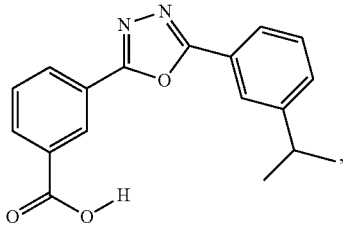
621
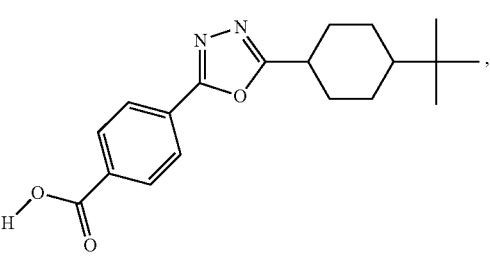
622
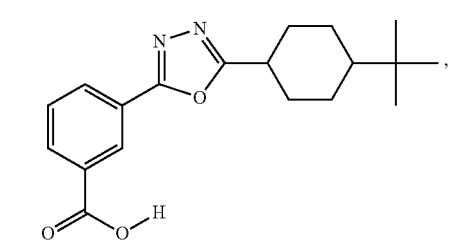
624
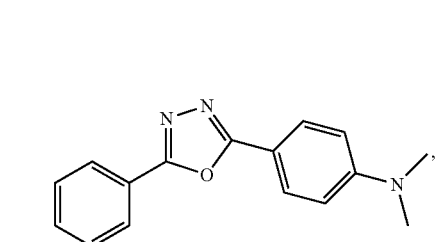
626
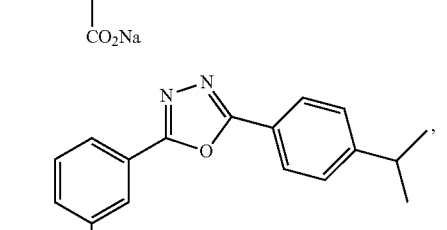
628
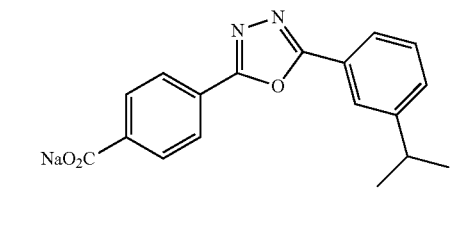
and a pharmaceutically acceptable salt thereof.

3. The compound of claim 2, wherein said compound is selected from the group consisting of:
1
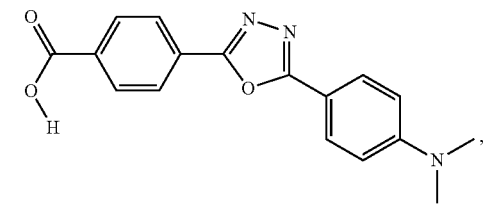
2
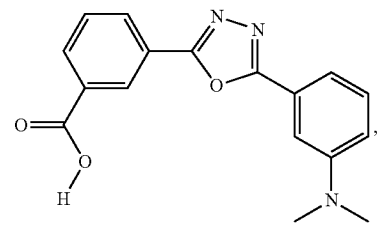
3
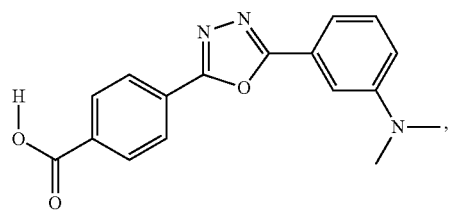
4
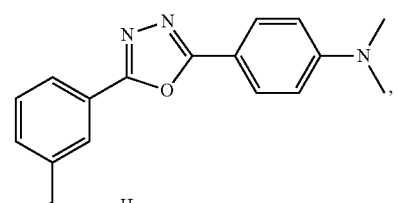
5
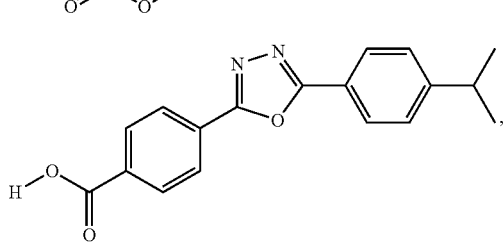
6
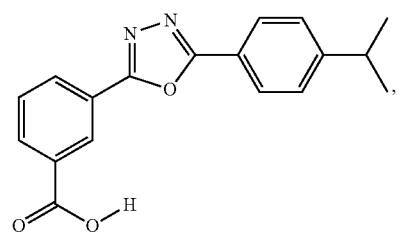
7
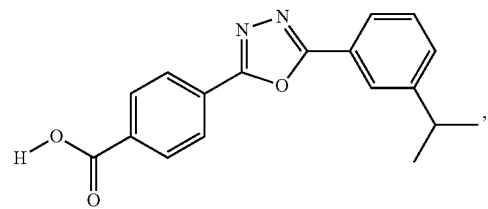
12
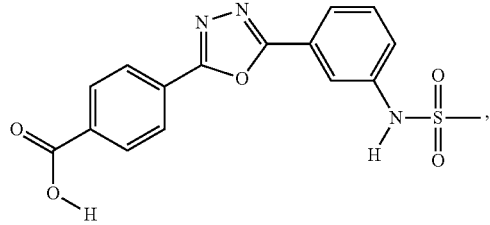
13
14
15
21
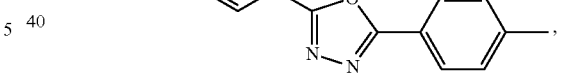
22
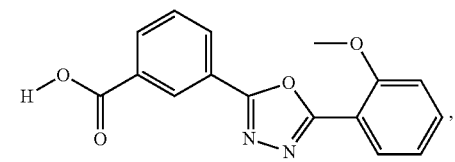
23
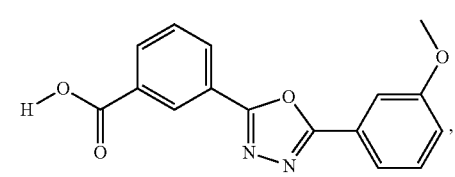
24
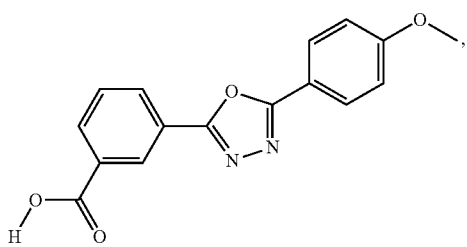

25
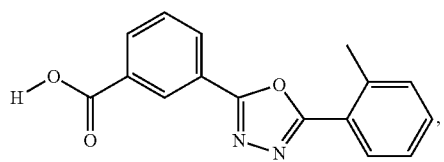
26
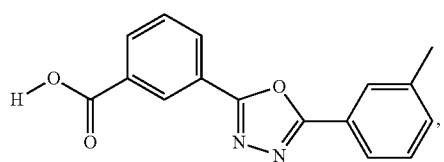
27
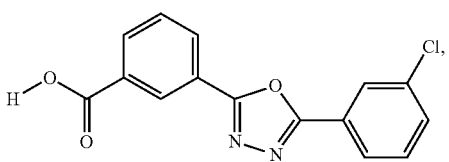
29
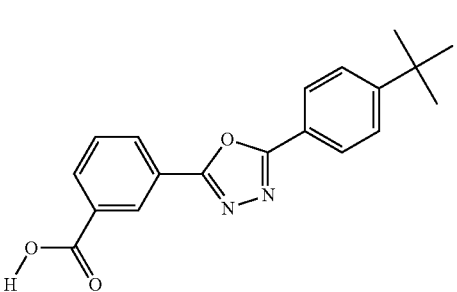
30
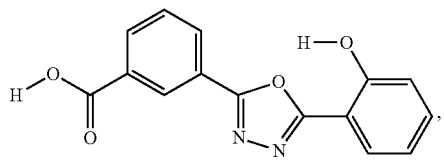
32
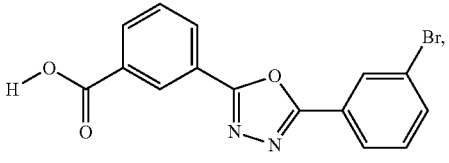
33
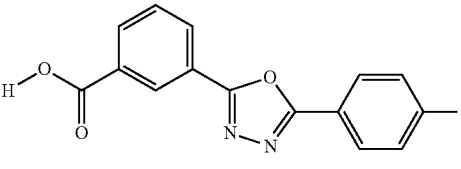
34
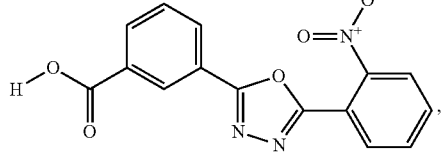
35
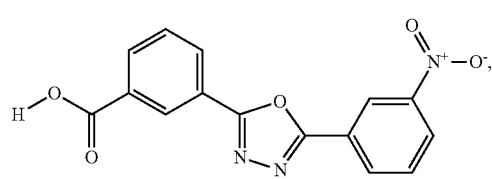
36
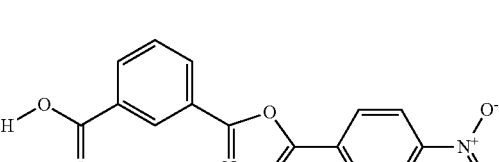
37
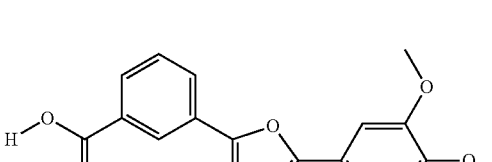
38
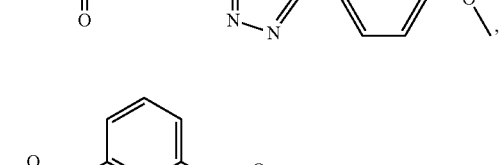
39
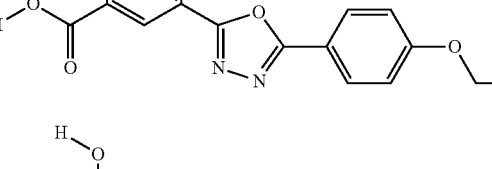
40
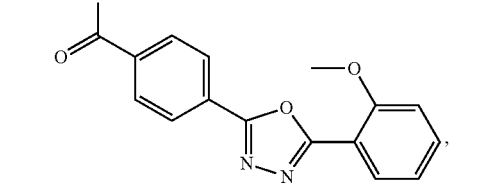
41
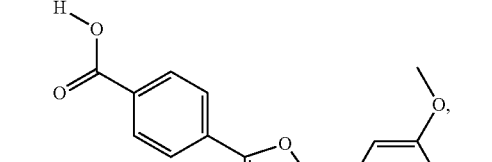
42
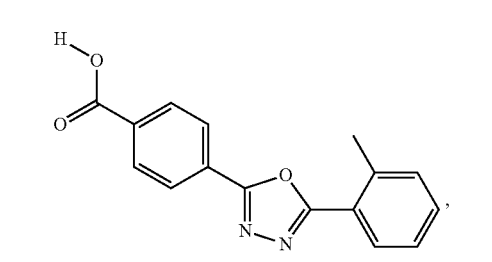

-continued
43
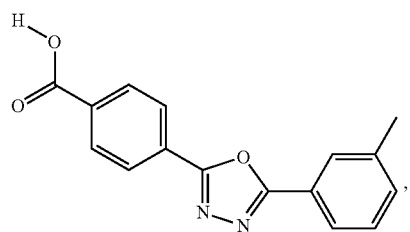
44
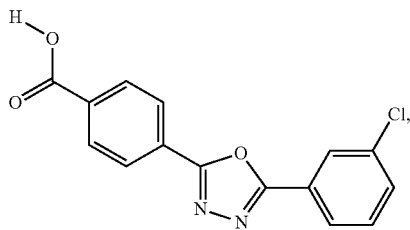
47
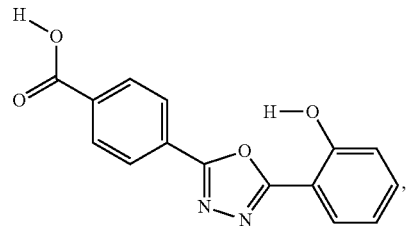
54
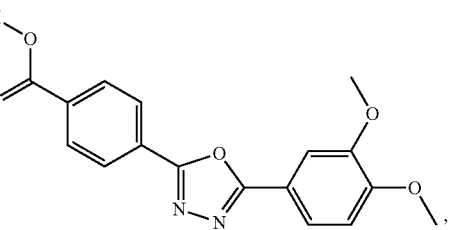
55
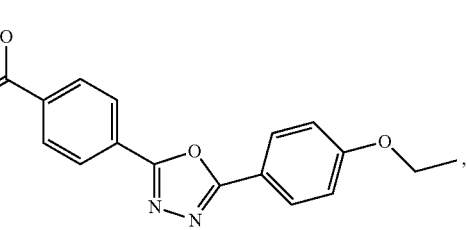
60
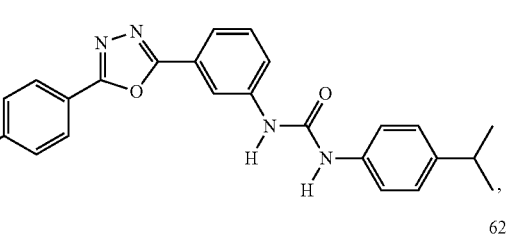
62
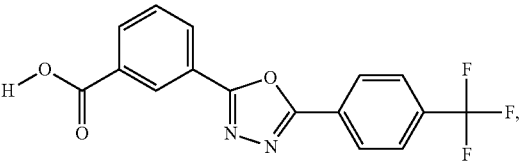
-continued
63
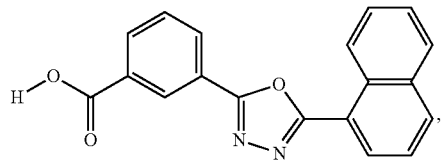
64
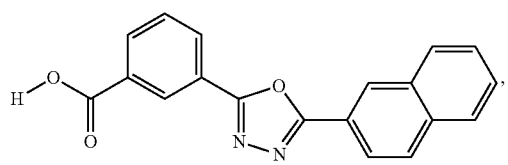
65
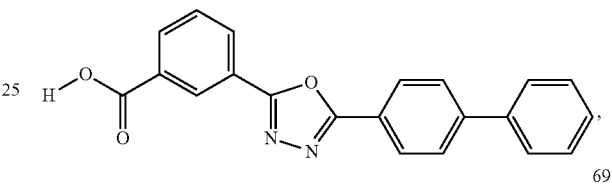
69
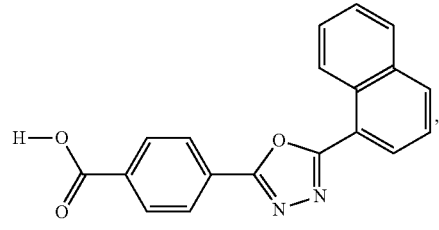
70
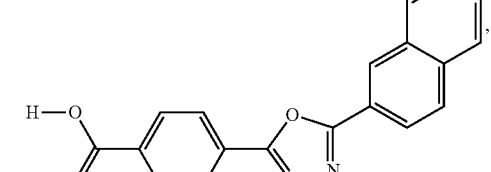
71
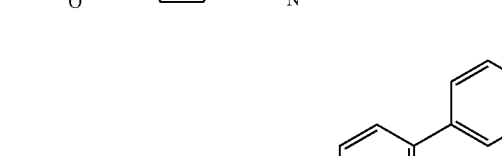
82
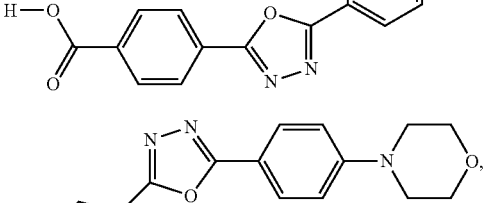
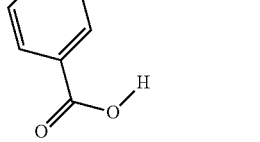

83
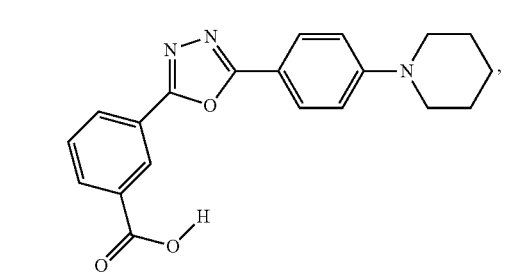
84
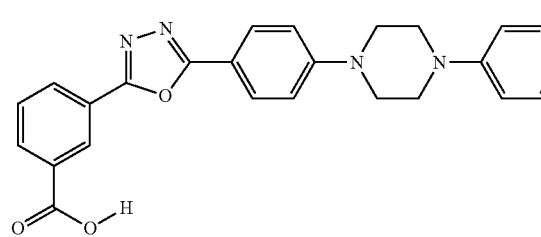
87
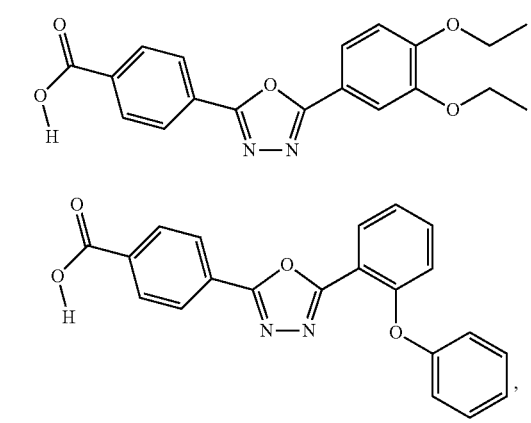
89
90
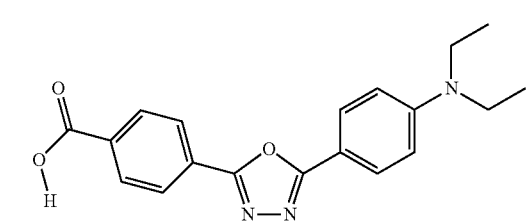
91
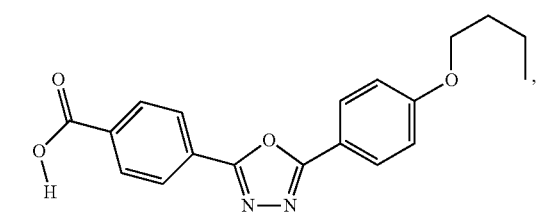
92
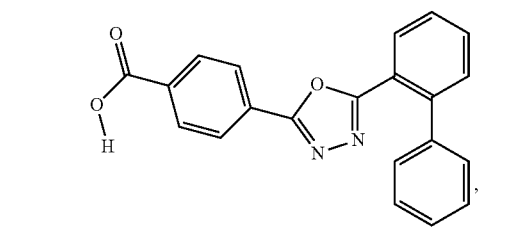
93
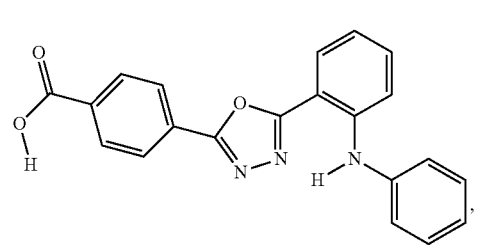
96
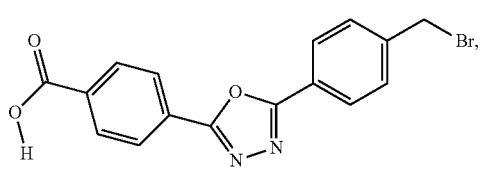
98
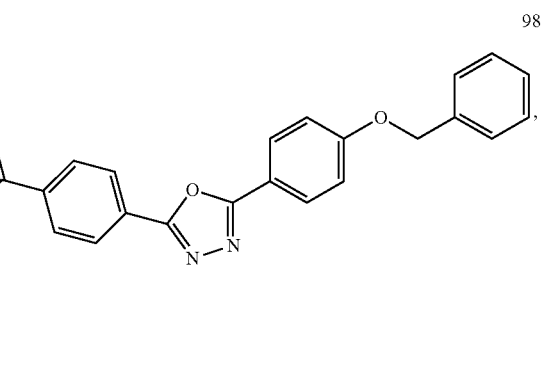
99
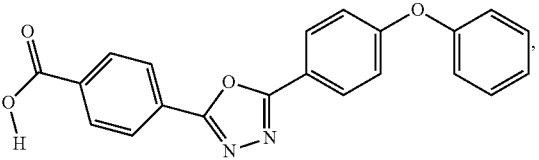
100
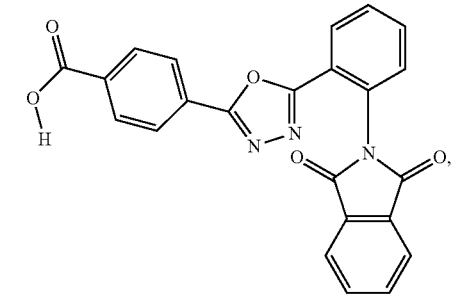
101
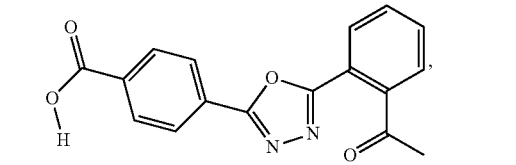

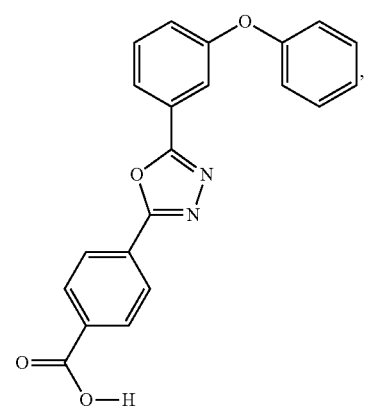
102
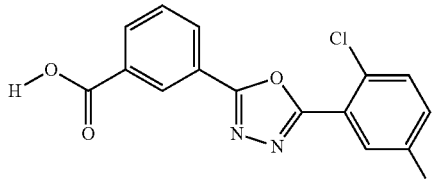
110
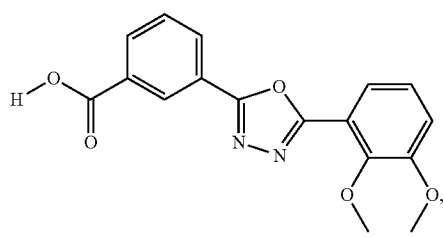
111
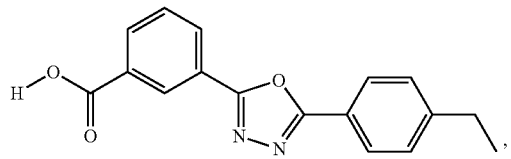
103
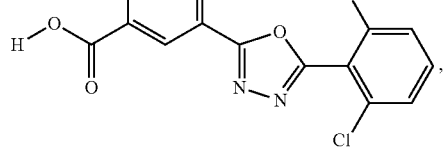
112
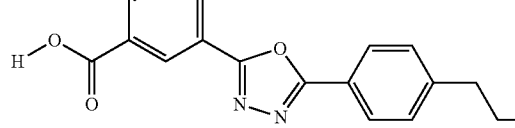
104
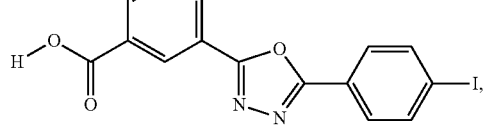
106
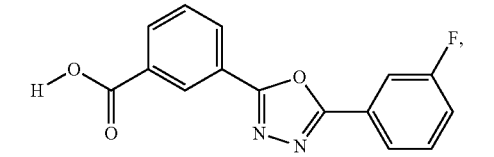
107
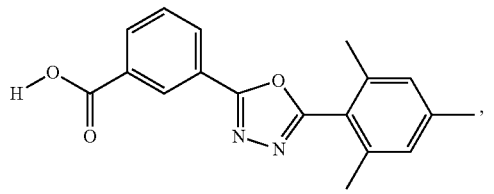
108
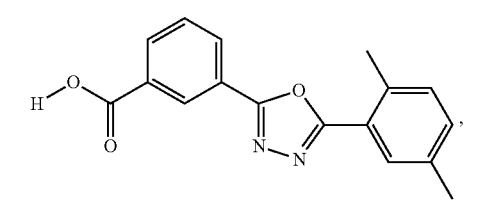
109
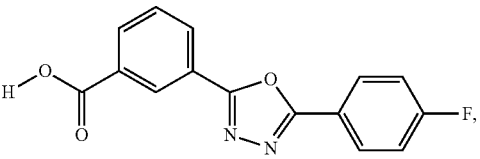
115
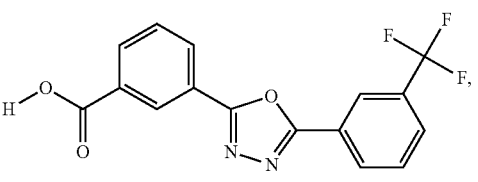
117

-continued
118
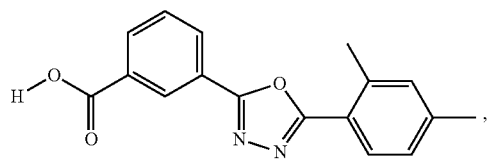
119
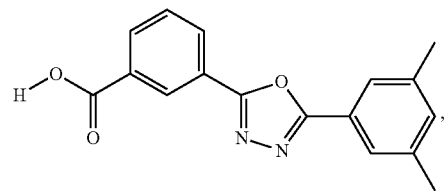
120
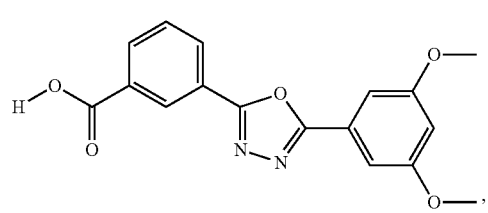
121
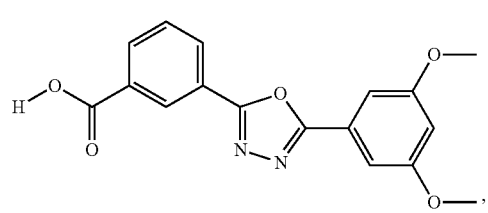
122
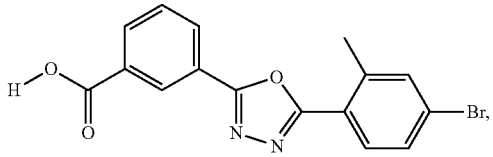
124
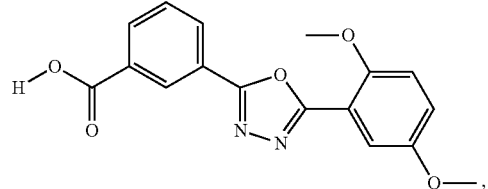
125
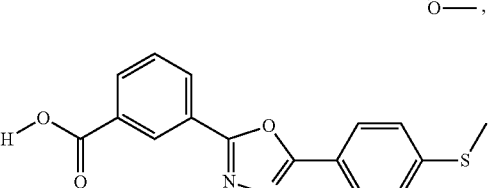
126
-continued
127
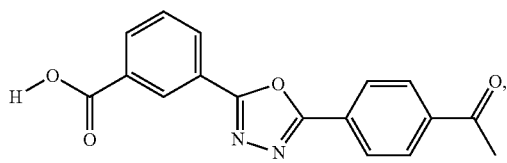
128
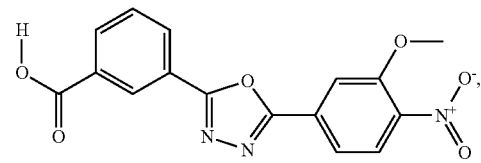
129
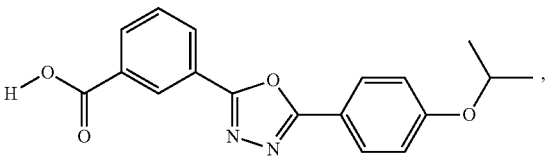
130
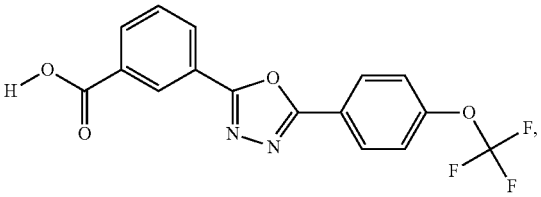
131
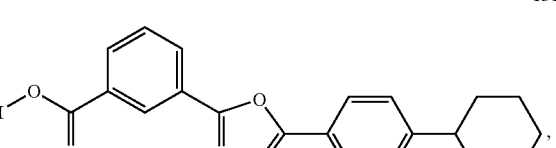
132
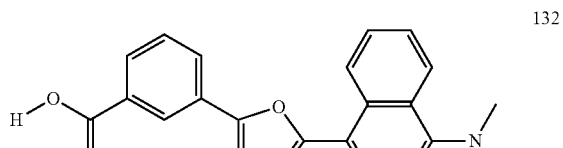
133
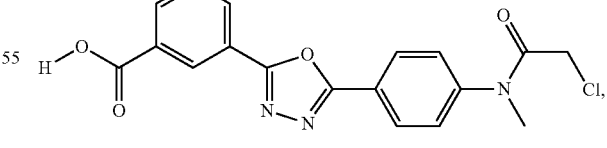
134
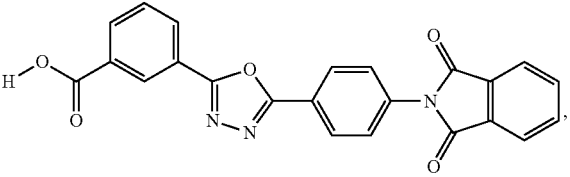

351
-continued
135
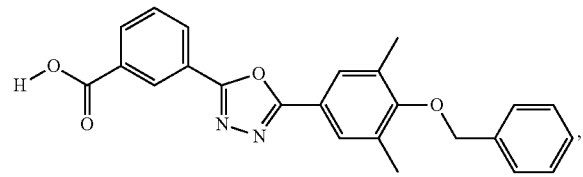
136
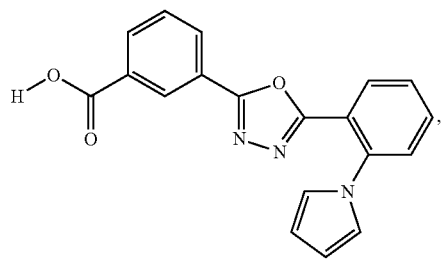
142
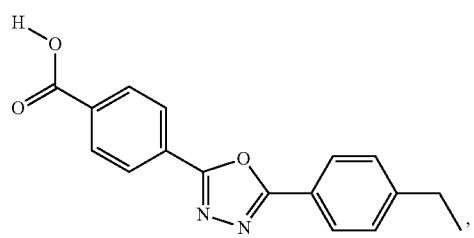
143
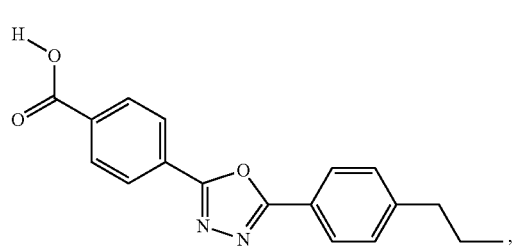
144
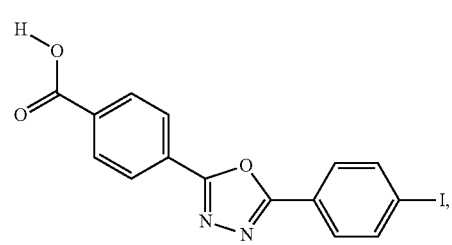
145
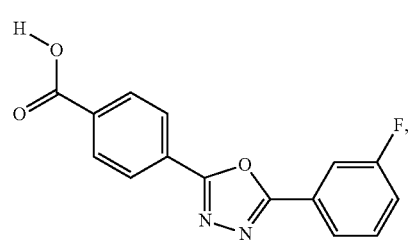
352
-continued
146
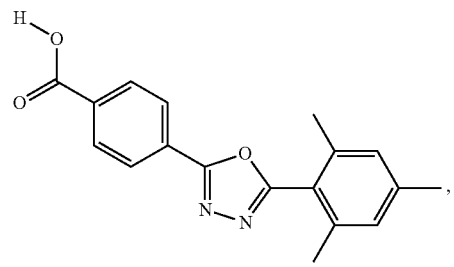
147
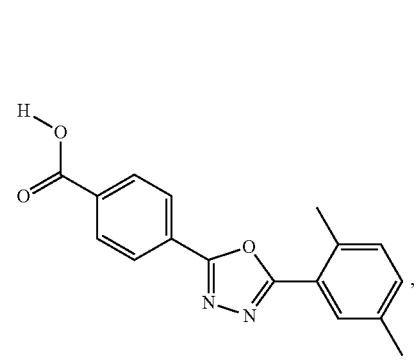
148
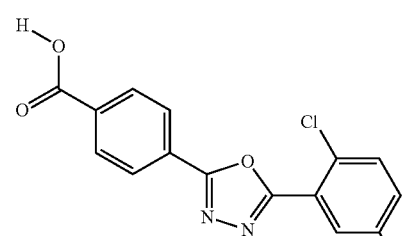
149
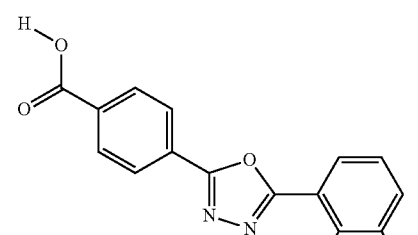
150
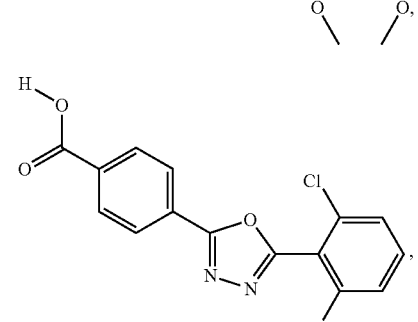

353
-continued
151
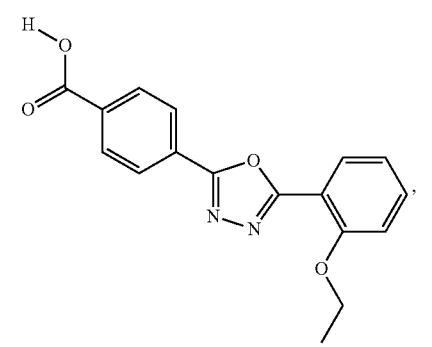
152
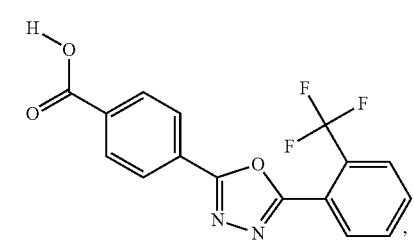
153
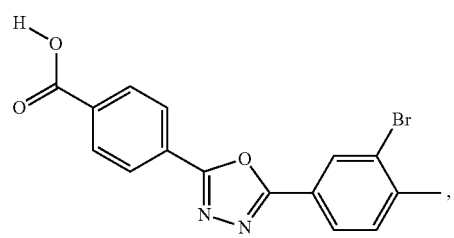
154
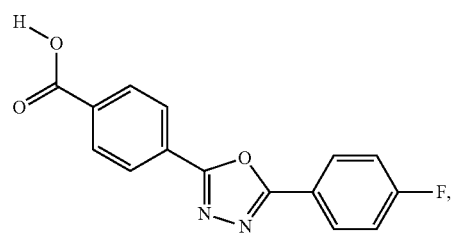
155
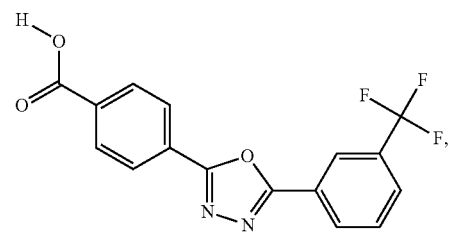
156
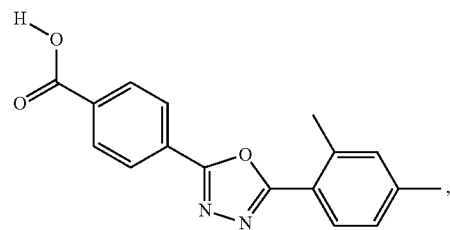
354
-continued
157
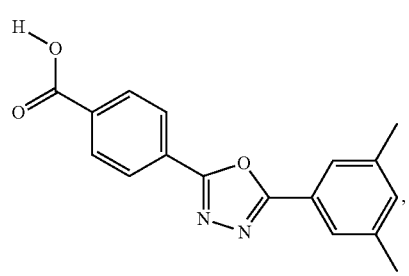
158
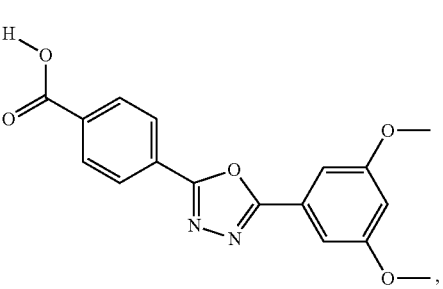
159
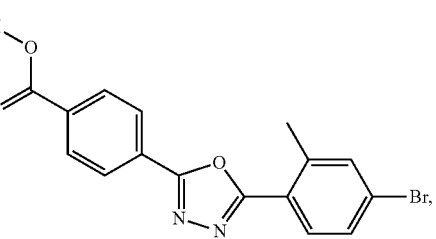
160
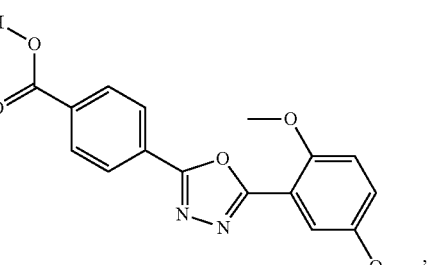
161
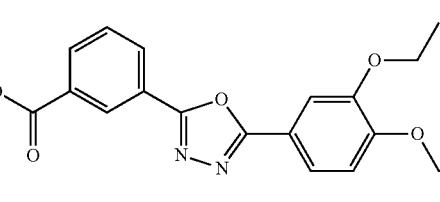
163
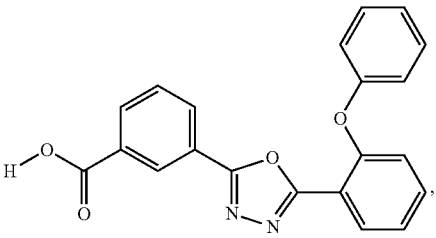

355
-continued
164
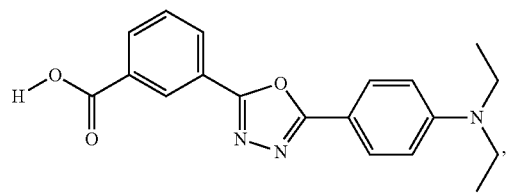
165
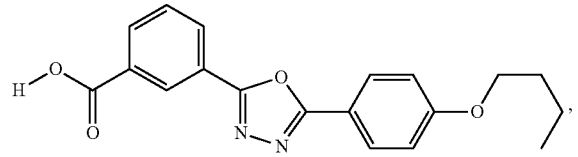
166
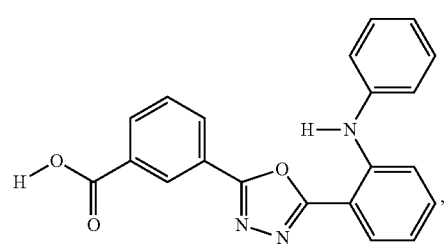
168
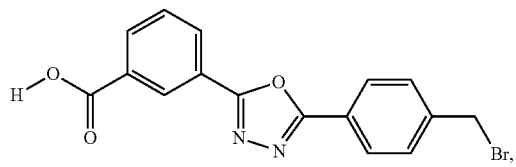
169
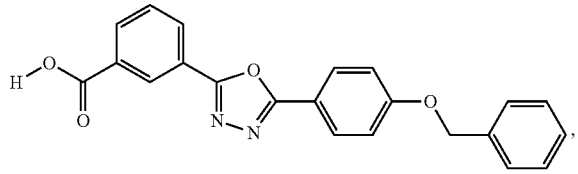
170
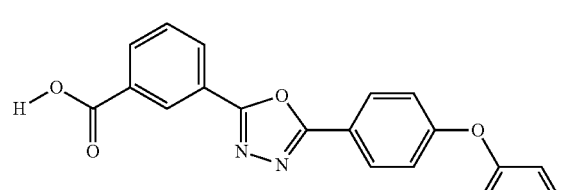
171
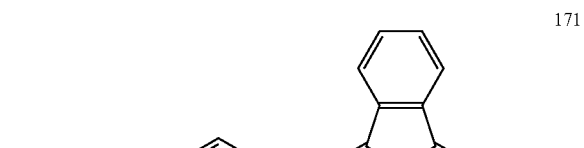
356
-continued
173
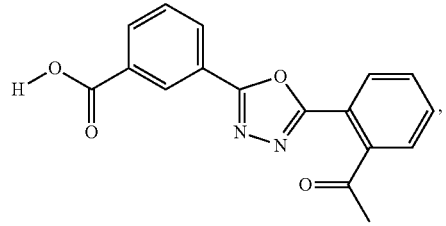
175
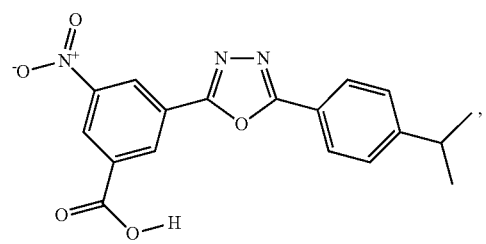
176
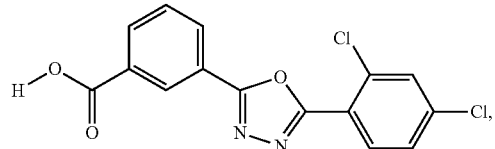
177
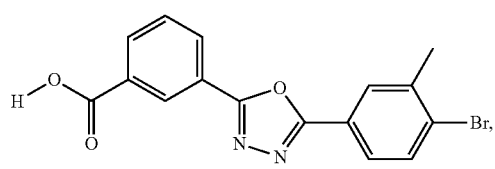
178
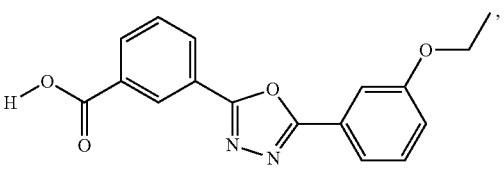
179
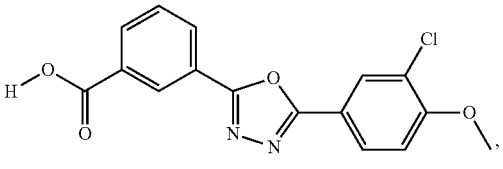
180
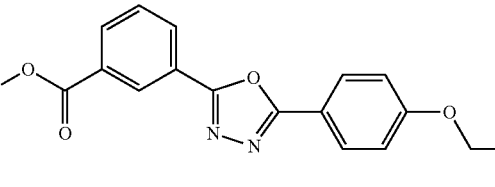
181
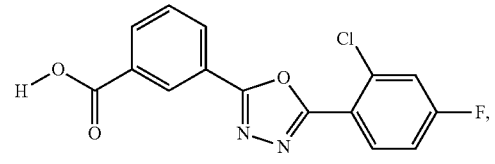

US 9,611,230 B2
-continued
182 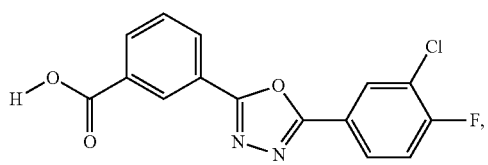
183 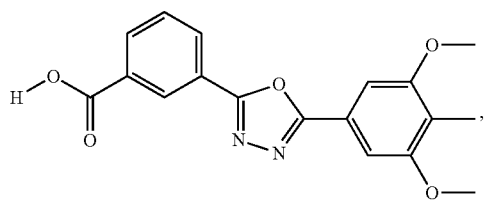
184 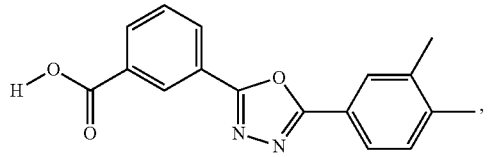
185 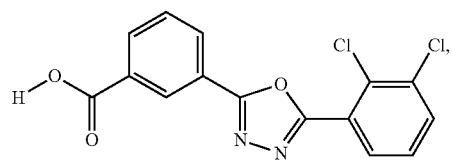
186 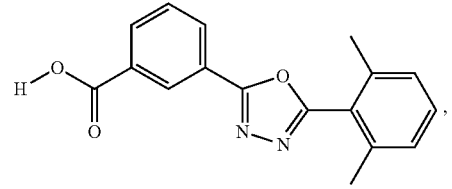
187 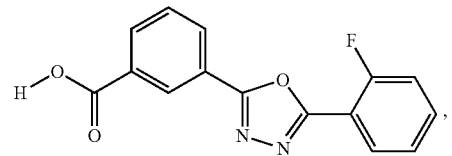
188 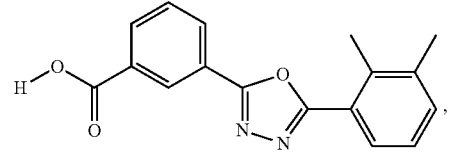
189 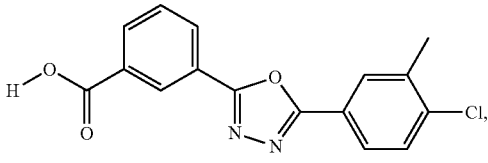
-continued
190 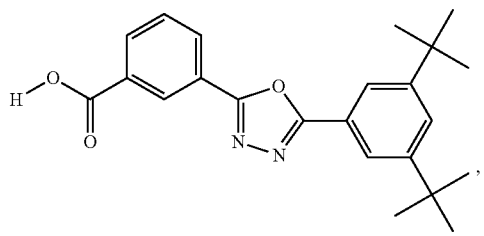
191 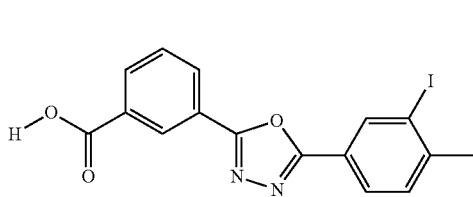
192 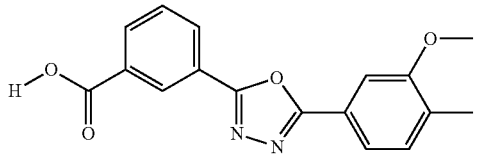
194 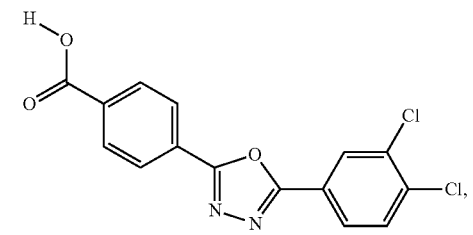
195 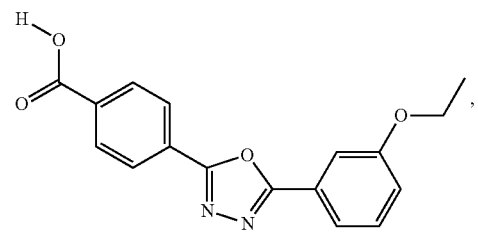
196 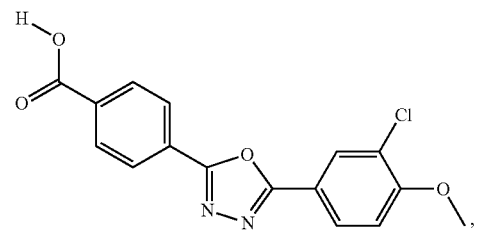
197 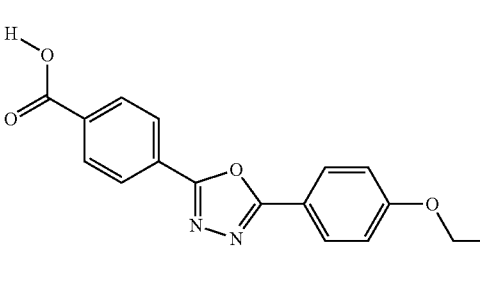

| | |
|---|---|
| 198 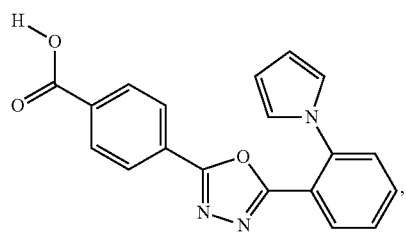 | 204 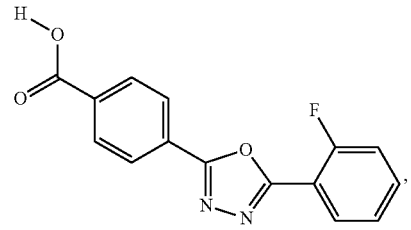 |
| 199 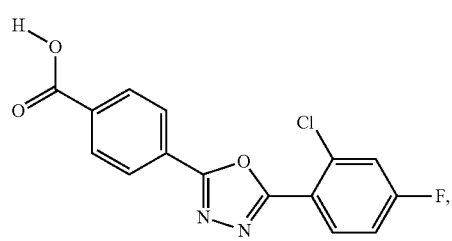 | 205 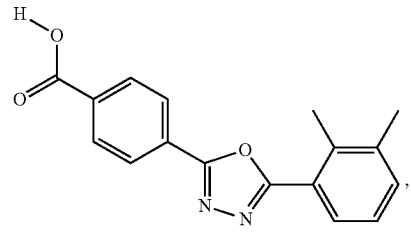 |
| 200 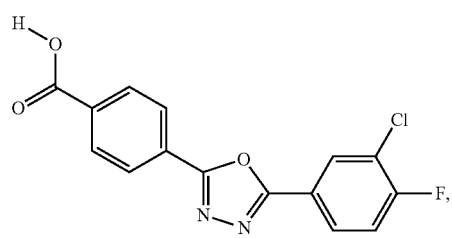 | 206 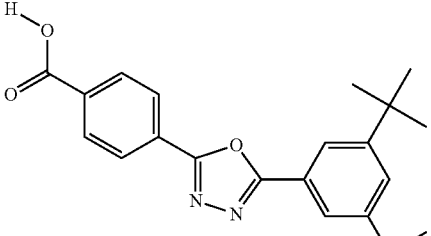 |
| 201 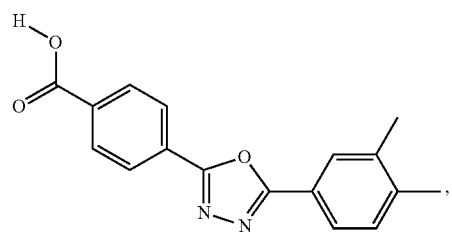 | 207 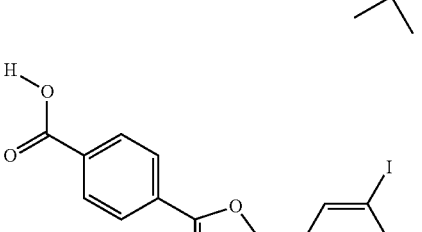 |
| 202 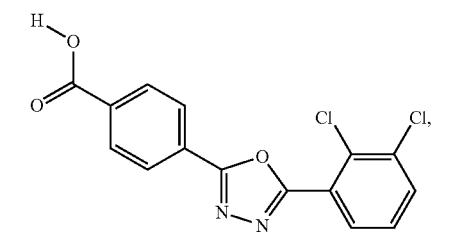 | 208 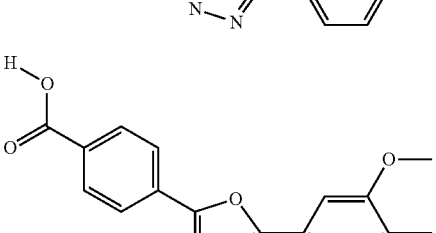 |
| 203 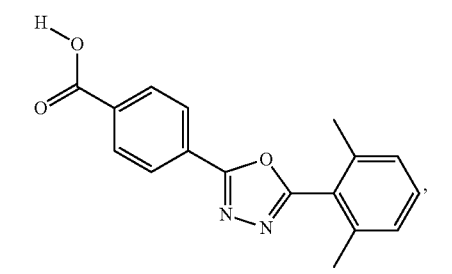 | 210 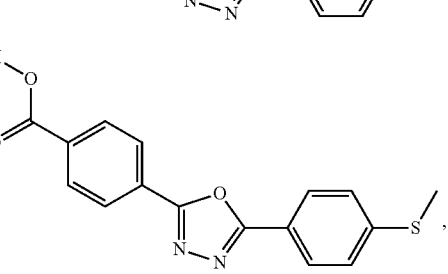 |

-continued
211
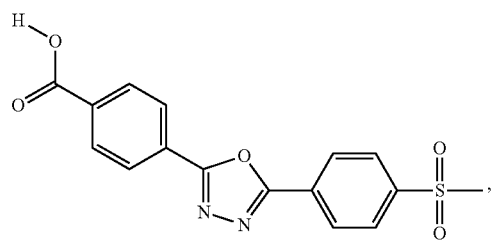
212
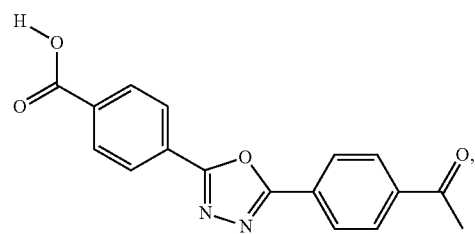
213
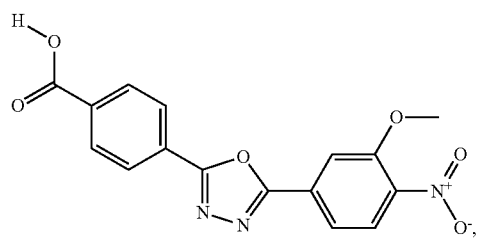
214
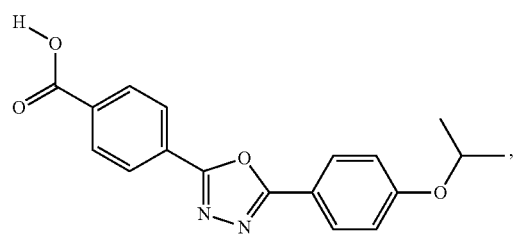
215
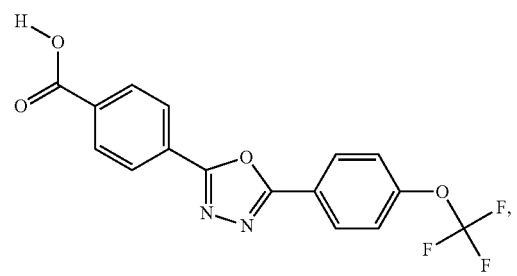
217
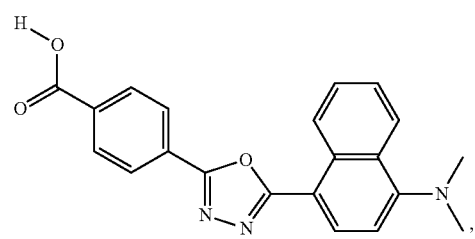
-continued
218
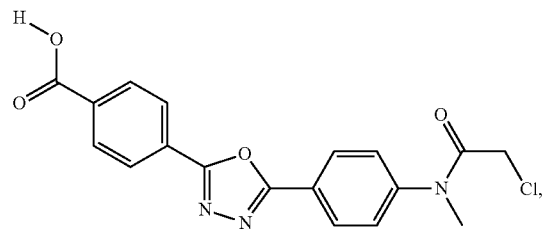
219
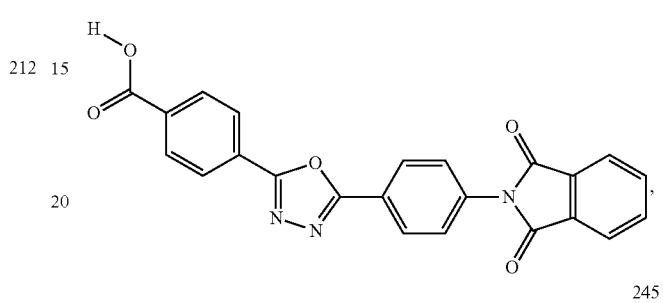
245
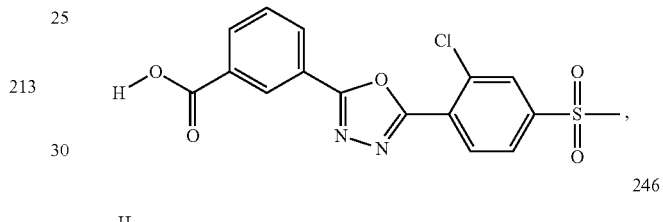
246
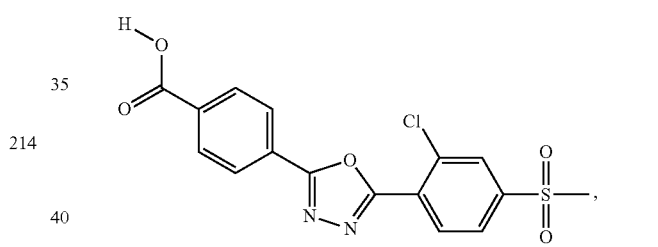
249
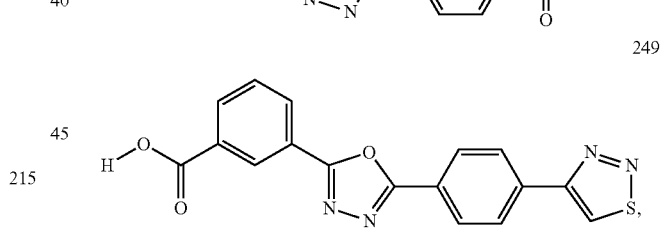
254
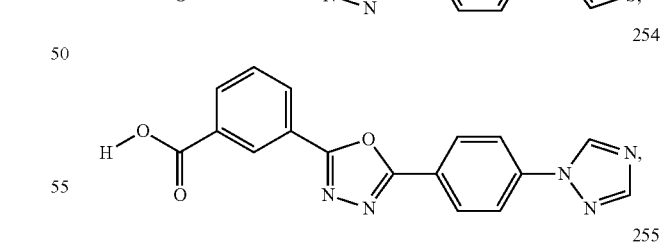
255
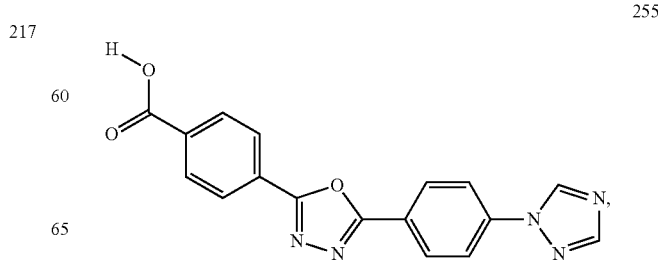

363
-continued
266
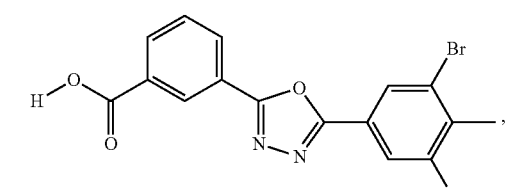
267
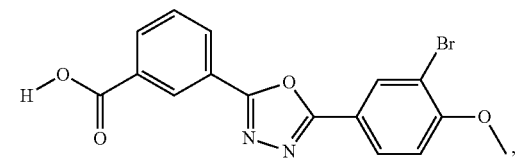
268
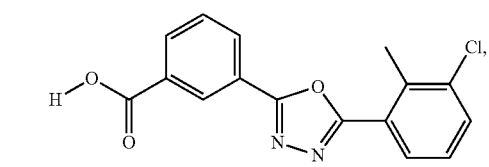
269
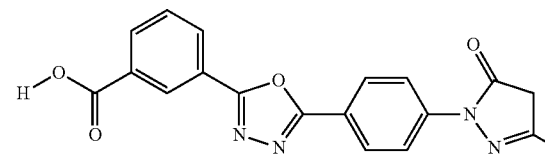
270
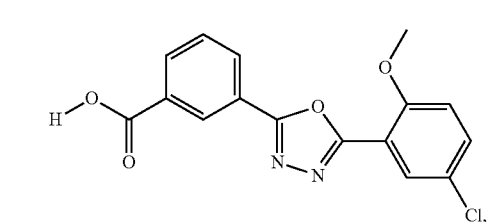
271
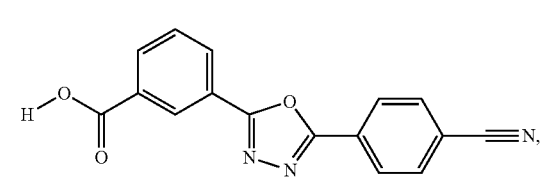
278
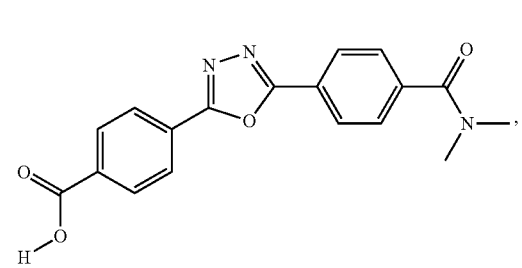
279
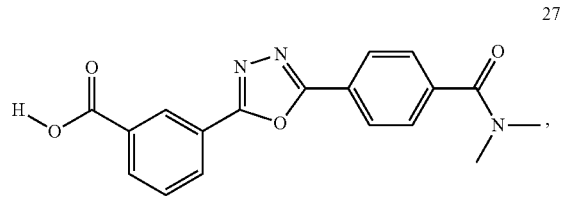
364
-continued
280
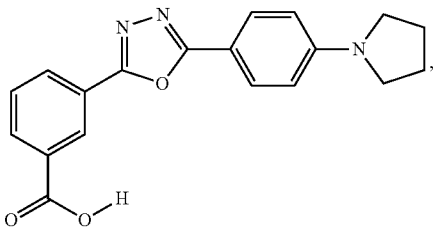
281
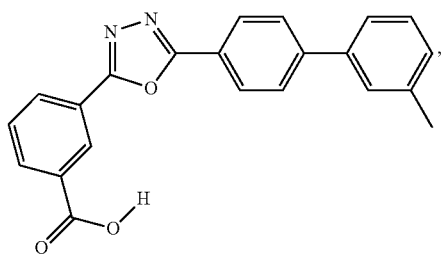
285
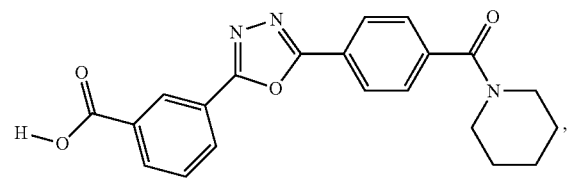
286
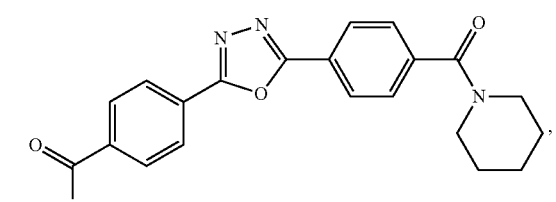
305
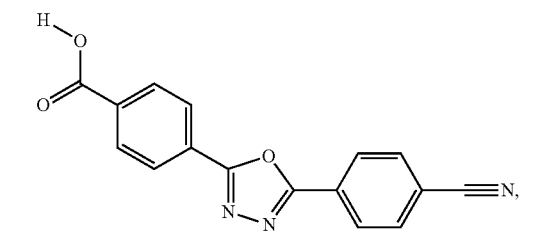
306
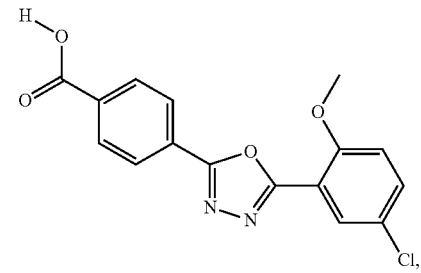

307 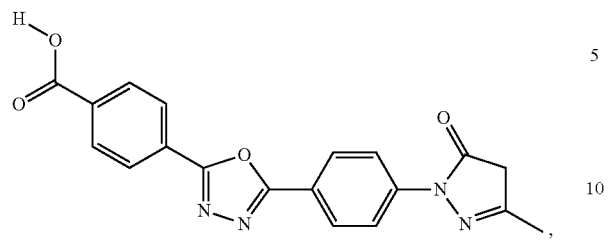
308 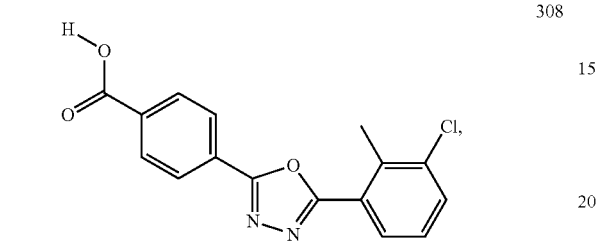
309 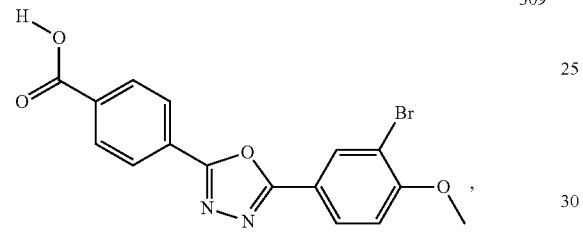
401 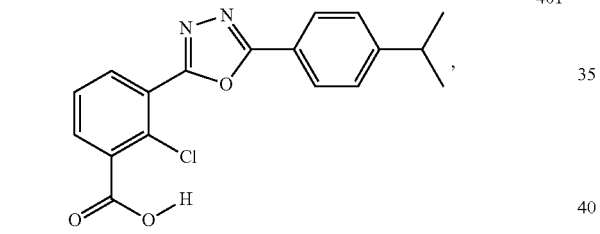
402 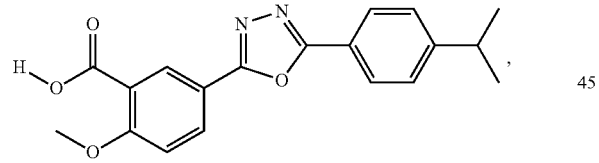
601 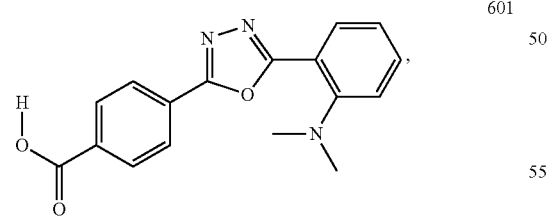
605 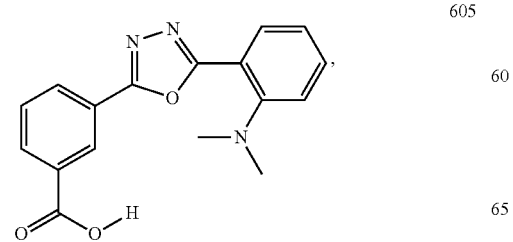
606 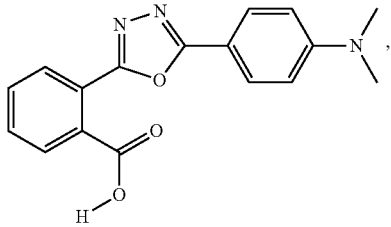
609 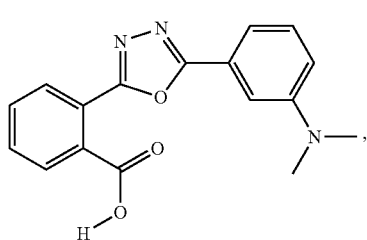
610 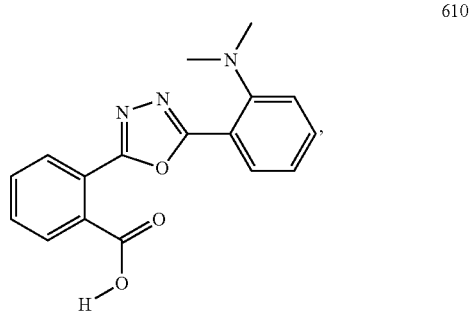
615 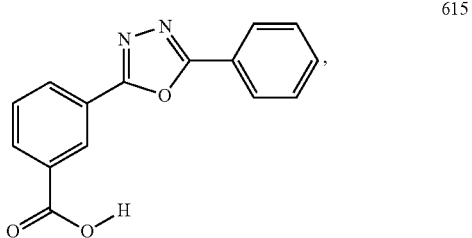
620 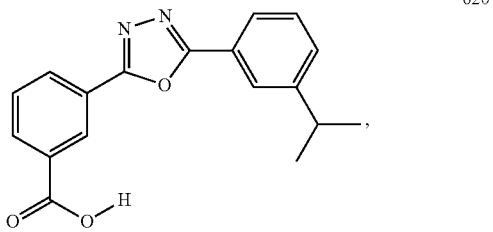
624 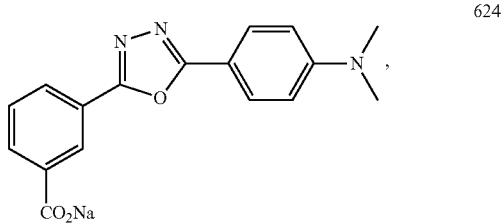

-continued
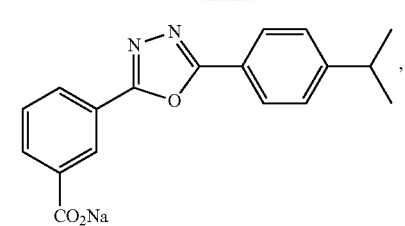 626
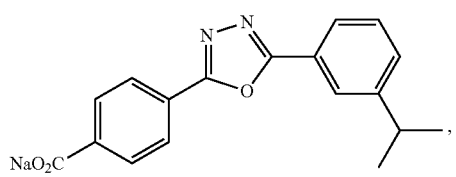 628
and a pharmaceutically acceptable salt thereof.
* * * * *

UNITED STATES PATENT AND TRADEMARK OFFICE
CERTIFICATE OF CORRECTION

PATENT NO. : 9,611,230 B2
APPLICATION NO. : 11/577191
DATED : April 4, 2017
INVENTOR(S) : Neil G. Almstead et al.

It is certified that error appears in the above-identified patent and that said Letters Patent is hereby corrected as shown below:

In the Specification

At Column 19 replace " 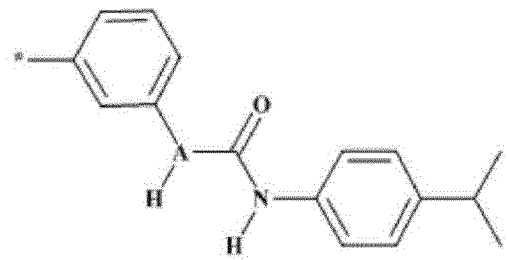 " with

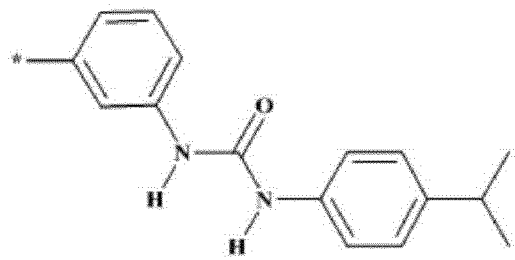 --;

Signed and Sealed this
Third Day of December, 2019

Andrei Iancu
*Director of the United States Patent and Trademark Office*

CERTIFICATE OF CORRECTION (continued)
U.S. Pat. No. 9,611,230 B2

At Column 21 replace " 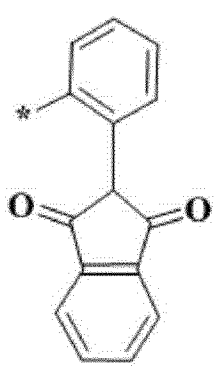 " with -- 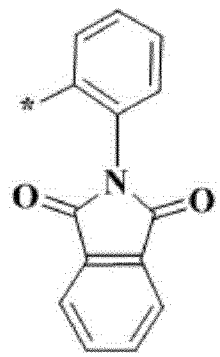 --;

At Column 154, compound 637, replace " 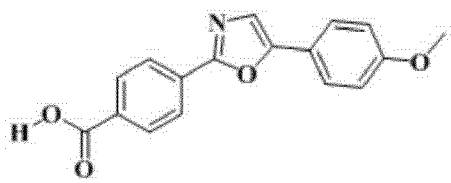 " with
-- 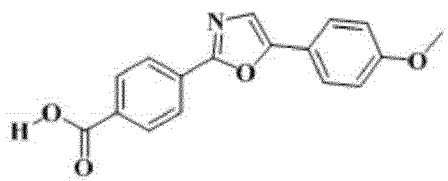 --;

In the Claims

At Column 283, Lines 55-60, in Claim 1 replace " 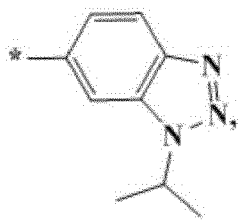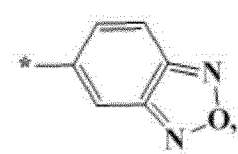 " with
-- 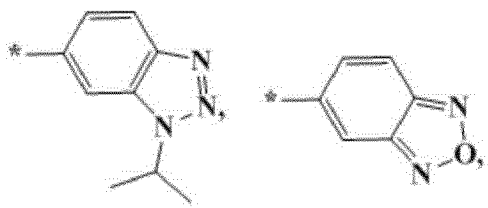 --;

At Column 285, Lines 34-44, in Claim 1 replace " 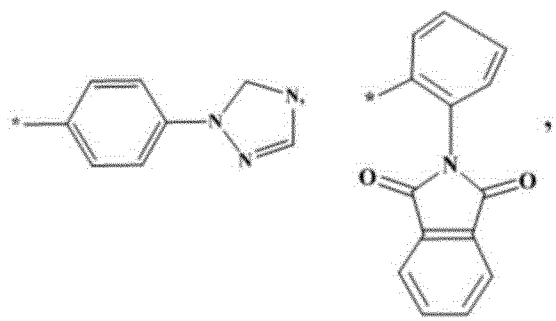 "
with -- 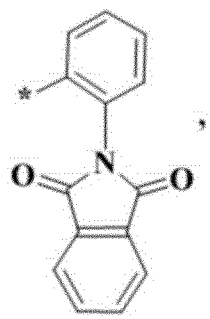 --;
At Column 287, Lines 18-23, in Claim 1 replace " 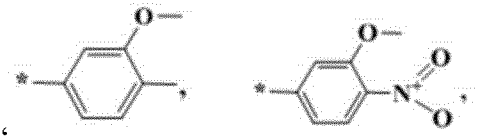 " with
-- 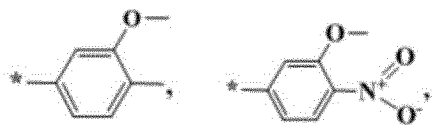 --;
At Column 289, Lines 13-18, in Claim 1 replace " 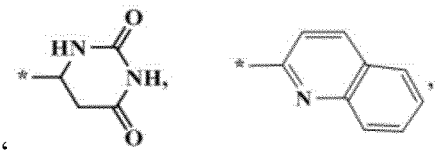 " with
-- 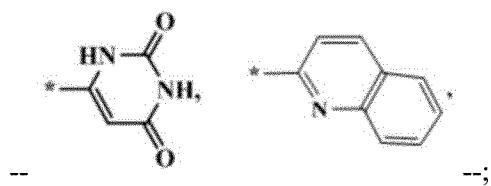 --;

CERTIFICATE OF CORRECTION (continued)
U.S. Pat. No. 9,611,230 B2

At Column 290, Lines 55-61, in Claim 1 replace " 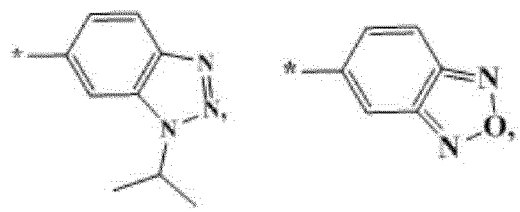 " with

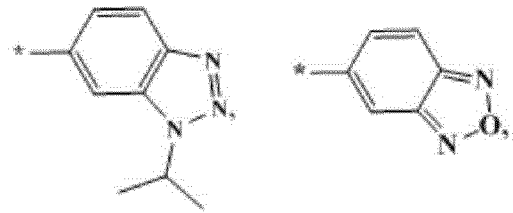

-- --;

At Column 292, Lines 34-43, in Claim 1 replace " 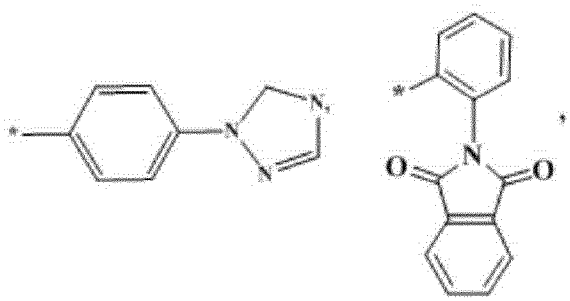 "

with -- 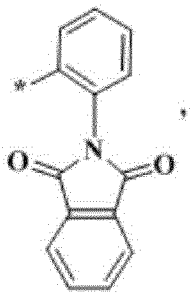 --;

At Column 294, Lines 16-20, in Claim 1 replace " 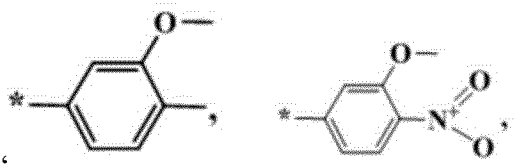 " with

-- --;

At Column 295, Lines 10-15, in Claim 1 replace " 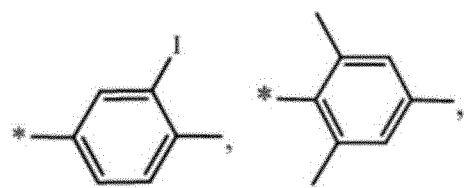 " with -- 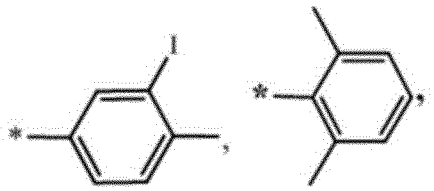 --;
At Column 296, Lines 27-33, in Claim 1 replace " 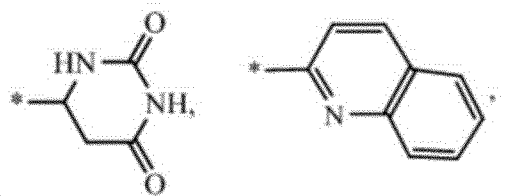 " with -- 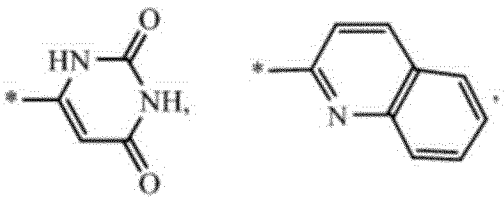 --;
At Column 306, compound 95 in Claim 2 replace " 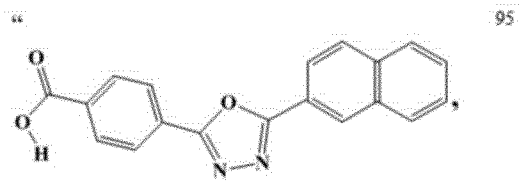 " with -- 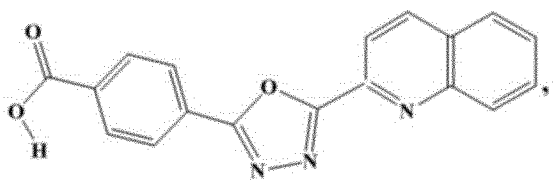 --;

At Column 306, compound 97 in Claim 2 replace " 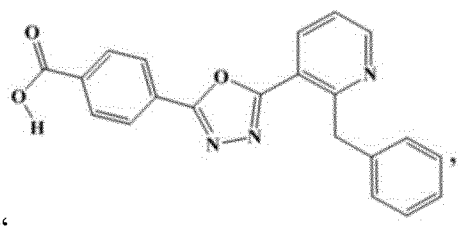 " with
-- 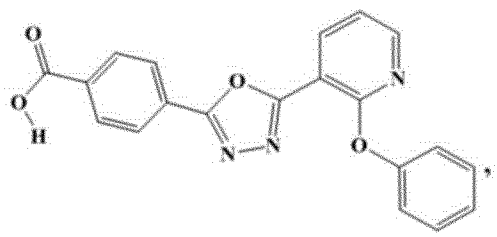 --;
At Column 309, compound 119 in Claim 2 replace " 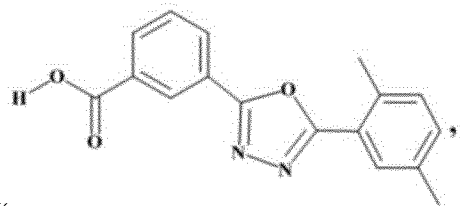 "
with -- 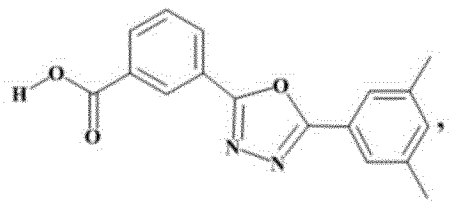 --;
At Column 310, compound 125 in Claim 2 replace " 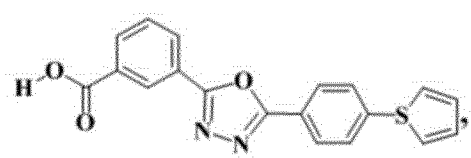 "
with -- 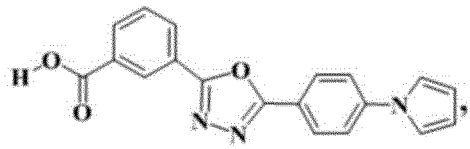 --;

At Column 311, compound 137 in Claim 2 replace " 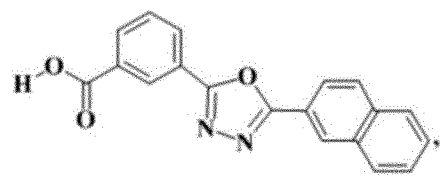 "
with -- 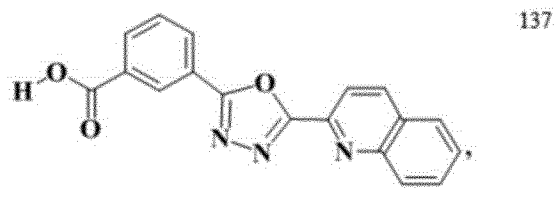 --;
At Column 312, compound 139 in Claim 2 replace " 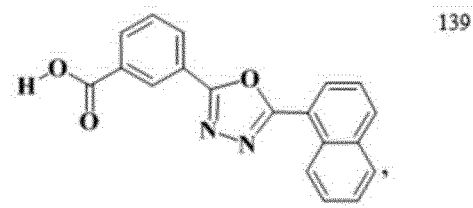 " with
-- 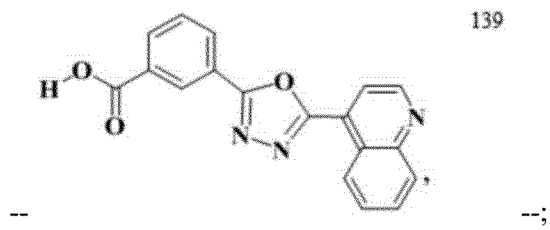 --;
At Column 315, compound 161 in Claim 2 replace " 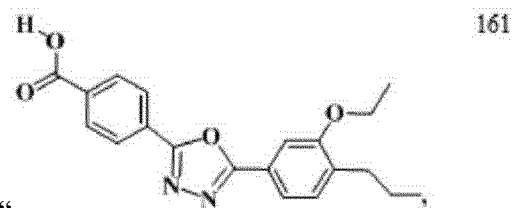 " with
-- 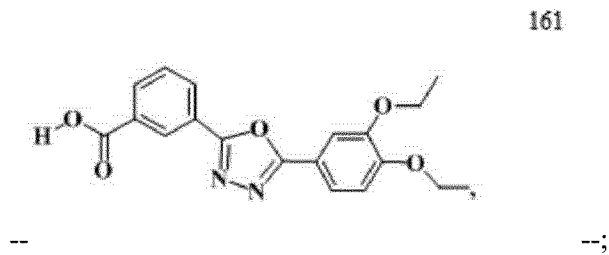 --;

At Column 316, compound 171 in Claim 2 replace " 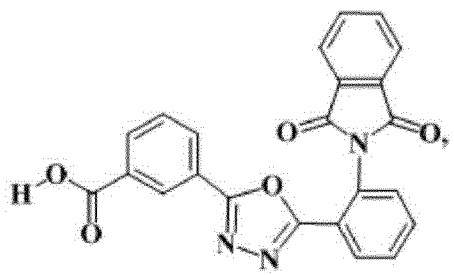 "
with -- 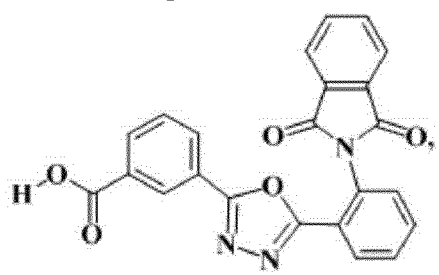 --;
At Column 322, compound 212 in Claim 2 replace " 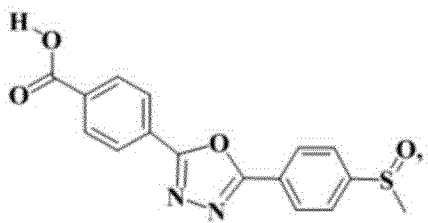 " with
-- 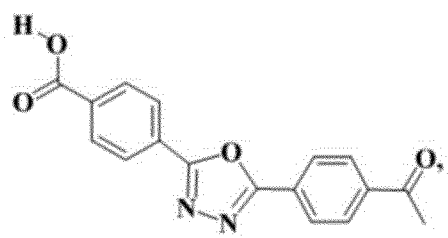 --;
At Column 324, Lines 40-48 in Claim 2 replace " 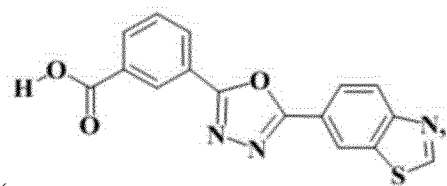 " with

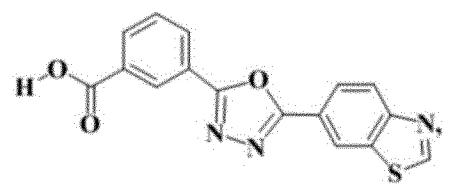
--                                        --;
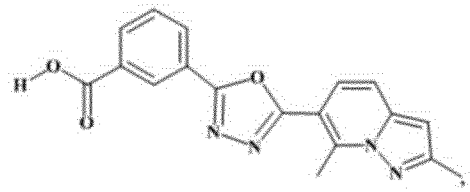
At Column 325, compound 234 in Claim 2 replace "                                        "
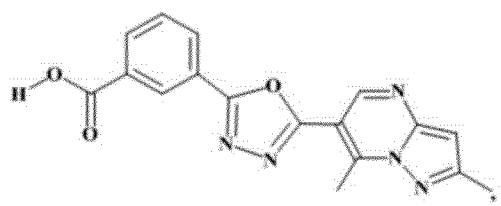
with --                                        --;
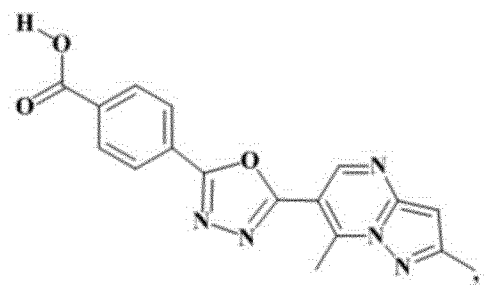
At Column 326, compound 235 in Claim 2 replace "                                        "
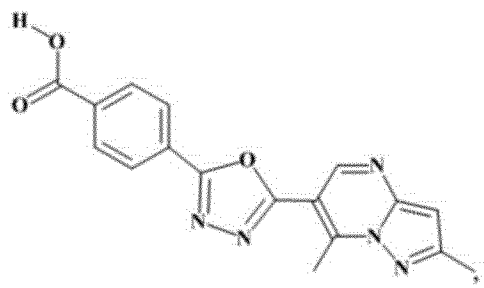
with --                                        --;

CERTIFICATE OF CORRECTION (continued)
U.S. Pat. No. 9,611,230 B2

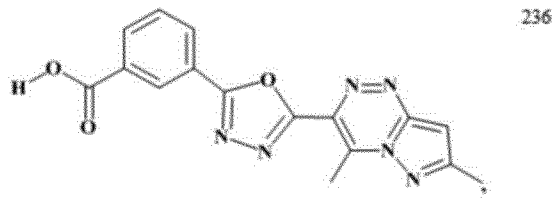

At Column 326, compound 236 in Claim 2 replace "

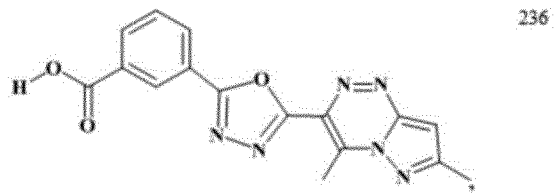

with -- --;

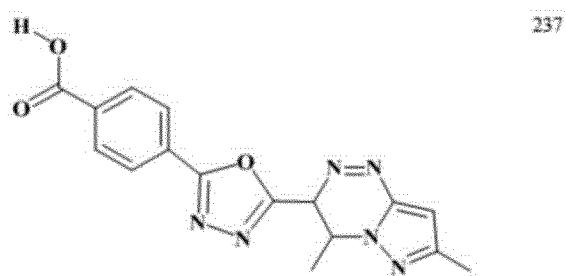

At Column 326, compound 237 in Claim 2 replace "

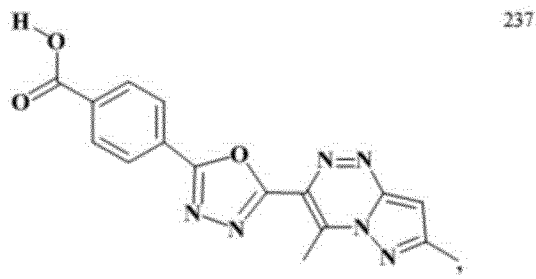

with -- --;

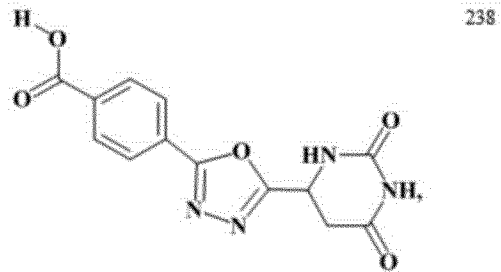

At Column 326, compound 238 in Claim 2 replace " " with

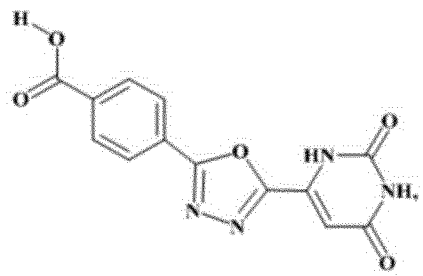
--                                          --;
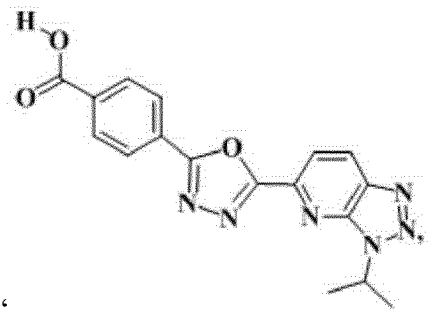
At Column 327, compound 244 in Claim 2 replace "                                          " with
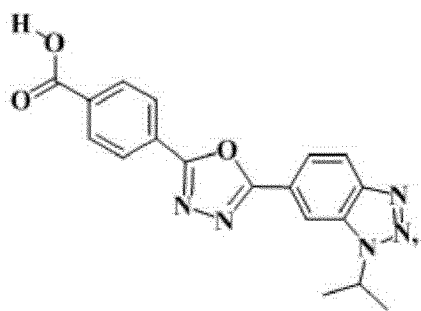
--                                          --;
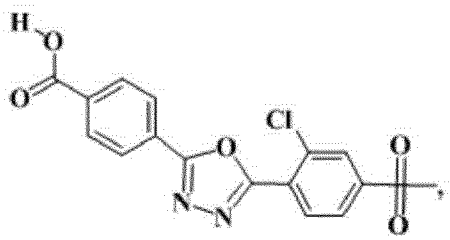
At Column 327, compound 246 in Claim 2 replace "                                          "

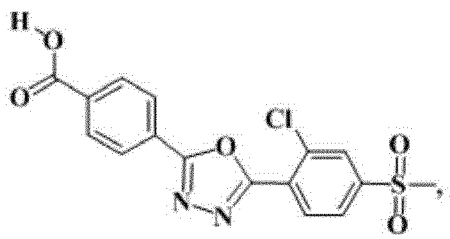
with -- -- ;
At Column 335, compound 305 in Claim 2 replace " 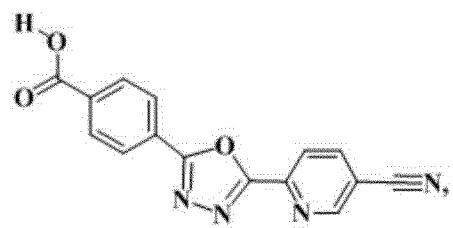 "
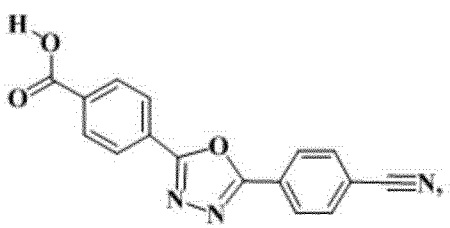
with -- -- ;
At Column 336, compound 317 in Claim 2 replace " 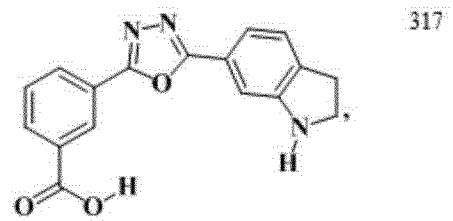 " with
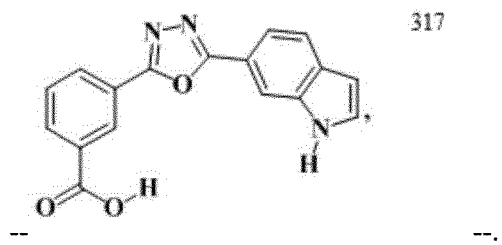
-- --.